United States Patent
Randolph et al.

(10) Patent No.: US 7,696,226 B2
(45) Date of Patent: Apr. 13, 2010

(54) HIV PROTEASE INHIBITING COMPOUNDS

(75) Inventors: John T. Randolph, Libertyville, IL (US); Hui-Ju Chen, Grayslake, IL (US); David A. DeGoey, Salem, WI (US); Charles A. Flentge, Salem, WI (US); William J. Flosi, Evanston, IL (US); David J. Grampovnik, Waukegan, IL (US); Peggy P. Huang, Lake Bluff, IL (US); Douglas K. Hutchinson, Antioch, IL (US); Dale J. Kempf, Libertyville, IL (US); Larry L. Klein, Lake Forest, IL (US); Ming C. Yeung, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 909 days.

(21) Appl. No.: 11/010,177

(22) Filed: Dec. 10, 2004

(65) Prior Publication Data

US 2005/0159469 A1   Jul. 21, 2005

Related U.S. Application Data

(60) Provisional application No. 60/528,679, filed on Dec. 11, 2003.

(51) Int. Cl.
| | |
|---|---|
| *A61K 31/4709* | (2006.01) |
| *A61K 31/4439* | (2006.01) |
| *A61K 31/444* | (2006.01) |
| *A61K 31/4436* | (2006.01) |
| *C07D 401/14* | (2006.01) |

(52) U.S. Cl. .................. 514/314; 546/256; 546/273.4; 546/269.7; 546/274.4; 546/152; 514/333; 514/338; 514/341; 514/342

(58) Field of Classification Search .............. None
See application file for complete search history.

(56) References Cited

U.S. PATENT DOCUMENTS

| 5,679,688 A | 10/1997 | Grobelny |
| 5,914,332 A | 6/1999 | Sham |
| 6,225,345 B1 | 5/2001 | Fässler et al. |

FOREIGN PATENT DOCUMENTS

| EP | 0346847 | 12/1989 |
| WO | 97/19055 | 5/1997 |
| WO | 98/03476 | 1/1998 |

OTHER PUBLICATIONS

Dunn et al., Genome Biology, Mar. 2002, 3(4), pp. 1-7.*
U.S. Appl. No. 10/733,227, filed Dec. 11, 2003.
Written Opinion from International Patent Application No. PCT/US2004/037711, Mar. 17, 2005.
J.T. Randolph et al., A-681799, a Novel HIV Protease Inhibitor, Poster # F-485, 44th Annual Interscience Conference on Antimicrobial Agents and Chemotherapy (2004).
J.F. Waring et al., Identification of Proteasome Gene Regulation in a Rat Model Analysis, Abstract 839, 12th Conference of Retroviruses and Opportunistic Infections (2005).
D.J. Kempf et al., Practical Preclinical Model for Assessing the Potential for Unconjugated Hyperbilirubinemia Produced by Human Immunodeficiency Virus Protease Inhibitors, Antimicrobial Agents and Chemotherapy 762-4 (2006), vol. 50, No. 2.

* cited by examiner

*Primary Examiner*—Laura L. Stockton
(74) *Attorney, Agent, or Firm*—Lydia N. Nanow

(57) ABSTRACT

A compound of the formula

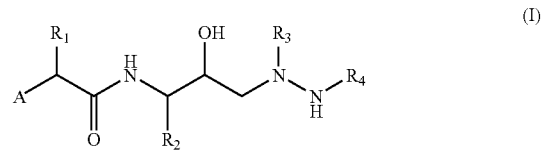

is disclosed as an HIV protease inhibitor. Methods and compositions for inhibiting an HIV infection are also disclosed.

49 Claims, No Drawings

HIV PROTEASE INHIBITING COMPOUNDS

This application claims priority to the provisional application Ser. No. 60/528,679 filed on Dec. 11, 2003.

TECHNICAL FIELD

The present invention relates to novel compounds and a composition and a method for inhibiting human immunodeficiency virus (HIV) protease, a composition and method for inhibiting or treating an HIV infection, processes for making the compounds and synthetic intermediates employed in the processes.

BACKGROUND OF THE INVENTION

The genome of the human immunodeficiency virus (HIV) encodes a protease that is responsible for the proteolytic processing of one or more polyprotein precursors such as the pol and gag gene products. HIV protease processes the gag precursor into core proteins and also processes the pol precursor into reverse transcriptase and protease.

The correct processing of the precursor polyproteins by HIV protease is necessary for the assembly of infectious virions. Therefore, inhibition of HIV protease provides a useful target for development of therapeutic agents for treatment of HIV infection.

In recent years, inhibitors of HIV protease have become an important class of therapeutic agents for inhibition and treatment of HIV infection in humans. HIV protease inhibitors are especially effective when administered in combination with other classes of HIV therapeutic agents, especially inhibitors of HIV reverse transcriptase, in "cocktails" of HIV therapeutic agents.

At the present time, the HIV protease inhibitors saquinavir, ritonavir, indinavir, nelfinavir, amprenavir, lopinavir/ritonavir, fosamprenavir, and atazanavir have been approved in the U.S. for treatment of HIV infection. There is a continuing need for improved HIV protease inhibitors that are very potent, that have reduced side-effects and that are effective against resistant strains of HIV.

SUMMARY OF THE INVENTION

The present invention provides a compound of formula (I)

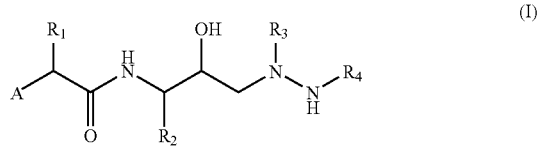

(I)

or a pharmaceutically acceptable salt form, stereoisomer, ester, salt of an ester, prodrug, salt of a prodrug or combination thereof, wherein:

A is

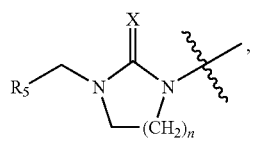

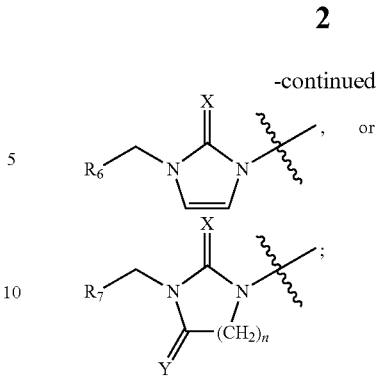

X is O, S or NH;

Y is O, S or NH;

$R_1$ is alkyl, alkenyl, alkynyl, cycloalkyl, cycloalkenyl, aryl, heteroaryl, arylalkyl, heteroarylalkyl, cycloalkylalkyl or cycloalkenylalkyl; wherein each $R_1$ is substituted with 0, 1 or 2 substituents independently selected from the group consisting of halo, haloalkyl, alkyl, alkenyl, cyano, nitro, —$OR_a$, —$OalkylC(=O)NR_aR_b$, —$SR_a$, —$SOR_a$, —$SO_2R_a$, —$SO_2NR_aR_b$, —$C(=O)R_a$, —$NR_aR_b$, —$N(R_b)C(=O)R_a$, —$N(R_b)C(=O)OR_a$, —$N(R_b)SO_2R_a$, —$N(R_b)SO_2NR_aR_b$, —$N(R_b)C(=NH)NR_aR_b$, —$N(R_b)C(=O)NR_aR_b$, —$C(=O)NR_aR_b$ and —$C(=O)OR_a$;

$R_2$ is alkyl, alkenyl, alkynyl, cycloalkyl, cycloalkenyl, cycloalkylalkyl, cycloalkenylalkyl, arylalkyl, heterocycle, heterocyclealkyl or heteroarylalkyl; wherein each $R_2$ is substituted with 0, 1, or 2 substituents independently selected from the group consisting of alkyl, alkenyl, alkynyl, cyano, halo, formyl, nitro, hydroxy, alkoxy, —$NH_2$, —N(H)alkyl, —$N(alkyl)_2$, —N(H)C(=O)Oalkyl, —N(alkyl)C(=O)Oalkyl, —C(=O)OH, —C(=O)Oalkyl, —C(=O)$NH_2$, —C(=O)N(H)(alkyl), —C(=O)$N(alkyl)_2$, —C(=O)alkyl, cyanoalkyl, nitroalkyl, formylalkyl, haloalkyl, hydroxyalkyl, alkoxyalkyl, -alkyl$NH_2$, -alkylN(H)alkyl, -alkyl$N(alkyl)_2$, -alkylN(H)C(=O)Oalkyl, -alkylN(alkyl)C(=O)Oalkyl, -alkylC(=O)OH, -alkylC(=O)Oalkyl, -alkylC(=O)$NH_2$, -alkylC(=O)N(H)(alkyl), -alkylC(=O)$N(alkyl)_2$ and -alkylC(=O)alkyl;

$R_3$ is hydrogen, alkyl, haloalkyl, alkenyl, haloalkenyl, alkynyl, haloalkynyl, cycloalkyl, cycloalkenyl, heterocycle, aryl, heteroaryl, cycloalkylalkyl, cycloalkenylalkyl, heterocyclealkyl, heteroarylalkyl, arylalkyl, hydroxyalkyl, alkoxyalkyl, -alkyl$SR_a$, -alkylS$OR_a$, -alkylS$O_2R_a$, -alkyl$NR_aR_b$, -alkylC(=O)$OR_a$, -alkylN($R_b$)C(=O)$OR_a$, -alkylN($R_b$)C(=O)$R_a$, -alkylN($R_b$)SO$_2R_a$ or -alkylN($R_b$)SO$_2NR_aR_b$; wherein the cycloalkyl, cycloalkenyl, heterocycle, aryl, heteroaryl, cycloalkyl moiety of cycloalkylalkyl, cycloalkenyl moiety of cycloalkenylalkyl, heterocycle moiety of heterocyclealkyl, heteroaryl moiety of heteroarylalkyl and aryl moiety of arylalkyl are independently substituted with 0, 1, 2 or 3 substituents independently selected from the group consisting of halo, nitro, cyano, formyl, alkyl, alkenyl, alkynyl, hydroxy, alkoxy, —SH, —S(alkyl), —S(haloalkyl), —$SO_2$(alkyl), —$SO_2$(haloalkyl), —$NH_2$, —N(H)(alkyl), —$N(alkyl)_2$, —N(H)C(=O)alkyl, —N(alkyl)C(=O)alkyl, —C(=O)OH, —C(=O)O(alkyl), —C(=O)$NH_2$, —C(=O)N(H)(alkyl), —C(=O)$N(alkyl)_2$, —C(=O)alkyl, haloalkyl, hydroxyalkyl, alkoxyalkyl, cyanoalkyl, formylalkyl, nitroalkyl, -alkylSH, -alkylS(alkyl), -alkylS$O_2$(alkyl), -alkyl$NH_2$, -alkylN(H)(alkyl), -alkyl$N(alkyl)_2$, -alkylN(H)C(=O)alkyl, -alkylN(alkyl)C(=O)alkyl, -alkylC(=O)OH, -alkylC(=O)O(alkyl), -alkylC(=O)NH₂, -alkylC(=O)N(H)(alkyl), -alkylC(=O)N(alkyl)₂, -alkylC(=O)alkyl and $R_{3a}$;

$R_{3a}$ is cycloalkyl, cycloalkenyl, aryl, heteroaryl, heterocycle, aryloxy, heteroaryloxy or heterocycleoxy, wherein each $R_{3a}$ is independently substituted with 0, 1, 2 or 3 substituents independently selected from the group consisting of halo, nitro, cyano, formyl, alkyl, alkenyl, alkynyl, hydroxyl, alkoxy, —SH, —S(alkyl), —SO₂(alkyl), —NH₂, —N(H)(alkyl), —N(alkyl)₂, —N(H)C(=O)alkyl, —N(alkyl)C(=O)alkyl, —C(=O)OH, —C(=O)O(alkyl), —C(=O)NH₂, —C(=O)N(H)(alkyl), —C(O)N(alkyl)₂, —C(=O)alkyl, haloalkyl, hydroxyalkyl, alkoxyalkyl, cyanoalkyl, formylalkyl, nitroalkyl, -alkylSH, -alkylS(alkyl), -alkylSO₂(alkyl), -alkylNH₂, -alkylN(H)(alkyl), -alkylN(alkyl)₂, -alkylN(H)C(=O)alkyl, -alkylN(alkyl)C(=O)alkyl, -alkylC(=O)OH, -alkylC(=O)O(alkyl), -alkylC(=O)NH₂, -alkylC(=O)N(H)(alkyl), -alkylC(=O)N(alkyl)₂ and -alkylC(=O)alkyl;

$R_4$ is a) —C(O)CH($R_8$)NHC(O)$R_9$, b) —C(O)$R_9$, c) —C(O)CH₂—O-aryl, substituted with 0, 1, 2 or 3 substituents selected from the group consisting of alkyl, alkenyl, halo, cynao, nitro, formyl, oxo, hydroxyl, alkoxy, hydroxyalky, alkoxyalkyl, haloalkyl, cyanoalkyl, aminoalkyl, alkylaminoalkyl, dialkylaminoalkyl, nitroalkyl, —NH₂, —N(H)alkyl, —N(alkyl)₂, —C(=O)alkyl, —C(=O)OH, —C(=O)Oalkyl, —C(=O)NH₂, —C(=O)N(H)(alkyl) and —C(=O)N(alkyl)₂, d) —C(O)CH₂—O-heteroaryl, substituted with 0, 1, 2 or 3 substituents selected from the group consisting of alkyl, alkenyl, halo, cynao, nitro, formyl, oxo, hydroxyl, alkoxy, hydroxyalky, alkoxyalkyl, haloalkyl, cyanoalkyl, aminoalkyl, alkylaminoalkyl, dialkylaminoalkyl, nitroalkyl, —NH₂, —N(H)alkyl, —N(alkyl)₂, —C(=O)alkyl, —C(=O)OH, —C(=O)Oalkyl, —C(=O)NH₂, —C(=O)N(H)(alkyl), and —C(=O)N(alkyl)₂, e) 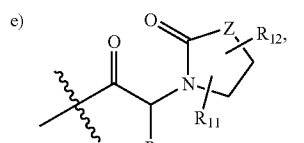

f) 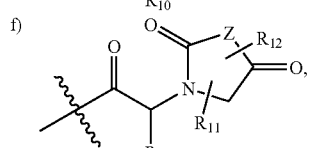

g) 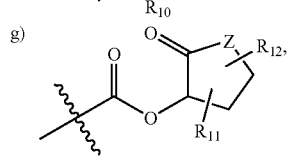

h) 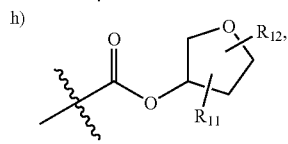

i), j), k) 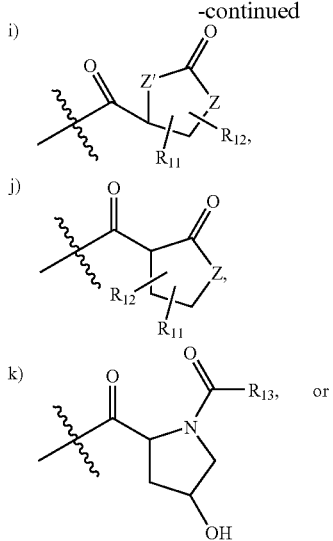

l) —SO₂$R_{14}$;

$R_5$ is alkyl, alkenyl, alkynyl, cycloalkyl, cycloalkenyl, aryl, heteroaryl or heterocycle; wherein each $R_5$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO₂R$_a$, —SO₂NR$_a$, —SO₂OR$_a$, —NR$_a$R$_b$, —N(R$_b$)NR$_a$R$_b$, —N(R$_b$)C(=O)R$_a$, —N(R$_b$)SO₂R$_a$, —N(R$_b$)C(=O)OR$_a$, —N(R$_b$)C(=O)NR$_a$R$_b$, —N(R$_b$)SO₂NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO₂R$_a$, -alkylSO₂NR$_a$, -alkylSO₂OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO₂NR$_a$R$_b$, -alkylN(R$_b$)SO₂R$_a$, -alkylC(=O)R$_a$, -alkylC(=O)OR$_a$, -alkylC(=O)NR$_a$R$_b$ and $R_{5a}$;

$R_{5a}$ is cycloalkyl, cycloalkenyl, heterocycle, aryl or heteroaryl; wherein each $R_{5a}$ is substituted with 0, 1, 2, 3 or 4 substituents independently selected from the group consisting of cyano, halo, nitro, oxo, alkyl, alkenyl, alkynyl, hydroxy, alkoxy, —NH₂, —N(H)(alkyl), —N(alkyl)₂, —SH, —S(alkyl), —SO₂(alkyl), —N(H)C(=O)alkyl, —N(alkyl)C(=O)alkyl, —N(H)C(=O)NH₂, —N(H)C(=O)N(H)(alkyl), —N(H)C(=O)N(alkyl)₂, —C(=O)OH, —C(=O)Oalkyl, —C(=O)NH₂, —C(=O)N(H)(alkyl), —C(=O)N(alkyl)₂, cyanoalkyl, formylalkyl, haloalkyl, hydroxyalkyl, alkoxyalkyl, -alkylNH₂, -alkylN(H)(alkyl), -alkylN(alkyl)₂, -alkylN(H)C(=O)alkyl, -alkylN(alkyl)C(=O)alkyl, -alkylN(H)C(=O)NH₂, -alkylN(H)C(=O)N(H)(alkyl), -alkylN(H)C(=O)N(alkyl)₂, -alkylC(=O)OH, -alkylC(=O)Oalkyl, -alkylC(=O)NH₂, -alkylC(=O)N(H)(alkyl) and -alkylC(=O)N(alkyl)₂;

$R_6$ is alkyl, alkenyl, alkynyl, cycloalkyl, cycloalkenyl, aryl, heteroaryl or heterocycle; wherein each $R_6$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO₂R$_a$, —SO₂NR$_a$, —SO₂OR$_a$, —NR$_a$R$_b$, —N(R$_b$)NR$_a$R$_b$, —N(R$_b$)C(=O)R$_a$, —N(R$_b$)SO₂R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and R$_{6a}$;

R$_{6a}$ is cycloalkyl, cycloalkenyl, heterocycle, aryl or heteroaryl; wherein each R$_{6a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)alkyl, -alkylN(alkyl)C(=O)alkyl, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

R$_7$ is alkyl, alkenyl, alkynyl, cycloalkyl, cycloalkenyl, aryl, heteroaryl or heterocycle; wherein each R$_7$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and R$_{7a}$;

R$_{7a}$ is cycloalkyl, cycloalkenyl, heterocycle, aryl or heteroaryl; wherein each R$_{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)alkyl, -alkylN(alkyl)C(=O)alkyl, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

R$_8$ is alkyl, alkenyl, alkynyl, cycloalkyl, aryl, heteroaryl, cycloalkylalkyl or arylalkyl; wherein each R$_8$ is substituted with 0, 1 or 2 substituents independently selected from the group consisting of halo, cyano, formyl, nitro, alkyl, alkenyl, alkynyl, hydroxy, alkoxy, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), —C(=O)N(alkyl)$_2$, —C(=O)alkyl, hydroxyalkyl, alkoxyalkyl, -alkylNH$_2$, -alkylN(H)alkyl, -alkylN(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

R$_9$ is alkyl, cycloalkyl, cycloalkylalkyl, aryl, heterocycle, heteroaryl or OR$_{9a}$, wherein each R$_9$ is substituted with 0, 1, 2 or 3 substituents selected from the group consisting of hydroxy, alkoxy, halo, cyano, nitro, formyl, alkyl, alkenyl, alkynyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), and —C(=O)N(alkyl)$_2$;

R$_{9a}$ is alkyl, cycloalkyl, cycloalkylalkyl, aryl, arylalkyl, heterocycle, heteroaryl, heteroarylalkyl or heterocyclealkyl; wherein each R$_{9a}$ is substituted with 0, 1, 2 or 3 substituents independently selected from the group consisting of hydroxy, alkoxy, halo, cyano, nitro, formyl, alkyl, alkenyl, alkynyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl) and —C(=O)N(alkyl)$_2$;

R$_{10}$ is alkyl, alkenyl, alkynyl, cycloalkyl or cycloalkenyl, aryl, heteroaryl, arylalkyl, cycloalkylalkyl or heteroarylalkyl; wherein each R$_{10}$ is substituted with 0, 1, 2 or 3 substituents selected from the group consisting of halo, cyano, nitro, formyl, alkyl, alkenyl, hydroxy, alkoxy, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_b$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$ and —C(=O)OR$_a$;

R$_{11}$ is hydrogen, alkyl, haloalkyl, hydroxyalkyl or alkoxyalkyl;

R$_{12}$ is hydrogen, alkyl, haloalkyl, hydroxyalkyl or alkoxyalkyl;

R$_{13}$ is alkyl or haloalkyl;

R$_{14}$ is alkyl, cycloalkyl, cycloalkylalkyl, aryl, heteroaryl or heterocycle; wherein each R$_{14}$ is substituted with 0, 1, 2 or 3 substituents selected from the group consisting of halo, cyano, nitro, formyl, alkyl, alkenyl, hydroxy, alkoxy, haloalkyl, —NH$_2$, —N(H)alkyl, —N(alkyl)$_2$, —C(=O)OH, —C(=O)Oalkyl, —C(=O)NH$_2$, —C(=O)N(H)(alkyl), and —C(=O)N(alkyl)$_2$;

Z is —CH$_2$—, —NH—, —O— or —S—;

Z' is —CH$_2$—, —NH—, —O— or —S—;

R$_a$ and R$_b$ at each occurrence are independently selected from the group consisting of hydrogen, alkyl, haloalkyl, alkenyl, alkynyl, cycloalkyl, aryl, heteroaryl, heterocycle, arylalkyl and heteroarylalkyl; wherein each R$_a$ and R$_b$, at each occurrence, is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, —C(=O)alkyl, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC (=O)OH, -alkylC(=O)Oalkyl, -alkylC(=O)NH₂, -alkylC(=O)N(H)(alkyl), -alkylC(=O)N(alkyl)₂ and -alkylC(=O)alkyl; and n is 1 or 2.

The present invention also provides the processes of making a compound of the present invention and intermediates employed in the processes.

The present invention further provides a pharmaceutical composition comprising a therapeutically effective amount of a compound or combination of compounds of the present invention, or a pharmaceutically acceptable salt form, stereoisomer, ester, salt of an ester, prodrug, salt of a prodrug, or combination thereof, and a pharmaceutically acceptable carrier.

The present invention yet further provides a pharmaceutical composition comprising a therapeutically effective amount of a compound or combination of compounds of the present invention, or a pharmaceutically acceptable salt form, stereoisomer, ester, salt of an ester, prodrug, salt of a prodrug, or combination thereof, and one, two, three, four, five or six agents selected from the group consisting of a second HIV protease inhibitor, a HIV reverse transcriptase inhibitor, an HIV entry/fusion inhibitor, an HIV integrase inhibitor and an HIV budding/maturation inhibitor, and a pharmaceutically acceptable carrier.

The present invention also provides a pharmaceutical composition comprising a therapeutically effective amount of a compound or combination of compounds of the present invention, or a pharmaceutically acceptable salt form, stereoisomer, ester, salt of an ester, prodrug, salt of a prodrug, or combination thereof, ritonavir, and a pharmaceutically acceptable carrier.

The present invention still further provides a method of inhibiting the replication of an HIV virus comprising contacting said virus with a therapeuctially effective amount of a compound or combination of compounds of the present invention, or a pharmaceutically acceptable salt form, stereoisomer, ester, salt of an ester, prodrug, salt of a prodrug, or combination thereof.

The present invention still further provides a method of inhibiting the replication of an HIV virus comprising contacting said virus with the pharmaceutical composition of the present invention.

The present invention still further provides a method of inhibiting an HIV protease comprising contacting said HIV protease with a therapeuctially effective amount of a compound or combination of compounds of the present invention, or a pharmaceutically acceptable salt form, stereoisomer, ester, salt of an ester, prodrug, salt of a prodrug, or combination thereof.

The present invention still further provides a method of inhibiting an HIV protease comprising contacting said HIV protease with the pharmaceutical composition of the present invention.

The present invention also provides a method of treating or preventing an HIV infection comprising administering to a patient in need of such treatment a therapeuctially effective amount of a compound or combination of compounds of the present invention, or a pharmaceutically acceptable salt form, stereoisomer, ester, salt of an ester, prodrug, salt of a prodrug or combination thereof.

The present invention also provides a method of treating or preventing an HIV infection comprising administering to a patient in need of such treatment the pharmaceutical composition of the present invention.

DETAILED DESCRIPTION OF THE INVENTION

As used in the present specification the following terms have the meanings indicated:

As used herein, the singular forms "a", "an", and "the" may include plural reference unless the context clearly dictates otherwise.

The term "activated carboxylic acid group" as used herein refers to acid halides such as acid chlorides and also refers to activated ester derivatives including, but not limited to, formic and acetic acid derived anhydrides, anhydrides derived from alkoxycarbonyl halides such as isobutyloxycarbonylchloride and the like, anhydrides derived from reaction of the carboxylic acid with N,N'-carbonyldiimidazole and the like, N-hydroxysuccinimide derived esters, N hydroxyphthalimide derived esters, N-hydroxybenzotriazole derived esters, N-hydroxy-5-norbornene-2,3-dicarboximide derived esters, 2,4,5-trichlorophenol derived esters, p-nitrophenol derived esters, phenol derived esters, pentachlorophenol derived esters, 8-hydroxyquinoline derived esters and the like.

The term "alkanoyl" as used herein, refers to an alkyl group, as defined herein, attached to the parent molecular moiety through a carbonyl group. Representative examples of alkanoyl include, but not limited to, methylcarbonyl, ethylcarbonyl and tert-butylcarbonyl.

The term "alkyl," as used herein, refers to a group derived from a straight or branched chain saturated hydrocarbon containing 1, 2, 3, 4, 5, 6, 7, 8, 9 or 10 carbon atoms. Representative examples of alkyl groups include, but not limited to, butyl, methyl, 1-methylpropyl, 1-methylbutyl, isopropyl (1-methylethyl), 2-methylbutyl, 1,3-dimethylbutyl, 2-ethylbutyl, 3-methylbutyl, 3,3-dimethylbutyl, tert-butyl and isopropyl (1-methylethyl).

The term "alkylamino" as used herein refers to —N(H)(alkyl).

The term "alkylaminocarbonyl", as used herein, refers to an alkylamino group, as defined herein, attached to the parent molecular moiety through a carbonyl group. Representative example of alkylaminocarbonyl includes, but not limited to, acetylamino.

The term "alkenyl", as used herein, refers to a straight or branched chain group of 2, 3, 4, 5, 6, 7, 8, 9 or 10 carbon atoms containing at least one carbon-carbon double bond. Representative examples of alkenyl groups include, but not limited to, allyl, propenyl, 3-methyl-2-butenyl and 3,7-dimethyl-6-octenyl.

The term "alkynyl," as used herein, refers to a straight or branched chain hydrocarbon of 2, 3, 4, 5, 6, 7, 8, 9 or 10 carbon atoms containing at least one carbon-carbon triple bond. Representative examples of alkynyl groups include, but not limited to, ethynyl, 2-methyl-3-butynyl, 3-pentynyl and 2-octynyl.

The term "alkoxy", as used herein, refers to an alkyl group, as defined herein, attached to the parent molecular moiety through an oxygen atom. Representative examples of alkoxy groups include, but not limited to, tert-butoxy, methoxy and isopropoxy.

The term "alkoxyalkyl", as used herein, refers to an alkyl group substituted by at least one alkoxy group. Representative examples of alkoxyalkyl include, but not limited to, methoxymethyl and 1-methyoxyethyl.

The term "alkoxycarbonyl", as used herein, refers to an alkoxy group attached to the parent molecular moiety through a carbonyl group. Representative examples of alkoxycarbonyl groups include, but not limited to, tert-butoxycarbonyl, ethoxycarbonyl and methoxycarbonyl.

The term "amino" as used herein, refers to —NH₂.

The term "aminoalkyl" as used herein, refers to an amino group appended to the parent molecular moiety through an alkyl group as defined herein.

The term "aryl" as used herein, refers to a phenyl group, or a bicyclic or tricyclic hydrocarbon fused ring systems wherein one or more of the rings is a phenyl group. Bicyclic fused ring systems have a phenyl group fused to a monocyclic cycloalkenyl group, as defined herein, a monocyclic cycloalkyl group, as defined herein, or another phenyl group. Tricyclic fused ring systems are exemplified by a bicyclic fused ring system fused to a monocyclic cycloalkenyl group, as defined herein, a monocyclic cycloalkyl group, as defined herein, or another phenyl group. Representative examples of aryl groups include, but not limited to, anthracenyl, azulenyl, fluorenyl, indanyl, indenyl, naphthyl, phenyl and tetrahydronaphthyl. The aryl groups of the present invention can be connected to the parent molecular moiety through any substitutable carbon atom of the group. The aryl groups of the compounds of the present invention can be substituted or unsubstituted.

The term "arylalkyl," as used herein, refers to an aryl group attached to the parent molecular moiety through an alkyl group. Representative examples of arylalkyl include, but not limited to, phenylmethyl, phenylethyl and naphthylmethyl.

The term "aryloxy", as used herein, refers to an aryl group, as defined herein, appended to the parent molecular moiety through an oxygen atom. Representative examples of aryloxy include, but not limited to, phenoxy, naphthyloxy, 3-bromophenoxy, 4-chlorophenoxy, 4-methylphenoxy, 3,5-dimethoxyphenoxy, 4-methoxyphenoxy and 4-methylphenoxy.

The term "carbonyl" as used herein, refers to —C(=O).

The term "cyano," as used herein, refers to —CN.

The term "cyanoalkyl," as used herein, refers to a cyano group attached to the parent molecular moiety through an alkyl group.

The term "cycloalkenyl," as used herein, refers to a non-aromatic, partially unsaturated, monocyclic, bicyclic or tricyclic ring system, having three to fourteen carbon atoms and zero heteroatom. Representative examples of cycloalkenyl groups include, but not limited to, cyclohexenyl, octahydronaphthalenyl and norbornylenyl. The cycloalkenyl groups of the compounds of the present invention can be unsubstituted or substituted.

The term "cycloalkenylalkyl," as used herein, refers to a cycloalkenyl group attached to the parent molecular moiety through an alkyl group as defined herein.

The term "cycloalkyl," as used herein, refers to a saturated monocyclic, bicyclic, or tricyclic hydrocarbon ring system having three to fourteen carbon atoms and zero heteroatom. Representative examples of cycloalkyl groups include cyclopropyl, cyclobutyl, cyclopentyl, cyclohexyl, cycloheptyl, bicyclo[3.1.1]heptyl, 6,6-dimethylbcyclo[3.1.1]heptyl and adamantyl. The cycloalkyl groups of the compounds of the present invention can be unsubstituted or substituted.

The term "cycloalkylalkyl," as used herein, refers to a cycloalkyl group attached to the parent molecular moiety through an alkyl group as defined herein.

The term "dialkylamino" as used herein refers to —NR$^{90}$R$^{91}$, wherein R$^{90}$ and R$^{91}$ are alkyls.

The term "dialkylaminocarbonyl" as used herein refers to a dialkylamino group as defined herein, appended to the parent molecular moiety through a carbonyl group.

The term "formyl", as used herein, refers to a —C(O)H group.

The term "formylalkyl" as used herein, refers to a formyl group appended to the parent molecular moiety through an alkyl group.

The terms "halo," and "halogen", as used herein, refer to F, Cl, Br, and I.

The term "haloalkenyl", as used herein, refers to an alkenyl group, as defined herein, substituted by one, two, three, or four halogen atoms.

The term "haloalkoxy", as used herein, refers to a haloalkyl group attached to the parent molecular moiety through an oxygen atom.

The term "haloalkyl", as used herein, refers to an alkyl group substituted by one, two, three, or four halogen atoms.

The term "haloalkynyl", as used herein, refers to an alkynyl group, as defined herein, substituted by one, two, three, or four halogen atoms.

The term "heteroaryl," as used herein, refers to an aromatic five or six-membered ring where at least one atom is selected from the group consisting of N, O, and S, and the remaining atoms are carbon. The term "heteroaryl" also includes bicyclic systems where a heteroaryl ring is fused to a phenyl group, a monocyclic cycloalkyl group, as defined herein, a heterocycle group, as defined herein, or an additional heteroaryl group. The term "heteroaryl" also includes tricyclic systems where a bicyclic system is fused to a phenyl group, a monocyclic cycloalkyl group, as defined herein, a heterocycle group, as defined herein, or an additional heteroaryl group. The heteroaryl groups are connected to the parent molecular moiety through any substitutable carbon or nitrogen atom in the groups. Examples of heteroaryl groups include benzothienyl, benzoxazolyl, benzimidazolyl, benzoxadiazolyl, dibenzofuranyl, dihydrobenzothiazolyl, furanyl (furyl), imidazolyl, imidazopyridinyl, indazolyl, indolyl, isoindolyl, isoxazolyl, isoquinolinyl, isothiazolyl, oxadiazolyl, oxazolyl, thiazolyl, thienopyridinyl, thienyl, triazolyl, thiadiazolyl, tetrazolyl, pyridoimidazolyl, pyridyl, pyridazinyl, pyrimidinyl, pyrazinyl, pyrazolyl, pyrrolyl, quinolinyl, tetrahydroquinolinyl, tetrahydropyranyl and triazinyl. The heteroaryl groups of the present invention can be substituted or unsubstituted. In addition, the nitrogen heteroatoms can be optionally quaternized or oxidized to the N-oxide. Also, the nitrogen containing rings can be optionally N-protected.

The term "heteroaryloxy", as used herein, refers to a heteroaryl group, as defined herein, appended to the parent molecular moiety through an oxygen atom. Representative examples of heteroaryloxy include, but not limited to, pyridin-3-yloxy and quinolin-3-yloxy.

The term "heteroarylalkyl", as used herein, refers to a heteroaryl group attached to the parent molecular moiety through an alkyl group. Representative examples of heteroarylalkyl groups include, but are not limited to, thiazolylmethyl, thienylmethyl, furylmethyl, imidazolylmethyl and pyridylmethyl.

The term "heterocycle," as used herein, refers to cyclic, non-aromatic, saturated or partially unsaturated, three, four, five-, six-, or seven-membered rings containing at least one atom selected from the group consisting of oxygen, nitrogen, and sulfur. The term "heterocycle" also includes bicyclic systems where a heterocycle ring is fused to a phenyl group, a monocyclic cycloalkenyl group, as defined herein, a monocyclic cycloalkyl group, as defined herein, or an additional monocyclic heterocycle group. The term "heterocycle" also includes tricyclic systems where a bicyclic system is fused to a phenyl group, a monocyclic cycloalkenyl group, as defined herein, a monocyclic cycloalkyl group, as defined herein, or an additional monocyclic heterocycle group. The heterocycle groups of the invention are connected to the parent molecular moiety through any substitutable carbon or nitrogen atom in the group. Representative examples of heterocycle groups include, but not limited to, benzoxazinyl, dihydroindolyl, dihydropyridinyl, 1,3-dioxanyl, 1,4-dioxanyl, 1,3-dioxolanyl, 1,3-benzodioxolyl, 2,3-dihydro-1,4-benzodioxinyl, 2,3-dihydrobenzofuranyl, hexahydrofurofuranyl, isoindolinyl, morpholinyl, piperazinyl, pyrrolidinyl, tetrahydropyridinyl, piperidinyl, thiomorpholinyl, tetrahydropyranyl. The heterocycle groups of the present invention can be substituted or substituted. In addition, the nitrogen heteroatoms can be optionally quaternized or oxidized to the N-oxide. Also, the nitrogen containing heterocyclic rings can be optionally N-protected.

The term "heterocycleoxy", as used herein, refers to a heterocycle group, as defined herein, appended to the parent molecular moiety through an oxygen atom.

The term "heterocyclealkyl", as used herein, refers to refers to a heterocycle group attached to the parent molecular moiety through an alkyl group, as defined herein. Representative examples of heterocyclealkyl groups include, 1,3-dioxolanyl, 1,3-benzodioxolylmethyl, 2,3-dihydro-1,4-benzodioxinylmethyl and 2,3-dihydrobenzofuranylmethyl.

The term "hydroxy" or "hydroxyl" as used herein, refer to —OH.

The term "hydroxyalkyl" as used herein, refers to an alkyl group as substituted by at least one hydroxy group. Representative examples of hydroxyalkyl groups include, but not limited to, 1-methyl-1-hydroxyethyl and 1-hydroxyethyl.

The term "nitro" as used herein, refers to $NO_2$.

The term "nitroalkyl", as used herein, refers to an alkyl group substituted by at least one nitro group.

The term "oxo," as used herein, refers to =O.

The term "thioalkoxy", as used herein, refers to an alkyl group as defined herein, appended to the parent molecular moiety through a sulfur atom.

The term "thioalkoxyalkyl", as used herein, refers to a thioalkoxy group as defined herein, appended to the parent molecular moiety through a alkyl group as defined herein.

It is understood that each of the terms alkanoyl, alkenyl, alkoxy, alkoxyalkyl, alkoxycarbonyl, alkyl, alkylamino, alkylaminocarbonyl, alkynyl, aminoalkyl, aryl, arylalkyl, aryloxy, cyanoalkyl, cycloalkenyl, cycloalkenylalkyl, cycloalkyl, cycloalkylalkyl, dialkylamino, dialkylaminocarbonyl, formylalkyl, haloalkenyl, haloalkoxy, haloalkyl, haloalkynyl, heteroaryl, heteroarylalkyl, heteroaryloxy, heterocycle, heterocyclealkyl, heterocycleoxy, hydroxyalkyl, nitroalkyl, thioalkoxy and thioalkoxyalkyl used herein may be unsubstituted or substituted.

In a first embodiment, the present invention provides a compound of formula (I),

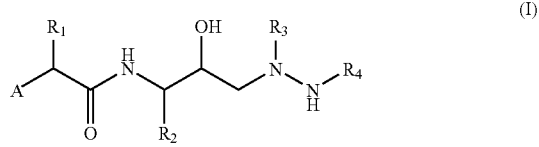

(I)

or a pharmaceutically acceptable salt form, stereoisomer, ester, salt of an ester, prodrug, salt of a prodrug or combination thereof, wherein:

A is

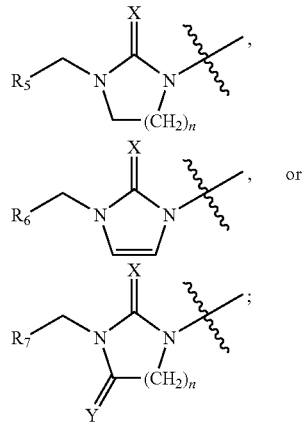

X is O, S or NH;

Y is O, S or NH;

$R_1$ is alkyl, alkenyl, alkynyl, cycloalkyl, cycloalkenyl, aryl, heteroaryl, arylalkyl, heteroarylalkyl, cycloalkylalkyl or cycloalkenylalkyl; wherein each $R_1$ is substituted with 0, 1 or 2 substituents independently selected from the group consisting of halo, haloalkyl, alkyl, alkenyl, cyano, nitro, —$OR_a$, —OalkylC(=O)$NR_aR_b$, —$SR_a$, —$SOR_a$, —$SO_2R_a$, —$SO_2NR_aR_b$, —C(=O)$R_a$, —$NR_aR_b$, —N($R_b$)C(=O)$R_a$, —N($R_b$)C(=O)$OR_a$, —N($R_b$)$SO_2R_a$, —N($R_b$)$SO_2NR_aR_b$, —N($R_b$)C(=NH)$NR_aR_b$, —N($R_b$)C(=O)$NR_aR_b$, —C(=O)$NR_aR_b$ and —C(=O)$OR_a$;

$R_2$ is alkyl, alkenyl, alkynyl, cycloalkyl, cycloalkenyl, cycloalkylalkyl, cycloalkenylalkyl, arylalkyl, heterocycle, heterocyclealkyl or heteroarylalkyl; wherein each $R_2$ is substituted with 0, 1, or 2 substituents independently selected from the group consisting of alkyl, alkenyl, alkynyl, cyano, halo, formyl, nitro, hydroxy, alkoxy, —$NH_2$, —N(H)alkyl, —N(alkyl)$_2$, —N(H)C(=O)Oalkyl, —N(alkyl)C(=O) Oalkyl, —C(=O)OH, —C(=O)Oalkyl, —C(=O)$NH_2$, —C(=O)N(H)(alkyl), —C(=O)N(alkyl)$_2$, —C(=O)alkyl, cyanoalkyl, nitroalkyl, formylalkyl, haloalkyl, hydroxyalkyl, alkoxyalkyl, -alkyl$NH_2$, -alkylN(H)alkyl, -alkylN(alkyl)$_2$, -alkylN(H)C(=O)Oalkyl, -alkylN(alkyl)C(=O)Oalkyl, -alkylC(=O)OH, -alkylC(=O)Oalkyl, -alkylC(=O)$NH_2$, -alkylC(=O)N(H)(alkyl), -alkylC(=O)N(alkyl)$_2$ and -alkylC(=O)alkyl;

$R_3$ is hydrogen, alkyl, haloalkyl, alkenyl, haloalkenyl, alkynyl, haloalkynyl, cycloalkyl, cycloalkenyl, heterocycle, aryl, heteroaryl, cycloalkylalkyl, cycloalkenylalkyl, heterocyclealkyl, heteroarylalkyl, arylalkyl, hydroxyalkyl, alkoxyalkyl, -alkyl$SR_a$, -alkylSO$R_a$, -alkyl$SO_2R_a$, -alkyl$NR_aR_b$, -alkylC(=O)$OR_a$, -alkylN($R_b$)C(=O)$OR_a$, -alkylN($R_b$)C(=O)$R_a$, -alkylN($R_b$)$SO_2R_a$ or -alkylN($R_b$)$SO_2NR_aR_b$; wherein the cycloalkyl, cycloalkenyl, heterocycle, aryl, heteroaryl, cycloalkyl moiety of cycloalkylalkyl, cycloalkenyl moiety of cycloalkenylalkyl, heterocycle moiety of heterocyclealkyl, heteroaryl moiety of heteroarylalkyl and aryl moiety of arylalkyl are independently substituted with 0, 1, 2 or 3 substituents independently selected from the group consisting of halo, nitro, cyano, formyl, alkyl, alkenyl, alkynyl, hydroxy, alkoxy, —SH, —S(alkyl), —S(haloalkyl), —$SO_2$(alkyl), —$SO_2$(haloalkyl), —$NH_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$, -alkylC(=O)alkyl and R$_{3a}$;

R$_{3a}$ is cycloalkyl, cycloalkenyl, aryl, heteroaryl, heterocycle, aryloxy, heteroaryloxy or heterocycleoxy, wherein each R$_{3a}$ is independently substituted with 0, 1, 2 or 3 substituents independently selected from the group consisting of halo, nitro, cyano, formyl, alkyl, alkenyl, alkynyl, hydroxyl, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$ and -alkylC(=O)alkyl;

R$_4$ is a) —C(O)CH(R$_8$)NHC(O)R$_9$, b) —C(O)R$_9$, c) —C(O)CH$_2$—O-aryl, substituted with 0, 1, 2 or 3 substituents selected from the group consisting of alkyl, alkenyl, halo, cynao, nitro, formyl, oxo, hydroxyl, alkoxy, hydroxyalky, alkoxyalkyl, haloalkyl, cyanoalkyl, aminoalkyl, alkylaminoalkyl, dialkylaminoalkyl, nitroalkyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl) and —C(=O)N(alkyl)$_2$, d) —C(O)CH$_2$—O-heteroaryl, substituted with 0, 1, 2 or 3 substituents selected from the group consisting of alkyl, alkenyl, halo, cynao, nitro, formyl, oxo, hydroxyl, alkoxy, hydroxyalky, alkoxyalkyl, haloalkyl, cyanoalkyl, aminoalkyl, alkylaminoalkyl, dialkylaminoalkyl, nitroalkyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), and —C(=O)N(alkyl)$_2$, e) 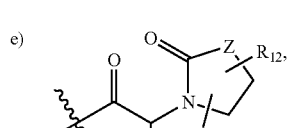

f) 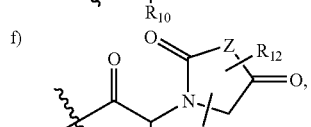

g) 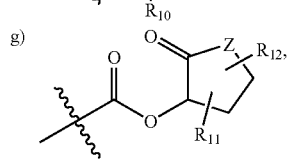

-continued h) 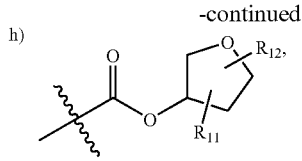

i) 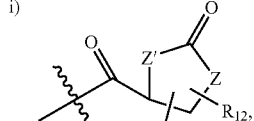

j) 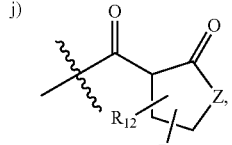

k) 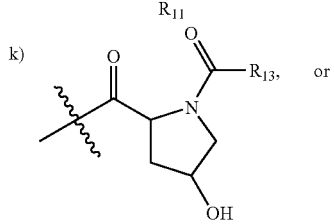, or l) —SO$_2$R$_{14}$;

R$_5$ is alkyl, alkenyl, alkynyl, cycloalkyl, cycloalkenyl, aryl, heteroaryl or heterocycle; wherein each R$_5$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, SO$_2$R$_a$, —SO$_2$NR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and R$_{5a}$;

R$_{5a}$ is cycloalkyl, cycloalkenyl, heterocycle, aryl or heteroaryl; wherein each R$_{5a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)alkyl, -alkylN(alkyl)C(=O)alkyl, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_6$ is alkyl, alkenyl, alkynyl, cycloalkyl, cycloalkenyl, aryl, heteroaryl or heterocycle; wherein each $R_6$ is substituted with 0, 1, 2 or 3 substituents independently selected from the group consisting of alkyl, alkenyl, alkynyl, cyano, halo, nitro, oxo, —$OR_a$, —$OC(=O)R_a$, —$SR_a$, —$SOR_a$, $SO_2R_a$, —$SO_2NR_a$, $SO_2OR_a$, —$NR_aR_b$, —$N(R_b)NR_aR_b$, —$N(R_b)C(=O)R_a$, —$N(R_b)SO_2R_a$, —$N(R_b)C(=O)OR_a$, —$N(R_b)C(=O)NR_aR_b$, —$N(R_b)SO_2NR_aR_b$, —$C(=O)R_a$, —$C(=O)NR_aR_b$, —$C(=O)OR_a$, azidoalkyl, haloalkyl, nitroalkyl, cyanoalkyl, -alkyl$OR_a$, -alkylOC(=O)$R_a$, -alkylS$R_a$, -alkyl-SO$R_a$, -alkylSO$_2R_a$, -alkylSO$_2NR_a$, -alkylSO$_2OR_a$, -alkylN-$R_aR_b$, —C(H)=N(O$R_a$), —C(alkyl)=N(O$R_a$), —C(H)=NN$R_aR_b$, —C(alkyl)=NN$R_aR_b$, —C(H)(=NO$R_a$)N$R_aR_b$, —C(alkyl)(=NO$R_a$)N$R_aR_b$, -alkylN(R$_b$)N$R_aR_b$, -alkylN(R$_b$)C(=O)$R_a$, -alkylN(R$_b$)C(=O)O$R_a$, -alkylN(R$_b$)C(=O)N$R_aR_b$, -alkylN(R$_b$)SO$_2$N$R_aR_b$, -alkylN(R$_b$)SO$_2R_a$, -alkylC(=O)$R_a$, -alkylC(=O)O$R_a$, -alkylC(=O)N$R_aR_b$ and $R_{6a}$;

$R_{6a}$ is cycloalkyl, cycloalkenyl, heterocycle, aryl or heteroaryl; wherein each $R_{6a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)alkyl, -alkylN(alkyl)C(=O)alkyl, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_7$ is alkyl, alkenyl, alkynyl, cycloalkyl, cycloalkenyl, aryl, heteroaryl or heterocycle; wherein each $R_7$ is substituted with 0, 1, 2 or 3 substituents independently selected from the group consisting of alkyl, alkenyl, alkynyl, cyano, halo, nitro, oxo, —$OR_a$, —$OC(=O)R_a$, —$SR_a$, —$SOR_a$, —$SO_2R_a$, —$SO_2NR_a$, —$SO_2OR_a$, —$NR_aR_b$, —$N(R_b)NR_aR_b$, —$N(R_b)C(=O)R_a$, —$N(R_b)SO_2R_a$, —$N(R_b)C(=O)OR_a$, —$N(R_b)C(=O)NR_aR_b$, —$N(R_b)SO_2NR_aR_b$, —$C(=O)R_a$, —$C(=O)NR_aR_b$, —$C(=O)OR_a$, azidoalkyl, haloalkyl, nitroalkyl, cyanoalkyl, -alkyl$OR_a$, -alkylOC(=O)$R_a$, -alkylS$R_a$, -alkylSO$R_a$, -alkylSO$_2R_a$, -alkylSO$_2NR_a$, -alkylSO$_2OR_a$, -alkylN$R_aR_b$, —C(H)=N(O$R_a$), —C(alkyl)=N(O$R_a$), —C(H)=NN$R_aR_b$, —C(alkyl)=NN$R_aR_b$, —C(H)(=NO$R_a$)N$R_aR_b$, —C(alkyl)(=NO$R_a$)N$R_aR_b$, -alkylN(R$_b$)N$R_aR_b$, -alkylN(R$_b$)C(=O)$R_a$, -alkylN(R$_b$)C(=O)O$R_a$, -alkylN(R$_b$)C(=O)N$R_aR_b$, -alkylN(R$_b$)SO$_2$N$R_aR_b$, -alkylN(R$_b$)SO$_2R_a$, -alkylC(=O)$R_a$, -alkylC(=O)O$R_a$, -alkylC(=O)N$R_aR_b$ and $R_{7a}$;

$R_{7a}$ is cycloalkyl, cycloalkenyl, heterocycle, aryl or heteroaryl; wherein each $R_{7a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)alkyl, -alkylN(alkyl)C(=O)alkyl, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_8$ is alkyl, alkenyl, alkynyl, cycloalkyl, aryl, heteroaryl, cycloalkylalkyl or arylalkyl; wherein each $R_8$ is substituted with 0, 1 or 2 substituents independently selected from the group consisting of halo, cyano, formyl, nitro, alkyl, alkenyl, alkynyl, hydroxy, alkoxy, —$NH_2$, —N(H)alkyl, —N(alkyl)$_2$, —C(=O)alkyl, —C(=O)OH, —C(=O)Oalkyl, —C(=O)NH$_2$, —C(=O)N(H)(alkyl), —C(=O)N(alkyl)$_2$, —C(=O)alkyl, hydroxyalkyl, alkoxyalkyl, -alkylNH$_2$, -alkylN(H)alkyl, -alkylN(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_9$ is alkyl, cycloalkyl, cycloalkylalkyl, aryl, heterocycle, heteroaryl or O$R_{9a}$, wherein each $R_9$ is substituted with 0, 1, 2 or 3 substituents selected from the group consisting of hydroxy, alkoxy, halo, cyano, nitro, formyl, alkyl, alkenyl, alkynyl, —$NH_2$, —N(H)alkyl, —N(alkyl)$_2$, —C(=O)alkyl, —C(=O)OH, —C(=O)Oalkyl, —C(=O)NH$_2$, —C(=O)N(H)(alkyl), and —C(=O)N(alkyl)$_2$;

$R_{9a}$ is alkyl, cycloalkyl, cycloalkylalkyl, aryl, arylalkyl, heterocycle, heteroaryl, heteroarylalkyl or heterocyclealkyl; wherein each $R_{9a}$ is substituted with 0, 1, 2 or 3 substituents independently selected from the group consisting of hydroxy, alkoxy, halo, cyano, nitro, formyl, alkyl, alkenyl, alkynyl, —$NH_2$, —N(H)alkyl, —N(alkyl)$_2$, —C(=O)alkyl, —C(=O)OH, —C(=O)Oalkyl, —C(=O)NH$_2$, —C(=O)N(H)(alkyl) and —C(=O)N(alkyl)$_2$;

$R_{10}$ is alkyl, alkenyl, alkynyl, cycloalkyl or cycloalkenyl, aryl, heteroaryl, arylalkyl, cycloalkylalkyl or heteroarylalkyl; wherein each $R_{10}$ is substituted with 0, 1, 2 or 3 substituents selected from the group consisting of halo, cyano, nitro, formyl, alkyl, alkenyl, hydroxy, alkoxy, —$SR_a$, —$SOR_a$, —$SO_2R_a$, —$SO_2NR_aR_b$, —$C(=O)R_a$, —$NR_aR_b$, —$N(R_b)C(=O)R_a$, —$N(R_b)C(=O)OR_a$, —$N(R_b)SO_2R_a$, —$N(R_b)SO_2NR_aR_b$, —$N(R_b)C(=NH)NR_aR_b$, —$N(R_b)C(=O)NR_aR_b$, —$C(=O)NR_aR_b$ and —$C(=O)OR_a$;

$R_{11}$ is hydrogen, alkyl, haloalkyl, hydroxyalkyl or alkoxyalkyl;

$R_{12}$ is hydrogen, alkyl, haloalkyl, hydroxyalkyl or alkoxyalkyl;

$R_{13}$ is alkyl or haloalkyl;

$R_{14}$ is alkyl, cycloalkyl, cycloalkylalkyl, aryl, heteroaryl or heterocycle; wherein each $R_{14}$ is substituted with 0, 1, 2 or 3 substituents selected from the group consisting of halo, cyano, nitro, formyl, alkyl, alkenyl, hydroxy, alkoxy, haloalkyl, —$NH_2$, —N(H)(alkyl), —N(alkyl)$_2$, —C(=O)OH, —C(=O)Oalkyl, —C(=O)NH$_2$, —C(=O)N(H)(alkyl), and —C(=O)N(alkyl)$_2$;

Z is —CH$_2$—, —NH—, —O— or —S—;

Z' is —CH$_2$—, —NH—, —O— or —S—;

$R_a$ and $R_b$ at each occurrence are independently selected from the group consisting of hydrogen, alkyl, haloalkyl, alkenyl, alkynyl, cycloalkyl, aryl, heteroaryl, heterocycle, arylalkyl and heteroarylalkyl; wherein each $R_a$ and $R_b$, at each occurrence, is independently substituted with 0, 1, 2 or 3 substituents independently selected from the group consisting of alkyl, alkenyl, alkynyl, cyano, formyl, nitro, halo, oxo, hydroxy, alkoxy, —$NH_2$, —N(H)(alkyl), —N(alkyl)$_2$, —SH, —S(alkyl), —SO$_2$(alkyl), —N(H)C(=O)alkyl, —N(alkyl)C (=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, —C(=O)alkyl, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), -alkylC(=O)N(alkyl)$_2$ and -alkylC(=O)alkyl; and n is 1 or 2.

For example, the present invention provides a compound of formula (I) wherein $R_1$ is alkyl.

For example, the present invention provides a compound of formula (I) wherein $R_1$ is alkyl and $R_4$ is —C(O)C(H)($R_8$)NHC(O)$R_9$.

For example, the present invention provides a compound of formula (I) wherein $R_1$ is alkyl, $R_4$ is —C(O)C(H)($R_8$)NHC(O)$R_9$ and $R_9$ is —O$R_{9a}$.

For example, the present invention provides a compound of formula (I) wherein $R_1$ is alkyl, $R_4$ is —C(O)C(H)($R_8$)NHC(O)$R_9$, $R_8$ is alkyl and $R_9$ is —O$R_{9a}$.

For example, the present invention provides a compound of formula (I) wherein $R_1$ is alkyl, $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is alkyl and $R_9$ is —O$R_{9a}$.

For example, the present invention provides a compound of formula (I) wherein $R_1$ is alkyl, $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is alkyl, $R_9$ is —O$R_{9a}$ and $R_2$ is arylalkyl.

For example, the present invention provides a compound of formula (I) wherein $R_1$ is alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is alkyl, $R_9$ is —O$R_{9a}$, $R_{9a}$ is alkyl and $R_2$ is arylalkyl.

For example, the present invention provides a compound of formula (I) wherein $R_1$ is alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is alkyl, $R_9$ is —O$R_{9a}$, $R_{9a}$ is alkyl, $R_2$ is arylalkyl, and $R_5$, $R_6$ and $R_7$ are heteroaryl.

For example, the present invention provides a compound of formula (I) wherein X is O, Y is O, $R_1$ is alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, 4 is —C(O)C(H)($R_8$)NHC(O)$R_9$, $R_8$ is alkyl, $R_9$ is —O$R_{9a}$, $R_{9a}$ is alkyl, $R_2$ is arylalkyl, and $R_5$, $R_6$ and $R_7$ are heteroaryl.

For example, the present invention provides a compound of formula (I) wherein X is O, Y is O, $R_1$ is C3 alkyl, C4 alkyl or C5 alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is C3 alkyl, C4 alkyl or C5 alkyl, $R_9$ is —O$R_{9a}$, $R_{9a}$ is alkyl, $R_2$ is arylalkyl, and $R_5$, $R_6$ and $R_7$ are heteroaryl.

For example, the present invention provides a compound of formula (I) wherein X is O, Y is O, $R_1$ is C3 alkyl, C4 alkyl or C5 alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is C3 alkyl, C4 alkyl or C5 alkyl, $R_9$ is —O$R_{9a}$, $R_{9a}$ is methyl, $R_2$ is arylalkyl, and $R_5$, $R_6$ and $R_7$ are heteroaryl.

For example, the present invention provides a compound of formula (I) wherein X is O, Y is O, $R_1$ is C3 alkyl, C4 alkyl or C5 alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is C3 alkyl, C4 alkyl or C5 alkyl, $R_9$ is —O$R_{9a}$, $R_{9a}$ is methyl, $R_2$ is arylalkyl, and $R_5$, $R_6$ and $R_7$ are independently selected from the group consisting of thienyl, furyl, oxazolyl, isoxazolyl, thiazolyl, pyridyl, pyridazinyl, indazolyl, imidazopyridinyl, indolyl, benzimidazolyl, isoquinolinyl and quinolinyl.

For example, the present invention provides a compound of formula (I) wherein X is O, Y is O, $R_1$ is C3 alkyl, C4 alkyl or C5 alkyl; $R_3$ is arylalkyl, $R_4$ is —C(O)C(H)($R_8$)NHC(O)$R_9$, $R_8$ is C3 alkyl, C4 alkyl or C5 alkyl, $R_9$ is —O$R_{9a}$, $R_{9a}$ is methyl, $R_2$ is phenylmethyl, and $R_5$, $R_6$ and $R_7$ are independently selected from the group consisting of thienyl, furyl, oxazolyl, isoxazolyl, thiazolyl, pyridyl, pyridazinyl, indazolyl, imidazopyridinyl, indolyl, benzimidazolyl, isoquinolinyl and quinolinyl.

For example, the present invention provides a compound of formula (I) wherein X is O, Y is O, $R_1$ is C3 alkyl, C4 alkyl or C5 alkyl; $R_3$ is arylalkyl substituted with $R_{3a}$, $R_4$ is —C(O)C(H)($R_8$)NHC(O)$R_9$, $R_8$ is C3 alkyl, C4 alkyl or C5 alkyl, $R_9$ is —O$R_{9a}$, $R_{9a}$ is methyl, $R_2$ is phenylmethyl, $R_5$, $R_6$ and $R_7$ are independently selected from the group consisting of thienyl, furyl, oxazolyl, isoxazolyl, thiazolyl, pyridyl, pyridazinyl, indazolyl, imidazopyridinyl, indolyl, benzimidazolyl, isoquinolinyl and quinolinyl, and $R_{3a}$ is heteroaryl.

For example, the present invention provides a compound of formula (I) wherein X is O, Y is O, $R_1$ is C3 alkyl, C4 alkyl or C5 alkyl; $R_3$ is phenylmethyl substituted with $R_{3a}$, $R_4$ is —C(O)C(H)($R_8$)NHC(O)$R_9$, $R_8$ is C3 alkyl, C4 alkyl or C5 alkyl, $R_9$ is —O$R_{9a}$, $R_{9a}$ is methyl, $R_2$ is phenylmethyl, and $R_5$, $R_6$ and $R_7$ are independently selected from the group consisting of thienyl, furyl, oxazolyl, isoxazolyl, thiazolyl, pyridyl, pyridazinyl, indazolyl, imidazopyridinyl, indolyl, benzimidazolyl, isoquinolinyl and quinolinyl, and $R_{3a}$ is pyridyl, oxazolyl or thiazolyl.

For example, the present invention provides a compound of formula (I) wherein X is O, Y is O, $R_1$ is C3 alkyl, C4 alkyl or C5 alkyl; $R_3$ is phenylmethyl substituted with $R_{3a}$, $R_4$ is —C(O)C(H)($R_9$)NHC(O)$R_9$, $R_8$ is C3 alkyl, C4 alkyl or C5 alkyl, $R_9$ is —O$R_{9a}$, $R_{9a}$ is methyl, $R_2$ is phenylmethyl, and $R_5$, $R_6$ and $R_7$ are independently selected from the group consisting of thienyl, furyl, oxazolyl, isoxazolyl, thiazolyl, pyridyl, pyridazinyl, indazolyl, imidazopyridinyl, indolyl, benzimidazolyl, isoquinolinyl and quinolinyl, and $R_{3a}$ is pyridyl.

For example, the present invention provides a compound of formula (I) wherein X is O, Y is O, $R_1$ is C3 alkyl, C4 alkyl or C5 alkyl; $R_3$ is phenylmethyl substituted with $R_{3a}$, $R_4$ is —C(O)C(H)($R_8$)NHC(O)$R_9$, $R_8$ is C3 alkyl, C4 alkyl or C5 alkyl, $R_9$ is —O$R_{9a}$, $R_{9a}$ is methyl, $R_2$ is phenylmethyl, and $R_5$, $R_6$ and $R_7$ are pyridyl, and $R_{3a}$ is 2-pyridyl.

For example, the present invention provides a compound of formula (I) wherein X is O, Y is O, $R_1$ is C3 alkyl, C4 alkyl or C5 alkyl; $R_3$ is phenylmethyl substituted with $R_{3a}$, $R_4$ is —C(O)C(H)($R_8$)NHC(O)$R_9$, $R_8$ is C3 alkyl, C4 alkyl or C5 alkyl, $R_9$ is —O$R_{9a}$, $R_{9a}$ is methyl, $R_2$ is phenylmethyl, and $R_5$, $R_6$ and $R_7$ are 2-pyridyl substituted with one alkyl substituent, and $R_{3a}$ is 2-pyridyl.

For example, the present invention provides a compound of formula (I) wherein X is O, Y is O, $R_1$ is C3 alkyl, C4 alkyl or C5 alkyl; $R_3$ is phenylmethyl substituted with $R_{3a}$, $R_4$ is —C(O)C(H)($R_8$)NHC(O)$R_9$, $R_8$ is C3 alkyl, C4 alkyl or C5 alkyl, $R_9$ is —O$R_{9a}$, $R_{9a}$ is methyl, $R_2$ is phenylmethyl, and $R_5$, $R_6$ and $R_7$ are 2-pyridyl substituted with one methyl substituent, and $R_{3a}$ is 2-pyridyl.

Exemplary compounds of the present invention of formula (I) include, but not limited to, the following:

methyl 1-({2-{2-hydroxy-3-[(3-methyl-2-{3-[2-(6-methyl-2-pyridinyl)ethyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate;

methyl 1-({2-{3-[(3,3-dimethyl-2-{3-[(1-methyl-1H-benzimidazol-2-yl)methyl]-2-oxo-1-imidazolidinyl}butanoyl)amino]-2-hydroxy-4-phenylbutyl}-2-[4-(2-pyridinyl)benzyl]hydrazino}carbonyl)-2,2-dimethylpropylcarbamate;

methyl 1-({2-[2-hydroxy-3-({3-methyl-2-[2-oxo-3-(3-pyridinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

methyl 1-({2-{2-hydroxy-3-[(3-methyl-2-{3-[(6-methyl-2-pyridinyl)methyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate;

methyl 1-({2-(2-hydroxy-3-{[2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}carbonyl)-2-methylbutylcarbamate;

tert-butyl 2-[2-hydroxy-3-({3-methyl-2-[2-oxo-3-(4-quinolinylmethyl)-1-imidazolidinyl]pentanoyl}amino)-4-phenylbutyl]-2-[4-(2-pyridinyl)benzyl]hydrazinecarboxylate;

methyl 1-({2-{3-[(3,3-dimethyl-2-{3-[(1-methyl-1H-benzimidazol-2-yl)methyl]-2-oxo-1-imidazolidinyl}butanoyl)amino]-2-hydroxy-4-phenylbutyl}-2-[4-(2-pyridinyl)benzyl]hydrazino}carbonyl)-2-methylbutylcarbamate;

methyl 1-({2-(2-hydroxy-3-{[2-(3-{[2-(methoxymethyl)-1,3-thiazol-4-yl]methyl}-2-oxo-1-imidazolidinyl)-3,3-dimethylbutanoyl]amino}-4-phenylbutyl)-2-[4-(2-pyridinyl)benzyl]hydrazino}carbonyl)-2-methylbutylcarbamate;

methyl 1-({2-(2-hydroxy-3-{[2-(3-{[2-(methoxymethyl)-1,3-thiazol-4-yl]methyl}-2-oxo-1-imidazolidinyl)-3,3-dimethylbutanoyl]amino}-4-phenylbutyl)-2-[4-(2-pyridinyl)benzyl]hydrazino}carbonyl)-2,2-dimethylpropylcarbamate;

methyl 1-({2-(4-bromobenzyl)-2-[2-hydroxy-3-({3-methyl-2-[2-oxo-3-(4-quinolinylmethyl)-1-imidazolidinyl]pentanoyl}amino)-4-phenylbutyl]hydrazino}carbonyl)-2-methylbutylcarbamate;

methyl 1-({2-benzyl-2-[2-hydroxy-3-({3-methyl-2-[2-oxo-3-(3-pyridinylmethyl)-1-imidazolidinyl]pentanoyl}amino)-4-phenylbutyl]hydrazino}carbonyl)-2,2-dimethylpropylcarbamate;

methyl 1-[(2-benzyl-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-({2-benzyl-2-[2-hydroxy-3-({3-methyl-2-[2-oxo-3-(3-pyridinylmethyl)-1-imidazolidinyl]pentanoyl}amino)-4-phenylbutyl]hydrazino}carbonyl)-2-methylbutylcarbamate;

methyl 1-({2-(3-{[3,3-dimethyl-2-(3-{[2-(5-methyl-3-isoxazolyl)-1,3-thiazol-4-yl]methyl}-2-oxo-1-imidazolidinyl)butanoyl]amino}-2-hydroxy-4-phenylbutyl)-2-[4-(2-pyridinyl)benzyl]hydrazino}carbonyl)-2,2-dimethylpropylcarbamate;

methyl 1-{[2-{2-hydroxy-3-[(3-methyl-2-{3-[(6-methyl-2-pyridinyl)methyl]-2-oxo-1-imidazolidinyl}pentanoyl)amino]-4-phenylbutyl}-2-(4-methoxybenzyl)hydrazino]carbonyl}-2,2-dimethylpropylcarbamate;

methyl 1-({2-(3-{[3,3-dimethyl-2-(2-oxo-3-{[2-(3-pyridinyl)-1,3-thiazol-4-yl]methyl}-1-imidazolidinyl)butanoyl]amino}-2-hydroxy-4-phenylbutyl)-2-[4-(2-pyridinyl)benzyl]hydrazino}carbonyl)-2,2-dimethylpropylcarbamate;

methyl 1-({2-(2-hydroxy-3-{[2-(3-{[6-(hydroxymethyl)-2-pyridinyl]methyl}-2-oxo-1-imidazolidinyl)-3,3-dimethylbutanoyl]amino}-4-phenylbutyl)-2-[4-(2-pyridinyl)benzyl]hydrazino}carbonyl)-2,2-dimethylpropylcarbamate;

methyl 1-({2-[2-hydroxy-3-({3-methyl-2-[2-oxo-3-((2-methyl-1,3-thiazol-4-yl) 1,3-thiazol-4-ylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

methyl 1-({2-{3-[(3,3-dimethyl-2-{3-[(6-methyl-3-pyridinyl)methyl]-2-oxo-1-imidazolidinyl}butanoyl)amino]-2-hydroxy-4-phenylbutyl}-2-[4-(2-pyridinyl)benzyl]hydrazino}carbonyl)-2,2-dimethylpropylcarbamate;

methyl 1-({2-(2-hydroxy-3-{[2-(3-{[6-(1-hydroxy-1-methylethyl)-2-pyridinyl]methyl}-2-oxo-1-imidazolidinyl)-3,3-dimethylbutanoyl]amino}-4-phenylbutyl)-2-[4-(2-pyridinyl)benzyl]hydrazino}carbonyl)-2,2-dimethylpropylcarbamate;

methyl 1-({2-(3-{[2-(3-{[2-(2-ethyl-4-pyridinyl)-1,3-thiazol-4-yl]methyl}-2-oxo-1-imidazolidinyl)-3-methylpentanoyl]amino}-2-hydroxy-4-phenylbutyl)-2-[4-(2-pyridinyl)benzyl]hydrazino}carbonyl)-2,2-dimethylpropylcarbamate;

methyl 1-({2-[2-hydroxy-3-({3-methyl-2-[2-oxo-3-(2-pyridinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

methyl 1-({2-[3-({2-[2,4-dioxo-3-(2-pyridinylmethyl)-1-imidazolidinyl]-3-methylpentanoyl}amino)-2-hydroxy-4-phenylbutyl]-2-[4-(2-pyridinyl)benzyl]hydrazino}carbonyl)-2,2-dimethylpropylcarbamate;

methyl 1-({2-{2-hydroxy-3-[(3-methyl-2-{3-[(4-methyl-3-pyridinyl)methyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate;

methyl 1-({2-{3-[(3,3-dimethyl-2-{3-[(4-methyl-3-pyridinyl)methyl]-2-oxo-1-imidazolidinyl}butanoyl)amino]-2-hydroxy-4-phenylbutyl}-2-[4-(2-pyridinyl)benzyl]hydrazino}carbonyl)-2,2-dimethylpropylcarbamate;

methyl 1-({2-[3-({3,3-dimethyl-2-[2-oxo-3-(4-quinolinylmethyl)-1-imidazolidinyl]butanoyl}amino)-2-hydroxy-4-phenylbutyl]-2-[4-(2-pyridinyl)benzyl]hydrazino}carbonyl)-2,2-dimethylpropylcarbamate;

methyl 1-({2-(2-hydroxy-3-{[3-methyl-2-(2-oxo-3-{[2-(3-pyridinyl)-1,3-thiazol-4-yl]methyl}-1-imidazolidinyl)pentanoyl]amino}-4-phenylbutyl)-2-[4-(2-pyridinyl)benzyl]hydrazino}carbonyl)-2,2-dimethylpropylcarbamate;

methyl 1-{[2-(2-hydroxy-3-{[2-(3-{[2-(methoxymethyl)-1,3-thiazol-4-yl]methyl}-2-oxo-1-imidazolidinyl)-3,3-dimethylbutanoyl]amino}-4-phenylbutyl)-2-(4-methoxybenzyl)hydrazino]carbonyl}-2,2-dimethylpropylcarbamate;

methyl 1-({2-[2-hydroxy-3-({3-methyl-2-[2-oxo-3-(4-pyridazinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

methyl 1-({2-(2-hydroxy-3-{[3-methyl-2-(2-oxo-3-{[2-(trifluoromethyl)-1,3-thiazol-4-yl]methyl}-1-imidazolidinyl)pentanoyl]amino}-4-phenylbutyl)-2-[4-(2-pyridinyl)benzyl]hydrazino}carbonyl)-2,2-dimethylpropylcarbamate;

methyl 1-({2-{2-hydroxy-3-[(2-{3-[(2-isopropyl-1,3-thiazol-4-yl)methyl]-2-oxo-1-imidazolidinyl}-3,3-dimethylbutanoyl)amino]-4-phenylbutyl}-2-[4-(2-pyridinyl)benzyl]hydrazino}carbonyl)-2,2-dimethylpropylcarbamate;

methyl 1-[(2-{2-hydroxy-3-[(3-methyl-2-{3-[(6-methyl-2-pyridinyl)methyl]-2-oxo-1-imidazolidinyl}pentanoyl)amino]-4-phenylbutyl}-2-{[2-(5-methyl-3-isoxazolyl)-1,3-thiazol-4-yl]methyl}hydrazino)carbonyl]-2,2-dimethylpropylcarbamate;

methyl 1-({2-{2-hydroxy-3-[(3-methyl-2-{3-[(2-methyl-1,3-thiazol-4-yl)methyl]-2-oxo-1-imidazolidinyl}butanoyl)amino]-4-phenylbutyl}-2-[4-(2-pyridinyl)benzyl]hydrazino}carbonyl)-2-methylbutylcarbamate;

methyl 1-({2-{3-[(3,3-dimethyl-2-{3-[(2-methyl-1,3-thiazol-4-yl)methyl]-2-oxo-1-imidazolidinyl}butanoyl)amino]-2-hydroxy-4-phenylbutyl}-2-[4-(2-pyridinyl)benzyl]hydrazino}carbonyl)-2-methylbutylcarbamate;

methyl 1-[(2-{2-hydroxy-3-[(3-methyl-2-{3-[(6-methyl-2-pyridinyl)methyl]-2-oxo-1-imidazolidinyl}pentanoyl)amino]-4-phenylbutyl}-2-{[2-(2-pyridinyl)-1,3-thiazol-4-yl]methyl}hydrazino)carbonyl]-2,2-dimethylpropylcarbamate;

methyl 1-({2-{2-hydroxy-3-[(3-methyl-2-{3-[(2-methyl-1,3-thiazol-4-yl)methyl]-2-oxo-1-imidazolidinyl}butanoyl)amino]-4-phenylbutyl}-2-[4-(2-pyridinyl)benzyl]hydrazino}carbonyl)-2-methylpropylcarbamate;

methyl 1-({2-{3-[(3,3-dimethyl-2-{3-[(2-methyl-1,3-thiazol-4-yl)methyl]-2-oxo-1-imidazolidinyl}butanoyl)amino]-2-hydroxy-4-phenylbutyl}-2-[4-(2-pyridinyl)benzyl]hydrazino}carbonyl)-2-methylpropylcarbamate;

methyl 1-({2-{2-hydroxy-3-[(3-methyl-2-{3-[(2-methyl-1,3-thiazol-4-yl)methyl]-2-oxo-1-imidazolidinyl}pentanoyl)amino]-4-phenylbutyl}-2-[4-(2-pyridinyl)benzyl]hydrazino}carbonyl)-2-methylbutylcarbamate;

methyl 1-({2-{2-hydroxy-3-[(3-methyl-2-{3-[(2-methyl-1,3-thiazol-4-yl)methyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate;

methyl 1-({2-{3-[(3,3-dimethyl-2-{3-[(2-methyl-1,3-thiazol-4-yl)methyl]-2-oxo-1-imidazolidinyl}butanoyl)amino]-2-hydroxy-4-phenylbutyl}-2-[4-(2-pyridinyl)benzyl]hydrazino}carbonyl)-2,2-dimethylpropylcarbamate;

methyl 1-{[2-(2-hydroxy-3-{[2-(3-{[2-(methoxymethyl)-1,3-thiazol-4-yl]methyl}-2-oxo-1-imidazolidinyl)-3-methylpentanoyl]amino}-4-phenylbutyl)-2-(4-methoxybenzyl)hydrazino]carbonyl}-2,2-dimethylpropylcarbamate;

methyl 1-{[2-[2-hydroxy-3-({3-methyl-2-[2-oxo-3-(4-quinolinylmethyl)-1-imidazolidinyl]pentanoyl}amino)-4-phenylbutyl]-2-(4-methoxybenzyl)hydrazino]carbonyl}-2,2-dimethylpropylcarbamate;

N-(1-benzyl-2-hydroxy-3-{2-[3-methyl-2-(2-oxo-1-pyrrolidinyl)butanoyl]-1-[4-(2-pyridinyl)benzyl]hydrazino}propyl)-3-methyl-2-{3-[(6-methyl-2-pyridinyl)methyl]-2-oxo-1-imidazolidinyl}pentanamide;

methyl 1-({2-[2-hydroxy-3-({3-methyl-2-[2-oxo-3-(3-pyridazinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

methyl 1-({2-{3-[(2-{3-[(6-acetyl-2-pyridinyl)methyl]-2-oxo-1-imidazolidinyl}-3,3-dimethylbutanoyl)amino]-2-hydroxy-4-phenylbutyl}-2-[4-(2-pyridinyl)benzyl]hydrazino}carbonyl)-2,2-dimethylpropylcarbamate;

methyl 6-[(3-{4-benzyl-1,10-ditert-butyl-5-hydroxy-2,9,12-trioxo-7-[4-(2-pyridinyl)benzyl]-13-oxa-3,7,8,11-tetraazatetradec-1-yl}-2-oxo-1-imidazolidinyl)methyl]-2-pyridinecarboxylate;

methyl 1-({2-{2-hydroxy-3-[(3-methyl-2-{3-[(6-methyl-2-pyridinyl)methyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate;

N-(1-benzyl-2-hydroxy-3-{2-[3-methyl-2-(2-oxo-1-imidazolidinyl)pentanoyl]-1-[4-(2-pyridinyl)benzyl]hydrazino}propyl)-3-methyl-2-{3-[(6-methyl-2-pyridinyl)methyl]-2-oxo-1-imidazolidinyl}pentanamide;

methyl 1-{[2-(2-hydroxy-3-{[2-(3-{[6-(1-hydroxy-1-methylethyl)-2-pyridinyl]methyl}-2-oxo-1-imidazolidinyl)-3,3-dimethylbutanoyl]amino}-4-phenylbutyl)-2-(4-methoxybenzyl)hydrazino]carbonyl}-2,2-dimethylpropylcarbamate;

methyl 1-{[2-(2-hydroxy-3-{[2-(3-{[6-(1-hydroxy-1-methylethyl)-2-pyridinyl]methyl}-2-oxo-1-imidazolidinyl)-3-methylpentanoyl]amino}-4-phenylbutyl)-2-(4-methoxybenzyl)hydrazino]carbonyl}-2,2-dimethylpropylcarbamate;

methyl 1-{[2-(2-hydroxy-3-{[2-(3-{[6-(hydroxymethyl)-2-pyridinyl]methyl}-2-oxo-1-imidazolidinyl)-3,3-dimethylbutanoyl]amino}-4-phenylbutyl)-2-(4-methoxybenzyl)hydrazino]carbonyl}-2,2-dimethylpropylcarbamate;

methyl 1-{[2-(2-hydroxy-3-{[2-(3-{[6-(hydroxymethyl)-2-pyridinyl]methyl}-2-oxo-1-imidazolidinyl)-3-methylpentanoyl]amino}-4-phenylbutyl)-2-(4-methoxybenzyl)hydrazino]carbonyl}-2,2-dimethylpropylcarbamate;

methyl 1-{[2-[2-hydroxy-3-({3-methyl-2-[2-oxo-3-(8-quinolinylmethyl)-1-imidazolidinyl]pentanoyl}amino)-4-phenylbutyl]-2-(4-methoxybenzyl)hydrazino]carbonyl}-2,2-dimethylpropylcarbamate;

methyl 1-{[2-{2-hydroxy-3-[(3-methyl-2-{3-[(2-methyl-4-quinolinyl)methyl]-2-oxo-1-imidazolidinyl}pentanoyl)amino]-4-phenylbutyl}-2-(4-methoxybenzyl)hydrazino]carbonyl}-2,2-dimethylpropylcarbamate;

methyl 1-{[2-{2-hydroxy-3-[(3-methyl-2-{3-[(3-methyl-3H-imidazo[4,5-b]pyridin-2-yl)methyl]-2-oxo-1-imidazolidinyl}pentanoyl)amino]-4-phenylbutyl}-2-(4-methoxybenzyl)hydrazino]carbonyl}-2,2-dimethylpropylcarbamate;

methyl 1-{[2-[2-hydroxy-3-({3-methyl-2-[2-oxo-3-(3-pyridazinylmethyl)-1-imidazolidinyl]pentanoyl}amino)-4-phenylbutyl]-2-(4-methoxybenzyl)hydrazino]carbonyl}-2,2-dimethylpropylcarbamate;

methyl 1-({2-{2-hydroxy-3-[(3-methyl-2-{3-[(5-methyl-2-thienyl)methyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate;

methyl 1-[(2-benzyl-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2-methylbutylcarbamate;

methyl 1-({2-[3-({2-[3-({2-[1-(acetylamino)ethyl]-1,3-thiazol-4-yl}methyl)-2-oxo-1-imidazolidinyl]-3-methylpentanoyl}amino)-2-hydroxy-4-phenylbutyl]-2-[4-(2-pyridinyl)benzyl]hydrazino}carbonyl)-2,2-dimethylpropylcarbamate;

N-(1-benzyl-2-hydroxy-3-{2-{[5-methyl-2-oxo-1,3-oxazolidin-4-yl]carbonyl}-1-[4-(2-pyridinyl)benzyl]hydrazino}propyl)-3-methyl-2-{3-[(6-methyl-2-pyridinyl)methyl]-2-oxo-1-imidazolidinyl}pentanamide;

methyl 1-{[2-(2-hydroxy-3-{[2-(3-{[6-(1-hydroxy-1-methylethyl)-2-pyridinyl]methyl}-2-oxo-1-imidazolidinyl)-3,3-dimethylbutanoyl]amino}-4-phenylbutyl)-2-isopentylhydrazino]carbonyl}-2,2-dimethylpropylcarbamate;

methyl 1-{[2-(2-hydroxy-3-{[2-(3-{[6-(1-hydroxy-1-methylethyl)-2-pyridinyl]methyl}-2-oxo-1-imidazolidinyl)-3- methylpentanoyl]amino}-4-phenylbutyl)-2-isopentylhydrazino]carbonyl}-2,2-dimethylpropylcarbamate;

methyl 1-{[2-(2-hydroxy-3-{[2-(3-{[6-(hydroxymethyl)-2-pyridinyl]methyl}-2-oxo-1-imidazolidinyl)-3,3-dimethylbutanoyl]amino}-4-phenylbutyl)-2-isopentylhydrazino]carbonyl}-2,2-dimethylpropylcarbamate;

methyl 1-{[2-(2-hydroxy-3-{[2-(3-{[6-(hydroxymethyl)-2-pyridinyl]methyl}-2-oxo-1-imidazolidinyl)-3-methylpentanoyl]amino}-4-phenylbutyl)-2-isopentylhydrazino]carbonyl}-2,2-dimethylpropylcarbamate;

N-(1-benzyl-3-{2-[(2,2-dimethyl-5-oxotetrahydro-3-furanyl)carbonyl]-1-[4-(2-pyridinyl)benzyl]hydrazino}-2-hydroxypropyl)-3-methyl-2-{3-[(6-methyl-2-pyridinyl)methyl]-2-oxo-1-imidazolidinyl}pentanamide;

methyl 1-{[2-[2-hydroxy-3-({2-[3-(imidazo[1,5-a]pyridin-3-ylmethyl)-2-oxo-1-imidazolidinyl]-3-methylpentanoyl}amino)-4-phenylbutyl]-2-(4-methoxybenzyl)hydrazino]carbonyl}-2,2-dimethylpropylcarbamate;

N-(1-benzyl-2-hydroxy-3-{2-{[5-oxopyrrolidinyl]carbonyl}-1-[4-(2-pyridinyl)benzyl]hydrazino}propyl)-3-methyl-2-{3-[(6-methyl-2-pyridinyl)methyl]-2-oxo-1-imidazolidinyl}pentanamide;

4,4-dimethyl-2-oxotetrahydro-3-furanyl 2-{2-hydroxy-3-[(3-methyl-2-{3-[(6-methyl-2-pyridinyl)methyl]-2-oxo-1-imidazolidinyl}pentanoyl)amino]-4-phenylbutyl}-2-[4-(2-pyridinyl)benzyl]hydrazinecarboxylate;

4,4-dimethyl-2-oxotetrahydro-3-furanyl 2-{2-hydroxy-3-[(3-methyl-2-{3-[(6-methyl-2-pyridinyl)methyl]-2-oxo-1-imidazolidinyl}pentanoyl)amino]-4-phenylbutyl}-2-[4-(2-pyridinyl)benzyl]hydrazinecarboxylate;

methyl 1-({2-{3-[(3,3-dimethyl-2-{3-[(6-methyl-2-pyridinyl)methyl]-2-oxo-1-imidazolidinyl}butanoyl)amino]-2-hydroxy-4-phenylbutyl}-2-[4-(2-pyridinyl)benzyl]hydrazino}carbonyl)-2,2-dimethylpropylcarbamate;

methyl 1-{[2-(2,3-dihydro-1,4-benzodioxin-6-ylmethyl)-2-(2-hydroxy-3-{[2-(3-{[2-(methoxymethyl)-1,3-thiazol-4-yl]methyl}-2-oxo-1-imidazolidinyl)-3-methylpentanoyl]amino}-4-phenylbutyl)hydrazino]carbonyl}-2,2-dimethylpropylcarbamate;

methyl 1-{[2-(3,3-dimethylbutyl)-2-(2-hydroxy-3-{[2-(3-{[2-(methoxymethyl)-1,3-thiazol-4-yl]methyl}-2-oxo-1-imidazolidinyl)-3-methylpentanoyl]amino}-4-phenylbutyl)hydrazino]carbonyl}-2,2-dimethylpropylcarbamate;

(3R)-2-oxotetrahydro-3-furanyl 2-{2-hydroxy-3-[(3-methyl-2-{3-[(6-methyl-2-pyridinyl)methyl]-2-oxo-1-imidazolidinyl}pentanoyl)amino]-4-phenylbutyl}-2-[4-(2-pyridinyl)benzyl]hydrazinecarboxylate;

2-oxotetrahydro-3-furanyl 2-{2-hydroxy-3-[(3-methyl-2-{3-[(6-methyl-2-pyridinyl)methyl]-2-oxo-1-imidazolidinyl}pentanoyl)amino]-4-phenylbutyl}-2-[4-(2-pyridinyl)benzyl]hydrazinecarboxylate;

methyl 1-[(2-[4-(diethylamino)benzyl]-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

N-(1-benzyl-3-{2-[3,3-dimethyl-2-(2-oxo-1-imidazolidinyl)butanoyl]-1-[4-(2-pyridinyl)benzyl]hydrazino}-2-hydroxypropyl)-3-methyl-2-{3-[(6-methyl-2-pyridinyl)methyl]-2-oxo-1-imidazolidinyl}pentanamide;

methyl 1-{[2-(2,3-dihydro-1,4-benzodioxin-6-ylmethyl)-2-(2-hydroxy-3-{[2-(3-{[6-(1-hydroxy-1-methylethyl)-2-pyridinyl]methyl}-2-oxo-1-imidazolidinyl)-3,3-dimethylbutanoyl]amino}-4-phenylbutyl)hydrazino]carbonyl}-2,2-dimethylpropylcarbamate;

methyl 1-{[2-(2,3-dihydro-1,4-benzodioxin-6-ylmethyl)-2-(2-hydroxy-3-{[2-(3-{[6-(1-hydroxy-1-methylethyl)-2-pyridinyl]methyl}-2-oxo-1-imidazolidinyl)-3-methylpentanoyl]amino}-4-phenylbutyl)hydrazino]carbonyl}-2,2-dimethylpropylcarbamate;

methyl 1-{[2-(2,3-dihydro-1,4-benzodioxin-6-ylmethyl)-2-(2-hydroxy-3-{[2-(3-{[6-(hydroxymethyl)-2-pyridinyl]methyl}-2-oxo-1-imidazolidinyl)-3,3-dimethylbutanoyl]amino}-4-phenylbutyl)hydrazino]carbonyl}-2,2-dimethylpropylcarbamate;

methyl 1-{[2-(2,3-dihydro-1,4-benzodioxin-6-ylmethyl)-2-(2-hydroxy-3-{[2-(3-{[6-(hydroxymethyl)-2-pyridinyl]methyl}-2-oxo-1-imidazolidinyl)-3-methylpentanoyl]amino}-4-phenylbutyl)hydrazino]carbonyl}-2,2-dimethylpropylcarbamate;

N-(1-benzyl-3-{2-[(4,4-dimethyl-2-oxotetrahydro-3-furanyl)carbonyl]-1-[4-(2-pyridinyl)benzyl]hydrazino}-2-hydroxypropyl)-3-methyl-2-{3-[(6-methyl-2-pyridinyl)methyl]-2-oxo-1-imidazolidinyl}pentanamide;

methyl 1-[(2-benzyl-2-{3-[(3,3-dimethyl-2-{3-[(4-methyl-3-pyridinyl)methyl]-2-oxo-1-imidazolidinyl}butanoyl)amino]-2-hydroxy-4-phenylbutyl}hydrazino)carbonyl]-2,2-dimethylpropylcarbamate;

methyl 1-{[2-(3,3-dimethylbutyl)-2-(2-hydroxy-3-{[2-(3-{[6-(1-hydroxy-1-methylethyl)-2-pyridinyl]methyl}-2-oxo-1-imidazolidinyl)-3,3-dimethylbutanoyl]amino}-4-phenylbutyl)hydrazino]carbonyl}-2,2-dimethylpropylcarbamate;

methyl 1-{[2-(3,3-dimethylbutyl)-2-(2-hydroxy-3-{[2-(3-{[6-(1-hydroxy-1-methylethyl)-2-pyridinyl]methyl}-2-oxo-1-imidazolidinyl)-3-methylpentanoyl]amino}-4-phenylbutyl)hydrazino]carbonyl}-2,2-dimethylpropylcarbamate;

methyl 1-{[2-(3,3-dimethylbutyl)-2-(2-hydroxy-3-{[2-(3-{[6-(hydroxymethyl)-2-pyridinyl]methyl}-2-oxo-1-imidazolidinyl)-3,3-dimethylbutanoyl]amino}-4-phenylbutyl)hydrazino]carbonyl}-2,2-dimethylpropylcarbamate;

methyl 1-{[2-(3,3-dimethylbutyl)-2-(2-hydroxy-3-{[2-(3-{[6-(hydroxymethyl)-2-pyridinyl]methyl}-2-oxo-1-imidazolidinyl)-3-methylpentanoyl]amino}-4-phenylbutyl)hydrazino]carbonyl}-2,2-dimethylpropylcarbamate;

methyl 1-{[2-(cyclopropylmethyl)-2-(2-hydroxy-3-{[2-(3-{[6-(1-hydroxy-1-methylethyl)-2-pyridinyl]methyl}-2-oxo-1-imidazolidinyl)-3,3-dimethylbutanoyl]amino}-4-phenylbutyl)hydrazino]carbonyl}-2,2-dimethylpropylcarbamate;

methyl 1-{[2-(cyclopropylmethyl)-2-(2-hydroxy-3-{[2-(3-{[6-(1-hydroxy-1-methylethyl)-2-pyridinyl]methyl}-2-oxo-1-imidazolidinyl)-3-methylpentanoyl]amino}-4-phenylbutyl)hydrazino]carbonyl}-2,2-dimethylpropylcarbamate;

methyl 1-{[2-(cyclopropylmethyl)-2-(2-hydroxy-3-{[2-(3-{[6-(hydroxymethyl)-2-pyridinyl]methyl}-2-oxo-1-imidazolidinyl)-3,3-dimethylbutanoyl]amino}-4-phenylbutyl)hydrazino]carbonyl}-2,2-dimethylpropylcarbamate;

methyl 1-{[2-(cyclopropylmethyl)-2-(2-hydroxy-3-{[2-(3-{[6-(hydroxymethyl)-2-pyridinyl]methyl}-2-oxo-1-imidazolidinyl)-3-methylpentanoyl]amino}-4-phenylbutyl)hydrazino]carbonyl}-2,2-dimethylpropylcarbamate;

methyl 1-[(2-benzyl-2-{2-hydroxy-3-[(3-methyl-2-{3-[(2-methyl-1,3-thiazol-4-yl)methyl]-2-oxo-1-imidazolidinyl}pentanoyl)amino]-4-phenylbutyl}hydrazino)carbonyl]-2-methylbutylcarbamate;

methyl 1-{[2-[2-hydroxy-3-({3-methyl-2-[2-oxo-3-(3-quinolinylmethyl)-1-imidazolidinyl]pentanoyl}amino)-4- phenylbutyl]-2-(4-methoxybenzyl)hydrazino]carbonyl}-2,2-dimethylpropylcarbamate;

methyl 1-{[2-[2-hydroxy-3-({3-methyl-2-[2-oxo-3-(2-quinolinylmethyl)-1-imidazolidinyl]pentanoyl}amino)-4-phenylbutyl]-2-(4-methoxybenzyl)hydrazino]carbonyl}-2,2-dimethylpropylcarbamate;

methyl 1-{[2-{2-hydroxy-3-[(4-(methylamino)-2-{3-[(2-methyl-1,3-thiazol-4-yl)methyl]-2-oxo-1-imidazolidinyl}-4-oxobutanoyl)amino]-4-phenylbutyl}-2-(4-methoxybenzyl)hydrazino]carbonyl}-2,2-dimethylpropylcarbamate;

methyl 1-{[2-{3-[(4-(ethylamino)-2-{3-[(2-methyl-1,3-thiazol-4-yl)methyl]-2-oxo-1-imidazolidinyl}-4-oxobutanoyl)amino]-2-hydroxy-4-phenylbutyl]-2-(4-methoxybenzyl)hydrazino]carbonyl}-2,2-dimethylpropylcarbamate;

methyl 1-[(2-benzyl-2-{3-[(3,3-dimethyl-2-{3-[(6-methyl-2-pyridinyl)methyl]-2-oxo-1-imidazolidinyl}butanoyl)amino]-2-hydroxy-4-phenylbutyl}hydrazino)carbonyl]-2,2-dimethylpropylcarbamate;

methyl 1-[(2-{3-[(3,3-dimethyl-2-{3-[(6-methyl-2-pyridinyl)methyl]-2-oxo-1-imidazolidinyl}butanoyl)amino]-2-hydroxy-4-phenylbutyl]-2-{[2-(3-pyridinyl)-1,3-thiazol-4-yl]methyl}hydrazino)carbonyl]-2,2-dimethylpropylcarbamate;

methyl 1-{[2-benzyl-2-(2-hydroxy-3-{[3-methyl-2-(2-oxo-3-{[2-(3-pyridinyl)-1,3-thiazol-4-yl]methyl}-1-imidazolidinyl)pentanoyl]amino}-4-phenylbutyl)hydrazino]carbonyl}-2,2-dimethylpropylcarbamate;

methyl 1-({2-(3,3-dimethylbutyl)-2-[2-hydroxy-3-({2-[3-(imidazo[1,5-a]pyridin-3-ylmethyl)-2-oxo-1-imidazolidinyl]-3-methylpentanoyl}amino)-4-phenylbutyl]hydrazino}carbonyl)-2,2-dimethylpropylcarbamate;

methyl 1-({2-(3,3-dimethylbutyl)-2-[2-hydroxy-3-({2-[3-(imidazo[1,5-a]pyridin-3-ylmethyl)-2-oxo-1-imidazolidinyl]-3,3-dimethylbutanoyl}amino)-4-phenylbutyl]hydrazino}carbonyl)-2,2-dimethylpropylcarbamate;

methyl 1-{[2-[2-hydroxy-3-({2-[3-(imidazo[1,5-a]pyridin-3-ylmethyl)-2-oxo-1-imidazolidinyl]-3,3-dimethylbutanoyl}amino)-4-phenylbutyl]-2-(4-methoxybenzyl)hydrazino]carbonyl}-2,2-dimethylpropylcarbamate;

methyl 1-({2-(3,3-dimethylbutyl)-2-[2-hydroxy-3-({3-methyl-2-[2-oxo-3-(4-quinolinylmethyl)-1-imidazolidinyl]pentanoyl}amino)-4-phenylbutyl]hydrazino}carbonyl)-2,2-dimethylpropylcarbamate;

methyl 1-{[2-{2-hydroxy-3-[(3-methyl-2-{3-[(2-methyl-1,3-thiazol-4-yl)methyl]-2-oxo-1-imidazolidinyl}pentanoyl)amino]-4-phenylbutyl}-2-(4-methoxybenzyl)hydrazino]carbonyl}-2-methylbutylcarbamate;

methyl 1-({2-benzyl-2-[2-hydroxy-3-({3-methyl-2-[2-oxo-3-(4-quinolinylmethyl)-1-imidazolidinyl]pentanoyl}amino)-4-phenylbutyl]hydrazino}carbonyl)-2-methylbutylcarbamate;

methyl 1-[(2-(3,3-dimethylbutyl)-2-{2-hydroxy-3-[(2-{3-[(2-isopropyl-1,3-thiazol-4-yl)methyl]-2-oxo-1-imidazolidinyl}-3-methylpentanoyl)amino]-4-phenylbutyl}hydrazino)carbonyl]-2,2-dimethylpropylcarbamate;

methyl 1-[(2-(3,3-dimethylbutyl)-2-{3-[(3,3-dimethyl-2-{3-[(6-methyl-2-pyridinyl)methyl]-2-oxo-1-imidazolidinyl}butanoyl)amino]-2-hydroxy-4-phenylbutyl}hydrazino)carbonyl]-2,2-dimethylpropylcarbamate;

methyl 1-{[2-{2-hydroxy-3-[(2-{3-[(2-isopropyl-1,3-thiazol-4-yl)methyl]-2-oxo-1-imidazolidinyl}-3-methylpentanoyl)amino]-4-phenylbutyl}-2-(4-methoxybenzyl)hydrazino]carbonyl}-2,2-dimethylpropylcarbamate;

methyl 1-({2-{2-hydroxy-3-[(2-{3-[(2-isopropyl-1,3-thiazol-4-yl)methyl]-2-oxo-1-imidazolidinyl}-3-methylpentanoyl)amino]-4-phenylbutyl}-2-[4-(2-pyridinyl)benzyl]hydrazino}carbonyl)-2,2-dimethylpropylcarbamate;

methyl 1-({2-{2-hydroxy-3-[(3-methyl-2-{3-[(6-methyl-3-pyridinyl)methyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate;

methyl 1-{[2-(2-hydroxy-3-{[3-methyl-2-(2-oxo-3-{[2-(3-pyridinyl)-1,3-thiazol-4-yl]methyl}-1-imidazolidinyl)pentanoyl]amino}-4-phenylbutyl)-2-(4-methoxybenzyl)hydrazino]carbonyl}-2,2-dimethylpropylcarbamate;

methyl 1-{[2-(2-hydroxy-3-{[3-methyl-2-(2-oxo-3-{[2-(3-pyridinyl)-1,3-thiazol-4-yl]methyl}-1-imidazolidinyl)pentanoyl]amino}-4-phenylbutyl)-2-isopentylhydrazino]carbonyl}-2,2-dimethylpropylcarbamate;

methyl 1-{[2-(3,3-dimethylbutyl)-2-(2-hydroxy-3-{[3-methyl-2-(2-oxo-3-{[2-(3-pyridinyl)-1,3-thiazol-4-yl]methyl}-1-imidazolidinyl)pentanoyl]amino}-4-phenylbutyl)hydrazino]carbonyl}-2,2-dimethylpropylcarbamate;

methyl 1-{[2-{3-[(3,3-dimethyl-2-{3-[(3-methylimidazo[1,5-a]pyridin-1-yl)methyl]-2-oxo-1-imidazolidinyl}butanoyl)amino]-2-hydroxy-4-phenylbutyl}-2-(4-methoxybenzyl)hydrazino]carbonyl}-2,2-dimethylpropylcarbamate;

methyl 1-[(2-(3,3-dimethylbutyl)-2-{3-[(3,3-dimethyl-2-{3-[(3-methylimidazo[1,5-a]pyridin-1-yl)methyl]-2-oxo-1-imidazolidinyl}butanoyl)amino]-2-hydroxy-4-phenylbutyl}hydrazino)carbonyl]-2,2-dimethylpropylcarbamate;

methyl 1-{[2-[2-hydroxy-3-({2-[3-(1H-indazol-3-ylmethyl)-2-oxo-1-imidazolidinyl]-3,3-dimethylbutanoyl}amino)-4-phenylbutyl]-2-(4-methoxybenzyl)hydrazino]carbonyl}-2,2-dimethylpropylcarbamate;

methyl 1-({2-(3,3-dimethylbutyl)-2-[2-hydroxy-3-({2-[3-(1H-indazol-3-ylmethyl)-2-oxo-1-imidazolidinyl]-3,3-dimethylbutanoyl}amino)-4-phenylbutyl]hydrazino}carbonyl)-2,2-dimethylpropylcarbamate;

methyl 1-({2-{2-hydroxy-3-[(2-{3-[(6-isopropyl-2-pyridinyl)methyl]-2-oxo-1-imidazolidinyl}-3-methylpentanoyl)amino]-4-phenylbutyl}-2-[4-(2-pyridinyl)benzyl]hydrazino}carbonyl)-2,2-dimethylpropylcarbamate;

methyl 1-{[2-{3-[(3,3-dimethyl-2-{3-[(1-methyl-1H-indazol-3-yl)methyl]-2-oxo-1-imidazolidinyl}butanoyl)amino]-2-hydroxy-4-phenylbutyl}-2-(4-methoxybenzyl)hydrazino]carbonyl}-2,2-dimethylpropylcarbamate;

methyl 1-[(2-(3,3-dimethylbutyl)-2-{3-[(3,3-dimethyl-2-{3-[(1-methyl-1H-indazol-3-yl)methyl]-2-oxo-1-imidazolidinyl}butanoyl)amino]-2-hydroxy-4-phenylbutyl}hydrazino)carbonyl]-2,2-dimethylpropylcarbamate;

methyl 1-[(2-(3,3-dimethylbutyl)-2-{3-[(3,3-dimethyl-2-{3-[(2-methyl-1H-benzimidazol-5-yl)methyl]-2-oxo-1-imidazolidinyl}butanoyl)amino]-2-hydroxy-4-phenylbutyl}hydrazino)carbonyl]-2,2-dimethylpropylcarbamate;

methyl 1-({2-{3-[(2-{3-[(6-tert-butyl-2-pyridinyl)methyl]-2-oxo-1-imidazolidinyl}-3,3-dimethylbutanoyl)amino]-2-hydroxy-4-phenylbutyl}-2-[4-(2-pyridinyl)benzyl]hydrazino}carbonyl)-2,2-dimethylpropylcarbamate;

methyl 1-({2-(2-hydroxy-3-{[2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}carbonyl)-2,2-dimethylpropylcarbamate;

methyl 1-({2-(2-hydroxy-3-{[2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}carbonyl)-2-methylpropylcarbamate;

methyl 4-hydroxy-2-({2-(2-hydroxy-3-{[2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}carbonyl)-1-pyrrolidinecarboxylate;

methyl (1S,2R)-2-hydroxy-1-({2-(2-hydroxy-3-{[2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}carbonyl)propylcarbamate;

methyl 1-cyclohexyl-2-{2-(2-hydroxy-3-{[2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}-2-oxoethylcarbamate;

methyl 1-benzyl-2-{2-(2-hydroxy-3-{[2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}-2-oxoethylcarbamate;

methyl 1-(cyclohexylmethyl)-2-{2-(2-hydroxy-3-{[2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}-2-oxoethylcarbamate;

methyl 1-({2-{2-hydroxy-3-[(3-methyl-2-{3-[(2-methyl-1,3-thiazol-4-yl)methyl]-2-oxo-1-imidazolidinyl}butanoyl)amino]-4-phenylbutyl}-2-[4-(2-pyridinyl)benzyl]hydrazino}carbonyl)-2,2-dimethylpropylcarbamate;

tert-butyl 1-({2-[2-hydroxy-3-({3-methyl-2-[2-oxo-3-(4-quinolinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

methyl 1-({2-[2-hydroxy-3-({3-methyl-2-[2-oxo-3-(4-quinolinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

tetrahydro-3-furanyl 2-[2-hydroxy-3-({3-methyl-2-[2-oxo-3-(4-quinolinylmethyl)-1-imidazolidinyl]pentanoyl}amino)-4-phenylbutyl]-2-[4-(2-pyridinyl)benzyl]hydrazinecarboxylate;

N-(1-benzyl-3-{2-[3,3-dimethyl-2-(2-oxo-1-imidazolidinyl)butanoyl]-1-[4-(2-pyridinyl)benzyl]hydrazino}-2-hydroxypropyl)-3-methyl-2-[2-oxo-3-(4-quinolinylmethyl)-1-imidazolidinyl]pentanamide;

N-(1-benzyl-3-{2-[(2,6-dimethylphenoxy)acetyl]-1-[4-(2-pyridinyl)benzyl]hydrazino}-2-hydroxypropyl)-3-methyl-2-[2-oxo-3-(4-quinolinylmethyl)-1-imidazolidinyl]pentanamide;

N-(1-benzyl-2-hydroxy-3-{2-[(2-methylphenoxy)acetyl]-1-[4-(2-pyridinyl)benzyl]hydrazino}propyl)-3-methyl-2-[2-oxo-3-(4-quinolinylmethyl)-1-imidazolidinyl]pentanamide;

N-(1-benzyl-2-hydroxy-3-{2-(3-hydroxy-2-methylbenzoyl)-1-[4-(2-pyridinyl)benzyl]hydrazino}propyl)-3-methyl-2-[2-oxo-3-(4-quinolinylmethyl)-1-imidazolidinyl]pentanamide;

N-(1-benzyl-2-hydroxy-3-{2-[3-methyl-2-(2-oxo-1-imidazolidinyl)pentanoyl]-1-[4-(2-pyridinyl)benzyl]hydrazino}propyl)-3-methyl-2-[2-oxo-3-(4-quinolinylmethyl)-1-imidazolidinyl]pentanamide;

N-(1-benzyl-3-{2-[2-(2,4-dioxo-1-imidazolidinyl)-3-methylpentanoyl]-1-[4-(2-pyridinyl)benzyl]hydrazino}-2-hydroxypropyl)-3-methyl-2-[2-oxo-3-(4-quinolinylmethyl)-1-imidazolidinyl]pentanamide;

benzyl 2-[2-hydroxy-3-({3-methyl-2-[2-oxo-3-(4-quinolinylmethyl)-1-imidazolidinyl]pentanoyl}amino)-4-phenylbutyl]-2-[4-(2-pyridinyl)benzyl]hydrazinecarboxylate;

ethyl 1-({2-[2-hydroxy-3-({3-methyl-2-[2-oxo-3-(4-quinolinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

N-(3-{2-[2-(acetylamino)-3,3-dimethylbutanoyl]-1-[4-(2-pyridinyl)benzyl]hydrazino}-1-benzyl-2-hydroxypropyl)-3-methyl-2-[2-oxo-3-(4-quinolinylmethyl)-1-imidazolidinyl]pentanamide;

methyl 1-({2-[2-hydroxy-3-({3-methyl-2-[2-oxo-3-(4-quinolinylmethyl)-1-imidazolidinyl]pentanoyl}amino)-4-phenylbutyl]-2-[4-(3-pyridinyl)benzyl]hydrazino}carbonyl)-2-methylbutylcarbamate;

methyl 1-({2-[4-(1,3-benzodioxol-5-yl)benzyl]-2-[2-hydroxy-3-({3-methyl-2-[2-oxo-3-(4-quinolinylmethyl)-1-imidazolidinyl]pentanoyl}amino)-4-phenylbutyl]hydrazino}carbonyl)-2-methylbutylcarbamate;

methyl 1-({2-[4-(3,5-dimethyl-4-isoxazolyl)benzyl]-2-[2-hydroxy-3-({3-methyl-2-[2-oxo-3-(4-quinolinylmethyl)-1-imidazolidinyl]pentanoyl}amino)-4-phenylbutyl]hydrazino}carbonyl)-2-methylbutylcarbamate;

methyl 1-({2-[2-hydroxy-3-({3-methyl-2-[2-oxo-3-(4-quinolinylmethyl)-1-imidazolidinyl]pentanoyl}amino)-4-phenylbutyl]-2-[4-(4-pyridinyl)benzyl]hydrazino}carbonyl)-2-methylbutylcarbamate;

methyl 1-[(2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-{2-hydroxy-3-[(3-methyl-2-{3-[2-(6-methyl-2-pyridinyl)ethyl]-2-oxo-1-imidazolidinyl}pentanoyl)amino]-4-phenylbutyl}-2-isopentylhydrazino)carbonyl]-2,2-dimethylpropylcarbamate;

methyl 1-{[2-{2-hydroxy-3-[(3-methyl-2-{3-[(6-methyl-2-pyridinyl)methyl]-2-oxo-1-imidazolidinyl}pentanoyl)amino]-4-phenylbutyl}-2-(4-methylbenzyl)hydrazino]carbonyl}-2,2-dimethylpropylcarbamate;

methyl 1-[(2-(cyclohexylmethyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-{2-hydroxy-3-[(3-methyl-2-{3-[(6-methyl-2-pyridinyl)methyl]-2-oxo-1-imidazolidinyl}pentanoyl)amino]-4-phenylbutyl}-2-isobutylhydrazino)carbonyl]-2,2-dimethylpropylcarbamate;

methyl 1-{[2-{2-hydroxy-3-[(3-methyl-2-{3-[(6-methyl-2-pyridinyl)methyl]-2-oxo-1-imidazolidinyl}pentanoyl)amino]-4-phenylbutyl}-2-(2-phenylethyl)hydrazino]carbonyl}-2,2-dimethylpropylcarbamate;

methyl 1-{[2-{2-hydroxy-3-[(3-methyl-2-{3-[(6-methyl-2-pyridinyl)methyl]-2-oxo-1-imidazolidinyl}pentanoyl)amino]-4-phenylbutyl}-2-(2-thienylmethyl)hydrazino]carbonyl}-2,2-dimethylpropylcarbamate;

methyl 1-{[2-{2-hydroxy-3-[(3-methyl-2-{3-[(6-methyl-2-pyridinyl)methyl]-2-oxo-1-imidazolidinyl}pentanoyl)amino]-4-phenylbutyl}-2-(2-naphthylmethyl)hydrazino]carbonyl}-2,2-dimethylpropylcarbamate;

methyl 1-{[2-{2-hydroxy-3-[(3-methyl-2-{3-[(6-methyl-2-pyridinyl)methyl]-2-oxo-1-imidazolidinyl}pentanoyl)

amino]-4-phenylbutyl}-2-(4-isopropylbenzyl)hydrazino]carbonyl}-2,2-dimethylpropylcarbamate;

methyl 1-{[2-{2-hydroxy-3-[(3-methyl-2-{3-[(6-methyl-2-pyridinyl)methyl]-2-oxo-1-imidazolidinyl}pentanoyl)amino]-4-phenylbutyl}-2-(4-isopropoxybenzyl)hydrazino]carbonyl}-2,2-dimethylpropylcarbamate;

methyl 1-[(2-(3,4-dimethylbenzyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-{[2-{2-hydroxy-3-[(3-methyl-2-{3-[(6-methyl-2-pyridinyl)methyl]-2-oxo-1-imidazolidinyl}pentanoyl)amino]-4-phenylbutyl}-2-(3-methoxybenzyl)hydrazino]carbonyl}-2,2-dimethylpropylcarbamate;

methyl 1-[(2-(2-ethylbutyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-(4-ethylbenzyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-{[2-{2-hydroxy-3-[(3-methyl-2-{3-[(6-methyl-2-pyridinyl)methyl]-2-oxo-1-imidazolidinyl}pentanoyl)amino]-4-phenylbutyl}-2-(3-methylbenzyl)hydrazino]carbonyl}-2,2-dimethylpropylcarbamate;

methyl 1-({2-{2-hydroxy-3-[(3-methyl-2-{3-[(6-methyl-2-pyridinyl)methyl]-2-oxo-1-imidazolidinyl}pentanoyl)amino]-4-phenylbutyl}-2-[4-(trifluoromethyl)benzyl]hydrazino}carbonyl)-2,2-dimethylpropylcarbamate;

methyl 1-[(2-(4-hydroxybenzyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-(4-fluorobenzyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-({2-{2-hydroxy-3-[(3-methyl-2-{3-[(6-methyl-2-pyridinyl)methyl]-2-oxo-1-imidazolidinyl}pentanoyl)amino]-4-phenylbutyl}-2-[3-(4-methylphenoxy)benzyl]hydrazino}carbonyl)-2,2-dimethylpropylcarbamate;

methyl 1-[(2-[3-(4-chlorophenoxy)benzyl]-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-{[2-{2-hydroxy-3-[(3-methyl-2-{3-[(6-methyl-2-pyridinyl)methyl]-2-oxo-1-imidazolidinyl}pentanoyl)amino]-4-phenylbutyl}-2-(2-quinolinylmethyl)hydrazino]carbonyl}-2,2-dimethylpropylcarbamate;

methyl 1-[(2-[(5-ethyl-2-thienyl)methyl]-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-{[2-{2-hydroxy-3-[(3-methyl-2-{3-[(6-methyl-2-pyridinyl)methyl]-2-oxo-1-imidazolidinyl}pentanoyl)amino]-4-phenylbutyl}-2-(2-octynyl)hydrazino]carbonyl}-2,2-dimethylpropylcarbamate;

methyl 6-(1-{2-hydroxy-3-[(3-methyl-2-{3-[(6-methyl-2-pyridinyl)methyl]-2-oxo-1-imidazolidinyl}pentanoyl)amino]-4-phenylbutyl}-2-{2-[(methoxycarbonyl)amino]-3,3-dimethylbutanoyl}hydrazino)hexanoate;

methyl 1-[(2-[(5-ethyl-2-furyl)methyl]-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-({2-{2-hydroxy-3-[(3-methyl-2-{3-[(6-methyl-2-pyridinyl)methyl]-2-oxo-1-imidazolidinyl}pentanoyl)amino]-4-phenylbutyl}-2-[4-(1H-imidazol-1-yl)benzyl]hydrazino}carbonyl)-2,2-dimethylpropylcarbamate;

methyl 1-[(2-(3,3-dimethylbutyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-[4-(acetylamino)benzyl]-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 4-[(1-{2-hydroxy-3-[(3-methyl-2-{3-[(6-methyl-2-pyridinyl)methyl]-2-oxo-1-imidazolidinyl}pentanoyl)amino]-4-phenylbutyl}-2-{2-[(methoxycarbonyl)amino]-3,3-dimethylbutanoyl}hydrazino)methyl]benzoate;

methyl 1-{[2-{2-hydroxy-3-[(3-methyl-2-{3-[(6-methyl-2-pyridinyl)methyl]-2-oxo-1-imidazolidinyl}pentanoyl)amino]-4-phenylbutyl}-2-(3-phenoxybenzyl)hydrazino]carbonyl}-2,2-dimethylpropylcarbamate;

methyl 1-({2-{2-hydroxy-3-[(3-methyl-2-{3-[(6-methyl-2-pyridinyl)methyl]-2-oxo-1-imidazolidinyl}pentanoyl)amino]-4-phenylbutyl}-2-[3-(4-methoxyphenoxy)benzyl]hydrazino}carbonyl)-2,2-dimethylpropylcarbamate;

methyl 1-[(2-(4-tert-butylbenzyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-(2,3-dihydro-1,4-benzodioxin-6-ylmethyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-{2-hydroxy-3-[(3-methyl-2-{3-[(6-methyl-2-pyridinyl)methyl]-2-oxo-1-imidazolidinyl}pentanoyl)amino]-4-phenylbutyl}-2-{4-[(trifluoromethyl)sulfanyl]benzyl}hydrazino)carbonyl]-2,2-dimethylpropylcarbamate;

methyl 1-[(2-(3,7-dimethyl-6-octenyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-(cyclopropylmethyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-[(2-ethyl-1H-imidazol-5-yl)methyl]-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-(2,3-dihydro-1-benzofuran-5-ylmethyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-(4-chlorobenzyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-(3,4-dimethoxybenzyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-(3-fluoro-4-methoxybenzyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-(1,3-benzodioxol-5-ylmethyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-{[2-{2-hydroxy-3-[(3-methyl-2-{3-[(6-methyl-2-pyridinyl)methyl]-2-oxo-1-imidazolidinyl}pentanoyl)amino]-4-phenylbutyl}-2-(4-methoxy-3-methylbenzyl)hydrazino]carbonyl}-2,2-dimethylpropylcarbamate;

methyl 1-[(2-(4-hydroxy-3-methoxybenzyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-({2-{2-hydroxy-3-[(3-methyl-2-{3-[(6-methyl-2-pyridinyl)methyl]-2-oxo-1-imidazolidinyl}pentanoyl)amino]-4-phenylbutyl}-2-[4-(methylsulfonyl)benzyl]hydrazino}carbonyl)-2,2-dimethylpropylcarbamate;

methyl 1-{[2-{2-hydroxy-3-[(3-methyl-2-{3-[(6-methyl-2-pyridinyl)methyl]-2-oxo-1-imidazolidinyl}pentanoyl)amino]-4-phenylbutyl}-2-(1H-imidazol-2-ylmethyl)hydrazino]carbonyl}-2,2-dimethylpropylcarbamate;

methyl 1-{[2-{2-hydroxy-3-[(3-methyl-2-{3-[(6-methyl-2-pyridinyl)methyl]-2-oxo-1-imidazolidinyl}pentanoyl)amino]-4-phenylbutyl}-2-(5-hydroxypentyl)hydrazino]carbonyl}-2,2-dimethylpropylcarbamate;

methyl 1-[(2-[(4,5-dimethyl-2-furyl)methyl]-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-(3-chlorobenzyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-(3,5-dimethylbenzyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-{2-hydroxy-3-[(3-methyl-2-{3-[(6-methyl-2-pyridinyl)methyl]-2-oxo-1-imidazolidinyl}pentanoyl)amino]-4-phenylbutyl}-2-neopentylhydrazino)carbonyl]-2,2-dimethylpropylcarbamate;

methyl 1-[(2-(1,3-dimethylbutyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-(4-cyanobenzyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-cyclohexyl-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-(3,4-dichlorobenzyl)-2-{2-hydroxy-3-[(3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 1-[(2-(2-hydroxy-3-{[2-(3-{[2-(methoxymethyl)-1,3-thiazol-4-yl]methyl}-2-oxo-1-imidazolidinyl)-3,3-dimethylbutanoyl]amino}-4-phenylbutyl)-2-{[2-(4-pyridinyl)-1,3-thiazol-4-yl]methyl}hydrazino)carbonyl]-2,2-dimethylpropylcarbamate;

methyl 1-({2-(2-hydroxy-3-{[2-(3-{[2-(methoxymethyl)-1,3-thiazol-4-yl]methyl}-2-oxo-1-imidazolidinyl)-3,3-dimethylbutanoyl]amino}-4-phenylbutyl)-2-[3-(5-pyrimidinyl)benzyl]hydrazino}carbonyl)-2,2-dimethylpropylcarbamate;

methyl 1-[(2-(2-hydroxy-3-{[2-(3-{[2-(methoxymethyl)-1,3-thiazol-4-yl]methyl}-2-oxo-1-imidazolidinyl)-3,3-dimethylbutanoyl]amino}-4-phenylbutyl)-2-{[2-(5-methyl-3-isoxazolyl)-1,3-thiazol-4-yl]methyl}hydrazino)carbonyl]-2,2-dimethylpropylcarbamate;

methyl 1-[(2-(2-hydroxy-3-{[2-(3-{[2-(methoxymethyl)-1,3-thiazol-4-yl]methyl}-2-oxo-1-imidazolidinyl)-3,3-dimethylbutanoyl]amino}-4-phenylbutyl)-2-{[2-(2-pyridinyl)-1,3-thiazol-4-yl]methyl}hydrazino)carbonyl]-2,2-dimethylpropylcarbamate;

methyl 1-({2-(2-hydroxy-3-{[2-(3-{[2-(methoxymethyl)-1,3-thiazol-4-yl]methyl}-2-oxo-1-imidazolidinyl)-3,3-dimethylbutanoyl]amino}-4-phenylbutyl)-2-[(2-isopropyl-1,3-thiazol-4-yl)methyl]hydrazino}carbonyl)-2,2-dimethylpropylcarbamate;

methyl 1-{[2-(2-hydroxy-3-{[2-(3-{[2-(methoxymethyl)-1,3-thiazol-4-yl]methyl}-2-oxo-1-imidazolidinyl)-3-methylpentanoyl]amino}-4-phenylbutyl)-2-isopentylhydrazino]carbonyl}-2,2-dimethylpropylcarbamate;

methyl 1-{[2-(3,4-dimethoxybenzyl)-2-(2-hydroxy-3-{[2-(3-{[2-(methoxymethyl)-1,3-thiazol-4-yl]methyl}-2-oxo-1-imidazolidinyl)-3-methylpentanoyl]amino}-4-phenylbutyl)hydrazino]carbonyl}-2,2-dimethylpropylcarbamate;

methyl 1-{[2-(3,4-dimethylbenzyl)-2-(2-hydroxy-3-{[2-(3-{[2-(methoxymethyl)-1,3-thiazol-4-yl]methyl}-2-oxo-1-imidazolidinyl)-3-methylpentanoyl]amino}-4-phenylbutyl)hydrazino]carbonyl}-2,2-dimethylpropylcarbamate;

methyl 1-{[2-{2-hydroxy-3-[(3-methyl-2-{3-[(6-methyl-2-pyridinyl)methyl]-2-oxo-1-imidazolidinyl}pentanoyl)amino]-4-phenylbutyl}-2-(4-methoxybenzyl)hydrazino]carbonyl}-2-methylbutylcarbamate;

methyl 1-[(2-{2-hydroxy-3-[(3-methyl-2-{3-[(6-methyl-2-pyridinyl)methyl]-2-oxo-1-imidazolidinyl}pentanoyl)amino]-4-phenylbutyl}-2-isopentylhydrazino)carbonyl]-2-methylbutylcarbamate;

methyl 1-({2-{2-hydroxy-3-[(3-methyl-2-{3-[(6-methyl-2-pyridinyl)methyl]-2-oxo-1-imidazolidinyl}pentanoyl)

amino]-4-phenylbutyl}-2-[4-(2-pyridinyl)benzyl]
hydrazino}carbonyl)-2-methylbutylcarbamate;

methyl 1-{[2-{3-[(3,3-dimethyl-2-{3-[2-(6-methyl-2-pyridinyl)ethyl]-2-oxo-1-imidazolidinyl}butanoyl)amino]-2-hydroxy-4-phenylbutyl}-2-(4-methoxybenzyl)hydrazino]carbonyl}-2,2-dimethylpropylcarbamate;

methyl 1-[(2-{3-[(3,3-dimethyl-2-{3-[2-(6-methyl-2-pyridinyl)ethyl]-2-oxo-1-imidazolidinyl}butanoyl)amino]-2-hydroxy-4-phenylbutyl}-2-isopentylhydrazino)carbonyl]-2,2-dimethylpropylcarbamate;

methyl 1-{[2-{3-[(3,3-dimethyl-2-{3-[(4-methyl-3-pyridinyl)methyl]-2-oxo-1-imidazolidinyl}butanoyl)amino]-2-hydroxy-4-phenylbutyl}-2-(4-methoxybenzyl)hydrazino]carbonyl}-2,2-dimethylpropylcarbamate;

methyl 1-[(2-{3-[(3,3-dimethyl-2-{3-[(4-methyl-3-pyridinyl)methyl]-2-oxo-1-imidazolidinyl}butanoyl)amino]-2-hydroxy-4-phenylbutyl}-2-isopentylhydrazino)carbonyl]-2,2-dimethylpropylcarbamate; and methyl 1-{[2-{2-hydroxy-3-[(3-methyl-2-{3-[2-(6-methyl-2-pyridinyl)ethyl]-2-oxo-1-imidazolidinyl}pentanoyl)amino]-4-phenylbutyl}-2-(4-pyridinylmethyl)hydrazino]carbonyl}-2,2-dimethylpropylcarbamate; or a pharmaceutically acceptable salt form, ester, salt of an ester, stereoisomer, prodrug, salt of a prodrug, or combination thereof.

In a second embodiment, the present invention provides a compound of formula (II)

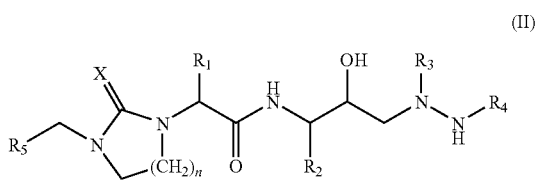

(II)

or a pharmaceutically acceptable salt form, stereoisomer, ester, salt of an ester, prodrug, salt of a prodrug or combination thereof, wherein:

X is O, S or NH;

$R_1$ is alkyl, alkenyl, alkynyl, cycloalkyl, cycloalkenyl, aryl, heteroaryl, arylalkyl, heteroarylalkyl, cycloalkylalkyl or cycloalkenylalkyl; wherein each $R_1$ is substituted with 0, 1 or 2 substituents independently selected from the group consisting of halo, haloalkyl, alkyl, alkenyl, cyano, nitro, —$OR_a$, —Oalkyl$C(=O)NR_aR_b$, —$SR_a$, —$SOR_a$, —$SO_2R_a$, —$SO_2NR_aR_b$, —$C(=O)R_a$, —$NR_aR_b$, —$N(R_b)C(=O)R_a$, —$N(R_b)C(=O)OR_a$, —$N(R_b)SO_2R_a$, —$N(R_b)SO_2NR_aR_b$, —$N(R_b)C(=NH)NR_aR_b$, —$N(R_b)C(=O)NR_aR_b$, —$C(=O)NR_aR_b$ and —$C(=O)OR_a$;

$R_2$ is alkyl, alkenyl, alkynyl, cycloalkyl, cycloalkenyl, cycloalkylalkyl, cycloalkenylalkyl, arylalkyl, heterocycle, heterocyclealkyl or heteroarylalkyl; wherein each $R_2$ is substituted with 0, 1, or 2 substituents independently selected from the group consisting of alkyl, alkenyl, alkynyl, cyano, halo, formyl, nitro, hydroxy, alkoxy, —$NH_2$, —N(H)alkyl, —N(alkyl)$_2$, —N(H)C(=O)Oalkyl, —N(alkyl)C(=O)Oalkyl, —C(=O)OH, —C(=O)Oalkyl, —C(=O)NH$_2$, —C(=O)N(H)(alkyl), —C(=O)N(alkyl)$_2$, —C(=O)alkyl, cyanoalkyl, nitroalkyl, formylalkyl, haloalkyl, hydroxyalkyl, alkoxyalkyl, -alkylNH$_2$, -alkylN(H)alkyl, -alkylN(alkyl)$_2$, -alkylN(H)C(=O)Oalkyl, -alkylN(alkyl)C(=O)Oalkyl,
-alkylC(=O)OH, -alkylC(=O)Oalkyl, -alkylC(=O)NH$_2$, -alkylC(=O)N(H)(alkyl), -alkylC(=O)N(alkyl)$_2$ and -alkylC(=O)alkyl;

$R_3$ is hydrogen, alkyl, haloalkyl, alkenyl, haloalkenyl, alkynyl, haloalkynyl, cycloalkyl, cycloalkenyl, heterocycle, aryl, heteroaryl, cycloalkylalkyl, cycloalkenylalkyl, heterocyclealkyl, heteroarylalkyl, arylalkyl, hydroxyalkyl, alkoxyalkyl, -alkylSR$_a$, -alkylSOR$_a$, -alkylSO$_2$R$_a$, -alkylNR$_a$R$_b$, -alkylC(=O)OR$_a$, -alkylN(R$_b$)C(=O)OR$_a$, -alkylN(R$_b$)C(=O)R$_a$, -alkylN(R$_b$)SO$_2$R$_a$ or -alkylN(R$_b$)SO$_2$NR$_a$R$_b$; wherein the cycloalkyl, cycloalkenyl, heterocycle, aryl, heteroaryl, cycloalkyl moiety of cycloalkylalkyl, cycloalkenyl moiety of cycloalkenylalkyl, heterocycle moiety of heterocyclealkyl, heteroaryl moiety of heteroarylalkyl and aryl moiety of arylalkyl are independently substituted with 0, 1, 2 or 3 substituents independently selected from the group consisting of halo, nitro, cyano, formyl, alkyl, alkenyl, alkynyl, hydroxy, alkoxy, —SH, —S(alkyl), —S(haloalkyl), —SO$_2$(alkyl), —SO$_2$(haloalkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$, -alkylC(=O)alkyl and $R_{3a}$;

$R_{3a}$ is cycloalkyl, cycloalkenyl, aryl, heteroaryl, heterocycle, aryloxy, heteroaryloxy or heterocycleoxy, wherein each $R_{3a}$ is independently substituted with 0, 1, 2 or 3 substituents independently selected from the group consisting of halo, nitro, cyano, formyl, alkyl, alkenyl, alkynyl, hydroxyl, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$ and -alkylC(=O)alkyl;

$R_4$ is a) —C(O)CH($R_8$)NHC(O)$R_9$, b) —C(O)$R_9$, c) —C(O)CH$_2$—O-aryl, substituted with 0, 1, 2 or 3 substituents selected from the group consisting of alkyl, alkenyl, halo, cynao, nitro, formyl, oxo, hydroxyl, alkoxy, hydroxyalky, alkoxyalkyl, haloalkyl, cyanoalkyl, aminoalkyl, alkylaminoalkyl, dialkylaminoalkyl, nitroalkyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl) and —C(=O)N(alkyl)$_2$, d) —C(O)CH$_2$—O-heteroaryl, substituted with 0, 1, 2 or 3 substituents selected from the group consisting of alkyl, alkenyl, halo, cynao, nitro, formyl, oxo, hydroxyl, alkoxy, hydroxyalky, alkoxyalkyl, haloalkyl, cyanoalkyl, aminoalkyl, alkylaminoalkyl, dialkylaminoalkyl, nitroalkyl, —NH$_2$, —N(H)alkyl, —N(alkyl)$_2$, —C(=O)alkyl, —C(=O)OH, —C(=O)Oalkyl, —C(=O)NH₂, —C(=O)N(H)(alkyl), and —C(=O)N(alkyl)₂,

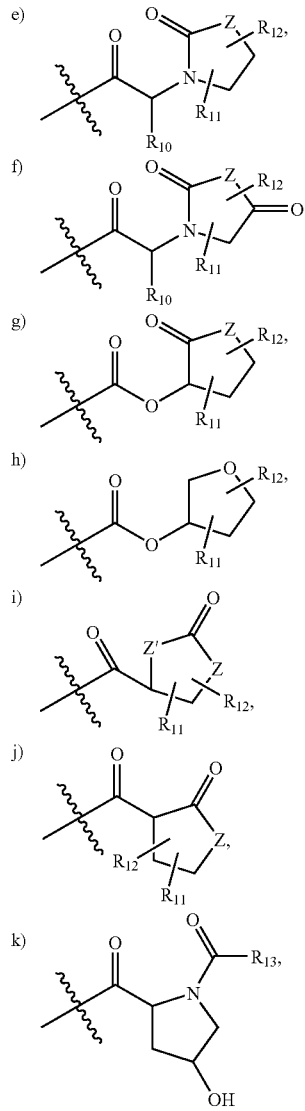

l) —SO₂R₁₄;

R₅ is alkyl, alkenyl, alkynyl, cycloalkyl, cycloalkenyl, aryl, heteroaryl or heterocycle; wherein each R₅ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO₂R$_a$, —SO₂NR$_a$R$_b$, —SO₂OR$_a$, —NR$_a$R$_b$, —N(R$_b$)NR$_a$R$_b$, —N(R$_b$)C(=O)R$_a$, —N(R$_b$)SO₂R$_a$, —N(R$_b$)C(=O)OR$_a$, —N(R$_b$)C(=O)NR$_a$R$_b$, —N(R$_b$)SO₂NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO₂R$_a$, -alkylSO₂NR$_a$, -alkylSO₂R$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO₂NR$_a$R$_b$, -alkylN(R$_b$)SO₂R$_a$, -alkylC(=O)R$_a$, -alkylC(=O)OR$_a$, -alkylC(=O)NR$_a$R$_b$ and R$_{5a}$;

R$_{5a}$ is cycloalkyl, cycloalkenyl, heterocycle, aryl or heteroaryl; wherein each R$_{5a}$ is substituted with 0, 1, 2, 3 or 4 substituents independently selected from the group consisting of cyano, halo, nitro, oxo, alkyl, alkenyl, alkynyl, hydroxy, alkoxy, —NH₂, —N(H)(alkyl), —N(alkyl)₂, —SH, —S(alkyl), —SO₂(alkyl), —N(H)C(=O)alkyl, —N(alkyl)C(=O)alkyl, —N(H)C(=O)NH₂, —N(H)C(=O)N(H)(alkyl), —N(H)C(=O)N(alkyl)₂, —C(=O)OH, —C(=O)Oalkyl, —C(=O)NH₂, —C(=O)N(H)(alkyl), —C(=O)N(alkyl)₂, cyanoalkyl, formylalkyl, haloalkyl, hydroxyalkyl, alkoxyalkyl, -alkylNH₂, -alkylN(H)(alkyl), -alkylN(alkyl)₂, -alkylN(H)C(=O)alkyl, -alkylN(alkyl)C(=O)alkyl, -alkylN(H)C(=O)NH₂, -alkylN(H)C(=O)N(H)(alkyl), -alkylN(H)C(=O)N(alkyl)₂, -alkylC(=O)OH, -alkylC(=O)Oalkyl, -alkylC(=O)NH₂, -alkylC(=O)N(H)(alkyl) and -alkylC(=O)N(alkyl)₂;

R₈ is alkyl, alkenyl, alkynyl, cycloalkyl, aryl, heteroaryl, cycloalkylalkyl or arylalkyl; wherein each R₈ is substituted with 0, 1 or 2 substituents independently selected from the group consisting of halo, cyano, formyl, nitro, alkyl, alkenyl, alkynyl, hydroxy, alkoxy, —NH₂, —N(H)alkyl, —N(alkyl)₂, —C(=O)alkyl, —C(=O)OH, —C(=O)Oalkyl, —C(=O)NH₂, —C(=O)N(H)(alkyl), —C(=O)N(alkyl)₂, —C(=O)alkyl, hydroxyalkyl, alkoxyalkyl, -alkylNH₂, -alkylN(H)alkyl, -alkylN(alkyl)₂, -alkylC(=O)OH, -alkylC(=O)Oalkyl, -alkylC(=O)NH₂, -alkylC(=O)N(H)(alkyl) and -alkylC(=O)N(alkyl)₂;

R₉ is alkyl, cycloalkyl, cycloalkylalkyl, aryl, heterocycle, heteroaryl or OR$_{9a}$, wherein each R₉ is substituted with 0, 1, 2 or 3 substituents selected from the group consisting of hydroxy, alkoxy, halo, cyano, nitro, formyl, alkyl, alkenyl, alkynyl, —NH₂, —N(H)alkyl, —N(alkyl)₂, —C(=O)alkyl, —C(=O)OH, —C(=O)Oalkyl, —C(=O)NH₂, —C(=O)N(H)(alkyl), and —C(=O)N(alkyl)₂;

R$_{9a}$ is alkyl, cycloalkyl, cycloalkylalkyl, aryl, arylalkyl, heterocycle, heteroaryl, heteroarylalkyl or heterocyclealkyl; wherein each R$_{9a}$ is substituted with 0, 1, 2 or 3 substituents independently selected from the group consisting of hydroxy, alkoxy, halo, cyano, nitro, formyl, alkyl, alkenyl, alkynyl, —NH₂, —N(H)alkyl, —N(alkyl)₂, —C(=O)alkyl, —C(=O)OH, —C(=O)Oalkyl, —C(=O)NH₂, —C(=O)N(H)(alkyl) and —C(=O)N(alkyl)₂;

R₁₀ is alkyl, alkenyl, alkynyl, cycloalkyl or cycloalkenyl, aryl, heteroaryl, arylalkyl, cycloalkylalkyl or heteroarylalkyl; wherein each R₁₀ is substituted with 0, 1, 2 or 3 substituents selected from the group consisting of halo, cyano, nitro, formyl, alkyl, alkenyl, hydroxy, alkoxy, —SR$_a$, —SOR$_a$, —SO₂R$_a$, —SO₂NR$_a$R$_b$, —C(=O)R$_a$, —NR$_a$R$_b$, —N(R$_b$)C(=O)R$_a$, —N(R$_b$)C(=O)OR$_a$, —N(R$_b$)SO₂R$_a$, —N(R$_b$)SO₂NR$_a$R$_b$, —N(R$_b$)C(=NH)NR$_a$R$_b$, —N(R$_b$)C(=O)NR$_a$R$_b$, C(=O)NR$_a$R$_b$ and —C(=O)OR$_a$;

R₁₁ is hydrogen, alkyl, haloalkyl, hydroxyalkyl or alkoxyalkyl;

R₁₂ is hydrogen, alkyl, haloalkyl, hydroxyalkyl or alkoxyalkyl;

R₁₃ is alkyl or haloalkyl;

R₁₄ is alkyl, cycloalkyl, cycloalkylalkyl, aryl, heteroaryl or heterocycle; wherein each R₁₄ is substituted with 0, 1, 2 or 3 substituents selected from the group consisting of halo, cyano, nitro, formyl, alkyl, alkenyl, hydroxy, alkoxy, haloalkyl, —NH₂, —N(H)alkyl, —N(alkyl)₂, —C(=O)OH, —C(=O)Oalkyl, —C(=O)NH₂, —C(=O)N(H)(alkyl), and —C(=O)N(alkyl)₂;

Z is —$CH_2$—, —NH—, —O— or —S—;

Z' is —$CH_2$—, —NH—, —O— or —S—;

$R_a$ and $R_b$ at each occurrence are independently selected from the group consisting of hydrogen, alkyl, haloalkyl, alkenyl, alkynyl, cycloalkyl, aryl, heteroaryl, heterocycle, arylalkyl and heteroarylalkyl; wherein each $R_a$ and $R_b$, at each occurrence, is independently substituted with 0, 1, 2 or 3 substituents independently selected from the group consisting of alkyl, alkenyl, alkynyl, cyano, formyl, nitro, halo, oxo, hydroxy, alkoxy, —$NH_2$, —N(H)(alkyl), —N(alkyl)$_2$, —SH, —S(alkyl), —$SO_2$(alkyl), —N(H)C(=O)alkyl, —N(alkyl)C(=O)alkyl, —N(H)C(=O)$NH_2$, —N(H)C(=O)N(H)(alkyl), —N(H)C(=O)N(alkyl)$_2$, —C(=O)OH, —C(=O)Oalkyl, —C(=O)$NH_2$, —C(=O)N(H)(alkyl), —C(=O)N(alkyl)$_2$, —C(=O)alkyl, cyanoalkyl, formylalkyl, nitroalkyl, haloalkyl, hydroxyalkyl, alkoxyalkyl, -alkyl$NH_2$, -alkylN(H)(alkyl), -alkylN(alkyl)$_2$, -alkylN(H)C(=O)$NH_2$, -alkylN(H)C(=O)N(H)(alkyl), -alkylN(H)C(=O)N(alkyl)$_2$, -alkylC(=O)OH, -alkylC(=O)Oalkyl, -alkylC(=O)$NH_2$, -alkylC(=O)N(H)(alkyl), -alkylC(=O)N(alkyl)$_2$ and -alkylC(=O)alkyl; and n is 1 or 2.

For example, the present invention provides a compound of formula (II) wherein X is O.

For example, the present invention provides a compound of formula (II) wherein X is O and $R_1$ is alkyl.

For example, the present invention provides a compound of formula (II) wherein X is O, $R_1$ is alkyl and $R_4$ is —C(O)C(H)($R_8$)NHC(O)$R_{9a}$.

For example, the present invention provides a compound of formula (II) wherein X is O, $R_1$ is alkyl, $R_4$ is —C(O)C(H)($R_8$)NHC(O)$R_9$ and $R_9$ is —$OR_{9a}$.

For example, the present invention provides a compound of formula (II) wherein X is O, $R_1$ is alkyl, $R_4$ is —C(O)C(H)($R_8$)NHC(O)$R_9$, $R_8$ is alkyl and $R_9$ is —$OR_{9a}$.

For example, the present invention provides a compound of formula (II) wherein X is O, $R_1$ is alkyl, $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is alkyl and $R_9$ is —$OR_{9a}$.

For example, the present invention provides a compound of formula (II) wherein X is O, $R_1$ is alkyl, $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is alkyl, $R_9$ is —$OR_{9a}$ and $R_2$ is arylalkyl.

For example, the present invention provides a compound of formula (II) wherein X is O, $R_1$ is alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is alkyl, $R_9$ is —$OR_{9a}$, $R_{9a}$ is alkyl and $R_2$ is arylalkyl.

For example, the present invention provides a compound of formula (II) wherein X is O, $R_1$ is alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is alkyl, $R_9$ is —$OR_{9a}$, $R_{9a}$ is alkyl, $R_2$ is arylalkyl and $R_5$ is heteroaryl.

For example, the present invention provides a compound of formula (II) wherein X is O, $R_1$ is C3 alkyl, C4 alkyl or C5 alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is alkyl, $R_2$ is arylalkyl, and $R_5$ is heteroaryl.

For example, the present invention provides a compound of formula (II) wherein X is O, $R_1$ is C3 alkyl, C4 alkyl or C5 alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is arylalkyl, and $R_5$ is heteroaryl.

For example, the present invention provides a compound of formula (II) wherein X is O, $R_1$ is C3 alkyl, C4 alkyl or C5 alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, and $R_5$ is heteroaryl.

For example, the present invention provides a compound of formula (II) wherein X is O, $R_1$ is C3 alkyl, C4 alkyl or C5 alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, and $R_5$ is thienyl, furyl, oxazolyl, isoxazolyl, thiazolyl, pyridyl, pyridazinyl, indazolyl, imidazopyridinyl, indolyl, benzimidazolyl, isoquinolinyl or quinolinyl.

For example, the present invention provides a compound of formula (II) wherein X is O, $R_1$ is C3 alkyl, C4 alkyl or C5 alkyl; $R_3$ is arylalkyl, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, and $R_5$ is thienyl, furyl, oxazolyl, isoxazolyl, thiazolyl, pyridyl, pyridazinyl, indazolyl, imidazopyridinyl, indolyl, benzimidazolyl, isoquinolinyl or quinolinyl.

For example, the present invention provides a compound of formula (II) wherein X is O, $R_1$ is C3 alkyl, C4 alkyl or C5 alkyl; $R_3$ is arylalkyl substituted with $R_{3a}$, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, and $R_5$ is thienyl, furyl, oxazolyl, isoxazolyl, thiazolyl, pyridyl, pyridazinyl, indazolyl, imidazopyridinyl, indolyl, benzimidazolyl, isoquinolinyl or quinolinyl.

For example, the present invention provides a compound of formula (II) wherein X is O, $R_1$ is C3 alkyl, C4 alkyl or C5 alkyl; $R_3$ is arylalkyl substituted with $R_{3a}$, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, $R_5$ is thienyl, furyl, oxazolyl, isoxazolyl, thiazolyl, pyridyl, pyridazinyl, indazolyl, imidazopyridinyl, indolyl, benzimidazolyl, isoquinolinyl or quinolinyl, and $R_{3a}$ is heteroaryl.

For example, the present invention provides a compound of formula (II) wherein X is O, $R_1$ is C3 alkyl, C4 alkyl or C5 alkyl; $R_3$ is phenylmethyl substituted with $R_{3a}$, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, $R_5$ is thienyl, furyl, oxazolyl, isoxazolyl, thiazolyl, pyridyl, pyridazinyl, indazolyl, imidazopyridinyl, indolyl, benzimidazolyl, isoquinolinyl or quinolinyl, and $R_{3a}$ is pyridyl, thiazolyl or isoxaolyl.

For example, the present invention provides a compound of formula (II) wherein X is O, $R_1$ is C3 alkyl, C4 alkyl or C5 alkyl; $R_3$ is phenylmethyl substituted with $R_{3a}$, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, $R_5$ is pyridyl, and $R_{3a}$ is pyridyl.

For example, the present invention provides a compound of formula (II) wherein X is O, $R_1$ is C3 alkyl, C4 alkyl or C5 alkyl; $R_3$ is phenylmethyl substituted with $R_{3a}$, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, $R_5$ is pyridyl substituted with one alkyl substituent, and $R_{3a}$ is pyridyl.

For example, the present invention provides a compound of formula (II) wherein X is O, $R_1$ is C3 alkyl, C4 alkyl or C5 alkyl; $R_3$ is phenylmethyl substituted with $R_{3a}$, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, $R_5$ is pyridyl substituted with one methyl substituent, and $R_{3a}$ is pyridyl.

For example, the present invention provides a compound of formula (II) wherein X is O, $R_1$ is C3 alkyl, C4 alkyl or C5 alkyl; $R_3$ is phenylmethyl substituted with $R_{3a}$, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, $R_5$ is 2-pyridyl substituted with one methyl substituent, and $R_{3a}$ is 2-pyridyl.

Exemplary compounds of the present invention of formula (II) include, but not limited to, the following:

methyl (1S)-1-({2-{(2S,3S)-2-hydroxy-3-[((2S,3S)-3-methyl-2-{3-[2-(6-methyl-2-pyridinyl)ethyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate;

methyl (1S)-1-({2-{(2S,3S)-3-[((2S)-3,3-dimethyl-2-{3-[(1-methyl-1H-benzimidazol-2-yl)methyl]-2-oxo-1-imidazolidinyl}butanoyl)amino]-2-hydroxy-4-phenylbutyl}-2-[4-(2-pyridinyl)benzyl]hydrazino}carbonyl)-2,2-dimethylpropylcarbamate;

methyl (1S)-1-({2-[(2S,3S)-2-hydroxy-3-({(2S,3S)-3-methyl-2-[2-oxo-3-(3-pyridinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

methyl (1S)-1-({2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate;

methyl (1S,2S)-1-({2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}carbonyl)-2-methylbutylcarbamate;

tert-butyl 2-[(2S,3S)-2-hydroxy-3-({(2S)-3-methyl-2-[2-oxo-3-(4-quinolinylmethyl)-1-imidazolidinyl]pentanoyl}amino)-4-phenylbutyl]-2-[4-(2-pyridinyl)benzyl]hydrazinecarboxylate;

methyl (1S,2S)-1-({2-{(2S,3S)-3-[((2S)-3,3-dimethyl-2-{3-[(1-methyl-1H-benzimidazol-2-yl)methyl]-2-oxo-1-imidazolidinyl}butanoyl)amino]-2-hydroxy-4-phenylbutyl}-2-[4-(2-pyridinyl)benzyl]hydrazino}carbonyl)-2-methylbutylcarbamate;

methyl (1S,2S)-1-({2-((2S,3S)-2-hydroxy-3-{[(2S)-2-(3-{[2-(methoxymethyl)-1,3-thiazol-4-yl]methyl}-2-oxo-1-imidazolidinyl)-3,3-dimethylbutanoyl]amino}-4-phenylbutyl)-2-[4-(2-pyridinyl)benzyl]hydrazino}carbonyl)-2-methylbutylcarbamate;

methyl (1S)-1-({2-((2S,3S)-2-hydroxy-3-{[(2S)-2-(3-{[2-(methoxymethyl)-1,3-thiazol-4-yl]methyl}-2-oxo-1-imidazolidinyl)-3,3-dimethylbutanoyl]amino}-4-phenylbutyl)-2-[4-(2-pyridinyl)benzyl]hydrazino}carbonyl)-2,2-dimethylpropylcarbamate;

methyl (1S,2S)-1-({2-(4-bromobenzyl)-2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]hydrazino}carbonyl)-2-methylbutylcarbamate;

methyl (1S)-1-({2-benzyl-2-[(2S,3S)-2-hydroxy-3-({(2S,3S)-3-methyl-2-[2-oxo-3-(3-pyridinylmethyl)-1-imidazolidinyl]pentanoyl}amino)-4-phenylbutyl]hydrazino}carbonyl)-2,2-dimethylpropylcarbamate;

methyl (1S)-1-[(2-benzyl-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S,2S)-1-({2-benzyl-2-[(2S,3S)-2-hydroxy-3-({(2S,3S)-3-methyl-2-[2-oxo-3-(3-pyridinylmethyl)-1-imidazolidinyl]pentanoyl}amino)-4-phenylbutyl]hydrazino}carbonyl)-2-methylbutylcarbamate;

methyl (1S)-1-({2-((2S,3S)-3-{[(2S)-3,3-dimethyl-2-(3-{[2-(5-methyl-3-isoxazolyl)-1,3-thiazol-4-yl]methyl}-2-oxo-1-imidazolidinyl)butanoyl]amino}-2-hydroxy-4-phenylbutyl)-2-[4-(2-pyridinyl)benzyl]hydrazino}carbonyl)-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(4-methoxybenzyl)hydrazino]carbonyl}-2,2-dimethylpropylcarbamate;

methyl (1S)-1-({2-((2S,3S)-3-{[(2S)-3,3-dimethyl-2-(2-oxo-3-{[2-(3-pyridinyl)-1,3-thiazol-4-yl]methyl}-1-imidazolidinyl)butanoyl]amino}-2-hydroxy-4-phenylbutyl)-2-[4-(2-pyridinyl)benzyl]hydrazino}carbonyl)-2,2-dimethylpropylcarbamate;

methyl (1S)-1-({2-((2S,3S)-2-hydroxy-3-{[(2S)-2-(3-{[6-(hydroxymethyl)-2-pyridinyl]methyl}-2-oxo-1-imidazolidinyl)-3,3-dimethylbutanoyl]amino}-4-phenylbutyl)-2-[4-(2-pyridinyl)benzyl]hydrazino}carbonyl)-2,2-dimethylpropylcarbamate;

methyl (1S)-1-({2-[(2S,3S)-2-hydroxy-3-({(2S,3S)-3-methyl-2-[2-oxo-3-((2-methyl-1,3-thiazol-4-yl) 1,3-thiazol-4-ylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

methyl (1S)-1-({2-{(2S,3S)-3-[((2S)-3,3-dimethyl-2-{3-[(6-methyl-3-pyridinyl)methyl]-2-oxo-1-imidazolidinyl}butanoyl)amino]-2-hydroxy-4-phenylbutyl}-2-[4-(2-pyridinyl)benzyl]hydrazino}carbonyl)-2,2-dimethylpropylcarbamate;

methyl (1S)-1-({2-((2S,3S)-2-hydroxy-3-{[(2S)-2-(3-{[6-(1-hydroxy-1-methylethyl)-2-pyridinyl]methyl}-2-oxo-1-imidazolidinyl)-3,3-dimethylbutanoyl]amino}-4-phenylbutyl)-2-[4-(2-pyridinyl)benzyl]hydrazino}carbonyl)-2,2-dimethylpropylcarbamate;

methyl (1S)-1-({2-((2S,3S)-3-{[(2S,3S)-2-(3-{[2-(2-ethyl-4-pyridinyl)-1,3-thiazol-4-yl]methyl}-2-oxo-1-imidazolidinyl)-3-methylpentanoyl]amino}-2-hydroxy-4-phenylbutyl)-2-[4-(2-pyridinyl)benzyl]hydrazino}carbonyl)-2,2-dimethylpropylcarbamate;

methyl (1S)-1-({2-[(2S,3S)-2-hydroxy-3-({(2S,3S)-3-methyl-2-[2-oxo-3-(2-pyridinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

methyl (1S)-1-({2-{(2S,3S)-2-hydroxy-3-[((2S,3S)-3-methyl-2-{3-[(4-methyl-3-pyridinyl)methyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate;

methyl (1S)-1-({2-{(2S,3S)-3-[((2S)-3,3-dimethyl-2-{3-[(4-methyl-3-pyridinyl)methyl]-2-oxo-1-imidazolidinyl}butanoyl)amino]-2-hydroxy-4-phenylbutyl}-2-[4-(2-pyridinyl)benzyl]hydrazino}carbonyl)-2,2-dimethylpropylcarbamate;

methyl (1S)-1-({2-[(2S,3S)-3-({(2S)-3,3-dimethyl-2-[2-oxo-3-(4-quinolinylmethyl)-1-imidazolidinyl]butanoyl}amino)-2-hydroxy-4-phenylbutyl]-2-[4-(2-pyridinyl)benzyl]hydrazino}carbonyl)-2,2-dimethylpropylcarbamate;

methyl (1S)-1-({2-((2S,3S)-2-hydroxy-3-{[(2S,3S)-3-methyl-2-(2-oxo-3-{[2-(3-pyridinyl)-1,3-thiazol-4-yl]methyl}-1-imidazolidinyl)pentanoyl]amino}-4-phenylbutyl)-2-[4-(2-pyridinyl)benzyl]hydrazino}carbonyl)-2,2-dimethylpropylcarbamate;

methyl (1S)-1-{[2-((2S,3S)-2-hydroxy-3-{[(2S)-2-(3-{[2-(methoxymethyl)-1,3-thiazol-4-yl]methyl}-2-oxo-1-imidazolidinyl)-3,3-dimethylbutanoyl]amino}-4-phenylbutyl)-2-(4-methoxybenzyl)hydrazino]carbonyl}-2,2-dimethylpropylcarbamate;

methyl (1S)-1-({2-[(2S,3S)-2-hydroxy-3-({(2S,3S)-3-methyl-2-[2-oxo-3-(4-pyridazinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

methyl (1S)-1-({2-((2S,3S)-2-hydroxy-3-{[(2S,3S)-3-methyl-2-(2-oxo-3-{[2-(trifluoromethyl)-1,3-thiazol-4-yl]methyl}-1-imidazolidinyl)pentanoyl]amino}-4-phenylbutyl)-2-[4-(2-pyridinyl)benzyl]hydrazino}carbonyl)-2,2-dimethylpropylcarbamate;

methyl (1S)-1-({2-{(2S,3S)-2-hydroxy-3-[((2S)-2-{3-[(2-isopropyl-1,3-thiazol-4-yl)methyl]-2-oxo-1-imidazolidinyl}-3,3-dimethylbutanoyl)amino]-4-phenylbutyl}-2-[4-(2-pyridinyl)benzyl]hydrazino}carbonyl)-2,2-dimethylpropylcarbamate;

methyl (1S)-1-[(2-{(2S,3S)-2-hydroxy-3-[((2S)-3-methyl-2-{3-[(6-methyl-2-pyridinyl)methyl]-2-oxo-1-imidazolidinyl}pentanoyl)amino]-4-phenylbutyl}-2-{[2-(5-methyl-3-isoxazolyl)-1,3-thiazol-4-yl]methyl}hydrazino)carbonyl]-2,2-dimethylpropylcarbamate;

methyl (1S,2S)-1-({2-{(2S,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}-2-[4-(2-pyridinyl)benzyl]hydrazino}carbonyl)-2-methylbutylcarbamate;

methyl (1S,2S)-1-({2-{(2S,3S)-3-[((2S)-3,3-dimethyl-2-{3-[(2-methyl-1,3-thiazol-4-yl)methyl]-2-oxo-1-imidazolidinyl}butanoyl)amino]-2-hydroxy-4-phenylbutyl}-2-[4-(2-pyridinyl)benzyl]hydrazino}carbonyl)-2-methylbutylcarbamate;

methyl (1S)-1-[(2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-{[2-(2-pyridinyl)-1,3-thiazol-4-yl]methyl}hydrazino)carbonyl]-2,2-dimethylpropylcarbamate;

methyl (1S)-1-({2-{(2S,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}-2-[4-(2-pyridinyl)benzyl]hydrazino}carbonyl)-2-methylpropylcarbamate;

methyl (1S)-1-({2-{(2S,3S)-3-[((2S)-3,3-dimethyl-2-{3-[(2-methyl-1,3-thiazol-4-yl)methyl]-2-oxo-1-imidazolidinyl}butanoyl)amino]-2-hydroxy-4-phenylbutyl}-2-[4-(2-pyridinyl)benzyl]hydrazino}carbonyl)-2-methylpropylcarbamate;

methyl (1S,2S)-1-({2-{(2S,3S)-2-hydroxy-3-[((2S,3S)-3-methyl-2-{3-[(2-methyl-1,3-thiazol-4-yl)methyl]-2-oxo-1-imidazolidinyl}pentanoyl)amino]-4-phenylbutyl}-2-[4-(2-pyridinyl)benzyl]hydrazino}carbonyl)-2-methylbutylcarbamate;

methyl (1S)-1-({2-{(2S,3S)-2-hydroxy-3-[((2S,3S)-3-methyl-2-{3-[(2-methyl-1,3-thiazol-4-yl)methyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate;

methyl (1S)-1-({2-{(2S,3S)-3-[((2S)-3,3-dimethyl-2-{3-[(2-methyl-1,3-thiazol-4-yl)methyl]-2-oxo-1-imidazolidinyl}butanoyl)amino]-2-hydroxy-4-phenylbutyl}-2-[4-(2-pyridinyl)benzyl]hydrazino}carbonyl)-2,2-dimethylpropylcarbamate;

methyl (1S)-1-{[2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)-2-(4-methoxybenzyl)hydrazino]carbonyl}-2,2-dimethylpropylcarbamate;

methyl (1S)-1-{[2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]-2-(4-methoxybenzyl)hydrazino]carbonyl}-2,2-dimethylpropylcarbamate;

(2S,3S)—N-((1S,2S)-1-benzyl-2-hydroxy-3-{2-[3-methyl-2-(2-oxo-1-pyrrolidinyl)butanoyl]-1-[4-(2-pyridinyl)benzyl]hydrazino}propyl)-3-methyl-2-{3-[(6-methyl-2-pyridinyl)methyl]-2-oxo-1-imidazolidinyl}pentanamide;

methyl (1S)-1-({2-[(2S,3S)-2-hydroxy-3-({(2S,3S)-3-methyl-2-[2-oxo-3-(3-pyridazinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

methyl (1S)-1-({2-{(2S,3S)-3-[((2S)-2-{3-[(6-acetyl-2-pyridinyl)methyl]-2-oxo-1-imidazolidinyl}-3,3-dimethylbutanoyl)amino]-2-hydroxy-4-phenylbutyl}-2-[4-(2-pyridinyl)benzyl]hydrazino}carbonyl)-2,2-dimethylpropylcarbamate;

methyl 6-[(3-{(1S,4S,5S,10S)-4-benzyl-1,10-ditert-butyl-5-hydroxy-2,9,12-trioxo-7-[4-(2-pyridinyl)benzyl]-13-oxa-3,7,8,11-tetraazatetradec-1-yl]-2-oxo-1-imidazolidinyl)methyl]-2-pyridinecarboxylate;

methyl (1S)-1-({2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate;

(2S,3S)—N-((1S,2S)-1-benzyl-2-hydroxy-3-{2-[(2S,3S)-3-methyl-2-(2-oxo-1-imidazolidinyl)pentanoyl]-1-[4-(2-pyridinyl)benzyl]hydrazino}propyl)-3-methyl-2-{3-[(6-methyl-2-pyridinyl)methyl]-2-oxo-1-imidazolidinyl}pentanamide;

methyl (1S)-1-{[2-((2S,3S)-2-hydroxy-3-{[(2S)-2-(3-{[6-(1-hydroxy-1-methylethyl)-2-pyridinyl]methyl}-2-oxo-1-imidazolidinyl)-3,3-dimethylbutanoyl]amino}-4-phenylbutyl)-2-(4-methoxybenzyl)hydrazino]carbonyl}-2,2-dimethylpropylcarbamate;

methyl (1S)-1-{[2-((2S,3S)-2-hydroxy-3-{[(2S)-2-(3-{[6-(1-hydroxy-1-methylethyl)-2-pyridinyl]methyl}-2-oxo-1-imidazolidinyl)-3-methylpentanoyl]amino}-4-phenylbutyl)-2-(4-methoxybenzyl)hydrazino]carbonyl}-2,2-dimethylpropylcarbamate;

methyl (1S)-1-{[2-((2S,3S)-2-hydroxy-3-{[(2S)-2-(3-{[6-(hydroxymethyl)-2-pyridinyl]methyl}-2-oxo-1-imidazolidinyl)-3,3-dimethylbutanoyl]amino}-4-phenylbutyl)-2-(4-methoxybenzyl)hydrazino]carbonyl}-2,2-dimethylpropylcarbamate;

methyl (1S)-1-{[2-((2S,3S)-2-hydroxy-3-{[(2S)-2-(3-{[6-(hydroxymethyl)-2-pyridinyl]methyl}-2-oxo-1-imidazolidinyl)-3-methylpentanoyl]amino}-4-phenylbutyl)-2-(4-methoxybenzyl)hydrazino]carbonyl}-2,2-dimethylpropylcarbamate;

methyl (1S)-1-{[2-[(2S,3S)-2-hydroxy-3-({(2S,3S)-3-methyl-2-[2-oxo-3-(8-quinolinylmethyl)-1-imidazolidinyl]pentanoyl}amino)-4-phenylbutyl]-2-(4-methoxybenzyl)hydrazino]carbonyl}-2,2-dimethylpropylcarbamate;

methyl (1S)-1-{[2-{(2S,3S)-2-hydroxy-3-[((2S,3S)-3-methyl-2-{3-[(2-methyl-4-quinolinyl)methyl]-2-oxo-1- imidazolidinyl}pentanoyl)amino]-4-phenylbutyl}-2-(4-methoxybenzyl)hydrazino]carbonyl}-2,2-dimethylpropylcarbamate;

methyl (1S)-1-{[2-{(2S,3S)-2-hydroxy-3-[((2S,3S)-3-methyl-2-{[(3-methyl-3H-imidazo[4,5-b]pyridin-2-yl)methyl]-2-oxo-1-imidazolidinyl}pentanoyl)amino]-4-phenylbutyl}-2-(4-methoxybenzyl)hydrazino]carbonyl}-2,2-dimethylpropylcarbamate;

methyl (1S)-1-{[2-[(2S,3S)-2-hydroxy-3-({(2S,3S)-3-methyl-2-[2-oxo-3-(3-pyridazinylmethyl)-1-imidazolidinyl]pentanoyl}amino)-4-phenylbutyl]-2-(4-methoxybenzyl)hydrazino]carbonyl}-2,2-dimethylpropylcarbamate;

methyl (1S)-1-({2-{(2S,3S)-2-hydroxy-3-[((2S,3S)-3-methyl-2-{3-[(5-methyl-2-thienyl)methyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate;

methyl (1S,2S)-1-[(2-benzyl-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2-methylbutylcarbamate;

methyl (1S)-1-({2-[(2S,3S)-3-({(2S,3S)-2-[3-({2-[(1S)-1-(acetylamino)ethyl]-1,3-thiazol-4-yl}methyl)-2-oxo-1-imidazolidinyl]-3-methylpentanoyl}amino)-2-hydroxy-4-phenylbutyl]-2-[4-(2-pyridinyl)benzyl]hydrazino}carbonyl)-2,2-dimethylpropylcarbamate;

(2S,3S)—N-((1S,2S)-1-benzyl-2-hydroxy-3-{2-{[(4S,5R)-5-methyl-2-oxo-1,3-oxazolidin-4-yl]carbonyl}-1-[4-(2-pyridinyl)benzyl]hydrazino}propyl)-3-methyl-2-{3-[(6-methyl-2-pyridinyl)methyl]-2-oxo-1-imidazolidinyl}pentanamide;

methyl (1S)-1-{[2-((2S,3S)-2-hydroxy-3-{[(2S)-2-(3-{[6-(1-hydroxy-1-methylethyl)-2-pyridinyl]methyl}-2-oxo-1-imidazolidinyl)-3,3-dimethylbutanoyl]amino}-4-phenylbutyl)-2-isopentylhydrazino]carbonyl}-2,2-dimethylpropylcarbamate;

methyl (1S)-1-{[2-((2S,3S)-2-hydroxy-3-{[(2S,3S)-2-(3-{[6-(1-hydroxy-1-methylethyl)-2-pyridinyl]methyl}-2-oxo-1-imidazolidinyl)-3-methylpentanoyl]amino}-4-phenylbutyl)-2-isopentylhydrazino]carbonyl}-2,2-dimethylpropylcarbamate;

methyl (1S)-1-{[2-((2S,3S)-2-hydroxy-3-{[(2S)-2-(3-{[6-(hydroxymethyl)-2-pyridinyl]methyl}-2-oxo-1-imidazolidinyl)-3,3-dimethylbutanoyl]amino}-4-phenylbutyl)-2-isopentylhydrazino]carbonyl}-2,2-dimethylpropylcarbamate;

methyl (1S)-1-{[2-((2S,3S)-2-hydroxy-3-{[(2S)-2-(3-{[6-(hydroxymethyl)-2-pyridinyl]methyl}-2-oxo-1-imidazolidinyl)-3-methylpentanoyl]amino}-4-phenylbutyl)-2-isopentylhydrazino]carbonyl}-2,2-dimethylpropylcarbamate;

(2S,3S)—N-((1S,2S)-1-benzyl-3-{2-[(2,2-dimethyl-5-oxotetrahydro-3-furanyl)carbonyl]-1-[4-(2-pyridinyl)benzyl]hydrazino}-2-hydroxypropyl)-3-methyl-2-{3-[(6-methyl-2-pyridinyl)methyl]-2-oxo-1-imidazolidinyl}pentanamide;

methyl (1S)-1-{[2-[(2S,3S)-2-hydroxy-3-({(2S,3S)-2-[3-(imidazo[1,5-a]pyridin-3-ylmethyl)-2-oxo-1-imidazolidinyl]-3-methylpentanoyl}amino)-4-phenylbutyl]-2-(4-methoxybenzyl)hydrazino]carbonyl}-2,2-dimethylpropylcarbamate;

(2S,3S)—N-((1S,2S)-1-benzyl-2-hydroxy-3-{2-{[(2S)-5-oxopyrrolidinyl]carbonyl}-1-[4-(2-pyridinyl)benzyl]hydrazino}propyl)-3-methyl-2-{3-[(6-methyl-2-pyridinyl)methyl]-2-oxo-1-imidazolidinyl}pentanamide;

(3S)-4,4-dimethyl-2-oxotetrahydro-3-furanyl 2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-[4-(2-pyridinyl)benzyl]hydrazinecarboxylate;

(3R)-4,4-dimethyl-2-oxotetrahydro-3-furanyl 2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-[4-(2-pyridinyl)benzyl]hydrazinecarboxylate;

methyl (1S)-1-({2-{(2S,3S)-3-[((2S)-3,3-dimethyl-2-{3-[(6-methyl-2-pyridinyl)methyl]-2-oxo-1-imidazolidinyl}butanoyl)amino]-2-hydroxy-4-phenylbutyl}-2-[4-(2-pyridinyl)benzyl]hydrazino}carbonyl)-2,2-dimethylpropylcarbamate;

methyl (1S)-1-{[2-(2,3-dihydro-1,4-benzodioxin-6-ylmethyl)-2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)hydrazino]carbonyl}-2,2-dimethylpropylcarbamate;

methyl (1S)-1-{[2-(3,3-dimethylbutyl)-2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)hydrazino]carbonyl}-2,2-dimethylpropylcarbamate;

(3R)-2-oxotetrahydro-3-furanyl 2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-[4-(2-pyridinyl)benzyl]hydrazinecarboxylate;

(3S)-2-oxotetrahydro-3-furanyl 2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-[4-(2-pyridinyl)benzyl]hydrazinecarboxylate;

methyl (1S)-1-[(2-[4-(diethylamino)benzyl]-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

(2S,3S)—N-((1S,2S)-1-benzyl-3-{2-[(2S)-3,3-dimethyl-2-(2-oxo-1-imidazolidinyl)butanoyl]-1-[4-(2-pyridinyl)benzyl]hydrazino}-2-hydroxypropyl)-3-methyl-2-{3-[(6-methyl-2-pyridinyl)methyl]-2-oxo-1-imidazolidinyl}pentanamide;

methyl (1S)-1-{[2-(2,3-dihydro-1,4-benzodioxin-6-ylmethyl)-2-((2S,3S)-2-hydroxy-3-{[(2S)-2-(3-{[6-(1-hydroxy-1-methylethyl)-2-pyridinyl]methyl}-2-oxo-1-imidazolidinyl)-3,3-dimethylbutanoyl]amino}-4-phenylbutyl)hydrazino]carbonyl}-2,2-dimethylpropylcarbamate;

methyl (1S)-1-{[2-(2,3-dihydro-1,4-benzodioxin-6-ylmethyl)-2-((2S,3S)-2-hydroxy-3-{[(2S,3S)-2-(3-{[6-(1-hydroxy-1-methylethyl)-2-pyridinyl]methyl}-2-oxo-1-imidazolidinyl)-3-methylpentanoyl]amino}-4-phenylbutyl)hydrazino]carbonyl}-2,2-dimethylpropylcarbamate;

methyl (1S)-1-{[2-(2,3-dihydro-1,4-benzodioxin-6-ylmethyl)-2-((2S,3S)-2-hydroxy-3-{[(2S)-2-(3-{[6-(hydroxymethyl)-2-pyridinyl]methyl}-2-oxo-1-imidazolidinyl)-3,3-dimethylbutanoyl]amino}-4-phenylbutyl)hydrazino]carbonyl}-2,2-dimethylpropylcarbamate;

methyl (1S)-1-{[2-(2,3-dihydro-1,4-benzodioxin-6-ylmethyl)-2-((2S,3S)-2-hydroxy-3-{[(2S)-2-(3-{[6-(hydroxymethyl)-2-pyridinyl]methyl}-2-oxo-1-imidazolidinyl)-3-methylpentanoyl]amino}-4-phenylbutyl)hydrazino]carbonyl}-2,2-dimethylpropylcarbamate;

(2S,3S)—N-((1S,2S)-1-benzyl-3-{2-[(4,4-dimethyl-2-oxotetrahydro-3-furanyl)carbonyl]-1-[4-(2-pyridinyl)benzyl]hydrazino}-2-hydroxypropyl)-3-methyl-2-{3-[(6-methyl-2-pyridinyl)methyl]-2-oxo-1-imidazolidinyl}pentanamide;

methyl (1S)-1-[(2-benzyl-2-{(2S,3S)-3-[((2S)-3,3-dimethyl-2-{3-[(4-methyl-3-pyridinyl)methyl]-2-oxo-1-imidazolidinyl}butanoyl)amino]-2-hydroxy-4-phenylbutyl}hydrazino)carbonyl]-2,2-dimethylpropylcarbamate;

methyl (1S)-1-{[2-(3,3-dimethylbutyl)-2-((2S,3S)-2-hydroxy-3-{[(2S)-2-(3-{[6-(1-hydroxy-1-methylethyl)-2-pyridinyl]methyl}-2-oxo-1-imidazolidinyl)-3,3-dimethylbutanoyl]amino}-4-phenylbutyl)hydrazino]carbonyl}-2,2-dimethylpropylcarbamate;

methyl (1S)-1-{[2-(3,3-dimethylbutyl)-2-((2S,3S)-2-hydroxy-3-{[(2S,3S)-2-(3-{[6-(1-hydroxy-1-methylethyl)-2-pyridinyl]methyl}-2-oxo-1-imidazolidinyl)-3-methylpentanoyl]amino}-4-phenylbutyl)hydrazino]carbonyl}-2,2-dimethylpropylcarbamate;

methyl (1S)-1-{[2-(3,3-dimethylbutyl)-2-((2S,3S)-2-hydroxy-3-{[(2S)-2-(3-{[6-(hydroxymethyl)-2-pyridinyl]methyl}-2-oxo-1-imidazolidinyl)-3,3-dimethylbutanoyl]amino}-4-phenylbutyl)hydrazino]carbonyl}-2,2-dimethylpropylcarbamate;

methyl (1S)-1-{[2-(3,3-dimethylbutyl)-2-((2S,3S)-2-hydroxy-3-{[(2S,3S)-2-(3-{[6-(hydroxymethyl)-2-pyridinyl]methyl}-2-oxo-1-imidazolidinyl)-3-methylpentanoyl]amino}-4-phenylbutyl)hydrazino]carbonyl}-2,2-dimethylpropylcarbamate;

methyl (1S)-1-{[2-(cyclopropylmethyl)-2-((2S,3S)-2-hydroxy-3-{[(2S)-2-(3-{[6-(1-hydroxy-1-methylethyl)-2-pyridinyl]methyl}-2-oxo-1-imidazolidinyl)-3,3-dimethylbutanoyl]amino}-4-phenylbutyl)hydrazino]carbonyl}-2,2-dimethylpropylcarbamate;

methyl (1S)-1-{[2-(cyclopropylmethyl)-2-((2S,3S)-2-hydroxy-3-{[(2S,3S)-2-(3-{[6-(1-hydroxy-1-methylethyl)-2-pyridinyl]methyl}-2-oxo-1-imidazolidinyl)-3-methylpentanoyl]amino}-4-phenylbutyl)hydrazino]carbonyl}-2,2-dimethylpropylcarbamate;

methyl (1S)-1-{[2-(cyclopropylmethyl)-2-((2S,3S)-2-hydroxy-3-{[(2S)-2-(3-{[6-(hydroxymethyl)-2-pyridinyl]methyl}-2-oxo-1-imidazolidinyl)-3,3-dimethylbutanoyl]amino}-4-phenylbutyl)hydrazino]carbonyl}-2,2-dimethylpropylcarbamate;

methyl (1S)-1-{[2-(cyclopropylmethyl)-2-((2S,3S)-2-hydroxy-3-{[(2S,3S)-2-(3-{[6-(hydroxymethyl)-2-pyridinyl]methyl}-2-oxo-1-imidazolidinyl)-3-methylpentanoyl]amino}-4-phenylbutyl)hydrazino]carbonyl}-2,2-dimethylpropylcarbamate;

methyl (1S,2S)-1-[(2-benzyl-2-{(2S,3S)-2-hydroxy-3-[((2S,3S)-3-methyl-2-{3-[(2-methyl-1,3-thiazol-4-yl)methyl]-2-oxo-1-imidazolidinyl}pentanoyl)amino]-4-phenylbutyl}hydrazino)carbonyl]-2-methylbutylcarbamate;

methyl (1S)-1-{[2-[(2S,3S)-2-hydroxy-3-({(2S,3S)-3-methyl-2-[2-oxo-3-(3-quinolinylmethyl)-1-imidazolidinyl]pentanoyl}amino)-4-phenylbutyl]-2-(4-methoxybenzyl)hydrazino]carbonyl}-2,2-dimethylpropylcarbamate;

methyl (1S)-1-{[2-[(2S,3S)-2-hydroxy-3-({(2S,3S)-3-methyl-2-[2-oxo-3-(2-quinolinylmethyl)-1-imidazolidinyl]pentanoyl}amino)-4-phenylbutyl]-2-(4-methoxybenzyl)hydrazino]carbonyl}-2,2-dimethylpropylcarbamate;

methyl (1S)-1-{[2-{(2S,3S)-2-hydroxy-3-[((2S)-4-(methylamino)-2-{3-[(2-methyl-1,3-thiazol-4-yl)methyl]-2-oxo-1-imidazolidinyl}-4-oxobutanoyl)amino]-4-phenylbutyl}-2-(4-methoxybenzyl)hydrazino]carbonyl}-2,2-dimethylpropylcarbamate;

methyl (1S)-1-{[2-{(2S,3S)-3-[((2S)-4-(ethylamino)-2-{3-[(2-methyl-1,3-thiazol-4-yl)methyl]-2-oxo-1-imidazolidinyl}-4-oxobutanoyl)amino]-2-hydroxy-4-phenylbutyl}-2-(4-methoxybenzyl)hydrazino]carbonyl}-2,2-dimethylpropylcarbamate;

methyl (1S)-1-[(2-benzyl-2-{(2S,3S)-3-[((2S)-3,3-dimethyl-2-{3-[(6-methyl-2-pyridinyl)methyl]-2-oxo-1-imidazolidinyl}butanoyl)amino]-2-hydroxy-4-phenylbutyl}hydrazino)carbonyl]-2,2-dimethylpropylcarbamate;

methyl (1S)-1-[(2-{(2S,3S)-3-[((2S)-3,3-dimethyl-2-{3-[(6-methyl-2-pyridinyl)methyl]-2-oxo-1-imidazolidinyl}butanoyl)amino]-2-hydroxy-4-phenylbutyl}-2-{[2-(3-pyridinyl)-1,3-thiazol-4-yl]methyl}hydrazino)carbonyl]-2,2-dimethylpropylcarbamate;

methyl (1S)-1-{[2-benzyl-2-((2S,3S)-2-hydroxy-3-{[(2S,3S)-3-methyl-2-(2-oxo-3-{[2-(3-pyridinyl)-1,3-thiazol-4-yl]methyl}-1-imidazolidinyl)pentanoyl]amino}-4-phenylbutyl)hydrazino]carbonyl}-2,2-dimethylpropylcarbamate;

methyl (1S)-1-({2-(3,3-dimethylbutyl)-2-[(2S,3S)-2-hydroxy-3-({(2S,3S)-2-[3-(imidazo[1,5-a]pyridin-3-ylmethyl)-2-oxo-1-imidazolidinyl]-3-methylpentanoyl}amino)-4-phenylbutyl]hydrazino}carbonyl)-2,2-dimethylpropylcarbamate;

methyl (1S)-1-({2-(3,3-dimethylbutyl)-2-[(2S,3S)-2-hydroxy-3-({(2S)-2-[3-(imidazo[1,5-a]pyridin-3-ylmethyl)-2-oxo-1-imidazolidinyl]-3,3-dimethylbutanoyl}amino)-4-phenylbutyl]hydrazino}carbonyl)-2,2-dimethylpropylcarbamate;

methyl (1S)-1-{[2-[(2S,3S)-2-hydroxy-3-({(2S)-2-[3-(imidazo[1,5-a]pyridin-3-ylmethyl)-2-oxo-1-imidazolidinyl]-3,3-dimethylbutanoyl}amino)-4-phenylbutyl]-2-(4-methoxybenzyl)hydrazino]carbonyl}-2,2-dimethylpropylcarbamate;

methyl (1S)-1-({2-(3,3-dimethylbutyl)-2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]hydrazino}carbonyl)-2,2-dimethylpropylcarbamate;

methyl (1S,2S)-1-{[2-{(2S,3S)-2-hydroxy-3-[((2S,3S)-3-methyl-2-{3-[(2-methyl-1,3-thiazol-4-yl)methyl]-2-oxo-1-imidazolidinyl}pentanoyl)amino]-4-phenylbutyl}-2-(4-methoxybenzyl)hydrazino]carbonyl}-2-methylbutylcarbamate;

methyl (1S,2S)-1-({2-benzyl-2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]hydrazino}carbonyl)-2-methylbutylcarbamate;

methyl (1S)-1-[(2-(3,3-dimethylbutyl)-2-{(2S,3S)-2-hydroxy-3-[((2S,3S)-2-{3-[(2-isopropyl-1,3-thiazol-4-yl)methyl]-2-oxo-1-imidazolidinyl}-3-methylpentanoyl)amino]-4-phenylbutyl}hydrazino)carbonyl]-2,2-dimethylpropylcarbamate;

methyl (1S)-1-[(2-(3,3-dimethylbutyl)-2-{(2S,3S)-3-[((2S)-3,3-dimethyl-2-{3-[(6-methyl-2-pyridinyl)methyl]-2-oxo-1-imidazolidinyl}butanoyl)amino]-2-hydroxy-4-phenylbutyl}hydrazino)carbonyl]-2,2-dimethylpropylcarbamate;

methyl (1S)-1-{[2-{(2S,3S)-2-hydroxy-3-[((2S,3S)-2-{3-[(2-isopropyl-1,3-thiazol-4-yl)methyl]-2-oxo-1-imidazolidinyl}-3-methylpentanoyl)amino]-4-phenylbutyl}-2-(4-methoxybenzyl)hydrazino]carbonyl}-2,2-dimethylpropylcarbamate;

methyl (1S)-1-({2-{(2S,3S)-2-hydroxy-3-[((2S,3S)-2-{3-[(2-isopropyl-1,3-thiazol-4-yl)methyl]-2-oxo-1-imidazolidinyl}-3-methylpentanoyl)amino]-4-phenylbutyl}-2-[4-(2-pyridinyl)benzyl]hydrazino}carbonyl)-2,2-dimethylpropylcarbamate;

methyl (1S)-1-({2-{(2S,3S)-2-hydroxy-3-[((2S,3S)-3-methyl-2-{3-[(6-methyl-3-pyridinyl)methyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate;

methyl (1S)-1-{[2-((2S,3S)-2-hydroxy-3-{[(2S,3S)-3-methyl-2-(2-oxo-3-{[2-(3-pyridinyl)-1,3-thiazol-4-yl]methyl}-1-imidazolidinyl)pentanoyl]amino}-4-phenylbutyl)-2-(4-methoxybenzyl)hydrazino]carbonyl}-2,2-dimethylpropylcarbamate;

methyl (1S)-1-{[2-((2S,3S)-2-hydroxy-3-{[(2S,3S)-3-methyl-2-(2-oxo-3-{[2-(3-pyridinyl)-1,3-thiazol-4-yl]methyl}-1-imidazolidinyl)pentanoyl]amino}-4-phenylbutyl)-2-isopentylhydrazino]carbonyl}-2,2-dimethylpropylcarbamate;

methyl (1S)-1-{[2-(3,3-dimethylbutyl)-2-((2S,3S)-2-hydroxy-3-{[(2S,3S)-3-methyl-2-(2-oxo-3-{[2-(3-pyridinyl)-1,3-thiazol-4-yl]methyl}-1-imidazolidinyl)pentanoyl]amino}-4-phenylbutyl)hydrazino]carbonyl}-2,2-dimethylpropylcarbamate;

methyl (1S)-1-{[2-{(2S,3S)-3-[((2S)-3,3-dimethyl-2-{3-[(3-methylimidazo[1,5-a]pyridin-1-yl)methyl]-2-oxo-1-imidazolidinyl}butanoyl)amino]-2-hydroxy-4-phenylbutyl}-2-(4-methoxybenzyl)hydrazino]carbonyl}-2,2-dimethylpropylcarbamate;

methyl (1S)-1-[(2-(3,3-dimethylbutyl)-2-{(2S,3S)-3-[((2S)-3,3-dimethyl-2-{3-[(3-methylimidazo[1,5-a]pyridin-1-yl)methyl]-2-oxo-1-imidazolidinyl}butanoyl)amino]-2-hydroxy-4-phenylbutyl}hydrazino)carbonyl]-2,2-dimethylpropylcarbamate;

methyl (1S)-1-{[2-[(2S,3S)-2-hydroxy-3-({(2S)-2-[3-(1H-indazol-3-ylmethyl)-2-oxo-1-imidazolidinyl]-3,3-dimethylbutanoyl}amino)-4-phenylbutyl]-2-(4-methoxybenzyl)hydrazino]carbonyl}-2,2-dimethylpropylcarbamate;

methyl (1S)-1-({2-(3,3-dimethylbutyl)-2-[(2S,3S)-2-hydroxy-3-({(2S)-2-[3-(1H-indazol-3-ylmethyl)-2-oxo-1-imidazolidinyl]-3,3-dimethylbutanoyl}amino)-4-phenylbutyl]hydrazino}carbonyl)-2,2-dimethylpropylcarbamate;

methyl (1S)-1-({2-{(2S,3S)-2-hydroxy-3-[((2S,3S)-2-{3-[(6-isopropyl-2-pyridinyl)methyl]-2-oxo-1-imidazolidinyl}-3-methylpentanoyl)amino]-4-phenylbutyl}-2-[4-(2-pyridinyl)benzyl]hydrazino}carbonyl)-2,2-dimethylpropylcarbamate;

methyl (1S)-1-{[2-{(2S,3S)-3-[((2S)-3,3-dimethyl-2-{3-[(1-methyl-1H-indazol-3-yl)methyl]-2-oxo-1-imidazolidinyl}butanoyl)amino]-2-hydroxy-4-phenylbutyl}-2-(4-methoxybenzyl)hydrazino]carbonyl}-2,2-dimethylpropylcarbamate;

methyl (1S)-1-[(2-(3,3-dimethylbutyl)-2-{(2S,3S)-3-[((2S)-3,3-dimethyl-2-{3-[(1-methyl-1H-indazol-3-yl)methyl]-2-oxo-1-imidazolidinyl}butanoyl)amino]-2-hydroxy-4-phenylbutyl}hydrazino)carbonyl]-2,2-dimethylpropylcarbamate;

methyl (1S)-1-[(2-(3,3-dimethylbutyl)-2-{(2S,3S)-3-[((2S)-3,3-dimethyl-2-{3-[(2-methyl-1H-benzimidazol-5-yl)methyl]-2-oxo-1-imidazolidinyl}butanoyl)amino]-2-hydroxy-4-phenylbutyl}hydrazino)carbonyl]-2,2-dimethylpropylcarbamate;

methyl (1S)-1-({2-{(2S,3S)-3-[((2S)-2-{3-[(6-tert-butyl-2-pyridinyl)methyl]-2-oxo-1-imidazolidinyl}-3,3-dimethylbutanoyl)amino]-2-hydroxy-4-phenylbutyl}-2-[4-(2-pyridinyl)benzyl]hydrazino}carbonyl)-2,2-dimethylpropylcarbamate;

methyl (1S)-1-({2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}carbonyl)-2,2-dimethylpropylcarbamate;

methyl (1S)-1-({2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}carbonyl)-2-methylpropylcarbamate;

methyl 4-hydroxy-2-({2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}carbonyl)-1-pyrrolidinecarboxylate;

methyl (1S,2R)-2-hydroxy-1-({2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}carbonyl)propylcarbamate;

methyl (1S)-1-cyclohexyl-2-{2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}-2-oxoethylcarbamate;

methyl (1S)-1-benzyl-2-{2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}-2-oxoethylcarbamate;

methyl (1S)-1-(cyclohexylmethyl)-2-{2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}-2-oxoethylcarbamate;

methyl (1S)-1-({2-{(2S,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}-2-[4-(2-pyridinyl)benzyl]hydrazino}carbonyl)-2,2-dimethylpropylcarbamate;

tert-butyl (1S)-1-({2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

methyl (1S)-1-({2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

(3S)-tetrahydro-3-furanyl 2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]-2-[4-(2-pyridinyl)benzyl]hydrazinecarboxylate;

(2S,3S)—N-((1S,2S)-1-benzyl-3-{2-[(2S)-3,3-dimethyl-2-(2-oxo-1-imidazolidinyl)butanoyl]-1-[4-(2-pyridinyl)benzyl]hydrazino}-2-hydroxypropyl)-3-methyl-2-[2-oxo-3-(4-quinolinylmethyl)-1-imidazolidinyl]pentanamide;

(2S,3S)—N-((1S,2S)-1-benzyl-3-{2-[(2,6-dimethylphenoxy)acetyl]-1-[4-(2-pyridinyl)benzyl]hydrazino}-2-hydroxypropyl)-3-methyl-2-[2-oxo-3-(4-quinolinylmethyl)-1-imidazolidinyl]pentanamide;

(2S,3S)—N-((1S,2S)-1-benzyl-2-hydroxy-3-{2-[(2-methylphenoxy)acetyl]-1-[4-(2-pyridinyl)benzyl]hydrazino}propyl)-3-methyl-2-[2-oxo-3-(4-quinolinylmethyl)-1-imidazolidinyl]pentanamide;

(2S,3S)—N-((1S,2S)-1-benzyl-2-hydroxy-3-{2-(3-hydroxy-2-methylbenzoyl)-1-[4-(2-pyridinyl)benzyl]hydrazino}propyl)-3-methyl-2-[2-oxo-3-(4-quinolinylmethyl)-1-imidazolidinyl]pentanamide;

(2S,3S)—N-((1S,2S)-1-benzyl-2-hydroxy-3-{2-[(2S,3S)-3-methyl-2-(2-oxo-1-imidazolidinyl)pentanoyl]-1-[4-(2-pyridinyl)benzyl]hydrazino}propyl)-3-methyl-2-[2-oxo-3-(4-quinolinylmethyl)-1-imidazolidinyl]pentanamide;

(2S,3S)—N-((1S,2S)-1-benzyl-3-{2-[(2S,3S)-2-(2,4-dioxo-1-imidazolidinyl)-3-methylpentanoyl]-1-[4-(2-pyridinyl)benzyl]hydrazino}-2-hydroxypropyl)-3-methyl-2-[2-oxo-3-(4-quinolinylmethyl)-1-imidazolidinyl]pentanamide;

benzyl 2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]-2-[4-(2-pyridinyl)benzyl]hydrazinecarboxylate;

ethyl (1S)-1-({2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

(2S,3S)—N-((1S,2S)-3-{2-[(2S)-2-(acetylamino)-3,3-dimethylbutanoyl]-1-[4-(2-pyridinyl)benzyl]hydrazino}-1-benzyl-2-hydroxypropyl)-3-methyl-2-[2-oxo-3-(4-quinolinylmethyl)-1-imidazolidinyl]pentanamide;

methyl (1S,2S)-1-({2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]-2-[4-(3-pyridinyl)benzyl]hydrazino}carbonyl)-2-methylbutylcarbamate;

methyl (1S,2S)-1-({2-[4-(1,3-benzodioxol-5-yl)benzyl]-2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]hydrazino}carbonyl)-2-methylbutylcarbamate;

methyl (1S,2S)-1-({2-[4-(3,5-dimethyl-4-isoxazolyl)benzyl]-2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]hydrazino}carbonyl)-2-methylbutylcarbamate;

methyl (1S,2S)-1-({2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]-2-[4-(4-pyridinyl)benzyl]hydrazino}carbonyl)-2-methylbutylcarbamate;

methyl (1S)-1-[(2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-{(2S,3S)-2-hydroxy-3-[((2S,3S)-3-methyl-2-{3-[2-(6-methyl-2-pyridinyl)ethyl]-2-oxo-1-imidazolidinyl}pentanoyl)amino]-4-phenylbutyl}-2-isopentylhydrazino)carbonyl]-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(4-methylbenzyl)hydrazino]carbonyl}-2,2-dimethylpropylcarbamate;

methyl (1S)-1-[(2-(cyclohexylmethyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-isobutylhydrazino)carbonyl]-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(2-phenylethyl)hydrazino]carbonyl}-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(2-thienylmethyl)hydrazino]carbonyl}-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(2-naphthylmethyl)hydrazino]carbonyl}-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(4-isopropylbenzyl)hydrazino]carbonyl}-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(4-isopropoxybenzyl)hydrazino]carbonyl}-2,2-dimethylpropylcarbamate;

methyl (1S)-1-[(2-(3,4-dimethylbenzyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(3-methoxybenzyl)hydrazino]carbonyl}-2,2-dimethylpropylcarbamate;

methyl (1S)-1-[(2-(2-ethylbutyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(4-ethylbenzyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(3-methylbenzyl)hydrazino]carbonyl}-2,2-dimethylpropylcarbamate;

methyl (1S)-1-({2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-[4-(trifluoromethyl)benzyl]hydrazino}carbonyl)-2,2-dimethylpropylcarbamate;

methyl (1S)-1-[(2-(4-hydroxybenzyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(4-fluorobenzyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-({2-{(2S,3S)-2-hydroxy-3-[((2S,3S)-3-methyl-2-{3-[(6-methyl-2-pyridinyl)methyl]-2-oxo-1- imidazolidinyl}pentanoyl)amino]-4-phenylbutyl}-2-[3-(4-methylphenoxy)benzyl]hydrazino}carbonyl)-2,2-dimethylpropylcarbamate;

methyl (1S)-1-[(2-[3-(4-chlorophenoxy)benzyl]-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(2-quinolinylmethyl)hydrazino]carbonyl}-2,2-dimethylpropylcarbamate;

methyl (1S)-1-[(2-[(5-ethyl-2-thienyl)methyl]-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(2-octynyl)hydrazino]carbonyl}-2,2-dimethylpropylcarbamate;

methyl 6-(1-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-{(2S)-2-[(methoxycarbonyl)amino]-3,3-dimethylbutanoyl}hydrazino)hexanoate;

methyl (1S)-1-[(2-[(5-ethyl-2-furyl)methyl]-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-({2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-[4-(1H-imidazol-1-yl)benzyl]hydrazino}carbonyl)-2,2-dimethylpropylcarbamate;

methyl (1S)-1-[(2-(3,3-dimethylbutyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-[4-(acetylamino)benzyl]-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 4-[(1-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-{(2S)-2-[(methoxycarbonyl)amino]-3,3-dimethylbutanoyl}hydrazino)methyl]benzoate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(3-phenoxybenzyl)hydrazino]carbonyl}-2,2-dimethylpropylcarbamate;

methyl (1S)-1-({2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-[3-(4-methoxyphenoxy)benzyl]hydrazino}carbonyl)-2,2-dimethylpropylcarbamate;

methyl (1S)-1-[(2-(4-tert-butylbenzyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(2,3-dihydro-1,4-benzodioxin-6-ylmethyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-{4-[(trifluoromethyl)sulfanyl]benzyl}hydrazino)carbonyl]-2,2-dimethylpropylcarbamate;

methyl (1S)-1-[(2-(3,7-dimethyl-6-octenyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(cyclopropylmethyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-[(2-ethyl-1H-imidazol-5-yl)methyl]-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(2,3-dihydro-1-benzofuran-5-ylmethyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(4-chlorobenzyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(3,4-dimethoxybenzyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(3-fluoro-4-methoxybenzyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(1,3-benzodioxol-5-ylmethyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(4-methoxy-3-methylbenzyl)hydrazino]carbonyl}-2,2-dimethylpropylcarbamate;

methyl (1S)-1-[(2-(4-hydroxy-3-methoxybenzyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-({2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-[4-(methylsulfonyl)benzyl]hydrazino}carbonyl)-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(1H-imidazol-2-ylmethyl)hydrazino]carbonyl}-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(5-hydroxypentyl)hydrazino]carbonyl}-2,2-dimethylpropylcarbamate;

methyl (1S)-1-[2-[(4,5-dimethyl-2-furyl)methyl]-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(3-chlorobenzyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(3,5-dimethylbenzyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-neopentylhydrazino)carbonyl]-2,2-dimethylpropylcarbamate;

methyl (1S)-1-[(2-(1,3-dimethylbutyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(4-cyanobenzyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-cyclohexyl-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(3,4-dichlorobenzyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-((2S,3S)-2-hydroxy-3-{[(2S)-2-(3-{[2-(methoxymethyl)-1,3-thiazol-4-yl]methyl}-2-oxo-1-imidazolidinyl)-3,3-dimethylbutanoyl]amino}-4-phenylbutyl)-2-{[2-(4-pyridinyl)-1,3-thiazol-4-yl]methyl}hydrazino)carbonyl]-2,2-dimethylpropylcarbamate;

methyl (1S)-1-({2-((2S,3S)-2-hydroxy-3-{[(2S)-2-(3-{[2-(methoxymethyl)-1,3-thiazol-4-yl]methyl}-2-oxo-1-imidazolidinyl)-3,3-dimethylbutanoyl]amino}-4-phenylbutyl)-2-[3-(5-pyrimidinyl)benzyl]hydrazino}carbonyl)-2,2-dimethylpropylcarbamate;

methyl (1S)-1-[(2-((2S,3S)-2-hydroxy-3-{[(2S)-2-(3-{[2-(methoxymethyl)-1,3-thiazol-4-yl]methyl}-2-oxo-1-imidazolidinyl)-3,3-dimethylbutanoyl]amino}-4-phenylbutyl)-2-{[2-(5-methyl-3-isoxazolyl)-1,3-thiazol-4-yl]methyl}hydrazino)carbonyl]-2,2-dimethylpropylcarbamate;

methyl (1S)-1-[(2-((2S,3S)-2-hydroxy-3-{[(2S)-2-(3-{[2-(methoxymethyl)-1,3-thiazol-4-yl]methyl}-2-oxo-1-imidazolidinyl)-3,3-dimethylbutanoyl]amino}-4-phenylbutyl)-2-{[2-(2-pyridinyl)-1,3-thiazol-4-yl]methyl}hydrazino)carbonyl]-2,2-dimethylpropylcarbamate;

methyl (1S)-1-({2-((2S,3S)-2-hydroxy-3-{[(2S)-2-(3-{[2-(methoxymethyl)-1,3-thiazol-4-yl]methyl}-2-oxo-1-imidazolidinyl)-3,3-dimethylbutanoyl]amino}-4-phenylbutyl)-2-[(2-isopropyl-1,3-thiazol-4-yl)methyl]hydrazino}carbonyl)-2,2-dimethylpropylcarbamate;

methyl (1S)-1-{[2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)-2-isopentylhydrazino]carbonyl}-2,2-dimethylpropylcarbamate;

methyl (1S)-1-{[2-(3,4-dimethoxybenzyl)-2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)hydrazino]carbonyl}-2,2-dimethylpropylcarbamate;

methyl (1S)-1-{[2-(3,4-dimethylbenzyl)-2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)hydrazino]carbonyl}-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(4-methoxybenzyl)hydrazino]carbonyl}-2-methylbutylcarbamate;

methyl (1S,2S)-1-[(2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-isopentylhydrazino)carbonyl]-2-methylbutylcarbamate;

methyl (1S,2S)-1-({2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-[4-(2-pyridinyl)benzyl]hydrazino}carbonyl)-2-methylbutylcarbamate;

methyl (1S)-1-{[2-{(2S,3S)-3-[((2S)-3,3-dimethyl-2-{3-[2-(6-methyl-2-pyridinyl)ethyl]-2-oxo-1-imidazolidinyl}butanoyl)amino]-2-hydroxy-4-phenylbutyl}-2-(4-methoxybenzyl)hydrazino]carbonyl}-2,2-dimethylpropylcarbamate;

methyl (1S)-1-[(2-{(2S,3S)-3-[((2S)-3,3-dimethyl-2-{3-[2-(6-methyl-2-pyridinyl)ethyl]-2-oxo-1-imidazolidinyl}butanoyl)amino]-2-hydroxy-4-phenylbutyl}-2-isopentylhydrazino)carbonyl]-2,2-dimethylpropylcarbamate;

methyl (1S)-1-{[2-{(2S,3S)-3-[((2S)-3,3-dimethyl-2-{3-[(4-methyl-3-pyridinyl)methyl]-2-oxo-1-imidazolidinyl}butanoyl)amino]-2-hydroxy-4-phenylbutyl}-2-(4-methoxybenzyl)hydrazino]carbonyl}-2,2-dimethylpropylcarbamate;

methyl (1S)-1-[(2-{(2S,3S)-3-[((2S)-3,3-dimethyl-2-{3-[(4-methyl-3-pyridinyl)methyl]-2-oxo-1-imidazolidinyl}butanoyl)amino]-2-hydroxy-4-phenylbutyl}-2-isopentylhydrazino)carbonyl]-2,2-dimethylpropylcarbamate; and methyl (1S)-1-{[2-{(2S,3S)-2-hydroxy-3-[((2S,3S)-3-methyl-2-{3-[2-(6-methyl-2-pyridinyl)ethyl]-2-oxo-1-imidazolidinyl}pentanoyl)amino]-4-phenylbutyl}-2-(4-pyridinylmethyl)hydrazino]carbonyl}-2,2-dimethylpropylcarbamate; or a pharmaceutically acceptable salt form, stereoisomer, ester, salt of an ester, prodrug, salt of a prodrug or combination thereof.

In a third embodiment, the present invention provides a compound of formula (III),

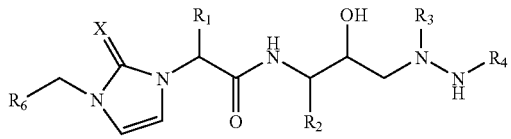

(III)

or a pharmaceutically acceptable salt form, stereoisomer, ester, salt of an ester, prodrug, salt of a prodrug or combination thereof, wherein:

X is O, S or NH;

$R_1$ is alkyl, alkenyl, alkynyl, cycloalkyl, cycloalkenyl, aryl, heteroaryl, arylalkyl, heteroarylalkyl, cycloalkylalkyl or cycloalkenylalkyl; wherein each $R_1$ is substituted with 0, 1 or 2 substituents independently selected from the group consisting of halo, haloalkyl, alkyl, alkenyl, cyano, nitro, —$OR_a$, —$OalkylC(=O)NR_aR_b$, —$SR_a$, —$SOR_a$, —$SO_2R_a$, —$SO_2NR_aR_b$, —$C(=O)R_a$, —$NR_aR_b$, —$N(R_b)C(=O)R_a$, —$N(R_b)C(=O)OR_a$, —$N(R_b)SO_2R_a$, —$N(R_b)SO_2NR_aR_b$, —$N(R_b)C(=NH)NR_aR_b$, —$N(R_b)C(=O)NR_aR_b$, —$C(=O)NR_aR_b$ and —$C(=O)OR_a$;

$R_2$ is alkyl, alkenyl, alkynyl, cycloalkyl, cycloalkenyl, cycloalkylalkyl, cycloalkenylalkyl, arylalkyl, heterocycle, heterocyclealkyl or heteroarylalkyl; wherein each $R_2$ is substituted with 0, 1, or 2 substituents independently selected from the group consisting of alkyl, alkenyl, alkynyl, cyano, halo, formyl, nitro, hydroxy, alkoxy, —$NH_2$, —N(H)alkyl, —N(alkyl)$_2$, —N(H)C(=O)Oalkyl, —N(alkyl)C(=O)Oalkyl, —C(=O)OH, —C(=O)Oalkyl, —C(=O)NH$_2$, —C(=O)N(H)(alkyl), —C(=O)N(alkyl)$_2$, —C(=O)alkyl, cyanoalkyl, nitroalkyl, formylalkyl, haloalkyl, hydroxyalkyl, alkoxyalkyl, -alkylNH$_2$, -alkylN(H)alkyl, -alkylN(alkyl)$_2$, -alkylN(H)C(=O)Oalkyl, -alkylN(alkyl)C(=O)Oalkyl, -alkylC(=O)OH, -alkylC(=O)Oalkyl, -alkylC(=O)NH$_2$, -alkylC(=O)N(H)(alkyl), -alkylC(=O)N(alkyl)$_2$ and -alkylC(=O)alkyl;

$R_3$ is hydrogen, alkyl, haloalkyl, alkenyl, haloalkenyl, alkynyl, haloalkynyl, cycloalkyl, cycloalkenyl, heterocycle, aryl, heteroaryl, cycloalkylalkyl, cycloalkenylalkyl, heterocyclealkyl, heteroarylalkyl, arylalkyl, hydroxyalkyl, alkoxyalkyl, -alkylSR$_a$, -alkylSOR$_a$, -alkylSO$_2$R$_a$, -alkylNR$_a$R$_b$, -alkylC(=O)OR$_a$, -alkylN(R$_b$)C(=O)OR$_a$, -alkylN(R$_b$)C(=O)R$_a$, -alkylN(R$_b$)SO$_2$R$_a$ or -alkylN(R$_b$)SO$_2$NR$_a$R$_b$; wherein the cycloalkyl, cycloalkenyl, heterocycle, aryl, heteroaryl, cycloalkyl moiety of cycloalkylalkyl, cycloalkenyl moiety of cycloalkenylalkyl, heterocycle moiety of heterocyclealkyl, heteroaryl moiety of heteroarylalkyl and aryl moiety of arylalkyl are independently substituted with 0, 1, 2 or 3 substituents independently selected from the group consisting of halo, nitro, cyano, formyl, alkyl, alkenyl, alkynyl, hydroxy, alkoxy, —SH, —S(alkyl), —S(haloalkyl), —SO$_2$(alkyl), —SO$_2$(haloalkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$, -alkylC(=O)alkyl and $R_{3a}$;

$R_{3a}$ is cycloalkyl, cycloalkenyl, aryl, heteroaryl, heterocycle, aryloxy, heteroaryloxy or heterocycleoxy, wherein each $R_{3a}$ is independently substituted with 0, 1, 2 or 3 substituents independently selected from the group consisting of halo, nitro, cyano, formyl, alkyl, alkenyl, alkynyl, hydroxyl, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$ and -alkylC(=O)alkyl;

$R_4$ is a) —C(O)CH(R$_8$)NHC(O)R$_9$, b) —C(O)R$_9$, c) —C(O)CH$_2$—O-aryl, substituted with 0, 1, 2 or 3 substituents selected from the group consisting of alkyl, alkenyl, halo, cynao, nitro, formyl, oxo, hydroxyl, alkoxy, hydroxyalky, alkoxyalkyl, haloalkyl, cyanoalkyl, aminoalkyl, alkylaminoalkyl, dialkylaminoalkyl, nitroalkyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl) and —C(=O)N(alkyl)$_2$, d) —C(O)CH$_2$—O-heteroaryl, substituted with 0, 1, 2 or 3 substituents selected from the group consisting of alkyl, alkenyl, halo, cynao, nitro, formyl, oxo, hydroxyl, alkoxy, hydroxyalky, alkoxyalkyl, haloalkyl, cyanoalkyl, aminoalkyl, alkylaminoalkyl, dialkylaminoalkyl, nitroalkyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), and —C(=O)N(alkyl)$_2$,

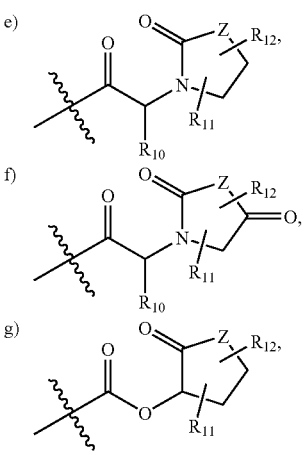

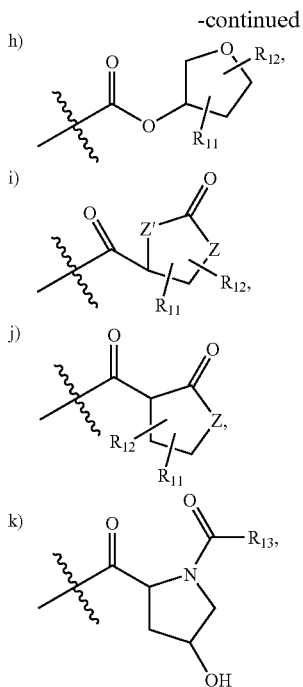

l) —SO$_2$R$_{14}$;

R$_6$ is alkyl, alkenyl, alkynyl, cycloalkyl, cycloalkenyl, aryl, heteroaryl or heterocycle; wherein each R$_6$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NR$_a$, -alkylSO$_{2O}$R$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and R$_{6a}$;

R$_{6a}$ is cycloalkyl, cycloalkenyl, heterocycle, aryl or heteroaryl; wherein each R$_{6a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)alkyl, -alkylN(alkyl)C(=O)alkyl, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

R$_8$ is alkyl, alkenyl, alkynyl, cycloalkyl, aryl, heteroaryl, cycloalkylalkyl or arylalkyl; wherein each R$_8$ is substituted with 0, 1 or 2 substituents independently selected from the group consisting of halo, cyano, formyl, nitro, alkyl, alkenyl, alkynyl, hydroxy, alkoxy, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), —C(=O)N(alkyl)$_2$, —C(=O)alkyl, hydroxyalkyl, alkoxyalkyl, -alkylNH$_2$, -alkylN(H)alkyl, -alkylN(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

R$_9$ is alkyl, cycloalkyl, cycloalkylalkyl, aryl, heterocycle, heteroaryl or OR$_{9a}$, wherein each R$_9$ is substituted with 0, 1, 2 or 3 substituents selected from the group consisting of hydroxy, alkoxy, halo, cyano, nitro, formyl, alkyl, alkenyl, alkynyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), and —C(=O)N(alkyl)$_2$;

R$_{9a}$ is alkyl, cycloalkyl, cycloalkylalkyl, aryl, arylalkyl, heterocycle, heteroaryl, heteroarylalkyl or heterocyclealkyl; wherein each R$_{9a}$ is substituted with 0, 1, 2 or 3 substituents independently selected from the group consisting of hydroxy, alkoxy, halo, cyano, nitro, formyl, alkyl, alkenyl, alkynyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl) and —C(=O)N(alkyl)$_2$;

R$_{10}$ is alkyl, alkenyl, alkynyl, cycloalkyl or cycloalkenyl, aryl, heteroaryl, arylalkyl, cycloalkylalkyl or heteroarylalkyl; wherein each R$_{10}$ is substituted with 0, 1, 2 or 3 substituents selected from the group consisting of halo, cyano, nitro, formyl, alkyl, alkenyl, hydroxy, alkoxy, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_b$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$ and —C(=O)OR$_a$;

R$_{11}$ is hydrogen, alkyl, haloalkyl, hydroxyalkyl or alkoxyalkyl;

R$_{12}$ is hydrogen, alkyl, haloalkyl, hydroxyalkyl or alkoxyalkyl;

R$_{13}$ is alkyl or haloalkyl;

R$_{14}$ is alkyl, cycloalkyl, cycloalkylalkyl, aryl, heteroaryl or heterocycle; wherein each R$_{14}$ is substituted with 0, 1, 2 or 3 substituents selected from the group consisting of halo, cyano, nitro, formyl, alkyl, alkenyl, hydroxy, alkoxy, haloalkyl, —NH$_2$, —N(H)alkyl, —N(alkyl)$_2$, —C(=O)OH, —C(=O)Oalkyl, —C(=O)NH$_2$, —C(=O)N(H)(alkyl), and —C(=O)N(alkyl)$_2$;

Z is —CH$_2$—, —NH—, —O— or —S—;

Z' is —CH$_2$—, —NH—, —O— or —S—; and

R$_a$ and R$_b$ at each occurrence are independently selected from the group consisting of hydrogen, alkyl, haloalkyl, alkenyl, alkynyl, cycloalkyl, aryl, heteroaryl, heterocycle, arylalkyl and heteroarylalkyl; wherein each R$_a$ and R$_b$, at each occurrence, is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, —C(=O)alkyl, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), -alkylC(=O)N(alkyl)$_2$ and -alkylC(=O)alkyl.

For example, the present invention provides a compound of formula (III) wherein X is O.

For example, the present invention provides a compound of formula (III) wherein X is O and R$_1$ is alkyl.

For example, the present invention provides a compound of formula (III) wherein X is O, R$_1$ is alkyl and R$_4$ is —C(O)C(H)(R$_8$)NHC(O)R$_9$.

For example, the present invention provides a compound of formula (III) wherein X is O, R$_1$ is alkyl, R$_4$ is —C(O)C(H)(R$_8$)NHC(O)R$_9$ and R$_9$ is —OR$_{9a}$.

For example, the present invention provides a compound of formula (III) wherein X is O, R$_1$ is alkyl, R$_4$ is —C(O)C(H)(R$_8$)NHC(O)R$_9$, R$_8$ is alkyl and R$_9$ is —OR$_{9a}$.

For example, the present invention provides a compound of formula (III) wherein X is O, R$_1$ is alkyl, R$_3$ is alkyl, alkenyl, alkynyl, cycloalkyl, cycloalkylalkyl, hydroxyalkyl, alkxoyalkyl, arylalkyl, heteroarylalkyl or heterocyclealkyl, R$_4$ is —C(O)C(H)(R$_8$)NHC(O)R$_9$, R$_8$ is alkyl and R$_9$ is —OR$_{9a}$.

For example, the present invention provides a compound of formula (III) wherein X is O, R$_1$ is alkyl, R$_3$ is alkyl, alkenyl, alkynyl, cycloalkyl, cycloalkylalkyl, hydroxyalkyl, alkxoyalkyl, arylalkyl, heteroarylalkyl or heterocyclealkyl, R$_4$ is —C(O)C(H)(R$_8$)NHC(O)R$_9$, R$_8$ is alkyl, R$_9$ is —OR$_{9a}$ and R$_2$ is arylalkyl.

For example, the present invention provides a compound of formula (III) wherein X is O, R$_1$ is alkyl; R$_3$ is alkyl, alkenyl, alkynyl, cycloalkyl, cycloalkylalkyl, hydroxyalkyl, alkoxyalkyl, arylalkyl, heteroarylalkyl or heterocyclealkyl, R$_4$ is —C(O)C(H)(R$_8$)NHC(O)R$_9$, R$_8$ is alkyl, R$_9$ is —OR$_a$, R$_{9a}$ is alkyl and R$_2$ is arylalkyl.

For example, the present invention provides a compound of formula (III) wherein X is O, R$_1$ is alkyl; R$_3$ is alkyl, alkenyl, alkynyl, cycloalkyl, cycloalkylalkyl, hydroxyalkyl, alkoxyalkyl, arylalkyl, heteroarylalkyl or heterocyclealkyl, R$_4$ is —C(O)C(H)(R$_8$)NHC(O)R$_9$, R$_8$ is alkyl, R$_9$ is —OR$_{9a}$, R$_{9a}$ is alkyl, R$_2$ is arylalkyl and R$_6$ is heteroaryl.

For example, the present invention provides a compound of formula (III) wherein X is O, R$_1$ is C3 alkyl, C4 alkyl or C5 alkyl; R$_3$ is alkyl, alkenyl, alkynyl, cycloalkyl, cycloalkylalkyl, hydroxyalkyl, alkoxyalkyl, arylalkyl, heteroarylalkyl or heterocyclealkyl, R$_4$ is —C(O)C(H)(R$_8$)NHC(O)R$_9$, R$_8$ is C3 alkyl, C4 alkyl or C5 alkyl, R$_9$ is —OR$_{9a}$, R$_{9a}$ is alkyl, R$_2$ is arylalkyl, and R$_6$ is heteroaryl.

For example, the present invention provides a compound of formula (III) wherein X is O, R$_1$ is C3 alkyl, C4 alkyl or C5 alkyl; R$_3$ is alkyl, alkenyl, alkynyl, cycloalkyl, cycloalkylalkyl, hydroxyalkyl, alkoxyalkyl, arylalkyl, heteroarylalkyl or heterocyclealkyl, R$_4$ is —C(O)C(H)(R$_8$)NHC(O)R$_9$, R$_8$ is C3 alkyl, C4 alkyl or C5 alkyl, R$_9$ is —OR$_{9a}$, R$_{9a}$ is methyl, R$_2$ is arylalkyl, and R$_6$ is heteroaryl.

For example, the present invention provides a compound of formula (III) X is O, wherein R$_1$ is C3 alkyl, C4 alkyl or C5 alkyl; R$_3$ is alkyl, alkenyl, alkynyl, cycloalkyl, cycloalkylalkyl, hydroxyalkyl, alkoxyalkyl, arylalkyl, heteroarylalkyl or heterocyclealkyl, R$_4$ is —C(O)C(H)(R$_8$)NHC(O)R$_9$, R$_8$ is C3 alkyl, C4 alkyl or C5 alkyl, R$_9$ is —OR$_{9a}$, R$_{9a}$ is methyl, R$_2$ is phenylmethyl, and R$_6$ is heteroaryl.

For example, the present invention provides a compound of formula (III) wherein X is O, R$_1$ is C3 alkyl, C4 alkyl or C5 alkyl; R$_3$ is alkyl, alkenyl, alkynyl, cycloalkyl, cycloalkylalkyl, hydroxyalkyl, alkoxyalkyl, arylalkyl, heteroarylalkyl or heterocyclealkyl, R$_4$ is —C(O)C(H)(R$_8$)NHC(O)R$_9$, R$_8$ is C3 alkyl, C4 alkyl or C5 alkyl, R$_9$ is —OR$_{9a}$, R$_{9a}$ is methyl, R$_2$ is phenylmethyl, and R$_6$ is thienyl, furyl, oxazolyl, isoxazolyl, thiazolyl, pyridyl, pyridazinyl, indazolyl, imidazopyridinyl, indolyl, benzimidazolyl, isoquinolinyl or quinolinyl.

For example, the present invention provides a compound of formula (III) wherein X is O, R$_1$ is C3 alkyl, C4 alkyl or C5 alkyl; R$_3$ is arylalkyl, R$_4$ is —C(O)C(H)(R$_8$)NHC(O)R$_9$, R$_9$ is C3 alkyl, C4 alkyl or C5 alkyl, R$_9$ is —OR$_{9a}$, R$_{9a}$ is methyl, R$_2$ is phenylmethyl, and R$_6$ is thienyl, furyl, oxazolyl, isoxazolyl, thiazolyl, pyridyl, pyridazinyl, indazolyl, imidazopyridinyl, indolyl, benzimidazolyl, isoquinolinyl or quinolinyl.

For example, the present invention provides a compound of formula (III) wherein X is O, R$_1$ is C3 alkyl, C4 alkyl or C5 alkyl; R$_3$ is arylalkyl substituted with R$_{3a}$, R$_4$ is —C(O)C(H)(R$_8$)NHC(O)R$_9$, R$_8$ is C3 alkyl, C4 alkyl or C5 alkyl, R$_9$ is —OR$_{9a}$, R$_{9a}$ is methyl, R$_2$ is phenylmethyl, and R$_5$ is thienyl, furyl, oxazolyl, isoxazolyl, thiazolyl, pyridyl, pyridazinyl, indazolyl, imidazopyridinyl, indolyl, benzimidazolyl, isoquinolinyl or quinolinyl.

For example, the present invention provides a compound of formula (III) wherein X is O, R$_1$ is C3 alkyl, C4 alkyl or C5 alkyl; R$_3$ is arylalkyl substituted with R$_{3a}$, R$_4$ is —C(O)C(H)(R$_8$)NHC(O)R$_9$, R$_8$ is C3 alkyl, C4 alkyl or C5 alkyl, R$_9$ is —OR$_{9a}$, R$_{9a}$ is methyl, R$_2$ is phenylmethyl, R$_6$ is thienyl, furyl, oxazolyl, isoxazolyl, thiazolyl, pyridyl, pyridazinyl, indazolyl, imidazopyridinyl, indolyl, benzimidazolyl, isoquinolinyl or quinolinyl, and R$_{3a}$ is heteroaryl.

For example, the present invention provides a compound of formula (III) wherein X is O, R$_1$ is C3 alkyl, C4 alkyl or C5 alkyl; R$_3$ is phenylmethyl substituted with R$_{3a}$, R$_4$ is —C(O)C(H)(R$_8$)NHC(O)R$_9$, R$_8$ is C3 alkyl, C4 alkyl or C5 alkyl, R$_9$ is —OR$_{9a}$, R$_{9a}$ is methyl, R$_2$ is phenylmethyl, R$_6$ is thienyl, furyl, oxazolyl, isoxazolyl, thiazolyl, pyridyl, pyridazinyl, indazolyl, imidazopyridinyl, indolyl, benzimidazolyl, isoquinolinyl or quinolinyl, and R$_{3a}$ is pyridyl, thiazolyl or isoxaolyl.

For example, the present invention provides a compound of formula (III) wherein X is O, R$_1$ is C3 alkyl, C4 alkyl or C5 alkyl; R$_3$ is phenylmethyl substituted with R$_{3a}$, R$_4$ is —C(O)C(H)(R$_8$)NHC(O)R$_9$, R$_8$ is C3 alkyl, C4 alkyl or C5 alkyl, R$_9$ is —OR$_{9a}$, R$_{9a}$ is methyl, R$_2$ is phenylmethyl, R$_6$ is pyridyl, and R$_{3a}$ is pyridyl.

For example, the present invention provides a compound of formula (III) wherein X is O, R$_1$ is C3 alkyl, C4 alkyl or C5 alkyl; R$_3$ is phenylmethyl substituted with R$_{3a}$, R$_4$ is —C(O)C(H)(R$_8$)NHC(O)R$_9$, R$_8$ is C3 alkyl, C4 alkyl or C5 alkyl, R$_9$ is —OR$_{9a}$, R$_{9a}$ is methyl, R$_2$ is phenylmethyl, R$_6$ is pyridyl substituted with one alkyl substituent, and R$_{3a}$ is pyridyl.

For example, the present invention provides a compound of formula (III) wherein X is O, R$_1$ is C3 alkyl, C4 alkyl or C5 alkyl; R$_3$ is phenylmethyl substituted with R$_{3a}$, R$_4$ is —C(O)C(H)(R$_8$)NHC(O)R$_9$, R$_8$ is C3 alkyl, C4 alkyl or C5 alkyl, R$_9$ is —OR$_{9a}$, R$_{9a}$ is methyl, R$_2$ is phenylmethyl, R$_6$ is pyridyl substituted with one methyl substituent, and R$_{3a}$ is pyridyl.

For example, the present invention provides a compound of formula (III) wherein X is O, R$_1$ is C3 alkyl, C4 alkyl or C5 alkyl; R$_3$ is phenylmethyl substituted with R$_{3a}$, R$_4$ is —C(O)C(H)(R$_8$)NHC(O)R$_9$, R$_8$ is C3 alkyl, C4 alkyl or C5 alkyl, R$_9$ is —OR$_{9a}$, R$_{9a}$ is methyl, R$_2$ is phenylmethyl, R$_6$ is 2-pyridyl substituted with one methyl substituent, and R$_{3a}$ is 2-pyridyl.

In a fourth embodiment, the present invention provides a compound of formula (IV),

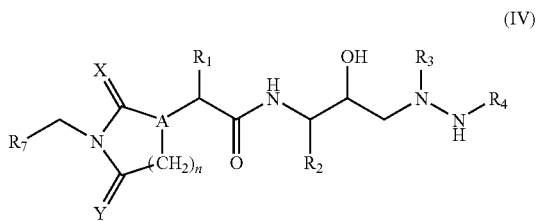

(IV)

or a pharmaceutically acceptable salt form, stereoisomer, ester, salt of an ester, prodrug, salt of a prodrug or combination thereof, wherein:

X is O, S or NH;

Y is O, S or NH;

$R_1$ is alkyl, alkenyl, alkynyl, cycloalkyl, cycloalkenyl, aryl, heteroaryl, arylalkyl, heteroarylalkyl, cycloalkylalkyl or cycloalkenylalkyl; wherein each $R_1$ is substituted with 0, 1 or 2 substituents independently selected from the group consisting of halo, haloalkyl, alkyl, alkenyl, cyano, nitro, —$OR_a$, —Oalkyl$C(=O)NR_aR_b$, —$SR_a$, —$SOR_a$, —$SO_2R_a$, —$SO_2NR_aR_b$, —$C(=O)R_a$, —$NR_aR_b$, —$N(R_b)C(=O)R_a$, —$N(R_b)C(=O)OR_a$, —$N(R_b)SO_2R_a$, —$N(R_b)SO_2NR_aR_b$, —$N(R_b)C(=NH)NR_aR_b$, —$N(R_b)C(=O)NR_aR_b$, —$C(=O)NR_aR_b$ and —$C(=O)OR_a$;

$R_2$ is alkyl, alkenyl, alkynyl, cycloalkyl, cycloalkenyl, cycloalkylalkyl, cycloalkenylalkyl, arylalkyl, heterocycle, heterocyclealkyl or heteroarylalkyl; wherein each $R_2$ is substituted with 0, 1, or 2 substituents independently selected from the group consisting of alkyl, alkenyl, alkynyl, cyano, halo, formyl, nitro, hydroxy, alkoxy, —$NH_2$, —N(H)alkyl, —N(alkyl)$_2$, —N(H)C(=O)Oalkyl, —N(alkyl)C(=O)Oalkyl, —C(=O)OH, —C(=O)Oalkyl, —C(=O)$NH_2$, —C(=O)N(H)(alkyl), —C(=O)N(alkyl)$_2$, —C(=O)alkyl, cyanoalkyl, nitroalkyl, formylalkyl, haloalkyl, hydroxyalkyl, alkoxyalkyl, -alkyl$NH_2$, -alkylN(H)alkyl, -alkylN(alkyl)$_2$, -alkylN(H)C(=O)Oalkyl, -alkylN(alkyl)C(=O)Oalkyl, -alkylC(=O)OH, -alkylC(=O)Oalkyl, -alkylC(=O)$NH_2$, -alkylC(=O)N(H)(alkyl), -alkylC(=O)N(alkyl)$_2$ and -alkylC(=O)alkyl;

$R_3$ is hydrogen, alkyl, haloalkyl, alkenyl, haloalkenyl, alkynyl, haloalkynyl, cycloalkyl, cycloalkenyl, heterocycle, aryl, heteroaryl, cycloalkylalkyl, cycloalkenylalkyl, heterocyclealkyl, heteroarylalkyl, arylalkyl, hydroxyalkyl, alkoxyalkyl, -alkyl$SR_a$, -alkyl$SOR_a$, -alkyl$SO_2R_a$, -alkyl$NR_aR_b$, -alkylC(=O)$OR_a$, -alkylN($R_b$)C(=O)$OR_a$, -alkylN($R_b$)C(=O)$R_a$, -alkylN($R_b$)$SO_2R_a$ or -alkylN($R_b$)$SO_2NR_aR_b$; wherein the cycloalkyl, cycloalkenyl, heterocycle, aryl, heteroaryl, cycloalkyl moiety of cycloalkylalkyl, cycloalkenyl moiety of cycloalkenylalkyl, heterocycle moiety of heterocyclealkyl, heteroaryl moiety of heteroarylalkyl and aryl moiety of arylalkyl are independently substituted with 0, 1, 2 or 3 substituents independently selected from the group consisting of halo, nitro, cyano, formyl, alkyl, alkenyl, alkynyl, hydroxy, alkoxy, —SH, —S(alkyl), —S(haloalkyl), —$SO_2$(alkyl), —$SO_2$(haloalkyl), —$NH_2$, —N(H)(alkyl), —N(alkyl)$_2$, —N(H)C(=O)alkyl, —N(alkyl)C(=O)alkyl, —C(=O)OH, —C(=O)O(alkyl), —C(=O)$NH_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkyl$SO_2$(alkyl), -alkyl$NH_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)$NH_2$, -alkylC(=O)N(H)(alkyl), -alkylC(=O)N(alkyl)$_2$, -alkylC(=O)alkyl and $R_{3a}$;

$R_{3a}$ is cycloalkyl, cycloalkenyl, aryl, heteroaryl, heterocycle, aryloxy, heteroaryloxy or heterocycleoxy, wherein each $R_{3a}$ is independently substituted with 0, 1, 2 or 3 substituents independently selected from the group consisting of halo, nitro, cyano, formyl, alkyl, alkenyl, alkynyl, hydroxyl, alkoxy, —SH, —S(alkyl), —$SO_2$(alkyl), —$NH_2$, —N(H)(alkyl), —N(alkyl)$_2$, —N(H)C(=O)alkyl, —N(alkyl)C(=O)alkyl, —C(=O)OH, —C(=O)O(alkyl), —C(=O)$NH_2$, —C(=O)N(H)(alkyl), —C(O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkyl$SO_2$(alkyl), -alkyl$NH_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)$NH_2$, -alkylC(=O)N(H)(alkyl), -alkylC(=O)N(alkyl)$_2$ and -alkylC(=O)alkyl;

$R_4$ is a) —C(O)CH($R_8$)NHC(O)$R_9$, b) —C(O)$R_9$, c) —C(O)$CH_2$—O-aryl, substituted with 0, 1, 2 or 3 substituents selected from the group consisting of alkyl, alkenyl, halo, cynao, nitro, formyl, oxo, hydroxyl, alkoxy, hydroxyalky, alkoxyalkyl, haloalkyl, cyanoalkyl, aminoalkyl, alkylaminoalkyl, dialkylaminoalkyl, nitroalkyl, —$NH_2$, —N(H)alkyl, —N(alkyl)$_2$, —C(=O)alkyl, —C(=O)OH, —C(=O)Oalkyl, —C(=O)$NH_2$, —C(=O)N(H)(alkyl) and —C(=O)N(alkyl)$_2$, d) —C(O)$CH_2$—O-heteroaryl, substituted with 0, 1, 2 or 3 substituents selected from the group consisting of alkyl, alkenyl, halo, cynao, nitro, formyl, oxo, hydroxyl, alkoxy, hydroxyalky, alkoxyalkyl, haloalkyl, cyanoalkyl, aminoalkyl, alkylaminoalkyl, dialkylaminoalkyl, nitroalkyl, —$NH_2$, —N(H)alkyl, —N(alkyl)$_2$, —C(=O)alkyl, —C(=O)OH, —C(=O)Oalkyl, —C(=O)$NH_2$, —C(=O)N(H)(alkyl), and —C(=O)N(alkyl)$_2$,

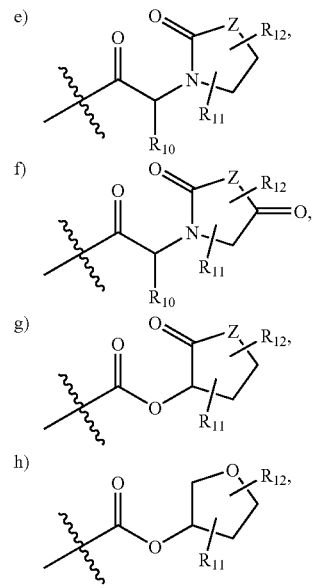

-continued

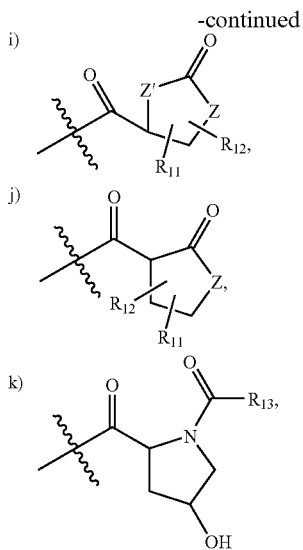

i)
j)
k) or l) —SO$_2$R$_{14}$;

R$_7$ is alkyl, alkenyl, alkynyl, cycloalkyl, cycloalkenyl, aryl, heteroaryl or heterocycle; wherein each R$_7$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and R$_{7a}$;

R$_{7a}$ is cycloalkyl, cycloalkenyl, heterocycle, aryl or heteroaryl; wherein each R$_{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)alkyl, -alkylN(alkyl)C(=O)alkyl, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

R$_8$ is alkyl, alkenyl, alkynyl, cycloalkyl, aryl, heteroaryl, cycloalkylalkyl or arylalkyl; wherein each R$_8$ is substituted with 0, 1 or 2 substituents independently selected from the group consisting of halo, cyano, formyl, nitro, alkyl, alkenyl, alkynyl, hydroxy, alkoxy, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), —C(=O)N(alkyl)$_2$, —C(=O)alkyl, hydroxyalkyl, alkoxyalkyl, -alkylNH$_2$, -alkylN(H)alkyl, -alkylN(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

R$_9$ is alkyl, cycloalkyl, cycloalkylalkyl, aryl, heterocycle, heteroaryl or OR$_{9a}$, wherein each R$_9$ is substituted with 0, 1, 2 or 3 substituents selected from the group consisting of hydroxy, alkoxy, halo, cyano, nitro, formyl, alkyl, alkenyl, alkynyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), and —C(=O)N(alkyl)$_2$;

R$_{9a}$ is alkyl, cycloalkyl, cycloalkylalkyl, aryl, arylalkyl, heterocycle, heteroaryl, heteroarylalkyl or heterocyclealkyl; wherein each R$_{9a}$ is substituted with 0, 1, 2 or 3 substituents independently selected from the group consisting of hydroxy, alkoxy, halo, cyano, nitro, formyl, alkyl, alkenyl, alkynyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl) and —C(=O)N(alkyl)$_2$;

R$_{10}$ is alkyl, alkenyl, alkynyl, cycloalkyl or cycloalkenyl, aryl, heteroaryl, arylalkyl, cycloalkylalkyl or heteroarylalkyl; wherein each R$_{10}$ is substituted with 0, 1, 2 or 3 substituents selected from the group consisting of halo, cyano, nitro, formyl, alkyl, alkenyl, hydroxy, alkoxy, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_b$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$ and —C(=O)OR$_a$;

R$_{11}$ is hydrogen, alkyl, haloalkyl, hydroxyalkyl or alkoxyalkyl;

R$_{12}$ is hydrogen, alkyl, haloalkyl, hydroxyalkyl or alkoxyalkyl;

R$_{13}$ is alkyl or haloalkyl;

R$_{14}$ is alkyl, cycloalkyl, cycloalkylalkyl, aryl, heteroaryl or heterocycle; wherein each R$_{14}$ is substituted with 0, 1, 2 or 3 substituents selected from the group consisting of halo, cyano, nitro, formyl, alkyl, alkenyl, hydroxy, alkoxy, haloalkyl, —NH$_2$, —N(H)alkyl, —N(alkyl)$_2$, —C(=O)OH, —C(=O)Oalkyl, —C(=O)NH$_2$, —C(=O)N(H)(alkyl), and —C(=O)N(alkyl)$_2$;

Z is —CH$_2$—, —NH—, —O— or —S—;

Z' is —CH$_2$—, —NH—, —O— or —S—;

R$_a$ and R$_b$ at each occurrence are independently selected from the group consisting of hydrogen, alkyl, haloalkyl, alkenyl, alkynyl, cycloalkyl, aryl, heteroaryl, heterocycle, arylalkyl and heteroarylalkyl; wherein each R$_a$ and R$_b$, at each occurrence, is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, —C(=O)alkyl, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), -alkylC(=O)N(alkyl)$_2$ and -alkylC(=O)alkyl; and n is 1 or 2.

For example, the present invention provides a compound of formula (IV) wherein X is O and Y is O.

For example, the present invention provides a compound of formula (IV) wherein X is O, Y is O and $R_1$ is alkyl.

For example, the present invention provides a compound of formula (IV) wherein X is O, Y is O, $R_1$ is alkyl and $R_4$ is —C(O)C(H)($R_8$)NHC(O)$R_9$.

For example, the present invention provides a compound of formula (IV) wherein X is O, Y is O, $R_1$ is alkyl, $R_4$ is —C(O)C(H)($R_8$)NHC(O)$R_9$ and $R_9$ is —$OR_{9a}$.

For example, the present invention provides a compound of formula (IV) wherein X is O, Y is O, $R_1$ is alkyl, $R_4$ is —C(O)C(H)($R_8$)NHC(O)$R_9$, $R_8$ is alkyl and $R_9$ is —$OR_{9a}$.

For example, the present invention provides a compound of formula (IV) wherein X is O, Y is O, $R_1$ is alkyl, $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is alkyl and $R_9$ is —$OR_{9a}$.

For example, the present invention provides a compound of formula (IV) wherein X is O, Y is O, $R_1$ is alkyl, $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is alkyl, $R_9$ is —$OR_{9a}$, and $R_2$ is arylalkyl.

For example, the present invention provides a compound of formula (IV) wherein X is O, Y is O, $R_1$ is alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is alkyl, $R_9$ is —$OR_{9a}$, $R_{9a}$ is alkyl and $R_2$ is arylalkyl.

For example, the present invention provides a compound of formula (IV) wherein X is O, Y is O, $R_1$ is alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is alkyl, $R_9$ is —$OR_{9a}$, $R_{9a}$ is alkyl, $R_2$ is arylalkyl and $R_7$ is heteroaryl.

For example, the present invention provides a compound of formula (IV) wherein X is O, Y is O, $R_1$ is C3 alkyl, C4 alkyl or C5 alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is alkyl, $R_2$ is arylalkyl, and $R_7$ is heteroaryl.

For example, the present invention provides a compound of formula (IV) wherein X is O, Y is O, $R_1$ is C3 alkyl, C4 alkyl or C5 alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is arylalkyl, and $R_7$ is heteroaryl.

For example, the present invention provides a compound of formula (IV) X is O, Y is O, wherein $R_1$ is C3 alkyl, C4 alkyl or C5 alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, and $R_7$ is heteroaryl.

For example, the present invention provides a compound of formula (IV) wherein X is O, Y is O, $R_1$ is C3 alkyl, C4 alkyl or C5 alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, and $R_7$ is thienyl, furyl, oxazolyl, isoxazolyl, thiazolyl, pyridyl, pyridazinyl, indazolyl, imidazopyridinyl, indolyl, benzimidazolyl, isoquinolinyl or quinolinyl.

For example, the present invention provides a compound of formula (IV) wherein X is O, Y is O, $R_1$ is C3 alkyl, C4 alkyl or C5 alkyl; $R_3$ is arylalkyl, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, and $R_7$ is thienyl, furyl, oxazolyl, isoxazolyl, thiazolyl, pyridyl, pyridazinyl, indazolyl, imidazopyridinyl, indolyl, benzimidazolyl, isoquinolinyl or quinolinyl.

For example, the present invention provides a compound of formula (IV) wherein X is O, Y is O, $R_1$ is C3 alkyl, C4 alkyl or C5 alkyl; $R_3$ is arylalkyl substituted with $R_{3a}$, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, and $R_7$ is thienyl, furyl, oxazolyl, isoxazolyl, thiazolyl, pyridyl, pyridazinyl, indazolyl, imidazopyridinyl, indolyl, benzimidazolyl, isoquinolinyl or quinolinyl.

For example, the present invention provides a compound of formula (IV) wherein X is O, Y is O, $R_1$ is C3 alkyl, C4 alkyl or C5 alkyl; $R_3$ is arylalkyl substituted with $R_{3a}$, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, $R_5$ is thienyl, furyl, oxazolyl, isoxazolyl, thiazolyl, pyridyl, pyridazinyl, indazolyl, imidazopyridinyl, indolyl, benzimidazolyl, isoquinolinyl or quinolinyl, and $R_{3a}$ is heteroaryl.

For example, the present invention provides a compound of formula (IV) wherein X is O, Y is O, $R_1$ is C3 alkyl, C4 alkyl or C5 alkyl; $R_3$ is phenylmethyl substituted with $R_{3a}$, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, $R_7$ is thienyl, furyl, oxazolyl, isoxazolyl, thiazolyl, pyridyl, pyridazinyl, indazolyl, imidazopyridinyl, indolyl, benzimidazolyl, isoquinolinyl or quinolinyl, and $R_{3a}$ is pyridyl, thiazolyl or isoxaolyl.

For example, the present invention provides a compound of formula (IV) wherein X is O, Y is O, $R_1$ is C3 alkyl, C4 alkyl or C5 alkyl; $R_3$ is phenylmethyl substituted with $R_{3a}$, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, $R_7$ is pyridyl, and $R_{3a}$ is pyridyl.

For example, the present invention provides a compound of formula (IV) wherein X is O, Y is O, $R_1$ is C3 alkyl, C4 alkyl or C5 alkyl; $R_3$ is phenylmethyl substituted with $R_{3a}$, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, $R_7$ is pyridyl substituted with one alkyl substituent, and $R_{3a}$ is pyridyl.

For example, the present invention provides a compound of formula (IV) wherein X is O, Y is O, $R_1$ is C3 alkyl, C4 alkyl or C5 alkyl; $R_3$ is phenylmethyl substituted with $R_{3a}$, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, $R_7$ is pyridyl substituted with one methyl substituent, and $R_{3a}$ is pyridyl.

For example, the present invention provides a compound of formula (IV) wherein X is O, Y is O, $R_1$ is C3 alkyl, C4 alkyl or C5 alkyl; $R_3$ is phenylmethyl substituted with $R_{3a}$, $R_4$ is —C(O)C(H)($R_8$)NHC(O)$R_9$, $R_8$ is C3 alkyl, C4 alkyl or C5 alkyl, $R_9$ is —$OR_{9a}$, $R_{9a}$ is methyl, $R_2$ is phenylmethyl, $R_7$ is 2-pyridyl substituted with one methyl substituent, and $R_{3a}$ is 2-pyridyl.

Exemplary compound of the present invention of formula (IV) includes, but not limited to, methyl (1S)-1-({2-[(2S,3S)-3-({(2S,3S)-2-[2,4-dioxo-3-(2-pyridinylmethyl)-1-imidazolidinyl]-3-methylpentanoyl}amino)-2-hydroxy-4-phenylbutyl]-2-[4-(2-pyridinyl)benzyl]hydrazino}carbonyl)-2,2-dimethylpropylcarbamate, or a pharmaceutically acceptable salt form, stereoisomer, ester, salt of an ester, prodrug, salt of a prodrug or combination thereof.

In a fifth embodiment, the present invention provides a compound of formula (V),

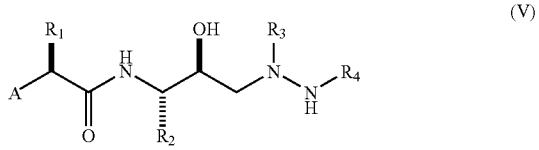

or a pharmaceutically acceptable salt form, stereoisomer, ester, salt of an ester, prodrug, salt of a prodrug or combination thereof, wherein:

A is

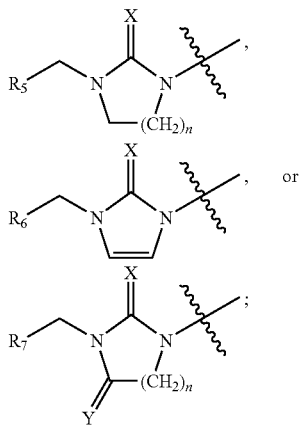

X is O, S or NH;

Y is O, S or NH;

$R_1$ is alkyl, alkenyl, alkynyl, cycloalkyl, cycloalkenyl, aryl, heteroaryl, arylalkyl, heteroarylalkyl, cycloalkylalkyl or cycloalkenylalkyl; wherein each $R_1$ is substituted with 0, 1 or 2 substituents independently selected from the group consisting of halo, haloalkyl, alkyl, alkenyl, cyano, nitro, —$OR_a$, —Oalkyl$C(=O)NR_aR_b$, —$SR_a$, —$SOR_a$, —$SO_2R_a$, —$SO_2NR_aR_b$, —$C(=O)R_a$, —$NR_aR_b$, —$N(R_b)C(=O)R_a$, —$N(R_b)C(=O)OR_a$, —$N(R_b)SO_2R_a$, —$N(R_b)SO_2NR_aR_b$, —$N(R_b)C(=NH)NR_aR_b$, —$N(R_b)C(=O)NR_aR_b$, —$C(=O)NR_aR_b$ and —$C(=O)OR_a$;

$R_2$ is alkyl, alkenyl, alkynyl, cycloalkyl, cycloalkenyl, cycloalkylalkyl, cycloalkenylalkyl, arylalkyl, heterocycle, heterocyclealkyl or heteroarylalkyl; wherein each $R_2$ is substituted with 0, 1, or 2 substituents independently selected from the group consisting of alkyl, alkenyl, alkynyl, cyano, halo, formyl, nitro, hydroxy, alkoxy, —$NH_2$, —N(H)alkyl, —N(alkyl)$_2$, —N(H)C(=O)Oalkyl, —N(alkyl)C(=O)Oalkyl, —C(=O)OH, —C(=O)Oalkyl, —C(=O)$NH_2$, —C(=O)N(H)(alkyl), —C(=O)N(alkyl)$_2$, —C(=O)alkyl, cyanoalkyl, nitroalkyl, formylalkyl, haloalkyl, hydroxyalkyl, alkoxyalkyl, -alkyl$NH_2$, -alkylN(H)alkyl, -alkylN(alkyl)$_2$, -alkylN(H)C(=O)Oalkyl, -alkylN(alkyl)C(=O)Oalkyl, -alkylC(=O)OH, -alkylC(=O)Oalkyl, -alkylC(=O)$NH_2$, -alkylC(=O)N(H)(alkyl), -alkylC(=O)N(alkyl)$_2$ and -alkylC(=O)alkyl;

$R_3$ is hydrogen, alkyl, haloalkyl, alkenyl, haloalkenyl, alkynyl, haloalkynyl, cycloalkyl, cycloalkenyl, heterocycle, aryl, heteroaryl, cycloalkylalkyl, cycloalkenylalkyl, heterocyclealkyl, heteroarylalkyl, arylalkyl, hydroxyalkyl, alkoxyalkyl, -alkyl$SR_a$, -alkylS$OR_a$, -alkylSO$_2R_a$, -alkylNR$_aR_b$, -alkylC(=O)$OR_a$, -alkylN(R$_b$)C(=O)$OR_a$, -alkylN(R$_b$)C(=O)$R_a$, -alkylN(R$_b$)SO$_2R_a$ or -alkylN(R$_b$)SO$_2NR_aR_b$; wherein the cycloalkyl, cycloalkenyl, heterocycle, aryl, heteroaryl, cycloalkyl moiety of cycloalkylalkyl, cycloalkenyl moiety of cycloalkenylalkyl, heterocycle moiety of heterocyclealkyl, heteroaryl moiety of heteroarylalkyl and aryl moiety of arylalkyl are independently substituted with 0, 1, 2 or 3 substituents independently selected from the group consisting of halo, nitro, cyano, formyl, alkyl, alkenyl, alkynyl, hydroxy, alkoxy, —SH, —S(alkyl), —S(haloalkyl), —SO$_2$(alkyl), —SO$_2$(haloalkyl), —$NH_2$, —N(H)(alkyl), —N(alkyl)$_2$, —N(H)C(=O)alkyl, —N(alkyl)C(=O)alkyl, —C(=O)OH, —C(=O)O(alkyl), —C(=O)$NH_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkyl$NH_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)$NH_2$, -alkylC(=O)N(H)(alkyl), -alkylC(=O)N(alkyl)$_2$, -alkylC(=O)alkyl and $R_{3a}$;

$R_{3a}$ is cycloalkyl, cycloalkenyl, aryl, heteroaryl, heterocycle, aryloxy, heteroaryloxy or heterocycleoxy, wherein each $R_{3a}$ is independently substituted with 0, 1, 2 or 3 substituents independently selected from the group consisting of halo, nitro, cyano, formyl, alkyl, alkenyl, alkynyl, hydroxyl, alkoxy, —SH, —S(alkyl), —SO$_2$(alkyl), —$NH_2$, —N(H)(alkyl), —N(alkyl)$_2$, —N(H)C(=O)alkyl, —N(alkyl)C(=O)alkyl, —C(=O)OH, —C(=O)O(alkyl), —C(=O)$NH_2$, —C(=O)N(H)(alkyl), —C(O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkyl$NH_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)$NH_2$, -alkylC(=O)N(H)(alkyl), -alkylC(=O)N(alkyl)$_2$ and -alkylC(=O)alkyl;

$R_4$ is a) —C(O)CH($R_8$)NHC(O)$R_9$, b) —C(O)$R_9$, c) —C(O)CH$_2$—O-aryl, substituted with 0, 1, 2 or 3 substituents selected from the group consisting of alkyl, alkenyl, halo, cynao, nitro, formyl, oxo, hydroxyl, alkoxy, hydroxyalky, alkoxyalkyl, haloalkyl, cyanoalkyl, aminoalkyl, alkylaminoalkyl, dialkylaminoalkyl, nitroalkyl, —$NH_2$, —N(H)alkyl, —N(alkyl)$_2$, —C(=O)alkyl, —C(=O)OH, —C(=O)Oalkyl, —C(=O)$NH_2$, —C(=O)N(H)(alkyl) and —C(=O)N(alkyl)$_2$, d) —C(O)CH$_2$—O-heteroaryl, substituted with 0, 1, 2 or 3 substituents selected from the group consisting of alkyl, alkenyl, halo, cynao, nitro, formyl, oxo, hydroxyl, alkoxy, hydroxyalky, alkoxyalkyl, haloalkyl, cyanoalkyl, aminoalkyl, alkylaminoalkyl, dialkylaminoalkyl, nitroalkyl, —$NH_2$, —N(H)alkyl, —N(alkyl)$_2$, —C(=O)alkyl, —C(=O)OH, —C(=O)Oalkyl, —C(=O)NH₂, —C(=O)N(H)(alkyl), and —C(=O)N(alkyl)₂,

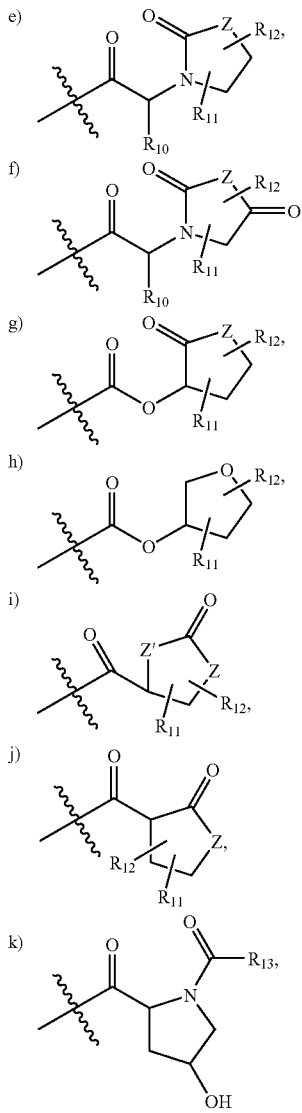

l) —SO₂R₁₄;

R₅ is alkyl, alkenyl, alkynyl, cycloalkyl, cycloalkenyl, aryl, heteroaryl or heterocycle; wherein each R₅ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO₂R$_a$, —SO₂NR$_a$, —SO₂OR$_a$, —NR$_a$R$_b$, —N(R$_b$)NR$_a$R$_b$, —N(R$_b$)C(=O)R$_a$, —N(R$_b$)SO₂R$_a$, —N(R$_b$)C(=O)OR$_a$, —N(R$_b$)C(=O)NR$_a$R$_b$, —N(R$_b$)SO₂NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO₂R$_a$, -alkylSO₂NR$_a$, -alkylSO₂OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO₂NR$_a$R$_b$, -alkylN(R$_b$)SO₂R$_a$, -alkylC(=O)R$_a$, -alkylC(=O)OR$_a$, -alkylC(=O)NR$_a$R$_b$ and R$_{5a}$;

R$_{5a}$ is cycloalkyl, cycloalkenyl, heterocycle, aryl or heteroaryl; wherein each R$_{5a}$ is substituted with 0, 1, 2, 3 or 4 substituents independently selected from the group consisting of cyano, halo, nitro, oxo, alkyl, alkenyl, alkynyl, hydroxy, alkoxy, —NH₂, —N(H)(alkyl), —N(alkyl)₂, —SH, —S(alkyl), —SO₂(alkyl), —N(H)C(=O)alkyl, —N(alkyl)C(=O)alkyl, —N(H)C(=O)NH₂, —N(H)C(=O)N(H)(alkyl), —N(H)C(=O)N(alkyl)₂, —C(=O)OH, —C(=O)Oalkyl, —C(=O)NH₂, —C(=O)N(H)(alkyl), —C(=O)N(alkyl)₂, cyanoalkyl, formylalkyl, haloalkyl, hydroxyalkyl, alkoxyalkyl, -alkylNH₂, -alkylN(H)(alkyl), -alkylN(alkyl)₂, -alkylN(H)C(=O)alkyl, -alkylN(alkyl)C(=O)alkyl, -alkylN(H)C(=O)NH₂, -alkylN(H)C(=O)N(H)(alkyl), -alkylN(H)C(=O)N(alkyl)₂, -alkylC(=O)OH, -alkylC(=O)Oalkyl, -alkylC(=O)NH₂, -alkylC(=O)N(H)(alkyl) and -alkylC(=O)N(alkyl)₂;

R₆ is alkyl, alkenyl, alkynyl, cycloalkyl, cycloalkenyl, aryl, heteroaryl or heterocycle; wherein each R₆ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO₂R$_a$, —SO₂NR$_a$, —SO₂OR$_a$, —NR$_a$R$_b$, —N(R$_b$)NR$_a$R$_b$, —N(R$_b$)C(=O)R$_a$, —N(R$_b$)SO₂R$_a$, —N(R$_b$)C(=O)OR$_a$, —N(R$_b$)C(=O)NR$_a$R$_b$, —N(R$_b$)SO₂NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO₂R$_a$, -alkylSO₂NR$_a$, -alkylSO₂OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO₂NR$_a$R$_b$, -alkylN(R$_b$)SO₂R$_a$, -alkylC(=O)R$_a$, -alkylC(=O)OR$_a$, -alkylC(=O)NR$_a$R$_b$ and R$_{6a}$;

R$_{6a}$ is cycloalkyl, cycloalkenyl, heterocycle, aryl or heteroaryl; wherein each R$_{6a}$ is substituted with 0, 1, 2, 3 or 4 substituents independently selected from the group consisting of cyano, halo, nitro, oxo, alkyl, alkenyl, alkynyl, hydroxy, alkoxy, —NH₂, —N(H)(alkyl), —N(alkyl)₂, —SH, —S(alkyl), —SO₂(alkyl), —N(H)C(=O)alkyl, —N(alkyl)C(=O)alkyl, —N(H)C(=O)NH₂, —N(H)C(=O)N(H)(alkyl), —N(H)C(=O)N(alkyl)₂, —C(=O)OH, —C(=O)Oalkyl, —C(=O)NH₂, —C(=O)N(H)(alkyl), —C(=O)N(alkyl)₂, cyanoalkyl, formylalkyl, haloalkyl, hydroxyalkyl, alkoxyalkyl, -alkylNH₂, -alkylN(H)(alkyl), -alkylN(alkyl)₂, -alkylN(H)C(=O)alkyl, -alkylN(alkyl)C(=O)alkyl, -alkylN(H)C(=O)NH₂, -alkylN(H)C(=O)N(H)(alkyl), -alkylN(H)C(=O)N(alkyl)₂, -alkylC(=O)OH, -alkylC(=O)Oalkyl, -alkylC(=O)NH₂, -alkylC(=O)N(H)(alkyl) and -alkylC(=O)N(alkyl)₂;

R₇ is alkyl, alkenyl, alkynyl, cycloalkyl, cycloalkenyl, aryl, heteroaryl or heterocycle; wherein each R₇ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO₂R$_a$, —SO₂NR$_a$, —SO₂OR$_a$, —NR$_a$R$_b$, —N(R$_b$)NR$_a$R$_b$, —N(R$_b$)C(=O)R$_a$, —N(R$_b$)SO₂R$_a$, —N(R$_b$)C(=O)OR$_a$, —N(R$_b$)C(=O)NR$_a$R$_b$, —N(R$_b$)SO₂NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO₂R$_a$, -alkylSO₂NR$_a$, -alkylSO₂OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C (=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and R$_{7a}$;

R$_{7a}$ is cycloalkyl, cycloalkenyl, heterocycle, aryl or heteroaryl; wherein each R$_{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)alkyl, -alkylN(alkyl)C(=O)alkyl, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

R$_8$ is alkyl, alkenyl, alkynyl, cycloalkyl, aryl, heteroaryl, cycloalkylalkyl or arylalkyl; wherein each R$_8$ is substituted with 0, 1 or 2 substituents independently selected from the group consisting of halo, cyano, formyl, nitro, alkyl, alkenyl, alkynyl, hydroxy, alkoxy, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), —C(=O)N(alkyl)$_2$, —C(=O)alkyl, hydroxyalkyl, alkoxyalkyl, -alkylNH$_2$, -alkylN(H)alkyl, -alkylN(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

R$_9$ is alkyl, cycloalkyl, cycloalkylalkyl, aryl, heterocycle, heteroaryl or OR$_{9a}$, wherein each R$_9$ is substituted with 0, 1, 2 or 3 substituents selected from the group consisting of hydroxy, alkoxy, halo, cyano, nitro, formyl, alkyl, alkenyl, alkynyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), and —C(=O)N(alkyl)$_2$;

R$_{9a}$ is alkyl, cycloalkyl, cycloalkylalkyl, aryl, arylalkyl, heterocycle, heteroaryl, heteroarylalkyl or heterocyclealkyl; wherein each R$_{9a}$ is substituted with 0, 1, 2 or 3 substituents independently selected from the group consisting of hydroxy, alkoxy, halo, cyano, nitro, formyl, alkyl, alkenyl, alkynyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl) and —C(=O)N(alkyl)$_2$;

R$_{10}$ is alkyl, alkenyl, alkynyl, cycloalkyl or cycloalkenyl, aryl, heteroaryl, arylalkyl, cycloalkylalkyl or heteroarylalkyl; wherein each R$_{10}$ is substituted with 0, 1, 2 or 3 substituents selected from the group consisting of halo, cyano, nitro, formyl, alkyl, alkenyl, hydroxy, alkoxy, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_b$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$ and —C(=O)OR$_a$;

R$_{11}$ is hydrogen, alkyl, haloalkyl, hydroxyalkyl or alkoxyalkyl;

R$_{12}$ is hydrogen, alkyl, haloalkyl, hydroxyalkyl or alkoxyalkyl;

R$_{13}$ is alkyl or haloalkyl;

R$_{14}$ is alkyl, cycloalkyl, cycloalkylalkyl, aryl, heteroaryl or heterocycle; wherein each R$_{14}$ is substituted with 0, 1, 2 or 3 substituents selected from the group consisting of halo, cyano, nitro, formyl, alkyl, alkenyl, hydroxy, alkoxy, haloalkyl, —NH$_2$, —N(H)alkyl, —N(alkyl)$_2$, —C(=O)OH, —C(=O)Oalkyl, —C(=O)NH$_2$, —C(=O)N(H)(alkyl), and —C(=O)N(alkyl)$_2$;

Z is —CH$_2$—, —NH—, —O— or —S—;

Z' is —CH$_2$—, —NH—, —O— or —S—;

R$_a$ and R$_b$ at each occurrence are independently selected from the group consisting of hydrogen, alkyl, haloalkyl, alkenyl, alkynyl, cycloalkyl, aryl, heteroaryl, heterocycle, arylalkyl and heteroarylalkyl; wherein each R$_a$ and R$_b$, at each occurrence, is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, —C(=O)alkyl, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), -alkylC(=O)N(alkyl)$_2$ and -alkylC(=O)alkyl; and n is 1 or 2.

For example, the present invention provides a compound of formula (V) wherein R$_1$ is alkyl.

For example, the present invention provides a compound of formula (V) wherein R$_1$ is alkyl and R$_4$ is —C(O)C(H)(R$_8$)NHC(O)R$_9$.

For example, the present invention provides a compound of formula (V) wherein R$_1$ is alkyl, R$_4$ is —C(O)C(H)(R$_8$)NHC(O)R$_9$ and R$_9$ is —OR$_{9a}$.

For example, the present invention provides a compound of formula (V) wherein R$_1$ is alkyl, R$_4$ is —C(O)C(H)(R$_8$)NHC(O)R$_9$, R$_8$ is alkyl and R$_9$ is OR$_{9a}$.

For example, the present invention provides a compound of formula (V) wherein R$_1$ is alkyl, R$_3$ is alkyl, alkenyl, alkynyl, cycloalkyl, cycloalkylalkyl, hydroxyalkyl, alkoxyalkyl, arylalkyl, heteroarylalkyl or heterocyclealkyl, R$_4$ is —C(O)C(H)(R$_8$)NHC(O)R$_9$, R$_8$ is alkyl and R$_9$ is —OR$_{9a}$.

For example, the present invention provides a compound of formula (V) wherein R$_1$ is alkyl, R$_3$ is alkyl, alkenyl, alkynyl, cycloalkyl, cycloalkylalkyl, hydroxyalkyl, alkoxyalkyl, arylalkyl, heteroarylalkyl or heterocyclealkyl, R$_4$ is —C(O)C(H)(R$_8$)NHC(O)R$_9$, R$_8$ is alkyl, R$_9$ is —OR$_{9a}$ and R$_2$ is arylalkyl.

For example, the present invention provides a compound of formula (V) wherein R$_1$ is alkyl; R$_3$ is alkyl, alkenyl, alkynyl, cycloalkyl, cycloalkylalkyl, hydroxyalkyl, alkoxyalkyl, arylalkyl, heteroarylalkyl or heterocyclealkyl, R$_4$ is —C(O)C(H)(R$_8$)NHC(O)R$_9$, R$_8$ is alkyl, R$_9$ is —OR$_{9a}$, R$_{9a}$ is alkyl and R$_2$ is arylalkyl.

For example, the present invention provides a compound of formula (V) wherein R$_1$ is alkyl; R$_3$ is alkyl, alkenyl, alkynyl, cycloalkyl, cycloalkylalkyl, hydroxyalkyl, alkoxyalkyl, arylalkyl, heteroarylalkyl or heterocyclealkyl, R$_4$ is —C(O)C(H)(R$_8$)NHC(O)R$_9$, R$_8$ is alkyl, R$_9$ is —OR$_{9a}$, R$_{9a}$ is alkyl, R$_2$ is arylalkyl, and R$_5$, R$_6$ and R$_7$ are heteroaryl.

For example, the present invention provides a compound of formula (V) wherein X is O, Y is O, R$_1$ is alkyl; R$_3$ is alkyl, alkenyl, alkynyl, cycloalkyl, cycloalkylalkyl, hydroxyalkyl, alkoxyalkyl, arylalkyl, heteroarylalkyl or heterocyclealkyl, R$_4$ is —C(O)C(H)(R$_8$)NHC(O)R$_9$, R$_8$ is alkyl, R$_9$ is —OR$_{9a}$, R$_{9a}$ is alkyl, R$_2$ is arylalkyl, and R$_5$, R$_6$ and R$_7$ are heteroaryl.

For example, the present invention provides a compound of formula (V) wherein X is O, Y is O, $R_1$ is C3 alkyl, C4 alkyl or C5 alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is C3 alkyl, C4 alkyl or C5 alkyl, $R_9$ is —O$R_{9a}$, $R_{9a}$ is alkyl, $R_2$ is arylalkyl, and $R_5$, $R_6$ and $R_7$ are heteroaryl.

For example, the present invention provides a compound of formula (V) wherein X is O, Y is O, $R_1$ is C3 alkyl, C4 alkyl or C5 alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is C3 alkyl, C4 alkyl or C5 alkyl, $R_9$ is O$R_{9a}$, $R_{9a}$ is methyl, $R_2$ is arylalkyl, and $R_5$, $R_6$ and $R_7$ are heteroaryl.

For example, the present invention provides a compound of formula (V) wherein X is O, Y is O, $R_1$ is C3 alkyl, C4 alkyl or C5 alkyl; $R_3$ is alkyl, alkenyl, alkynyl, cycloalkyl, cycloalkylalkyl, hydroxyalkyl, alkoxyalkyl, arylalkyl, heteroarylalkyl or heterocyclealkyl, $R_4$ is —C(O)C(H)($R_8$)NHC(O)$R_9$, $R_8$ is C3 alkyl, C4 alkyl or C5 alkyl, $R_9$ is O$R_{9a}$, $R_{9a}$ is methyl, $R_2$ is arylalkyl, and $R_5$, $R_6$ and $R_7$ are independently selected from the group consisting of thienyl, furyl, oxazolyl, isoxazolyl, thiazolyl, pyridyl, pyridazinyl, indazolyl, imidazopyridinyl, indolyl, benzimidazolyl, isoquinolinyl and quinolinyl.

For example, the present invention provides a compound of formula (V) wherein X is O, Y is O, $R_1$ is C3 alkyl, C4 alkyl or C5 alkyl; $R_3$ is arylalkyl, $R_4$ is —C(O)C(H)($R_8$)NHC(O)$R_9$, $R_8$ is C3 alkyl, C4 alkyl or C5 alkyl, $R_9$ is —O$R_{9a}$, $R_{9a}$ is methyl, $R_2$ is phenylmethyl, and $R_5$, $R_6$ and $R_7$ are independently selected from the group consisting of thienyl, furyl, oxazolyl, isoxazolyl, thiazolyl, pyridyl, pyridazinyl, indazolyl, imidazopyridinyl, indolyl, benzimidazolyl, isoquinolinyl and quinolinyl.

For example, the present invention provides a compound of formula (V) wherein X is O, Y is O, $R_1$ is C3 alkyl, C4 alkyl or C5 alkyl; $R_3$ is arylalkyl substituted with $R_{3a}$, $R_4$ is —C(O)C(H)($R_8$)NHC(O)$R_9$, $R_8$ is C3 alkyl, C4 alkyl or C5 alkyl, $R_9$ is —O$R_{9a}$, $R_{9a}$ is methyl, $R_2$ is phenylmethyl, $R_5$, $R_6$ and $R_7$ are independently selected from the group consisting of thienyl, furyl, oxazolyl, isoxazolyl, thiazolyl, pyridyl, pyridazinyl, indazolyl, imidazopyridinyl, indolyl, benzimidazolyl, isoquinolinyl and quinolinyl, and $R_{3a}$ is heteroaryl.

For example, the present invention provides a compound of formula (V) wherein X is O, Y is O, $R_1$ is C3 alkyl, C4 alkyl or C5 alkyl; $R_3$ is phenylmethyl substituted with $R_{3a}$, $R_4$ is —C(O)C(H)($R_8$)NHC(O)$R_9$, $R_8$ is C3 alkyl, C4 alkyl or C5 alkyl, $R_9$ is —O$R_{9a}$, $R_{9a}$ is methyl, $R_2$ is phenylmethyl, and $R_5$, $R_6$ and $R_7$ are independently selected from the group consisting of thienyl, furyl, oxazolyl, isoxazolyl, thiazolyl, pyridyl, pyridazinyl, indazolyl, imidazopyridinyl, indolyl, benzimidazolyl, isoquinolinyl and quinolinyl, and $R_{3a}$ is pyridyl, oxazolyl or thiazolyl.

For example, the present invention provides a compound of formula (V) wherein X is O, Y is O, $R_1$ is C3 alkyl, C4 alkyl or C5 alkyl; $R_3$ is phenylmethyl substituted with $R_{3a}$, $R_4$ is —C(O)C(H)($R_8$)NHC(O)$R_9$, $R_8$ is C3 alkyl, C4 alkyl or C5 alkyl, $R_9$ is —O$R_{9a}$, $R_{9a}$ is methyl, $R_2$ is phenylmethyl, and $R_5$, $R_6$ and $R_7$ are independently selected from the group consisting of thienyl, furyl, oxazolyl, isoxazolyl, thiazolyl, pyridyl, pyridazinyl, indazolyl, imidazopyridinyl, indolyl, benzimidazolyl, isoquinolinyl and quinolinyl, and $R_{3a}$ is pyridyl.

For example, the present invention provides a compound of formula (V) wherein X is O, Y is O, $R_1$ is C3 alkyl, C4 alkyl or C5 alkyl; $R_3$ is phenylmethyl substituted with $R_{3a}$, $R_4$ is —C(O)C(H)($R_8$)NHC(O)$R_9$, $R_8$ is C3 alkyl, C4 alkyl or C5 alkyl, $R_9$ is —O$R_{9a}$, $R_{9a}$ is methyl, $R_2$ is phenylmethyl, and $R_5$, $R_6$ and $R_7$ are pyridyl, and $R_{3a}$ is 2-pyridyl.

For example, the present invention provides a compound of formula (V) wherein X is O, Y is O, $R_1$ is C3 alkyl, C4 alkyl or C5 alkyl; $R_3$ is phenylmethyl substituted with $R_{3a}$, $R_4$ is —C(O)C(H)($R_8$)NHC(O)$R_9$, $R_8$ is C3 alkyl, C4 alkyl or C5 alkyl, $R_9$ is —O$R_{9a}$, $R_{9a}$ is methyl, $R_2$ is phenylmethyl, and $R_5$, $R_6$ and $R_7$ are 2-pyridyl substituted with one alkyl substituent, and $R_{3a}$ is 2-pyridyl.

For example, the present invention provides a compound of formula (V) wherein X is O, Y is O, $R_1$ is C3 alkyl, C4 alkyl or C5 alkyl; $R_3$ is phenylmethyl substituted with $R_{3a}$, $R_4$ is —C(O)C(H)($R_8$)NHC(O)$R_9$, $R_8$ is C3 alkyl, C4 alkyl or C5 alkyl, $R_9$ is —O$R_{9a}$, $R_{9a}$ is methyl, $R_2$ is phenylmethyl, and $R_5$, $R_6$ and $R_7$ are 2-pyridyl substituted with one methyl substituent, and $R_{3a}$ is 2-pyridyl.

In a sixth embodiment, the present invention provides pharmaceutical composition comprising a therapeutically effective amount of a compound or combination of compounds of formula (I), (II), (III), (IV) or (V), or a pharmaceutically acceptable salt form, stereoisomer, ester, salt of an ester, prodrug, salt of a prodrug, or combination thereof, and a pharmaceutically acceptable carrier.

In a seventh embodiment, the present invention provides a pharmaceutical composition comprising a therapeutically effective amount of a compound or combination of compounds of formula (I), (II), (III), (IV) or (V), or a pharmaceutically acceptable salt form, stereoisomer, ester, salt of an ester, prodrug, salt of a prodrug, or combination thereof, and one, two, three, four, five or six second HIV protease inhibitors, and a pharmaceutically acceptable carrier.

For example, the present invention provides a pharmaceutical composition comprising a therapeutically effective amount of a compound or combination of compounds of formula (I), (II), (III), (IV) or (V), or a pharmaceutically acceptable salt form, stereoisomer, ester, salt of an ester, prodrug, salt of a prodrug, or combination thereof, and one, two, three, four, five or six second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, and a pharmaceutically acceptable carrier.

In an eighth embodiment, the present invention provides a pharmaceutical composition comprising a therapeutically effective amount of a compound or combination of compounds of formula (I), (II), (III), (IV) or (V), or a pharmaceutically acceptable salt form, stereoisomer, ester, salt of an ester, prodrug, salt of a prodrug, or combination thereof, and one, two, three, four, five or six HIV reverse transcriptase inhibitors, and a pharmaceutically acceptable carrier.

For example, the present invention provides a pharmaceutical composition comprising a therapeutically effective amount of a compound or combination of compounds of formula (I), (II), (III), (IV) or (V), or a pharmaceutically acceptable salt form, stereoisomer, ester, salt of an ester, prodrug, salt of a prodrug, or combination thereof, and one, two, three, four, five or six HIV reverse transcriptase inhibitors selected from the group consisting of lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120 and TMC-125, and a pharmaceutically acceptable carrier.

In a ninth embodiment, the present invention provides a pharmaceutical composition comprising a therapeutically effective amount of a compound or combination of compounds of formula (I), (II), (III), (IV) or (V), or a pharmaceutically acceptable salt form, stereoisomer, ester, salt of an ester, prodrug, salt of a prodrug, or combination thereof, and one, two, three, four, five or six HIV entry/fusion inhibitors, and a pharmaceutically acceptable carrier.

For example, the present invention provides a pharmaceutical composition comprising a therapeutically effective amount of a compound or combination of compounds of formula (I), (II), (III), (IV) or (V), or a pharmaceutically acceptable salt form, stereoisomer, ester, salt of an ester, prodrug, salt of a prodrug, or combination thereof, and one, two, three, four, five or six HIV entry/fusion inhibitors selected from the group consisting of enfuvirtide (T-20), T-1249, PRO 2000, PRO 542, PRO 140, AMD-3100, BMS-806, FP21399, GW873140, Schering C (SCH-C), Schering D (SCH-D), TNX-355 and UK-427857, and a pharmaceutically acceptable carrier.

In a tenth embodiment, the present invention provides a pharmaceutical composition comprising a therapeutically effective amount of a compound or combination of compounds of formula (I), (II), (III), (IV) or (V), or a pharmaceutically acceptable salt form, stereoisomer, ester, salt of an ester, prodrug, salt of a prodrug, or combination thereof, and one, two, three, four, five or six HIV integrase inhibitors, and a pharmaceutically acceptable carrier.

For example, the present invention provides a pharmaceutical composition comprising a therapeutically effective amount of a compound or combination of compounds of formula (I), (II), (III), (IV) or (V), or a pharmaceutically acceptable salt form, stereoisomer, ester, salt of an ester, prodrug, salt of a prodrug, or combination thereof, and one, two, three or four HIV integrase inhibitors selected from the group consisting of S-1360, zintevir (AR-177), L-870812 and L-870810, and a pharmaceutically acceptable carrier.

In an eleventh embodiment, the present invention provides a pharmaceutical composition comprising a therapeutically effective amount of a compound or combination of compounds of formula (I), (II), (III), (IV) or (V), or a pharmaceutically acceptable salt form, stereoisomer, ester, salt of an ester, prodrug, salt of a prodrug, or combination thereof, and one, two, three, four, five or six HIV budding/maturation inhibitors, and a pharmaceutically acceptable carrier.

For example, the present invention provides a pharmaceutical composition comprising a therapeutically effective amount of a compound or combination of compounds of formula (I), (II), (III), (IV) or (V), or a pharmaceutically acceptable salt form, stereoisomer, ester, salt of an ester, prodrug, salt of a prodrug, or combination thereof, PA-457, and a pharmaceutically acceptable carrier.

In a twelfth embodiment the present invention provides a pharmaceutical composition comprising a therapeutically effective amount of a compound or combination of compounds of formula (I), (II), (III), (IV) or (V), or a pharmaceutically acceptable salt form, stereoisomer, ester, salt of an ester, prodrug, salt of a prodrug, or combination thereof, one, two or three second HIV protease inhibitors, one, two or three HIV reverese transcriptase inhibitors and a pharmaceutically acceptable carrier.

For example, the present invention provides a pharmaceutical composition comprising a therapeutically effective amount of a compound or combination of compounds of formula (I), (II), (III), (IV) or (V), or a pharmaceutically acceptable salt form, stereoisomer, ester, salt of an ester, prodrug, salt of a prodrug, or combination thereof, one, two or three second HIV protease inhibitors selected from the group consisting of ritonavir, lopinavir, saquinavir, amprenavir, fos-amprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, one, two or three HIV reverse transcriptase inhibitors selected from the group consisting of lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120 and TMC-125, and a pharmaceutically acceptable carrier.

In a thirteenth embodiment the present invention provides a pharmaceutical composition comprising a therapeutically effective amount of a compound or combination of compounds of formula (I), (II), (III), (IV) or (V), or a pharmaceutically acceptable salt form, stereoisomer, ester, salt of an ester, prodrug, salt of a prodrug, or combination thereof, one, two or three second HIV protease inhibitors, one, two or three HIV entry/fusion inhibitors, and a pharmaceutically acceptable carrier.

For example, the present invention provides a pharmaceutical composition comprising a therapeutically effective amount of a compound or combination of compounds of formula (I), (II), (III), (IV) or (V), or a pharmaceutically acceptable salt form, stereoisomer, ester, salt of an ester, prodrug, salt of a prodrug, or combination thereof, one, two or three second HIV protease inhibitors selected from the group consisting of ritonavir, lopinavir, saquinavir, amprenavir, fos-amprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, one, two or three HIV entry/fusion inhibitors selected from the group consisting of enfuvirtide (T-20), T-1249, PRO 2000, PRO 542, PRO 140, AMD-3100, BMS-806, FP21399, GW873140, Schering C (SCH-C), Schering D (SCH-D), TNX-355 and UK-427857, and a pharmaceutically acceptable carrier.

In a fourteenth embodiment the present invention provides a pharmaceutical composition comprising a therapeutically effective amount of a compound or combination of compounds of formula (I), (II), (III), (IV) or (V), or a pharmaceutically acceptable salt form, stereoisomer, ester, salt of an ester, prodrug, salt of a prodrug, or combination thereof, one, two or three second HIV protease inhibitors, one, two or three HIV integrase inhibitors, and a pharmaceutically acceptable carrier.

For example, the present invention provides a pharmaceutical composition comprising a therapeutically effective amount of a compound or combination of compounds of formula (I), (II), (III), (IV) or (V), or a pharmaceutically acceptable salt form, stereoisomer, ester, salt of an ester, prodrug, salt of a prodrug, or combination thereof, one, two or three second HIV protease inhibitors selected from the group consisting of ritonavir, lopinavir, saquinavir, amprenavir, fos-amprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, one, two or three HIV integrase inhibitors selected from the group consisting of S-1360, zintevir (AR-177), L-870812 and L-870810, and a pharmaceutically acceptable carrier.

In a fifteenth embodiment the present invention provides a pharmaceutical composition comprising a therapeutically effective amount of a compound, or combination of compounds of formula (I), (II), (III), (IV) or (V), or a pharmaceutically acceptable salt form, stereoisomer, ester, salt of an ester, prodrug, salt of a prodrug, or combination thereof, one, two or three second HIV protease inhibitors, one, two or three HIV budding/maturation inhibitors, and a pharmaceutically acceptable carrier.

For example, the present invention provides a pharmaceutical composition comprising a therapeutically effective amount of a compound or combination of compounds of formula (I), (II), (III), (IV) or (V), or a pharmaceutically acceptable salt form, stereoisomer, ester, salt of an ester, prodrug, salt of a prodrug, or combination thereof, one, two or three second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, and PA-457, and a pharmaceutically acceptable carrier.

In an sixteenth embodiment, the present invention provides a method of inhibiting the replication of HIV virus comprising contacting said virus with a therapeuctially effective amount of a compound, or combination of compounds, of formula (I), (II), (III), (IV) or (V), or a pharmaceutically acceptable salt form, stereoisomer, ester, salt of an ester, prodrug, salt of a prodrug, or combination thereof.

In a seventeenth embodiment, the present invention provides a method of inhibiting the replication of HIV virus comprising contacting said virus with any one of the pharmaceutical compositions as described hereinabove.

In an eighteenth embodiment, the present invention provides a method of treating or preventing an HIV infection comprising administering to a patient in need of such treatment a therapeutically effective amount of a compound or combination of compounds, of formula (I), (II), (III), (IV) or (V), or a pharmaceutically acceptable salt form, stereoisomer, ester, salt of an ester, prodrug, salt of a prodrug, or combination thereof.

In a ninteenth embodiment, the present invention provides a method of treating or preventing an HIV infection comprising administering to a patient in need of such treatment any one of the pharmaceutical compositions as disclosed hereinabove.

In a twentieth embodiment, the present invention provides a method of inhibiting an HIV protease comprising contacting said HIV protease with a therapeutically effective amount of a compound or combination of compounds of formula (I), (II), (III), (IV) or (V), or a pharmaceutically acceptable salt form, stereoisomer, ester, salt of an ester, prodrug, salt of a prodrug, or combination thereof.

In a twenty-first embodiment, the present invention provides a method of inhibiting an HIV protease comprising contacting said HIV protease with any one of the pharmaceutical composition as disclosed hereinabove.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in T. H. Greene and P. G. M. Wuts, *Protective Groups in Organic Synthesis,* 2nd edition, John Wiley & Sons, New York (1991). N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, benzoyl, 4-chlorobenzoyl, 4-bromobenzoyl, 4-nitrobenzoyl, and the like; sulfonyl groups such as benzenesulfonyl, p-toluenesulfonyl and the like; sulfenyl groups such as phenylsulfenyl (phenyl-S—), triphenylmethylsulfenyl (trityl-S—) and the like; sulfinyl groups such as p-methylphenylsulfinyl (p-methylphenyl-S(O)—), t-butylsulfinyl (t-Bu-S(O)—) and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloro-ethoxy-carbonyl, phenoxycarbonyl, 4-nitro-phenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, p-methoxybenzyl, triphenylmethyl, benzyloxymethyl and the like; p-methoxyphenyl and the like; and silyl groups such as trimethylsilyl and the like. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

As used herein, the terms "S" and "R" configuration are as defined by the IUPAC 1974 Recommendations for Section E, Fundamental Stereochemistry, Pure Appl. Chem. (1976) 45, 13-30.

The compounds of the invention can comprise asymmetrically substituted carbon atoms. As a result, all stereoisomers of the compounds of the invention are meant to be included in the invention, including racemic mixtures, mixtures of diastereomers, as well as individual optical isomers, including, enantiomers and single diastereomers of the compounds of the invention substantially free from their enantiomers or other diastereomers. By "substantially free" is meant greater than about 80% free of other enantiomers or diastereomers of the compound, more preferably greater than about 90% free of other enantiomers or diastereomers of the compound, even more preferably greater than about 95% free of other enantiomers or diastereomers of the compound, even more highly preferably greater than about 98% free of other enantiomers or diastereomers of the compound and most preferably greater than about 99% free of other enantiomers or diastereomers of the compound.

In addition, compounds comprising the possible geometric isomers of carbon-carbon double bonds and carbon-nitrogen double are also meant to be included in this invention.

Individual stereoisomers of the compounds of this invention can be prepared by any one of a number of methods which are within the knowledge of one of ordinary skill in the art. These methods include stereospecific synthesis, chromatographic separation of diastereomers, chromatographic resolution of enantiomers, conversion of enantiomers in an enantiomeric mixture to diastereomers and then chromatographically separating the diastereomers and regeneration of the individual enantiomers, enzymatic resolution and the like.

Stereospecific synthesis involves the use of appropriate chiral starting materials and synthetic reactions which do not cause racemization or inversion of stereochemistry at the chiral centers.

Diasteromeric mixtures of compounds resulting from a synthetic reaction can often be separated by chromatographic techniques which are well-known to those of ordinary skill in the art.

Chromatographic resolution of enantiomers can be accomplished on chiral chromatography resins. Chromatography columns containing chiral resins are commercially available. In practice, the racemate is placed in solution and loaded onto the column containing the chiral stationary phase. The enantiomers are then separated by HPLC.

Resolution of enantiomers can also be accomplished by converting the enantiomers in the mixture to diastereomers by reaction with chiral auxiliaries. The resulting diastereomers can then be separated by column chromatography. This technique is especially useful when the compounds to be separated contain a carboxyl, amino or hydroxyl group that will form a salt or covalent bond with the chiral auxiliary. Chirally pure amino acids, organic carboxylic acids or organosulfonic acids are especially useful as chiral auxiliaries. Once the diastereomers have been separated by chromatography, the individual enantiomers can be regenerated. Frequently, the chiral auxiliary can be recovered and used again.

Enzymes, such as esterases, phosphatases and lipases, can be useful for resolution of derivatives of the enantiomers in an enantiomeric mixture. For example, an ester derivative of a carboxyl group in the compounds to be separated can be prepared. Certain enzymes will selectively hydrolyze only one of the enantiomers in the mixture. Then the resulting enantiomerically pure acid can be separated from the unhydrolyzed ester.

In addition, solvates and hydrates of the compounds of formula (I), (II), (III), (IV) or (V), are meant to be included in this invention. When any variable (for example A, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_a$, $R_b$, $R_c$, n, Z, Z', X, Y, etc.) occurs more than one time in any substituent or in the compound of formula (I), (II), (III), (IV) or (V), or any other formula herein its definition on each occurrence is independent of its definition at every other occurrence. In addition, combinations of substituents are permissible only if such combinations result in stable compounds. Stable compounds are compounds which can be isolated in a useful degree of purity from a reaction mixture.

The compounds of the present invention can be used in the form of salts derived from inorganic or organic acids. These salts include but are not limited to the following: 4 acetamidobenzoate, acetate, adipate, alginate, carbonate, 4-chlorobenzenesulfonate, citrate, aspartate, benzoate, benzenesulfonate, bisulfate, butyrate, camphorate, camphorsulfonate, cholate, digluconate, cyclopentanepropionate, dichloroacetate, dodecylsulfate, ethanedisulfonate, ethanesulfonate, ethylsuccinate, formate, fumarate, galactarate, D-gluconate, D-glucuronate, glucoheptanoate, glutarate, lycerophosphate, glycolate, hemisulfate, heptanoate, hexanoate, hydrochloride, hydrobromide, hydroiodide, 2-hydroxyethanesulfonate (isethionate), 3-hydroxy-2-naphthoate, 1-hydroxy-2-naphthoate, lactate, lactobionate, laurate, maleate, malonate, mandelate, methanesulfonate, nicotinate, 1,5-naphthalene-disulfonate, 2-naphthalenesulfonate, oleate, oxalate, pamoate, palmitate, pectinate, persulfate, 3-phenylpropionate, picrate, pivalate, propionate, L-pyroglutamate, sebacate, stearate, succinate, tartrate, terephthalate, thiocyanate, p-toluenesulfonate, undecanoate, undecylenoate and valerate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as aluminum, sodium, lithium, potassium, calcium, magnesium or zinc or with organic bases such as diethylethanolamine, diethanolamine, ethylenediamine, guanidine, meglumine, olamine (ethnolamine), piperazine, piperidine, triethylamine, tromethamine, benzathine, benzene-ethanamine, adenine, cytosine, diethylamine, glucosamine, guanine, nicotinamide, hydrabamine, tributylamine, deanol, epolamine or triethanolamine.

Representative salts of the compounds of the present invention include, but not limited to, hydrochloride, methanesulfonate, sulfonate, phosphonate, isethionate and trifluoroacetate.

The compounds of the present invention can also be used in the form of prodrugs. Examples of such prodrugs include compounds wherein one, two or three hydroxy groups in the compound of this invention are functionalized with $R^{15}$ wherein $R^{15}$ is

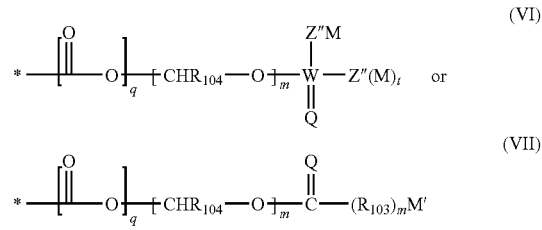

$R_{103}$ is $C(R_{105})_2$, O or $N(R_{105})$;

$R_{104}$ is hydrogen, alkyl, haloalkyl, alkoxycarbonyl, aminocarbonyl, alkylaminocarbonyl or dialkylaminocarbonyl, each M is independently selected from the group consisting of H, Li, Na, K, Mg, Ca, Ba, —$N(R_{105})_2$, alkyl, alkenyl, and $R_{106}$; wherein 1 to 4-$CH_2$ radicals of the alkyl or alkenyl, other than the —$CH_2$ radical that is bound to Z", is optionally replaced by a heteroatom group selected from the group consisting of O, S, S(O), $SO_2$ and $N(R_{105})$; and wherein any hydrogen in said alkyl, alkenyl or $R_{106}$ is optionally replaced with a substituent selected from the group consisting of oxo, —$OR_{105}$, —$R_{105}$, —$N(R_{105})_2$, —CN, —$C(O)OR_{105}$, —$C(O)N(R_{105})_2$, —$SO_2N(R_{105})$, —$N(R_{105})C(O)R_{105}$, —$C(O)R_{105}$, —$SR_{105}$, —$S(O)R_{105}$, —$SO_2R_{105}$, —$OCF_3$, —$SR_{106}$, —$SOR_{106}$, —$SO_2R_{106}$, —$N(R_{105})SO_2R_{105}$, halo, —$CF_3$ and $NO_2$;

Z" is $CH_2$, O, S, —$N(R_{105})$, or, when M is absent, H;

Q is O or S;

W is P or S; wherein when W is S, Z" is not S;

M' is H, alkyl, alkenyl or $R_{106}$; wherein 1 to 4-$CH_2$ radicals of the alkyl or alkenyl is optionally replaced by a heteroatom group selected from O, S, S(O), $SO_2$, or $N(R_{105})$; and wherein any hydrogen in said alkyl, alkenyl or $R_{106}$ is optionally replaced with a substituent selected from the group consisting of oxo, —$OR_{105}$, —$R_{105}$, —$N(R_{105})_2$, —CN, —$C(O)OR_{105}$, —C(O)N(R$_{105}$)$_2$, —SO$_2$N(R$_{105}$), —N(R$_{105}$)C(O)R$_{105}$, —C(O)R$_{105}$, —SR$_{105}$, —S(O)R$_{105}$, —SO$_2$R$_{105}$, —OCF$_3$, —SR$_{106}$, —SOR$_{106}$, —SO$_2$R$_{106}$, —N(R$_{105}$)SO$_2$R$_{105}$, halo, —CF$_3$ and NO$_2$;

R$_{106}$ is a monocyclic or bicyclic ring system selected from the group consisting of aryl, cycloalkyl, cycloalkenyl heteroaryl and heterocycle; wherein any of said heteroaryl and heterocycle ring systems contains one or more heteroatom selected from the group consisting of O, N, S, SO, SO$_2$ and N(R$_{105}$); and wherein any of said ring system is substituted with 0, 1, 2, 3, 4, 5 or 6 substituents selected from the group consisting of hydroxy, alkyl, alkoxy, and —OC(O)alkyl;

each R$_{105}$ is independently selected from the group consisting of H or alkyl; wherein said alkyl is optionally substituted with a ring system selected from the group consisting of aryl, cycloalkyl, cycloalkenyl, heteroaryl and heterocycle; wherein any of said heteroaryl and heterocycle ring systems contains one or more heteroatoms selected from the group consisting of O, N, S, SO, SO$_2$, and N(R$_{105}$); and wherein any one of said ring system is substituted with 0, 1, 2, 3 or 4 substituents selected from the group consisting of oxo, OR$_{105}$, —R$_{105}$, —N(R$_{105}$)$_2$, —N(R$_{105}$)C(O)R$_{105}$, —CN, —C(O)OR$_{105}$, —C(O)N(R$_{105}$)$_2$, halo and —CF$_3$;

q is 0 or 1;

m is 0 or 1; and t is 0 or 1.

Representative examples of R$^{15}$ of formula (VI) or (VII) that can be utilized for the functionalization of the hydroxy groups in the compound of the present invention include, but not limited to, the following:

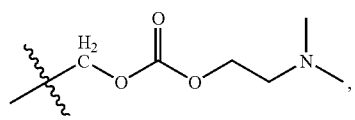

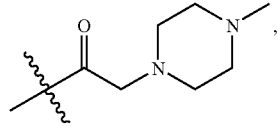

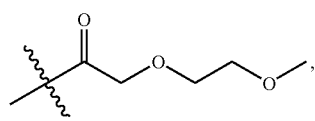

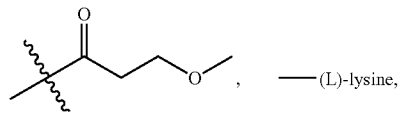

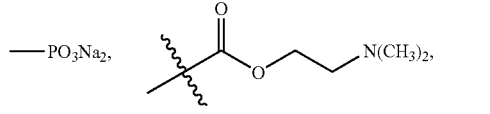

—PO$_3$Na$_2$, 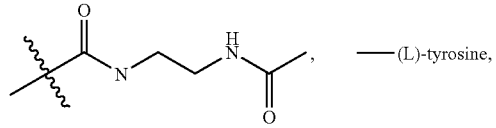

—(L)-tyrosine,

-continued

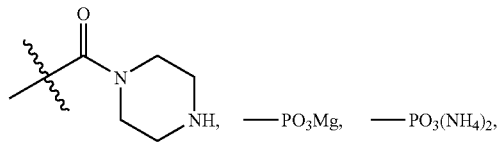, —PO$_3$Mg, —PO$_3$(NH$_4$)$_2$,

—CH$_2$—OPO$_3$Na, —(L)-serine,

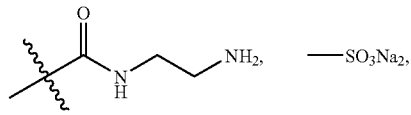, —SO$_3$Na$_2$,

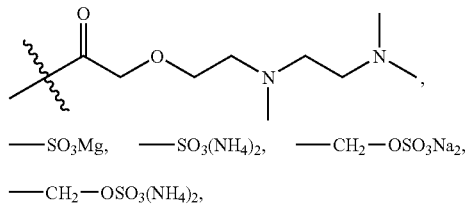

—SO$_3$Mg, —SO$_3$(NH$_4$)$_2$, —CH$_2$—OSO$_3$Na$_2$,

—CH$_2$—OSO$_3$(NH$_4$)$_2$,

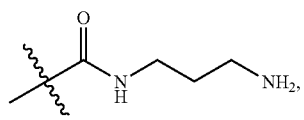

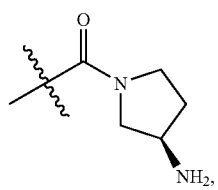

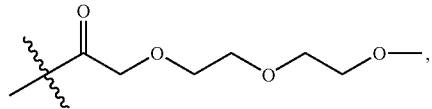

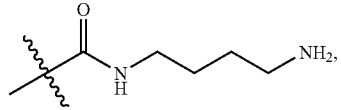

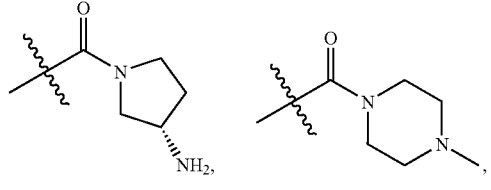

acetyl, 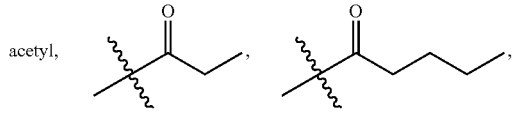

—(L)-valine, —(L)-glutamic acid, —(L)-aspartic acid,

—(L)-γ-tert-aspartic acid,

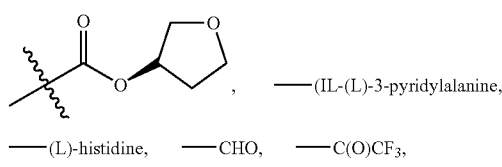, —(IL-(L)-3-pyridylalanine,

—(L)-histidine, —CHO, —C(O)CF$_3$,

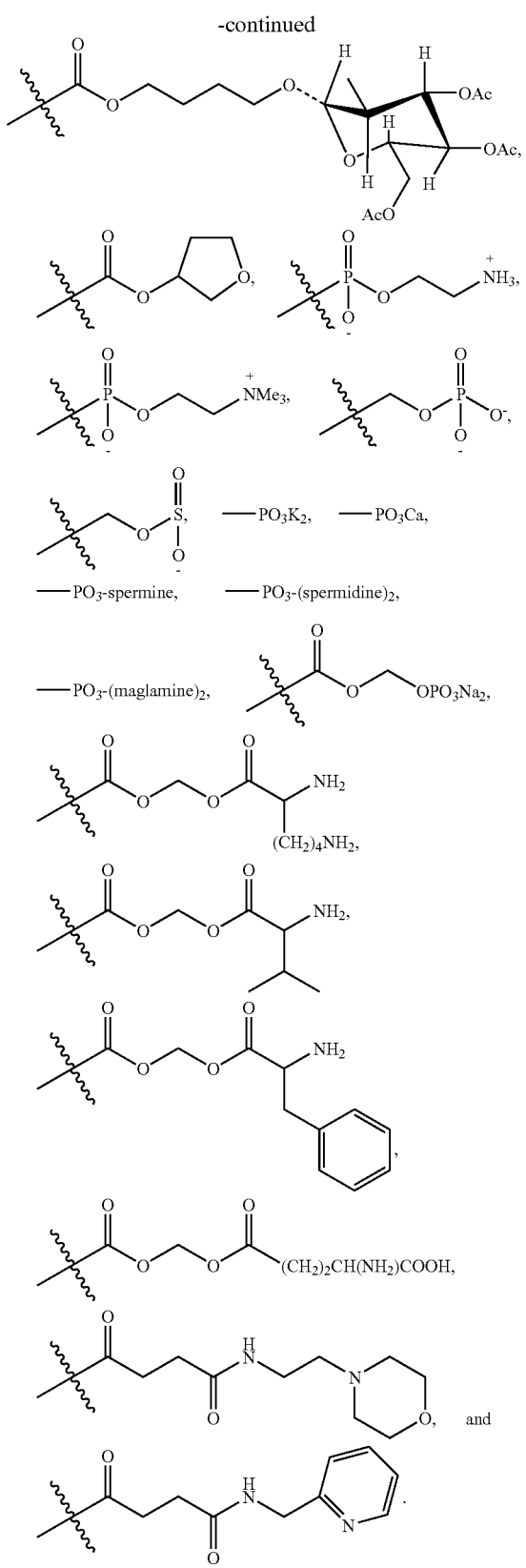

It will be understood by those of skill in the art that component M or M' in the formulae set forth herein will have either a covalent, a covalent/zwitterionic, or an ionic association with either Z" or $R_{103}$ depending upon the actual choice for M or M'. When M or M' is hydrogen, alkyl, alkenyl or $R_{106}$, then M or M', is covalently bound to $—R_{103}$ or Z". If M is a mono or bivalent metal or other charged species (i.e. $NH_4^+$), there is an ionic interaction between M and Z" and the resulting compound is a salt.

These prodrugs of the compound of the present invention serve to increase the solubility of these compounds in the gastrointestinal tract. These prodrugs also serve to increase solubility for intravenous administration of the compound. These prodrugs may be prepared by using conventional synthetic techniques. One of skill in the art would be well aware of conventional synthetic reagents to convert one or more of the hydroxy groups of the compounds of the present invention to a desired prodrug, functionalized by the substituents of formula (VI) or (VII) as defined above.

The prodrugs of this invention are metabolized in vivo to provide the compound of this invention.

The compounds of the invention are useful for inhibiting retroviral protease, in particular HIV protease, in vitro or in vivo (especially in mammals and in particular in humans). The compounds of the present invention are also useful for the inhibition of retroviruses in vivo, especially human immunodeficiency virus (HIV). The compounds of the present invention are also useful for the treatment or prophylaxis of diseases caused by retroviruses, especially acquired immune deficiency syndrome or an HIV infection in a human or other mammal.

Total daily dose administered to a human or other mammal host in single or divided doses may be in amounts, for example, from 0.001 to 300 mg/kg body weight daily and more usually 0.1 to 20 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically aceptable and metabolizable lipid capabale of forming liposomes can be used. The present compositions in liposome form can contain, in addition to the compound of the present invention, stabilizers, preservatives, excipients, and the like. The preferred lipids are the phospholipids and phosphatidyl cholines (lecithins), both natureal and synthetic.

Methods to form liposomes are known in the art. See, for example, Prescott, Ed., Methods in Cell Biology, Volume XIV, Academic Press, New York, N.Y. (1976), p. 33.

While the compound of the invention can be administered as the sole active pharmaceutical agent, it can also be used in combination with one or more immunomodulators, antiviral agents, other antiinfective agents or vaccines. Other antiviral agents to be administered in combination with a compound of the present invention include AL-721, beta interferon, polymannoacetate, reverse transcriptase inhibitors (for example, BCH-189, AzdU, carbovir, ddA, d4C, d4T (stavudine), 3TC (lamivudine) DP-AZT, FLT (fluorothymidine), BCH-189, 5-halo-3'-thia-dideoxycytidine, PMEA, bis-POMPMEA, zidovudine (AZT), MSA-300, trovirdine, R82193, L-697, 661, BI-RG-587 (nevirapine), abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120, and TMC-125 and the like), retroviral protease inhibitors (for example, HIV protease inhibitors such as ritonavir, lopinavir, saquinavir, amprenavir (VX-478), fosamprenavir, nelfinavir (AG1343), tipranavir, indinavir, atazanavir, TMC-126, TMC-114, mozenavir (DMP-450), JE-2147 (AG1776), L-756423, RO0334649, KNI-272, DPC-681, DPC-684, GW640385X, SC-52151, BMS 186,318, SC-55389a, BILA 1096 BS, DMP-323, KNI-227, and the like), HEPT compounds, L,697, 639, R82150, U-87201E and the like), HIV integrase inhibitors (S-1360, zintevir (AR-177), L-870812 L-870810 and the like), TAT inhibitors (for example, RO-24-7429 and the like), trisodium phosphonoformate, HPA-23, eflonithine, Peptide T, Reticulose (nucleophosphoprotein), ansamycin LM 427, trimetrexate, UA001, ribavirin, alpha interferon, oxetanocin, oxetanocin-G, cylobut-G, cyclobut-A, ara-M, BW882C87, foscarnet, BW256U87, BW348U87, L-693,989, BV ara-U, CMV triclonal antibodies, FIAC, HOE-602, HPMPC, MSL-109, TI-23, trifluridine, vidarabine, famciclovir, penciclovir, acyclovir, ganciclor, castanosperminem rCD4/CD4-IgG, CD4-PE40, butyl-DNJ, hypericin, oxamyristic acid, dextran sulfate and pentosan polysulfate. Other agents that can be administered in combination with the compound of the present invention include HIV entry/fusion inhibitor (for example, enfuvirtide (T-20), T-1249, PRO 2000, PRO 542, PRO 140, AMD-3100, BMS-806, FP21399, GW873140, Schering C (SCH-C), Schering D (SCH-D), TNX-355, UK-427857, and the like) and HIV budding/maturation inhibitor such as PA-457. Immunomodulators that can be administered in combination with the compound of the present invention include bropirimine, Ampligen, anti-human alpha interferon antibody, colony stimulting factor, CL246,738, Imreg-1, Imreg-2, diethydithiocarbamate, interleukin-2, alpha-interferon, inosine pranobex, methionine enkephalin, muramyl-tripeptide, TP-5, erythropoietin, naltrexone, tumor necrosis factor, beta interferon, gamma interferon, interleukin-3, interleukin-4, autologous CD8+ infusion, alpha interferon immunoglobulin, IGF-1, anti-Leu-3A, autovaccination, biostimulation, extracorporeal photophoresis, cyclosporin, rapamycin, FK-565, FK-506, G-CSF, GM-CSF, hyperthermia, isopinosine, IVIG, HIVIG, passive immunotherapy and polio vaccine hyperimmunization. Other antiinfective agents that can be administered in combination with the compound of the present invention include pentamidine isethionate. Any of a variety of HIV or AIDS vaccines (for example, gp120 (recombinant), Env 2-3 (gp120), HIVAC-1e (gp120), gp160 (recombinant), VaxSyn HIV-1 (gp160), Immuno-Ag (gp160), HGP-30, HIV-Immunogen, p24 (recombinant), VaxSyn HIV-1 (p24)) can be used in combination with the compound of the present invention.

Other agents that can be used in combination with the compound of this invention are ansamycin LM 427, apurinic acid, ABPP, AI-721, carrisyn, AS-101, avarol, azimexon, colchicine, compound Q, CS-85, N-acetyl cysteine, (2-oxothiazolidine-4-carboxylate), D-penicillamine, diphenylhydantoin, EL-10, erythropoieten, fusidic acid, glucan, HPA-23, human growth hormone, hydroxchloroquine, iscador, L-ofloxacin or other quinolone antibiotics, lentinan, lithium carbonate, MM-1, monolaurin, MTP-PE, naltrexone, neurotropin, ozone, PAI, panax ginseng, pentofylline, pentoxifylline, Peptide T, pine cone extract, polymannoacetate, reticulose, retrogen, ribavirin, ribozymes, RS-47, Sdc-28, silicotungstate, THA, thymic humoral factor, thymopentin, thymosin fraction 5, thymosin alpha one, thymostimulin, UA001, uridine, vitamin B12 and wobemugos.

Other agents that can be used in combination with the compound of this invention are antifungals such as amphotericin B, clotrimazole, flucytosine, fluconazole, itraconazole, ketoconazole and nystatin and the like.

Other agents that can be used in combination with the compound of this invention are antibacterials such as amikacin sulfate, azithromycin, ciprofloxacin, tosufloxacin, clarithromycin, clofazimine, ethambutol, isoniazid, pyrazinamide, rifabutin, rifampin, streptomycin and TLC G-65 and the like.

Other agents that can be used in combination with the compound of this invention are anti-neoplastics such as alpha interferon, COMP (cyclophosphamide, vincristine, methotrexate and prednisone), etoposide, mBACOD (methotrexate, bleomycin, doxorubicin, cyclophosphamide, vincristine and dexamethasone), PRO-MACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, pentosan polysulfate, platelet factor 4 and SP-PG and the like.

Other agents that can be used in combination with the compound of this invention are drugs for treating neurological disease such as peptide T, ritalin, lithium, elavil, phenyloin, carbamazipine, mexitetine, heparin and cytosine arabinoside and the like.

Other agents that can be used in combination with the compound of this invention are anti-protozoals such as albendazole, azithromycin, clarithromycin, clindamycin, corticosteroids, dapsone, DIMP, eflornithine, 566C80, fansidar, furazolidone, L,671,329, letrazuril, metronidazole, paromycin, pefloxacin, pentamidine, piritrexim, primaquine, pyrimethamine, somatostatin, spiramycin, sulfadiazine, trimethoprim, TMP/SMX, trimetrexate and WR 6026 and the like.

For example, a compound of this invention can be administered in combination with ritonavir. Such a combination is especially useful for inhibiting HIV protease in a human. Such a combination is also especially useful for inhibiting or treating an HIV infection in a human. When used in such a combination the compound of this invention and ritonavir can be administered as separate agents at the same or different times or they can be formulated as a single composition comprising both compounds.

When administered in combination with a compound, or combination of compounds of this invention, ritonavir causes an improvement in the pharmacokinetics (i.e., increases half-life, increases the time to peak plasma concentration, increases blood levels) of the compound of this invention.

Another combination can comprise of a compound, or combination of compounds of the present invention with ritonavir and one or more reverse transcriptase inhibitors (for example, lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150 TMC-120, TMC-125 and the like). Yet another combination can comprise of a compound, or combination of compounds of the present invention with ritonavir and one or more HIV entry/fusion inhibitors. Such combinations are useful for inhibiting or treating an HIV infection in a human. When used in such a combination the compound or combination of compounds of the present invention and ritonavir and one or more reverse transcriptase inhibitors or HIV entry/fusion inhibitors can be administered as separate agents at the same or different times or they can be formulated as compositions comprising two or more of the compounds.

It will be understood that agents which can be combined with the compound of the present invention for the inhibition, treatment or prophylaxis of AIDS or an HIV infection are not limited to those listed above, but include in principle any agents useful for the treatment or prophylaxis of AIDS or an HIV infection.

When administered as a combination, the therapeutic agents can be formulated as separate compositions which are given at the same time or different times, or the therapeutic agents can be given as a single composition.

Antiviral Activity

Determination of Activity Against Wild-Type HIV or the Passaged Variants

MT4 cells were infected with 0.003 multiplicity of infection (MOI) of wild-type HIV-1 or the passaged mutant variants at $1 \times 10^6$ cells/mL for 1 h, washed twice to remove unabsorbed virus and resuspended to $1 \times 10^5$ cells/mL of medium, seeded in a 96-well plate at 100 µL/well, and treated with an equal volume of solution of inhibitor in a series of half log dilutions in RPMI 1640 (Rosewell Park Memorial Institute) media (Gibco) containing 10% fetal bovine serum (FBS), in triplicate. The final concentration of DMSO in all wells was 0.5%. The virus control culture was treated in an identical manner except no inhibitor was added to the medium. The cell control was incubated in the absence of inhibitor or virus. Plates were incubated for 5 days in a $CO_2$ incubator at 37° C. On day 5, stock solution of 3-[4,5-dimethylthiazol-2-yl]-2,5-diphenyltetrazolium bromide (MTT) (4 mg/mL in PBS, Sigma cat. #M 5655) was added to each well at 25 µL per well. Plates were further incubated for 4 hrs, then treated with 20% sodium dodecyl sulfate (SDS) plus 0.02 N HCl at 50 µL per well to lyse the cells. After an overnight incubation, optical density (O.D.) was measured by reading the plates at 570/650 nm wavelengths on a Bio-Tek microtitre plate reader. Percent cytopathic effect (CPE) reduction was calculated from the formula below:

((O.D. test well–O.D. infected control well)/(O.D. uninfected control well–O.D. infected control well))×100

$EC_{50}$ values were determined from the plot of log (Fa/Fu) vs. log (compound concentration) using the median-effect equation (Chou, 1975, Proc. Int. Cong. Pharmacol. $6^{th}$ p. 619) wherein Fa is the fraction inhibited by the compound, and Fu is the fraction uninhibited (1-Fa).

When tested by the above method, the compounds of the present invention exhibit $EC_{50}$ in the range of 1 nM to 100 µM.

Determination of Anti-HIV Activity in the Presence of Human Serum

The above antiviral assay was performed in 96-well tissue culture plates containing 50% human serum (HS) (Sigma) plus 10% FBS (Gibco/BRL, Grand Island, N.Y.). Compounds were dissolved in DMSO, diluted at half log concentrations in DMSO, then transferred to media without serum at four times the final concentration. These solutions were added to 96 well plates at 50 µL per well, in triplicate. Cells were separately infected with 0.003 MOI of HIV-1 at $1 \times 10^6$ cells/mL for 1 h, washed twice to remove unadsorbed virus and resuspended to $2 \times 10^5$ cells/mL of media without serum. The cell suspension (50 µL) was seeded at $1 \times 10^4$ cells per well. Uninfected cells were included as control. Final DMSO concentration in all wells was 0.5% including uninfected and infected control wells. Cultures were incubated for 5 days in a $CO_2$ incubator at 37° C. $EC_{50}$ values were measured using MTT uptake as described above.

When tested by the above method, compounds of the present invention exhibit $EC_{50}$ in the range of 5 nM to 1 μM.

Generation of HIV-1 Resistant to ABT-378/r (A17) by In Vitro Passage

MT4 cells ($2\times10^6$ were infected with pNL4-3 at an MOI of 0.03 for 2 h, washed, then cultured in the presence of ABT-378 and ritonavir at concentration ratio of 5:1. The concentration of ABT-378 and ritonavir used in the initial passage was 1 nM and 0.2 nM respectively. Viral replication was monitored by determination of p24 antigen levels in the culture supernatant (Abbott Laboratories), as well as by observation for any cytopathic effect (CPE) present in the cultures. When p24 antigen levels were positive, the viral supernatant was harvested for the proceeding passage. Following each passage, the drug concentrations in the subsequent passage were gradually increased. After 5 months of selection, 1.5 μM of ABT-378 can be used in the final passage. The A17 virus was generated after 17 passages of pNL4-3 in the presence of ABT-378 and ritonavir at concentration ratio of 5:1.

When tested by the above method, compounds of the present invention inhibit the A17 virus with $EC_{50}$ in the range of 1 nM to 1 μM.

Synthetic Methods

Abbreviations which have been used in the descriptions of the scheme and the examples that follow are: DMF is N,N-dimethylformamide, DMSO is dimethylsulfoxide, THF is tetrahydrofuran, TEA is triethylamine, NMMO is 4-methylmorpholine N-oxide, HOBT is 1-hydroxybenzotriazole hydrate, DCC is 1,3-dicyclohexylcarbodiimide, EDAC is 1-(3-dimethylaminopropyl)-3-ethylcarbodiimide hydrochloride, DMAP is 4-(dimethylamino)pyridine, TFA is trifluoroacetic acid, DEPBT is 3-(diethoxyphosphoryloxy)-1,2,3-benzotriazin-4(3H)-one, DPPA is diphenylphosphine azide, NMM is N-methylmorpholine, DIBAL is diisobutyl aluminum hydride, EtOAc is ethyl acetate and TBAF is tetrabutyl ammonium fluoride.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. The groups A, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, X, Y, Z, Z', $R_a$, $R_b$, $R_c$ and n are as defined above unless otherwise noted below.

This invention is intended to encompass compounds having formula (I), (II), (III), (IV) or (V) when prepared by synthetic processes or by metabolic processes. Preparation of the compounds of the invention by metabolic processes includes those occurring in the human or animal body (in vivo) or processes occurring in vitro.

Compounds of the invention can be prepared according to the methods described in Schemes 1-3 as shown below.

Scheme 1

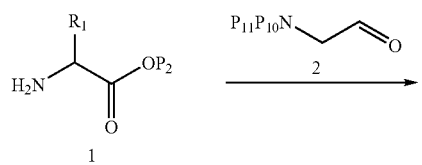

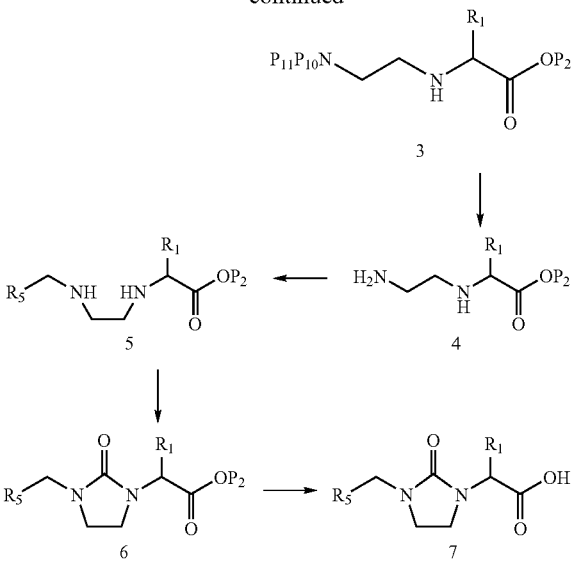

Amino acid esters of formula (1), wherein $P_2$ is lower alkyls (for example methyl, ethyl, tert-butyl and the like), can be treated with a suitably protected aldehyde of formula (2) (for example, $P_{10}$ and $P_{11}$ together with the nitrogen atom they are attached, form a phthalimido group) in the presence of a reducing agent under acidic conditions (for example, in the presence of acetic acid or hydrochloric acid) in an inert solvent, or mixture of solvents, such as DMSO, methanol, dichloromethane, and the like, at a temperature of about room temperature to about 50° C., to provide compounds of formula (3). Examples of the reducing agent include, but are not limited to, sodium triacetoxyborohydride, sodium borohydride, sodium cyanoborohydride, and $BH_3$-pyridine.

Removal of the phthalimido group can be achieved using hydrazine in a suitable solvent such as ethanol and the like, at a temperature of about room temperature to about 100° C., to provide compounds of formula (4).

Compounds of formula (4) can be converted to compounds of formula (5) by (a) treating compounds of formula (4) with an aldehyde having formula $R_5CHO$, optionally in the presence of a drying agent (for example, magnesium sulfate, silica gel and the like) in an inert solvent, or mixture of solvents, such as dichloromethane, benzene, toluene, methanol, ethanol, DMSO, and the like, at a temperature from about room temperature to about 100° C., and (b) reacting the product of step (a) with a reducing agent at about room temperature. Examples of the reducing agent include, but are not limited to, sodium triacetoxyborohydride, sodium borohydride, sodium cyanoborohydride, and $BH_3$-pyridine.

The diamine of formula (5) can be treated with a carbonylating agent in an inert solvent, or mixture of solvents, such as dichloromethane, 1,2 dichloroethane, toluene, acetonitrile, and the like, at a temperature of about room temperature to about 100° C., to provide compounds of formula (6). Examples of the carbonylating agent include, but not limited to, 4-nitrophenyl carbonate, phosphene, diphosgene, triphosgene, carbonyl diimidazole and disuccinimidyl carbonate.

Conversion of compounds of formula (6) to the corresponding acids having formula (7) can be achieved by acid hydrolysis (for example acetic acid, trifluoroacetic acid, toluenesulfonic acid, formic acid, hydrochloric acid and the like) or base hydrolysis (for example sodium hydroxide, potassium hydroxide, lithium hydroxide, cesium carbonate, and the like) in a solvent, or mixture of solvents such as DMF, toluene, benzene, dichloromethane, ethyl acetate, water, methanol and the like, at a temperature of about 0° C. to about 100° C.

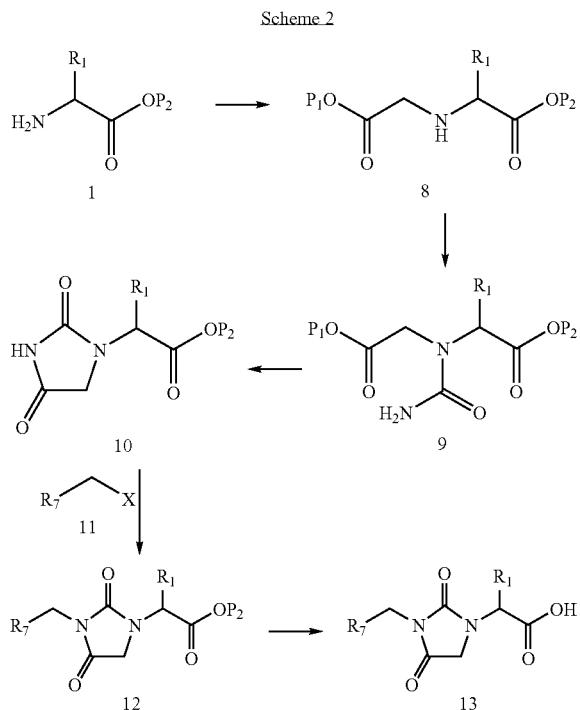

Amino acid esters having formula (1), wherein $P_2$ is lower alkyls (for example, methyl, ethyl, tert-butyl and the like) can be treated with compounds of formula $P_1OC(O)CH_2X$, wherein $P_1$ is lower alkyls and X is Br, Cl, or I, in an inert solvent, or mixture of solvents, such as DMF, dichloromethane, 1,2-dichloroethane, acetonitrile, toluene, benzene, diethyl ether and the like, at a temperature of about room temperature to about 50° C., to provide (8).

Compounds of formula (8) can be converted to compounds of formula (9) by (a) treating with chlorosulfonyl isocyanate (or compounds of formula $XSO_2NCO$, wherein X is Br, Cl, or I, and the like) in an inert solvent, or mixture of solvents, such as dichloromethane, 1,2-dichloroethane, dioxane, toluene, DMF, THF diethyl ether and the like, at a temperature of about −10° C. to about room temperature, and (b) treating the product of step (a) with water at about room temperature. Alternatively, (8) can be reacted with a carbonylating agent such as, but not are limited to, 4-nitrophenyl carbonate, phosphene, diphosgene, triphosgene, carbonyl diimidazole, disuccinimidyl carbonate, followed by reaction with ammonia.

Cyclization of the compounds of formula (9) to provide compounds of formula (10) can be achieved be treating with an organic amine base such as triethyl amine, diisopropylethyl amine, imidazole, pyridine, N-methylmorpholine and the like, or an inorganic base such as sodium bicarbonate, sodium carbonate, cesium carbonate and the like, in an inert solvent, or mixture of solvents, such as methanol, ethanol, DMF, dioxane, xylene, THF and the like, at a temperature of about room temperature to about 70° C.

Imides of formula (10) can be converted to compounds of formula (12) by (a) deprotonation with a base in an inert solvent, or mixture of solvents, such as dichloromethane, 1,2-dichloroethane, THF, diethyl ether, tert-butyl methyl ether, and the like, at a temperature of about −78 to about 0° C., and (b) treating product of step (a) with an alkyl halide of formula (11), wherein X is Cl, Br or I, at a temperature of about room temperature to about 100° C. Examples of the base include, but are not limited to, sodium hydride, potassium hydride, lithium diisopropyl amide, lithium bis(trimethylsilyl)amide.

Alternatively, compounds of formula (10) can be converted to compounds of formula (12) by treating with an alcohol having formula $R_7CH_2OH$, in the presence of triphenylphosphine and diethyl azodicarboxylate, in an inert solvent such as dichloromethane, THF, dioxane or DMF, at a temperature of about 0° C. to about 25° C.

Compounds of formula (12) can be converted to compounds of formula (13) using the conditions for the transformation of compounds of formula (6) to compounds of formula (7).

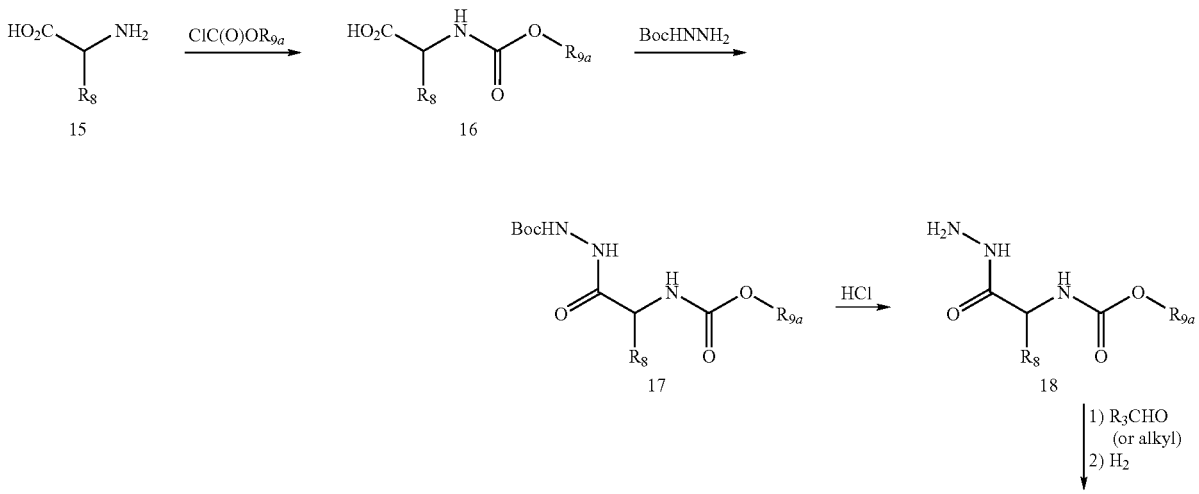

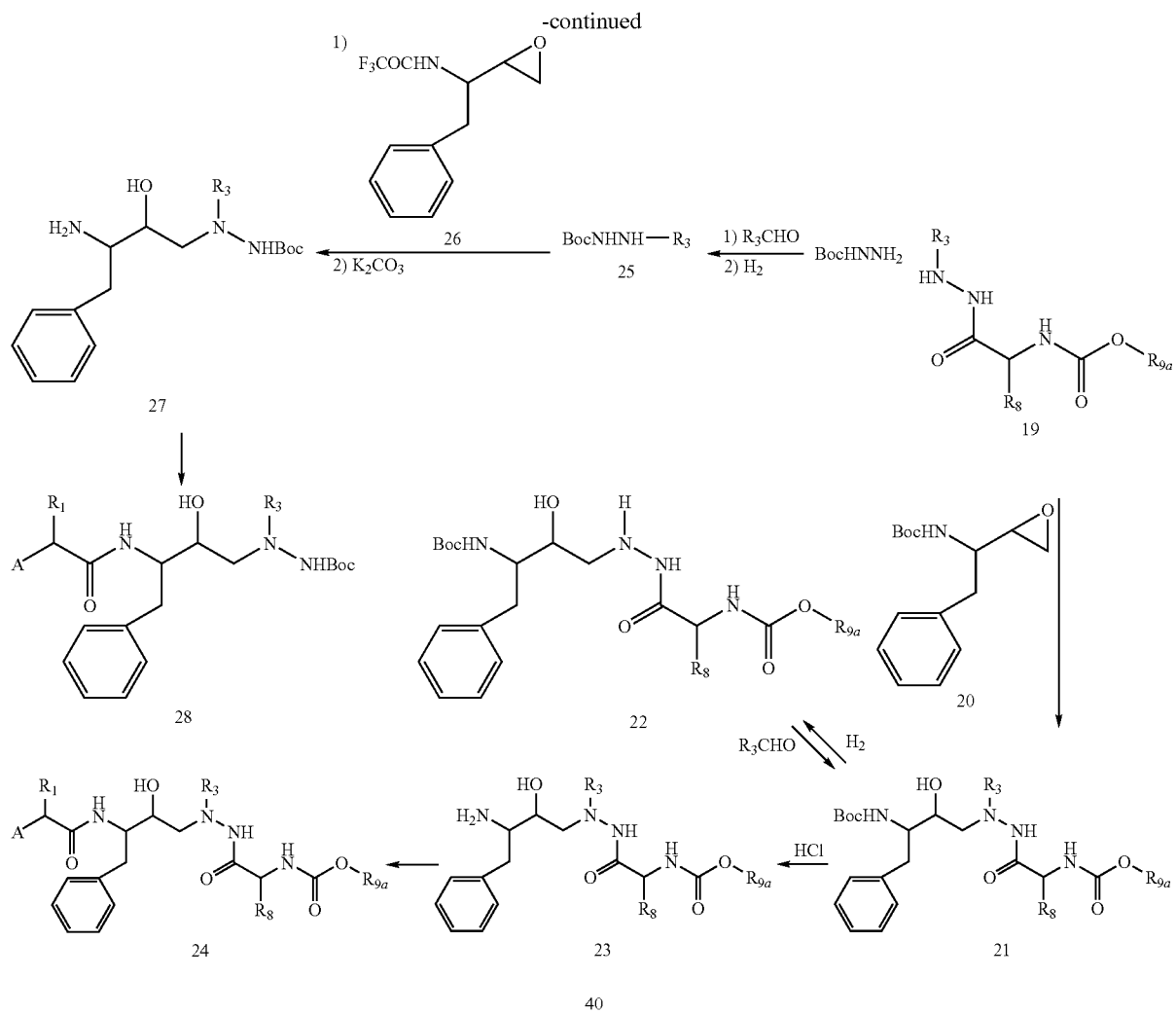

Compounds of formula (15) wherein $R_8$ is an alkyl or substituted alkyl residue can be treated with an organic amine base such as, but not limited to, triethylamine, diisobutylethylamine, pyridine, 2-methylimidazole, pyrrole and N-methylmorpholine, and a chloroformate of formula $R_{9a}OC(O)Cl$ (for example methyl chloroformate and the like) to give compounds of the formula (16). Compound (16) is treated with tert-butyl carbazate in the presence of an activating agent which includes, but is not limited to, 1,1'-carbonyldiimidazole (CDI), 1,3-dicyclohexylcarbodiimide (DCC), 1,3-diisopropylcarbodiimide, 1-(3-dimethylaminopropyl)-3-ethylcarbodiimide hydrochloride (EDAC), DEPBT (3-(diethoxyphosphoryloxy)-1,2,3-benzotriazin-4(3H)-one), PyBOP (benzotriazol-1-yl-oxy-tris-pyrrolidino-phosphoniumhexafluorophosphate), and 1,3-di-tert-butylcarbodiimide to afford compound of formula (17). Deprotection of compound (17) with acids such as, but not limited to, hydrochloric acid gives compound (18).

Treatment of compound (18) with an aldehyde having formula $R_3CHO$ provides a hydrazone which is in turn reduced with hydrogen gas using a metal catalyst such as, but not limited to, palladium, platinum, or rhodium on carbon in the presence of an alcoholic solvent such as methanol or ethanol, to give compound (19).

Epoxides of formula (20) can be treated with a hydrazine such as compound (19) in an alcoholic solvent such as, but not limited to, ethanol or methanol at a temperature of about 25° C. to about 80° C., to give compounds of formula (21). Compound (21) can be deprotected by using acids such as, but not limited to, hydrochloric acid to give compound (23). Alternatively compounds of formula (21) can be treated with hydrogen gas using a metal catalyst such as, but not limited to, palladium, platinum, or rhodium on carbon in the presence of an alcoholic solvent such as methanol or ethanol to give compound (22).

Compounds of formula (23) can also be obtained from compounds of formula (18) by (a) treating compounds of formula (18) with compounds of formula (20) to give compounds of formula (22), using the conditions for the transformation of (19) to (21), (b) treating compounds of formula (22) with an aldehyde of formula $R_3CHO$, optionally in the presence of drying agent (for example, magnesium sulfate, silica gel and the like) in an inert solvent, or mixture of solvents, such as dichloromethane, benzene, toluene, methanol, ethanol, methyl sulfoxide, and the like, at a temperature from about room temperature to about 100° C., and (c) reacting the product of step (b) with a reducing agent at about room temperature. Examples of the reducing agent include, but are not limited to, sodium triacetoxyborohydride, sodium borohydride, sodium cyanoborohydride, and $BH_3$-pyridine.

Tert-Butyl carbazate can be treated with aldehydes of formula $R_3CHO$ to form a hydrazone which is in turn reduced with hydrogen gas using a metal catalyst such as, but not limited to, palladium, platinum, or rhodium on carbon in the presence of an alcoholic solvent such as methanol or ethanol, to give compounds of formula (25). Compounds of formula (25) can be reacted with epoxides of formula (26) in an inert solvent such as, but not limited to, dichloromethane or dichloroethane, followed by treatment with bases such as, but not limited to, potassium carbonate to afford compounds of formula (27).

Compounds of formula (23) can be treated with carboxylic acids having formula AC(O)OH (examples of such carboxylic acids include compounds of formula (7), (13), and the like) or their salts, and an activating agent, optionally in the presence of 1-hydroxy-7-azabenzotriazole (HOAT), 1-hydroxybenzotriazole hydrate (HOBT) or 3-hydroxy-1,2,3-benzotriazin-4(3H)-one (HOOBT), and optionally in the presence of an inorganic base (for example, $NaHCO_3$, $Na_2CO_3$, $KHCO_3$, $K_2CO_3$, NaOH or KOH and the like) in an inert solvent (for example, 1:1 ethyl acetate/water or isopropyl acetate/water or toluene/water or THF/water and the like) at about room temperature, or an organic amine base (for example, imidazole, 1-methylimidazole, 2-methylimidazole, 2-isopropylimidazole, 4-methylimidazole, 4-nitroimidazole, pyridine, N,N-dimethylaminopyridine, 1,2,4-triazole, pyrrole, 3-methylpyrrole, triethylamine or N-methylmorpholine and the like) in an inert solvent (for example, ethyl acetate, isopropyl acetate, THF, toluene, acetonitrile, DMF, dichloromethane and the like) at a temperature of about 0° C. to about 50° C. to provide compounds of formula (24). Examples of the activating agent include, but are not limited to, 1,1'-carbonyldiimidazole (CDI), 1,3-dicyclohexylcarbodiimide (DCC), 1,3-diisopropylcarbodiimide, 1-(3-dimethylaminopropyl)-3-ethylcarbodiimide hydrochloride (EDAC), DEPBT (3-(diethoxyphosphoryloxy)-1,2,3-benzotriazin-4(3H)-one), PyBOP (benzotriazol-1-yl-oxy-tris-pyrrolidino-phosphoniumhexafluorophosphate), and 1,3-di-tert-butylcarbodiimide.

Alternatively, a salt or an activated ester derivative of acids of formula (7) or (13) (for example, the acid chloride, prepared by reaction of the carboxylic acid with thionyl chloride in ethyl acetate or THF or oxalyl chloride in toluene/DMF) can be reacted with compounds of formula (23).

Similarly, compounds of formula (27) can be treated with acids of formula AC(O)OH (for example acids of formula (7), (13), and the like) or their corresponding salts to provide compounds of formula (28).

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purpose of illustration of certain preferred embodiments and are presented to provide what is believed to be the most useful and readily understood description of its procedures and conceptual aspects.

It will be understood that the term "purification" used hereinafter, unless otherwise stated, means column chromatography using a silica gel column and eluting the column with a solvent system as specified in the experimental details.

Compounds of the invention were named by ACD/ChemSketch version 4.01 (developed by Advanced Chemistry Development, Inc., Toronto, ON, Canada) or were given names consistent with ACD nomenclature.

EXAMPLE 1 methyl (1S)-1-({2-[(2S,3S)-3-amino-2-hydroxy-4-phenylbutyl]-2-[4-(2-pyridinyl)benzyl] hydrazino}carbonyl)-2,2-dimethylpropylcarbamate

EXAMPLE 1A (2S)-2-[(methoxycarbonyl)amino]-3,3-dimethylbutanoic acid (L)-tert-Leucine (10 g, 0.076 mol) was dissolved in 1,4-dioxane (40 mL) and treated with 2M NaOH (125 mL, 3.2 equivalents) followed by dropwise addition of methyl chloroformate (11.2 mL, 1.9 equivalents) at 25° C. The mixture was heated at 60° C. for 22 hrs, cooled, and extracted twice with dichloromethane. The aqueous layer was separated, cooled in ice bath, and acidified with 4N HCl (60 mL). The mixture was extracted three times with ethyl acetate, and the organic layer was separated, dried with sodium sulfate, filtered, and the solvents were evaporated to give 14.1 g (98%) of the title compound.

EXAMPLE 1B tert-butyl 2-{(2S)-2-[(methoxycarbonyl)amino]-3,3-dimethylbutanoyl}hydrazinecarboxylate Example 1A (8 g, 42.3 mmol) was dissolved in DMF (200 mL) and treated with EDAC (11.96 g, 1.48 equivalent) and HOBT (8.8 g, 1.54 equivalents) at 25° C. After stirring this mixture for 15 min, t-butyl carbazate (6.1 g, 1.1 equivalent) was added, followed by N-methyl morpholine (8 mL, 1.72 equivalent) and stirring continued at 25° C. for 16 h. The mixture was quenched with 1N sodium bicarbonate and extracted twice with ethyl acetate. The solvents were evaporated, and the residue was purified using 30% ethyl acetate/hexanes to give 11.5 g (90%) of the title compound.

EXAMPLE 1C methyl (1S)-1-(hydrazinocarbonyl)-2,2-dimethylpropylcarbamate

Example 1B (11.5 g, 0.037 mol) was dissolved in THF (200 mL) and 4N HCl (70 mL) at 60° C. for 5 hrs. The solvents were evaporated to give 9.2 g (quant.) of the title compound as the hydrochloride salt.

EXAMPLE 1D methyl (1S)-2,2-dimethyl-1-({(2E)-2-[4-(2-pyridinyl)benzylidene]hydrazino}carbonyl)propylcarbamate Example 1C (9.2 g, 0.045 mol) was dissolved in 2-propanol (90 mL) and treated with 4 (2-pyridyl)benzaldehyde (7 g, 1 equivalent) for 10 min before heating to 80° C. for 4 hrs. The mixture was cooled, treated with hexanes (90 mL), and the solids were filtered and partitioned between 1N sodium bicarbonate and ethyl acetate. The organic layer was separated, dried with sodium sulfate, filtered, and the solvents were evaporated to give 12.8 g (91%) of the title compound.

EXAMPLE 1E methyl (1S)-2,2-dimethyl-1-({2-[4-(2-pyridinyl)benzyl]hydrazino}carbonyl)propylcarbamate Example 1D (6.4 g, 0.017 mol) was dissolved in methanol (64 mL) and treated with 10% Pd/C (0.64 g) and a hydrogen balloon at 25° C. for 16 hrs. The catalyst was filtered, and the solvents were evaporated. The solids were purified using 80% ethyl acetate/hexanes to give 10.7 g (83%) of the title compound.

EXAMPLE 1F tert-butyl (1S,2S)-1-benzyl-2-hydroxy-3-{2-{(2S)-2-[(methoxycarbonyl)amino]-3,3-dimethylbutanoyl}-1-[4-(2-pyridinyl)benzyl]hydrazino}propylcarbamate Example 1E (10.7 g, 0.029 mol) was dissolved in 2-propanol (30 mL) and hexanes (60 mL) and was combined with (2S,3S)-3-N-tert-butoxycarbonylamino-1,2-epoxy-4-phenylbutane (9.15 g, 1.2 equivalent) at 65° C. for 2.5 days. The solvents were evaporated, and the mixture was triturated with 40% ethyl acetate/hexanes (200 mL) and warmed to 60° C. for 4 min. The mixture was cooled and stirred at 25° C. for 30 min before filtering the white solids. The mother liquor was evaporated and purified using 80% ethyl acetate/hexanes to give another gram totaling 12 g (65%) of the title compound.

EXAMPLE 1G methyl (1S)-1-({2-[(2S,3S)-3-amino-2-hydroxy-4-phenylbutyl]-2-[4-(2-pyridinyl)benzyl]hydrazino}carbonyl)-2,2-dimethylpropylcarbamate Example 1F (12 g, 0.019 mol) was dissolved in THF (100 mL) and treated with 4N HCl (33 mL), and the mixture was heated at 60° C. for 4 h. The solvents was evaporated, the mixture was made alkaline with saturated sodium bicarbonate (220 mL), and was extracted twice with ethyl acetate. The organic layer was dried with $Na_2SO_4$ and the solvents were evaporated to give 9.5 g (94%) of the title compound.

EXAMPLE 2 methyl (1S)-1-{[2-[(2S,3S)-3-amino-2-hydroxy-4-phenylbutyl]-2-(4-methoxybenzyl)hydrazino]carbonyl}-2,2-dimethylpropylcarbamate

EXAMPLE 2A methyl (1S)-1-{[(2E)-2-(4-methoxybenzylidene)hydrazino]carbonyl}-2,2-dimethylpropylcarbamate p-Anisaldehyde (0.34 g, 2.5 mmol) was dissolved in isopropanol (2 mL) and treated with Example 1C (0.1 g, 1 equivalent) at 80° C. for 4 h. The mixture was partitioned between ethyl acetate and saturated sodium hydrosulfite, the organic layer was separated, washed with water, dried over sodium sulfate, filtered and the solvents were evaporated to give 0.69 g (86%) the title compound, used directly without purification.

EXAMPLE 2B methyl (1S)-1-{[2-(4-methoxybenzyl)hydrazino]carbonyl}-2,2-dimethylpropylcarbamate Example 2A (0.68 g, 2.1 mmol) was dissolved in dichloroethane (0.2 mL) and treated with sodium triacetoxyborohydride (0.86 g, 2 equivalent) and trifluoroacetic acid (25 uL, 1.5 equivalent) at 25° C. for 4 hrs. The solvents were evaporated and the crude residue was purified using ethyl acetate:hexanes (2:1)-ethyl acetate to give 0.4 g (57%) of the title compound.

EXAMPLE 2C tert-butyl (1S,2S)-1-benzyl-2-hydroxy-3-(1-(4-methoxybenzyl)-2-{(2S)-2-[(methoxycarbonyl)amino]-3,3-dimethylbutanoyl}hydrazino)propylcarbamate Example 2B (0.39 g, 1.23 mmol) was dissolved in isopropanol:hexanes (10 mL, 1:1) and treated with (2S,3S)-3-N-tert-butoxycarbonylamino-1,2-epoxy-4-phenylbutane (0.39 g, 1.1 equivalent) at 65° C. for 2 days. The solvents were evaporated, and the crude residue was crystallized using ethyl acetate:hexanes (1:1) to give 0.58 g (82%) of the title compound.

EXAMPLE 2D methyl (1S)-1-{[2-[(2S,3S)-3-amino-2-hydroxy-4-phenylbutyl]-2-(4-methoxybenzyl)hydrazino]carbonyl}-2,2-dimethylpropylcarbamate Example 2C (0.58 g, 0.99 mmol) was dissolved in THF (4.5 mL) and treated with 4N HCl (1.5 mL) at 60° C. for 3 h. The solvents were evaporated and the crude residue was partitioned between dichloromethane and saturated sodium bicarbonate. The organic layer was separated, dried over sodium sulfate and the solvents were evaporated to give 0.46 g (96%) of the crude title compound.

EXAMPLE 3 methyl (1S,2S)-1-{[2-[(2S,3S)-3-amino-2-hydroxy-4-phenylbutyl]-2-(4-bromobenzyl)hydrazino]carbonyl}-2-methylbutylcarbamate

EXAMPLE 3A (3S,4S)-3-[(methoxycarbonyl)amino]-4-methylhexanoic acid (L)-isoleucine (7.43 g, 57 mmol) was dissolved in dioxane (28 mL) and treated with 2N sodium hydroxide (93.5 mL, 3.3 equivalents) and methyl chloroformate (8.75 mL, 2 equivalents) at 60° C. for 16 hrs. The mixture was extracted with dichloromethane (2×). The mixture made acidic with 4N HCl, and extracted with ethyl acetate (3×), dried over sodium sulfate, filtered and the solvents were evaporated to give 8.6 g (80%) of the title compound.

EXAMPLE 3B tert-butyl 2-{(2S,3S)-2-[(methoxycarbonyl)amino]-3-methylpentanoyl}hydrazinecarboxylate Example 3A (0.54 g, 2.85 mmol) was dissolved in ethyl acetate (14 mL) and treated with EDAC (0.49 g, 1.1 equivalents), HOBT (0.42 g, 1.1 equivalents), NMM (0.48 mL, 1.2 equivalents), and t-butyl carbazate (0.45 g, 1.2 equivalents) at 25° C. for 16 hrs. The mixture was washed with saturated sodium bicarbonate, water, brine, dried over sodium sulfate, filtered and the solvents were evaporated. The crude residue was purified using dichloromethane-7% methanol/dichloromethane to give 0.77 g (89%) of the title compound.

EXAMPLE 3C methyl (1S,2S)-1-(hydrazinocarbonyl)-2-methylbutylcarbamate

Example 3B (0.86 g, 2.85 mmol) was dissolved in 4N HCl/dioxane (7.2 mL) at 25° C. for 2 hrs. The mixture was quenched with saturated sodium bicarbonate, and made basic with 1N sodium hydroxide. The mixture was extracted with dichloromethane, dried over magnesium sulfate, filtered and the solvents were evaporated to give 0.58 g (64%) of the title compound.

EXAMPLE 3D methyl (1S,2S)-1-{[2-(4-bromobenzyl)hydrazino]carbonyl}-2-methylbutylcarbamate Example 3C (0.32 g, 1.58 mmol) was dissolved in isopropanol (8 mL) and treated with 4-bromobenzaldehyde (0.29 g, 1 equivalent), and magnesium sulfate (0.95 g, 5 equivalent) at 80° C. for 3 hrs. The mixture was filtered, and the solvents were evaporated to give the crude imine which was dissolved in THF (8 mL) and treated with sodium cyanoborohydride (0.1 g, 1.05 equivalents) followed by toluenesulfonic acid (0.3 g, 1 equivalent) at 25° C. for 16 hrs. The mixture was quenched with saturated sodium bicarbonate, the organic layer was dried over sodium sulfate, filtered and the solvents were evaporated to give 0.36 g (61%) of the title compound.

EXAMPLE 3E tert-butyl (1S,2S)-1-benzyl-3-(1-(4-bromobenzyl)-2-{(2S,3S)-2-[(methoxycarbonyl)amino]-3-methylpentanoyl}hydrazino)-2-hydroxypropylcarbamate Example 3D (0.36 g, 0.96 mmol) was dissolved in isopropanol (4.8 mL) and treated with (2S,3S)-3-N-tert-butoxycarbonylamino-1,2-epoxy-4-phenylbutane (0.3 g, 1.2 equivalent) at 65° C. for 1 h. The mixture was heated to 50° C. for 2 days and cooled to room temperature. The solvents were evaporated, and the crude residue was purified using chloroform-3% methanol/chloroform to give 0.48 g (78%) of the title compound.

EXAMPLE 3F methyl (1S,2S)-1-{[2-[(2S,3S)-3-amino-2-hydroxy-4-phenylbutyl]-2-(4-bromobenzyl)hydrazino]carbonyl}-2-methylbutylcarbamate Example 3E (0.48 g, 0.755 mmol) was dissolved in THF (5 mL) and treated with 2N HCl (3.8 mL) at 50° C. for 16 hrs and cooled to room temperature. The solvents were concentrated, triturated with ethanol, and the solids were filtered and dried to give 0.4 g (97%) of the title compound.

EXAMPLE 4 tert-butyl 2-[(2S,3S)-3-amino-2-hydroxy-4-phenylbutyl]-2-[4-(2-pyridinyl)benzyl]hydrazinecarboxylate

EXAMPLE 4A tert-butyl (2E)-2-[4-(2-pyridinyl)benzylidene]hydrazinecarboxylate 4-(2-Pyridyl)benzaldehyde (15 g, 0.082 mol) was dissolved in ethanol (150 mL) and treated with t-butyl carbazate (10.3 g, 0.078 mol) at 80° C. for 4 h. The mixture was combined with water (200 mL), the solids were filtered, washed with water, and dried under vacuum to give 22.5 g (92%) of the title compound.

EXAMPLE 4B tert-butyl 2-[4-(2-pyridinyl)benzyl]hydrazinecarboxylate

Example 4A (15 g, 0.05 mol) was dissolved in methanol (100 mL) and treated with 10% Pd/C (1.5 g) and a hydrogen balloon for 4 h. The catalyst was filtered, and the solvents were evaporated to give 15 g (98%) of the title compound.

EXAMPLE 4C tert-butyl (1S)-1-benzyl-2-oxoethylcarbamate (S)—N-Bocphenylalaninol (5 g, 0.019 mol) was dissolved in dichloromethane (150 mL) and triethylamine (8.3 mL, 3 equivalents) at 0° C. and treated with a solution of pyridinesulfur trioxide complex (9.5 g, 3 equivalents) in DMSO (30 mL) over several minutes. After 1 h at 0° C., the mixture was added to ice water (200 mL). The dichloromethane was evaporated and the mixture was extracted with ether (100 mL, 4×). The organic layer was washed with 10% citric acid, water, saturated sodium bicarbonate, brine, dried over sodium sulfate, and the solvents were evaporated to give 5.3 g of the title compound.

EXAMPLE 4D tert-butyl (1S)-1-benzyl-2-propenylcarbamate

Triphenyl methylphosphonium bromide (13.1 g, 0.037 mol) was suspended in toluene (150 mL) and was treated with 1M potassium tert-butoxide in THF (28.8 mL, 0.8 equivalents) at 25° C. for 16 hrs. This solution was added dropwise to a suspension of Example 4C in toluene (100 mL) at −78° C. over 15 min. After 1.5 h, the mixture was warmed to 25° C. and partitioned between saturated ammonium chloride (100 mL) and ethyl acetate. The organic layer was washed with brine, dried over sodium sulfate, and the solvents were evaporated. The oil was redissolved in ether:hexanes (10 mL, 1:1) and filtered to remove triphenylphosphine oxide. The filtrate was evaporated and the crude residue was purified using ethyl acetate:hexanes (1:6) to give 2.4 g (49%) of the title compound.

EXAMPLE 4E (1S)-1-(2-oxiranyl)-2-phenyl-N-(trifluoromethyl)ethanamine

Example 4D (2.4 g, 9.7 mmol) was dissolved in 4N HCl/dioxane (18 mL) at 25° C. for 1 h. The solvents were evaporated. This residue was dissolved in dichloromethane (15 mL) and treated with pyridine (8 mL, 10 equivalents) and trifluoroacetic anhydride (3 g, 1.5 equivalents) at 25° C. for 1 h. The solvents were evaporated and the crude residue was partitioned between dichloromethane and saturated sodium bicarbonate. The organic layer was separated, dried over sodium sulfate and the solvents were evaporated to give 2.63 g crude olefin which was re-dissolved in dichloromethane (50 mL) and treated with m-chloroperbenzoic acid (8.36 g, 1.5 equivalents, 70%) at 0° C. The mixture was warmed to 25° C. over 16 hrs, diluted with ether (200 mL), and washed with 10% sodium sulfite, saturated sodium bicarbonate, brine, dried over sodium sulfate, and the solvents were evaporated. The crude residue was purified using chloroform-2% methanol/chloroform to give 1.5 g (59%) of the title compound.

EXAMPLE 4F tert-butyl 2-{(2S,3S)-2-hydroxy-4-phenyl-3-[(trifluoromethyl)amino]butyl}-2-[4-(2-pyridinyl)benzyl]hydrazinecarboxylate Example 4E (1.5 g, 5.8 mmol) was dissolved in isopropanol (22 mL) and treated with Example 4B (1.7 g, 1 equivalent) at 65° C. for 16 hrs. The solvents were evaporated and the crude residue was purified using 0-50% chloroform in ethyl acetate to give 0.86 g (28%) of the title compound.

EXAMPLE 4G tert-butyl 2-[(2S,3S)-3-amino-2-hydroxy-4-phenylbutyl]-2-[4-(2-pyridinyl)benzyl]hydrazinecarboxylate Example 4F (0.2 g, 0.36 mmol) was dissolved in methanol (3.7 mL) and treated with 10% potassium carbonate (1.5 mL) at 60° C. for 3 hrs. The mixture was diluted with chloroform and washed with brine, dried over magnesium sulfate, filtered and the solvents were evaporated. The crude residue was purified using chloroform—chloroform/5% methanol/0.2% ammonium hydroxide to give 0.17 g (100%) of the title compound.

EXAMPLE 5 methyl (1S)-1-({2-[(2S,3S)-3-amino-2-hydroxy-4-phenylbutyl]-2-benzylhydrazino}carbonyl)-2,2-dimethylpropylcarbamate

EXAMPLE 5A 1-({[2-(trimethylsilyl)ethoxy]carbonyl}oxy)-2,5-pyrrolidinedione

Trimethylsilylethanol (7.4 mL, 52 mmol) was dissolved in acetonitrile (260 mL) and treated with disuccinimoyl carbonate (20 g, 1.5 equivalents) and triethylamine (33 mL, 3 equivalents) at 25° C. for 16 h. The solvents were evaporated, and the residue was partitioned between ethyl acetate and saturated sodium bicarbonate, the organic layer was separated and washed with brine, dried over sodium sulfate, filtered and concentrated. The crude residue was triturated with ether to form a solid which was filtered and dried to give 11.12 g (82%) of the title compound.

EXAMPLE 5B 2-(trimethylsilyl)ethyl hydrazinecarboxylate

Hydrazine hydrate (1.87 mL, 38 mmol) was dissolved in THF (16 mL) at 0° C. and treated with Example 5A (2 g, 0.2 equivalent) in THF (7 mL) over 10 min. The mixture was warmed to 25° C. for 16 hrs and diluted with ethyl acetate and saturated sodium bicarbonate. The organic layer was washed with brine, dried over sodium sulfate and the solvents were evaporated to give 1.31 g (99%) of a crude oil which was redissolved in ethanol (14 mL) and treated with benzaldehyde (0.72 mL, 1 equivalent) at 25° C. for 2 days. The solvents were evaporated and the crude residue was partitioned between ethyl acetate and saturated sodium bicarbonate. The organic layer was separated, washed with brine, dried over sodium sulfate, filtered and the solvents were evaporated. The crude oil was crystallized by treatment with ether/hexane and filtered to give 1.85 g (99%) of the title compound.

EXAMPLE 5C 2-(trimethylsilyl)ethyl 2-benzylhydrazinecarboxylate

Example 5B (1.69 g, 6.4 mmol) was dissolved in THF (25 mL) and treated with sodium cyanoborohydride (0.48 g, 1.2 equivalents) followed by addition of a solution of toluenesulfonic acid (1.4 g, 1.2 equivalents) in THF (12 mL) at 25° C. for 1 day. The mixture was partitioned between ethyl acetate and saturated sodium bicarbonate, the organic layer was separated, washed with brine, dried over sodium sulfate, and the solvents were evaporated. The crude residue was dissolved in THF:methanol (10 mL, 5:1) and treated with 1N sodium hydroxide (35 mL) at 0° C. for 1 h. The mixture was extracted with ethyl acetate, the organic layer was separated, washed with brine, dried over sodium sulfate, filtered and the solvents were evaporated to give 1.74 g (100%) of the crude product.

EXAMPLE 5D 2-(trimethylsilyl)ethyl 2-benzyl-2-{(2S,3S)-3-[(tert-butoxycarbonyl)amino]-2-hydroxy-4-phenylbutyl}hydrazinecarboxylate Example 5C (1.7 g, 6.4 mmol) was dissolved in isopropanol (17 mL) and treated with (2S,3S)-3-N-tert-butoxycarbonylamino-1,2-epoxy-4-phenylbutane (1.68 g, 1 equivalent) at 65° C. for 16 hrs. The solvents were evaporated, and the crude residue was purified using hexane—8% acetone/hexane to give 1.61 g (48%) of the title compound.

EXAMPLE 5E tert-butyl (1S,2S)-1-benzyl-3-(1-benzylhydrazino)-2-hydroxypropylcarbamate Example 5D (1.42 g, 2.68 mmol) was dissolved in THF (26 mL) and treated with 1M tetrabutylammonium fluoride in THF (8.4 mL, 3 equivalents) at 25° C. for 1 h, followed by 50° C. for 3 h. The mixture was partitioned between chloroform and water, the organic layer was separated and washed with brine, dried over sodium sulfate, filtered and the solvents were evaporated to give 1.01 g (100%) of the title compound.

EXAMPLE 5F tert-butyl (1S,2S)-1-benzyl-3-(1-benzyl-2-{(2S)-2-[(methoxycarbonyl)amino]-3,3-dimethylbutanoyl}hydrazino)-2-hydroxypropylcarbamate A 0.2M solution of Example 5E (2 mL, 0.4 mmol) in THF was treated with Example 1A (79 mg, 1.1 equivalent), DEPBT (0.24 g, 2 equivalent), triethylamine (0.22 mL, 4 equivalent) at 25° C. for 16 hrs. The mixture was treated with 10% sodium carbonate and dichloromethane, the organic layer was separated, dried over sodium sulfate, filtered and the solvents were evaporated.

EXAMPLE 5G methyl (1S)-1-({2-[(2S,3S)-3-amino-2-hydroxy-4-phenylbutyl]-2-benzylhydrazino}carbonyl)-2,2-dimethylpropylcarbamate A solution of Example 5F in THF (4 mL) was treated with 4N HCl, and stirred at 70° C. for 3 hrs. The mixture was cooled to room temperature and quenched with saturated sodium bicarbonate and ethyl acetate. The organic layer was separated, washed with brine, dried over sodium sulfate, filtered and the solvents were evaporated to give 83 mg (100%) of the title compound.

EXAMPLE 6 methyl (1S,2S)-1-({2-[(2S,3S)-3-amino-2-hydroxy-4-phenylbutyl]-2-benzylhydrazino}carbonyl)-2-methylbutylcarbamate A solution of Example 5E (1.38 mL, 0.2 M solution in THF, 0.275 mmol) was treated with Example 3A (57 mg, 1.2 equivalents), DEPBT (99 mg, 1.2 equivalents), and triethylamine (92 uL, 2.4 equivalents) and stirred at 25° C. for 4 hrs. The mixture was treated with 10% sodium carbonate (2 mL) and dichloromethane. The organic layer was separated, washed with brine, dried over sodium sulfate, filtered and the solvents were evaporated. The crude residue was purified using ethyl acetate to give 79 mg (51%) of the crude product. This material was dissolved in THF (4 mL) and treated with 4N HCl (2 mL) at 70° C. for 3 hrs. The mixture was quenched with saturated sodium bicarbonate and ethyl acetate. The organic layer was separated, washed with brine, dried over sodium sulfate, filtered and the solvents were evaporated to give 65 mg (100%) of the title compound.

EXAMPLE 7A tert-butyl 2-{(2S,3S)-3-[(tert-butoxycarbonyl)amino]-2-hydroxy-4-phenylbutyl}-2-[4-(2-pyridinyl)benzyl]hydrazinecarboxylate A solution of Example 4B (0.84 g, 2.8 mmol) in isopropanol (9 mL) was treated with (2S,3S)-3-N-tert-butoxycarbonylamino-1,2-epoxy-4-phenylbutane (0.74 g, 1 equivalent), stirred at 65° C. for 16 hrs and cooled to room temperature. The mixture was partitioned between water and dichloromethane. The organic layer was separated, dried over sodium sulfate, filtered and the solvents were concentrated. Ether was added to precipitate the solid which was filtered to give 0.8 g (57%) of the title compound.

EXAMPLE 7B tert-butyl (1S,2S)-1-benzyl-2-hydroxy-3-{1-[4-(2-pyridinyl)benzyl]hydrazino}propylcarbamate A solution of Example 7A (0.6 g, 1.1 mmol) in THF (5.3 mL) was treated with 4N HCl (1.9 mL), stirred at 60° C. for 3 hrs, and cooled to room temperature. The solvents were evaporated, and the residue was azeotroped with ethanol twice to give 0.6 g (100%) of the hydrochloride salt of the title compound. This salt was dissolved in THF (20 mL) and treated with sodium bicarbonate (0.43 g, 4 equivalents) in water (5 mL) and $Boc_2O$ (0.295 µL, 1 equivalent) at 25° C. for 3 hrs. The solvents were evaporated, and the crude residue was partitioned between chloroform and water. The organic layer was separated, washed with brine, dried over sodium sulfate, filtered and the solvents were evaporated. The crude residue was purified using 2% methanol/chloroform to give 0.357 g (72%) of the title compound.

EXAMPLE 7C tert-butyl (1S,2S)-1-benzyl-2-hydroxy-3-{2-{(2S,3S)-2-[(methoxycarbonyl)amino]-3-methylpentanoyl}-1-[4-(2-pyridinyl)benzyl]hydrazino}propylcarbamate A solution of Example 7B (0.36 g, 0.77 mmol) in dichloromethane (5 mL) was treated with O-(1,2-dihydro-2-oxo-1-pyridyl)-N,N,N',N'-tetramethyluronium tetrafluoroborate (TPTU) (0.344 g, 1.5 equivalent), and diisopropylethyl amine (0.4 µL, 3 equivalents) at 0° C. over 20 min. A solution of Example 3A (0.22 g, 1.5 equivalent) in dichloromethane (5 mL) was added at 0° C. and the mixture was stirred at 25° C. for 16 hrs. The mixture was washed with water, 10% sodium bicarbonate, brine, the organic layer was separated, dried over sodium sulfate, filtered and the solvents were evaporated. The crude residue was purified using 1% methanol/chloroform to give 0.37 g (76%) of the title compound.

EXAMPLE 7D methyl (1S,2S)-1-({2-[(2S,3S)-3-amino-2-hydroxy-4-phenylbutyl]-2-[4-(2-pyridinyl)benzyl]hydrazino}carbonyl)-2-methylbutylcarbamate A solution of Example 7C (0/37 g, 0.59 mmol) in THF (4 mL) was treated with 4N HCl (1 mL), stirred at 60° C. for 3 hrs and cooled to room temperature. The solvents were evaporated, and the crude residue was partitioned between ethyl acetate and 10% sodium bicarbonate. The organic layer was separated and washed with brine, dried over sodium sulfate, filtered and the solvents were evaporated to give 0.28 g (89%) of the title compound.

EXAMPLE 8

(2S)—N'-[(2S,3S)-3-amino-2-hydroxy-4-phenylbutyl]-5-oxo-N-[4-(2-pyridinyl)benzyl]-2-pyrrolidinecarbohydrazide (L)-Pyroglutamic acid (14 mg, 0.11 mmol) was dissolved in THF (1.1 mL) and treated with Example 7B (50 mg, 1 equivalent), triethylamine (0.11 mL, 7 equivalent), and DEPBT (48 mg, 1.5 equivalents) at 25° C. for 16 hrs. The mixture was partitioned between ethyl acetate and 10% potassium carbonate, the organic layer was separated, washed with brine, dried over magnesium sulfate, filtered and the solvents were evaporated. The crude residue was purified using 0-10% methanol/chloroform to give 31 mg (48%) of the title compound. This material (28 mg, 0.049 mmol) was dissolved in dichloromethane:trifluoroacetic acid (0.6 mL, 1:1) at 25° C. for 2 hrs, and the solvents were evaporated to give 23 mg (100%) of the title compound as the trifluoroacetic acid salt.

The compounds listed in Table 1, wherein $X_4$ represents the point of connection to the core structure (A), were prepared by the procedures as exemplified in Example 8, substituting the corresponding acids for (L)-pyroglutamic acid:

TABLE 1

(A)

| Ex. | $R_4$ |
|---|---|
| 9 | (3-acyl-4,4-dimethyl-γ-butyrolactone structure) |
| 10 | (4-methyl-oxazolidinone-acyl structure) |
| 11 | (2-oxopyrrolidinyl-propanoyl structure) |
| 12 | (2-oxoimidazolidinyl-2-methylbutanoyl structure) |

TABLE 1-continued (A)

| Ex. | $R_4$ |
|---|---|
| 13 | (2-oxoimidazolidinyl-3,3-dimethylbutanoyl structure) |

EXAMPLE 14

(3R)-2-oxotetrahydro-3-furanyl 2-[(2S,3S)-3-amino-2-hydroxy-4-phenylbutyl]-2-[4-(2-pyridinyl)benzyl] hydrazinecarboxylate

EXAMPLE 14A

1-[({[(3R)-2-oxotetrahydro-3-furanyl]oxy}carbonyl) oxy]-2,5-pyrrolidinedione (R)-alpha-Hydroxybutyrolactone (8 μL, 0.11 mmol) was dissolved in acetonitrile (0.5 mL) and treated with triethylamine (45 μL, 1.5 equivalents), and disuccinimidyl carbonate (42 mg, 1.5 equivalent) at 25° C. for 16 hrs. The solvents were evaporated and the residue was partitioned between ethyl acetate and saturated sodium bicarbonate, the organic layer was separated, washed with brine, dried over magnesium sulfate, filtered and evaporated.

EXAMPLE 14B (3R)-2-oxotetrahydro-3-furanyl 2-[(2S,3S)-3-amino-2-hydroxy-4-phenylbutyl]-2-[4-(2-pyridinyl)benzyl] hydrazinecarboxylate A solution of Example 7B (50 mg, 0.11 mmol) in THF (1 mL) was treated with triethylamine (80 uL, 5 equivalent) and Example 14A (26 mg, 1 equivalent), stirred at 50° C. for 2 h and cooled to room temperature. The mixture was evaporated and purified using 20% chloroform/ethylacetate to give 23 mg (35%) of the title compound. This material was dissolved in dichloromethane:trifluoroacetic acid (0.4 mL, 1:1), stirred at 25° C. for 1 h, and the solvents were evaporated to give 23 mg (100%) of the title compound as the trifluoroacetic acid salt.

EXAMPLE 15

(3S)-2-oxotetrahydro-3-furanyl 2-[(2S,3R)-3-amino-2-hydroxy-4-phenylbutyl]-2-[4-(2-pyridinyl)benzyl]hydrazinecarboxylate Example 15 was prepared using the procedures of Examples 14A and 14B, substituting (S)-alpha-hydroxybutyrolactone for (R)-alpha-hydroxybutyrolactone.

EXAMPLE 16

(3R)-4,4-dimethyl-2-oxotetrahydro-3-furanyl 2-[(2S,3S)-3-amino-2-hydroxy-4-phenylbutyl]-2-[4-(2-pyridinyl)benzyl]hydrazinecarboxylate Example 16 was prepared using the procedures of Examples 14A and 14B, substituting (R)-alpha-pantolactone for (R)-alpha-hydroxybutyrolactone.

EXAMPLE 17

(3S)-4,4-dimethyl-2-oxotetrahydro-3-furanyl 2-[(2S,3S)-3-amino-2-hydroxy-4-phenylbutyl]-2-[4-(2-pyridinyl)benzyl]hydrazinecarboxylate Example 17 was prepared using the procedures of Examples 14A and 14B, substituting (S)-alpha-pantolactone for (R)-alpha-hydroxybutyrolactone.

EXAMPLE 18 methyl (1S)-1-({2-[(2S,3S)-3-amino-2-hydroxy-4-phenylbutyl]-2-benzylhydrazino}carbonyl)-2-methylpropylcarbamate

EXAMPLE 18A (2S)-2-[(methoxycarbonyl)amino]-3-methylbutanoic acid

A solution of (L)-Valine (7.43 g, 57 mmol) in dioxane (28 mL) was treated with 2N sodium hydroxide (93.5 mL, 3.3 equivalents) and methyl chloroformate (8.75 mL, 2 equivalents), stirred at 60° C. for 16 hrs and cooled to room temperature. The mixture was extracted with dichloromethane (2×). The mixture was acidified with 4N HCl, and extracted with ethyl acetate (3×), dried over sodium sulfate, filtered and the solvents were evaporated to give 8.6 g (80%) of the title compound.

EXAMPLE 18B methyl (1S)-2-methyl-1-({2-[4-(2-pyridinyl)benzyl]hydrazino}carbonyl)propylcarbamate A solution of Example 4B (0.18 g, 0.6 mmol) in dichloromethane:trifluoroacetic acid (4 mL, 1:1) was stirred at 25° C. for 1 h, and the solvents were evaporated. This material was dissolved in THF (1 mL) and treated with diisopropylethyl amine (0.31 mL, 3 equivalents), DEPBT (0.36 g, 2 equivalents), and Example 18A (0.105 g, 1 equivalent), stirred at 25° C. for 3 h. The mixture was partitioned between dichloromethane and 10% sodium carbonate, the organic layer was separated, washed with brine, dried over sodium sulfate, filtered and the solvents were evaporated. The crude residue was purified using 2% methanol/chloroform to give 0.1 g (47%) of the title compound.

EXAMPLE 18C tert-butyl (1S,2S)-1-benzyl-2-hydroxy-3-{2-{(2S)-2-[(methoxycarbonyl)amino]-3-methylbutanoyl}-1-[4-(2-pyridinyl)benzyl]hydrazino}propylcarbamate A solution of Example 18B (0.1 g, 0.28 mmol) in hexane:isopropanol (6 mL, 1:1) was treated with (2S,3S)-3-N-tert-butoxycarbonylamino-1,2-epoxy-4-phenylbutane (75 mg, 1 equivalent), stirred at 70° C. for 2 days and cooled to room temperature. The solvents were evaporated, and the crude residue was purified using 2% methanol/chloroform to give 0.11 g (63%) of the title compound.

EXAMPLE 18D methyl (1S)-1-({2-[(2S,3S)-3-amino-2-hydroxy-4-phenylbutyl]-2-[4-(2-pyridinyl)benzyl]hydrazino}carbonyl)-2-methylpropylcarbamate A solution of Example 18C (0.11 g, 0.18 mmol) in THF (2 mL) was treated with 4N HCl (0.3 mL), stirred at 60° C. for 3 hrs and cooled to room temperature. The mixture was concentrated, neutralized with 10% sodium bicarbonate, and extracted with ethyl acetate, the organic layer washed with brine, dried over sodium sulfate, filtered and the solvents were evaporated to give 92 mg (100%) of the title compound.

EXAMPLE 19 methyl (1S)-1-[(2-[(2S,3S)-3-amino-2-hydroxy-4-phenylbutyl]-2-{[2-(5-methyl-3-isoxazolyl)-1,3-thiazol-4-yl]methyl}hydrazino)carbonyl]-2,2-dimethylpropylcarbamate

EXAMPLE 19A tert-butyl (1S,2S)-1-benzyl-2-hydroxy-3-(2-{(2S)-2-[(methoxycarbonyl)amino]-3,3-dimethylbutanoyl}hydrazino)propylcarbamate A solution of Example 5F (0.115 g, 0.2 mmol) in methanol (2 mL) was treated with Pd(OH)$_2$ (38 mg) and 4N HCl (52 μL, 1 equivalent) and a hydrogen balloon at 25° C. for 3.5 hrs. The solvents were evaporated, and the crude residue was partitioned between ethyl acetate and saturated sodium bicarbonate. The organic layer was separated, washed with brine, dried over sodium sulfate and the solvents were evaporated to give 90 mg (93%) of the title compound.

EXAMPLE 19B tert-butyl (1S,2S)-1-benzyl-2-hydroxy-3-(2-{(2S)-2-[(methoxycarbonyl)amino]-3,3-dimethylbutanoyl}-1-{[2-(5-methyl-3-isoxazolyl)-1,3-thiazol-4-yl]methyl}hydrazino)propylcarbamate A solution of Example 19A (0.4 g, 0.86 mmol) in dichloroethane (5.7 mL) was treated with acetic acid (99 μL, 2 equivalents), 2-(5-methyl-3-isoxazolyl)thiazole 4-carboxaldehyde (0.199 g, 1.2 equivalents), and sodium triacetoxyborohydride (0.545 g, 3 equivalents) and stirred at 25° C. for 16 hrs. The mixture was diluted with dichloromethane and saturated sodium bicarbonate. The organic layer was separated, washed with brine, dried over magnesium sulfate, filtered and the solvents were evaporated. The crude residue was purified by HPLC reverse phase chromatography using water (0.1% trifluoroacetic acid):acetonitrile (95:5) to acetonitrile (100%) to give 0.55 g (60%) of the title compound.

EXAMPLE 19C methyl (1S)-1-[(2-[(2S,3S)-3-amino-2-hydroxy-4-phenylbutyl]-2-{[2-(5-methyl-3-isoxazolyl)-1,3-thiazol-4-yl]methyl}hydrazino)carbonyl]-2,2-dimethylpropylcarbamate A solution of Example 19B (0.268 g, 0.42 mmol) in THF (2.1 mL) was treated with 4N HCl (0.7 mL), stirred at 60° C. for 3 hrs and cooled to room temperature. The solvents were evaporated to give 0.2 g (100%) of the trifluoroacetic acid salt of the title compound.

The compounds listed in Table 2, wherein $X_3$ represents the point of connection to the core structure (B), were prepared by the procedures as exemplified in Examples 19B and 19C, substituting the corresponding aldehydes for 2-(5-methyl-3-isoxazolyl)thiazole 4-carboxaldehyde:

TABLE 2

| Ex. | $R_3$ |
|---|---|
| 20 | 4-[thiazol-2-(2-pyridyl)]methyl |
| 21 | isopentyl (CH(CH3)CH2-) |
| 22 | (2,3-dihydro-1,4-benzodioxin-6-yl)methyl |
| 23 | 3,3-dimethylbutyl |
| 24 | 4-(N,N-diethylamino)benzyl |
| 25 | [2-(3-pyridyl)thiazol-4-yl]methyl |

EXAMPLE 26 methyl (1S,2S)-1-({2-[(2S,3S)-3-amino-2-hydroxy-4-phenylbutyl]-2-benzylhydrazino}carbonyl)-2-methylbutylcarbamate

EXAMPLE 26A methyl (1S,2S)-1-[(2-benzylhydrazino)carbonyl]-2-methylbutylcarbamate A solution of Example 3A (3.32 g, 17.5 mmol) in THF (70 mL) was treated with benzylhydrazine di-HCl salt (3.42 g, 1 equivalent), diisopropylethyl amine (9.2 mL, 3 equivalents), EDAC (6.05 g, 1.8 equivalents), and HOBT (3.56 g, 1.5 equivalents), and stirred at 25° C. for 16 hrs. The solvents were evaporated, and the crude residue was partitioned between chloroform and 10% sodium bicarbonate. The organic layer was separated, washed with 10% sodium bicarbonate, brine, dried over sodium sulfate, filtered and the solvents were evaporated. The crude residue was purified using 1% methanol/chloroform to give 2.41 g (47%) of the title compound.

EXAMPLE 26B tert-butyl (1S,2S)-1-benzyl-3-(1-benzyl-2-{(2S,3S)-2-[(methoxycarbonyl)amino]-3-methylpentanoyl}hydrazino)-2-hydroxypropylcarbamate A solution of Example 26A (2.41 g, 8.2 mmol) in isopropanol:hexane (42 mL, 1:1) was treated with (2S,3S)-3-N-tert-butoxycarbonylamino-1,2-epoxy-4-phenylbutane (2.19 g, 1 equivalent), stirred at 65° C. for 16 hrs and cooled to room temperature. The mixture was combined with brine and extracted thrice with chloroform. The organic layers were combined and washed with brine, dried over sodium sulfate, filtered and the solvents were evaporated. The crude residue was purified using 2% methanol/chloroform to give 4.57 g (100%) of the title compound.

EXAMPLE 26C methyl (1S,2S)-1-({2-[(2S,3S)-3-amino-2-hydroxy-4-phenylbutyl]-2-benzylhydrazino}carbonyl)-2-methylbutylcarbamate A solution of Example 26B (4.57 g, 8.2 mmol) in THF (60 mL) was treated with 4N HCl (14.4 mL). stirred at 60° C. for 3 hrs, and cooled to room temperature. The solvents were evaporated, and the crude residue was partitioned between ethyl acetate and 10% sodium bicarbonate. The organic layer was separated, washed with 10% sodium bicarbonate, brine, dried over sodium sulfate, filtered and the solvents were evaporated to give 3.41 g (89%) of the title compound.

EXAMPLE 27 methyl (1S,2S)-1-{[2-[(2S,3S)-3-amino-2-hydroxy-4-phenylbutyl]-2-(4-methoxybenzyl)hydrazino]carbonyl}-2-methylbutylcarbamate

EXAMPLE 27A tert-butyl (1S,2S)-1-benzyl-2-hydroxy-3-(1-(4-methoxybenzyl)-2-{(2S,3S)-2-[(methoxycarbonyl)amino]-3-methylpentanoyl}hydrazino)propylcarbamate A solution of Example 26B (1.2 g, 2.2 mmol) in methanol (7 mL) was treated with Pd(OH)$_2$ (0.24 g), 4N HCl (0.54 mL), stirred under a hydrogen balloon at 25° C. for 16 hrs. The catalyst was filtered, washed with methanol, and the solvents were evaporated to give 1 g (100%) of the crude product used directly for the next step. This material (0.5 g, 1.1 mmol) was dissolved in dichloroethane (4 mL) and treated with acetic acid (0.12 mL, 2 equivalent), sodium triacetoxyborohydride (0.57 g, 2.5 equivalent), and p-anisaldehyde (0.26 mL, 2 equivalents) at 25° C. for 16 hrs. The mixture was quenched with 10% sodium bicarbonate and chloroform. The organic layer was separated, washed with brine, dried over sodium sulfate, filtered and the solvents were evaporated. The crude residue was purified using 1% methanol/chloroform to give 0.38 g (60%) of the title compound.

EXAMPLE 27B methyl (1S,2S)-1-{[2-[(2S,3S)-3-amino-2-hydroxy-4-phenylbutyl]-2-(4-methoxybenzyl)hydrazino]carbonyl}-2-methylbutylcarbamate Example 27A (0.38 g, 0.6 mmol) was dissolved in THF (5 mL) was treated with 4N HCl (1.1 mL), stirred at 60° C. for 3 hrs and cooled to room temperature. The solvents were evaporated, and the residue was triturated with ethanol, filtered and dried to give 0.29 g (100%) of the title compound.

EXAMPLE 28

(2S,3S)-3-methyl-2-{3-[(6-methyl-2-pyridinyl)methyl]-2-oxo-1-imidazolidinyl}pentanoic Acid

EXAMPLE 28A (1,3-dioxo-1,3-dihydro-2H-isoindol-2-yl)acetaldehyde

To a solution of phthalimide diethylacetal (15 g) in tetrahydrofuran (THF) (30 mL) was added 10% aqueous HCl (18 mL). After heating at 75° C. for 5 hrs, the solution was allowed to cool to room temperature, and ethyl acetate was separated and dried over magnesium sulfate (MgSO$_4$). The solution was filtered and evaporated to provide 11.2 g of the titled compound.

EXAMPLE 28B tert-butyl (2S,3S)-2-{[2-(1,3-dioxo-1,3-dihydro-2H-isoindol-2-yl)ethyl]amino}-3-methylpentanoate To a solution of Example 28A (12.1 g) in methanol (20 mL) was added L-isoleucine tert-butyl ester hydrochloride (13.0 g, 58 mmol), sodium cyanoborohydride (7.3 g, 116 mmol), and acetic acid (2 mL). The resulting solution was stirred for 3 hrs at 25° C. and the methanol removed under vacuum, dichloromethane (500 mL) added, and the solution washed with aqueous NaHCO$_3$ (2×300 mL). The organic layer was concentrated to give 12.9 g of the title compound.

EXAMPLE 28C tert-butyl (2S,3S)-2-[(2-aminoethyl)amino]-3-methylpentanoate

To a solution of Example 28B (12.9 g) in ethanol (400 mL) was added hydrazine hydrate (11.2 mL). The solution was then heated to 70° C. for 2 hrs. After cooling to 25° C., the resulting solid was dissolved in 1N NaOH solution (200 mL) and water (200 mL). The solution was then extracted with dichloromethane (3×200 mL), the organic extracts combined, dried and evaporated to provide 6.8 g of the title compound.

EXAMPLE 28D tert-butyl (2S,3S)-3-methyl-2-[(2-{[(6-methyl-2-pyridinyl)methyl]amino}ethyl)amino]pentanoate 6-Methyl-2-pyridinecarboxaldehyde (4.25 g) was dissolved in dichloromethane (80 mL) and combined with Example 28C (8 g, 1 equivalent) and MgSO$_4$ (15 g), and the mixture was stirred at 25° C. for 2.5 hrs. The mixture was filtered, rinsed with dichloromethane, and the solvents were evaporated. The residue was dissolved in methanol (80 mL) and treated with NaBH$_4$ at 0° C. for 0.5 h. The solvents were evaporated, and the residue was partitioned between satureated NaHCO$_3$ and ethyl acetate. The organic layer was separated, washed with brine, dried over Na$_2$SO$_4$, filtered and the solvents were evaporated to give 11 g of the title compound.

EXAMPLE 28E tert-butyl (2S,3S)-3-methyl-2-{3-[(6-methyl-2-pyridinyl)methyl]-2-oxo-1-imidazolidinyl}pentanoate A solution of the product of Example 28D in DMF (60 mL) was treated with bis(p-nitrophenyl)carbonate (12.6 g, 1.2 equivalents) at 50° C. for 5 hrs. The solvents were evaporated, and the residue was partitioned between water and ethyl acetate. The organic layer was separated, washed with brine, dried over $Na_2SO_4$ and the solvents were evaporated, and the residue was purified using ethyl acetate:hexanes (2:1) to give 7.3 g (57%) of the title compound.

EXAMPLE 28F (2S,3S)-3-methyl-2-{3-[(6-methyl-2-pyridinyl)methyl]-2-oxo-1-imidazolidinyl}pentanoic acid A solution of the product of Example 28E (7.3 g) in dichloromethane (50 mL) and trifluoroacetic acid (50 mL) was stirred at 25° C. for 3.5 hrs. The solvents were evaporated and the crude acid was used directly without purification.

The compounds listed in Table 3, wherein $X_1$ and $X_5$ represents the points of connection to the core structure (C), were prepared by the procedures as exemplified in Examples 28A-28F, substituting the corresponding aldehydes for 6-methyl-2-pyridinecarboxaldehyde, and substituting the corresponding amino acid esters for L-isoleucine tert-butyl ester hydrochloride:

TABLE 3

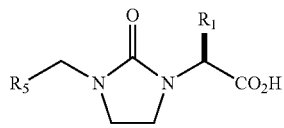

(C)

| Ex. | $R_5$ | $R_1$ |
|---|---|---|
| 29 | 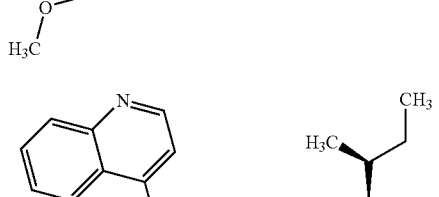 | |
| 30 | | |
| 31 | | |

TABLE 3-continued

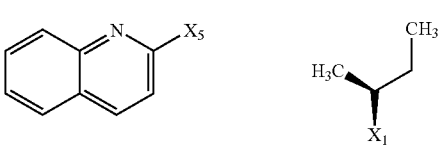

(C)

| Ex. | $R_5$ | $R_1$ |
|---|---|---|
| 32 |  | |
| 33 | | |
| 34 | | |
| 35 | | |
| 36 | 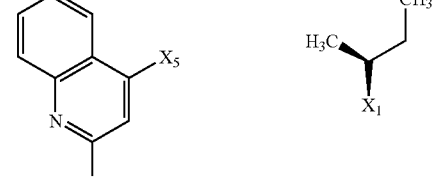 | |
| 37 | | |
| 38 | | |
| 39 | | |

TABLE 3-continued (C)

| Ex. | R₅ | R₁ |
|---|---|---|
| 40 | pyridazin-3-yl-X₅ | (S)-sec-butyl-X₁ |
| 41 | 6-isopropylpyridin-2-yl-X₅ | (S)-sec-butyl-X₁ |
| 42 | 6-acetylpyridin-2-yl-X₅ | tert-butyl-X₁ |
| 43 | 2-(pyridin-3-yl)thiazol-4-yl-X₅ | tert-butyl-X₁ |
| 44 | 6-(methoxycarbonyl)pyridin-2-yl-X₅ | tert-butyl-X₁ |
| 45 | quinolin-4-yl-X₅ | tert-butyl-X₁ |
| 46 | 6-(2-hydroxypropan-2-yl)pyridin-2-yl-X₅ | (S)-sec-butyl-X₁ |
| 47 | 6-((ethoxycarbonyl(methyl)amino)methyl)pyridin-2-yl-X₅ | (S)-sec-butyl-X₁ |
| 48 | 6-(hydroxymethyl)pyridin-2-yl-X₅ | (S)-sec-butyl-X₁ |
| 49 | 2'-methyl-[2,4'-bithiazol]-4-yl-X₅ | (S)-sec-butyl-X₁ |
| 50 | 2-methylquinolin-4-yl-X₅ | (S)-sec-butyl-X₁ |
| 51 | 6-methylpyridin-3-yl-X₅ | tert-butyl-X₁ |
| 52 | 5-methylthiophen-2-yl-X₅ | (S)-sec-butyl-X₁ |
| 53 | 6-(2-hydroxypropan-2-yl)pyridin-2-yl-X₅ | tert-butyl-X₁ |
| 54 | 2-((S)-1-acetamidoethyl)thiazol-4-yl-X₅ | (S)-sec-butyl-X₁ |

TABLE 3-continued

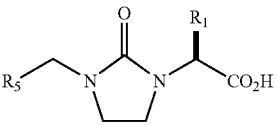
(C)

| Ex. | R5 | R1 |
|---|---|---|
| 55 | 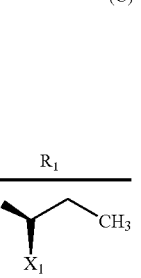 | 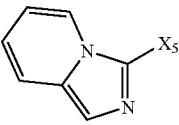 |
| 56 | 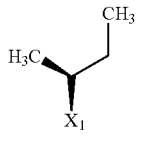 | 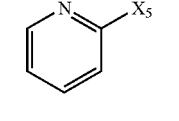 |
| 57 | 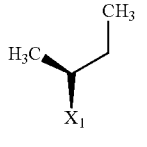 | 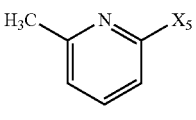 |
| 58 | 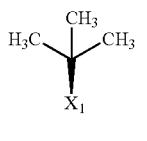 | 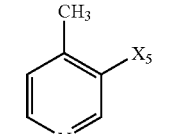 |
| 59 | 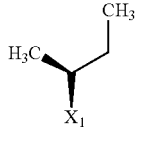 | 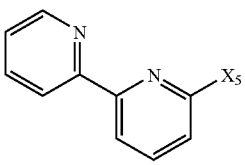 |
| 60 | 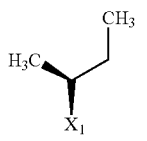 | |

EXAMPLE 61

(2S)-3-methyl-2-{3-[(2-methyl-1,3-thiazol-4-yl)methyl]-2-oxo-1-imidazolidinyl}butanoic acid

EXAMPLE 61A

2-{[(2-methyl-1,3-thiazol-4-yl)methyl]amino}ethanol

2-Methyl-4-(chloromethyl)thiazole (2.24 g) was treated with ethanolamine (11.6 mL, 10 equivalents) in dichloromethane at 25° C. for 16 hrs. The solvent was evaporated and the residue partitioned between ethyl acetate and brine. The organic layer was separated and extracted with ethyl acetate (5×). The organic layers were combined and washed with brine, dried over $Na_2SO_4$, and the solvents were evaporated to give 2.4 g (85%) of title compound.

EXAMPLE 61B tert-butyl 2-hydroxyethyl[(2-methyl-1,3-thiazol-4-yl)methyl]carbamate The product of Example 61A (2.4 g) was treated with di-t-butyl dicarbonate (2.85 g, 1 equivalent) in tetrahydrofuran/1M $NaHCO_3$ (2:1) and stirred at 25° C. for 16 hrs. The solvents were evaporated, and the residue was acidified with 10% citric acid and extracted with ethyl acetate (3×). The combined organic layer was washed with brine, dried over $Na_2SO_4$, filtered and evaporated. The crude product was purified using 1% methanol/dichloromethane to give 1.91 g (52%) of title compound.

EXAMPLE 61C methyl (2S)-3-methyl-2-[(2-{[(2-methyl-1,3-thiazol-4-yl)methyl]amino}ethyl)amino]butanoate A solution of the product of Example 61B (2.26 g) in dichloromethane (20 mL) was treated with oxalyl chloride (5.4 mL, 1.5 equivalents) at −78° C., and stirred for 15 min. DMSO (1.02 mL, 2 equivalents) was added dropwise at −78° C., stirred for 15 min, and quenched with triethylamine (4 mL, 4 equivalents) as the mixture warmed to 0° C. The mixture was quenched with 20% $KH_2PO_4$, and partitioned between dichloromethane and water. The organic layer was washed with brine, dried over $Na_2SO_4$, and the solvents were evaporated. To this crude product was added methanol/water (7:2), (L)-valine methyl ester (1.21 g, 1 equivalent), sodium acetate trihydrate (1.96 g, 2 equivalents), and $NaCNBH_3$ (0.95 g, 2 equivalents) was added portionwise over 30 min. After stirring for 1 hour, the mixture was partitioned between saturatued $NaHCO_3$, and extracted with ethyl acetate (2×). The combined organic layer was washed with brine, dried with $Na_2SO_4$, filtered, and evaporated. The residue was treated with dichloromethane/trifluoacetic acid (10 mL, 1:1), stirred at 25° C. for 2 hrs and concentrated to give the title compound isolated as the trifluoroacetic acid salt.

EXAMPLE 61D (2S)-3-methyl-2-{3-[(2-methyl-1,3-thiazol-4-yl)methyl]-2-oxo-1-imidazolidinyl}butanoic Acid A solution of the product of Example 61C (5.4 g) in tetrahydrofuran (80 mL) was treated with carbonydiimidazole (6.1 g, 2 equivalents) at 25° C. for 2 hrs. The mixture was quenched with 10% citric acid, the organic layer was separated, washed with water, brine, dried over $Na_2SO_4$, and the solvents were evaporated. A solution of the residue (3.3 g) in dioxane (20 mL) was treated with 1M LiOH (20 mL) at 25° C. for 2 hrs. The solvents were evaporated, and the residue was acidified with 10% HCl, extracted with dichloromethane/2-propanol (3:1), the organic layer was separated, dried over $Na_2SO_4$, filtered, and the solvents evaporated to give 1.5 g of the title compound.

The compounds listed in Table 4, wherein $X_1$ and $X_5$ represents the points of connection to the core structure (C), were prepared by the procedures as exemplified in Examples 61A-61D, substituting the corresponding halides for 6-methyl-4-

(chloromethyl)thiazole, and substituting the corresponding amino acid esters for L-valine methyl ester:

TABLE 4

| Example | Ex. | $R_5$ | $R_1$ |
|---|---|---|---|
| 365038 | 62 | thiazole with OCH3 substituent, $X_5$ | $H_3C-C(CH_3)-X_1$ |
| 428059 | 63 | thiazole with CH(CH3)2 substituent, $X_5$ | $H_3C-CH(CH_2CH_3)-X_1$ |

EXAMPLE 64

(2S)-3,3-dimethyl-2-{3-[(1-methyl-1H-benzimidazol-2-yl)methyl]-2-oxo-1-imidazolidinyl}butanoic acid

EXAMPLE 64A 2,2-dimethoxy-N-[(1-methyl-1H-benzimidazol-2-yl)methyl]ethanamine A solution of 1-methyl-2-formylbenzimidazole (1 g) in methanol (27 mL) and acetic acid (0.54 mL) was treated with aminoacetaldehyde diethylacetal (0.9 g, 1 equivalent) and NaCNBH$_3$ (0.85 g, 2 equivalents) at 25° C., stirred for 1 hour. The mixture was partitioned between water and ethyl acetate. The organic layer was separated, washed sequentially with saturated NaHCO$_3$ and brine, and concentrated. The residue was purified by eluting with 8% methanol/dichloromethane to give 1.2 g (64%) of the title compound.

EXAMPLE 64B 9H-fluoren-9-ylmethyl 2,2-dimethoxyethyl[(1-methyl-1H-benzimidazol-2-yl)methyl]carbamate A solution of the product of Example 64A (1.2 g) in dichloromethane (30 mL) was treated with 9-fluorenylmethyl succinimide (1.6 g, 1.05 eq.) at 0° C. for 16 hours. The mixture was partitioned between water and ethyl acetate. The organic layer was separated, washed sequentially with 10% NaHCO$_3$ and brine, dried over Na$_2$SO$_4$, filtered and concentrated. The residue was purified by eluting with ethyl acetate:dichloromethane (1:1) to give 1.83 g (84%) of the title compound.

EXAMPLE 64C 9H-fluoren-9-ylmethyl (1-methyl-1H-benzimidazol-2-yl)methyl(2-oxoethyl)carbamate A solution of the product of Example 64B (0.2 g) in tetrahydrofuran (0.2 mL) was treated with 30% HCl (0.2 mL), stirred at 75° C. for 6 hours, cooled to 25° C. and concentrated. The residue was partitioned between 10% NaHCO$_3$ and ethyl acetate, the organic layer was separated and washed with brine, dried over Na$_2$SO$_4$, filtered and concentrated to give the title compound (175 mg).

EXAMPLE 64D methyl (2S)-2-[(2-{[(9H-fluoren-9-ylmethoxy)carbonyl][(1-methyl-1H-benzimidazol-2-yl)methyl]amino}ethyl)amino]-3,3-dimethylbutanoate A solution of the product of Example 64C (0.178 g) and (L)-methyl t-leucinate hydrochloride (76.1 mg, 1 equivalent) in methanol (1.7 mL) and acetic acid (17 µL) was treated with NaCNBH$_3$ (54 mg, 2 equivalents) at 25° C. for 3.5 hours. The mixture was partitioned between water and ethyl acetate. The organic layer was separated and washed with 1N NaHCO$_3$ and brine, and concentrated. The residue was purified by ethyl acetate:dichloromethane (3:1) to give 0.19 g (83%) of the title compound.

EXAMPLE 64E methyl (2S)-3,3-dimethyl-2-{3-[(1-methyl-1H-benzimidazol-2-yl)methyl]-2-oxo-1-imidazolidinyl}butanoate A solution of the product of Example 64D (0.19 g) in N,N-dimethylformamide (3.5 mL) was treated with diethylamine (0.35 mL), stirred at 25° C. for 1.5 hours and concentrated. A solution of the residue in dichloroethane (7 mL) was treated with bis-(p-nitrophenyl)carbonate (0.128 g, 1.2 eq.), stirred at 60° C. for 16 hours and concentrated. The residue was purified by ethyl acetate:dichloromethane (3:2) to give 80 mg (64%) of the title compound.

EXAMPLE 64F (2S)-3,3-dimethyl-2-{3-[(1-methyl-1H-benzimidazol-2-yl)methyl]-2-oxo-1-imidazolidinyl}butanoic acid A solution of the product of Example 64E (37 mg) in tetrahydrofuran (0.26 mL) and water (0.13 mL) was treated with LiOH (6.1 mg, 1.4 equivalents), stirred at 25° C. for 16 hours, quenched with 1N HCl (0.15 mL) at 0° C., and the solvents were evaporated to give the title compound, to be used without further purification.

The compounds listed in Table 5, wherein $X_1$ and $X_5$ represent respectively the points of connection to the core structure (C), were prepared by the procedures as exemplified in Examples 64A-64F, substituting the corresponding for 1-methyl-2-formylbenzimidazole, and substituting the corresponding amino acid esters for (L)-methyl-t-leucinate.

TABLE 5

| Ex. | $R_5$ | $R_1$ |
|---|---|---|
| 65 | thiazole with CH3 and $X_5$ | $H_3C-C(CH_3)(CH_3)-X_1$ |

TABLE 5-continued

| Ex. | R₅ | R₁ |
|---|---|---|
| 66 | H₃C–[thiazole]–X₅ (2-methylthiazol-4-yl) | H₃C–CH₂–NH–C(=O)–CH₂–X₁ |
| 67 | H₃C–[thiazole]–X₅ (2-methylthiazol-4-yl) | H₃C–CH(CH₃)–X₁ (isopropyl via CH) |
| 68 | [3-methylimidazo[4,5-b]pyridin-2-yl]–X₅ | H₃C–CH(CH₃)–X₁ |
| 69 | H₃C–[thiazole]–X₅ (2-methylthiazol-4-yl) | H₃C–NH–C(=O)–CH₂–X₁ |

EXAMPLE 70 methyl (1S)-1-({2-{(2S,3S)-2-hydroxy-3-[((2S,3S)-3-methyl-2-{3-[2-(6-methyl-2-pyridinyl)ethyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate Example 28 (40 mg) is combined with HOBT (23 mg, 1.5 equivalents) and EDAC (32 mg, 1.5 equivalents) in DMF (2 mL) and stirred for 1 hour at 25° C. To this mixture is added N-methylmorpholine (40 μL, 3 equivalents) and Example 1 (65 mg, 1.1 equivalents). The mixture is stirred for 16 hrs, evaporated, and purified using 2% methanol/CHCl₃ to give 78 mg (86%) of the title compound. ¹H NMR (300 MHz, CDCl₃), δ ppm 0.78 (d, J=7.72 Hz, 12H), 0.85 (m, 3H), 1.03 (m, 1H), 1.40 (m, 1H), 1.91 (s, 1H), 2.54 (s, 3H), 2.61 (dd, J=12.32, 3.86 Hz, 1H), 2.81 (dd, J=12.69, 10.11 Hz, 1H), 2.92 (t, J=8.09 Hz, 3H), 3.11 (m, J=4.04 Hz, 1H), 3.17 (m, 3H), 3.59 (s, 3H), 3.64 (m, 2H), 3.91 (m, 1H), 3.97 (d, J=6.62 Hz, 1H), 4.07 (m, 1H), 4.48 (s, 2H), 4.79 (s, 1H), 5.26 (d, J=8.82 Hz, 1H), 6.59 (d, J=9.19 Hz, 1H), 7.06 (dd, J=12.13, 7.35 Hz, 2H), 7.19 (m, 6H), 7.42 (d, J=8.09 Hz, 2H), 7.54 (t, J=7.72 Hz, 1H), 7.74 (m, 2H), 7.94 (d, J=8.09 Hz, 2H), 8.68 (d, J=4.78 Hz, 1H).

The compounds listed in Table 6, wherein $X_1$, $X_3$, $X_4$, and $X_5$ represent respectively the points of connection to the core structure (E), were prepared by the procedure of Example 70 (Method A), coupling the corresponding acids (Examples 28-69) having formula (C), with the corresponding amines (Examples 1-27) having formula (D); or by the procedure as exemplified in Example 192 (Method D), substituting the corresponding amines (Examples 1-27) for Example 191D, and substituting the corresponding amino acid esters (prepared from the corresponding amino acids using the procedure of Example 18A) for Example 18A:

TABLE 6

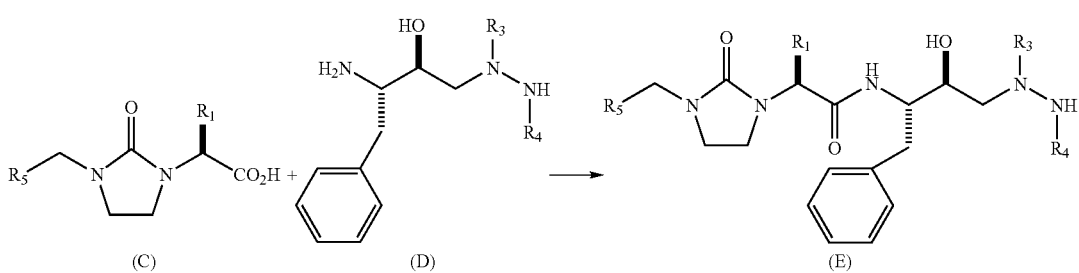

| Ex. | Method | R₅ | R₁ | R₃ | R₄ |
|---|---|---|---|---|---|
| 71 | A | 1-methylbenzimidazol-2-yl–X₅ | tert-butyl (C(CH₃)₃)–X₁ | 4-(2-pyridinyl)benzyl–X₃ | X₄–C(=O)–CH(C(CH₃)₃)–NH–C(=O)–O–CH₃ |

TABLE 6-continued

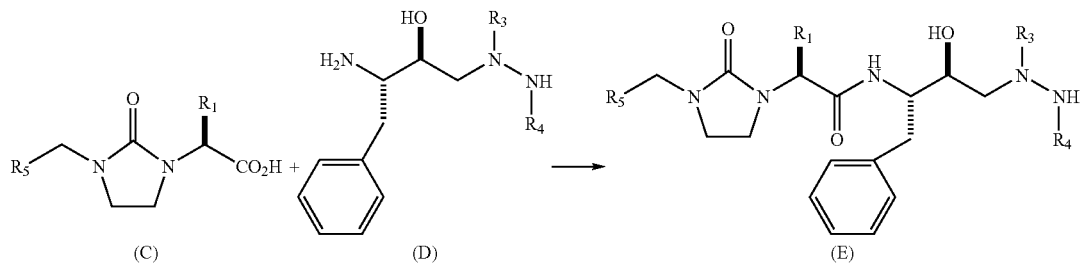

| Ex. | Method | R₅ | R₁ | R₃ | R₄ |
|---|---|---|---|---|---|
| 72 | A | 3-pyridyl-X₅ | (S)-sec-butyl-X₁ (CH₃, CH₂CH₃) | 4-(2-pyridyl)benzyl-X₃ | X₄-C(O)-CH(tBu)-NH-C(O)-OCH₃ |
| 73 | A | 6-methyl-2-pyridyl-X₅ | (S)-sec-butyl-X₁ | 4-(2-pyridyl)benzyl-X₃ | X₄-C(O)-CH(tBu)-NH-C(O)-OCH₃ |
| 74 | A | 2-(methoxymethyl)thiazol-4-yl-X₅ | (S)-sec-butyl-X₁ | 4-(2-pyridyl)benzyl-X₃ | X₄-C(O)-CH(sec-butyl)-NH-C(O)-OCH₃ |
| 75 | A | 4-quinolyl-X₅ | (S)-iso-butyl-X₁ | 4-(2-pyridyl)benzyl-X₃ | X₄-OC(O)-C(CH₃)₃ (Boc) |
| 76 | A | 1-methylbenzimidazol-2-yl-X₅ | tert-butyl-X₁ | 4-(2-pyridyl)benzyl-X₃ | X₄-C(O)-CH(sec-butyl)-NH-C(O)-OCH₃ |

TABLE 6-continued
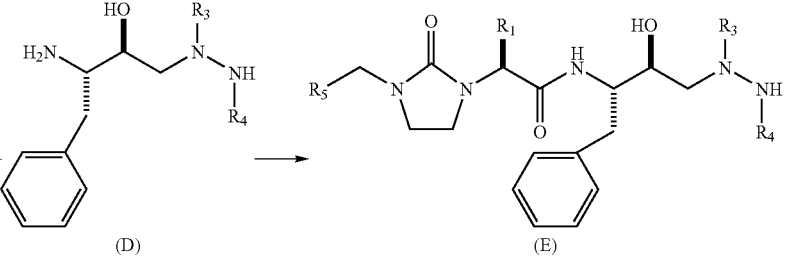
| Ex. | Method | R₅ | R₁ | R₃ | R₄ |
|---|---|---|---|---|---|
| 77 | A | 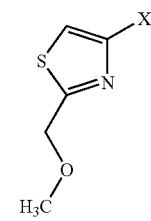 | 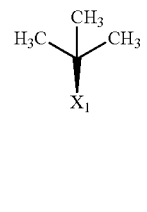 | 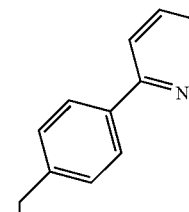 | 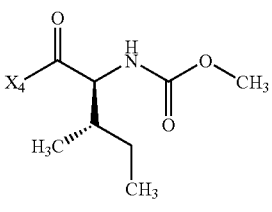 |
| 78 | A | 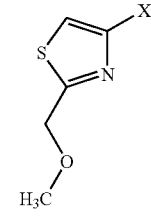 | 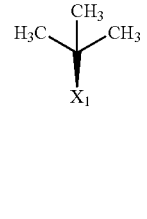 | 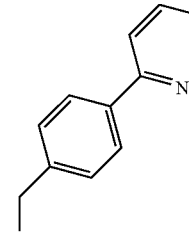 | 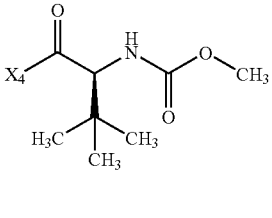 |
| 79 | A | 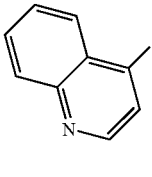 | 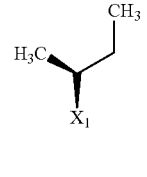 | 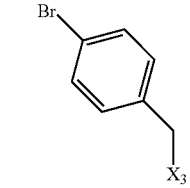 | 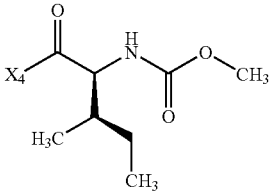 |
| 80 | D | 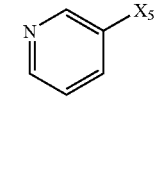 | 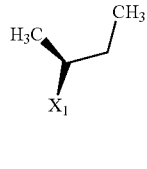 | 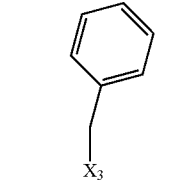 | 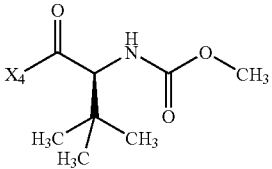 |
| 81 | D | 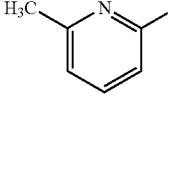 | 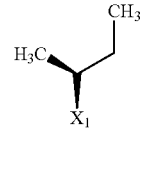 | 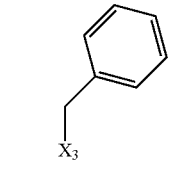 | 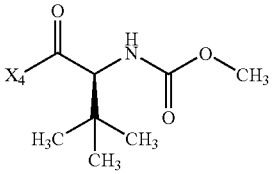 |

TABLE 6-continued

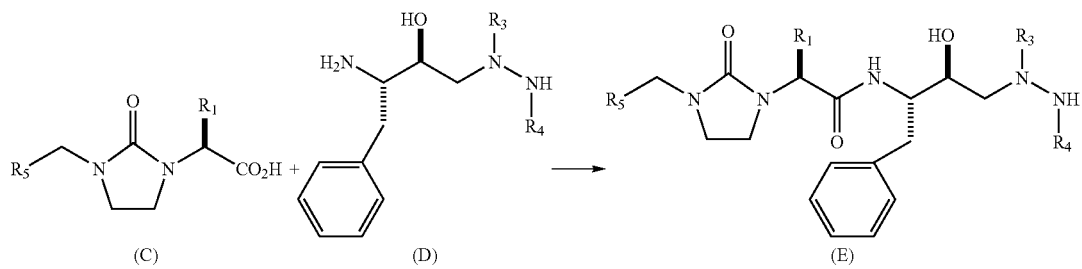

| Ex. | Method | R<sub>5</sub> | R<sub>1</sub> | R<sub>3</sub> | R<sub>4</sub> |
|-----|--------|---------------|---------------|---------------|---------------|
| 82 | D | 3-pyridyl-X<sub>5</sub> | sec-butyl-X<sub>1</sub> (CH<sub>3</sub>, CH<sub>3</sub>CH<sub>2</sub>) | benzyl-X<sub>3</sub> | X<sub>4</sub>-C(O)-CH(CH(CH<sub>3</sub>)CH<sub>2</sub>CH<sub>3</sub>)-NHC(O)OCH<sub>3</sub> |
| 83 | A | 5-methylisoxazol-3-yl-thiazol-2-yl-X<sub>5</sub> | tert-butyl-X<sub>1</sub> | (4-(pyridin-2-yl)benzyl)-X<sub>3</sub> | X<sub>4</sub>-C(O)-CH(C(CH<sub>3</sub>)<sub>3</sub>)-NHC(O)OCH<sub>3</sub> |
| 84 | A | 6-methylpyridin-2-yl-X<sub>5</sub> | sec-butyl-X<sub>1</sub> | 4-methoxybenzyl-X<sub>3</sub> | X<sub>4</sub>-C(O)-CH(C(CH<sub>3</sub>)<sub>3</sub>)-NHC(O)OCH<sub>3</sub> |
| 85 | D | 2-(pyridin-3-yl)thiazol-4-yl-X<sub>5</sub> | tert-butyl-X<sub>1</sub> | (4-(pyridin-2-yl)benzyl)-X<sub>3</sub> | X<sub>4</sub>-C(O)-CH(C(CH<sub>3</sub>)<sub>3</sub>)-NHC(O)OCH<sub>3</sub> |
| 86 | D | 6-(hydroxymethyl)pyridin-2-yl-X<sub>5</sub> | tert-butyl-X<sub>1</sub> | (4-(pyridin-2-yl)benzyl)-X<sub>3</sub> | X<sub>4</sub>-C(O)-CH(C(CH<sub>3</sub>)<sub>3</sub>)-NHC(O)OCH<sub>3</sub> |

TABLE 6-continued
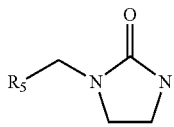
| Ex. | Method | R₅ | R₁ | R₃ | R₄ |
|---|---|---|---|---|---|
| 87 | D | 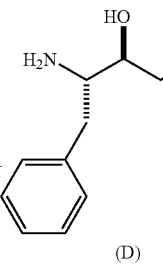 | 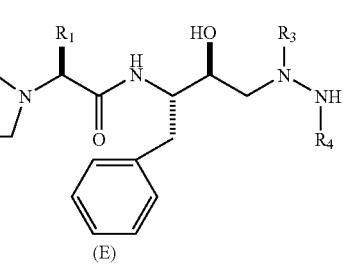 | 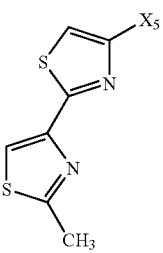 | 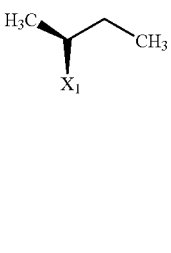 |
| 88 | A | 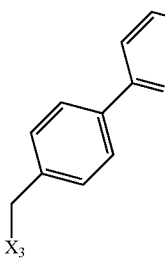 | 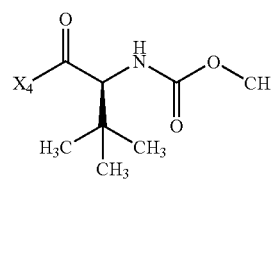 | 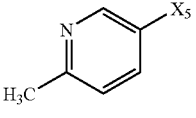 | 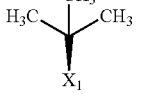 |
| 89 | D | 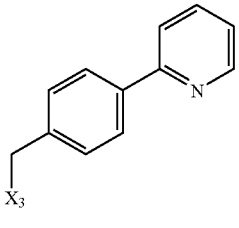 | 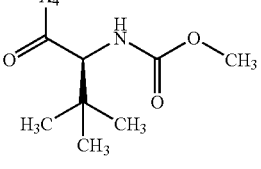 | 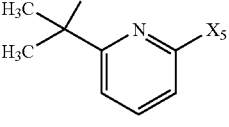 | 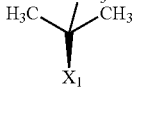 |
| 90 | D | 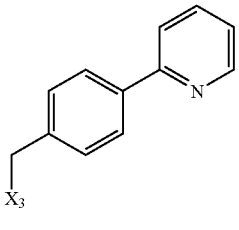 | 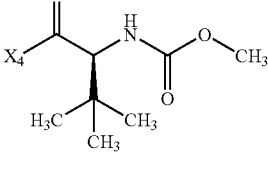 | 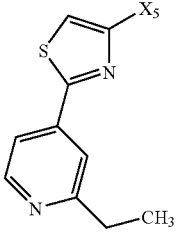 | 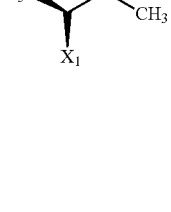 |
| 91 | A | 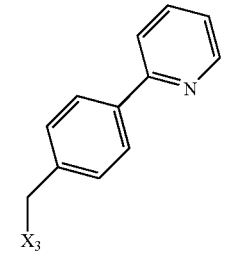 | 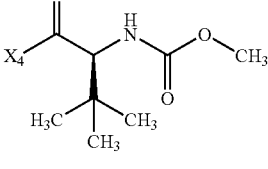 | 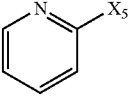 | 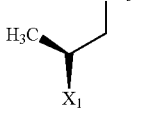 |

TABLE 6-continued

| Ex. | Method | R5 | R1 | R3 | R4 |
|---|---|---|---|---|---|
| 92 | A | 2-pyridyl-X5 | sec-butyl-X1 | 4-(2-pyridyl)benzyl-X3 | methyl carbamate of tert-leucine-X4 |
| 93 | A | 4-methyl-3-pyridyl-X5 | sec-butyl-X1 | 4-(2-pyridyl)benzyl-X3 | methyl carbamate of tert-leucine-X4 |
| 94 | A | 4-methyl-3-pyridyl-X5 | tert-butyl-X1 | 4-(2-pyridyl)benzyl-X3 | methyl carbamate of tert-leucine-X4 |
| 95 | D | 4-quinolinyl-X5 | tert-butyl-X1 | 4-(2-pyridyl)benzyl-X3 | methyl carbamate of tert-leucine-X4 |
| 96 | A | 2-(3-pyridyl)thiazol-4-yl-X5 | sec-butyl-X1 | 4-(2-pyridyl)benzyl-X3 | methyl carbamate of tert-leucine-X4 |

TABLE 6-continued
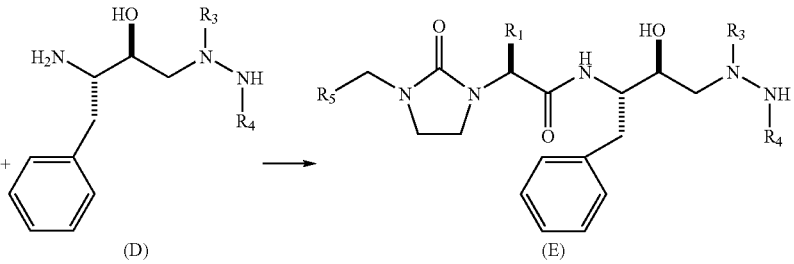
| Ex. | Method | R₅ | R₁ | R₃ | R₄ |
|---|---|---|---|---|---|
| 97 | D | 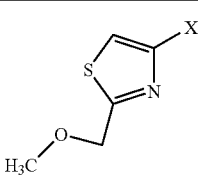 | 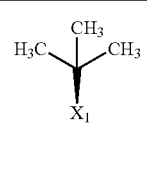 | 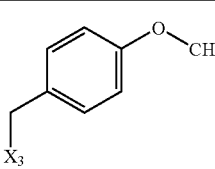 | 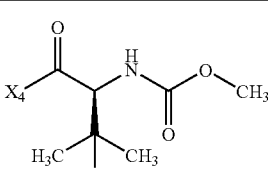 |
| 98 | A | 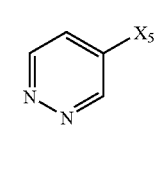 | 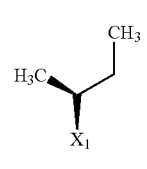 | 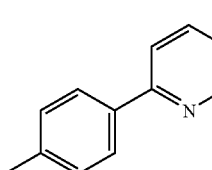 | 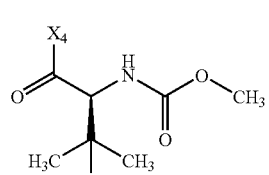 |
| 99 | D | 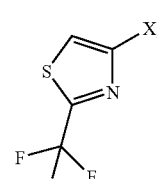 | 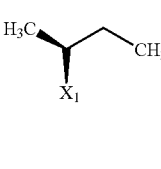 | 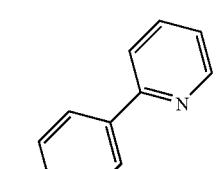 | 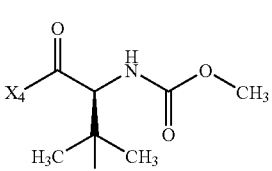 |
| 100 | D | 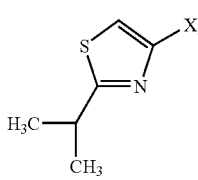 | 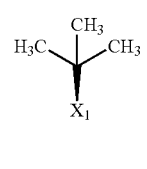 | 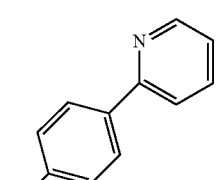 | 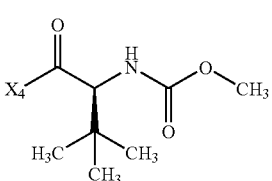 |
| 101 | A | 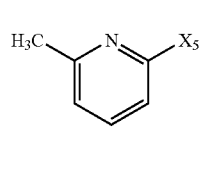 | 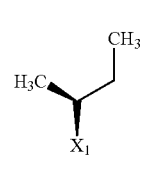 | 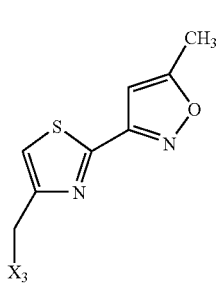 | 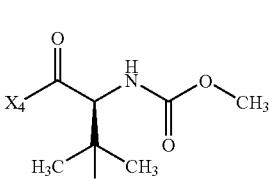 |

TABLE 6-continued
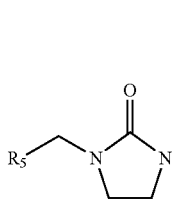
| Ex. | Method | R₅ | R₁ | R₃ | R₄ |
|---|---|---|---|---|---|
| 102 | D | 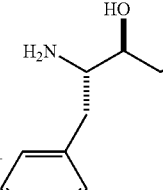 | 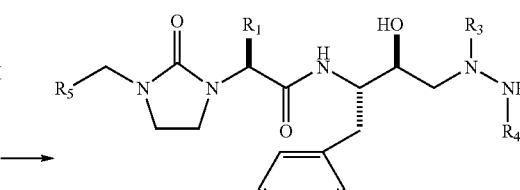 | 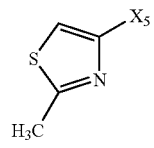 | 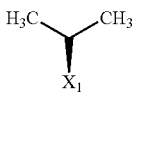 |
| 103 | D | 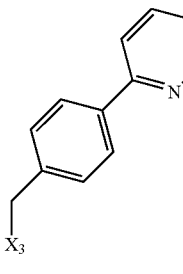 | 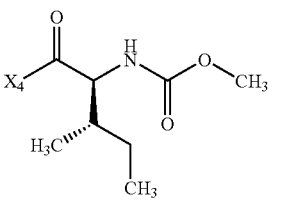 | 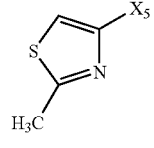 | 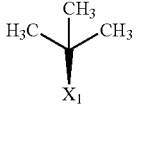 |
| 104 | A | 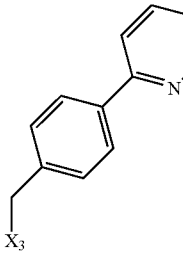 | 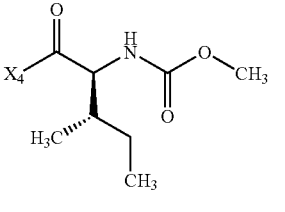 | 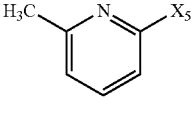 | 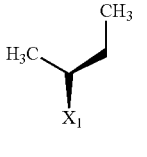 |
| 105 | D | 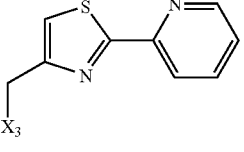 | 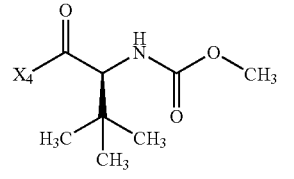 | 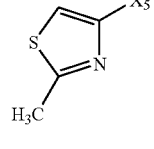 | 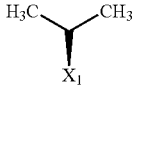 |
| 106 | D | 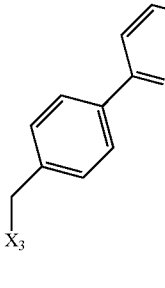 | 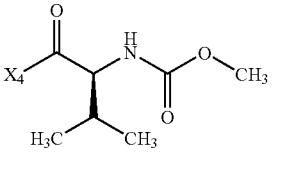 | 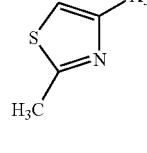 | 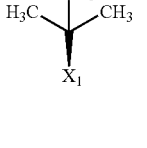 |

TABLE 6-continued
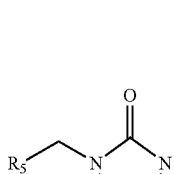
| Ex. | Method | R₅ | R₁ | R₃ | R₄ |
|---|---|---|---|---|---|
| 107 | D | 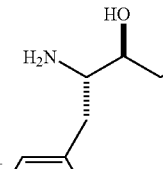 | 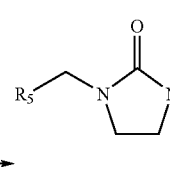 | 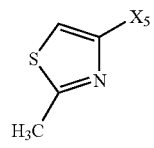 | 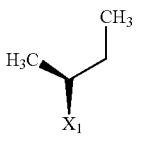 |
| 108 | D | 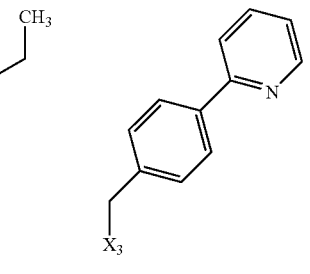 | 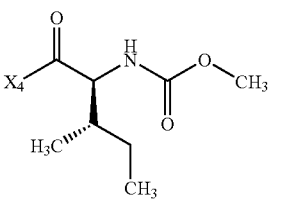 | 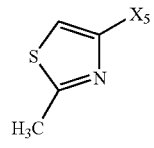 | 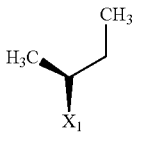 |
| 109 | D | 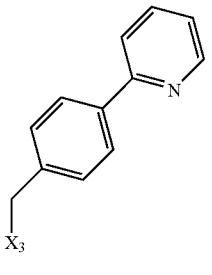 | 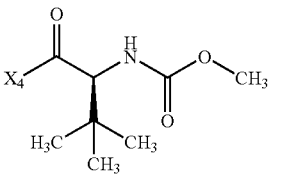 | 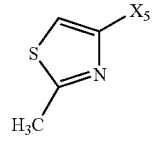 | 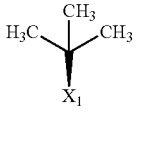 |
| 110 | A | 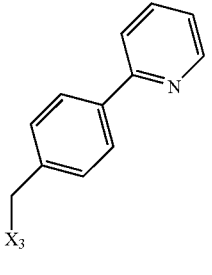 | 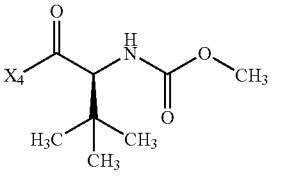 | 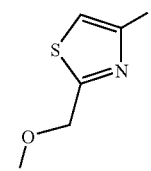 | 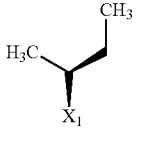 |
| 111 | A | 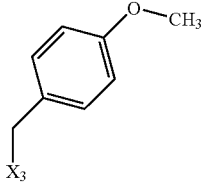 | 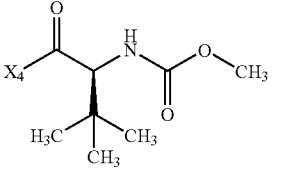 | 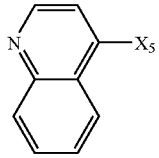 | 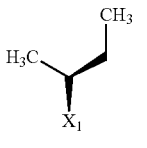 |

TABLE 6-continued
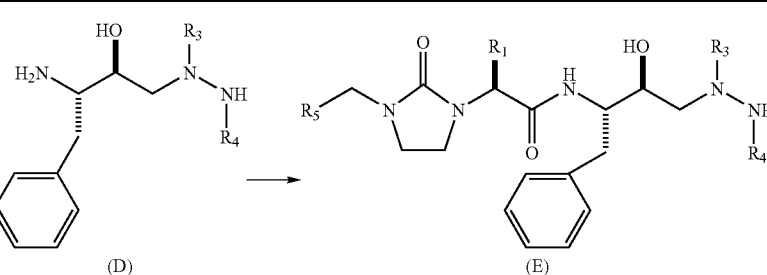
| Ex. | Method | R$_5$ | R$_1$ | R$_3$ | R$_4$ |
|---|---|---|---|---|---|
| 112 | A | 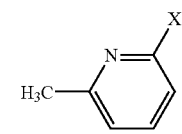 | 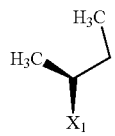 | 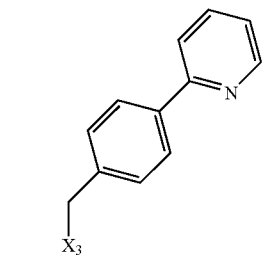 | 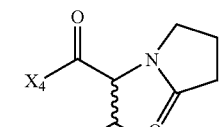 |
| 113 | A | 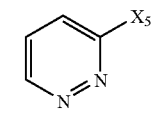 | 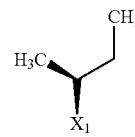 | 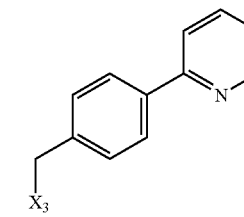 | 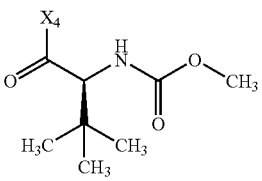 |
| 114 | A | 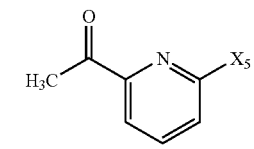 | 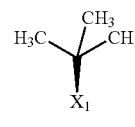 | 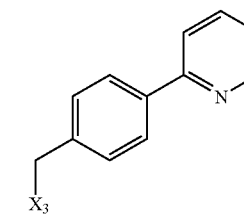 | 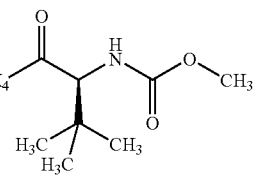 |
| 115 | A | 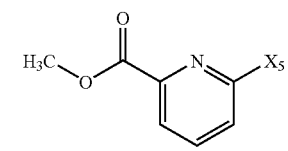 | 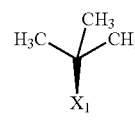 | 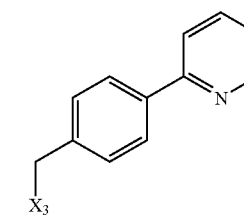 | 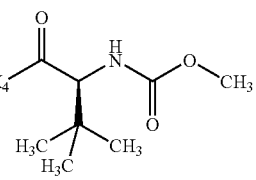 |
| 116 | A | 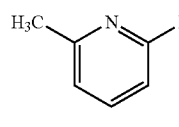 | 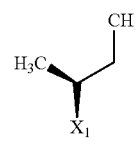 | 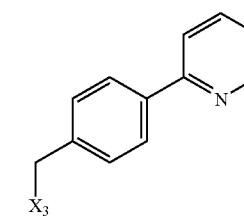 | 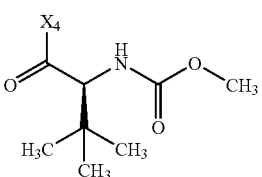 |

TABLE 6-continued

| Ex. | Method | R₅ | R₁ | R₃ | R₄ |
|-----|--------|----|----|----|----|
| 117 | A | 6-methylpyridin-2-yl (X₅) | sec-butyl (X₁) | 4-(pyridin-2-yl)benzyl (X₃) | (S)-2-(2-oxoimidazolidin-1-yl)-3-methylpentanoyl (X₄) |
| 118 | D | 6-(2-hydroxypropan-2-yl)pyridin-2-yl (X₅) | tert-butyl (X₁) | 4-methoxybenzyl (X₃) | (S)-2-(methoxycarbonylamino)-3,3-dimethylbutanoyl (X₄) |
| 119 | D | 6-(2-hydroxypropan-2-yl)pyridin-2-yl (X₅) | sec-butyl (X₁) | 4-methoxybenzyl (X₃) | (S)-2-(methoxycarbonylamino)-3,3-dimethylbutanoyl (X₄) |
| 120 | D | 6-(hydroxymethyl)pyridin-2-yl (X₅) | tert-butyl (X₁) | 4-methoxybenzyl (X₃) | (S)-2-(methoxycarbonylamino)-3,3-dimethylbutanoyl (X₄) |
| 121 | D | 6-(hydroxymethyl)pyridin-2-yl (X₅) | sec-butyl (X₁) | 4-methoxybenzyl (X₃) | (S)-2-(methoxycarbonylamino)-3,3-dimethylbutanoyl (X₄) |
| 122 | A | quinolin-8-yl (X₅) | sec-butyl (X₁) | 4-methoxybenzyl (X₃) | (S)-2-(methoxycarbonylamino)-3,3-dimethylbutanoyl (X₄) |

TABLE 6-continued
| Ex. | Method | R5 | R1 | R3 | R4 |
|---|---|---|---|---|---|
| 123 | A | 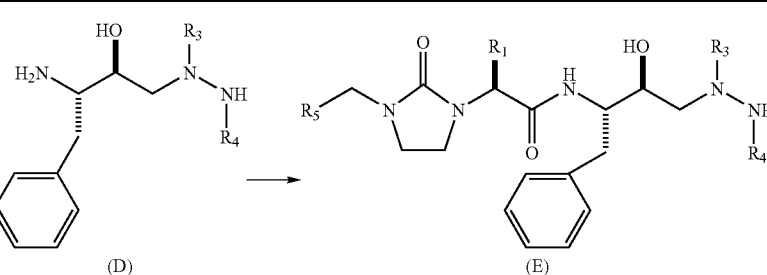 | 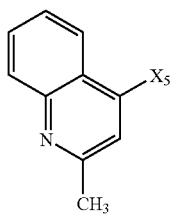 | 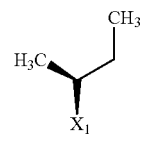 | 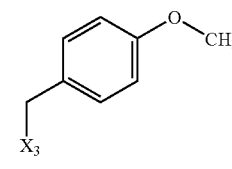 |
| 124 | A | 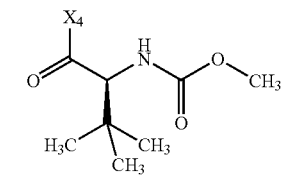 | 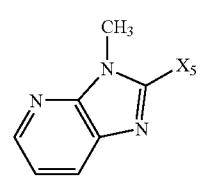 | 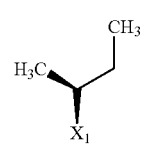 | 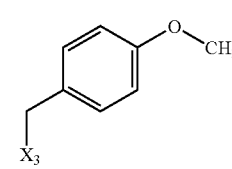 |
| 125 | A | 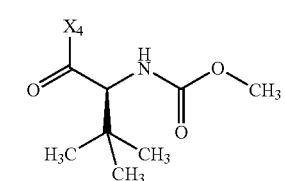 | 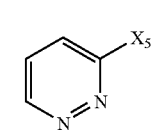 | 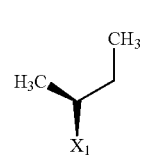 | 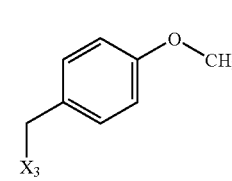 |
| 126 | D | 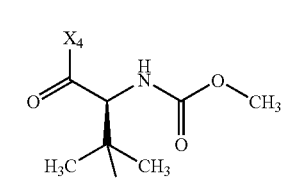 | 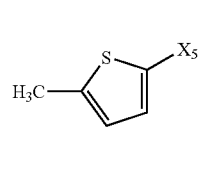 | 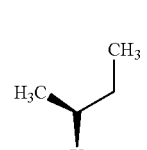 | 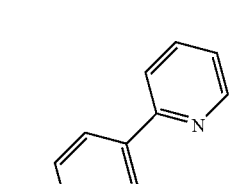 |
| 127 | A | 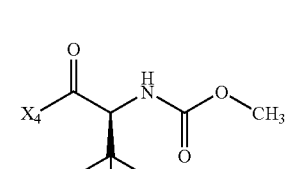 | 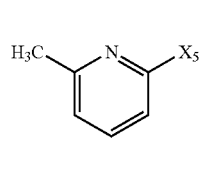 | 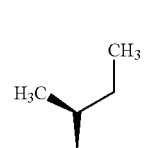 | 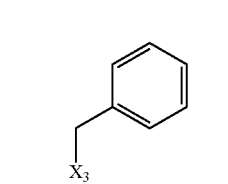 |

TABLE 6-continued

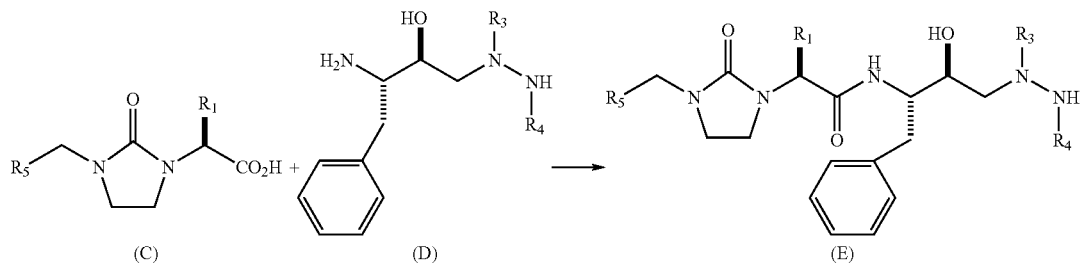

| Ex. | Method | R₅ | R₁ | R₃ | R₄ |
|---|---|---|---|---|---|
| 128 | D | thiazole-CH(CH₃)NHC(O)CH₃ with X₅ | sec-butyl (X₁) | 4-(2-pyridyl)benzyl-X₃ | X₄-C(O)-CH(tBu)-NHC(O)OCH₃ |
| 129 | D | 6-methylpyridin-2-yl-X₅ | sec-butyl (X₁) | 4-(2-pyridyl)benzyl-X₃ | X₄-C(O)-oxazolidinone (5-methyl) |
| 130 | D | 6-(2-hydroxypropan-2-yl)pyridin-2-yl-X₅ | tert-butyl (X₁) | isobutyl-X₃ | X₄-C(O)-CH(tBu)-NHC(O)OCH₃ |
| 131 | D | 6-(2-hydroxypropan-2-yl)pyridin-2-yl-X₅ | sec-butyl (X₁) | isobutyl-X₃ | X₄-C(O)-CH(tBu)-NHC(O)OCH₃ |
| 132 | D | 6-(hydroxymethyl)pyridin-2-yl-X₅ | tert-butyl (X₁) | isobutyl-X₃ | X₄-C(O)-CH(tBu)-NHC(O)OCH₃ |
| 133 | D | 6-(hydroxymethyl)pyridin-2-yl-X₅ | sec-butyl (X₁) | isobutyl-X₃ | X₄-C(O)-CH(tBu)-NHC(O)OCH₃ |

TABLE 6-continued

| Ex. | Method | R5 | R1 | R3 | R4 |
|---|---|---|---|---|---|
| 134 | D | 6-methylpyridin-2-yl (X5) | sec-butyl (X1) | 4-(pyridin-2-yl)benzyl (X3) | 5,5-dimethyl-2-oxotetrahydrofuran-3-carbonyl (X4) |
| 135 | A | imidazo[1,2-a]pyridin-3-yl (X5) | sec-butyl (X1) | 4-methoxybenzyl (X3) | N-(methoxycarbonyl)-tert-leucyl (X4) |
| 136 | A | 6-methylpyridin-2-yl (X5) | sec-butyl (X1) | 4-(pyridin-2-yl)benzyl (X3) | (S)-5-oxopyrrolidine-2-carbonyl (X4) |
| 137 | A | 6-methylpyridin-2-yl (X5) | sec-butyl (X1) | 4-(pyridin-2-yl)benzyl (X3) | (S)-4,4-dimethyl-2-oxotetrahydrofuran-3-yl carbonate (X4) |
| 138 | A | 6-methylpyridin-2-yl (X5) | sec-butyl (X1) | 4-(pyridin-2-yl)benzyl (X3) | (R)-4,4-dimethyl-2-oxotetrahydrofuran-3-yl carbonate (X4) |

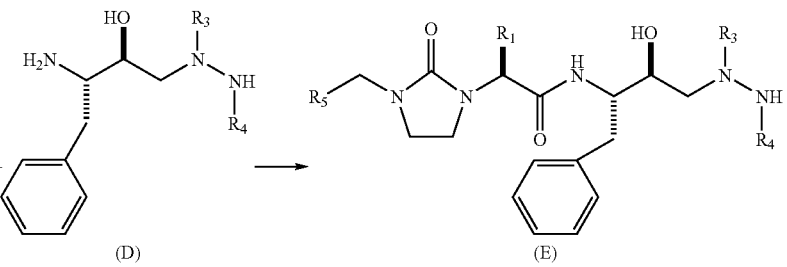

TABLE 6-continued
| Ex. | Method | R₅ | R₁ | R₃ | R₄ |
|---|---|---|---|---|---|
| 139 | A | 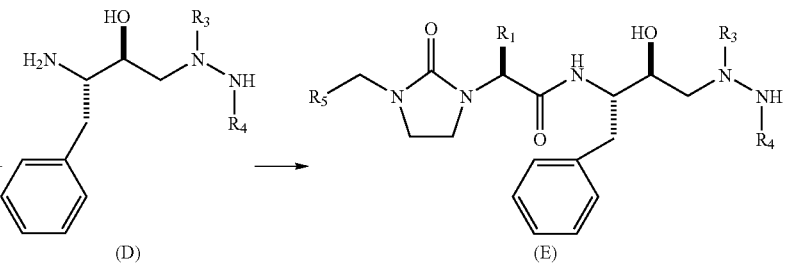 | 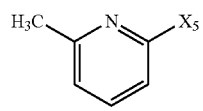 | 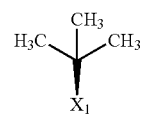 | 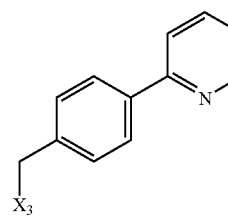 |
| 140 | A | 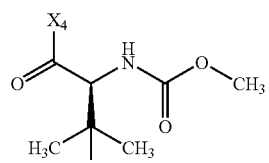 | 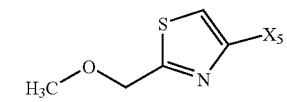 | 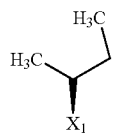 | 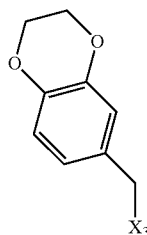 |
| 141 | A | 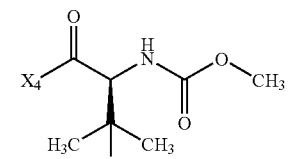 | 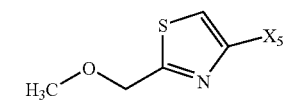 | 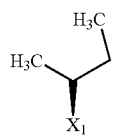 | 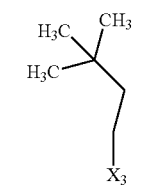 |
| 142 | A | 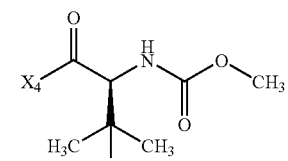 | 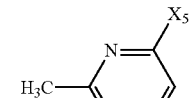 | 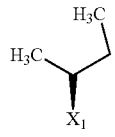 | 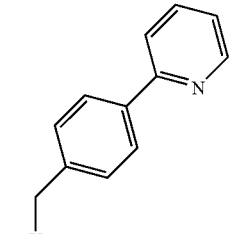 |
| 143 | A | 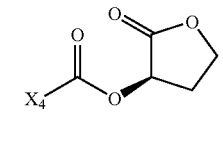 | 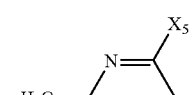 | 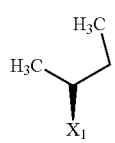 | 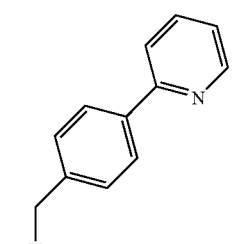 |

TABLE 6-continued

| Ex. | Method | R5 | R1 | R3 | R4 |
|---|---|---|---|---|---|
| 144 | A | 6-methylpyridin-2-yl (X5) | (S)-sec-butyl (X1) | 4-(diethylamino)benzyl (X3) | methyl N-carbamate-tert-leucyl (X4) |
| 145 | D | 6-methylpyridin-2-yl (X5) | (S)-sec-butyl (X1) | 4-(pyridin-2-yl)benzyl (X3) | 2-oxoimidazolidin-1-yl tert-leucyl (X4) |
| 146 | D | 6-(2-hydroxypropan-2-yl)pyridin-2-yl (X5) | tert-butyl (X1) | 2,3-dihydrobenzo[1,4]dioxin-6-ylmethyl (X3) | methyl N-carbamate-tert-leucyl (X4) |
| 147 | D | 6-(2-hydroxypropan-2-yl)pyridin-2-yl (X5) | (S)-sec-butyl (X1) | 2,3-dihydrobenzo[1,4]dioxin-6-ylmethyl (X3) | methyl N-carbamate-tert-leucyl (X4) |
| 148 | D | 6-(hydroxymethyl)pyridin-2-yl (X5) | tert-butyl (X1) | 2,3-dihydrobenzo[1,4]dioxin-6-ylmethyl (X3) | methyl N-carbamate-tert-leucyl (X4) |
| 149 | D | 6-(hydroxymethyl)pyridin-2-yl (X5) | (S)-sec-butyl (X1) | 2,3-dihydrobenzo[1,4]dioxin-6-ylmethyl (X3) | methyl N-carbamate-tert-leucyl (X4) |

TABLE 6-continued
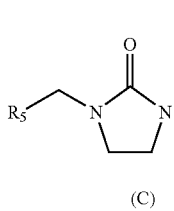
| Ex. | Method | R₅ | R₁ | R₃ | R₄ |
|---|---|---|---|---|---|
| 150 | D | 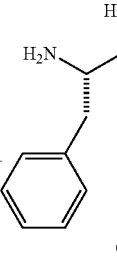 | 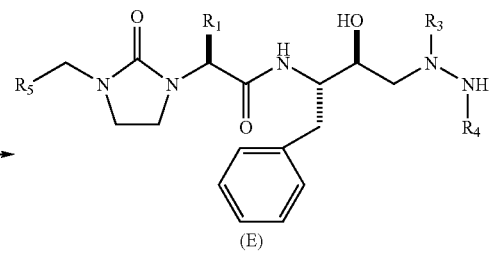 | 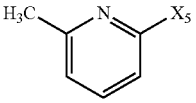 | 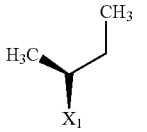 |
| 151 | D | 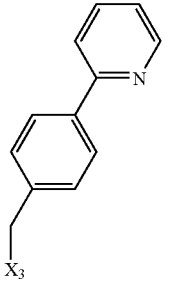 | 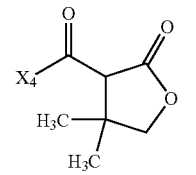 | 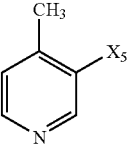 | 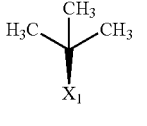 |
| 152 | D | 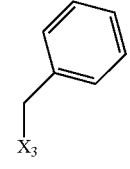 | 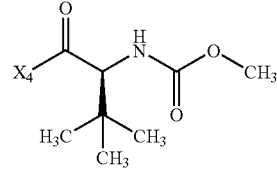 | 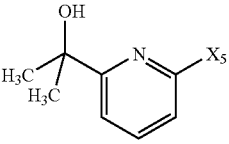 | 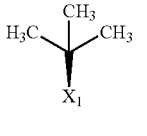 |
| 153 | D | 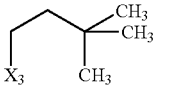 | 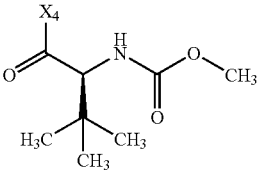 | 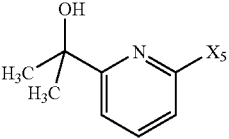 | 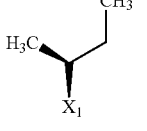 |
| 154 | D | 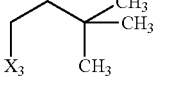 | 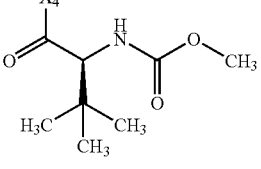 | 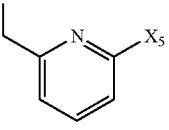 | 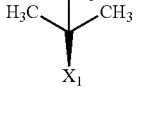 |
| 155 | D | 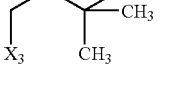 | 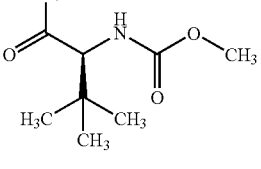 | 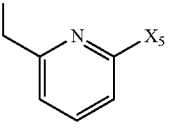 | 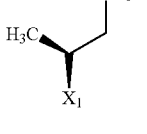 |

TABLE 6-continued
| Ex. | Method | R₅ | R₁ | R₃ | R₄ |
|---|---|---|---|---|---|
| 156 | D | 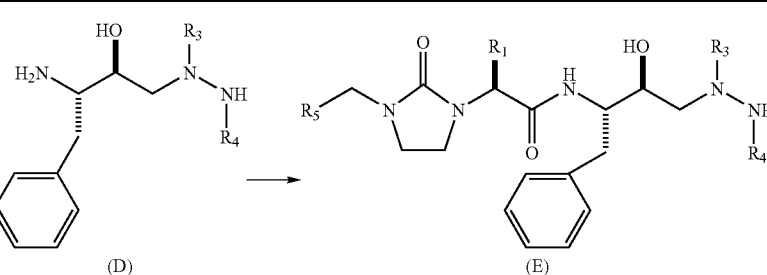 | 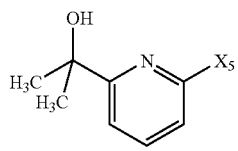 | 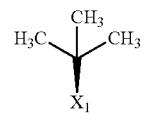 | 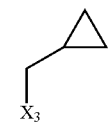 |
| 157 | D | 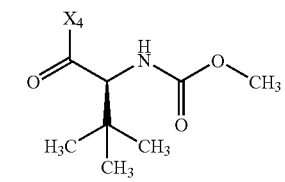 | 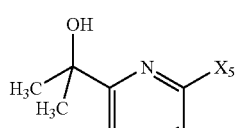 | 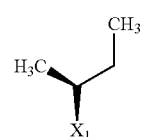 | 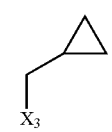 |
| 158 | D | 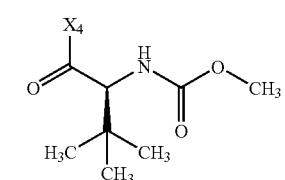 | 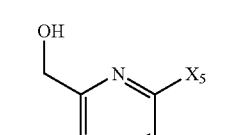 | 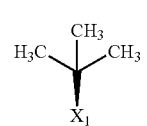 |  |
| 159 | D | 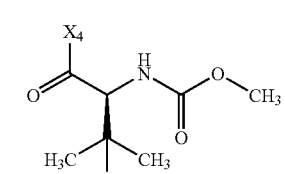 | 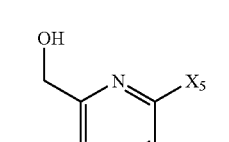 | 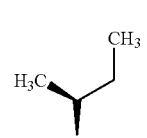 | 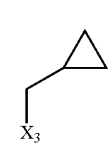 |
| 160 | D | 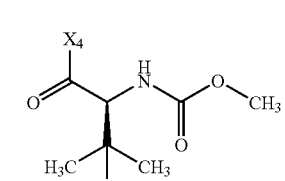 | 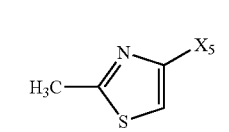 | 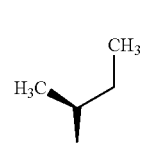 | 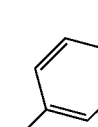 |
| 161 | A | 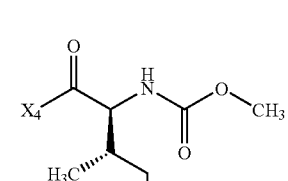 | 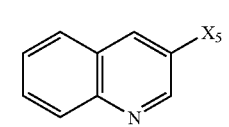 | 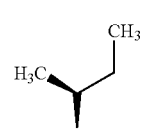 | 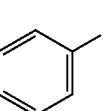 |

TABLE 6-continued

| Ex. | Method | R₅ | R₁ | R₃ | R₄ |
|---|---|---|---|---|---|
| 162 | A | quinolin-2-yl (X₅) | sec-butyl (CH₃CH₂CH(CH₃)-, X₁) | 4-methoxybenzyl (X₃) | methyl (S)-2-(methoxycarbonylamino)-3,3-dimethylbutanoyl (X₄) |
| 163 | A | 2-methylthiazol-4-yl (X₅) | -CH₂C(O)NHCH₃ (X₁) | 4-methoxybenzyl (X₃) | methyl (S)-2-(methoxycarbonylamino)-3,3-dimethylbutanoyl (X₄) |
| 164 | A | 2-methylthiazol-4-yl (X₅) | -CH₂C(O)NHCH₂CH₃ (X₁) | 4-methoxybenzyl (X₃) | methyl (S)-2-(methoxycarbonylamino)-3,3-dimethylbutanoyl (X₄) |
| 165 | D | 6-methylpyridin-2-yl (X₅) | tert-butyl (X₁) | benzyl (X₃) | methyl (S)-2-(methoxycarbonylamino)-3,3-dimethylbutanoyl (X₄) |
| 166 | A | 6-methylpyridin-2-yl (X₅) | tert-butyl (X₁) | (2-(pyridin-3-yl)thiazol-4-yl)methyl (X₃) | methyl (S)-2-(methoxycarbonylamino)-3,3-dimethylbutanoyl (X₄) |
| 167 | D | 2-(pyridin-3-yl)thiazol-4-yl (X₅) | sec-butyl (X₁) | benzyl (X₃) | methyl (S)-2-(methoxycarbonylamino)-3,3-dimethylbutanoyl (X₄) |

TABLE 6-continued

TABLE 6-continued

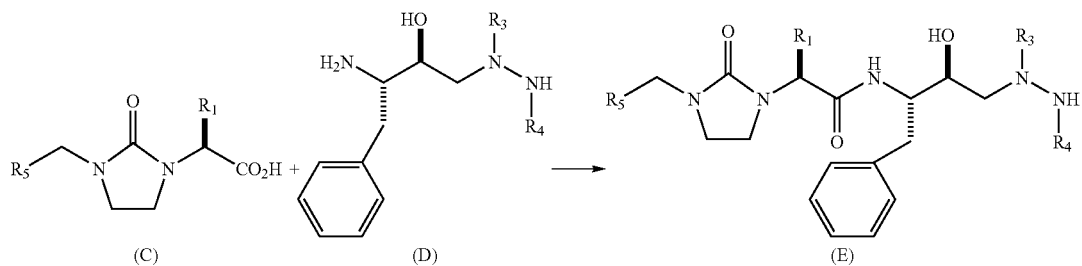

| Ex. | Method | R₅ | R₁ | R₃ | R₄ |
|-----|--------|----|----|----|----|
| 174 | A | 2-isopropylthiazol-4-yl (X₅) | (S)-sec-butyl (X₁) | 3,3-dimethylbutyl (X₃) | methyl (S)-2-(methoxycarbonylamino)-3,3-dimethylbutanoate (X₄) |
| 175 | D | 6-methylpyridin-2-yl (X₅) | tert-butyl (X₁) | 3,3-dimethylbutyl (X₃) | methyl (S)-2-(methoxycarbonylamino)-3,3-dimethylbutanoate (X₄) |
| 176 | A | 2-isopropylthiazol-4-yl (X₅) | (S)-sec-butyl (X₁) | 4-methoxybenzyl (X₃) | methyl (S)-2-(methoxycarbonylamino)-3,3-dimethylbutanoate (X₄) |
| 177 | A | 2-isopropylthiazol-4-yl (X₅) | (S)-sec-butyl (X₁) | 4-(pyridin-2-yl)benzyl (X₃) | methyl (S)-2-(methoxycarbonylamino)-3,3-dimethylbutanoate (X₄) |
| 178 | D | 6-methylpyridin-3-yl (X₅) | (S)-sec-butyl (X₁) | 4-(pyridin-2-yl)benzyl (X₃) | methyl (S)-2-(methoxycarbonylamino)-3,3-dimethylbutanoate (X₄) |

TABLE 6-continued
| Ex. | Method | R$_5$ | R$_1$ | R$_3$ | R$_4$ |
|---|---|---|---|---|---|
| 179 | A | 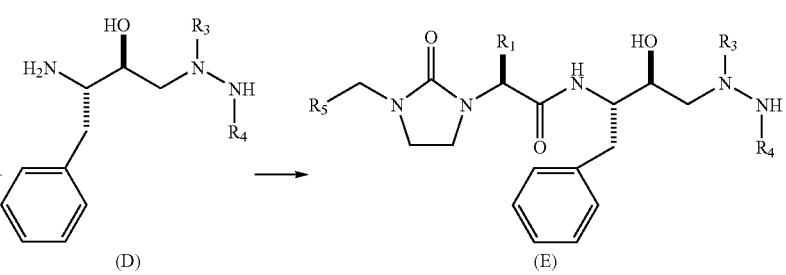 | 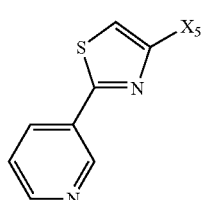 | 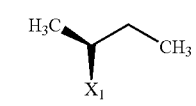 | 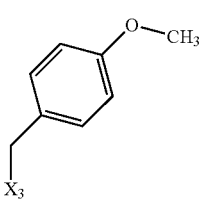 |
| 180 | A | 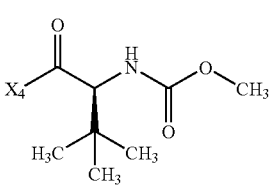 | 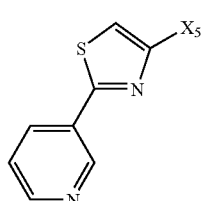 | 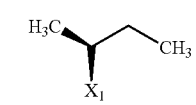 | 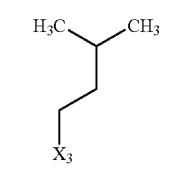 |
| 181 | A | 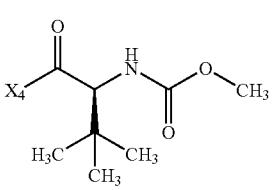 | 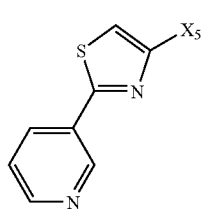 | 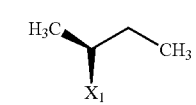 | 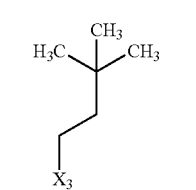 |
| 182 | A | 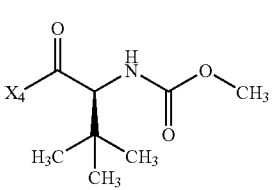 |  | 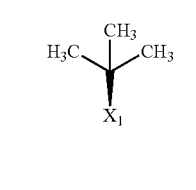 | 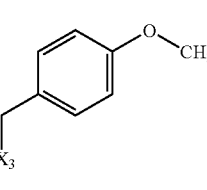 |
| 183 | A | 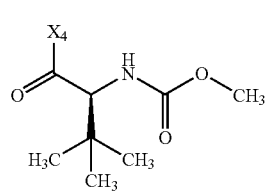 | 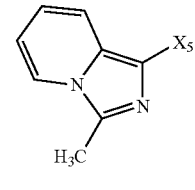 | 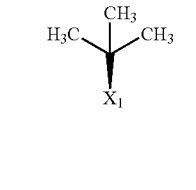 | 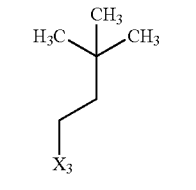 |
| 184 | A | 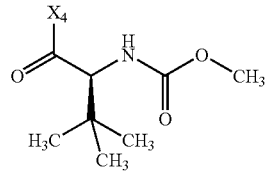 |  | 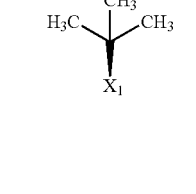 | 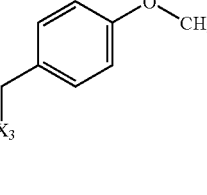 |

TABLE 6-continued
| Ex. | Method | R5 | R1 | R3 | R4 |
|---|---|---|---|---|---|
| 185 | A | 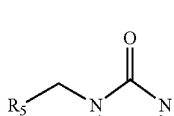 | 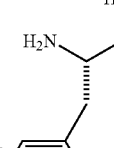 | 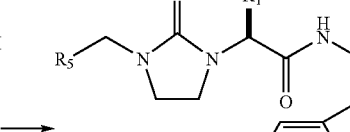 | 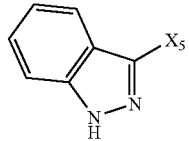 |
| 186 | A | 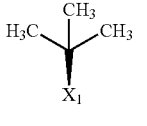 | 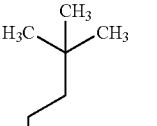 | 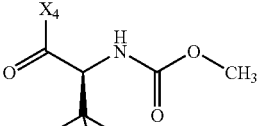 | 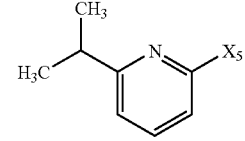 |
| 187 | A | 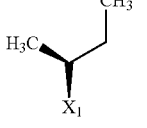 | 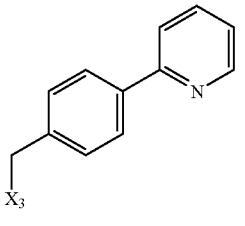 | 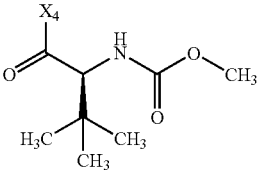 | 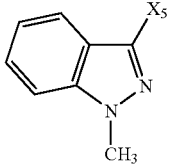 |
| 188 | A | 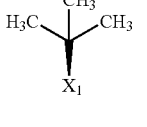 | 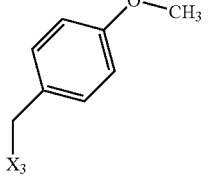 | 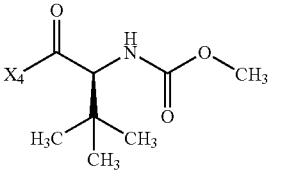 | 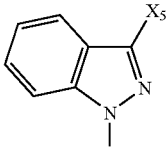 |
| 189 | A | 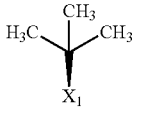 | 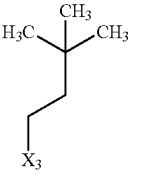 | 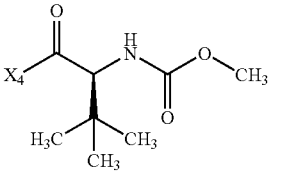 | 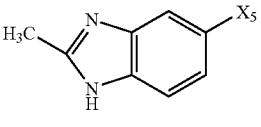 |
| 190 | D | 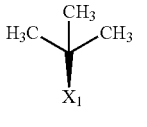 | 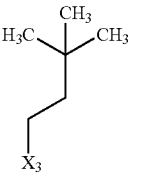 | 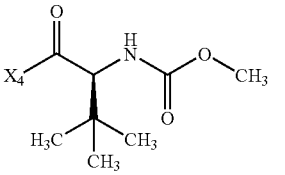 | 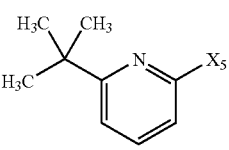 |

EXAMPLE 191 methyl (1S)-1-({2-((2S,3S)-2-hydroxy-3-{[(2S,3S)-
2-(3-{[2-(methoxymethyl)-1,3-thiazol-4-yl]methyl}-
2-oxo-1-imidazolidinyl)-3-methylpentanoyl]amino}-
4-phenylbutyl)-2-[4-(2-pyridinyl)benzyl]
hydrazino}carbonyl)-2,2-dimethylpropylcarbamate

EXAMPLE 191A tert-butyl 2-{(2S,3S)-3-[(tert-butoxycarbonyl)
amino]-2-hydroxy-4-phenylbutyl}-2-[4-(2-pyridinyl)
benzyl]hydrazinecarboxylate (2S,3S)-3-N-tert-butoxycarbonylamino-1,2-epoxy-4-phenylbutane (3 g, 0.011 mol) in isopropanol (50 mL) was combined with Example 4B (3.41 g, 1 equivalent), stirred at 85° C. for 16 hrs. The mixture was cooled to room temperature, evaporated and partitioned between $CHCl_3$ and brine. The organic layer was dried over sodium sulfate, filtered and evaporated to give an oil which was crystallized by trituration with diethyl ether, filtered, and dried in vacuo to give 2.27 g (35%) of the title compound.

EXAMPLE 191B (2S,3S)-3-amino-4-phenyl-1-{1-[4-(2-pyridinyl)
benzyl]hydrazino}-2-butanol Example 191A (2.27 g, 0.004 mol) was dissolved in THF (28 mL) and treated with 4N HCl (7.1 mL, 7 equivalents), heated at 60° C. for 3 hrs and cooled to room temperature. The mixture was evaporated and azeotroped in ethanol (30 mL) twice, and the residue was dissolved in THF (32 mL), treated with a solution of $NaHCO_3$ (1.36 g, 4 equivalents) in water (8 mL). The mixture was vigorously stirred for 3 hrs at 25° C. The solvents were evaporated and the concentrate partitioned between $CHCl_3$ and water. The organic layer was separated, washed with brine, dried over sodium sulfate, filtered and evaporated. The residue was purified using 1% methanol/$CHCl_3$ to give 1.14 g (61%) of the title compound.

EXAMPLE 191C 9H-fluoren-9-ylmethyl 2-[(2S,3S)-3-amino-2-hydroxy-4-phenylbutyl]-2-[4-(2-pyridinyl)benzyl]hydrazinecarboxylate Example 191B (0.25 g, 0.69 mmol) was dissolved in THF (3 mL) and combined with Fmoc-Osu (0.2 g, 1.1 equivalents) and DCC (0.13 g, 1.2 equivalents) and the mixture was stirred at 25° C. for 16 hrs. The mixture was filtered and evaporated and the residue was purified using 1% methanol/$CHCl_3$ to give 0.21 g (57%) of the title compound.

EXAMPLE 191D (2S,3S)—N-((1S,2S)-1-benzyl-2-hydroxy-3-{1-[4-
(2-pyridinyl)benzyl]hydrazino}propyl)-2-(3-{[2-
(methoxymethyl)-1,3-thiazol-4-yl]methyl}-2-oxo-1-
imidazolidinyl)-3-methylpentanamide Example 191C (0.21 g, 0.36 mmol) was dissolved in THF (2 mL) and combined with 4N HCl (0.5 mL, 7 equivalents) and heated to 60° C. was 3 hrs. The solvents were evaporated, and the residue was azeotroped with ethanol (20 mL) twice. The residue was dissolved in THF (2 mL) and treated with the Example 29 (105 mg, 1 equivalent), DEPBT (184 mg, 2 equivalents) and DIPEA (160 µL, 3 equivalens). The mixture was stirred at 25° C. for 2 h. This mixture was treated with 10% $Na_2CO_3$ (10 mL) at 25° C. for 20 min. and extracted with dichloromethane. The extracts were combined and washed with 10% $Na_2CO_3$, brine, and dried over sodium sulfate, filtered and evaporated. The crude residue was dissolved in THF (2 mL) and diethylamine (95 uL, 3 equivalens) and stirred at 25° C. for 16 hrs. The solvents were evaporated, and the residue was purified using 2% methanol/$CHCl_3$ to give 80 mg (38%) of the title compound.

EXAMPLE 191E methyl (1S)-1-({2-((2S,3S)-2-hydroxy-3-{[(2S,3S)-
2-(3-{[2-(methoxymethyl)-1,3-thiazol-4-yl]methyl}-
2-oxo-1-imidazolidinyl)-3-methylpentanoyl]amino}-
4-phenylbutyl)-2-[4-(2-pyridinyl)benzyl]
hydrazino}carbonyl)-2,2-dimethylpropylcarbamate Example 191D (26 mg, 0.037 mmol) was dissolved dichloromethane (1 mL) and treated with O-(1,2-dihydro-2-oxo-1-pyridyl)-N,N,N',N'-tetramethyluronium tetrafluoroborate (TPTU) (34 mg, 3 equivalents), N,N-di-isopropylethylamine (40 uL, 6 equivalent), followed by Example 1A (22 mg, 3 equivalents) at 0° C. for 0.5 h, then 25° C. for 16 hrs. The solvents were evaporated, and the residue was purified using 2% methanol/$CHCl_3$ to give 9 mg (28%) of the title compound.

EXAMPLE 192 methyl (1S)-1-({2-((2S,3S)-2-hydroxy-3-{[(2S,3S)-
2-(3-{[2-(methoxymethyl)-1,3-thiazol-4-yl]methyl}-
2-oxo-1-imidazolidinyl)-3-methylpentanoyl]
amino}4-phenylbutyl)-2-[4-(2-pyridinyl)benzyl]
hydrazino}carbonyl)-2-methylpropylcarbamate Example 191D (20 mg, 0.029 mmol) was dissolved in THF (1 mL) and treated with DEPBT (17.5 mg, 2 equivalents), Example 18A (5.1 mg, 1 equivalent), diisopropylethyl amine (15.3 µL, 3 equivalents) at 25° C. for 16 hrs. The mixture was combined with 10% sodium bicarbonate and dichloromethane. The organic layer was separated and washed with 10% sodium bicarbonate, brine, dried over sodium sulfate, filtered and the solvents were evaporated. The crude residue was purified using 1% methanol/chloroform to give 13.6 mg (35%) of the title compound. $^1$H NMR (300 MHz, $CDCl_3$) δ ppm 0.70 (m, 6H), 0.79 (d, J=6.62 Hz, 3H), 0.84 (m, 3H), 0.99 (s, 1H), 1.39 (d, J=25.00 Hz, 1H), 1.85 (dd, J=13.79, 7.17 Hz, 1H), 2.62 (s, 1H), 2.82 (m, 1H), 2.94 (m, 5H), 3.12 (m, 1H), 3.21 (m, 3H), 3.48 (m, 3H), 3.60 (s, 3H), 3.66 (dd, J=8.82, 6.99 Hz, 1H), 3.89 (m, 1H), 3.97 (d, J=19.85 Hz, 1H), 4.05 (s, 1H), 4.48 (s, 2H), 4.69 (s, 2H), 5.06 (d, J=8.46 Hz, 1H), 6.57 (d, J=8.09 Hz, 1H), 6.70 (s, 1H), 7.18 (m, 7H), 7.41 (d, J=8.46 Hz, 2H), 7.73 (m, 2H), 7.94 (d, J=8.46 Hz, 2H), 8.68 (d, J=4.78 Hz, 1H).

The compounds listed in Table 7, wherein $X_4$ represents the point of connection to the core structure (F), were prepared by the procedure as exemplified by Example 192, substituting the corresponding acids for Example 18A:

TABLE 7

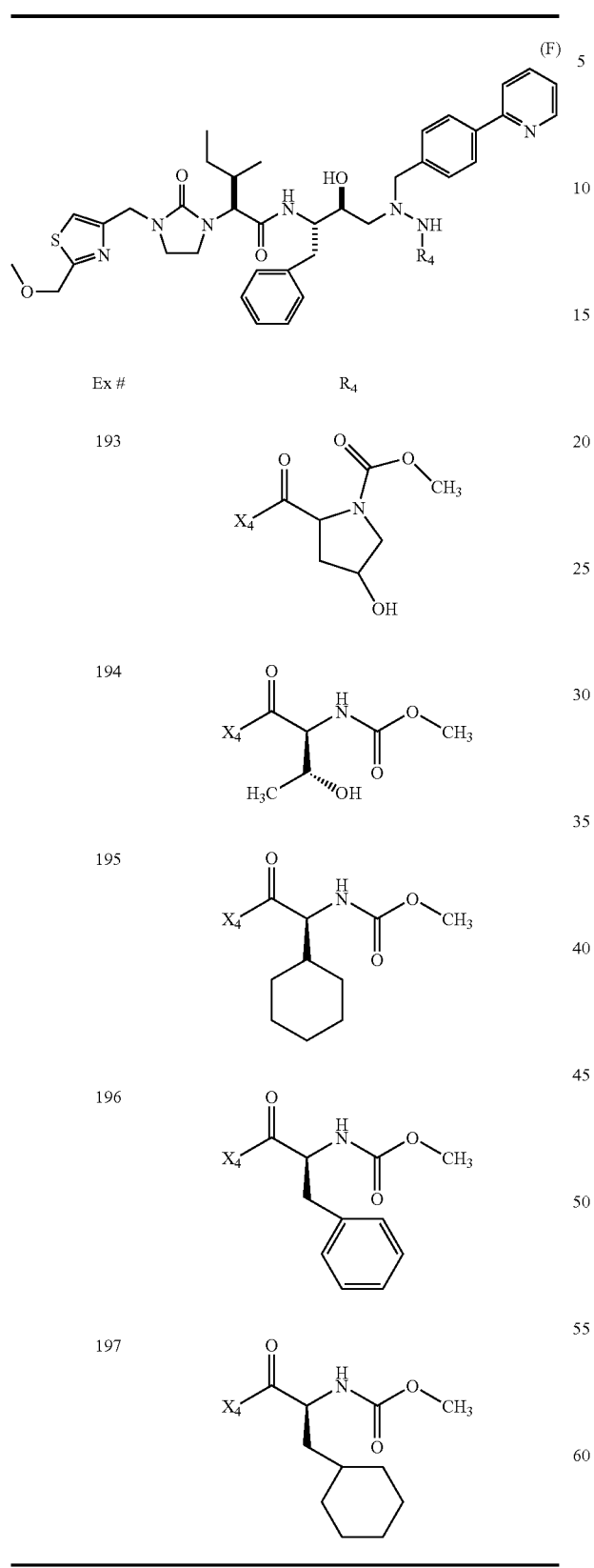

| Ex # | R₄ |
|---|---|
| 193 | (structure: methyl pyrrolidine carboxylate with OH) |
| 194 | (structure with CH₃, OH, NH-C(O)-OCH₃) |
| 195 | (structure with cyclohexyl, NH-C(O)-OCH₃) |
| 196 | (structure with benzyl, NH-C(O)-OCH₃) |
| 197 | (structure with cyclohexylmethyl, NH-C(O)-OCH₃) |

EXAMPLE 198 methyl (1S)-1-({2-{(2S,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}-2-[4-(2-pyridinyl)benzyl]hydrazino}carbonyl)-2,2-dimethylpropylcarbamate

EXAMPLE 198A tert-butyl 2-{(2S,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}-2-[4-(2-pyridinyl)benzyl]hydrazinecarboxylate Example 61 (64 mg, 0.22 mmol) was dissolved in THF (3 mL) and DMF (0.5 mL) and treated with HOBT (44 mg, 1.5 equivalents), EDAC (75 mg, 1.8 equivalent), and N,N-diisopropylethylamine (DIPEA)(38 µL, 1 equivalent) followed by Example 4G (100 mg, 1 equivalent). The mixture was stirred at 25° C. for 16 hrs. The solvents were evaporated and partitioned between ethyl acetate and saturated NaHCO₃. The organic layer was separated and washed with brine, dried over sodium sulfate and evaporated. The residue was purified using 2% methanol/CHCl₃ to give 120 mg (75%) of the title compound.

EXAMPLE 198B (2S)—N-((1S,2S)-1-benzyl-2-hydroxy-3-{1-[4-(2-pyridinyl)benzyl]hydrazino}propyl)-3-methyl-2-{3-[(2-methyl-1,3-thiazol-4-yl)methyl]-2-oxo-1-imidazolidinyl}butanamide Example 198A (120 mg, 0.16 mmol) was dissolved in THF (1 mL) and 4N HCl (0.3 mL) and the mixture was heated at 60° C. for 3 hrs. The mixture was cooled to room temperature and the solvents were evaporated. The residue was azetroped with ethanol (5 mL) twice and the title compound was used directly for the next step.

EXAMPLE 198C methyl (1S)-1-({2-{(2S,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}-2-[4-(2-pyridinyl)benzyl]hydrazino}carbonyl)-2,2-dimethylpropylcarbamate Example 198B (46 mg, 1.5 equivalent) was dissolved in dichloromethane (3 mL) and treated with O-(1,2-dihydro-2-oxo-1-pyridyl)-N,N,N',N'-tetramethyluronium tetrafluoroborate (TPTU) (72 mg, 1.5 equivalents) at 0° C. followed by DIPEA (85 uL, 3 equivalents). The mixture was stirred for 20 min. and combined with a solution of Example 1A, DIPEA (85 µL, 3 equivalents) in dichloromethane (2 mL), and stirred at 25° C. for 16 hours. The solvents were evaporated and partitioned between CHCl₃ and brine. The organic layer was dried over sodium sulfate, and the solvents were evaporated. The residue was purified using 2% methanol/CHCl₃ to give 38 mg (29%) of the title compound.

EXAMPLE 199 tert-butyl (1S)-1-({2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate

EXAMPLE 199A (2S,3S)—N-((1S,2S)-1-benzyl-2-hydroxy-3-{1-[4-(2-pyridinyl)benzyl]hydrazino}propyl)-3-methyl-2-[2-oxo-3-(4-quinolinylmethyl)-1-imidazolidinyl]pentanamide Example 75 (185 mg) was dissolved in THF (5 mL) and 4N HCl (1.1 mL, 20 equivalents) and heated to 60° C. for 2 hrs and cooled to room temperature. The solvents were evaporated and the residue was azetroped in ethanol (10 mL) twice to give 164 mg of the title compound.

EXAMPLE 199B tert-butyl (1S)-1-({2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate Example 199A (164 mg) was dissolved in THF:DMF (2.2 mL, 10:1) along with DEPBT (144 mg, 2 equivalents), TEA (230 μL, 7 equivalents) followed by Example 1A (61 mg, 1.1 equivalents). The mixture was stirred at 25° C. for 4 h. The mixture was partitioned between ethyl acetate and 10% NaHCO$_3$ and stirred vigorously for 30 min. The organic layer was separated, and the aqueous layer was re-extracted with ethyl acetate. The organic layer was combined, washed with brine, and dried over magnesium sulfate and evaporated. The residue was purified using chloroform:methanol (98:2) to give 156 mg (72%) of the title compound. $^1$HNMR (300 MHz, CDCl$_3$) δ ppm 0.75 (m, 3H), 0.82 (s, 9H), 0.93 (m, 3H), 1.33 (d, J=5.52 Hz, 1H), 1.43 (m, 9H), 1.89 (s, 1H), 2.85 (m, 8H), 3.57 (m, 1H), 3.61 (s, 1H), 3.91 (d, J=11.03 Hz, 1H), 4.00 (m, 2H), 4.13 (d, J=8.46 Hz, 1H), 4.25 (dd, J=15.44, 6.99 Hz, 1H), 4.80 (m, 2H), 5.09 (d, J=9.19 Hz, 1H), 6.48 (d, J=9.56 Hz, 1H), 6.56 (s, 1H), 7.05 (m, 3H), 7.20 (m, 2H), 7.35 (m, 1H), 7.43 (d, J=8.09 Hz, 2H), 7.74 (m, 4H), 7.95 (d, J=8.46 Hz, 2H), 7.95 (m, 1H), 8.14 (d, J=7.72 Hz, 1H), 8.21 (d, J=7.35 Hz, 1H), 8.68 (d, J=4.41 Hz, 1 H), 8.88 (d, J=4.41 Hz, 1H).

The compounds listed in Table 8, wherein X$_4$ represents the point of connection to the core structure (G), were prepared by coupling the corresponding acids (Examples 28-69) with the corresponding amine (Example 199A), using the procedure of Example 199B:

TABLE 8

(G) [core structure shown]

| Ex # | R$_4$ |
|------|-------|
| 200 | [structure: X$_4$–C(O)–CH(NHCO$_2$CH$_3$)–C(CH$_3$)$_3$] |
| 201 | [structure: X$_4$–O–C(O)–O–(tetrahydrofuran-3-yl)] |
| 202 | [structure: X$_4$–C(O)–CH(2-oxoimidazolidin-1-yl)–C(CH$_3$)$_3$] |
| 203 | [structure: X$_4$–C(O)–CH$_2$–O–(2,6-dimethylphenyl)] |
| 204 | [structure: X$_4$–C(O)–CH$_2$–O–(2-methylphenyl)] |
| 205 | [structure: X$_4$–C(O)–(2-methyl-3-hydroxyphenyl)] |
| 206 | [structure: X$_4$–C(O)–CH(2-oxoimidazolidin-1-yl)–CH(CH$_3$)(CH$_2$CH$_3$)] |

TABLE 8-continued

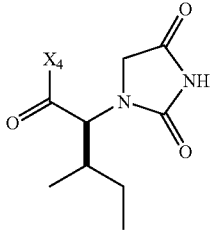

| Ex # | R4 |
|---|---|
| 207 | 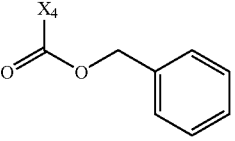 |
| 208 | (structure: X4-C(=O)-O-CH2-phenyl) |

EXAMPLE 209 ethyl (1S)-1-({2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate

EXAMPLE 209A (2S,3S)—N-((1S,2S)-3-{2-[(2S)-2-amino-3,3-dimethylbutanoyl]-1-[4-(2-pyridinyl)benzyl]hydrazino}-1-benzyl-2-hydroxypropyl)-3-methyl-2-[2-oxo-3-(4-quinolinylmethyl)-1-imidazolidinyl]pentanamide Example 199B (150 mg, 0.17 mmol) was dissolved in dichloromethane (1 mL) and trifluoroacetic acid (1 mL) and stirred at 25° C. for 1 h. The solvents were evaporated and the residue was partitioned between ethyl acetate and saturated NaHCO₃, the organic layer was washed with brine, dried over MgSO₄, filtered and evaporated to give the title compound, used directly for the next step.

EXAMPLE 209B ethyl (1S)-1-({2-[(2S,3S)-2-hydroxy-3-({(2S,3S)-3-methyl-2-[2-oxo-(4-quinolinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate Example 209A (20 mg, 0.025 mmol) was dissolved in dichloromethane (0.3 mL) and treated with trifluoroacetic acid (8 µL, 2.2 equivalents) and ethyl chloroformate ((3 µL, 1.1 equivalents) at 25° C. for 16 hours. The solvents were evaporated, and the crude residue was purified using ethyl acetate:methanol (9:1) with 0.2% ammonium hydroxide to give 9.2 mg (42%) of the title compound.

EXAMPLE 210

(2S,3S)—N-((1S,2S)-3-{2-[(2S)-2-(acetylamino)-3,3-dimethylbutanoyl]-1-[4-(2-pyridinyl)benzyl]hydrazino}-1-benzyl-2-hydroxypropyl)-3-methyl-2-[2-oxo-3-(4-quinolinylmethyl)-1-imidazolidinyl]pentanamide Example 209A (20 mg, 0.025 mmol) was dissolved in dichloromethane (0.3 mL) and treated with trifluoroacetic acid (8 µL, 2.2 equivalents) and acetic anhydride (3 µL, 1.1 equivalents) at 25° C. for 16 hours. The solvents were evaporated, and the residue was purified by preparative TLC using 0.5 mm silica gel plates and CHCl₃:methanol:NH₄OH (90:9.8:0.2) to give 3.5 mg (17%) of the title compound.

EXAMPLE 211 methyl (1S,2S)-1-({2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]-2-[4-(3-pyridinyl)benzyl]hydrazino}carbonyl)-2-methylbutylcarbamate Example 79 (22 mg, 0.025 mmol) was dissolved in toluene (0.2 mL) and treated with tetrakis(triphenylphosphine)-palladium(0) (3 mg, 10 mol %, 0.1 equivalent) followed by 2M Na₂CO₃ (26 µL, 2 equivalents). The mixture was stirred at 25° C. for 10 min. and a solution of 3-pyridine boronic acid (6.3 mg, 2 equivalents) in ethanol (0.2 mL) was added. The mixture was heated in microwave (150° C., 30 min.). The mixture was cooled to room temperature, diluted with dichloromethane and filtered. The solvents were evaporated, and the residue was purified by HPLC reverse phase chromatography using water (0.1% trifluoroacetic acid):acetonitrile (95:5) to acetonitrile (100%) to give 15 mg (68%) of the title compound. ¹H NMR (300 MHz, DMSO-d₆) δ ppm 0.51 (d, J=6.62 Hz, 3H), 0.65 (m, 6H), 0.77 (t, J=7.17 Hz, 3H), 1.00 (m, 3H), 1.21 (d, J=12.50 Hz, 3H), 1.50 (m, 1H), 1.78 (s, 1H), 2.68 (m, 4H), 3.06 (m, 3H), 3.48 (d, J=11.03 Hz, 3H), 3.63 (d, J=7.72 Hz, 2H), 3.98 (m, 2H), 4.46 (s, 4H), 4.87 (s, 2H), 7.08 (m, 5H), 7.52 (m, 3H), 7.69 (m, J=8.46 Hz, 3H), 7.87 (t, J=6.99 Hz, 1H), 8.11 (d, J=8.09 Hz, 1H), 8.29 (d, J=7.72 Hz, 1H), 8.37 (d, J=7.72 Hz, 1H), 8.66 (d, J=5.15 Hz, 1H), 8.99 (m, 2H), 9.12 (s, 1H).

The compounds listed in Table 9, wherein X₃ₐ represents the point of connection to the core structure (H), were prepared by the procedure as exemplified in Example 211, coupling Example 79 with the corresponding commercially available boronic acids:

TABLE 9

(H)

| Ex # | R$_{3a}$ |
|---|---|
| 212 | 1,3-benzodioxol-5-ylmethyl (X$_{3a}$) |
| 213 | 3,5-dimethylisoxazol-4-ylmethyl (X$_{3a}$) |
| 214 | pyridin-4-ylmethyl (X$_{3a}$) |

EXAMPLE 215 methyl (1S)-1-[(2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate Example 84 (0.26 g, 0.34 mmol) was dissolved in trifluoroacetic acid:dichloromethane (3:1) (10 mL) at 50° C. for 2 hrs. The solvents were evaporated, and the mixture was partitioned between saturated NaHCO$_3$ and dichloromethane. The organic layer was separated and dried over sodium sulfate, evaporated, and the residue was purified using 5% methanol/CHCl$_3$ to give 140 mg (64%) of the title compound.

EXAMPLE 216 methyl (1S)-1-[(2-{(2S,3S)-2-hydroxy-3-[((2S,3S)-3-methyl-2-{3-[2-(6-methyl-2-pyridinyl)ethyl]-2-oxo-1-imidazolidinyl}pentanoyl)amino]-4-phenylbutyl}-2-isopentylhydrazino)carbonyl]-2,2-dimethylpropylcarbamate Example 215 (60 mg, 0.091 mmol) was dissolved in 1,2-dichloroethane (1 mL) and treated with isovaleraldehyde (10 mg, 1.2 equivalents) and acetic acid (15 µL, 3 equivalents) followed by sodium triacetoxy borohydride (60 mg, 3 equivalents) at 25° C. for 16 hrs. The mixture was partitioned between saturated NaHCO$_3$ and dichloromethane, the organic layer was separated, dried over sodium sulfate, filtered and the solvents were evaporated. The residue was purified using 3% methanol/CHCl$_3$ to give 36 mg (55%) of the title compound. $^1$H NMR (300 MHz, CDCl$_3$) δ ppm 0.82 (d, J=6.25 Hz, 6H), 0.87 (m, 6H), 1.00 (s, 9H), 1.07 (m, 1H), 1.34 (m, 2H), 1.45 (m, 1H), 1.55 (m, 1H), 1.94 (d, J=11.03 Hz, 1H), 2.54 (s, 3H), 2.65 (d, J=9.19 Hz, 1H), 2.71 (m, 3H), 2.93 (d, J=7.72 Hz, 2H), 3.07 (m, 1H), 3.17 (m, 4H), 3.58 (s, 3H), 3.77 (d, J=9.56 Hz, 1H), 3.96 (m, J=11.03 Hz, 2H), 4.48 (m, 2H), 5.35 (d, J=9.56 Hz, 1H), 6.74 (d, J=8.46 Hz, 1H), 6.88 (d, J=18.02 Hz, 1H), 7.06 (dd, J=10.85, 7.54 Hz, 2H), 7.15 (m, 5H), 7.55 (t, J=7.72 Hz, 1H).

The compounds listed in Table 10, wherein X$_3$ represents the point of connection to the core structure (J), were prepared by the procedure as exemplified in Example 216, substituting the commercially available aldehydes for isovaleraldehyde:

TABLE 10

(J)

| Ex # | R$_3$ |
|---|---|
| 217 | 4-methylbenzyl (X$_3$) |
| 218 | cyclohexylmethyl (X$_3$) |
| 219 | isobutyl (X$_3$) |
| 220 | 2-phenylethyl (X$_3$) |
| 221 | thiophen-2-ylmethyl (X$_3$) |
| 222 | naphthalen-2-ylmethyl (X$_3$) |

TABLE 10-continued (J)

Structure shown with R₃ substituent position.

| Ex # | R₃ |
|------|-----|
| 223 | 4-isopropylbenzyl (X₃-CH₂-C₆H₄-iPr) |
| 224 | 4-isopropoxybenzyl |
| 225 | 3,4-dimethylbenzyl |
| 226 | 3-methoxybenzyl |
| 227 | 2-ethylbutyl |
| 228 | 4-ethylbenzyl |
| 229 | 3-methylbenzyl |
| 230 | 4-trifluoromethylbenzyl |
| 231 | 4-hydroxybenzyl |
| 232 | 4-fluorobenzyl |
| 233 | 3-(4-methylphenoxy)benzyl |
| 234 | 3-(4-chlorophenoxy)benzyl |
| 235 | quinolin-2-ylmethyl |
| 236 | 5-ethylthiophen-2-ylmethyl |
| 237 | oct-2-ynyl |

TABLE 10-continued (J)

| Ex # | R₃ |
|---|---|
| 238 | CH₃O₂C-(CH₂)₅-X₃ |
| 239 | 5-ethyl-furan-2-yl-CH₂-X₃ |
| 240 | 4-(imidazol-1-yl)benzyl-X₃ |
| 241 | 3,3-dimethylbutyl-X₃ |
| 242 | 4-(NHCOCH₃)benzyl-X₃ |
| 243 | 4-(CO₂CH₃)benzyl-X₃ |
| 244 | 3-phenoxybenzyl-X₃ |
| 245 | 3-(4-methoxyphenoxy)benzyl-X₃ |

TABLE 10-continued (J)

| Ex # | R₃ |
|---|---|
| 246 | 4-tert-butylbenzyl-X₃ |
| 247 | 2,3-dihydrobenzo[1,4]dioxin-6-ylmethyl-X₃ |
| 248 | 4-(SCF₃)benzyl-X₃ |
| 249 | 3,7-dimethyl-oct-6-enyl-X₃ |
| 250 | cyclopropylmethyl-X₃ |
| 251 | (2-ethyl-imidazol-5-yl)methyl-X₃ |
| 252 | 2,3-dihydrobenzofuran-5-ylmethyl-X₃ |
| 253 | 4-chlorobenzyl-X₃ |

TABLE 10-continued
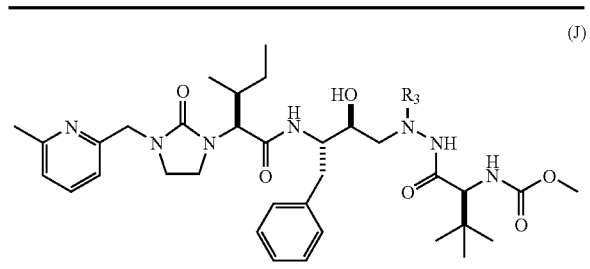
(J)
| Ex # | R₃ |
|---|---|
| 254 | 3,4-dimethoxybenzyl |
| 255 | 3-fluoro-4-methoxybenzyl |
| 256 | 1,3-benzodioxol-5-ylmethyl |
| 257 | 4-methoxy-3-methylbenzyl |
| 258 | 4-hydroxy-3-methoxybenzyl |
| 259 | 4-(methylsulfonyl)benzyl |
| 260 | (1H-imidazol-2-yl)methyl |
| 261 | 4-hydroxybutyl |
TABLE 10-continued
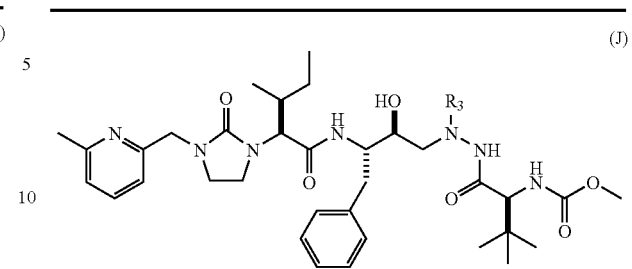
(J)
| Ex # | R₃ |
|---|---|
| 262 | (4,5-dimethylfuran-2-yl)methyl |
| 263 | 3-chlorobenzyl |
| 264 | 3,5-dimethylbenzyl |
| 265 | neopentyl |
| 266 | 2,4-dimethylpentyl |
| 267 | 4-cyanobenzyl |
| 268 | cyclohexyl |
| 269 | 3,4-dichlorobenzyl |

EXAMPLE 270

2-(4-pyridinyl)-1,3-thiazole-4-carbaldehyde

EXAMPLE 270A ethyl 2-(4-pyridinyl)-1,3-thiazole-4-carboxylate

A suspension of iso-thionicotinamide (5 g, 36.2 mmol) was dissolved in ethanol (90 mL) and treated with ethyl bromopyruvate (5 mL, 1 equivalent) and 20 g of powdered 3 A molecular sieves. The reaction was stirred at 70° C. under a nitrogen atmosphere for 48 h. The mixture was filtered and evaporated to give 12.5 g of crude material. This material was dissolved in THF (200 mL) and treated with 2,6-lutidine (17 mL, 4 equivalents). The reaction was cooled to 0° C. followed by the addition of trifluoroactetic acid (10.2 mL, 2 equivalents). Stirring was continued for 2 hrs under a nitrogen atmosphere. Water (200 mL) was added and the reaction was extracted twice with ethyl acetate (600 mL, 150 mL). The combined organic layers were washed with brined, dried over magnesium sulfate, filtered and the solvent was removed by evaporation. The crude material was purified using chloroform:ethyl acetate (1:1) to give 4.70 g (56%) of the title compound.

EXAMPLE 270B 2-(4-pyridinyl)-1,3-thiazole-4-carbaldehyde

Example 270A (4.7 g, 20.1 mmol) was dissolved in dichloromethane (67 mL) and treated with the slow addition of a 1 M solution of diisobutylaluminum hydride in dichloromethane (38 mL, 1.9 equivalents). The reaction was stirred under a nitrogen atmosphere for 1 h., followed by addition of acetic acid (3.8 mL). The reaction was warmed to 25° C., quenched with a 10% solution of sodium potassium tartrate (200 mL), and stirred for 1 h. The layers were separated and the aqueous layer was extracted twice with ethyl acetate. The combined organic layers were washed with brine, dried over magnesium sulfate, filtered and the solvent was removed by evaporation to give 3.73 g crude material which was purified using chloroform:ethyl acetate (1:1) to give 2.62 g (69%) of the title compound.

EXAMPLE 271

4-(5-pyrimidinyl)benzaldehyde

5-Bromopyrimidine (159 mg, 1 mmol) was dissolved in toluene (5 mL) and treated with tetrakis(triphenylphosphine)-palladium(0) (116 mg, 0.1 equivalent) and a 2 M solution of sodium carbonate (1 mL, 2 equivalents). The mixture was stirred under an argon atmosphere for 20 min. followed by addition of 3-formylphenyl boronic acid (165 mg, 1.1 equivalensts) in ethanol (1 mL). The reaction was heated to 80° C. and stirred for 16 hrs. The mixture was filtered and partitioned between ethyl acetate and water. The organic layer was washed with brine, dried over magnesium sulfate, filtered, and the solvent was removed by evaporation. This material was purified using hexanes:dichloromethane (1:1) followed by dichloromethane:methanol (97:3) to give 110 mg (60%) of the title compound.

EXAMPLE 272

2-(5-methyl-3-isoxazolyl)-1,3-thiazole-4-carbaldehyde

EXAMPLE 272A ethyl 2-(5-methyl-3-isoxazolyl)-1,3-thiazole-4-carboxylate

5-Methyl-isoxazole-3-carbothioamide (1.0 g, 7.0 mmol) was dissolved in acetone (16 mL) and treated with ethyl bromopyruvate (1 mL, 1 equivalent) and 3.9 g of powdered 3 A molecular sieves. The reaction was stirred at 55° C. under a nitrogen atmosphere for 18 h. The mixture was filtered and evaporated to give 1.06 g of crude material. This material was dissolved in THF (25 mL), cooled to 0° C., and treated with 2,6-lutidine (1.5 mL, 3 equivalents). Trifluoroactic acid (0.9 mL, 1.5 equivalents) was added and stirring was continued for 2 hrs under a nitrogen atmosphere. The reaction was poured into a 1 M solution of sodium bicarbonate and extracted twice with ethyl acetate (75 mL). The combined organic layers were washed with brine, dried over magnesium sulfate, filtered and the solvent was removed by evaporation. The crude material was purified using chloroform:ethyl acetate (1:1) to give 876 mg (53%) of the title compound.

EXAMPLE 272B 2-(5-methyl-3-isoxazolyl)-1,3-thiazole-4-carbaldehyde

Example 272A (870 mg, 3.7 mmol) was dissolved in dichloromethane (12 mL) and treated with the dropwise addition of a 1 M solution of diisobutyl aluminum hydride in dichloromethane (7.0 mL, 1.9 equivalents). The reaction was stirred under a nitrogen atmosphere for 1 h. followed by addition of acetic acid (0.7 mL). The reaction was warmed to 25° C., quenched with a 10% solution of sodium potassium tartrate (45 mL), and stirred for 1 h. The layers were separated and the aqueous layer was extracted twice with chloroform. The combined organic layers were washed with brine, dried over magnesium sulfate, filtered and the solvent was removed by evaporation to give 670 mg of crude material which was purified using chloroform:hexanes (4:1) to give 594 g (83%) of the title compound.

EXAMPLE 273

2-(2-pyridinyl)-1,3-thiazole-4-carbaldehyde

EXAMPLE 273A ethyl 2-(2-pyridinyl)-1,3-thiazole-4-carboxylate

2-Picolinamide (3.1 g, 25.4 mmol) was dissolved in toluene (25 mL) and treated with Lawesson's Reagent (5.1 g, 0.5 equivalents). The reaction was heated to 85° C. and stirred for 48 hrs. The reaction was quenched with water and extracted and extracted with ethyl acetate. The organic layer was washed with brine, dried over magnesium sulfate, filtered, and the solvent was removed by evaporation. This material was dissolved in ethanol (50 mL) and treated with ethyl bromopyruvate (3 mL, about 1 equivalent) and powdered 3 A molecular sieves (10 g). The reaction was refluxed for 16 hrs. The reaction was then filtered and the solvent was removed by evaporation. The material was dissolved in ethyl acetate, washed with a saturated solution of sodium bicarbonate, washed with brine, and dried over magnesium sulfate. The reaction was filtered and the solvents were removed by evaporation. This material was purified using dichloromethane: ethyl acetate (3:1) to give 1.98 g of the title compound (33%).

EXAMPLE 273B 2-(2-pyridinyl)-1,3-thiazole-4-carbaldehyde

Example 273A (910 mg, 3.9 mmol) was dissolved in dichloromethane (13 mL) and treated with the dropwise addition of a 1 M solution of diisobutyl aluminum hydride in dichloromethane (7.4 mL, 1.9 equivalents). The reaction was stirred under a nitrogen atmosphere for 1 h. followed by addition of acetic acid (0.8 mL). The reaction was warmed to 25° C., quenched with a 10% solution of sodium potassium tartrate (45 mL), and stirred for 1 h. The layers were separated and the aqueous layer was extracted twice with chloroform. The combined organic layers were washed with brine, dried over magnesium sulfate, filtered and the solvent was removed by evaporation to give 670 mg of crude material. The crude material was purified using chloroform:hexanes (4:1) to give 390 g (53%) of the title compound.

EXAMPLE 274

2-isopropyl-1,3-thiazole-4-carbaldehyde

Example 274 was prepared using the procedures as described in Journal of Medicinal Chemistry, 41, 4; 602-617 (1998).

EXAMPLE 275 methyl (1S)-1-[(2-((2S,3S)-2-hydroxy-3-{[(2S)-2-(3-{[2-(methoxymethyl)-1,3-thiazol-4-yl]methyl}-2-oxo-1-imidazolidinyl)-3,3-dimethylbutanoyl]amino}-4-phenylbutyl)-2-{[2-(4-pyridinyl)-1,3-thiazol-4-yl]methyl}hydrazino)carbonyl]-2,2-dimethylpropylcarbamate

EXAMPLE 275A tert-butyl 2-((2S,3S)-3-{[(benzyloxy)carbonyl]amino}-2-hydroxy-4-phenylbutyl)-2-(4-nitrobenzyl)hydrazinecarboxylate N'-(4-Nitro-benzyl)-hydrazinecarboxylic acid tert-butyl ester (1 g, 3.7 mmol) was dissolved in isopropanol (30 mL) and treated with (2S,3S)-3-N-benzyloxycarbonylamino-1,2-epoxy-4-phenylbutane (1.2 g, 1.1 equivalents) at 65° C. for 16 hrs. The mixture was cooled to 25° C., and the solids were filtered and dried in vacuo to give 1.5 g (71%) of the title compound.

EXAMPLE 275B benzyl (1S,2S)-1-benzyl-2-hydroxy-3-[2-{(2S)-2-[(methoxycarbonyl)amino]-3,3-dimethylbutanoyl}-1-(4-nitrobenzyl)hydrazino]propylcarbamate Example 275A (0.355 g, 0.63 mmol) was dissolved in THF (6.3 mL) and treated with 4N HCl (1.2 mL) at 60° C. for 16 hrs. The solvents were evaporated and the crude residue was dissolved in THF (3.2 mL) and treated with DEPBT (0.28 g, 1.5 equivalents), triethylamine (0.26 mL, 3 equivalents) at 25° C. for 3 hrs. The solvents were evaporated, and the crude residue was purified using HPLC reverse phase chromatography using water (0.1% trifluoroacetic acid):acetonitrile (95:5) to acetonitrile (100%) to give 344 mg (86%) of the title compound.

EXAMPLE 275C methyl (1S)-1-{[2-((2S,3S)-2-hydroxy-3-{[(2S)-2-(3-{[2-(methoxymethyl)-1,3-thiazol-4-yl]methyl}-2-oxo-1-imidazolidinyl)-3,3-dimethylbutanoyl]amino}-4-phenylbutyl)hydrazino]carbonyl}-2,2-dimethylpropylcarbamate A solution of Example 275B (0.29 g, 0.456 mmol) in methanol (4.6 mL) was treated with Pd/C (29 mg, 10%) stirred at 25° C. under a hydrogen balloon for 2.5 hrs. The catalyst was filtered, rinsed with methanol, and the solvents were evaporated to give 0.17 g of crude product which was used for the next step. The crude material was dissolved in DMF (3.6 mL) and treated with EDAC (112 mg, 2 equivalents), HOBT (97 mg, 2 equivalents), N-methyl morpholine (251 µL, 5 equivalents) and Example 32 (123 mg, 1 equivalent) at 25° C. for 16 hrs. The solvents were evaporated, and the residue was partitioned between 1N NaHCO$_3$ and ethyl acetate. The organic layer was separated, washed with brine, dried with magnesium sulfate, and the solvents were evaporated to give two products, one being the amine Example 275C and the other, the para-aminobenzyl compound. This mixture was submitted to THF: 4N HCl (1:2) at 50° C. for 3 hrs to give 85 mg (27%) of the title compound.

EXAMPLE 275D methyl (1S)-1-[(2-((2S,3S)-2-hydroxy-3-{[(2S)-2-(3-{[2-(methoxymethyl)-1,3-thiazol-4-yl]methyl}-2-oxo-1-imidazolidinyl)-3,3-dimethylbutanoyl]amino}-4-phenylbutyl)-2-{[2-(4-pyridinyl)-1,3-thiazol-4-yl]methyl}hydrazino)carbonyl]-2,2-dimethylpropylcarbamate A solution of Example 275C (13.8 mg, 0.02 mmol) in 1,2-dichloroethane (0.25 mL) was treated with 2-(4-pyridyl)thiazole 4-carboxaldehyde (4.6 mg, 1.2 equivalents), sodium triacetoxy borohydride (12.7 mg, 3 equivalents), and acetic acid (2.3 µL), and stirred at 25° C. for 16 hrs. The mixture was partitioned between dichloromethane and saturated NaHCO$_3$. The organic layer was separated, dried with magnesium sulfate, filtered, and the solvents were evaporated. The residue was purified by HPLC reverse phase chromatography using water (0.1% trifluoroacetic acid):acetonitrile (95:5) to acetonitrile (100%) to give 3 mg (14%) of the title compound. $^1$H NMR (300 MHz, CD$_3$OD) δ ppm 0.87 (s, 9H), 0.91 (s, 9H), 2.36 (d, J=8.82 Hz, 1H), 2.85 (m, 5H), 3.07 (m, 1H), 3.14 (m, 1H), 3.28 (m, 3H), 3.46 (s, 3H), 3.61 (s, 3H), 3.76 (s, 1H), 3.85 (s, 1H), 4.05 (s, 1H), 4.16 (m, 3H), 4.46 (m, 2H), 4.71 (s, 2H), 7.08 (m, 3H), 7.16 (m, 2H), 7.38 (s, 1H), 7.73 (s, 1H), 7.95 (m, 2H), 8.64 (m, 2H).

The compounds listed in Table 11, wherein X$_3$ represents the point of connection to the core structure (K), were prepared by the procedure as exemplified in Example 275D, substituting the corresponding commercially available aldehydes for 2-(4-pyridyl)thiazole 4-carboxaldehyde:

TABLE 11

(K) [Structure shown with R₃ substituent]

| Ex # | R₃ |
|---|---|
| 276 | benzyl-pyrimidine (3-pyrimidin-5-yl-benzyl), X₃ |
| 277 | 4-(5-methylisoxazol-3-yl)thiazol-2-yl methyl, X₃ |
| 278 | 2-(pyridin-2-yl)thiazol-4-ylmethyl, X₃ |
| 279 | 2-isopropylthiazol-4-ylmethyl, X₃ |

EXAMPLE 280 methyl (1S)-1-{[2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)-2-isopentylhydrazino]carbonyl}-2,2-dimethylpropylcarbamate

EXAMPLE 280A methyl (1S)-1-{[2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)hydrazino]carbonyl}-2,2-dimethylpropylcarbamate A solution of Example 19A (0.46 g, 0.987 mmol) in dichloromethane:trifluoroacetic acid (9 mL, 2:1) was stirred at 25° C. for 4 hrs. The solvents were evaporated and the crude residue was dissolved in DMF (10 mL) and treated with Example 29 (0.37 g, 1.1 equivalents), EDAC (0.338 g, 2 equivalents), HOBT (0.29 g, 2 equivalents), and N-methyl morpholine (0.76 mL, 5 equivalent) at 25° C. for 16 hrs. The solvents were evaporated, and the crude residue was partitioned between ethyl acetate and 1N sodium bicarbonate. The organic layer was separated, washed with brine, dried over magnesium sulfate, filtered, and the solvents were evaporated to give 0.475 g (70%) of the title compound.

EXAMPLE 280B methyl (1S)-1-{[2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)-2-isopentylhydrazino]carbonyl}-2,2-dimethylpropylcarbamate A solution of Example 280A (20 mg, 0.029 mmol) in 1,2-dichloroethane (0.3 mL) was treated with isovaleraldehyde (6.2 µL, 2 equivalents), acetic acid (3.3 µL, 2 equivalents), and sodium triacetoxyborohydride (18.5 mg, 3 equivalents) at 25° C. for 16 hrs. The mixture was partitioned between dichloromethane and saturated sodium bicarbonate. The organic layer was separated, washed with brine, dried over magnesium sulfate, filtered, and the solvents were evaporated. The residue was purified by HPLC reverse phase chromatography using water (0.1% TFA):acetonitrile (95:5) to acetonitrile (100%) to give 8 mg (36%) of the title compound. $^1$H NMR (300 MHz, DMSO-$d_6$) δ ppm 0.78 (dd, J=13.79, 6.43 Hz, 12H), 0.91 (m, 9H), 1.25 (m, 3H), 1.62 (m, 1H), 1.77 (d, J=8.82 Hz, 1H), 2.58 (m, 3H), 2.69 (m, 4H), 2.79 (m, 2H), 3.09 (m, 3H), 3.37 (s, 3H), 3.81 (m, 2H), 3.95 (m, 2H), 4.10 (s, 1H), 4.36 (m, 2H), 4.66 (s, 1H), 7.06 (m, 5H), 7.20 (m, 1H), 7.44 (m, 1H), 8.96 (s, 2H), 9.17 (s, 1H), 9.48 (s, 1H).

The compounds listed in Table 12, wherein $X_3$ represents the point of connection to the core structure (L), were prepared by the procedure as exemplified in Example 280B, substituting the corresponding commercially available aldehydes for isovaleraldehyde:

TABLE 12

(L) [Structure shown with R₃ substituent]

| Ex # | R₃ |
|---|---|
| 281 | 3,4-dimethoxybenzyl (OCH₃, OCH₃), X₃ |
| 282 | 3,4-dimethylbenzyl (CH₃, CH₃), X₃ |

EXAMPLE 283 methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(4-methoxybenzyl)hydrazino]carbonyl}-2-methylbutylcarbamate

EXAMPLE 283A methyl (1S,2S)-1-[(2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2-methylbutylcarbamate A solution of Example 127 (0.74 g) in methanol (5 mL) was treated with 4N HCl (0.25 mL, 1 equivalent) and Pearlman's catalyst (150 mg, 20 wt %) and stirred under a hydrogen balloon at 25° C. for 4 hrs. The mixture was filtered, rinsed with methanol (10 mL), and the solvents were evaporated. The residue was purified using 10% methanol/CHCl₃ to give 0.47 g (73%) of the title compound.

EXAMPLE 283B methyl (1S,2S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(4-methoxybenzyl)hydrazino]carbonyl}-2-methylbutylcarbamate A solution of Example 283A (50 mg, 0.45 mmol) in 1,2-dichloroethane (1 mL) and treated with p-anisaldehyde (16 mg, 1.5 equivalents), acetic acid (5 μL, 2 equivalents), and sodium triacetoxy borohydride (32 mg, 2 equivalents) at 25° C. for 16 hrs. The mixture was quenched with 10% NaHCO₃ (2 mL) and CHCl₃. The organic layer was separated, dried over sodium sulfate, filtered and the solvents were evaporated. The residue was purified using 5% methanol/CHCl₃ to give 53 mg (90%) of the title compound.

EXAMPLE 284 methyl (1S,2S)-1-[(2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-isopentylhydrazino)carbonyl]-2-methylbutylcarbamate A solution of Example 283A (50 mg, 0.075 mmol) in dichloroethane (1 mL) was treated with isovaleraldehyde (10 mg, 1.5 equivalents), acetic acid (5 μL, 2 equivalents), and sodium triacetoxy borohydride (32 mg, 2 equivalents), stirred at 25° C. for 16 hrs. The mixture was quenched with 10% NaHCO₃ (2 mL) and CHCl₃. The organic layer was separated, dried over sodium sulfate, and the solvents were evaporated. The residue was purified using 5% methanol/CHCl₃ to give 49 mg (89%) of the title compound.

EXAMPLE 285 methyl (1S,2S)-1-({2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-[4-(2-pyridinyl)benzyl]hydrazino}carbonyl)-2-methylbutylcarbamate Example 283A (300 mg, 0.45 mmol) was dissolved in dichloroethane (1 mL) and treated with 4-(2-pyridyl)benzaldehyde (0.125 g, 1.5 equivalents), acetic acid (40 μL, 2 equivalent), and sodium triacetoxy borohydride (0.19 g, 2 equivalents) at 25° C. for 16 hrs. The mixture was quenched with 10% NaHCO₃ (2 mL) and CHCl₃. The organic layer was separated, dried over sodium sulfate, and the solvents were evaporated. The residue was purified using 5% methanol/CHCl₃ to give 0.273 g (72%) of the title compound.

EXAMPLE 286 methyl (1S)-1-{[2-{(2S,3S)-3-[((2S)-3,3-dimethyl-2-{3-[2-(6-methyl-2-pyridinyl)ethyl]-2-oxo-1-imidazolidinyl}butanoyl)amino]-2-hydroxy-4-phenylbutyl}-2-(4-methoxybenzyl)hydrazino]carbonyl}-2,2-dimethylpropylcarbamate

EXAMPLE 286A methyl (1S)-1-{[2-{(2S,3S)-3-[((2S)-3,3-dimethyl-2-{3-[2-(6-methyl-2-pyridinyl)ethyl]-2-oxo-1-imidazolidinyl}butanoyl)amino]-2-hydroxy-4-phenylbutyl}-2-(4-methoxybenzyl)hydrazino]carbonyl}-2,2-dimethylpropylcarbamate Example 139 (0.122 g, 0.146 mmol) was dissolved in methanol (4 mL) and treated with Pearlman's catalyst (30 mg) and 4N HCl (40 μL) with a hydrogen balloon at 25° C. for 4 hrs. The mixture is filtered, rinsed with methanol, and the solvents were evaporated. The residue was purified using 10% methanol/CHCl₃ to give 98 mg (100%) of the title compound.

EXAMPLE 286B methyl (1S)-1-{[2-{(2S,3R)-3-[((2S)-3,3-dimethyl-2-{3-[2-(6-methyl-2-pyridinyl)ethyl]-2-oxo-1-imidazolidinyl}butanoyl)amino]-2-hydroxy-4-phenylbutyl}-2-(4-methoxybenzyl)hydrazino]carbonyl}-2,2-dimethylpropylcarbamate Example 286A (45 mg, 0.067 mmol) was dissolved in 1,2-dichloroethane (1 mL) and treated with p-anisaldehyde (15 mg, 1.2 equivalents) and acetic acid (5 μL, 3 equivalents) followed by sodium triacetoxy borohydride (30 mg, 3 equivalents) at 25° C. for 16 hrs. The mixture was partitioned between saturated NaHCO₃ and dichloromethane, the organic layer was separated, dried over sodium sulfate, filtered, and the solvents were evaporated. The residue was purified using 3% methanol/CHCl₃ to give 36 mg (55%) of the title compound.

EXAMPLE 287 methyl (1S)-1-[(2-{(2S,3S)-3-[((2S)-3,3-dimethyl-2-{3-[2-(6-methyl-2-pyridinyl)ethyl]-2-oxo-1-imidazolidinyl}butanoyl)amino]-2-hydroxy-4-phenylbutyl}-2-isopentylhydrazino)carbonyl]-2,2-dimethylpropylcarbamate Example 287 was prepared using the procedure of Example 286B, substituting isovaleraldehyde for p-anisaldehyde.

EXAMPLE 288 methyl (1S)-1-{[2-{(2S,3S)-3-[((2S)-3,3-dimethyl-2-{3-[(4-methyl-3-pyridinyl)methyl]-2-oxo-1-imidazolidinyl}butanoyl)amino]-2-hydroxy-4-phenylbutyl}-2-(4-methoxybenzyl)hydrazino]carbonyl}-2,2-dimethylpropylcarbamate

EXAMPLE 288A methyl (1S)-1-[(2-{(2S,3S)-3-[((2S)-3,3-dimethyl-2-{3-[(4-methyl-3-pyridinyl)methyl]-2-oxo-1-imidazolidinyl}butanoyl)amino]-2-hydroxy-4-phenylbutyl}hydrazino)carbonyl]-2,2-dimethylpropylcarbamate Example 94 (0.17 g, 0.2 mmol) was dissolved in methanol (5 mL) and treated with 4N HCl (52 µL, 1 equivalent) and Pd(OH)$_2$ (34 mg, 20 wt %) and a hydrogen balloon at 25° C. for 16 hrs. The mixture was filtered, rinsed with methanol (10 mL), and the solvents were evaporated. The residue was purified using 3% methanol/CHCl$_3$ to give 100 mg (74%) of the title compound.

EXAMPLE 288B methyl (1S)-1-{[2-{(2S,3S)-3-[((2S)-3,3-dimethyl-2-{3-[(4-methyl-3-pyridinyl)methyl]-2-oxo-1-imidazolidinyl}butanoyl)amino]-2-hydroxy-4-phenylbutyl}-2-(4-methoxybenzyl)hydrazino]carbonyl}-2,2-dimethylpropylcarbamate Example 288A (40 mg) was dissolved in dichloroethane (1 mL) and treated with p-anisaldehyde (12 µL, 1.5 equivalent), acetic acid (7 µL, 2 equivalents), and sodium triacetoxy borohydride at 25° C. for 16 hrs. The mixture was quenched with 10% NaHCO$_3$ (2 mL) and CHCl$_3$. The organic layer was separated, dried over sodium sulfate, filtered and the solvents were evaporated. The residue was purified using 5% methanol/CHCl$_3$ to give 22 mg (46%) of the title compound.

EXAMPLE 289 methyl (1S)-1-[(2-{(2S,3S)-3-[((2S)-3,3-dimethyl-2-{3-[(4-methyl-3-pyridinyl)methyl]-2-oxo-1-imidazolidinyl}butanoyl)amino]-2-hydroxy-4-phenylbutyl}-2-isopentylhydrazino)carbonyl]-2,2-dimethylpropylcarbamate Example 289 was prepared using the procedure of Example 288B, substituting isovaleraldehyde for p-anisaldehyde.

EXAMPLE 290 methyl (1S)-1-{[2-{(2S,3S)-2-hydroxy-3-[((2S,3S)-3-methyl-2-{3-[2-(6-methyl-2-pyridinyl)ethyl]-2-oxo-1-imidazolidinyl}pentanoyl)amino]-4-phenylbutyl}-2-(4-pyridinylmethyl)hydrazino]carbonyl}-2,2-dimethylpropylcarbamate Example 209 was dissolved in DMF (0.15 mL) and treated with 4-bromomethylpyridine (5 mg, 1.3 equivalents) and N,N-diisopropylethylamine (8 µL, 3 equivalents) at 25° C. for 1 h, followed by 50° C. for 16 hrs. The mixture is partitioned between water and ethyl acetate. The organic layer was separated, dried over sodium sulfate, filtered and the solvents were evaporated. The residue was purified using 10% methanol/CHCl$_3$ to give 7 mg (61%) of the title compound.

NMR Data

Example 71 $^1$H NMR (300 MHz, CDCl$_3$) δ ppm 0.80 (s, 9H), 0.93 (m, 9H), 2.62 (dd, J=12.13, 2.94 Hz, 2H), 2.82 (m, 2H), 2.86 (d, J=1.84 Hz, 1H), 3.10 (m, 2H), 3.31 (m, J=9.19 Hz, 1H), 3.59 (d, J=9.19 Hz, 1H), 3.63 (s, 3H), 3.85 (s, 3H), 3.99 (s, 1H), 4.00 (m, 2H), 4.12 (m, 1H), 4.69 (d, J=8.46 Hz, 2H), 4.74 (s, 1H), 5.28 (d, J=8.09 Hz, 1H), 6.22 (d, J=9.56 Hz, 1H), 6.41 (s, 1H), 7.01 (m, 3H), 7.10 (m, 2H), 7.30 (m, 4H), 7.43 (d, J=8.09 Hz, 2H), 7.74 (m, 3H), 7.96 (d, J=8.46 Hz, 2H), 8.69 (d, J=4.41 Hz, 1H).

Example 72 $^1$H NMR (300 MHz, CDCl$_3$) δ ppm 0.75 (d, J=6.25 Hz, 3H), 0.82 (m, 9H), 0.98 (m, 1H), 1.32 (m, 1H), 1.90 (d, J=6.99 Hz, 1H), 2.63 (dd, J=12.50, 2.94 Hz, 1H), 2.82 (dd, J=12.50, 10.30 Hz, 2H), 2.91 (d, J=6.62 Hz, 3H), 3.01 (dd, J=7.72, 3.31 Hz, 2H), 3.06 (m, 3H), 3.60 (s, 3H), 3.63 (d, J=3.31 Hz, 1H), 3.84 (d, J=11.03 Hz, 1H), 4.00 (m, 2H), 4.12 (m, 1H), 4.28 (d, J=15.08 Hz, 1H), 4.46 (d, J=15.08 Hz, 1H), 4.75 (s, 1H), 5.27 (d, J=8.82 Hz, 1 H), 6.57 (d, J=9.56 Hz, 1H), 6.71 (s, 1H), 7.18 (m, 7H), 7.43 (d, 8.46 Hz, 2H), 7.63 (m, 2H), 7.74 (m, 2H), 7.95 (d, J=8.09 Hz, 2H), 8.53 (m, 2H).

Example 73 $^1$H NMR (300 MHz, CDCl$_3$) δ ppm 0.78 (d, J=7.72 Hz, 12H), 0.85 (m, 3H), 1.03 (m, 1H), 1.40 (m, 1H), 1.91 (s, 1H), 2.54 (s, 3H), 2.61 (dd, J=12.32, 3.86 Hz, 1H), 2.81 (dd, J=12.69, 10.11 Hz, 1H), 2.92 (t, J=8.09 Hz, 3H), 3.11 (m, J=4.04 Hz, 1H), 3.17 (m, 3H), 3.59 (s, 3H), 3.64 (m, 2H), 3.91 (m, 1H), 3.97 (d, J=6.62 Hz, 1H), 4.07 (m, 1H), 4.48 (s, 2H), 4.79 (s, 1H), 5.26 (d, J=8.82 Hz, 1H), 6.59 (d, J=9.19 Hz, 1H), 7.06 (dd, J=12.13, 7.35 Hz, 2H), 7.19 (m, 6H), 7.42 (d, J=8.09 Hz, 2H), 7.54 (t, J=7.72 Hz, 1H), 7.74 (m, 2H), 7.94 (d, J=8.09 Hz, 2H), 8.68 (d, J=4.78 Hz, 1H).

Example 74 $^1$H NMR (300 MHz, CDCl$_3$) δ ppm 0.64 (d, J=6.62 Hz, 3H), 0.75 (m, 3H), 0.78 (m, 3H), 0.84 (m, 3H), 0.96 (m, 2H), 1.63 (d, J=3.31 Hz, 2H), 2.62 (dd, J=12.50, 3.68 Hz, 1H), 2.88 (m, 5H), 3.10 (m, 1H), 3.22 (m, 2H), 3.47 (s, 3H), 3.59 (s, 3H), 3.69 (m, 1H), 3.88 (d, J=11.03 Hz, 1H), 3.97 (d, J=18.02 Hz, 2H), 4.08 (m, 2H), 4.47 (s, 4H), 4.69 (s, 2H), 5.10 (d, J=8.82 Hz, 1H), 6.57 (d, J=9.19 Hz, 1H), 6.75 (s, 1H), 7.14 (m, 7H), 7.44 (d, J=8.46 Hz, 2H), 7.72 (d, J=7.72 Hz, 1H), 7.79 (m, 1H), 7.94 (d, J=8.46 Hz, 2H), 8.72 (d, J=4.04 Hz, 1 H).

Example 75 $^1$H NMR (300 MHz, CDCl$_3$) δ ppm 0.76 (d, J=6.62 Hz, 3H), 0.81 (t, J=7.35 Hz, 3H), 1.00 (m, 1H), 1.38 (s, 9H), 1.92 (s, 1H), 2.52 (s, 1H), 2.71 (d, J=11.03 Hz, 1H), 2.80 (m, 1H), 2.86 (d, J=7.72 Hz, 1H), 2.92 (d, J=7.72 Hz, 1H), 3.04 (m, 2H), 3.08 (m, 1H), 3.66 (d, J=12.50 Hz, 1H), 3.91 (d, J=11.03 Hz, 1H), 3.98 (s, 2H), 4.09 (d, J=9.93 Hz, 1H), 4.48 (s, 1H), 4.75 (d, J=15.44 Hz, 1H), 4.88 (m, 1H), 5.33 (s, 1H), 6.44 (d, J=8.82 Hz, 1H), 7.08 (m, 3H), 7.14 (m, 2H), 7.22 (m, 1H), 7.28 (s, 1H), 7.41 (d, J=8.09 Hz, 2H), 7.58 (m, 1H), 7.74 (m, 4H), 7.96 (d, J=8.09 Hz, 2H), 8.12 (d, J=8.46 Hz, 1H), 8.19 (d, J=8.09 Hz, 1H), 8.69 (d, J=4.78 Hz, 1H), 8.86 (d, J=4.41 Hz, 1H).

Example 76 $^1$H NMR (300 MHz, CDCl$_3$) δ ppm 0.65 (d, J=6.99 Hz, 3H), 0.75 (t, J=7.17 Hz, 3H), 0.95 (s, 9H), 1.28 (m, 2H), 1.68 (m, 1H), 2.62 (m, 2H), 2.83 (m, 3H), 3.11 (m, 2H), 3.32 (m, 1H), 3.62 (s, 3H), 3.68 (m, 1H), 3.85 (s, 3H), 3.93 (d, J=13.60 Hz, 1H), 4.00 (s, 1H), 4.05 (m, 1H), 4.15 (q, J=8.33 Hz, 1H), 4.69 (m, 3H), 5.10 (d, J=8.09 Hz, 1H), 6.26 (d, J=9.56 Hz, 1H), 6.58 (s, 1H), 7.01 (m, 3H), 7.10 (m, 2H), 7.29 (m, 3H), 7.43 (d, J=8.09 Hz, 2H), 7.74 (m, 4H), 7.96 (d, J=8.46 Hz, 2H), 8.68 (d, J=4.78 Hz, 1H).

Example 77 $^1$H NMR (300 MHz, CDCl$_3$) δ ppm 0.65 (d, J=6.62 Hz, 3H), 0.74 (t, J=7.17 Hz, 3H), 0.88 (dd, J=13.05, 3.86 Hz, 1H), 0.96 (s, 9H), 1.30 (s, 1H), 1.64 (s, 1H), 2.65 (m, 3H), 2.85 (m, 4H), 3.14 (m, 2H), 3.35 (m, 1H), 3.48 (s, 3H), 3.62 (s, 3H), 3.68 (m, 1H), 3.92 (d, J=13.60 Hz, 1H), 4.03 (s, 1H), 4.10 (m, 1H), 4.50 (s, 2H), 4.71 (s, 3H), 5.09 (d, J=8.46 Hz, 1H), 6.30 (d, J=9.19 Hz, 1H), 6.59 (s, 1H), 7.16 (m, 7H), 7.42 (d, J=8.09 Hz, 2H), 7.74 (m, 2H), 7.95 (d, J=8.46 Hz, 2H).

Example 78 $^1$H NMR (300 MHz, CDCl$_3$) δ ppm 0.80 (s, 9H), 0.95 (s, 9H), 2.61 (dd, J=12.50, 2.94 Hz, 2H), 2.84 (m, 4H), 3.14 (m, 2H), 3.34 (d, J=4.04 Hz, 1H), 3.48 (d, J=2.57 Hz, 3H), 3.62 (s, 3H), 3.94 (d, J=13.60 Hz, 1H), 4.02 (s, 2H), 4.09 (m, 1H), 4.50 (s, 2H), 4.71 (s, 3H), 5.27 (d, J=8.46 Hz, 1H), 6.27 (d, J=9.56 Hz, 1H), 6.44 (s, 1H), 7.10 (m, 6H), 7.23 (m, 1H), 7.43 (d, J=8.09 Hz, 2H), 7.74 (m, 2H), 7.95 (d, J=8.46 Hz, 2H), 8.69 (d, J=4.78 Hz, 1H).

Example 79 $^1$H NMR (300 MHz, CDCl$_3$) δ ppm 0.64 (d, J=6.62 Hz, 3H), 0.77 (q, J=6.50 Hz, 9H), 0.88 (m, 4H), 1.04 (m, 1H), 1.35 (m, 2H), 1.90 (s, 1H), 2.59 (m, 1H), 2.78 (m, 1H), 2.88 (d, J=6.99 Hz, 3H), 3.08 (m, 2H), 3.61 (s, 3H), 3.67 (m, 1H), 3.84 (m, 2H), 3.94 (d, J=11.03 Hz, 1H), 4.10 (d, J=7.72 Hz, 1H), 4.81 (m, 2H), 5.09 (d, J=9.19 Hz, 1H), 6.56 (d, J=9.56 Hz, 1H), 6.72 (s, 1H), 7.09 (m, 5H), 7.24 (m, 3H), 7.42 (d, J=8.09 Hz, 2H), 7.59 (m, 1H), 7.72 (t, J=6.99 Hz, 1H), 8.14 (d, J=7.72 Hz, 1H), 8.19 (d, J=7.72 Hz, 1H), 8.88 (d, J=4.04 Hz, 1H).

Example 80 $^1$H NMR (300 MHz, CDCl$_3$) δ ppm 0.78 (d, J=2.94 Hz, 9H), 0.87 (m, 6H), 0.97 (d, J=6.62 Hz, 1H), 1.38 (m, 1H), 1.89 (s, 1H), 2.60 (dd, J=12.50, 3.31 Hz, 1H), 2.79 (m, 1H), 2.90 (d, J=8.09 Hz, 3H), 3.05 (m, 3H), 3.58 (s, 1H), 3.62 (s, 3H), 3.87 (m, 2H), 3.99 (m, 1H), 4.12 (m, 1H), 4.29 (d, J=15.08 Hz, 1H), 4.46 (m, 1H), 4.72 (s, 1H), 5.27 (d, J=8.46 Hz, 1H), 6.54 (d, J=9.93 Hz, 1H), 6.60 (s, 1H), 7.15 (m, 5H), 7.30 (m, 6H), 7.63 (m, 1H), 8.54 (m, 1H).

Example 81 $^1$H NMR (300 MHz, CDCl$_3$) δ ppm 0.79 (m, 12H), 0.87 (m, 3H), 1.02 (m, 1H), 1.27 (d, J=3.68 Hz, 1H), 1.41 (m, 1H), 1.89 (s, 1H), 2.54 (s, 3H), 2.59 (m, 1H), 2.78 (dd, J=12.50, 10.30 Hz, 1H), 2.91 (m, 2H), 3.16 (m, 2H), 3.59 (s, 2H), 3.61 (s, 3H), 3.89 (m, 1H), 3.95 (m, 2H), 4.07 (q, J=8.70 Hz, 1H), 4.47 (m, 2H), 4.75 (s, 1H), 5.26 (d, J=9.93 Hz, 1H), 6.54 (d, J=9.93 Hz, 2H), 7.06 (dd, J=12.50, 7.72 Hz, 2H), 7.12 (m, 1H), 7.19 (m, 4H), 7.29 (m, 5H), 7.54 (t, J=7.72 Hz, 1H).

Example 82 $^1$H NMR (300 MHz, CDCl$_3$) δ ppm 0.62 (t, J=6.80 Hz, 3H), 0.77 (m, 6H), 0.86 (t, J=7.35 Hz, 3H), 1.02 (m, 1H), 1.37 (m, 1H), 1.91 (m, 1H), 2.60 (dd, 12.32, 2.76 Hz, 1 H), 2.80 (m, 1H), 2.93 (m, 4H), 3.06 (m, 4H), 3.58 (s, 1H), 3.61 (s, 3H), 3.70 (m, 1H), 3.85 (m, 2H), 3.99 (m, 1H), 4.13 (m, 1H), 4.29 (d, J=15.08 Hz, 1H), 4.45 (m, 1H), 4.73 (s, 1H), 5.10 (d, J=8.09 Hz, 1H), 6.57 (d, J=9.19 Hz, 1H), 6.74 (s, 1H), 7.14 (m, 5H), 7.29 (m, 6H), 7.63 (t, J=7.54 Hz, 1H), 8.53 (m, 2H).

Example 83 $^1$H NMR (300 MHz, CDCl$_3$) δ ppm 0.80 (s, 9H), 0.95 (s, 9H), 1.27 (d, J=3.68 Hz, 1H), 2.48 (s, 3H), 2.64 (d, J=2.94 Hz, 2H), 2.87 (m, 2H), 3.14 (m, 2H), 3.34 (s, 1H), 3.58 (s, 1H), 3.62 (s, 3H), 3.99 (m, 2H), 4.02 (s, 1H), 4.11 (d, J=6.62 Hz, 1H), 4.57 (s, 2H), 4.73 (s, 1H), 5.27 (d, J=9.19 Hz, 1H), 6.27 (d, J=9.56 Hz, 1H), 6.44 (s, 1H), 6.55 (s, 1H), 7.10 (m, 5H), 7.22 (m, 1H), 7.26 (s, 1H), 7.43 (d, J=8.46 Hz, 2H), 7.74 (m, 2H), 7.95 (d, J=8.46 Hz, 2H), 8.69 (d, J=4.04 Hz, 1H).

Example 84 $^1$H NMR (300 MHz, CDCl$_3$) δ ppm 0.80 (d, J=8.82 Hz, 12H), 0.86 (m, 5H), 0.88 (m, 3H), 1.05 (m, 1H), 1.42 (m, 1H), 1.94 (m, 1H), 2.54 (s, 3H), 2.54 (dd, J=12.32, 3.49 Hz, 1H), 2.75 (m, 1H), 2.89 (d, J=6.62 Hz, 2H), 3.14 (m, 2H), 3.54 (s, 1H), 3.61 (s, 3H), 3.78 (s, 3H), 3.85 (d, J=7.72 Hz, 1H), 3.91 (m, 1H), 4.06 (m, 1H), 4.47 (m, 1H), 4.71 (s, 1H), 4.82 (d, J=8.82 Hz, 1H), 5.26 (d, J=10.30 Hz, 1H), 6.54 (d, J=9.56 Hz, 2H), 6.83 (d, J=8.82 Hz, 2H), 7.08 (m, 2H), 7.16 (m, 3H), 7.20 (d, J=8.82 Hz, 2H), 7.54 (t, J=7.54 Hz, 1H).

Example 85 $^1$H NMR (300 MHz, DMSO-d$_6$) δ ppm 0.68 (s, 9H), 0.86 (s, 9H), 2.72 (m, 4H), 2.72 (m, 3H), 3.09 (m, 1H), 3.24 (m, 1H), 3.50 (s, 3H), 3.67 (d, J=9.19 Hz, 2H), 3.98 (s, 1H), 4.04 (s, 1H), 4.12 (s, 1H), 4.42 (d, J=15.44 Hz, 1H), 4.53 (d, J=15.08 Hz, 1H), 4.85 (d, J=3.31 Hz, 1H), 6.98 (m, 1H), 7.09 (m, 5H), 7.32 (m, 1H), 7.45 (d, J=8.09 Hz, 1H), 7.53 (dd, J=8.82, 4.78 Hz, 1H), 7.60 (s, 1H), 7.65 (d, J=9.19 Hz, 1H), 7.87 (m, 2H), 7.98 (d, J=8.46 Hz, 2H), 8.29 (m, 1H), 8.66 (m, 2H), 9.13 (s, 2H).

Example 86 $^1$H NMR (300 MHz, MeOH-d$_4$) δ ppm 0.78 (s, 9H), 0.91 (s, 9H), 0.98 (m, 1H), 2.42 (t, J=9.01 Hz, 1H), 2.82 (m, 5H), 3.06 (m, 1H), 3.16 (q, J=9.19 Hz, 1H), 3.59 (s, 3H), 3.73 (m, 1H), 3.83 (s, 1H), 3.99 (m, 2H), 4.07 (m, 1H), 4.19 (m, 1H), 4.47 (m, 2H), 4.55 (s, 3H), 4.69 (s, 2H), 7.09 (m, 4H), 7.18 (m, 3H), 7.23 (d, J=7.35 Hz, 1H), 7.35 (m, 1H), 7.45 (d, J=7.72 Hz, 1H), 7.54 (d, J=8.46 Hz, 2H), 7.81 (m, 2H), 7.86 (d, J=2.21 Hz, 1H), 7.89 (d, J=1.84 Hz, 1H).

Example 87 $^1$H NMR (500 MHz, DMSO-d$_6$) δ ppm 0.66 (m, 12H), 0.75 (t, J=7.63 Hz, 3H), 0.92 (m, 1H), 1.27 (m, 2H), 1.76 (m, 1H), 2.65 (dd, J=13.43, 9.77 Hz, 1H), 2.71 (s, 3H), 2.76 (m, 9H), 3.03 (m, 1H), 3.15 (m, 1H), 3.21 (q, J=8.54 Hz, 1H), 3.65 (m, 2H), 3.95 (m, 2H), 4.01 (m, 2H), 4.09 (s, 1H), 4.38 (d, J=15.87 Hz, 1H), 4.47 (d, J=15.87 Hz, 1H), 6.90 (d, J=9.16 Hz, 1H), 7.03 (t, J=6.41 Hz, 1H), 7.10 (m, 4H), 7.40 (m, 2H), 7.44 (s, 1H), 7.48 (d, J=8.54 Hz, 2H), 7.97 (d, J=7.93 Hz, 2H), 8.68 (d, J=4.88 Hz, 1H), 9.12 (s, 1H).

Example 88 $^1$H NMR (500 MHz, CDCl$_3$) δ ppm 0.80 (s, 9H), 0.94 (s, 9H), 1.63 (m, 2H), 2.55 (s, 3H), 2.65 (m, 2H), 2.81 (m, 1H), 2.90 (m, 3H), 2.99 (q, J=8.95 Hz, 1H), 3.32 (m, 1H), 4.00 (m, 4H), 4.12 (q, J=7.93 Hz, 1H), 4.31 (d, J=15.26 Hz, 1H), 4.38 (d, J=15.26 Hz, 1 H), 4.72 (s, 1H), 5.29 (m, 1H), 6.29 (d, J=9.16 Hz, 1H), 6.51 (s, 1H), 7.09 (m, 3H), 7.16 (d, J=6.10 Hz, 4H), 7.23 (m, 1H), 7.43 (d, J=7.93 Hz, 2H), 7.55 (dd, J=7.93, 2.44 Hz, 1H), 7.70 (d, J=7.93 Hz, 1H), 7.75 (m, 1H), 7.95 (d, J=8.54 Hz, 2H), 8.40 (s, 1H), 8.69 (d, J=3.66 Hz, 1H).

Example 89 $^1$H NMR (300 MHz, MeOH-d$_4$) δ ppm 0.78 (s, 9H), 0.91 (s, 9H), 1.35 (m, 1H), 1.52 (s, 3H), 1.53 (s, 3H), 2.36 (m, 1H), 2.82 (m, 6H), 3.06 (m, 1H), 3.22 (dd, J=17.83, 8.64 Hz, 1H), 3.29 (m, 3H), 3.59 (s, 3H), 3.83 (m, 1H), 3.97 (d, J=13.60 Hz, 1H), 4.04 (t, #5.33 Hz, 2H), 4.20 (m, 1H), 4.41 (d, J=15.81 Hz, 1H), 4.59 (d, J=15.44 Hz, 1H), 7.09 (m, 2H), 7.18 (m, 3H), 7.35 (m, 1H), 7.53 (m, 2H), 7.76 (d, J=7.72 Hz, 2H), 7.82 (m, 3H), 7.88 (m, 2H), 8.59 (d, J=4.78 Hz, 1H).

Example 90 $^1$H NMR (300 MHz, DMSO-d$_6$) δ ppm 0.66 (m, J=8.09 Hz, 12H), 0.74 (t, #7.17 Hz, 3H), 0.89 (m, 3H), 1.25 (m, 5H), 1.75 (s, 1H), 2.76 (m, 5H), 3.04 (s, 1H), 3.19 (m, 1H), 3.50 (s, 3H), 3.67 (d, J=9.93 Hz, 2H), 3.96 (m, 2H), 4.03 (s, 1H), 4.15 (m, 1H), 4.48 (m, 2H), 4.95 (d, J=3.31 Hz, 1H), 7.04 (m, 5H), 7.32 (m, 1H), 7.45 (d, J=8.46 Hz, 3H), 7.67 (m, 2H), 7.72 (s, 1H), 7.86 (m, 2H), 7.99 (d, J=8.09 Hz, 2H), 8.57 (d, J=5.15 Hz, 1H), 8.64 (d, J=4.04 Hz, 1H), 9.13 (s, 1H).

Example 91 $^1$H NMR (300 MHz, CDCl$_3$) δ ppm 0.78 (d, J=7.35 Hz, 12H), 0.86 (m, 3H), 1.28 (m, 6H), 1.39 (m, 2H), 1.96 (d, J=38.24 Hz, 1H), 2.63 (d, J=2.57 Hz, 1H), 2.81 (m, 1H), 2.90 (m, 3H), 3.16 (m, 2H), 3.90 (d, J=11.40 Hz, 1H), 3.98 (d, J=9.56 Hz, 1H), 4.07 (s, 1H), 4.50 (s, 2H), 4.80 (s, 1H), 5.30 (m, 1H), 6.59 (m, 2H), 7.17 (m, 5H), 7.23 (m, 3H), 7.30 (d, J=7.72 Hz, 1H), 7.42 (d, J=8.09 Hz, 2H), 7.71 (m, 2H), 7.94 (d, J=8.46 Hz, 2H), 8.54 (m, 1H), 8.69 (d, J=4.78 Hz, 1H).

Example 92 $^1$H NMR (300 MHz, CDCl$_3$) δ ppm 0.72 (d, J=6.62 Hz, 3H), 0.81 (m, 3H), 0.81 (s, 9H), 0.94 (m, 1H), 1.26 (m, 1H), 1.84 (s, 1H), 2.60 (dd, J=9.56, 2.94 Hz, 1H), 2.76 (m, 1H), 2.90 (m, 2H), 3.35 (d, J=18.02 Hz, 1H), 3.61 (m, 2H), 3.63 (s, 3H), 3.99 (m, 4H), 4.16 (m, J=6.62 Hz, 1H), 4.81 (m, 3H), 5.26 (d, J=8.46 Hz, 1H), 6.29 (d, J=9.56 Hz, 1H), 6.44 (s, 1H), 7.14 (m, 6H), 7.22 (t, J=3.31 Hz, 2H), 7.43 (d, J=8.09 Hz, 2H), 7.64 (m, 1H), 7.75 (m, 2H), 7.96 (d, J=8.09 Hz, 2H), 8.52 (d, J=4.78 Hz, 1H), 8.69 (d, J=4.78 Hz, 1H).

Example 93 $^1$H NMR (300 MHz, CDCl$_3$) δ ppm 0.75 (d, J=6.62 Hz, 3H), 0.82 (m, 12H), 0.97 (m, 1H), 1.34 (m, 1H), 1.88 (d, J=10.30 Hz, 1H), 2.53 (s, 3H), 2.62 (m, 1H), 2.81 (m, 1H), 2.88 (m, 3H), 3.02 (m, 3H), 3.60 (s, 3H), 3.63 (s, 1H), 3.85 (d, J=11.40 Hz, 1H), 4.00 (m, 2H), 4.09 (m, 1H), 4.24 (d, J=15.08 Hz, 1H), 4.41 (m, 1H), 4.78 (s, 1H), 5.28 (d, J=12.87 Hz, 1H), 6.57 (d, J=9.56 Hz, 1H), 6.68 (s, 1H), 7.13 (m, 6H), 7.22 (m, 1H), 7.43 (d, J=8.46 Hz, 2H), 7.52 (dd, J=7.91, 2.39 Hz, 1H), 7.74 (m, 2H), 7.95 (d, J=8.09 Hz, 2H), 8.38 (d, J=1.84 Hz, 1H), 8.69 (d, J=4.78 Hz, 1H).

Example 94 $^1$H NMR (300 MHz, CDCl$_3$) δ ppm 0.80 (s, 9H), 0.94 (s, 9H), 2.55 (s, 3H), 2.63 (m, 2H), 2.86 (m, 4H), 2.98 (m, 2H), 3.32 (m, 1H), 3.62 (s, 3H), 4.00 (m, 3H), 4.09 (d, J=10.66 Hz, 1H), 4.34 (m, 2H), 4.74 (s, 1H), 5.29 (d, J=7.72 Hz, 1H), 6.29 (d, J=9.19 Hz, 1H), 6.47 (s, 1H), 7.08 (m, 2H), 7.16 (m, 4H), 7.23 (dd, J=6.80, 2.02 Hz, 1H), 7.43 (d, J=8.09 Hz, 2H), 7.54 (dd, J=7.72, 2.21 Hz, 1H), 7.75 (m, 2H), 7.95 (d, J=8.46 Hz, 2H), 8.39 (d, J=1.84 Hz, 1H), 8.69 (d, J=4.78 Hz, 1H).

Example 95 $^1$H NMR (300 MHz, MeOH-d$_4$) δ ppm 0.78 (s, 9H), 0.90 (d, J=5.52 Hz, 9H), 2.31 (t, J=9.38 Hz, 1H), 2.81 (m, 8H), 2.95 (m, 1H), 3.07 (q, J=8.82 Hz, 1H), 3.59 (s, 3H), 3.72 (s, 1H), 3.84 (d, J=8.82 Hz, 1H), 3.99 (m, 2H), 4.08 (d, J=3.68 Hz, 1H), 4.18 (m, 1H), 4.74 (d, J=15.08 Hz, 1H), 5.02 (d, J=15.44 Hz, 1H), 6.82 (t, J=7.17 Hz, 2H), 6.91 (t, J=7.17 Hz, 1H), 7.04 (d, J=6.99 Hz, 2H), 7.34 (m, 1H), 7.49 (d, J=4.41 Hz, 1H), 7.54 (d, J=8.09 Hz, 2H), 7.70 (m, 1H), 7.85 (m, 5H), 8.09 (d, J=8.46 Hz, 1H), 8.35 (d, J=8.46 Hz, 1H), 8.59 (d, J=4.78 Hz, 1H), 8.85 (d, J=4.78 Hz, 1H).

Example 96 $^1$H NMR (300 MHz, CDCl$_3$) δ ppm 0.79 (m, 12H), 0.83 (t, J=7.35 Hz, 3H), 1.00 (m, 1H), 1.26 (d, J=2.94 Hz, 1H), 1.39 (m, 1H), 1.92 (s, 1H), 2.68 (dd, J=13.05, 3.49 Hz, 1H), 2.79 (d, J=9.56 Hz, 1H), 2.87 (m, 2H), 3.08 (t, J=9.01 Hz, 1H), 3.21 (m, 1H), 3.35 (m, 2H), 3.58 (s, 3H), 3.64 (m, 2H), 3.91 (d, J=11.03 Hz, 1H), 4.04 (m, 3H), 4.57 (m, 2H), 5.32 (d, J=9.19 Hz, 2H), 6.74 (d, J=9.93 Hz, 1H), 7.11 (m, 5H), 7.36 (s, 1H), 7.56 (d, J=8.46 Hz, 2H), 7.71 (m, 2H), 7.84 (d, J=8.46 Hz, 2H), 7.97 (d, J=8.09 Hz, 1H), 8.28 (m, 1H), 8.57 (d, J=8.46 Hz, 1H), 8.74 (dd, J=5.52, 1.47 Hz, 1H), 9.04 (d, J=4.78 Hz, 1H), 9.28 (d, J=1.47 Hz, 1H).

Example 97 $^1$H NMR (300 MHz, CDCl$_3$) δ ppm 0.82 (s, 9H), 0.97 (s, 9H), 2.54 (dd, J=12.32, 2.76 Hz, 1H), 2.75 (m, 1H), 2.86 (m, 2H), 3.11 (m, 2H), 3.35 (m, 1H), 3.48 (s, 3H), 3.58 (t, #9.19 Hz, 2H), 3.64 (s, 3H), 3.79 (s, 3H), 3.87 (m, 2H), 4.02 (s, 1H), 4.10 (m, 1H), 4.50 (s, 2H), 4.67 (s, 1H), 4.71 (s, 2H), 5.29 (d, J=7.72 Hz, 1H), 6.25 (d, J=9.56 Hz, 1H), 6.40 (s, 1H), 6.84 (m, 2H), 7.10 (m, 5H), 7.21 (d, J=8.46 Hz, 2H), 7.26 (s, 1H).

Example 98 $^1$H NMR (300 MHz, CDCl$_3$) δ ppm 0.78 (m, 15H), 0.98 (m, 2H), 1.32 (m, 1H), 1.94 (m, 1H), 2.62 (dd, #12.13, 2.94 Hz, 2H), 2.81 (m, 2H), 2.92 (d, J=7.72 Hz, 3H), 3.14 (m, 3H), 3.61 (s, 3H), 3.84 (m, 1H), 4.15 (m, 1H), 4.24 (d, J=16.18 Hz, 1H), 4.50 (d, J=16.18 Hz, 1H), 4.79 (s, 1H), 5.28 (d, J=9.19 Hz, 1H), 6.50 (d, J=9.56 Hz, 1H), 6.66 (s, 1H), 7.17 (m, 6H), 7.37 (dd, J=5.15, 2.21 Hz, 1H), 7.43 (d, J=8.46 Hz, 2H), 7.74 (m, 2H), 7.95 (d, J=8.09 Hz, 2H), 8.68 (d, J=4.78 Hz, 1H), 9.11 (s, 1H), 9.15 (d, J=5.15 Hz, 1H).

Example 99 $^1$H NMR (300 MHz, DMSO-d$_6$) δ ppm 0.66 (m, 12H), 0.74 (t, J=7.17 Hz, 3H), 0.88 (d, J=5.52 Hz, 9H), 1.05 (dd, #20.22, 6.62 Hz, 1H), 1.28 (m, 1H), 1.75 (s, 1H), 2.68 (m, 5H), 3.10 (m, 3H), 3.50 (s, 3H), 3.67 (d, J=8.82 Hz, 2H), 3.95 (m, 2H), 4.03 (s, 1H), 4.49 (m, 2H), 4.93 (d, J=2.94 Hz, 1H), 6.93 (d, J=9.56 Hz, 1H), 7.10 (m, 3H), 7.32 (m, 1H), 7.43 (t, J=8.64 Hz, 3H), 7.86 (m, 2H), 7.97 (m, 3H), 8.65 (d, J=4.41 Hz, 1H), 9.12 (s, 1H).

Example 100 $^1$H NMR (300 MHz, CDCl$_3$) δ ppm 0.82 (s, 9H), 0.96 (s, 9H), 1.39 (d, J=6.99 Hz, 6H), 1.80 (s, 5H), 2.63 (s, 2H), 2.86 (d, J=7.35 Hz, 2H), 3.14 (m, 2H), 3.31 (m, 1H), 3.63 (s, 3H), 4.04 (s, 2H), 4.12 (m, 1H), 4.48 (t, J=15.44 Hz, 2H), 5.30 (s, 1H), 6.33 (s, 1H), 6.58 (s, 1H), 7.00 (s, 1H), 7.10 (m, 4H), 7.22 (m, 1H), 7.41 (d, J=8.09 Hz, 2H), 7.75 (m, 3H), 7.96 (d, J=8.09 Hz, 2H), 8.69 (d, J=4.41 Hz, 1H).

Example 101 $^1$H NMR (300 MHz, CDCl$_3$) δ ppm 0.82 (d, J=6.62 Hz, 3H), 0.87 (t, J=7.35 Hz, 3H), 0.96 (s, 9H), 1.07 (m, 3H), 1.43 (m, 1H), 1.71 (s, 3H), 1.91 (m, 1H), 2.63 (m, 1H), 2.90 (m, 2H), 3.11 (m, 2H), 3.15 (m, 2H), 3.57 (d, J=1.47 Hz, 1H), 3.65 (s, 3H), 3.76 (d, J=9.19 Hz, 1H), 3.93 (d, J=11.03 Hz, 1H), 4.06 (m, 2H), 4.13 (d, J=1.84 Hz, 1H), 4.23 (m, 1H), 4.46 (m, 2H), 4.79 (s, 1H), 5.39 (d, J=9.93 Hz, 1H), 6.52 (m, J=7.72 Hz, 2H), 7.03 (d, J=7.72 Hz, 1H), 7.07 (d, J=7.35 Hz, 1H), 7.15 (m, 5H), 7.27 (s, 1H), 7.54 (t, J=7.72 Hz, 1H), 7.97 (s, 1H).

Example 102 $^1$H NMR (300 MHz, CDCl$_3$) δ ppm 0.64 (d, J=6.62 Hz, 3H), 0.74 (t, J=7.35 Hz, 3H), 0.83 (dd, J=6.62, 2.21 Hz, 6H), 0.92 (m, 1H), 1.26 (d, J=4.04 Hz, 1H), 2.10 (m, 2H), 2.62 (m, 1H), 2.68 (m, 1H), 2.80 (m, 1H), 2.88 (m, 4H), 3.12 (m, 1H), 3.23 (m, 2H), 3.59 (s, 3H), 3.69 (m, 1H), 3.79 (d, J=10.66 Hz, 1H), 3.97 (m, 2H), 4.10 (d, J=8.09 Hz, 1H), 4.44 (m, 2H), 5.07 (m, 1H), 6.58 (d, J=9.19 Hz, 1H), 6.72 (s, 1H), 6.97 (s, 1H), 7.11 (m, 6H), 7.22 (m, 2H), 7.42 (d, J=8.46 Hz, 2H), 7.74 (m, 2H), 7.94 (d, J=8.09 Hz, 2H), 8.68 (d, J=4.78 Hz, 1H).

Example 103 $^1$H NMR (300 MHz, CDCl$_3$) δ ppm 0.65 (d, J=6.62 Hz, 3H), 0.74 (t, J=7.17 Hz, 3H), 0.85 (m, 2H), 0.96 (s, 9H), 1.31 (m, 1H), 1.65 (m, 1H), 2.63 (d, J=9.19 Hz, 1H), 2.69 (d, J=4.78 Hz, 3H), 2.86 (m, 3H), 3.14 (m, 1H), 3.35 (m, 1H), 3.60 (d, 6.25 Hz, 3H), 3.68 (m, 2H), 3.92 (d, J=13.97 Hz, 1H), 4.03 (m, 2H), 4.11 (d, J=8.46 Hz, 1H), 4.46 (m, 2H), 4.71 (s, 1H), 5.10 (d, J=7.72 Hz, 1H), 6.31 (d, J=9.56 Hz, 1H), 6.61 (s, 1H), 6.97 (d, J=2.94 Hz, 1H), 7.15 (m, 6H), 7.42 (d, J=8.09 Hz, 2H), 7.74 (m, 2H), 7.95 (d, J=8.09 Hz, 2H), 8.68 (d, J=4.78 Hz, 1H).

Example 104 $^1$H NMR (300 MHz, CDCl$_3$) δ ppm 0.83 (d, J=6.62 Hz, 3H), 0.87 (m, 3H), 1.00 (s, 9H), 1.07 (m, 2H), 1.42 (m, 2H), 1.91 (m, 1H), 2.53 (s, 3H), 2.64 (m, 2H), 2.88 (m, 1H), 3.15 (m, 2H), 3.59 (d, J=11.40 Hz, 2H), 3.65 (s, 3H), 3.81 (m, 3H), 3.91 (m, 1H), 4.09 (m, 2H), 4.26 (m, 1H), 4.47 (m, 2H), 4.80 (s, 1H), 5.40 (s, 1H), 6.48 (d, J=9.56 Hz, 1H), 7.02 (d, J=7.72 Hz, 1H), 7.07 (d, J=7.72 Hz, 2H), 7.16 (m, 5H), 7.23 (s, 1H), 7.35 (dd, J=7.72, 4.78 Hz, 1H), 7.53 (t, J=7.54 Hz, 1H), 7.84 (m, 1H), 8.10 (d, J=8. Hz, 1H), 8.18 (s, 1H), 8.63 (d, J=4.04 Hz, 1H).

Example 105 $^1$H NMR (300 MHz, CDCl$_3$) δ ppm 0.70 (m, 6H), 0.83 (dd, J=6.62, 1.84 Hz, 6H), 1.56 (s, 1H), 1.84 (m, 1H), 2.12 (m, 1H), 2.61 (m, 1H), 2.69 (m, 3H), 2.81 (dd, J=12.50, 10.30 Hz, 1H), 2.91 (m, 2H), 3.14 (m, 1H), 3.24 (m, 1H), 3.60 (s, 3H), 3.66 (dd, J=8.64, 6.80 Hz, 1H), 3.91 (m, J=13.60 Hz, 1H), 4.02 (m, 1H), 4.09 (d, J=8.46 Hz, 1H), 4.45 (m, 2H), 4.74 (s, 1H), 5.06 (s, 1H), 6.59 (d, J=8.82 Hz, 1H), 6.73 (s, 1H), 6.95 (d, J=8.46 Hz, 1H), 7.12 (m, 6H), 7.21 (m, 2H), 7.41 (d, J=8.46 Hz, 1H), 7.73 (m, 2H), 7.93 (t, J=8.27 Hz, 3H), 8.68 (d, J=4.04 Hz, 1H).

Example 106 $^1$H NMR (300 MHz, CDCl$_3$) δ ppm 0.71 (t, J=6.25 Hz, 6H), 0.96 (d, J=5.52 Hz, 9H), 1.86 (m, 1H), 2.61 (dd, J=12.13, 2.94 Hz, 1H), 2.70 (m, 3H), 2.80 (d, J=10.30 Hz, 1H), 2.90 (m, 2H), 3.16 (m, 1H), 3.35 (m, 1H), 3.64 (m, 2H), 3.63 (m, 3H), 3.92 (d, J=13.60 Hz, 1H), 4.05 (m, 2H), 4.09 (m, 1H), 4.47 (m, 2H), 4.70 (s, 1H), 5.09 (d, J=9.56 Hz, 1H), 6.32 (d, J=9.56 Hz, 1H), 6.61 (s, 1H), 6.98 (s, 1H), 7.11

(m, 6H), 7.22 (m, 2H), 7.41 (d, J=8.09 Hz, 2H), 7.74 (m, 2H), 7.95 (d, J=8.09 Hz, 2H), 8.68 (d, J=4.04 Hz, 1H).

Example 107 $^1$H NMR (300 MHz, CDCl$_3$) δ ppm 0.64 (d, J=6.62 Hz, 3H), 0.78 (m, 9H), 0.96 (m, 2H), 1.38 (m, 2H), 1.90 (s, 1H), 2.61 (m, 1H), 2.66 (d, J=11.77 Hz, 3H), 2.86 (m, 3H), 3.11 (m, 1H), 3.23 (m, 1H), 3.61 (m, 3H), 3.70 (m, 1H), 3.88 (d, J=11.03 Hz, 1H), 3.97 (d, J=17.28 Hz, 1H), 4.04 (s, 1H), 4.44 (m, 2H), 4.76 (s, 1H), 5.12 (s, 1H), 6.60 (s, 2H), 6.79 (s, 2H), 6.94 (d, J=15.81 Hz, 1H), 7.16 (m, 7H), 7.42 (d, J=8.46 Hz, 2H), 7.74 (m, 2H), 7.95 (d, J=8.46 Hz, 2H), 8.68 (d, J=4.04 Hz, 1H).

Example 108 $^1$H NMR (300 MHz, CDCl$_3$) δ ppm 0.80 (m, 15H), 0.85 (m, 2H), 0.97 (m, 1H), 1.37 (m, 1H), 1.89 (s, 1H), 2.61 (dd, J=12.69, 3.49 Hz, 1H), 2.69 (m, 3H), 2.78 (d, J=9.93 Hz, 1H), 2.87 (m, 2H), 3.09 (m, 1H), 3.23 (m, 1H), 3.62 (m, 3H), 3.64 (m, 2H), 3.65 (m, 1H), 3.88 (m, 1H), 3.98 (d, J=8.46 Hz, 1H), 4.06 (m, 1H), 4.44 (m, 2H), 4.78 (s, 1H), 5.25 (s, 1H), 6.55 (d, J=9.19 Hz, 1H), 6.64 (s, 1H), 6.96 (s, 1H), 7.17 (m, 7H), 7.43 (d, J=8.46 Hz, 2H), 7.94 (d, J=8.09 Hz, 2H), 8.68 (d, J=4.78 Hz, 1H).

Example 109 $^1$H NMR (300 MHz, CDCl$_3$) δ ppm 0.78 (d, J=13.24 Hz, 9H), 0.96 (m, 9H), 2.61 (m, 2H), 2.70 (s, 3H), 2.79 (d, J=10.66 Hz, 1H), 2.88 (m, 2H), 3.13 (m, 2H), 3.34 (m, 1H), 3.58 (s, 1H), 3.63 (m, 3H), 3.96 (m, 1H), 4.04 (m, 2H), 4.10 (m, 1H), 4.46 (m, 2H), 4.72 (s, 1H), 5.28 (d, J=9.19 Hz, 1H), 6.29 (d, J=9.56 Hz, 1H), 6.48 (s, 1H), 6.97 (s, 1H), 7.10 (m, 5H), 7.21 (m, 2H), 7.43 (d, J=8.46 Hz, 2H), 7.74 (m, 2H), 7.95 (d, J=8.46 Hz, 2H), 8.69 (d, J=4.78 Hz, 1H).

Example 110 $^1$H NMR (300 MHz, CDCl$_3$) δ ppm 0.79 (d, J=6.62 Hz, 3H), 0.81 (s, 9H), 0.86 (m, 3H), 1.01 (m, 1H), 1.38 (m, 1H), 1.91 (m, 1H), 2.54 (dd, J=12.32, 3.13 Hz, 1H), 2.74 (m, 1H), 2.86 (t, J=7.17 Hz, 2H), 2.94 (m, 1H), 3.10 (m, 1H), 3.21 (m, 2H), 3.47 (s, 2H), 3.57 (m, 2H), 3.62 (s, 3H), 3.66 (s, 1H), 3.78 (s, 3H), 3.87 (m, 1H), 4.06 (m, 1H), 4.48 (s, 2H), 4.69 (s, 2H), 4.71 (s, 1H), 5.27 (d, J=8.82 Hz, 1H), 6.51 (m, 2H), 6.83 (d, J=8.46 Hz, 2H), 7.12 (m, 6H), 7.21 (d, J=8.46 Hz, 2H).

Example 111 $^1$H NMR (300 MHz, CDCl$_3$) δ ppm 0.78 (d, J=4.41 Hz, 3H), 0.82 (s, 9H), 0.87 (m, 3H), 1.02 (m, 2H), 1.37 (m, 1H), 1.94 (m, 2H), 2.55 (dd, J=12.13, 2.94 Hz, 1H), 2.76 (m, 1H), 2.88 (t, J=6.99 Hz, 1H), 3.57 (d, J=9.93 Hz, 2H), 3.63 (s, 3H), 3.66 (d, J=4.78 Hz, 2H), 3.78 (s, 3H), 3.89 (d, J=19.12 Hz, 1H), 3.90 (s, 1H), 3.95 (d, J=5.15 Hz, 1H), 4.07 (m, 1H), 4.83 (m, 2H), 5.29 (d, J=8.82 Hz, 1H), 6.49 (m, 2H), 6.84 (d, J=8.82 Hz, 2H), 7.07 (m, 6H), 7.21 (d, J=8.46 Hz, 2H), 7.34 (d, J=4.78 Hz, 1H), 7.64 (t, J=7.72 Hz, 1H), 7.77 (m, 1H), 8.21 (t, J=9.01 Hz, 2H), 8.93 (d, J=4.41 Hz, 1H).

Example 112 $^1$H NMR (300 MHz, MeOH-d$_4$) δ ppm 0.66 (d, J=6.62 Hz, 3H), 0.73 (d, J=6.62 Hz, 3H), 0.77 (d, J=6.62 Hz, 3H), 0.84 (t, J=7.35 Hz, 3H), 1.00 (m, 1H), 1.37 (m, 2H), 1.70 (s, 1H), 1.76 (s, 1H), 1.87 (m, 2H), 2.09 (m, 1H), 2.24 (m, 1H), 2.53 (s, 3H), 2.72 (m, 1H), 2.87 (m, 4H), 3.13 (m, 4H), 3.24 (m, 2H), 3.76 (s, 1H), 3.87 (d, J=11.03 Hz, 1H), 3.93 (d, J=11.03 Hz, 1H), 4.06 (d, J=13.24 Hz, 1H), 4.35 (m, J=15.44 Hz, 2H), 4.53 (m, 1H), 7.12 (m, 4H), 7.17 (s, 1H), 7.22 (m, 3H), 7.34 (m, 1H), 7.53 (d, J=8.46 Hz, 2H), 7.69 (t, #7.72 Hz, 1H), 7.84 (d, J=7.72 Hz, 2H), 7.91 (d, J=8.46 Hz, 2H), 8.60 (d, J=4.41 Hz, 1H).

Example 113 $^1$H NMR (300 MHz, CDCl$_3$) δ ppm 0.74 (d, J=6.62 Hz, 3H), 0.78 (s, 9H), 0.81 (m, 3H), 0.96 (m, 1H), 1.33 (m, 1H), 1.95 (m, 4H), 2.65 (dd, J=12.50, 2.94 Hz, 1H), 2.80 (m, 1H), 2.92 (m, 2H), 3.15 (m, 2H), 3.64 (m, 3H), 3.65 (d, J=9.56 Hz, 2H), 3.83 (d, J=11.03 Hz, 1H), 4.00 (m, 2H), 4.12 (q, J=8.46 Hz, 2H), 4.68 (m, 2H), 5.36 (d, J=9.19 Hz, 1 H), 6.63 (d, J=9.56 Hz, 1H), 7.15 (m, 6H), 7.45 (d, J=8.09 Hz, 2H), 7.49 (m, 1H), 7.59 (m, 1H), 7.72 (d, J=8.09 Hz, 1H), 7.80 (m, 1H), 7.92 (d, J=8.09 Hz, 2H), 8.72 (d, J=4.04 Hz, 1H), 9.12 (dd, J=4.78, 1.84 Hz, 1H).

Example 114 $^1$H NMR (300 MHz, MeOH-d$_4$) δ ppm 0.78 (s, 9H), 0.91 (s, 9H), 2.44 (d, J=8.09 Hz, 1H), 2.66 (d, J=3.31 Hz, 3H), 2.78 (m, 2H), 2.86 (m, 3H), 3.11 (dd, J=7.54, 2.39 Hz, 1H), 3.35 (m, 2H), 3.59 (s, 3H), 3.72 (s, 1H), 3.85 (d, J=10.30 Hz, 1H), 4.01 (d, J=11.40 Hz, 2H), 4.07 (m, 2H), 4.16 (m, 1H), 4.49 (d, J=16.18 Hz, 1H), 4.69 (m, 1H), 7.09 (m, 3H), 7.18 (m, 2H), 7.35 (m, 1H), 7.55 (m, 2H), 7.82 (d, J=8.09 Hz, 1H), 7.88 (d, J=8.46 Hz, 4H), 7.92 (m, 2H), 7.95 (m, 1H), 8.59 (m, 1H).

Example 115 $^1$H NMR (300 MHz, MeOH-d$_4$) δ ppm 0.78 (s, 9H), 0.91 (s, 9H), 2.41 (d, J=8.46 Hz, 1H), 2.41 (d, J=8.46 Hz, 1H), 2.83 (m, 4H), 3.09 (t, J=9.01 Hz, 1H), 3.20 (t, J=9.19 Hz, 1H), 3.34 (s, 2H), 3.59 (s, 3H), 3.72 (s, 1H), 3.83 (d, J=1.47 Hz, 1H), 3.97 (m, 3H), 4.01 (d, J=11.03 Hz, 1H), 4.03 (m, 3H), 4.20 (d, J=7.35 Hz, 1H), 4.56 (m, 2H), 7.11 (m, 3H), 7.16 (m, 2H), 7.35 (m, 1H), 7.56 (m, 3H), 7.87 (m, 4H), 8.03 (m, 2H), 8.60 (m, 1H).

Example 116 $^1$H NMR (300 MHz, MeOH-d$_4$) δ ppm 0.59 (d, J=6.25 Hz, 3H), 0.75 (d, J=6.62 Hz, 3H), 0.83 (m, 6H), 0.97 (m, 3H), 1.34 (m, 3H), 1.87 (m, 2H), 2.52 (d, J=5.88 Hz, 3H), 2.66 (m, 1H), 2.85 (m, 4H), 3.09 (m, 4H), 3.21 (m, 3H), 3.34 (s, 1H), 3.74 (m, 2H), 3.89 (m, 2H), 4.03 (m, 1H), 4.34 (d, J=15.81 Hz, 1H), 4.54 (m, 1H), 7.12 (m, 4H), 7.21 (m, 3H), 7.35 (m, 1H), 7.54 (d, J=8.46 Hz, 2H), 7.70 (t, #7.72 Hz, 1H), 7.85 (m, 3H), 7.90 (d, J=8.09 Hz, 2H), 8.59 (d, J=4.78 Hz, 1H).

Example 117 $^1$H NMR (300 MHz, MeOH-d$_4$) δ ppm 0.79 (s, 9H), 0.92 (s, 9H), 1.53 (d, J=3.68 Hz, 6H), 2.33 (t, #8.82 Hz, 1H), 2.69 (m, 2H), 2.80 (m, 2H), 2.84 (s, 1H), 3.06 (m, 1H), 3.21 (t, #9.19 Hz, 1H), 3.27 (d, J=2.57 Hz, 1H), 3.33 (s, 1H), 3.64 (s, 3H), 3.72 (s, 1 H), 3.76 (s, 3H), 3.81 (d, J=13.24 Hz, 2H), 3.89 (m, 1H), 4.05 (m, 1H), 4.13 (m, 1H), 4.41 (d, J=15.44 Hz, 1H), 4.59 (m, 1H), 6.82 (m, 2H), 7.08 (m, 3H), 7.15 (d, J=1.84 Hz, 1H), 7.19 (m, 2H), 7.28 (m, 2H), 7.53 (d, J=6.99 Hz, 1H), 7.77 (t, J=7.72 Hz, 1H), 7.83 (s, 1H).

Example 118 $^1$H NMR (300 MHz, MeOH-d$_4$) δ ppm 0.72 (d, J=6.62 Hz, 3H), 0.79 (s, 9H), 0.86 (t, J=7.35 Hz, 3H), 0.98 (m, 1H), 1.39 (m, 1H), 1.52 (d, J=2.57 Hz, 6H), 1.86 (m, 1H), 2.65 (d, J=15.44 Hz, 2H), 2.74 (m, 1H), 2.84 (m, 2H), 3.07 (dd, J=9.74, 4.60 Hz, 1H), 3.13 (s, 1H), 3.18 (m, 1H), 3.26 (d, J=7.72 Hz, 1H), 3.64 (s, 3H), 3.71 (s, 1H), 3.75 (s, 3H), 3.79 (s, 1H), 3.87 (m, 3H), 4.16 (m, 1H), 4.37 (d, J=15.81 Hz, 1H), 4.61 (d, J=15.44 Hz, 1H), 6.82 (m, 2H), 7.09 (dd, #6.62, 4.04 Hz, 4H), 7.16 (m, 4H), 7.28 (m, 2H) 7.52 (d, J=6.99 Hz, 1H), 7.75 (t, J=7.91 Hz, 1H).

Example 119 $^1$H NMR (300 MHz, MeOH-d$_4$) δ ppm 0.79 (s, 9H), 0.92 (s, 9H), 2.39 (d, J=9.56 Hz, 1H), 2.70 (m, 2H), 2.83 (m, 2H), 3.05 (m, 1H), 3.16 (q, J=9.07 Hz, 2H), 3.65 (s, 3H), 3.72 (s, 1H), 3.76 (s, 3H), 3.85 (m, 3H), 4.05 (s, 1H), 4.12 (m, 1H), 4.47 (m, 2H), 4.69 (s, 2H), 6.82 (m, 2H), 7.08 (m, 4H), 7.15 (m, 3H), 7.23 (d, J=7.72 Hz, 1H), 7.29 (m, 2H), 7.45 (d, J=7.35 Hz, 1H), 7.84 (m, 2H).

Example 120 $^1$H NMR (300 MHz, MeOH-d$_4$) δ ppm 0.79 (s, 9H), 0.92 (s, 9H), 2.39 (d, J=9.56 Hz, 1H), 2.70 (m, 2H), 2.83 (m, 2H, 3.05 (m, 1H), 3.16 (q, J=9.07 Hz, 2H), 3.65 (s, 3H), 3.72 (s, 1H), 3.76 (s, 3H), 3.85 (m, 3H), 4.05 (s, 1H), 4.12 (m, 1H), 4.47 (m, 2H), 4.69 (s, 2H), 6.82 (m, 2H), 7.08 (m, 4H), 7.15 (m, 3H), 7.23 (d, J=7.72 Hz, 1H), 7.29 (m, 2H), 7.45 (d, J=7.35 Hz, 1H), 7.84 (m, 2H).

Example 121 $^1$H NMR (300 MHz, MeOH-d$_4$) δ ppm 0.72 (d, J=6.62 Hz, 3H), 0.79 (s, 9H), 0.86 (t, J=7.35 Hz, 3H), 0.99 (m, 1H), 1.37 (m, 1H), 1.86 (m, 1H), 2.66 (dd, J=12.13, 3.31 Hz, 2H), 2.75 (m, 1H), 2.83 (dd, J=10.66, 4.04 Hz, 2H), 3.13 (m, 3H), 3.24 (d, J=9.19 Hz, 1 H), 3.64 (s, 3H), 3.72 (s, 1H), 3.75 (s, 3H), 3.79 (s, 1H), 3.87 (m, 3H), 3.91 (s, 1H), 4.18 (m, 1H), 4.36 (d, J=15.81 Hz, 1H), 4.57 (m, 1H), 4.68 (s, 2H), 6.82 (d, J=8.82 Hz, 2H), 7.14 (m, 6H), 7.21 (d, J=7.72 Hz, 1H), 7.29 (d, J=8.46 Hz, 2H), 7.44 (d, J=7.72 Hz, 1H), 7.81 (t, J=7.72 Hz, 1H).

Example 122 $^1$H NMR (300 MHz, CDCl$_3$) δ ppm 0.82 (m, 12H), 0.89 (m, 3H), 1.04 (m, 2H), 1.44 (m, 2H), 1.93 (d, J=10.30 Hz, 1H), 2.54 (m, 1H), 2.76 (m, 2H), 3.09 (m, 1H), 3.22 (m, 1H), 3.59 (m, 3H), 3.78 (m, 3H), 3.83 (m, 2H), 3.93 (m, 1H), 4.06 (m, 1H), 4.77 (s, 1H), 5.12 (m, 2H), 5.28 (d, J=8.82 Hz, 1H), 6.59 (s, 2H), 6.82 (d, J=8.46 Hz, 2H), 7.08 (m, 6H), 7.19 (m, 2H), 7.42 (m, 1H), 7.53 (m, 1H), 7.73 (m, 2H), 8.16 (dd, 8.46, 1.84 Hz, 1H), 8.94 (dd, J=4.04, 1.84 Hz, 1H).

Example 123 $^1$H NMR (300 MHz, CDCl$_3$) δ ppm 0.82 (m, 12H), 0.86 (t, #7.35 Hz, 3H), 1.05 (m, 2H), 1.36 (m, 2H), 1.91 (m, 1H), 2.53 (m, 1H), 2.72 (d, 2.94 Hz, 3H), 2.77 (d, J=12.50 Hz, 1H), 2.87 (m, 2H), 3.03 (m, 2H), 3.57 (d, J=13.97 Hz, 2H), 3.63 (s, 3H), 3.79 (s, 3H), 3.87 (d, J=11.03 Hz, 1H), 3.94 (m, 1H), 4.07 (m, 1H), 4.74 (s, 1H), 4.77 (d, J=2.94 Hz, 2H), 5.28 (d, J=9.93 Hz, 1H), 6.48 (m, 2H), 6.84 (d, J=8.82 Hz, 2H), 7.06 (m, 3H), 7.10 (m, 2H), 7.17 (s, 1H), 7.20 (m, 2H), 7.52 (t, J=6.99 Hz, 1H), 7.67 (m, 1H), 804 (d, J=7.72 Hz, 1H), 8.13 (d, J=7.35 Hz, 1H).

Example 124 $^1$H NMR (300 MHz, CDCl$_3$) δ ppm 0.78 (d, J=6.62 Hz, 3H), 0.84 (m, 12H), 0.99 (m, 2H), 1.32 (m, 2H), 1.94 (m, 1H), 2.54 (dd, J=11.95, 2.39 Hz, 1H), 2.74 (m, 1H), 2.87 (d, J=7.35 Hz, 2H), 3.07 (m, 1H), 3.17 (m, 2H), 3.57 (t, J=9.01 Hz, 2H), 3.64 (s, 3H), 3.79 (m, 3H), 3.89 (m, 3H), 3.88 (m, 2H), 4.11 (m, 1H), 4.60 (d, J=15.44 Hz, 1H), 4.71 (m, 1H), 4.77 (m, 1H), 5.28 (d, J=9.19 Hz, 1H), 6.39 (m, 2H), 6.83 (m, 2H), 7.09 (m, 5H), 7.22 (m, 2H), 7.24 (s, 1H), 7.99 (dd, J=8.09, 1.47 Hz, 1H), 8.38 (dd, J=4.78, 1.47 Hz, 1H).

Example 125 $^1$H NMR (300 MHz, CDCl$_3$) δ ppm 0.76 (m, 3H), 0.82 (s, 9H), 0.86 (m, 3H), 1.01 (m, 1H), 1.37 (m, 1H), 1.94 (m, 1H), 2.55 (dd, J=12.32, 2.76 Hz, 1H), 2.75 (m, 1H), 2.89 (t, J=7.54 Hz, 2H), 3.15 (m, 1H), 3.54 (s, 1H), 3.60 (d, J=9.56 Hz, 2H), 3.63 (s, 3H), 3.71 (d, J=5.52 Hz, 1H), 3.79 (s, 3H), 3.86 (m, 3H), 4.09 (m, 1H), 4.70 (m, 3H), 5.27 (d, J=9.19 Hz, 1H), 6.48 (m, 2H), 6.84 (m, 2H), 7.15 (m, 5H), 7.20 (m, 2H), 7.47 (m, 1H), 7.57 (m, 1H), 9.13 (dd, J=4.78, 1.47 Hz, 1H).

Example 126 $^1$H NMR (300 MHz, CDCl$_3$) δ ppm 0.77 (m, 3H), 0.82 (m, 12H), 0.98 (m, 1H), 1.37 (m, 1H), 1.87 (s, 1H), 2.43 (s, 3H), 2.60 (dd, J=12.69, 3.49 Hz, 1H), 2.82 (m, 2H), 2.89 (t, J=8.27 Hz, 2H), 3.08 (m, 1H), 3.59 (s, 3H), 3.64 (d, J=9.93 Hz, 2H), 3.89 (d, J=11.03 Hz, 1H), 3.99 (d, J=8.09 Hz, 2H), 4.07 (m, 1H), 4.44 (s, 2H), 4.80 (s, 1H), 5.25 (s, 1H), 6.58 (d, J=2.21 Hz, 2H), 6.66 (s, 1H), 6.73 (d, J=3.31 Hz, 1H), 7.12 (m, 6H), 7.22 (m, 2H), 7.44 (d, J=8.09 Hz, 2H), 7.74 (m, 3H), 7.95 (d, J=8.09 Hz, 2H), 8.69 (d, J=4.78 Hz, 1H).

Example 127 $^1$H NMR (300 MHz, CDCl$_3$) δ ppm 0.63 (d, J=6.99 Hz, 3H), 0.78 (dd, J=13.05, 6.80 Hz, 6H), 0.87 (t, J=7.35 Hz, 3H), 1.04 (m, 1H), 1.30 (m, 1H), 1.40 (dd, J=10.85, 2.76 Hz, 1H), 1.63 (d, J=4.04 Hz, 1H), 1.92 (s, 1H), 2.54 (s, 3H), 2.59 (m, 1H), 2.80 (dd, J=12.32, 10.11 Hz, 1H), 2.90 (d, J=7.72 Hz, 2H), 2.94 (s, 1H), 3.14 (m, 2H), 3.22 (m, 1H), 3.57 (s, 1H), 3.60 (s, 3H), 3.68 (m, 3H), 3.84 (d, J=13.60 Hz, 1H), 3.91 (d, J=11.03 Hz, 1H), 3.96 (m, 1H), 4.08 (m, 1H), 4.45 (m, 2H), 4.75 (s, 1H), 5.07 (s, 1H), 6.9 (d, J=18.75 Hz, 2H), 7.09 (m, 4H), 7.18 (m, 4H), 7.29 (m, 4H), 7.54 (t, J=7.72 Hz, 1H).

Example 128 $^1$H NMR (300 MHz, DMSO-d$_6$) δ ppm 0.64 (m, 3H), 0.68 (s, 9H), 0.74 (t, J=7.35 Hz, 3H), 0.92 (m, 1H), 0.93 (m, 1H), 1.24 (m, 2H), 1.47 (m, 1H), 1.54 (dd, J=8.64, 6.07 Hz, 1H), 1.74 (s, 1H), 1.87 (s, 2H), 2.50 (m, 3H), 2.69 (m, 4H), 3.12 (m, 1H), 3.48 (d, J=13.97 Hz, 1H), 3.67 (d, J=9.93 Hz, 2H), 3.95 (m, 2H), 4.04 (dd, J=9.38, 6.43 Hz, 1H), 4.35 (m, 2H), 4.94 (d, J=3.68 Hz, 1H), 5.13 (m, 1H), 6.95 (d, J=9.93 Hz, 1H), 7.07 (m, 5H), 7.26 (s, 1H), 7.35 (m, 1H), 7.45 (d, J=8.09 Hz, 2H), 7.87 (m, 1H), 7.99 (d, J=8.09 Hz, 1H), 8.63 (m, 1H), 9.12 (s, 1H).

Example 129 $^1$H NMR (300 MHz, CDCl$_3$) δ ppm 0.82 (m, 3H), 0.88 (m, 3H), 1.04 (m, 1H), 1.25 (m, 2H), 1.32 (d, J=6.25 Hz, 3H), 1.42 (m, 2H), 1.95 (m, 1H), 2.52 (d, J=5.15 Hz, 3H), 2.87 (m, 2H), 2.96 (m, 2H), 3.23 (m, 2H), 3.63 (m, 2H), 3.91 (d, J=10.66 Hz, 1H), 4.02 (m, 2H), 4.20 (d, J=8.09 Hz, 1H), 4.45 (m, 2H), 4.83 (s, 1H), 6.51 (s, 1H), 6.84 (d, J=8.82 Hz, 1 H), 7.03 (m, 2H), 7.18 (m, 4H), 7.38 (d, J=8.09 Hz, 2H), 7.55 (m, 1H), 7.73 (m, 3H), 7.90 (d, J=8.09 Hz, 2H), 7.95 (m, 1H), 8.66 (d, J=4.78 Hz, 1H).

Example 130 $^1$H NMR (300 MHz, MeOH-d$_4$) δ ppm 0.88 (d, J=6.62 Hz, 6H), 0.99 (s, 9H), 1.00 (s, 9H), 1.37 (q, J=7.11 Hz, 2H), 1.52 (s, 3H), 1.53 (s, 3H), 1.66 (m, 1H), 2.37 (d, J=8.82 Hz, 1H), 2.70 (m, 3H), 2.74 (m, 1H), 2.77 (d, J=5.15 Hz, 1H), 2.81 (t, J=4.23 Hz, 1 H), 2.85 (s, 1H), 2.87 (s, 1H), 3.07 (m, 2H), 3.23 (m, 2H), 3.66 (s, 3H), 3.74 (s, 1H), 3.84 (s, 1H), 4.10 (s, 1H), 4.13 (s, 1H), 4.41 (d, J=15.44 Hz, 1H), 4.60 (m, 1H), 7.10 (m, 3H), 7.15 (d, J=1.47 Hz, 2H), 7.19 (d, J=7.72 Hz, 1H), 7.53 (d, J=6.99 Hz, 1H), 7.77 (t, J=7.91 Hz, 1H), 7.88 (d, J=9.93 Hz, 1H).

Example 131 $^1$H NMR (300 MHz, MeOH-d$_4$) δ ppm 0.87 (m, 12H), 1.00 (s, 9H), 1.06 (m, 1H), 1.40 (m, 4H), 1.52 (d, J=2.21 Hz, 6H), 1.64 (m, 1H), 1.92 (m, 1H), 2.67 (d, J=6.62 Hz, 3 H), 2.75 (m, 3H), 2.85 (m, 3H), 3.13 (m, 4H), 3.66 (s, 3H), 3.73 (s, 1H), 3.83 (s, 1H), 3.93 (d, J=11.03 Hz, 1H), 4.14 (dd, J=5.70, 3.86 Hz, 1H), 4.37 (d, J=15.81 Hz, 1H), 4.62 (d, J=15.81 Hz, 1H), 7.10 (m, 3H), 7.16 (m, 3H), 7.52 (d, J=6.99 Hz, 1H), 7.76 (t, J=7.72 Hz, 1 H).

Example 132 $^1$H NMR (300 MHz, MeOH-d$_4$) δ ppm 0.88 (d, J=6.62 Hz, 6H), 099 (s, 9H), 1.01 (s, 9H), 1.37 (q, J=7.35 Hz, 2H), 1.66 (m, 1H), 2.41 (m, 1H), 2.69 (m, 3H), 2.76 (m, 2H), 2.84 (m, 3H), 3.05 (m, 2H), 3.17 (q, J=9.07 Hz, 1H), 3.35 (m, 1H), 3.66 (s, 3H), 3.74 (s, 1H), 3.84 (s, 1H), 4.10 (s, 1H), 4.13 (m, 1H), 4.42 (d, J=15.81 Hz, 1H), 4.54 (m, 1H), 4.70 (s, 2H), 7.09 (m, 4H), 7.17 (m, 2H), 7.23 (d, J=7.35 Hz, 1H), 7.45 (d, J=7.72 Hz, 1H), 7.83 (t, J=7.72 Hz, 1H).

Example 133 $^1$H NMR (300 MHz, MeOH-d$_4$) δ ppm 0.85 (m, 6H), 0.90 (m, 6H), 1.00 (s, 9H), 1.06 (m, 1H), 1.39 (m, 4H), 1.64 (m, 1H), 1.91 (m, 1H), 2.68 (m, 3H), 2.74 (m, 2H), 2.79 (m, 1H), 2.85 (m, 2H), 3.13 (m, 2H), 3.18 (m, 1H), 3.25 (m, 1H), 3.66 (s, 3H), 3.72 (d, J=6.25 Hz, 1H), 3.83 (s, 1H), 3.94 (d, J=11.40 Hz, 1H), 4.15 (m, H), 4.37 (d, J=15.81 Hz, 1 H), 4.57 (m, 1H), 4.69 (s, 2H), 7.12 (m, 3H), 7.17 (m, 3H), 7.21 (d, J=7.72 Hz, 1H), 7.44 (d, J=7.72 Hz, 1H), 7.82 (t, #7.72 Hz, 1H).

Example 134 $^1$H NMR (300 MHz, DMSO-d$_6$) δ ppm 0.72 (dd, J=6.43, 2.76 Hz, 3H), 0.84 (m, 6H), 1.20 (m, 5H), 1.31 (m, 2H), 1.83 (m, 1H), 2.45 (m, 3H), 2.64 (dd, J=8.09, 3.68 Hz, 2H), 2.80 (m, 3H), 3.14 (m, 2H), 3.58 (m, 1H), 4.03 (m, 3H), 4.35 (s, 2H), 4.84 (m, 1H), 7.03 (d, J=7.72 Hz, 1H), 7.12 (m, 6H), 7.21 (m, 1H), 7.34 (m, 1H), 7.46 (m, 3H), 7.66 (m, 1H), 7.88 (m, 2H), 8.04 (m, 3H), 8.65 (d, J=4.04 Hz, 1H), 9.18 (d, J=9.19 Hz, 1H).

Example 135 $^1$H NMR (300 MHz, CDCl$_3$), δ ppm 0.77 (d, J=6.62 Hz, 3H), 0.85 (m, 12H), 0.97 (m, 1H), 1.30 (m, 1H), 1.89 (m, 1H), 2.54 (d, J=9.19 Hz, 2H), 2.71 (d, J=10.66 Hz, 1 H), 2.80 (m, 2H), 3.01 (m, 2H), 3.56 (dd, 17.46, 8.64 Hz, 2H), 3.63 (s, 3H), 3.79 (s, 3H), 3.85 (m, 2H), 3.94 (m, 1H), 4.11 (d, J=7.72 Hz, 1H), 4.69 (m, 2H), 4.88 (m, 1H), 5.26 (m, 1H), 6.33 (d, J=9.93 Hz, 1H), 6.39 (s, 1H), 6.61 (m, 1H), 6.72 (m, 1H), 6.86 (m, 2H), 6.92 (m, 2H), 7.01 (m, 3H), 7.22 (d, J=8.46 Hz, 2H), 7.37 (d, J=6.99 Hz, 1H), 7.42 (d, J=8.82 Hz, 1H), 8.32 (d, J=7.35 Hz, 1H).

Example 136 ¹H NMR (300 MHz, CF₃COOD), δ ppm 0.74 (d, J=6.62 Hz, 3H), 0.82 (t, J=7.35 Hz, 3H), 0.98 (m, 1H), 1.35 (m, 1H), 1.54 (m, 1H), 1.86 (m, 1H), 2.11 (m, 1H), 2.18 (m, 3H), 2.22 (m, 1H), 2.52 (s, 3H), 2.73 (m, 1H), 2.80 (dd, J=13.60, 2.21 Hz, 2H), 2.89 (m, 2H), 3.13 (m, 2H), 3.25 (m, 1H), 3.28 (m, 1H), 3.33 (m, 1H), 3.79 (m, 1H), 3.90 (d, J=11.03 Hz, 1H), 3.97 (m, 1H), 4.02 (d, J=3.68 Hz, 2H), 4.24 (m, 1H), 4.35 (d, J=15.81 Hz, 1H), 4.53 (m, 1H), 7.12 (m, 3H), 7.18 (m, 3H), 7.35 (m, 1H), 7.54 (d, 8.46 Hz, 2H), 7.70 (t, J=7.72 Hz, 1H), 7.85 (m, 2H), 7.91 (m, 2H), 8.60 (d, J=4.41 Hz, 1H).

Example 137 ¹H NMR (300 MHz, MeOH-d₄), δ ppm 0.41 (s, 2H), 0.70 (s, 2H), 0.82 (m, 6H), 1.00 (s, 3H), 1.33 (d, J=25.37 Hz, 1H), 1.88 (m, 1H), 2.53 (s, 3H), 2.73 (m, 1H), 2.84 (d, J=18.75 Hz, 2H), 3.11 (m, 2H), 3.21 (m, 3H), 3.34 (s, 3H), 3.38 (m, 1H), 3.91 (m, 2H), 3.96 (m, 1H), 4.27 (d, J=12.87 Hz, 1H), 4.35 (d, J=15.81 Hz, 1H), 4.47 (d, J=8.09 Hz, 1H), 4.54 (d, J=15.81 Hz, 1H), 4.59 (s, 1H), 4.68 (s, 1H), 7.13 (d, J=7.35 Hz, 3H), 7.19 (d, J=7.72 Hz, 3H), 7.35 (dd, J=7.72, 5.52 Hz, 1H), 7.58 (d, J=7.72 Hz, 2H), 7.73 (m, 1H), 7.85 (m, 4H), 8.59 (d, J=5.15 Hz, 1H).

Example 138 ¹H NMR (300 MHz, MeOH-d₄), δ ppm 0.50 (s, 1H), 0.81 (s, 5H), 0.86 (d, J=7.35 Hz, 4H), 1.02 (d, J=6.25 Hz, 2H), 1.01 (s, 1H), 1.38 (s, 1H), 1.89 (s, 1H), 2.45 (m, 3H), 2.79 (m, 2H), 3.20 (m, 3H), 3.34 (s, 1H), 3.79 (d, J=18.38 Hz, 2H), 3.88 (d, J=11.40 Hz, 1H), 4.37 (d, J=32.36 Hz, 4H), 4.53 (m, 1H), 4.73 (s, 1H), 7.13 (d, J=6.62 Hz, 4H), 7.20 (m, 3H), 7.36 (m, 1H), 7.56 (d, J=7.72 Hz, 3H), 7.70 (t, J=7.72 Hz, 1H), 7.86 (m, 5H), 8.60 (d, J=5.15 Hz, 1H).

Example 139 ¹H NMR (300 MHz, CDCl₃), δ ppm 0.80 (m, 9H), 0.97 (m, 9H), 1.24 (t, J=6.99 Hz, 1H), 2.55 (s, 3H), 2.62 (d, J=9.56 Hz, 2H), 2.80 (m, 1H), 2.88 (m, 2H), 3.13 (m, 2H), 3.34 (s, 1H), 3.60 (d, J=10.30 Hz, 4H), 3.97 (m, 2H), 4.05 (m, 1H), 4.13 (m, 1H), 4.49 (s, 2H), 4.74 (s, 1H), 5.29 (m, 1H), 6.31 (d, J=9.56 Hz, 1H), 6.46 (s, 1H), 7.11 (m, 6H), 7.23 (m, 1H), 7.43 (d, J=8.09 Hz, 2H), 7.58 (m, 1H), 7.74 (m, 2H), 7.95 (d, J=8.09 Hz, 2H), 8.69 (d, J=4.04 Hz, 1H).

Example 140 ¹H NMR (300 MHz, DMSO-d₆), δ ppm 0.69 (m, 12H), 0.79 (t, J=7.35 Hz, 3H), 0.95 (m, 1H), 1.28 (s, 1H), 1.76 (s, 1H), 2.69 (m, 4H), 3.07 (m, 2H), 3.37 (m, 3H), 3.54 (s, 3H), 3.70 (m, 8H), 3.95 (d, J=11.03 Hz, 2H), 4.02 (s, 1H), 4.17 (m, 3H), 4.36 (m, 2H), 6.73 (m, 2H), 6.83 (s, 1H), 6.95 (d, J=9.19 Hz, 1H), 7.07 (m, 5H), 7.41 (d, J=7.35 Hz, 2H), 9.01 (s, 1H).

Example 141 ¹H NMR (300 MHz, DMSO-d₆), δ ppm 0.79 (m, 15H), 0.94 (m, 9H), 1.31 (m, 3H), 1.77 (d, J=11.40 Hz, 1H), 2.63 (m, 6H), 2.83 (m, 2H), 3.09 (m, 3H), 3.37 (s, 3H), 3.57 (m, 4H), 3.78 (d, J=9.19 Hz, 2H), 4.00 (m, 5H), 4.36 (m, 2H), 7.07 (m, 5H), 7.43 (m, 1H), 8.98 (s, 1H).

Example 142 ¹H NMR (300 MHz, CF₃COOD), δ ppm 0.84 (m, 5H), 1.01 (s, 1H), 1.29 (s, 2H), 1.76 (s, 1H), 1.89 (s, 2H), 2.06 (s, 1H), 2.53 (s, 3H), 2.70 (d, J=8.82 Hz, 2H), 2.85 (d, J=6.25 Hz, 2H), 2.99 (s, 1H), 3.14 (m, 4H), 3.45 (s, 1H), 3.68 (s, 1H), 3.83 (s, 2H), 4.36 (m, 2H), 4.54 (d, J=15.44 Hz, 2H), 4.87 (s, 2H), 7.12 (s, 3H), 7.20 (t, J=7.17 Hz, 3H), 7.37 (d, J=5.88 Hz, 1H), 7.50 (s, 1H), 7.55 (d, J=8.09 Hz, 2H), 7.70 (t, J=7.72 Hz, 1H), 7.87 (m, 4H), 8.60 (d, J=4.78 Hz, 1H).

Example 143 ¹H NMR (300 MHz, BENZENE-d₆), δ ppm 0.80 (m, 3H), 0.85 (t, J=7.35 Hz, 3H), 1.01 (s, 1H), 1.29 (s, 3H), 1.89 (s, 2H), 2.05 (s, 1H), 2.53 (s, 3H), 2.70 (d, J=9.93 Hz, 3H), 2.86 (s, 2H), 2.99 (s, 2H), 3.15 (m, 4H), 3.49 (s, 1H), 3.67 (s, 1H), 3.88 (d, J=11.03 Hz, 2H), 4.34 (d, J=15.81 Hz, 3H), 4.53 (m, 1H), 4.88 (s, 2H), 7.13 (m, 3H), 7.19 (m, 3H), 7.36 (m, 1H), 7.56 (s, 2H), 7.70 (t, J=7.72 Hz, 1H), 7.88 (m, 3H), 8.60 (d, J=5.15 Hz, 1H).

Example 144 ¹H NMR (300 MHz, CDCl₃), δ ppm 0.86 (m, 15H), 0.94 (s, 1H), 1.01 (s, 1H), 1.13 (m, 6H), 1.42 (m, 1H), 1.93 (s, 1H), 2.49 (d, J=2.94 Hz, 1H), 2.54 (s, 3H), 2.74 (m, 1H), 2.92 (m, 2H), 3.15 (m, 3H), 3.33 (m, 4H), 3.52 (d, J=9.93 Hz, 1H), 3.62 (m, 4H), 3.83 (m, 2H), 3.92 (d, J=11.40 Hz, 1H), 4.06 (t, J=8.27 Hz, 1H), 4.46 (m, 2H), 4.75 (s, 1H), 5.31 (d, J=9.19 Hz, 1H), 6.43 (s, 1H), 6.52 (d, J=9.56 Hz, 1H), 6.59 (d, J=8.46 Hz, 2H), 7.05 (m, 3H), 7.11 (d, J=2.21 Hz, 1H), 7.17 (m, 4H), 7.55 (m, 1H).

Example 145 ¹H NMR (300 MHz, MeOH-d₄), δ ppm 0.75 (d, J=6.62 Hz, 3H), 0.83 (t, J=7.35 Hz, 3H), 0.87 (s, 9H), 0.98 (dd, J=15.63, 6.07 Hz, 1H), 1.35 (s, 1H), 1.84 (s, 1H), 2.53 (s, 3H), 2.72 (m, 2H), 2.81 (d, J=6.99 Hz, 2H), 2.88 (m, 2H), 3.02 (s, 2H), 3.17 (m, 7H), 3.57 (s, 1H), 3.82 (d, J=15.44 Hz, 1H), 3.90 (m, 2H), 4.04 (m, 1H), 4.35 (d, J=15.44 Hz, 2H), 4.53 (m, 1H), 4.91 (s, 2H), 7.13 (m, 3H), 7.19 (m, 3H), 7.25 (m, 1H), 7.53 (d, J=8.46 Hz, 2H), 7.70 (t, J=7.72 Hz, 1H), 7.85 (m, 2H), 7.90 (d, J=8.46 Hz, 2H).

Example 146 ¹H NMR (300 MHz, MeOH-d₄), δ ppm 0.81 (s, 9H), 0.93 (s, 9H), 1.52 (s, 3H), 1.53 (s, 3H), 2.35 (d, J=8.82 Hz, 1H), 2.66 (dd, J=12.69, 2.76 Hz, 1H), 2.76 (m, 1H), 2.82 (d, J=3.68 Hz, 2H), 2.86 (m, 2H), 3.06 (m, 1H), 3.21 (t, J=9.19 Hz, 1H), 3.27 (d, J=2.57 Hz, 1H), 3.33 (s, 1H), 3.65 (s, 2H), 3.72 (s, 1H), 3.80 (m, 2H), 4.05 (s, 1H), 4.12 (dd, J=5.88, 4.04 Hz, 1H), 4.19 (s, 4H), 4.41 (d, J=15.81 Hz, 1H), 4.60 (m, 1H), 4.91 (s, 2H), 6.71 (d, J=8.46 Hz, 1H), 6.81 (m, 1H), 6.89 (d, J=1.84 Hz, 1H), 7.09 (m, 2H), 7.15 (m, 1H), 7.19 (d, J=8.82 Hz, 1H), 7.53 (d, J=8.09 Hz, 1H), 7.77 (t, J=7.72 Hz, 1H), 7.82 (d, J=9.56 Hz, 1H).

Example 147 ¹H NMR (300 MHz, MeOH-d₄), δ ppm 0.74 (d, J=6.62 Hz, 3H), 0.80 (s, 9H), 0.87 (t, J=7.35 Hz, 3H), 1.01 (m, 1H), 1.37 (m, 1H), 1.88 (d, J=8.09 Hz, 1H), 2.64 (dd, J=12.32, 3.13 Hz, 2H), 2.71 (d, J=6.62 Hz, 1H), 2.77 (m, 1H), 2.84 (m, 2H), 3.12 (m, 2H), 3.24 (m, 1H), 3.65 (s, 3H), 3.72 (s, 1H), 3.78 (m, 3H), 3.89 (m, 1H), 4.16 (m, 1H), 4.19 (s, 4H), 4.36 (d, J=15.44 Hz, 1H), 4.57 (m, 1H), 4.68 (s, 2H), 4.91 (s, 2H), 6.71 (d, J=8.09 Hz, 1H), 6.81 (m, 1H), 6.89 (d, J=2.21 Hz, 1H), 7.11 (m, 3H), 7.17 (m, 2H), 7.21 (d, J=7.72 Hz, 1H), 7.44 (d, J=7.72 Hz, 1H), 7.81 (t, J=7.72 Hz, 1H), 7.84 (d, J=10.30 Hz, 1H).

Example 148 ¹H NMR (300 MHz, MeOH-d₄), δ ppm 0.81 (s, 9H), 0.93 (s, 9H), 2.39 (q, J=9.80 Hz, 1H), 2.66 (m, 1H), 2.75 (d, J=9.93 Hz, 1H), 2.82 (d, J=2.94 Hz, 1H), 2.86 (m, 1H), 3.05 (m, 2H), 3.16 (q, J=9.07 Hz, 2H), 3.34 (s, 1H), 3.65 (s, 3H), 3.72 (s, 1H), 3.80 (m, 3H), 4.05 (s, 1H), 4.13 (m, 1H), 4.19 (s, 4H), 4.41 (d, J=15.81 Hz, 1H), 4.53 (m, 1H), 4.69 (s, 2H), 4.91 (s, 1H), 6.71 (d, J=8.09 Hz, 1H), 6.81 (m, 1H), 6.89 (d, J=2.21 Hz, 1H), 7.08 (m, 2H), 7.16 (m, 2H), 7.23 (d, J=7.72 Hz, 1H), 7.45 (d, J=7.35 Hz, 1H), 7.83 (m, 2H).

Example 149 ¹H NMR (300 MHz, MeOH-d₄), δ ppm 0.74 (d, J=6.62 Hz, 3H), 0.80 (s, 9H), 0.86 (t, J=7.35 Hz, 3H), 1.01 (m, 1H), 1.39 (m, 1H), 1.84 (m, 1H), 2.64 (m, 4H), 2.75 (m, 1H), 2.83 (m, 3H), 3.14 (m, 2H), 3.27 (d, J=7.72 Hz, 1H), 3.65 (s, 3H), 3.72 (s, 1H), 3.75 (s, 1H), 3.80 (d, J=4.04 Hz, 2H), 3.88 (d, J=11.40 Hz, 1H), 4.16 (d, J=5.52 Hz, 1H), 4.18 (d, J=7.35 Hz, 4H), 4.37 (d, J=15.81 Hz, 1H), 4.61 (d, J=15.81 Hz, 1H), 4.91 (s, 2H), 6.71 (d, J=8.09 Hz, 1H), 6.81 (m, 1H), 6.89 (d, J=1.84 Hz, 1H), 7.10 (m, 2H), 7.16 (m, 3H), 7.52 (d, J=8.09 Hz, 1H), 7.76 (t, #7.91 Hz, 1H), 7.82 (s, 1H).

Example 150 ¹H NMR (300 MHz, DMSO-d₆), δ ppm 0.71 (dd, J=5.15, 2.94 Hz, 6H), 0.79 (m, 3H), 0.86 (t, J=7.91 Hz, 1H), 0.93 (dd, J=17.46, 8.27 Hz, 3H), 1.15 (m, 1H), 1.22 (m, 2H), 1.80 (s, 1H), 2.45 (s, 2H), 2.54 (s, 1H), 2.76 (d, J=30.89 Hz, 3H), 2.96 (d, J=2.94 Hz, 1H), 3.14 (m, 3H), 3.32 (s, 2H), 3.64 (s, 1H), 3.96 (m, 4H), 4.34 (d, J=11.03 Hz, 2H), 4.82 (t, J=4.04 Hz, 1H), 7.03 (d, J=7.35 Hz, 1H), 7.17 (m, 5H), 7.35 (m, 2H), 7.45 (m, 2H), 7.65 (t, J=7.72 Hz, 1H), 7.87 (d, J=6.99 Hz, 1H), 7.93 (m, 1H), 8.02 (d, J=8.09 Hz, 2H), 8.65 (d, J=4.78 Hz, 1H), 9.28 (d, J=15.08 Hz, 1H).

Example 151 $^1$H NMR (300 MHz, CDCl$_3$), δ ppm 0.75 (m, 9H), 0.94 (m, 10H), 2.38 (s, 3H), 2.58 (m, 1H), 2.78 (m, 1H), 2.88 (t, J=8.46 Hz, 2H), 2.96 (m, 1H), 3.31 (m, 1H), 3.58 (d, J=9.19 Hz, 2H), 3.64 (s, 3H), 3.88 (d, J=13.97 Hz, 1H), 4.00 (t, J=6.99 Hz, 2H), 4.13 (d, J=8.82 Hz, 1H), 4.30 (d, J=15.08 Hz, 1H), 4.50 (m, 1H), 4.71 (s, 1H), 5.29 (d, J=9.56 Hz, 1 H), 6.28 (d, J=9.56 Hz, 1H), 6.44 (s, 1H), 7.05 (m, 3H), 7.15 (m, 3H), 7.30 (m, 5H), 8.39 (s, 1H), 8.43 (d, J=4.78 Hz, 1H).

Example 152 $^1$H NMR (300 MHz, MeOH-d$_4$), δ ppm 0.89 (s, 6H), 0.99 (s, 9H), 1.01 (s, 9H), 1.24 (t, J=7.17 Hz, 1H), 1.43 (t, J=8.27 Hz, 3H), 1.53 (d, J=3.68 Hz, 6H), 2.37 (d, J=8.82 Hz, 1H), 2.68 (m, 2H), 2.76 (m, 2H), 2.83 (m, 2H), 3.07 (m, 1H), 3.23 (dd, J=18.20, 8.64 Hz, 2H), 3.34 (m, 1H), 3.66 (s, 3H), 3.73 (m, 1H), 3.84 (s, 1H), 4.11 (m, 2H), 4.13 (s, 1H), 4.41 (d, J=15.81 Hz, 1H), 4.60 (m, 1H), 4.91 (s, 2H), 7.08 (m, 2H), 7.16 (m, 2H), 7.21 (s, 1H), 7.53 (d, J=6.99 Hz, 1H), 7.77 (t, J=7.72 Hz, 1H), 7.88 (d, J=9.56 Hz, 1H).

Example 153 $^1$H NMR (300 MHz, MeOH-d$_4$), δ ppm 0.87 (m, 21H), 1.00 (s, 9H), 1.06 (m, 1H), 1.41 (m, 2H), 1.89 (s, 1H), 2.67 (m, 4H), 2.74 (m, 4H), 2.85 (m, 2H), 3.15 (m, 2H), 3.26 (s, 1H), 3.27 (s, 1H), 3.66 (s, 3H), 3.72 (t, J=6.07 Hz, 1H), 3.83 (s, 1H), 3.94 (d, J=11.03 Hz, 1H), 4.12 (m, 1H), 4.37 (d, J=15.81 Hz, 1H), 4.62 (d, J=15.81 Hz, 1H), 7.10 (m, 2H), 7.17 (m, 3H), 7.52 (d, J=8.09 Hz, 1H), 7.76 (t, J=7.91 Hz, 1H), 7.85 (d, J=9.56 Hz, 1 H).

Example 154 $^1$H NMR (300 MHz, MeOH-d$_4$), δ ppm 0.89 (s, 6H), 0.99 (s, 9H), 1.01 (s, 9H), 1.43 (t, J=8.27 Hz, 2H), 2.42 (d, J=9.56 Hz, 1H), 2.68 (m, 3H), 2.76 (m, 2H), 2.82 (m, 2H), 3.05 (m, 1H), 3.17 (q, J=9.19 Hz, 2H), 3.34 (d, J=2.94 Hz, 2H), 3.66 (s, 3H), 3.74 (t, J=6.43 Hz, 1H), 3.84 (s, 1H), 4.10 (d, J=6.62 Hz, 2H), 4.42 (d, J=15.81 Hz, 1H), 4.54 (m, 1H), 4.70 (s, 2H), 4.91 (s, 1H), 7.10 (q, J=5.52 Hz, 3H), 7.17 (m, 3H), 7.23 (d, J=7.72 Hz, 1H), 7.45 (d, J=7.72 Hz, 1H), 7.84 (t, J=7.72 Hz, 1H), 7.89 (d, J=9.19 Hz, 1H).

Example 155 $^1$H NMR (300 MHz, MeOH-d$_4$), δ ppm 0.85 (d, J=6.62 Hz, 3H), 0.90 (m, 12H), 0.98 (d, J=11.77 Hz, 9H), 1.04 (d, J=1.47 Hz, 1H), 1.42 (m, 3H), 1.87 (d, J=10.66 Hz, 1 H), 2.69 (m, 2H), 2.77 (m, 3H), 2.85 (m, 2H), 3.12 (m, 2H), 3.24 (m, 2H), 3.66 (s, 3H), 3.73 (m, 1H), 3.84 (s, 1H), 3.94 (d, J=11.40 Hz, 1H), 4.15 (d, J=1.84 Hz, 1H), 4.37 (d, J=15.81 Hz, 1H), 4.57 (m, 1H), 4.69 (s, 2H), 4.87 (s, 2H), 7.12 (m, 3H), 7.17 (m, 2H), 7.22 (d, J=7.72 Hz, 1H), 7.44 (d, J=7.35 Hz, 1H), 7.82 (t, J=7.72 Hz, 1H).

Example 156 $^1$H NMR (300 MHz, MeOH-d$_4$), δ ppm 0.13 (m, 2H), 0.46 (m, 2H), 0.91 (s, 1H), 0.99 (s, 9H), 1.00 (s, 9H), 1.52 (s, 3H), 1.53 (s, 3H), 2.41 (d, J=9.19 Hz, 1H), 2.53 (dd, J=12.87, 6.62 Hz, 1H), 2.70 (m, 2H), 2.75 (m, 2H), 2.84 (m, 3H), 3.08 (m, 1H), 3.24 (m, 2H), 3.34 (m, 1H), 3.66 (s, 3H), 3.76 (s, 1H), 3.87 (s, 1H), 4.10 (s, 1H), 4.14 (m, 1H), 4.41 (d, J=15.44 Hz, 1H), 4.60 (m, 1H), 7.09 (m, 3H), 7.16 (m, 2H), 7.20 (s, 1H), 7.53 (d, J=6.99 Hz, 1H), 7.77 (t, J=7.91 Hz, 1H), 7.86 (d, J=9.19 Hz, 1H).

Example 157 $^1$H NMR (300 MHz, MeOH-d$_4$), δ ppm 0.14 (m, 2H), 0.46 (m, 2H), 0.84 (d, J=6.25 Hz, 3H), 0.90 (m, 6H), 0.99 (s, 9H), 1.05 (m, 1H), 1.41 (m, 1H), 1.52 (d, J=2.57 Hz, 6H), 1.89 (s, 1H), 2.52 (dd, J=12.87, 6.99 Hz, 1H), 2.71 (m, 3H), 2.86 (m, 2H), 3.14 (m, 3H), 3.26 (d, J=3.31 Hz, 1H), 3.66 (s, 3H), 3.76 (s, 1H), 3.87 (s, 1H), 3.93 (d, J=11.40 Hz, 1 H), 4.17 (m, 1H), 4.37 (d, J=15.81 Hz, 1H), 4.61 (d, J=15.81 Hz, 1H), 4.91 (s, 1H), 7.11 (m, 2H), 7.17 (m, 3H), 7.52 (d, J=6.99 Hz, 1H), 7.76 (t, J=7.72 Hz, 1H), 7.83 (d, J=9.19 Hz, 1 H).

Example 158 $^1$H NMR (300 MHz, MeOH-d$_4$), δ ppm 0.15 (m, 2H), 0.47 (m, 2H), 0.90 (m, 1H), 0.99 (s, 9H), 1.00 (s, 9H), 2.45 (d, J=9.56 Hz, 1H), 2.53 (dd, J=12.69, 6.80 Hz, 2H), 2.69 (m, 1H), 2.75 (m, 2H), 2.84 (m, 2H), 3.06 (m, 1H), 3.18 (q, =J=9.07 Hz, 2H), 3.36 (m, 1H), 3.66 (s, 3H), 3.76 (s, 1H), 3.87 (s, 1H), 4.11 (s, 1H), 4.14 (m, 1H), 4.42 (d, J=15.44 Hz, 1 H), 4.54 (m, 1H), 4.69 (s, 2H), 7.10 (m, 3H), 7.16 (m, 2H), 7.23 (d, J=7.72 Hz, 1H), 7.45 (d, J=7.72 Hz, 1H), 7.85 (m, 2H).

Example 159 $^1$H NMR (300 MHz, MeOH-d$_4$), δ ppm 0.84 (d, J=6.62 Hz, 3H), 0.89 (m, 3H), 0.97 (s, 1H), 0.98 (d, J=6.62 Hz, 9H), 1.06 (m, 1H), 1.40 (m, 1H), 1.89 (m, 2H), 2.52 (dd, J=12.69, 6.80 Hz, 1H), 2.73 (m, 4H), 2.81 (m, 1H), 2.88 (m, 2H), 3.13 (m, 4H), 3.24 (t, J=9.01 Hz, 3H), 3.66 (s, 3H), 3.77 (s, 1H), 3.87 (s, 1H), 3.94 (d, J=11.03 Hz, 1H), 4.17 (m, 1H), 4.37 (d, J=15.81 Hz, 1H), 4.57 (m, 1H), 4.69 (s, 2H), 4.91 (s, 1H), 4.91 (s, 1H), 7.12 (m, 3H), 7.17 (m, 2H), 7.21 (d, J=8.09 Hz, 1H), 7.44 (d, J=7.72 Hz, 1H), 7.82 (t, J=7.72 Hz, 1H), 7.87 (d, J=8.46 Hz, 1H).

Example 160 $^1$H NMR (300 MHz, CDCl$_3$), δ ppm 0.63 (d, J=6.62 Hz, 3H), 0.92 (m, 14H), 1.35 (m, 3H), 1.92 (m, 1H), 2.59 (dd, J=12.32, 3.13 Hz, 1H), 2.69 (s, 3H), 2.84 (m, 3H), 3.10 (m, 3H), 3.22 (m, 2H), 3.64 (m, 3H), 3.95 (m, 4H), 4.43 (m, 2H), 4.74 (s, 1H), 5.11 (d, J=8.09 Hz, 1H), 6.58 (d, J=9.56 Hz, 1H), 6.68 (s, 1H), 6.97 (s, 1H), 7.18 (m, 5H), 7.30 (m, 5H).

Example 161 $^1$H NMR (300 MHz, CDCl$_3$), δ ppm 0.79 (d, J=6.25 Hz, 3H), 0.82 (s, 9H), 0.87 (t, J=7.35 Hz, 3H), 1.04 (m, 1H), 1.38 (m, 1H), 1.93 (m, 1H), 2.58 (dd, J=12.50, 2.94 Hz, 1 H), 2.77 (m, 1H), 2.91 (m, 4H), 3.09 (m, 3H), 3.60 (m, 1H), 3.62 (s, 3H), 3.78 (s, 3H), 3.88 (m, 2H), 4.10 (m, 1H), 4.45 (d, J=15.08 Hz, 1H), 4.67 (d, J=15.08 Hz, 1H), 5.30 (br d, J=7.54 Hz, 1H), 6.59 (br d, J=9.56 Hz, 1H), 6.64 (br s, 1H), 6.83 (d, J=8.82 Hz, 2H), 7.08-7.22 (m, 7H), 7.54 (m, 1H), 7.71 (m, 1H), 7.80 (m, 1H), 8.06 (d, 1.84 Hz, 1H), 8.09 (d, J=8.46 Hz, 1H), 8.85 (d, J=2.21 Hz, 1H).

Example 162 $^1$H NMR (300 MHz, CDCl$_3$), δ ppm 0.80-0.82 (m, 12H), 0.88 (t, J=7.35 Hz, 3H), 1.05 (m, 1H), 1.44 (m, 1H), 1.95 (m, 1H), 2.55 (dd, J=12.32, 3.13 Hz, 1H), 2.77 (m, 1H), 2.93 (m, 4H), 3.16 (m, 3H), 3.60 (m, 1H), 3.62 (s, 3H), 3.78 (s, 3H), 3.86 (d, J=8.46 Hz, 1H), 3.94 (d, J=11.40 Hz, 1H), 4.09 (m, 1H), 4.64 (d, J=15.44 Hz, 1H), 4.73 (d, J=15.44 Hz, 1H), 5.29 (br d, J=9.19 Hz, 1H), 6.51 (br s, 1H), 6.58 (br d, J=9.56 Hz, 1H), 6.82 (d, J=8.82 Hz, 2H), 7.10-7.21 (m, 7H), 7.44 (d, J=8.46 Hz, 1H), 7.54 (m, 1H), 7.71 (m, 1H), 7.80 (m, 1H), 8.06 (br d, J=8.46 Hz, 1H), 8.14 (d, J=8.09 Hz, 1H).

Example 163 $^1$H NMR (300 MHz, CDCl$_3$), δ ppm 0.80 (s, 9H), 2.44 (dd, J=14.52, 6.80 Hz, 1 H), 2.58 (dd, J=12.69, 3.13 Hz, 2H), 2.70 (s, 3H), 2.73 (m, 1H), 2.73 (d, J=4.78 Hz, 3H), 2.87 (m, 4H), 3.12 (m, 1H), 3.23 (m, 2H), 3.60 (m, 3H), 3.64 (s, 3H), 3.79 (s, 3H), 3.86 (d, J=13.60 Hz, 1H), 4.01 (d, J=13.60 Hz, 1H), 4.12 (m, 1H), 4.45 (s, 2H), 4.66 (t, J=7.35 Hz, 1 H), 5.30 (br d, J=8.82 Hz, 1H), 5.99 (m, 1H), 6.55 (s, 1H), 6.68 (br d, J=9.19 Hz, 1H), 6.84 (d, J=8.46 Hz, 2H), 7.02 (s, 1H), 7.14 (m, 5H), 7.26 (d, J=8.46 Hz, 2H).

Example 164 $^1$H NMR (300 MHz, CDCl$_3$), δ ppm 0.80 (s, 9H), 1.07 (t, #7.17 Hz, 3H), 2.43 (dd, J=14.71, 6.99 Hz, 1H), 2.58 (dd, J=12.69, 3.13 Hz, 2H), 2.70 (s, 3H), 2.74 (m, 1H), 2.87 (m, 4H), 3.13-3.29 (m, 5H), 3.58 (m, 3H), 3.64 (s, 3H), 3.78 (s, 3H), 3.85 (d, J=13.60 Hz, 1H), 4.02 (d, J=13.60 Hz, 1H), 4.13 (m, 1H), 4.45 (s, 2H), 4.67 (t, J=7.54 Hz, 1H), 5.30 (br d, J=9.19 Hz, 1H), 5.96 (m, 1H), 6.53 (br s, 1H), 6.68 (br d, J=8.82 Hz, 1H), 6.84 (m, 2H), 7.02 (s, 1H), 7.15 (m, 5H) 7.26 (m, 1H).

Example 165 $^1$H NMR (300 MHz, CDCl$_3$), δ ppm 0.80 (m, 9H), 0.96 (d, J=13.97 Hz, 9H), 1.62 (s, 3H), 2.60 (m, 1H), 2.83 (m, 4H), 3.10 (m, 2H), 3.34 (s, 1H), 3.60 (m, 4H), 3.98 (m, 4H), 4.49 (d, J=2.57 Hz, 3H), 4.71 (s, 1H), 5.29 (d, J=9.19 Hz, 1H), 6.28 (d, J=9.56 Hz, 1 H), 6.40 (s, 1H), 7.10 (m, 7H), 7.28 (m, 5H), 7.56 (t, J=7.72 Hz, 1H).

Example 166 $^1$H NMR (300 MHz, CDCl$_3$) δ ppm 0.90-0.82 (m, 6H), 0.99 (s, 9H), 1.07-0.96 (m, 1H), 1.45-1.39 (m, 1H), 2.00-1.86 (m, 1H), 2.54 (s, 3H), 2.69-2.61 (m, 2H), 2.90-2.87 (m, 3H), 3.23-3.08 (m, 3H), 3.66-3.54 (m, 1H), 3.63 (s, 3H), 3.79-3.76 (m, 1H), 3.95-3.92 (d, J=11.03, 1H), 4.16-4.03 (m, 1H), 4.28-4.07 (dd, J=48.9, 15.44 Hz, 2H), 4.49-4.47 (m, 2H), 4.82 (s, 1H), 5.40-5.37 (m, 1H), 6.53-6.49 (d, J=9.56, 1H), 7.18-7.02 (m, 6H), 7.23 (s, 1H), 7.44-7.40 (m, 1H), 7.54 (t, J=7.72, 1H), 8.20-8.15 (m, 2H), 8.70-8.68 (m, 1H), 9.14 (d, J=1.84 Hz, 1H).

Example 167 $^1$H NMR (300 MHz, DMSO-d$_6$) δ ppm 0.65 (s, 9H), 0.70-0.65 (m, 3H), 0.81-0.77 (m, 3H), 0.88-0.84 (m, 2H), 0.98-0.94 (m, 1H), 1.77 (m, 1H), 2.79-2.62 (m, 4H), 3.08-2.99 (m, 1H), 3.25-3.16 (m, 2H), 3.53 (s, 3H), 3.67-3.55 (m, 2H), 3.98-3.84 (m, 2H), 3.99-3.96 (d, J=10.67 Hz, 1H), 4.05 (m, 1H), 4.54-4.41 (dd, J=15.81, 21.7 Hz, 2H), 4.93-4.92 (d, J=3.31 Hz, 1H), 6.96-6.93 (d, J=9.56 Hz, 1H), 7.01-7.10 (m, 5H), 7.28-7.19 (m, 3H), 7.35-7.32 (m, 2H), 7.45-7.42 (d, J=9.56 Hz, 1H) 7.54-7.50 (dd, J=8.82, 4.78 Hz, 1H) 7.60 (s, 1H) 8.30-8.26 (ddd, J=8.27, 2.02, 1.84 Hz, 1H) 8.67-8.64 (dd, J=4.78, 1.47 Hz, 1H) 9.06 (s, 1H) 9.13-9.12 (d, J=1.47 Hz, 1H).

Example 168 $^1$H NMR (300 MHz, CD$_3$OD), δ ppm 0.83 (m, 6H), 0.89 (s, 9H), 0.97 (m, 1H), 1.01 (s, 9H), 1.30 (m, 1H), 1.42 (t, J=8.27 Hz, 2H), 1.86 (m, 1H), 2.44 (m, 1H), 2.65-2.84 (m, 6H), 3.04 (m, 3H), 3.65 (s, 3H), 3.72 (m, 1H), 3.83 (s, 1H), 3.93 (d, J=11.03 Hz, 1H), 4.14 (m, 1H), 4.73 (d, J=15.44 Hz, 1H), 4.86 (d, J=15.44 Hz, 1H), 6.74 (m, 1H), 6.83 (m, 3H), 6.94 (br t, J=7.35 Hz, 1H), 7.01 (m, 2H), 7.41 (br s, 1H), 7.56 (m, 1H), 8.36 (br d, J=7.35 Hz, 1H).

Example 169 $^1$H NMR (300 MHz, CD$_3$OD), δ ppm 0.89 (s, 9H), 0.95 (s, 9H), 1.01 (s, 9H), 1.43 (t, J=8.27 Hz, 2H), 2.05 (m, 1H), 2.66-2.81 (m, 6H), 2.96 (m, 2H), 3.20 (m, 1H), 3.65 (s, 3H), 3.73 (m, 1H), 3.84 (br s, 1H), 4.08 (br s, 1H), 4.11 (m, 1H), 4.64 (d, J=15.81 Hz, 1H), 4.95 (d, J=15.81 Hz, 1H), 6.69 (t, J=7.54 Hz, 2H), 6.76 (m, 1H), 6.86 (m, 2H), 6.98 (br d, J=7.35 Hz, 2H), 7.43 (br s, 1H), 7.58 (m, 1H), 7.83 (br d, J=9.93 Hz, 1H), 8.38 (br d, J=6.99 Hz, 1H).

Example 170 $^1$H NMR (300 MHz, CDCl$_3$), δ ppm 0.84 (s, 9H), 0.93 (s, 9H), 2.14 (m, 1H), 2.55 (dd, J=12.50, 2.21 Hz, 1H), 2.74 (m, 4H), 2.97 (m, 2H), 3.18 (m, 1H), 3.59 (br d, J=9.19 Hz, 2H), 3.63 (s, 3H), 3.80 (s, 3H), 3.84 (d, J=13.60 Hz, 1H), 3.94 (d, J=13.60 Hz, 1H), 4.12 (m, 1H), 4.62 (d, J=15.44 Hz, 1H), 4.69 (s, 1H), 4.99 (d, J=15.44 Hz, 1H), 5.28 (br d, J=9.56 Hz, 1H), 6.10 (br d, J=9.56 Hz, 1H), 6.32 (br s, 1H), 6.65 (m, 1H), 6.75 (m, 3H), 6.89 (m, 5H), 7.22 (d, J=8.82 Hz, 2H), 7.40 (br s, 1H), 7.45 (m, 1H), 8.35 (m, 1H).

Example 171 $^1$H NMR (300 MHz, CDCl$_3$) δ ppm 0.83 (s, 9H), 0.90-0.83 (m, 6H), 1.02 (s, 9H), 1.11-1.00 (m, 1H), 1.42-1.35 (m, 2H), 1.99-1.89 (m, 1H), 2.58-2.53 (m, 1H), 2.78-2.64 (m, 4H), 3.14-2.28 (m, 4H), 3.61 (s, 3H), 3.77-3.59 (m, 3H), 4.09-3.96 (m, 2H), 4.73 (bs, 1H), 4.82 (s, 2H), 5.37-5.34 (m, 1H), 6.64-6.61 (m, 1H), 6.71 (bs, 1H), 7.13-7.05 (m, 5H), 7.30-7.28 (d, J=4.41 Hz, 1H), 7.63-7.57 (t, J=6.99 Hz, 1H), 7.76-7.70 (t, J=6.99 Hz, 1H), 8.15-8.12 (d, J=8.45 Hz, 1H), 8.21-8.18 (d, J=8.45 Hz, 1H), 8.89-8.88 (d, J=4.42 Hz, 1H).

Example 172 $^1$H NMR (300 MHz, CDCl$_3$), δ ppm 0.67 (d, J=6.99 Hz, 3H), 0.93 (m, 11H), 1.39 (m, 2H), 1.61 (m, 1H), 1.90 (s, 1H), 2.54 (dd, J=12.32, 3.13 Hz, 1H), 2.81 (m, 8H), 3.10 (m, 1H), 3.22 (m, 2H), 3.77 (m, 11H), 4.08 (d, J=8.09 Hz, 1H), 4.44 (m, 2H), 4.70 (s, 1H), 5.08 (s, 1), 6.56 (m, 2H), 6.85 (m, 2H), 6.97 (s, 1H), 7.14 (m, 6H).

Example 173 $^1$H NMR (300 MHz, CDCl$_3$) δ ppm 0.64-0.62 (d, J=6.61 Hz, 3H), 0.89-0.75 (m, 12H), 1.10-0.93 (m, 1H), 1.99-1.89 (m, 1H), 2.61-2.56 (m, 2H), 2.89-2.76 (m, 4H), 3.10-2.98 (m, 3H), 3.70-3.57 (m, 2H), 3.62 (s, 3H), 4.01-3.83 (m, 3H), 4.16-4.06 (m, 2H), 4.89-4.74 (dd, J=15.44, 29.05 Hz, 2H), 4.76 (bs, 1H), 5.10-5.08 (m, 1H), 6.54-6.51 (d, J=9.2 Hz, 1H), 6.59 (bs, 1H), 7.12-7.04 (m, 5H) 7.31-7.28 (m, 6H), 7.63-7.58 (ddd, J=8.27, 6.99, 1.29 Hz, 1H), 7.75-7.70 (ddd, J=8.36, 6.89, 1.29 Hz, 1H), 8.15-8.12 (d, J=8.46, 1H) 8.22-8.19 (d, J=8.45, 1H) 8.88-8.87 (d, J=4.41 Hz, 1H).

Example 174 $^1$H NMR (300 MHz, CDCl$_3$) δ ppm 0.83 (s, 9H), 0.89-0.83 (m, 6H), 1.01 (s, 9H), 1.12-0.97 (m, 1H), 1.39-1.37 (d, J=6.62 Hz, 6H), 1.48-1.36 (m, 2H), 1.92 (m, 1H), 2.5&2.52 (m, 1H), 2.78-2.64 (m, 3H), 2.93-2.90 (d, J=7.35 Hz, 2H), 3.02-2.99 (m, 1H), 3.16-3.09 (m, 1H), 3.34-3.22 (m, 3H), 3.57 (s, 3H), 3.63-3.54 (m, 1H), 3.80-3.77 (d, J=9.56 Hz, 1H), 4.0-3.93 (m, 2H) 4.55-4.40, (dd, J=15.84, 29.42 Hz, 2H), 4.82 (bs, 1H), 5.37-5.33 (d, J=9.56 Hz, 1H), 6.70 (m, 1H), 6.88 (bs, 1H), 6.97 (s, 1H), 7.18-7.08 (m, 5H).

Example 175 $^1$H NMR (300 MHz, CD$_3$OD) δ ppm 0.89 (s, 9H), 0.99 (s, 9H), 1.01 (s, 9H), 1.24 (t, J=8.30 Hz, 2H), 2.42 (m, 1H), 2.54 (s, 3H), 2.75 (m, 6H), 3.04 (m, 1H), 3.16 (m, 1H), 3.66 (s, 3H), 3.74 (m, 1H), 3.84 (s, 1H), 4.13 (m, 2H), 4.45 (dd, J=15.8, 13.24 Hz, 2H), 7.14 (m, 7H), 7.72 (t, J=7.72 Hz, 1H).

Example 176 $^1$H NMR (300 MHz, CDCl$_3$) δ ppm 0.88-0.78 (m, 15H), 1.07-0.95 (m, 1H), 1.39-1.37 (d, J=6.99 Hz, 6H), 1.93-1.89 (m, 1H), 2.56-2.51 (m, 1H), 2.89-2.71 (m, 4H), 3.12-3.05 (m, 1H), 3.34-3.20 (m, 3H), 3.62 (s, 3H), 3.63-3.54 (m, 2H), 3.79 (s, 3H), 3.92-3.82 (m, 3H), 4.10-4.02 (m, 1H) 4.53-4.40 (dd, J=15.45, 23.54 Hz, 2H), 4.72 (bs, 1H), 5.30-5.20 (m, 1H), 6.52-6.49 (m, 2H), 6.86-6.81 (m, 2H), 6.97 (s, 1H), 7.23-7.05 (m, 7H).

Example 177 $^1$H NMR (300 MHz, CDCl$_3$) δ ppm 0.84-0.76 (m, 15H), 1.03-0.91 (m, 1H), 1.39-1.37 (d, J=6.99 Hz, 6H), 1.92-1.86 (m, 1H), 2.64-2.58 (m, 1H), 2.90-2.76 (m, 4H), 3.12-3.05 (m, 1H), 3.34-3.20 (m, 3H), 3.59 (s, 3H), 3.64-3.59 (m, 2H), 4.12-3.86 (m, 4H), 4.53-4.40 (dd, J=15.81, 25.74 Hz, 2H), 4.79 (bs, 1H), 5.29-5.26 (d, J=8.83 Hz, 1H), 6.56-6.53 (d, J=9.56 Hz, 1H), 6.66 (bs, 1H), 6.97 (s, 1H), 7.25-7.05 (m, 6H), 7.44-7.41 (d, J=8.45 Hz, 2H), 7.78-7.69 (m, 1H), 7.96-7.93 (d, J=8.45 Hz, 2H), 8.70-8.67 (m, 1H).

Example 178 $^1$H NMR (300 MHz, DMSO-d$_6$) δ ppm 0.68 (s, 9H), 0.77-0.64 (m, 6H), 0.96-0.84 (m, 2H) 1.80-1.70 (m, 1H), 2.44 (s, 3H), 2.81-2.60 (m, 5H), 3.03-2.93 (m, 3H), 3.50 (s, 3H), 3.69-3.63 (m, 2H), 4.12-3.92 (m, 4H), 4.29 (s, 2H), 4.95-4.94 (d, J=3.31 Hz, 1H), 6.98-6.95 (d, J=9.56 Hz, 1H), 7.13-7.05 (m, 5H), 7.24-7.21 (m, 1H), 7.35-7.31 (m, 1H), 7.46-7.44 (d, J=8.09 Hz, 3H), 7.56-7.52 (dd, J=7.91, 2.39 Hz, 1H), 7.93-7.83 (m, 2H), 8.00-7.97 (d, J=8.46 Hz, 2H), 8.36 (d, J=2.21 Hz, 1H), 8.65 (d, J=4.78 Hz, 1H), 9.13 (s, 1H).

Example 179 $^1$H NMR (300 MHz, CDCl$_3$) δ ppm 0.80 (d, J=6.62 Hz, 3H), 0.82 (s, 9H), 0.87 (d, J=7.35 Hz, 3H), 1.00 (m, 2H), 2.52 (d, J=3.31 Hz, 1H), 2.56 (d, J=2.94 Hz, 1H), 2.75 (m, 2H), 2.87 (d, J=8.09 Hz, 3H), 2.94 (d, J=12.87 Hz, 1H), 3.12 (d, J=4.78 Hz, 1H), 3.30 (m, 2H), 3.62 (s, 3H), 3.78 (s, 3H), 3.86 (d, J=7.35 Hz, 1H), 3.91 (m, 1H), 4.06 (m, 1H), 4.55 (s, 2H), 4.72 (s, 1H), 5.28 (d, J=8.82 Hz, 1H), 6.50 (d, J=9.93 Hz, 2H), 6.82 (d, J=2.94 Hz, 1 H), 6.85 (s, 1H), 7.09 (m, 1H), 7.15 (m, 2H), 7.18 (d, J=6.25 Hz, 2H), 7.22 (d, J=2.21 Hz, 3H), 7.34 (d, J=5.15 Hz, 1H), 7.37 (d, J=4.78 Hz, 1H), 8.21 (m, 2H), 8.64 (dd, J=4.78, 1.84 Hz, 2H), 9.15 (d, J=2.21 Hz, 1H).

Example 180 $^1$H NMR (300 MHz, CDCl$_3$) δ ppm 0.86 (m, 12H), 1.03 (m, 9H), 1.31 (m, 2H), 1.44 (m, 1H), 1.91 (d, J=6.99 Hz, 1H), 2.53 (dd, J=12.87, 4.04 Hz, 1H), 2.71 (m, 2H), 2.90 (d, J=7.35 Hz, 2H), 3.02 (d, J=9.19 Hz, 1H), 3.16 (m, 2H), 3.31 (m, 1H), 3.60 (m, 3H), 3.76 (d, J=9.56 Hz, 1H), 3.94 (d, J=11.03 Hz, 1H), 4.02 (d, J=7.72 Hz, 1H), 4.56 (s, 3H), 4.77 (s, 1H), 5.35 (d, J=9.19 Hz, 1H), 6.65 (d, J=8.09 Hz, 1H), 6.73 (s, 1H), 7.11 (m, 1H), 7.17 (m, 5H), 7.21 (s, 1H), 7.35 (d, J=4.78 Hz, 1H), 7.38 (d, J=4.78 Hz, 1H), 8.22 (m, 2H), 8.65 (dd, J=4.78, 1.84 Hz, 2H), 9.15 (d, J=1.47 Hz, 1H).

Example 181 $^1$H NMR (300 MHz, CDCl$_3$) δ ppm 0.84 (s, 12H), 0.88 (m, 3H), 1.02 (s, 9H), 1.94 (d, J=9.56 Hz, 1H), 2.56 (m, 2H), 2.66 (m, 2H), 2.74 (m, 2H), 2.91 (d, J=7.35 Hz, 2H), 3.17 (m, 1H), 3.31 (m, 2H), 3.59 (s, 3H), 3.77 (d, J=9.56 Hz, 1H), 3.95 (d, J=11.03 Hz, 1H), 4.01 (d, J=6.99 Hz, 1H), 4.56 (s, 3H), 5.33 (s, 1H), 6.66 (s, 1H), 6.79 (s, 1H), 7.11 (m, 2H), 7.16 (m, 5H), 7.21 (s, 1H), 7.35 (d, J=4.78 Hz, 1H), 7.38 (d, J=4.78 Hz, 1H), 8.22 (m, 2H), 8.65 (dd, J=4.96, 1.65 Hz, 1H), 9.15 (d, J=2.21 Hz, 1H).

Example 182 $^1$H NMR (300 MHz, CDCl$_3$), δ ppm 0.83 (s, 9H), 0.93 (s, 9H), 2.51 (m, 2H), 2.63 (s, 3H), 2.75 (m, 4H), 3.07 (m, 2H), 3.24 (m, 1H), 3.59 (m, 2H), 3.64 (s, 3H), 3.79 (s, 3H), 3.83 (d, J=13.97 Hz, 1H), 3.92 (d, J=13.97 Hz, 1H), 4.04 (m, 1H), 4.61 (d, J=15.08 Hz, 1H), 4.69 (d, J=15.08 Hz, 1H), 5.29 (br d, J=8.82 Hz, 1H), 6.21 (br d, J=9.56 Hz, 1H), 6.38 (br s, 1H), 6.54 (m, 1H), 6.66 (m, 1H), 6.85 (d, J=8.82 Hz, 2H), 7.00 (m, 5H), 7.21 (d, J=8.46 Hz, 2H), 7.60 (d, J=7.35 Hz, 1H), 7.67 (m, 1H).

Example 183 $^1$H NMR (300 MHz, CDCl$_3$), δ ppm 0.86 (s, 9H), 0.98 (s, 9H), 1.02 (s, 9H), 1.39 (dd, J=10.30, 5.88 Hz, 2H), 2.53 (m, 2H), 2.63 (s, 3H), 2.76 (m, 4H), 3.08 (dd, J=9.38, 6.43 Hz, 2H), 3.25 (m, 1H), 3.56 (br d, J=9.19 Hz, 1H), 3.64 (s, 3H), 3.73 (d, J=9.56 Hz, 1H), 4.03 (m, 1H), 4.56 (br s, 1H), 4.66 (m, 2H), 5.37 (br d, J=9.19 Hz, 1H), 6.30 (d, J=9.56 Hz, 1H), 6.55 (m, 2H), 6.66 (m, 1H), 7.01 (m, 5H), 7.60 (m, 1H), 7.67 (m, 1H).

Example 184 $^1$H NMR (300 MHz, CDCl$_3$), δ ppm 0.82 (s, 9H), 1.00 (s, 9H), 2.40 (m, 1H), 2.62 (dd, J=12.32, 2.39 Hz, 1H), 2.77-2.92 (m, 4H), 3.07 (m, 2H), 3.24 (m, 1H), 3.62 (m, 1H), 3.64 (s, 3H), 3.78 (s, 3H), 3.82 (d, J=14.71 Hz, 1H), 3.95 (d, J=14.71 Hz, 1H), 4.17 (s, 1H), 4.25 (br q, J=8.58 Hz, 1H), 4.63 (d, J=15.44 Hz, 1H), 4.91 (m, 2H), 5.30 (br d, J=18.82 Hz, 1H), 6.42 (br s, 1H), 6.83 (m, 3H), 7.03 (s, 5H), 7.18 (m, 3H), 7.40 (m, 1H), 7.51 (d, J=8.09 Hz, 1H), 7.83 (d, J=8.09 Hz, 1H), 10.86 (br s, 1H).

Example 185 $^1$H NMR (300 MHz, CDCl$_3$), δ ppm 0.83 (s, 9H), 1.02 (s, 18H), 1.37 (m, 2H), 2.46 (m, 1H), 2.61 (br dd, J=12.69, 3.13 Hz, 1H), 2.75 (m, 3H), 2.90 (d, J=8.09 Hz, 2H), 3.10 (m, 2H), 3.24 (m, 1H), 3.64 (m, 1H), 3.65 (s, 3H), 3.76 (d, J=9.19 Hz, 1H), 4.19 (s, 1H), 4.24 (m, 1H), 4.65 (d, J=15.44 Hz, 1H), 4.84 (br s, 1H), 4.89 (d, J=15.81 Hz, 1H), 5.38 (br d, J=8.82 Hz, 1H), 6.53 (br s, 1H), 6.90 (m, 1H), 7.05 (s, 5H), 7.16 (m, 1H), 7.39 (m, 1H), 7.49 (m, 1H), 7.81 (d, J=8.09 Hz, 1H), 10.92 (br s, 1H).

Example 186 $^1$H NMR (300 MHz, CDCl$_3$), δ ppm 0.81 (m, 15H), 1.00 (m, 1H), 1.27 (m, 7H), 1.41 (m, 1H), 1.57 (m, 2H), 1.80-2.00 (m, 1H), 2.60 (dd, J=12.32, 3.49 Hz, 1H), 3.05 (m, 7H), 3.62 (m, 4H), 3.98 (m, 4H), 4.48 (m, 2H), 4.79 (br s, 1H), 5.26 (d, J=8.46 Hz, 1H), 6.59 (m, 2H), 7.18 (m, 8H), 7.42 (d, J=8.09 Hz, 2H), 7.57 (t, J=7.72 Hz, 1H), 7.74 (m, 2H), 7.94 (d, J=8.46 Hz, 2H), 8.68 (d, J=4.78 Hz, 1H).

Example 187 $^1$H NMR (300 MHz, CDCl$_3$), δ ppm 0.83 (s, 9H), 0.95 (s, 9H), 2.40 (m, 1H), 2.54 (dd, J=12.50, 2.21 Hz, 1H), 2.69-2.80 (m, 4H), 2.92-3.00 (m, 2H), 3.23 (m, 1H), 3.55 (m, 1H), 3.59 (d, J=9.19 Hz, 2H), 3.64 (s, 3H), 3.80 (s, 3H), 3.83 (d, 1H), 3.92 (d, 1H), 4.05 (s, 3H), 4.06-4.12 (m, 1H), 4.66 (br s, 1H), 4.75 (s, 2H), 6.22 (br d, J=9.56 Hz, 1H), 6.34 (s, 1H), 6.85 (m, 2H), 6.99 (m, 5H), 7.14 (m, 1H), 7.22 (m, 2H), 7.37 (m, 2H), 7.88 (m, 1H).

Example 188 $^1$H NMR (300 MHz, CDCl$_3$) δ ppm 0.86 (s, 9H), 0.99 (s, 9H), 1.03 (s, 9H), 1.39 (dd, J=10.11, 6.07 Hz, 2H), 2.47-2.57 (m, 2H), 2.61-2.70 (m, 1H), 2.72-2.83 (m, 4H), 2.92-3.01 (m, 2H), 3.23 (m, 1H), 3.58 (m, 1H), 3.64 (s, 3H), 3.73 (d, J=9.56 Hz, 1H), 4.05 (s, 3H), 4.01-4.07 (m, 1H), 4.10 (s, 1H), 4.58 (br s, 1H), 4.72 (s, 1H), 4.79 (s, 1H), 5.37 (m, 1H), 6.30 (br d, 1H), 6.51 (br s, 1H), 7.01 (m, 5H), 7.14 (m, 1H), 7.37 (m, 2H), 7.88 (m, 1H).

Example 189 $^1$H NMR (300 MHz, CDCl$_3$), δ ppm 0.88 (s, 9H), 0.94 (s, 9H), 1.04 (s, 9H), 2.23 (m, 1H), 2.50-2.58 (m, 1H), 2.61 (s, 3H), 2.62-2.69 (m, 1H), 2.71-2.80 (m, 4H), 2.89-3.04 (m, 2H), 3.20 (m, 1H), 3.59 (m, 1H), 3.67 (s, 3H), 3.71 (d, J=9.19 Hz, 1H), 4.04 (s, 1H), 4.13 (m, 1H), 4.37 (d, J=14.71 Hz, 1H), 4.59 (br s, 1H), 4.70 (br d, J=14.71 Hz, 1H), 5.37 (m, 1H), 6.10 (br d, 1H), 6.44 (br s, 1H), 6.90 (m, 5H), 7.01 (m, 2H), 7.15 (t, 1H), 7.65 (d, J=8.09 Hz, 1H).

Example 190 $^1$H NMR (300 MHz, CDCl$_3$), δ ppm 0.76 (d, J=19.85 Hz, 9H), 0.96 (m, 9H), 1.35 (s, 9H), 1.60 (s, 3H), 2.61 (dd, J=12.13, 2.94 Hz, 2H), 2.84 (m, 4H), 3.11 (s, 1H), 3.30 (m, 2H), 4.03 (m, 5H), 4.48 (m, 2H), 4.73 (s, 1H), 5.29 (d, J=9.19 Hz, 1H), 6.31 (d, J=9.56 Hz, 1H), 6.48 (s, 1H), 7.14 (m, 8H), 7.43 (d, J=8.09 Hz, 2H), 7.57 (t, J=7.72 Hz, 1H), 7.74 (m, 2H), 7.95 (d, J=8.46 Hz, 2H), 8.69 (d, J=4.78 Hz, 1H).

Example 191 $^1$H NMR (300 MHz, CDCl$_3$) δ ppm 0.80 (m, 15H), 0.93 (m, 2H), 1.04 (s, 2H), 1.91 (s, 1H), 2.04 (s, 1H), 2.63 (d, #4.07 Hz, 1H), 2.78 (d, J=11.19 Hz, 1H), 2.89 (d, J=7.46 Hz, 2H), 3.08 (s, 1H), 3.21 (m, 2H), 3.35 (s, 1H), 3.48 (m, 3H), 3.60 (s, 3H), 3.63 (s, 2H), 3.88 (d, J=11.19 Hz, 1H), 3.98 (d, J=9.49 Hz, 1H), 4.04 (s, 1H), 4.48 (s, 2H), 4.70 (m, 2H), 5.27 (m, 1H), 6.58 (m, #7.12 Hz, 2H), 7.17 (m, 5H), 7.43 (d, J=8.48 Hz, 2H), 7.74 (m, 2H), 7.95 (d, J=8.48 Hz, 2H), 8.68 (d, J=4.75 Hz, 1H).

Example 193 $^1$H NMR (300 MHz, CDCl$_3$) δ ppm 0.84 (m, 4H), 1.44 (d, J=6.62 Hz, 3H), 1.53 (m, 6H), 1.90 (s, 1H), 2.48 (s, 8H), 3.11 (m, 4H), 3.48 (s, 3H), 3.52 (s, 3H), 3.68 (m, 1H), 3.92 (d, J=11.40 Hz, 2H), 4.12 (s, 2H), 4.25 (s, 1H), 4.47 (m, 1H), 4.70 (s, 2H), 7.15 (m, 6H), 7.60 (m, 2H), 7.67 (s, 1H), 7.91 (d, J=7.72 Hz, 3H), 8.24 (s, 1H), 8.87 (s, 1H).

Example 194 $^1$H NMR (300 MHz, CDCl$_3$) δ ppm 0.85 (t, J=7.17 Hz, 3H), 1.04 (d, J=4.41 Hz, 1H), 1.39 (d, J=6.62 Hz, 3H), 1.45 (t, #6.62 Hz, 6H), 1.95 (s, 1H), 2.46 (s, 7H), 2.90 (s, 2H), 2.90 (s, 1H), 3.12 (m, 2H), 3.22 (s, 2H), 3.45 (m, 3H), 3.71 (m, 2H), 3.92 (s, 1H), 4.06 (s, 2H), 4.48 (s, 1H), 4.68 (m, 2H), 5.65 (s, 1H), 6.91 (s, 1H), 7.15 (m, 7H), 7.41 (m, 2H), 7.80 (d, J=8.09 Hz, 1H), 7.92 (m, 3H), 8.81 (s, 1H).

Example 195 $^1$H NMR (300 MHz, CDCl$_3$) δ ppm 0.82 (m, 6H), 0.99 (s, 2H), 1.25 (s, 1H), 1.49 (s, 4H), 2.09 (s, 11H), 2.65 (s, 1H), 2.90 (d, J=7.35 Hz, 2H), 3.10 (s, 1H), 3.22 (t, J=9.01 Hz, 2H), 3.48 (m, 3H), 3.59 (s, 3H), 3.62 (s, 2H), 3.89 (m, 2H), 4.09 (m, 1H), 4.47 (d, J=4.04 Hz, 2H), 4.69 (d, J=6.25 Hz, 2H), 5.17 (s, 1H), 6.61 (s, 1H), 7.14 (m, 6H), 7.39 (d, J=12.50 Hz, 1H), 7.48 (d, J=8.09 Hz, 2H), 7.78 (d, J=7.72 Hz, 1H), 7.93 (m, 3H), 8.83 (d, J=5.15 Hz, 1H).

Example 196 $^1$H NMR (300 MHz, CDCl$_3$) δ ppm 0.75 (d, J=6.62 Hz, 3H), 0.81 (t, J=7.35 Hz, 3H), 1.00 (m, 1H), 1.38 (m, 1H), 1.90 (d, J=6.99 Hz, 1H), 2.42 (dd, J=12.50, 3.68 Hz, 1H), 2.71 (dd, J=12.32, 9.74 Hz, 1H), 2.90 (d, J=7.72 Hz, 4H), 3.01 (d, J=9.56 Hz, 1H), 3.12 (m, 1H), 3.23 (m, 2H), 3.48 (m, 3H), 3.57 (m, 3H), 3.71 (d, J=8.46 Hz, 2H), 3.86 (d, J=11.03 Hz, 1H), 3.99 (s, 1H), 4.17 (d, J=7.72 Hz, 1H), 4.46 (s, 3H), 4.69 (m, 2H), 5.12 (s, 1H), 6.64 (s, 1H), 6.75 (s, 1H), 7.11 (m, 10H), 7.22 (m, 2H), 7.30 (m, 2H), 7.73 (m, 2H), 7.90 (d, J=8.46 Hz, 2H), 8.67 (d, J=3.68 Hz, 1H).

Example 197 $^1$H NMR (300 MHz, CDCl$_3$) δ ppm 0.81 (m, 6H), 1.08 (d, #10.30 Hz, 6H), 1.32 (m, 5H), 1.59 (s, 3H), 1.91 (s, 1H), 2.58 (s, 1H), 2.82 (d, J=9.56 Hz, 1H), 2.92 (d, J=7.72 Hz, 2H), 3.01 (d, J=8.82 Hz, 1H), 3.13 (s, 1H), 3.22 (d, J=8.09 Hz, 2H), 3.47 (s, 3H), 3.56 (s, 3H), 3.60 (s, 2H), 3.90 (m, 3H), 4.02 (d, J=13.97 Hz, 2H), 4.46 (m, 2H), 4.69 (s, 2H), 4.89 (s, 1H), 6.71 (s, 1H), 6.96 (s, 1H), 7.12 (s, 1H), 7.14 (m, 6H), 7.41 (d, J=8.09 Hz, 2H), 7.73 (m, 2H), 7.96 (d, J=7.72 Hz, 2H), 8.68 (d, J=4.41 Hz, 1H).

Example 198 ¹H NMR (300 MHz, CDCl₃) δ ppm 0.79 (m, 12H), 1.56 (s, 1H), 2.12 (m, 1H), 2.61 (m, 1H), 2.68 (s, 3H), 2.80 (dd, J=12.50, 9.93 Hz, 1H), 2.88 (t, J=7.17 Hz, 2H), 3.13 (m, 1H), 3.23 (m, 2H), 3.59 (s, 3H), 3.65 (m, 2H), 3.78 (d, J=11.03 Hz, 1H), 3.93 (d, J=13.97 Hz, 1H), 3.98 (d, J=11.40 Hz, 2H), 4.07 (m, 2H), 4.45 (d, J=4.78 Hz, 2H), 4.76 (s, 1H), 5.25 (d, J=8.82 Hz, 1H), 6.55 (m, #9.93 Hz, 2H), 6.96 (s, 1H), 7.17 (m, 5H), 7.43 (d, J=8.09 Hz, 2H), 7.74 (m, 3H), 7.94 (d, J=8.46 Hz, 2H), 8.68 (d, J=4.78 Hz, 1H).

Example 200 ¹H NMR (300 MHz, CDCl₃) δ ppm 0.83 (m, 15H), 1.00 (m, 1H), 1.31 (s, 1H), 1.90 (s, 1H), 2.61 (dd, #12.32, 2.76 Hz, 1H), 2.84 (m, 5H), 3.03 (m, 3H), 3.61 (m, 3H), 3.92 (m, 1H), 3.99 (d, J=12.50 Hz, 2H), 4.09 (m, 1H), 4.81 (m, 3H), 5.26 (d, J=9.93 Hz, 1H), 6.51 (d, J=9.56 Hz, 2H), 7.08 (m, 8H), 7.24 (m, 2H), 7.43 (d, J=8.09 Hz, 2H), 7.60 (dd, J=7.72, 6.25 Hz, 1H), 7.74 (m, 3H), 7.95 (d, J=8.09 Hz, 2H), 8.14 (d, J=7.72 Hz, 1H), 8.20 (d, J=7.72 Hz, 1H), 8.68 (d, J=4.04 Hz, 1H), 8.88 (d, J=4.41 Hz, 1H).

Example 201 ¹H NMR (300 MHz, CDCl₃) δ ppm 0.81 (m, 6H), 1.27 (s, 3H), 1.92 (s, 2H), 2.08 (s, 1H), 2.58 (d, J=10.66 Hz, 1H), 2.89 (m, 3H), 3.01 (s, 1H), 3.06 (d, J=10.66 Hz, 2H), 3.68 (d, J=10.66 Hz, 2H), 3.76 (s, 2H), 3.84 (m, 1H), 3.91 (d, J=11.03 Hz, 1H), 3.99 (d, J=9.19 Hz, 1H), 4.13 (d, J=8.82 Hz, 1H), 4.26 (s, 1H), 4.76 (d, J=15.44 Hz, 1H), 4.87 (m, 1H), 5.21 (s, 1H), 5.53 (s, 1H), 6.42 (d, J=9.93 Hz, 1H), 7.10 (m, 5H), 7.23 (m, 1H), 7.28 (s, 1H), 7.41 (d, J=8.09 Hz, 2H), 7.59 (m, 1H), 7.74 (m, 3H), 7.97 (d, J=8.09 Hz, 2H), 8.13 (d, J=7.72 Hz, 1H), 8.20 (d, J=8.46 Hz, 1H), 8.69 (d, J=4.41 Hz, 1H), 8.87 (d, J=4.04 Hz, 1H).

Example 202 ¹H NMR (300 MHz, CDCl₃) δ ppm 0.83 (dd, J=11.95, 7.17 Hz, 6H), 0.89 (s, 9H), 1.35 (s, 1H), 1.96 (s, 1H), 2.69 (s, 1H), 2.89 (d, J=8.46 Hz, 5H), 3.06 (dd, J=6.62, 2.94 Hz, 5H), 3.23 (s, 1H), 3.42 (s, 1H), 3.57 (s, 2H), 3.75 (s, 1H), 3.95 (m, 2H), 4.14 (m, 1H), 4.43 (s, 1H), 4.81 (d, J=10.30 Hz, 1H), 4.88 (s, 1H), 6.56 (d, J=9.93 Hz, 1H), 6.99 (s, 1H), 7.10 (m, 5H), 7.22 (m, 2H), 7.44 (d, J=8.09 Hz, 2H), 7.60 (m, 1H), 7.72 (m, 3H), 7.93 (d, J=8.09 Hz, 2H), 8.14 (d, J=8.46 Hz, 1H), 8.19 (m, 1H), 8.68 (d, J=4.04 Hz, 1H), 8.88 (t, J=3.68 Hz, 1H).

Example 203 ¹H NMR (300 MHz, CDCl₃) δ ppm 0.86 (m, 6H), 0.98 (m, 2H), 1.26 (s, 2H), 1.38 (m, 2H), 1.99 (m, 6H), 2.00 (m, 3H), 2.67 (dd, J=12.13, 2.21 Hz, 1H), 2.91 (m, 2H), 3.08 (m, 1H), 3.69 (d, J=9.19 Hz, 1H), 3.96 (d, J=11.03 Hz, 1H), 4.05 (d, J=13.97 Hz, 1H), 4.12 (d, J=10.66 Hz, 1H), 4.18 (m, 2H), 4.75 (m, 1H), 4.89 (m, 1H), 6.52 (d, J=9.56 Hz, 1 H), 6.93 (m, 2H), 7.10 (m, 3H), 7.16 (m, 2H), 7.23 (m, 1H), 7.28 (d, J=4.41 Hz, 1H), 7.45 (s, 1H), 7.48 (d, J=8.09 Hz, 2H), 7.59 (m, 1H), 7.74 (m, 3H), 7.97 (m, 2H), 8.13 (d, J=7.72 Hz, 1H), 8.20 (d, J=7.72 Hz, 1H), 8.69 (d, J=4.78 Hz, 1H), 8.87 (d, J=4.41 Hz, 1H).

Example 204 ¹H NMR (300 MHz, CDCl₃) δ ppm 0.84 (m, 6H), 1.01 (m, 2H), 1.35 (m, 2H), 1.92 (s, 1H), 2.14 (s, 3H), 2.58 (dd, J=12.50, 2.21 Hz, 1H), 2.86 (m, 3H), 3.03 (m, 2H), 3.60 (s, 3H), 3.93 (d, J=11.03 Hz, 1H), 4.02 (d, J=14.34 Hz, 1H), 4.09 (s, 1H), 4.44 (m, 2H), 4.65 (s, 1H), 4.76 (d, J=15.44 Hz, 1H), 4.87 (m, 1H), 6.45 (d, J=9.93 Hz, 1H), 6.57 (d, J=8.09 Hz, 1H), 6.90 (t, J=6.99 Hz, 1H), 7.05 (m, 4H), 7.12 (m, 5H), 7.23 (dd, J=6.80, 2.02 Hz, 1H), 7.28 (s, 1H), 7.33 (d, J=8.09 Hz, 2H), 7.61 (m, 1H), 7.75 (m, 3H), 7.95 (m, 2H), 8.13 (d, J=8.46 Hz, 1H), 8.20 (d, J=7.72 Hz, 1H), 8.69 (d, J=4.78 Hz, 1H), 8.87 (d, J=4.41 Hz, 1H).

Example 205 ¹H NMR (300 MHz, CDCl₃) δ ppm 0.83 (d, J=6.62 Hz, 3H), 0.87 (m, 3H), 1.05 (s, 1H), 1.24 (m, 1H), 1.40 (s, 1H), 1.95 (s, 3H), 2.58 (d, J=12.87 Hz, 1H), 2.84 (s, 1H), 2.93 (m, 2H), 3.09 (m, 3H), 3.74 (d, J=10.66 Hz, 1H), 3.99 (m, 2H), 4.14 (m, 1H), 4.75 (d, J=15.44 Hz, 1H), 4.91 (d, J=15.08 Hz, 1H), 5.76 (s, 1H), 6.32 (d, J=6.99 Hz, 1H), 6.44 (d, J=1.84 Hz, 1H), 6.61 (d, J=9.19 Hz, 1H), 6.78 (d, J=7.72 Hz, 1H), 6.90 (t, J=7.72 Hz, 1H), 7.13 (m, 3H), 7.20 (m, 3H), 7.23 (d, J=1.84 Hz, 1H), 7.28 (d, J=4.41 Hz, 1H), 7.49 (d, J=8.09 Hz, 2H), 7.59 (m, 1H), 7.73 (m, 3H), 7.97 (d, J=8.09 Hz, 2H), 8.12 (d, J=8.46 Hz, 1H), 8.19 (d, J=8.46 Hz, 1H), 8.67 (d, J=4.78 Hz, 1H), 8.86 (d, J=4.41 Hz, 1H).

Example 206 ¹H NMR (300 MHz, CDCl₃) δ ppm 0.55 (t, J=6.43 Hz, 3H), 0.82 (m, 9H), 0.88 (m, 2H), 0.97 (m, 1H), 1.38 (m, 2H), 1.54 (s, 2H), 1.94 (s, 1H), 2.71 (s, 1H), 2.84 (m, 3H), 2.97 (m, 1H), 3.07 (m, 2H), 3.12 (m, 1H), 3.24 (m, 2H), 3.33 (s, 1H), 3.51 (d, J=11.40 Hz, 1 H), 3.64 (m, 1H), 3.95 (m, 2H), 4.15 (m, 1H), 4.42 (s, 1H), 4.82 (m, 3H), 6.55 (d, J=9.56 Hz, 1H), 7.09 (m, 5H), 7.22 (m, 2H), 7.46 (d, J=8.09 Hz, 2H), 7.61 (m, 1H), 7.74 (m, 3H), 7.93 (d, J=8.46 Hz, 2H), 8.14 (d, J=8.46 Hz, 1H), 8.20 (d, J=8.82 Hz, 1H), 8.67 (d, #4.78 Hz, 1H), 8.88 (d, J=4.04 Hz, 1H).

Example 207 ¹H NMR (300 MHz, CDCl₃) δ ppm 0.58 (d, J=6.25 Hz, 3H), 0.83 (d, J=13.97 Hz, 9H), 1.03 (s, 1H), 1.26 (s, 4H), 1.95 (s, 1H), 2.98 (d, J=50.37 Hz, 10H), 3.70 (s, 2H), 3.95 (s, 2H), 4.11 (s, 2H), 4.51 (s, 1H), 4.80 (d, J=42.65 Hz, 2H), 5.32 (m, 1H), 6.59 (d, J=9.56 Hz, 1H), 7.11 (d, J=2.21 Hz, 6H), 7.39 (d, J=7.72 Hz, 1H), 7.74 (d, J=38.24 Hz, 7H), 7.95 (s, 1H), 8.17 (m, 2H), 8.69 (s, 1H), 8.87 (s, 1H).

Example 208 ¹H NMR (300 MHz, CDCl₃) δ ppm 0.78 (m, 6H), 0.90 (d, #4.78 Hz, 2H), 1.38 (m, 2H), 1.90 (s, 1H), 2.61 (d, J=2.57 Hz, 2H), 2.87 (m, 1H), 3.02 (m, 2H), 3.68 (s, 1H), 3.89 (d, J=11.03 Hz, 1H), 4.00 (s, 2H), 4.12 (q, J=6.99 Hz, 2H), 4.53 (d, J=13.24 Hz, 1H), 4.77 (d, J=15.08 Hz, 1H), 4.85 (m, 1H), 5.08 (s, 2H), 5.62 (s, 1H), 6.40 (d, J=110 Hz, 1 H), 7.09 (m, 7H), 7.23 (m, 2H), 7.28 (d, J=4.41 Hz, 3H), 7.39 (d, J=8.09 Hz, 2H), 7.60 (m, 1H), 7.75 (m, 3H), 7.95 (d, J=8.09 Hz, 2H), 8.14 (m, 1H), 8.20 (d, J=7.72 Hz, 1H), 8.69 (d, J=4.78 Hz, 1H), 8.88 (d, J=4.04 Hz, 1H).

Example 209 ¹H NMR (300 MHz, CDCl₃) δ ppm 0.76 (t, J=6.43 Hz, 3H), 0.85 (m, 12H), 0.99 (m, 1H), 1.22 (t, J=6.99 Hz, 2H), 1.29 (m, 2H), 1.89 (s, 1H), 2.63 (d, J=3.31 Hz, 1H), 2.84 (m, 4H), 3.02 (m, 3H), 3.02 (m, 2H), 3.61 (d, J=9.56 Hz, 2H), 3.95 (m, 2H), 4.09 (m, 2H), 4.81 (m, 2H), 5.22 (d, J=8.09 Hz, 1H), 6.50 (d, J=9.56 Hz, 2H), 7.08 (m, 5H), 7.22 (m, 2H), 7.43 (d, J=8.09 Hz, 2H), 7.60 (t, #6.99 Hz, 1H), 7.73 (m, 3H), 7.95 (d, J=8.46 Hz, 2H), 8.14 (d, J=7.72 Hz, 1H), 8.20 (d, J=8.09 Hz, 1H), 8.68 (d, J=4.41 Hz, 1H), 8.88 (d, J=4.41 Hz, 1H).

Example 210 ¹H NMR (300 MHz, CDCl₃) δ ppm 0.81 (m, 15H), 0.98 (m, 1H), 1.33 (m, 1H), 1.93 (s, 3H), 2.64 (dd, J=12.50, 2.94 Hz, 1H), 2.84 (m, 5H), 3.04 (m, 3H), 3.58 (s, 1H), 3.96 (m, 4H), 4.09 (m, 1H), 4.81 (m, 2H), 6.04 (d, J=9.19 Hz, 1H), 6.55 (d, J=9.19 Hz, 2H), 6.83 (s, 1H), 7.09 (m, 5H), 7.22 (m, 1H), 7.43 (d, J=8.09 Hz, 2H), 7.60 (m, 1H), 7.73 (m, 4H), 7.94 (d, J=8.46 Hz, 2H), 8.14 (d, J=7.35 Hz, 1H), 8.19 (d, J=7.72 Hz, 1H), 8.68 (d, J=4.78 Hz, 1H), 8.87 (d, J=4.41 Hz, 1H).

Example 212 ¹H NMR (300 MHz, MeOH-d) δ ppm 0.65 (d, J=6.62 Hz, 3H), 0.70 (d, J=6.62 Hz, 3H), 0.76 (t, J=7.35 Hz, 3H), 0.82 (t, J=7.35 Hz, 3H), 0.96 (m, 2H), 1.32 (m, 2H), 1.59 (m, 1H), 1.84 (m, J=14.71, 14.71 Hz, 1H), 2.76 (m, 8H), 3.08 (m, 4H), 3.62 (s, 3H), 3.73 (d, J=7.72 Hz, 1H), 3.83 (d, J=8.09 Hz, 1H), 3.95 (s, 2H), 4.20 (m, 1H), 4.88 (s, 2H), 5.97 (s, 2H), 6.86 (m, 1H), 6.95 (d, J=7.35 Hz, 1H), 7.06 (m, 4H), 7.43 (m, 5H), 7.47 (d, J=4.41 Hz, 2H), 7.67 (t, J=7.72 Hz, 1H), 7.80 (m, 1H), 8.08 (d, J=7.72 Hz, 1H), 8.32 (d, J=7.72 Hz, 1H), 8.83 (d, J=4.41 Hz, 1H).

Example 213 ¹H NMR (300 MHz, MeOH-d₄) δ ppm 0.60 (m, 3H), 0.77 (m, 6H), 0.87 (m, 3H), 1.03 (m, 2H), 1.33 (m, 2H), 1.54 (d, J=17.65 Hz, 1H), 1.89 (s, 3H), 2.23 (s, 3H), 2.39 (s, 3H), 2.81 (m, 8H), 3.19 (m, 3H), 3.63 (m, 3H), 3.70 (d, J=8.09 Hz, 1H), 3.85 (s, 1H), 3.95 (m, 3H), 4.25 (s, 1H), 5.05

(m, 2H), 7.05 (m, 3H), 7.15 (m, 2H), 7.26 (d, J=8.09 Hz, 2H), 7.52 (d, J=8.09 Hz, 2H), 7.78 (d, J=5.15 Hz, 1H), 7.89 (m, 2H), 8.05 (m, 1H), 8.19 (d, J=8.46 Hz, 1H), 8.52 (d, J=8.46 Hz, 1H), 9.05 (d, J=5.15 Hz, 1H).

Example 214 $^1$H NMR (300 MHz, MeOH-d$_4$) δ ppm 0.63 (d, J=6.99 Hz, 3H), 0.73 (m, 6H), 0.82 (m, 3H), 0.98 (s, 2H), 1.29 (s, 2H), 1.56 (s, 1H), 1.85 (s, 1H), 2.62 (s, 1H), 2.76 (m, 3H), 2.84 (m, 2H), 3.07 (m, 2H), 3.31 (m, 2H), 3.60 (s, 3H), 3.71 (d, J=8.09 Hz, 1H), 3.84 (s, 1H), 3.93 (d, J=11.03 Hz, 1H), 4.00 (s, 2H), 4.23 (s, 1H), 4.89 (s, 3H), 6.97 (m, 2H), 7.09 (d, J=6.62 Hz, 2H), 7.48 (d, J=4.41 Hz, 1H), 7.57 (d, J=8.46 Hz, 2H), 7.68 (m, 5H), 7.81 (m, 2H), 8.08 (d, J=8.46 Hz, 1H), 8.32 (d, J=7.72 Hz, 1H), 8.57 (d, J=6.25 Hz, 2H), 8.84 (d, J=4.41 Hz, 1H).

Example 215 $^1$H NMR (300 MHz, CDCl$_3$) δ ppm 0.85 (m, 3H), 0.91 (m, J=5.52 Hz, 12H), 1.02 (m, 1H), 1.42 (m, 1H), 1.98 (m, 1H), 2.54 (s, 3H), 2.78 (m, 2H), 2.92 (d, J=17.72 Hz, 2H), 3.06 (q, J=8.33 Hz, 1H), 3.21 (m, 3H), 3.63 (s, 3H), 3.67 (s, 2H), 3.78 (d, J=8.82 Hz, 1 H), 4.00 (d, J=11.40 Hz, 1H), 4.11 (m, 1H), 4.49 (m, 2H), 4.80 (s, 2H), 5.41 (d, J=9.56 Hz, 1H), 7.04 (m, 2H), 7.15 (m, 5H), 7.54 (t, J=7.72 Hz, 1H).

Example 217 $^1$H NMR (300 MHz, CDCl$_3$) δ ppm 0.78 (d, J=6.44 Hz, 3H), 0.82 (s, 9H), 0.86 (t, J=7.12 Hz, 3H), 1.01 (s, 1H), 1.03 (m, 4H), 1.43 (s, 1H), 1.93 (s, 1H), 2.31 (s, 3H), 2.53 (d, J=12.54 Hz, 1H), 2.74 (s, 1H), 2.87 (d, J=7.46 Hz, 2H), 2.94 (s, 1H), 3.14 (s, 1H), 3.24 (s, 1H), 3.62 (m, 4H), 3.62 (s, 3H), 3.86 (m, 2H), 4.11 (m, 2H), 4.71 (s, 1H), 5.26 (d, J=9.15 Hz, 1H), 6.44 (s, 1H), 7.12 (m, 12H).

Example 218 $^1$H NMR (300 MHz, CDCl$_3$) δ ppm 0.85 (m, 3H), 0.89 (m, 3H), 0.95 (s, 1H), 1.00 (s, 9H), 1.06 (m, 2H), 1.13 (s, 3H), 1.26 (s, 1H), 1.70 (s, 4H), 1.89 (s, 1H), 1.93 (s, 1H), 2.49 (dd, J=6.99, 3.68 Hz, 2H), 2.54 (s, 3H), 2.63 (m, 1H), 2.90 (d, J=7.72 Hz, 3H), 3.15 (m, 4H), 3.55 (d, J=9.19 Hz, 1H), 3.63 (s, 3H), 3.70 (d, J=9.19 Hz, 1H), 3.93 (d, J=11.03 Hz, 1H), 4.06 (s, 1H), 4.47 (m, 2H), 4.65 (s, 1H), 5.35 (m, 1H), 6.41 (s, 1H), 6.50 (d, J=9.19 Hz, 1H), 7.05 (dd, J=11.58, 7.54 Hz, 2H), 7.12 (m, 1H), 7.17 (m, 4H), 7.53 (t, J=7.72 Hz, 1H).

Example 219 $^1$H NMR (300 MHz, CDCl$_3$) δ ppm 0.87 (m, 9H), 0.93 (d, #6.62 Hz, 3H), 0.99 (s, 9H), 1.07 (m, 1H), 1.42 (m, 1H), 1.68 (d, J=7.35 Hz, 1H), 1.97 (s, 1H), 2.45 (m, 2H), 2.56 (m, 4H), 2.63 (m, 1H), 2.90 (d, J=7.35 Hz, 2H), 3.15 (m, 3H), 3.56 (d, J=8.82 Hz, 1H), 3.63 (s, 3H), 3.70 (d, J=9.93 Hz, 1H), 3.93 (d, J=11.03 Hz, 1H), 4.09 (d, J=8.82 Hz, 1H), 4.47 (m, 2H), 4.66 (s, 1H), 5.32 (d, J=13.97 Hz, 1H), 6.44 (s, 1H), 6.51 (d, J=9.56 Hz, 1H), 7.05 (dd, J=11.77, 7.72 Hz, 2H), 7.14 (m, 5H), 7.53 (t, J=7.72 Hz, 1H).

Example 220 $^1$H NMR (300 MHz, CDCl$_3$) δ ppm 0.86 (m, 3H), 0.92 (d, 110.30 Hz, 3H), 1.01 (d, J=5.88 Hz, 9H), 1.07 (m, 1H), 1.50 (s, 1H), 1.92 (s, 1H), 2.49 (s, 3H), 2.72 (m, 5H), 2.96 (t, J=7.91 Hz, 4H), 3.23 (m, 4H), 3.55 (s, 3H), 3.66 (m, 1H), 3.80 (d, J=8.46 Hz, 1H), 3.93 (s, 1H), 3.98 (d, J=11.40 Hz, 1H), 4.47 (m, 2H), 5.30 (m, 1H), 6.85 (s, 1H), 6.99 (d, J=7.72 Hz, 1H), 7.07 (m, 3H), 7.17 (m, 8H), 7.52 (m, 1H).

Example 221 $^1$H NMR (300 MHz, CDCl$_3$) δ ppm 0.87 (m, 6H), 0.92 (s, 9H), 1.44 (m, 1H), 1.94 (s, 1H), 2.54 (s, 3H), 2.60 (dd, J=12.32, 3.49 Hz, 1H), 2.73 (m, 1H), 2.90 (d, J=7.72 Hz, 2H), 2.96 (d, J=8.82 Hz, 1H), 3.16 (m, 3H), 3.55 (d, J=8.09 Hz, 1H), 3.62 (s, 3H), 3.66 (d, J=9.19 Hz, 1H), 3.94 (d, J=11.03 Hz, 1H), 4.07 (m, 1H), 4.16 (m, 2H), 4.46 (s, 2H), 4.65 (s, 1H), 5.28 (d, J=8.46 Hz, 1H), 6.57 (d, J=8.82 Hz, 1H), 6.72 (s, 1H), 6.90 (m, 1H), 6.96 (m, 1H), 7.05 (dd, J=11.95, 7.54 Hz, 2H), 7.14 (m, 5H), 7.23 (d, J=1.47 Hz, 1H), 7.54 (t, J=7.72 Hz, 1H).

Example 222 $^1$H NMR (300 MHz, CDCl$_3$) δ ppm 0.65 (d, J=6.62 Hz, 3H), 0.73 (m, 6H), 0.81 (t, J=7.35 Hz, 3H), 0.98 (m, 1H), 1.38 (m, 1H), 1.87 (s, 1H), 2.54 (s, 3H), 2.61 (m, 1H), 2.82 (m, 1H), 2.90 (m, 6H), 3.08 (m, 1H), 3.18 (m, 3H), 3.56 (s, 2H), 3.60 (d, J=9.93 Hz, 1H), 3.85 (d, J=11.03 Hz, 1H), 4.06 (d, J=5.52 Hz, 2H), 4.47 (s, 1H), 5.24 (d, J=6.99 Hz, 1H), 6.55 (d, J=8.09 Hz, 1H), 6.62 (s, 1H), 7.06 (dd, J=10.30, 7.72 Hz, 1H), 7.13 (m, 1H), 7.15 (m, 5H), 7.46 (m, 2H), 7.68 (s, 1H), 7.75 (s, 1H), 7.79 (m, 2H).

Example 223 $^1$H NMR (300 MHz, CDCl$_3$) δ ppm 0.77 (s, 9H), 0.81 (d, J=6.62 Hz, 3H), 0.87 (t, J=7.35 Hz, 3H), 1.22 (m, 6H), 1.39 (m, 2H), 1.94 (s, 1H), 2.56 (m, 3H), 2.78 (dd, J=12.50, 10.30 Hz, 1H), 2.88 (m, 4H), 3.16 (m, 3H), 3.58 (s, 2H), 3.62 (m, 3H), 3.81 (d, J=13.60 Hz, 1H), 3.93 (m, 2H), 4.07 (m, 1H), 4.48 (s, 2H), 4.75 (s, 1H), 5.25 (m, 1H), 6.42 (s, 1H), 6.52 (d, J=9.56 Hz, 1H), 7.14 (m, 11H), 7.55 (s, 1H).

Example 224 $^1$H NMR (300 MHz, CDCl$_3$) δ ppm 0.80 (m, 12H), 0.87 (t, #7.35 Hz, 3H), 1.07 (m, 1H), 1.32 (dd, #5.88, 1.84 Hz, 6H), 1.43 (m, 1H), 1.92 (s, 1H), 2.54 (s, 3H), 2.56 (d, J=3.31 Hz, 1H), 2.76 (dd, J=12.13, 10.30 Hz, 1H), 2.89 (d, J=7.72 Hz, 5H), 3.15 (m, 2H), 3.60 (s, 2H), 3.62 (s, 3H), 3.84 (m, 2H), 3.91 (d, J=11.03 Hz, 1H), 4.07 (t, J=6.62 Hz, 1H), 4.48 (m, 3H), 4.73 (s, 1H), 5.28 (d, J=13.24 Hz, 1H), 6.46 (s, 1H), 6.53 (d, J=9.19 Hz, 1H), 6.81 (d, J=8.82 Hz, 2H), 7.06 (m, 2H), 7.19 (m, 5H), 7.54 (t, J=7.72 Hz, 1H).

Example 225 $^1$H NMR (300 MHz, CDCl$_3$) δ ppm 0.79 (d, J=6.62 Hz, 3H), 0.82 (s, 9H), 0.87 (t, J=7.35 Hz, 3H), 1.06 (m, 1H), 1.44 (m, 1H), 1.95 (s, 1H), 2.22 (s, 6H), 2.50 (d, J=2.94 Hz, 1H), 2.54 (s, 3H), 2.75 (m, 1H), 2.90 (t, J=8.09 Hz, 3H), 3.16 (m, 2H), 3.54 (d, J=10.30 Hz, 1H), 3.61 (d, J=4.78 Hz, 3H), 3.85 (d, J=5.52 Hz, 2H), 3.91 (m, 1H), 4.05 (d, J=7.72 Hz, 1H), 4.47 (s, 2H), 4.72 (s, 1H), 5.30 (s, 1H), 6.52 (m, J=9.19 Hz, 2H), 7.05 (m, 7H), 7.18 (m, 4H), 7.54 (t, J=7.72 Hz, 1H).

Example 226 $^1$H NMR (300 MHz, CDCl$_3$) δ ppm 0.80 (m, 12H), 0.87 (t, #7.17 Hz, 3H), 1.04 (m, 1H), 1.26 (s, 1H), 1.41 (m, 1H), 1.95 (m, 1H), 2.54 (s, 3H), 2.58 (dd, J=12.87, 2.94 Hz, 1H), 2.78 (m, 1H), 2.90 (d, J=7.72 Hz, 3H), 3.16 (m, 2H), 3.59 (s, 1H), 3.61 (s, 3H), 3.79 (s, 3H), 3.83 (d, J=13.97 Hz, 1H), 3.91 (d, J=7.72 Hz, 1H), 3.95 (m, 1H), 4.09 (m, 1H), 4.47 (m, 2H), 4.78 (d, J=1.47 Hz, 1H), 5.28 (m, 1H), 6.50 (s, 1H), 6.55 (d, J=9.56 Hz, 1H), 6.79 (dd, J=8.09, 2.57 Hz, 1H), 6.84 (d, J=7.72 Hz, 1H), 6.92 (d, J=552 Hz, 1H), 7.05 (dd, J=12.50, 7.72 Hz, 2H), 7.15 (m, 6H), 7.54 (t, J=7.72 Hz, 1H).

Example 227 $^1$H NMR (300 MHz, CDCl$_3$) δ ppm 0.83 (dd, J=13.42, 6.80 Hz, 9H), 0.88 (m, 3H), 1.00 (s, 9H), 1.05 (m, 1H), 1.31 (m, 5H), 1.42 (s, 1H), 1.53 (m, 1H), 1.93 (s, 1H), 2.51 (s, 2H), 2.54 (s, 3H), 2.62 (m, 1H), 2.90 (d, J=7.72 Hz, 2H), 3.17 (m, 3H), 3.55 (d, J=8.09 Hz, 1H), 3.64 (s, 3H), 3.71 (d, J=9.56 Hz, 1H), 3.92 (d, J=11.40 Hz, 1H), 4.07 (s, 1H), 4.47 (m, 2H), 4.63 (s, 1H), 5.32 (d, J=9.56 Hz, 1H), 6.40 (s, 1H), 6.50 (d, J=9.19 Hz, 1H), 7.05 (dd, J=12.32, 7.54 Hz, 2H), 7.14 (m, 5H), 7.54 (t, J=7.72 Hz, 1H).

Example 228 $^1$H NMR (300 MHz, CDCl$_3$) δ ppm 0.80 (m, 12H), 0.87 (t, #7.35 Hz, 3H), 0.87 (t, J=7.35 Hz, 3H), 1.02 (m, 1H), 1.21 (t, J=7.72 Hz, 3H), 1.42 (m, 1H), 1.91 (m, J=6.25 Hz, 1H), 2.54 (s, 3H), 2.90 (m, 3H), 3.14 (m, 3H), 3.56 (d, J=12.87 Hz, 2H), 3.61 (s, 3H), 3.83 (m, 1H), 3.90 (d, J=5.15 Hz, 1H), 3.94 (m, 1H), 4.07 (m, J=8.09 Hz, 1H), 4.47 (m, 2H), 4.73 (s, 1H), 5.26 (d, J=8.46 Hz, 1H), 6.46 (s, 1H), 6.52 (d, J=9.56 Hz, 1H), 7.06 (m, 2H), 7.15 (m, 9H), 7.54 (t, J=7.72 Hz, 1H).s Example 229 $^1$H NMR (300 MHz, CDCl$_3$) δ ppm 0.80 (m, 12H), 0.87 (t, #7.35 Hz, 3H), 1.03 (m, 1H), 1.42 (m, 1H), 1.95 (s, 1H), 2.31 (s, 3H), 2.54 (s, 3H), 2.57 (d, J=3.31 Hz, 1 H), 2.77 (m, 1H), 2.89 (d, J=7.72 Hz, 3H), 3.16 (m, 2H), 3.61 (d, J=9.19 Hz, 2H), 3.60 (d, J=4.41 Hz, 3H), 3.88 (m, 3H), 4.05 (m, 1H), 4.47 (m, 2H), 4.75 (s, 1H), 5.27 (d, J=9.19 Hz, 1 H), 6.50 (s, 1H), 6.54 (d, J=9.19 Hz, 1H), 7.08 (m, 6H), 7.18 (m, 5H), 7.54 (t, J=7.72 Hz, 1 H).

Example 230 ¹H NMR (300 MHz, CDCl₃) δ ppm 0.75 (m, 12H), 0.86 (t, #7.35 Hz, 3H), 1.05 (m, 1H), 1.40 (m, 2H), 1.93 (d, J=6.25 Hz, 1H), 2.54 (s, 3H), 2.62 (dd, J=12.69, 3.86 Hz, 1H), 2.79 (m, 1H), 2.92 (m, 2H), 3.16 (m, 2H), 3.59 (s, 3H), 3.92 (t, J=10.66 Hz, 3H), 4.06 (m, 1H), 4.48 (s, 2H), 4.80 (s, 1H), 5.22 (d, J=9.19 Hz, 1H), 6.63 (d, J=8.82 Hz, 1H), 6.71 (s, 1H), 7.06 (t, J=8.27 Hz, 2H), 7.06 (t, J=8.27 Hz, 2H), 7.16 (m, 5H), 7.49 (t, J=9.01 Hz, 2H), 7.55 (m, 3H).

Example 231 ¹H NMR (300 MHz, CDCl₃) δ ppm 0.77 (d, J=6.25 Hz, 3H), 0.87 (m, 12H), 1.02 (m, 2H), 1.39 (d, J=24.27 Hz, 1H), 1.91 (s, 1H), 2.47 (s, 1H), 2.56 (s, 3H), 2.74 (dd, J=12.50, 9.93 Hz, 1H), 2.90 (d, J=7.72 Hz, 2H), 2.97 (s, 1H), 3.18 (m, 3H), 3.59 (s, 3H), 3.66 (d, J=9.19 Hz, 1H), 3.85 (m, 3H), 3.89 (s, 1H), 4.01 (m, 1H), 4.48 (m, 2H), 4.87 (s, 1H), 5.31 (d, J=9.93 Hz, 1H), 6.68 (m, 2H), 6.80 (d, J=8.82 Hz, 2H), 7.07 (t, J=6.80 Hz, 2H), 7.15 (m, 7H), 7.57 (t, J=7.72 Hz, 1H).

Example 232 ¹H NMR (300 MHz, CDCl₃) δ ppm 0.79 (m, 12H), 0.87 (t, #7.35 Hz, 3H), 1.05 (dd, J=8.09, 5.88 Hz, 1H), 1.26 (m, 1H), 1.42 (m, 1H), 1.93 (s, 1H), 2.55 (s, 3H), 2.60 (m, J=3.31 Hz, 1H), 2.77 (m, 1H), 2.90 (d, J=7.72 Hz, 2H), 2.95 (s, 1H), 3.16 (m, 2H), 3.57 (s, 1H), 3.62 (s, 2H), 3.60 (s, 3H), 3.89 (m, 2H), 4.07 (m, J=7.72 Hz, 1H), 4.48 (s, 2H), 5.24 (d, J=8.82 Hz, 1H), 6.57 (d, J=4.41 Hz, 2H), 6.97 (m, 2H), 7.11 (m, 1H), 7.17 (m, 4H), 7.30 (m, 4H), 7.55 (m, 1H).

Example 233 ¹H NMR (300 MHz, CDCl₃) δ ppm 0.77 (m, 12H), 0.85 (t, #7.35 Hz, 3H), 1.00 (m, 1H), 1.37 (m, 1H), 1.93 (m, 1H), 2.34 (s, 3H), 2.60 (dd, J=12.69, 3.13 Hz, 1H), 2.75 (d, J=10.66 Hz, 1H), 2.82 (s, 3H), 2.87 (t, J=7.17 Hz, 2H), 3.07 (s, 1H), 3.23 (m, 3H), 3.59 (d, J=9.19 Hz, 2H), 3.63 (s, 3H), 3.84 (m, 2H), 3.94 (m, 1H), 4.11 (m, J=8.09 Hz, 1H), 4.77 (s, 3H), 5.28 (d, J=8.82 Hz, 1H), 6.60 (d, J=9.19 Hz, 1H), 6.86 (m, 2H), 6.90 (s, 2H), 7.02 (d, J=7.35 Hz, 1H), 7.13 (s, 1H), 7.17 (s, 6H), 7.21 (d, J=8.09 Hz, 1H), 7.46 (d, J=7.72 Hz, 1H), 7.67 (d, J=7.72 Hz, 1H), 8.15 (t, J=7.91 Hz, 1H).

Example 234 ¹H NMR (300 MHz, CDCl₃) δ ppm 0.76 (d, J=6.62 Hz, 3H), 0.79 (s, 9H), 0.85 (t, J=7.17 Hz, 3H), 1.00 (m, 1H), 1.36 (m, 1H), 1.91 (m, 1H), 2.61 (dd, J=12.50, 2.94 Hz, 1 H), 2.75 (d, J=10.66 Hz, 1H), 2.82 (s, 3H), 2.88 (d, J=6.99 Hz, 2H), 3.04 (d, J=8.46 Hz, 1H), 3.23 (m, 4H), 3.58 (s, 1H), 3.62 (s, 3H), 3.82 (m, 2H), 3.95 (m, 1H), 4.12 (m, J=7.72 Hz, 1H), 4.76 (s, 2H), 5.28 (d, J=10.30 Hz, 1H), 6.57 (d, J=9.19 Hz, 1H), 6.87 (m, 1H), 6.92 (m, 2H), 6.96 (s, 1H), 7.07 (t, J=7.72 Hz, 1H), 7.14 (m, 1H), 7.29 (m, 1H), 7.46 (d, J=7.72 Hz, 1 H), 7.66 (d, J=7.72 Hz, 1H), 8.15 (t, #7.91 Hz, 1H).

Example 235 ¹H NMR (300 MHz, MeOH-d₄) δ ppm 0.52 (d, J=6.62 Hz, 3H), 0.72 (s, 9H), 0.77 (t, J=7.54 Hz, 3H), 0.87 (s, 1H), 0.93 (m, 1H), 0.98 (d, J=9.19 Hz, 1H), 1.30 (m, 1H), 1.32 (m, 1H), 1.79 (s, 1H), 2.52 (s, 3H), 2.71 (m, 1H), 2.85 (m, 3H), 3.11 (m, 2H), 3.20 (t, J=9.01 Hz, 1H), 3.23 (s, 1H), 3.55 (s, 3H), 3.70 (s, 1H), 3.82 (m, J=11.03 Hz, 2H), 4.22 (s, 1H), 4.30 (m, 2H), 4.33 (d, J=15.81 Hz, 1H), 4.52 (m, 1H), 7.11 (m, 4H), 7.18 (m, 2H), 7.58 (t, J=6.99 Hz, 1H), 7.69 (m, 2H), 7.75 (m, 1H), 7.90 (s, 1H), 7.93 (d, J=8.46 Hz, 1H), 7.98 (d, J=8.09 Hz, 1H), 8.30 (d, J=8.46 Hz, 1H).

Example 236 ¹H NMR (300 MHz, MeOH-d₄) δ ppm 0.79 (d, J=6.25 Hz, 3H), 0.87 (m, 12H), 1.01 (m, 1H), 1.38 (m, 1H), 1.87 (m, 1H), 2.53 (s, 3H), 2.70 (m, 3H), 2.77 (d, J=8.46 Hz, 3H), 2.85 (m, 3H), 3.10 (m, 2H), 3.11 (m, 2H), 3.20 (m, 2H), 3.22 (m, 1H), 3.65 (s, 3H), 3.76 (s, 2H), 3.90 (d, J=11.03 Hz, 2H), 4.04 (s, 2H), 4.15 (m, 1H), 4.35 (d, J=15.81 Hz, 1H), 4.53 (m, 1H), 6.59 (d, J=3.68 Hz, 1H), 6.75 (d, J=3.31 Hz, 1H), 7.14 (m, 7H), 7.70 (t, J=7.72 Hz, 1H).

Example 237 ¹H NMR (300 MHz, MeOH-d₄) δ ppm 0.86 (d, J=6.62 Hz, 3H), 0.91 (t, J=7.72 Hz, 3H), 0.97 (d, J=2.94 Hz, 3H), 1.01 (s, 9H), 1.06 (m, 1H), 1.36 (m, 4H), 1.42 (m, 1H), 1.49 (m, 2H), 1.91 (m, J=14.52 Hz, 1H), 2.18 (t, J=6.99 Hz, 2H), 2.53 (s, 3H), 2.66 (dd, J=12.50, 9.56 Hz, 1H), 2.76 (m, 1H), 2.86 (m, 4H), 3.11 (m, 2H), 3.18 (m, 1H), 3.24 (m, 1H), 3.55 (m, 2H), 3.64 (m, 3H), 3.66 (s, 3H), 3.74 (d, J=9.19 Hz, 1H), 3.90 (s, 1H), 3.94 (d, J=11.03 Hz, 1H), 4.17 (m, 1H), 4.35 (d, J=15.81 Hz, 1H), 4.53 (m, 1H), 7.11 (m, 3H), 7.17 (m, 4H), 7.70 (t, J=7.72 Hz, 1H).

Example 238 ¹H NMR (300 MHz, MeOH-d₄) δ ppm 0.84 (d, J=6.62 Hz, 3H), 0.89 (m, 3H), 1.00 (s, 9H), 1.06 (m, 1H), 1.33 (s, 1H), 1.37 (m, 2H), 1.45 (m, 2H), 1.59 (m, 2H), 1.88 (m, 1H), 2.31 (t, J=7.54 Hz, 2H), 2.53 (s, 3H), 2.67 (m, 4H), 2.73 (m, 2H), 2.78 (m, 1H), 2.85 (m, 2H), 3.13 (m, 3H), 3.22 (m, 1H), 3.65 (s, 3H), 3.66 (s, 3H), 3.72 (m, J=6.99 Hz, 1H), 3.83 (s, 1H), 3.94 (d, J=11.03 Hz, 1H), 4.16 (m, 1H), 4.35 (d, J=15.44 Hz, 1H), 4.53 (m, 1H), 7.11 (m, 3H), 7.17 (m, 4H), 7.70 (t, J=7.72 Hz, 1H).

Example 239 ¹H NMR (300 MHz, MeOH-d₄) δ ppm 0.84 (d, J=6.62 Hz, 3H), 0.88 (m, 3H), 0.93 (s, 9H), 1.04 (m, 1H), 1.06 (m, 1H), 1.21 (m, 3H), 1.40 (m, 1H), 1.87 (m, 1H), 2.53 (s, 3H), 2.59 (q, J=7.60 Hz, 2H), 2.75 (m, 4H), 2.84 (m, 3H), 3.13 (m, 2H), 3.24 (m, 1H), 3.66 (s, 3H), 3.74 (d, J=9.93 Hz, 1H), 3.80 (s, 1H), 3.87 (s, 2H), 3.93 (d, J=11.40 Hz, 1H), 4.14 (m, 1H), 4.35 (d, J=15.81 Hz, 1H), 4.53 (m, 1H), 5.91 (d, J=3.31 Hz, 1H), 6.15 (d, J=2.94 Hz, 1H), 7.14 (m, 7H), 7.70 (t, J=7.72 Hz, 1H).

Example 240 ¹H NMR (300 MHz, MeOH-d₄) δ ppm 0.71 (d, J=6.62 Hz, 3H), 0.79 (s, 9H), 0.84 (m, 3H), 0.90 (m, 2H), 0.98 (s, 1H), 1.01 (m, 1H), 1.36 (m, 1H), 1.88 (m, J=14.34 Hz, 1H), 2.52 (s, 3H), 2.70 (m, 1H), 2.79 (m, 2H), 2.87 (m, 2H), 3.10 (m, 2H), 3.22 (t, J=9.38 Hz, 1H), 3.58 (s, 3H), 3.67 (d, J=15.08 Hz, 1H), 3.85 (s, 1H), 3.89 (d, J=11.40 Hz, 1H), 3.98 (m, 2H), 4.25 (s, 1H), 4.35 (m, 1H), 4.52 (m, 1H), 7.12 (m, 4H), 7.19 (m, 3H), 7.48 (d, J=8.46 Hz, 2H), 7.56 (m, 3H), 7.69 (t, J=7.72 Hz, 1H), 7.80 (m, 1H), 8.10 (s, 1H).

Example 241 ¹H NMR (300 MHz, MeOH-d₄) δ ppm 0.85 (d, J=6.62 Hz, 3H), 0.89 (m, 12H), 1.00 (s, 9H), 1.07 (m, 1H), 1.41 (m, 3H), 1.91 (m, 1H), 2.53 (s, 3H), 2.69 (m, 4H), 2.77 (m, 3H), 2.84 (dd, J=9.56, 4.04 Hz, 2H), 3.11 (m, 2H), 3.16 (m, 1H), 3.22 (m, 1H), 3.66 (s, 3H), 3.72 (s, 1H), 3.84 (s, 1H), 3.94 (d, J=11.03 Hz, 1H), 4.15 (m, 1H), 4.35 (d, J=15.81 Hz, 1H), 4.53 (m, 1H), 7.12 (m, 3H), 7.17 (m, 4H), 7.70 (t, J=7.72 Hz, 1H).

Example 242 ¹H NMR (300 MHz, MeOH-d₄) δ ppm 0.71 (d, J=6.25 Hz, 3H), 0.80 (s, 9H), 0.85 (t, J=7.35 Hz, 3H), 0.97 (d, J=5.88 Hz, 1H), 1.02 (m, 1H), 1.35 (m, 1H), 1.88 (m, 1H), 2.10 (s, 3H), 2.53 (s, 3H), 2.68 (m, 2H), 2.76 (m, 2H), 2.85 (m, 3H), 3.11 (m, 2H), 3.22 (t, J=8.82 Hz, 1H), 3.64 (s, 3H), 3.72 (s, 1H), 3.80 (d, J=16.55 Hz, 1H), 3.88 (m, 3H), 4.18 (m, 1H), 4.34 (d, J=15.81 Hz, 1H), 4.53 (m, 1H), 7.11 (m, 4H), 7.17 (m, 4H), 7.32 (d, J=8.82 Hz, 2H), 7.48 (d, J=8.46 Hz, 2H), 7.70 (t, J=7.72 Hz, 1H).

Example 243 ¹H NMR (300 MHz, MeOH-d₄) δ ppm 0.70 (d, J=6.62 Hz, 3H), 0.76 (s, 9H), 0.85 (t, J=7.35 Hz, 3H), 0.99 (m, 1H), 1.36 (m, 1H), 1.85 (m, 1H), 2.53 (s, 3H), 2.71 (m, 1H), 2.78 (m, 2H), 2.83 (d, J=4.04 Hz, 1H), 2.88 (m, 2H), 3.11 (m, 3H), 3.22 (t, J=8.64 Hz, 1 H), 3.28 (s, 1H), 3.63 (s, 3H), 3.68 (s, 1H), 3.82 (s, 1H), 3.86 (s, 1H), 3.89 (s, 3H), 4.01 (m, 2H), 4.22 (m, 1H), 4.34 (d, J=15.44 Hz, 1H), 4.53 (m, 1H), 7.11 (m, 3H), 7.18 (m, 4H), 7.53 (d, J=8.46 Hz, 2H), 7.70 (t, J=7.72 Hz, 1H), 7.92 (d, J=8.09 Hz, 2H).

Example 244 ¹H NMR (300 MHz, CDCl₃) δ ppm 0.82 (s, 12H), 0.88 (m, 3H), 1.03 (m, 1H), 1.44 (m, 1H), 2.04 (m, 4H), 2.54 (s, 3H), 2.61 (s, 1H), 2.89 (d, J=6.99 Hz, 4H), 3.17 (d, J=6.62 Hz, 1H), 3.65 (m, 3H), 3.94 (s, 3H), 4.10 (d, J=7.35 Hz, 1H), 4.47 (s, 2H), 5.26 (s, 1H), 6.64 (s, 2H), 6.91 (s, 1H), 7.02 (t, J=8.46 Hz, 2H), 7.13 (dd, J=14.71, 7.35 Hz, 10H), 7.35 (m, 3H), 7.55 (t, J=7.54 Hz, 1H).

Example 245 ¹H NMR (300 MHz, CDCl₃) δ ppm 0.82 (m, 12H), 0.88 (m, 3H), 1.03 (m, 1H), 1.42 (m, 1H), 1.94 (m, 1H), 2.53 (s, 3H), 2.58 (d, J=2.57 Hz, 1H), 2.75 (d, J=4.78 Hz, 1 H), 2.91 (t, #8.09 Hz, 3H), 3.16 (m, 3H), 3.62 (m, 1H), 3.61 (s, 3H), 3.81 (m, 3H), 3.88 (s, 1H), 3.92 (d, J=11.03 Hz, 1H), 4.05 (m, 1H), 4.47 (s, 3H), 4.75 (s, 1H), 5.27 (d, J=8.82 Hz, 1H), 6.58 (s, 2H), 6.82 (d, J=8.09 Hz, 1H), 6.89 (m, 3H), 6.96 (m, 3H), 7.05 (m, 2H), 7.16 (d, J=6.62 Hz, 4H), 7.22 (m, 2H), 7.53 (t, J=7.72 Hz, 1H).

Example 246 ¹H NMR (300 MHz, MeOH-d₄) δ ppm 0.72 (d, J=6.62 Hz, 3H), 0.73 (s, 9H), 0.86 (t, J=7.35 Hz, 3H), 0.99 (m, 1H), 1.29 (s, 9H), 1.37 (m, 1H), 1.86 (m, 1H), 2.53 (s, 3H), 2.67 (dd, J=12.50, 3.31 Hz, 1H), 2.77 (m, 1H), 2.84 (m, 1H), 3.09 (m, 1H), 3.16 (m, 1H), 3.24 (m, 1H), 3.65 (s, 3H), 3.67 (m, 1H), 3.79 (d, J=8.82 Hz, 1H), 3.88 (d, J=10.66 Hz, 1H), 3.90 (s, 3H), 4.17 (m, 1H), 4.34 (d, J=15.81 Hz, 1H), 4.53 (d, J=15.81 Hz, 1H), 7.14 (m, 10H), 7.31 (m, 5H), 7.70 (t, J=7.72 Hz, 1H).

Example 247 ¹H NMR (300 MHz, MeOH-d₄) δ ppm 0.74 (d, J=6.62 Hz, 3H), 0.81 (s, 9H), 0.87 (t, J=7.17 Hz, 3H), 1.01 (m, 1H), 1.38 (m, 1H), 1.87 (m, 1H), 2.53 (s, 3H), 2.64 (dd, J=12.32, 3.13 Hz, 1H), 2.73 (m, 2H), 2.82 (m, 2H), 3.12 (m, 4H), 3.20 (d, J=9.56 Hz, 1H), 3.25 (s, 1H), 3.65 (s, 3H), 3.73 (m, 1H), 3.75 (s, 1H), 3.80 (d, J=4.04 Hz, 2H), 3.89 (d, J=11.03 Hz, 1H), 4.15 (m, 4H), 4.34 (d, J=15.81 Hz, 1H), 4.53 (m, 1H), 6.71 (d, J=8.46 Hz, 1H), 6.81 (m, 1H), 6.89 (d, J=2.21 Hz, 1H), 7.14 (m, 7H), 7.70 (t, J=7.72 Hz, 1H).

Example 248 ¹H NMR (300 MHz, MeOH-d₄) δ ppm 0.71 (s, 9H), 0.74 (d, J=6.62 Hz, 3H), 0.86 (t, J=7.17 Hz, 3H), 1.01 (m, 1H), 1.37 (m, 1H), 1.87 (m, 1H), 2.53 (s, 3H), 2.73 (m, 1H), 2.80 (m, 2H), 2.87 (m, 2H), 3.11 (m, 3H), 3.22 (t, J=9.01 Hz, 1H), 3.26 (m, 1H), 3.64 (s, 3H), 3.67 (s, 1H), 3.82 (s, 3H), 3.89 (d, J=11.03 Hz, 1H), 4.02 (m, 2H), 4.24 (m, 1H), 4.34 (d, J=15.81 Hz, 1H), 4.53 (m, 1H), 7.14 (m, 7H), 7.58 (m, 4H), 7.70 (t, J=7.72 Hz, 1H).

Example 249 ¹H NMR (300 MHz, MeOH-d₄) δ ppm 0.87 (q, J=6.86 Hz, 9H), 1.00 (s, 9H), 1.11 (m, 1H), 1.28 (m, 2H), 1.33 (m, 2H), 1.39 (m, 1H), 1.43 (d, J=2.94 Hz, 1H), 1.53 (m, 2H), 1.60 (s, 3H), 1.68 (m, 3H), 1.88 (d, J=14.34 Hz, 2H), 1.94 (m, 2H), 2.53 (s, 3H), 2.67 (d, J=6.99 Hz, 2H), 2.75 (t, #7.35 Hz, 3H), 2.85 (m, 2H), 3.14 (m, 2H), 3.22 (m, 1H), 3.65 (s, 3H), 3.73 (s, 1H), 3.84 (s, 1H), 3.94 (d, J=11.03 Hz, 1H), 4.15 (m, 1H), 4.35 (d, J=15.81 Hz, 1H), 4.53 (m, 1H), 5.10 (m, 1H), 7.15 (m, 7H), 7.70 (t, J=7.72 Hz, 1H).

Example 250 ¹H NMR (300 MHz, MeOH-d₄) δ ppm 0.13 (m, 3H), 0.47 (m, 3H), 0.84 (d, J=6.62 Hz, 3H), 0.88 (m, 3H), 0.99 (s, 9H), 1.40 (m, 1H), 1.89 (m, 1H), 2.52 (d, J=3.31 Hz, 3H), 2.73 (m, 5H), 2.86 (m, 3H), 3.17 (m, 5H), 3.66 (s, 3H), 3.74 (s, 1H), 3.87 (s, 1H), 3.94 (d, J=11.40 Hz, 1H), 4.17 (m, 1H), 4.35 (d, J=15.44 Hz, 1H), 4.53 (m, 1H), 7.14 (m, 7H), 7.70 (t, J=7.72 Hz, 1H).

Example 251 ¹H NMR (300 MHz, MeOH-d₄) δ ppm 0.75 (d, J=6.62 Hz, 3H), 0.86 (d, J=10.66 Hz, 12H), 1.00 (m, 1H), 1.27 (t, J=7.72 Hz, 3H), 1.36 (dd, J=6.62, 3.68 Hz, 1H), 1.86 (m, 1H), 2.53 (s, 3H), 2.67 (q, J=7.72 Hz, 5H), 2.82 (m, 3H), 2.87 (m, 1H), 3.13 (m, 3H), 3.22 (t, #9.01 Hz, 1H), 3.66 (s, 3H), 3.76 (s, 1H), 3.79 (s, 1H), 3.89 (m, 3H), 4.20 (s, 1H), 4.34 (d, J=15.81 Hz, 1H), 4.53 (m, 1H), 6.78 (s, 1H), 7.15 (m, 8H), 7.69 (t, J=7.72 Hz, 1 H).

Example 252 ¹H NMR (300 MHz, MeOH-d₄) δ ppm 0.73 (d, J=6.62 Hz, 3H), 0.80 (s, 9H), 0.86 (t, J=7.35 Hz, 3H), 1.01 (m, 1H), 1.38 (m, 1H), 1.84 (d, J=11.03 Hz, 1H), 2.53 (s, 3H), 2.67 (m, 2H), 2.75 (dd, #13.05, 3.49 Hz, 1H), 2.84 (m, 1H), 3.12 (m, 4H), 3.22 (t, J=8.82 Hz, 1H), 3.64 (s, 3H), 3.72 (s, 1H), 3.78 (m, 1H), 3.83 (m, 1H), 3.89 (m, 1H), 4.18 (m, 1H), 4.34 (d, J=15.81 Hz, 1H), 4.49 (m, 3H), 4.54 (d, J=9.19 Hz, 1H), 6.60 (d, J=8.09 Hz, 1H), 7.04 (dd, J=8.09, 1.84 Hz, 1H), 7.15 (m, 8H), 7.26 (s, 1H), 7.70 (t, J=7.72 Hz, 1H).

Example 253 ¹H NMR (300 MHz, CDCl₃) δ ppm 0.77 (d, J=6.62 Hz, 3H), 0.78 (d, J=2.94 Hz, 9H), 0.85 (s, 1H), 0.87 (t, J=7.35 Hz, 3H), 1.05 (m, 1H), 1.43 (m, 1H), 1.94 (s, 1H), 2.53 (d, J=4.78 Hz, 3H), 2.57 (s, 1H), 2.60 (m, 1H), 2.76 (m, 1H), 2.93 (m, 3H), 2.98 (m, 1H), 3.16 (m, 3H), 3.61 (m, 5H), 3.81 (m, 1H), 3.87 (m, 2H), 3.90 (d, J=11.03 Hz, 1H), 4.06 (d, J=8.82 Hz, 1H), 4.76 (s, 1H), 5.23 (d, J=8.09 Hz, 1H), 6.61 (s, 2H), 7.07 (m, 3H), 7.15 (m, 5H), 7.54 (t, J=7.72 Hz, 1H).

Example 254 ¹H NMR (300 MHz, CDCl₃) δ ppm 0.78 (s, 9H), 0.81 (d, J=6.62 Hz, 3H), 0.87 (t, J=7.35 Hz, 3H), 1.03 (m, 1H), 1.42 (m, 1H), 1.95 (s, 1H), 2.53 (d, J=4.78 Hz, 3H), 2.59 (m, 2H), 2.78 (dd, J=12.69, 10.11 Hz, 1H), 2.90 (d, J=7.35 Hz, 3H), 3.16 (m, 3H), 3.59 (s, 1 H), 3.62 (s, 3H), 3.85 (s, 3H), 3.87 (s, 3H), 3.92 (m, 1H), 4.08 (d, J=9.19 Hz, 1H), 4.47 (m, 2H), 4.81 (s, 1H), 5.30 (s, 1H), 6.47 (s, 1H), 6.56 (d, J=9.56 Hz, 1H), 6.76 (s, 2H), 6.97 (s, 1H), 7.04 (m, 1H), 7.10 (m, 1H), 7.11 (m, 2H), 7.18 (m, 4H), 7.54 (t, J=7.72 Hz, 1H).

Example 255 ¹H NMR (300 MHz, CDCl₃) δ ppm 0.78 (m, 3H), 0.81 (s, 9H), 0.87 (t, J=7.54 Hz, 3H), 1.02 (m, 1H), 1.41 (m, 1H), 1.91 (s, 1H), 2.54 (s, 3H), 2.59 (m, 1H), 2.75 (m, 1H), 2.93 (m, 2H), 3.18 (m, 3H), 3.56 (s, 1H), 3.60 (s, 3H), 3.64 (s, 1H), 3.82 (d, J=4.41 Hz, 2H), 3.86 (s, 3H), 3.91 (d, J=11.03 Hz, 1H), 4.07 (s, 1H), 4.47 (s, 2H), 4.75 (s, 1H), 5.27 (d, 1H), 6.61 (s, 2H), 6.89 (m, 1H), 7.03 (m, 3H), 7.11 (m, 2H), 7.18 (m, 4H), 7.54 (t, J=7.72 Hz, 1H).

Example 256 ¹H NMR (300 MHz, CDCl₃) δ ppm 0.85 (m, 15H), 1.07 (m, 1H), 1.42 (m, 1H), 2.00 (m, 1H), 2.55 (m, 2H), 2.54 (m, 3H), 2.75 (dd, J=12.32, 10.11 Hz, 1H), 2.92 (m, 3H), 3.17 (m, 3H), 3.56 (d, J=11.03 Hz, 1H), 3.61 (s, 3H), 3.65 (s, 1H), 3.81 (d, J=4.78 Hz, 2H), 3.92 (d, J=11.03 Hz, 1H), 4.06 (d, J=8.46 Hz, 1H), 4.47 (s, 2H), 4.73 (s, 1H), 5.26 (d, J=8.09 Hz, 1H), 5.93 (m, 2H), 6.58 (d, J=2.21 Hz, 2H), 6.83 (s, 1H), 7.06 (dd, J=11.40, 7.72 Hz, 2H), 7.15 (m, 5H), 7.54 (t, J=7.72 Hz, 1H).

Example 257 ¹H NMR (300 MHz, CDCl₃) δ ppm 0.80 (d, J=6.25 Hz, 3H), 0.83 (s, 9H), 0.89 (m, 3H), 1.02 (m, 1H), 1.43 (s, 1H), 1.96 (s, 1H), 2.17 (s, 3H), 2.50 (s, 1H), 2.54 (s, 3H), 2.74 (m, 1H), 2.89 (d, J=7.72 Hz, 3H), 3.17 (m, 2H), 3.55 (d, J=9.56 Hz, 1H), 3.62 (m, 3H), 3.63 (s, 1H), 3.81 (s, 3H), 3.83 (d, J=5.88 Hz, 2H), 3.91 (d, J=11.40 Hz, 1H), 4.05 (s, 1H), 4.47 (s, 2H), 4.73 (s, 1H), 5.30 (s, 1H), 6.47 (s, 1H), 6.51 (s, 1H), 6.75 (d, J=8.46 Hz, 1H), 7.06 (dd, J=13.97, 6.99 Hz, 4H), 7.15 (m, 5H), 7.54 (t, J=7.72 Hz, 1H).

Example 258 ¹H NMR (300 MHz, CDCl₃) δ ppm 0.78 (s, 9H), 0.81 (m, 3H), 0.87 (t, J=7.35 Hz, 3H), 1.03 (m, 1H), 1.41 (s, 1H), 1.91 (s, 1H), 2.54 (s, 3H), 2.77 (dd, 12.69, 10.11 Hz, 1H), 2.90 (d, J=7.72 Hz, 2H), 3.14 (m, 2H), 3.22 (m, 1H), 3.60 (s, 2H), 3.61 (s, 3H), 3.82 (m, 2H), 3.88 (s, 3H), 3.91 (m, 1H), 4.07 (d, J=8.09 Hz, 1H), 4.47 (d, J=2.57 Hz, 2H), 4.80 (s, 1H), 5.25 (d, J=9.56 Hz, 1H), 5.60 (s, 1H), 6.48 (s, 1H), 6.54 (s, 1H), 6.66 (dd, J=8.09, 1.84 Hz, 1H), 6.79 (d, J=8.09 Hz, 1H), 7.00 (d, J=1.47 Hz, 1H), 7.03 (d, J=7.72 Hz, 1H), 7.07 (d, J=7.35 Hz, 1H), 7.15 (m, 5H), 7.54 (t, J=7.72 Hz, 1H).

Example 259 ¹H NMR (300 MHz, CD₃OD) δ ppm 0.73 (m, 3H), 0.75 (s, 9H), 0.86 (t, J=7.17 Hz, 3H), 1.06 (t, J=7.17 Hz, 1H), 1.36 (m, 1H), 1.87 (s, 1H), 2.53 (s, 3H), 2.69 (m, 1H), 2.82 (m, 3H), 2.87 (m, 2H), 3.08 (s, 3H), 3.13 (m, 3H), 3.22 (t, J=8.82 Hz, 1H), 3.64 (s, 3H), 3.66 (d, J=3.31 Hz, 1H), 3.84 (d, J=4.04 Hz, 1H), 3.90 (d, J=11.03 Hz, 1H), 4.05 (s, 2H), 4.27 (s, 1H), 4.34 (d, J=15.81 Hz, 1H), 4.53 (m, 1H), 7.11 (m, 4H), 7.15 (s, 1H), 7.19 (m, 3H), 7.70 (m, 3H), 7.86 (d, J=8.46 Hz, 2H).

Example 260 ¹H NMR (300 MHz, CD₃OD) δ ppm 0.74 (d, J=6.62 Hz, 3H), 0.84 (s, 9H), 0.87 (m, 3H), 0.94 (s, 1H), 1.00

(m, 1H), 1.37 (m, 1H), 1.83 (d, J=11.03 Hz, 1H), 1.84 (m, 1H), 2.53 (s, 3H), 2.67 (m, 1H), 2.76 (dd, J=9.93, 5.88 Hz, 3H), 2.86 (m, 1H), 3.09 (m, 1H), 3.15 (m, 1H), 3.25 (m, 1H), 3.65 (s, 3H), 3.74 (s, 1H), 3.80 (s, 1H), 3.88 (d, J=1.40 Hz, 1 H), 4.02 (s, 2H), 4.27 (d, J=8.46 Hz, 1H), 4.34 (d, J=15.81 Hz, 1H), 4.53 (m, 1H), 6.96 (s, 1H), 7.12 (m, 5H), 7.18 (m, 4H), 7.69 (t, J=7.72 Hz, 1H).

Example 261 $^1$H NMR (300 MHz, CD$_3$OD) δ ppm 0.87 (m, 6H), 1.00 (s, 9H), 1.05 (d, J=8.82 Hz, 1H), 1.29 (s, 1H), 1.40 (m, 4H), 1.50 (m, 5H), 1.90 (m, 1H), 2.53 (s, 3H), 2.71 (m, 3H), 2.80 (m, 1H), 2.86 (m, 1H), 3.13 (m, 2H), 3.22 (m, 1H), 3.53 (t, J=6.43 Hz, 1H), 3.65 (s, 1H), 3.65 (d, J=4.04 Hz, 3H), 3.75 (s, 1H), 3.84 (m, 1H), 3.93 (m, 1H), 4.17 (m, 1H), 4.34 (m, 1H), 4.54 (m, 1H), 7.11 (dd, J=4.96, 2.02 Hz, 5H), 7.17 (m, 3H), 7.70 (t, J=7.72 Hz, 1H), 7.86 (d, J=9.56 Hz, 1H).

Example 262 $^1$H NMR (300 MHz, CD$_3$OD) δ ppm 0.84 (m, 3H), 0.89 (m, 3H), 0.91 (s, 1H), 0.93 (s, 9H), 1.04 (m, 1H), 1.40 (m, 1H), 1.87 (s, 3H), 1.92 (s, 1H), 2.13 (s, 3H), 2.53 (s, 3H), 2.69 (m, 3H), 2.77 (s, 1H), 2.84 (m, 2H), 3.13 (m, 2H), 3.17 (m, 1H), 3.24 (m, 1H), 3.66 (s, 3H), 3.72 (s, 1H), 3.80 (m, 3H), 3.93 (d, J=11.40 Hz, 1H), 4.15 (m, 1H), 4.35 (d, J=15.44 Hz, 1H), 4.53 (m, 1H), 6.02 (s, 1H), 7.11 (m, 6H), 7.18 (m, 1H), 7.70 (t, J=7.72 Hz, 1H).

Example 263 $^1$H NMR (300 MHz, CDCl$_3$), δ ppm 0.84 (m, 15H), 1.03 (m, 2H), 1.35 (m, 2H), 1.91 (m, 1H), 2.61 (m, 3H), 2.77 (m, 1H), 2.91 (d, J=7.72 Hz, 2H), 2.98 (m, J=9.19 Hz, 1 H), 3.19 (m, 3H), 3.62 (m, 4H), 3.89 (t, J=11.03 Hz, 3H), 4.06 (q, J=7.72 Hz, 1H), 4.53 (br s, 2H), 5.25 (d, J=9.56 Hz, 1H), 6.66 (s, 2H), 7.20 (m, 11H), 7.61 (s, 1H).

Example 264 $^1$H NMR (300 MHz, CDCl$_3$), δ ppm 0.83 (m, 15H), 1.03 (m, 2H), 1.36 (m, 2H), 1.96 (m, 1H), 2.27 (s, 6H), 2.53 (m, 4H), 2.76 (dd, J=12.50, 10.30 Hz, 1H), 2.91 (m, 3H), 3.16 (m, 3H), 3.59 (m, 4H), 3.86 (m, 3H), 4.06 (m, 1H), 4.50 (br s, 2H), 5.29 (d, J=9.19 Hz, 1H), 6.53 (m, 2H), 6.90 (m, 3H), 7.14 (m, 7H), 7.57 (m, 1H).

Example 265 $^1$H NMR (300 MHz, CDCl$_3$), δ ppm 0.96 (m, 24H), 1.40 (m, 1H), 1.54 (m, 1H), 1.96 (s, 1H), 2.52 (m, 6H), 2.82 (m, 4H), 3.14 (m, 3H), 3.49 (d, J=9.56 Hz, 1H), 3.66 (m, 4H), 3.87 (d, J=11.03 Hz, 1H), 4.09 (m, 1H), 4.47 (m, 2H), 4.72 (s, 1H), 5.33 (d, J=9.93 Hz, 1H), 6.47 (d, J=9.56 Hz, 1H), 6.70 (s, 1H), 7.11 (m, 7H), 753 (t, J=7.72 Hz, 1H).

Example 266 $^1$H NMR (300 MHz, CDCl$_3$), δ ppm 0.93 (m, 27H), 1.32 (m, 1H), 1.94 (m, J=8.82 Hz, 1H), 2.56 (m, 5H), 2.90 (m, 4H), 3.16 (m, 3H), 3.60 (m, J=7.72 Hz, 4H), 3.77 (dd, J=9.74, 4.96 Hz, 1H), 3.98 (m, 2H), 4.47 (m, 2H), 4.73 (s, 0.5H), 4.92 (s, 0.5H), 5.30 (s, 1H), 6.57 (m, 1H), 6.65 (s, 0.5H), 6.91 (s, 0.5H), 7.11 (m, 7H), 7.55 (t, J=7.54 Hz, 1H).

Example 267 $^1$H NMR (300 MHz, CDCl$_3$), δ ppm 0.77 (m, 12H), 0.87 (t, J=7.35 Hz, 3H), 1.05 (m, 1H), 1.43 (m, 1H), 1.91 (s, 1H), 2.55 (s, 3H), 2.65 (dd, J=12.50, 4.04 Hz, 1H), 2.77 (m, 1H), 2.92 (d, J=7.72 Hz, 2H), 3.01 (t, J=8.82 Hz, 1H), 3.17 (m, 3H), 3.60 (m, 5H), 3.91 (m, 3H), 4.06 (m, 1H), 4.48 (s, 2H), 4.84 (br s, 1H), 5.21 (d, J=8.82 Hz, 1H), 6.69 (d, J=8.82 Hz, 1H), 6.82 (br s, 1H), 7.06 (m, 2H), 7.15 (m, 5H), 7.54 (m, 5H).

Example 268 $^1$H NMR (300 MHz, CDCl$_3$) δ ppm 0.87 (m, 6H), 1.06 (m, 15H), 1.44 (m, 1H), 1.55 (m, 2H), 1.76 (m, 4H), 1.93 (m, 1H), 2.54 (m, 4H), 2.67 (m, 1H), 2.92 (m, 2H), 3.05 (m, 1H), 3.18 (m, 3H), 3.56 (s, 3H), 3.80 (d, J=9.56 Hz, 1H), 3.96 (m, J=11.03 Hz, 2H), 4.48 (m, 2H), 4.87 (s, 1H), 5.31 (m, 1H), 6.68 (s, 1H), 6.95 (s, 1H), 7.12 (m, 7H), 7.56 (t, J=7.54 Hz, 1H).

Example 269 $^1$H NMR (300 MHz, CDCl$_3$) δ ppm 0.81 (m, 15H), 1.04 (m, 1H), 1.43 (m, 1H), 1.92 (m, 1H), 2.59 (m, 4H), 2.76 (m, 1H), 2.92 (m, J=7.72 Hz, 1H), 3.02 (t, J=8.64 Hz, 1 H), 3.17 (m, 3H), 3.62 (m, 5H), 3.82 (m, 2H), 3.92 (d, J=11.03 Hz, 1H), 4.03 (q, J=8.21 Hz, 1 H), 4.48 (m, 2H), 4.82 (s, 1H), 5.24 (d, J=9.10 Hz, 1H), 6.68 (d, J=7.72 Hz, 1H), 6.79 (s, 1H), 7.15 (m, 8H), 7.39 (m, 2H), 7.55 (t, J=7.72 Hz, 1H).

Example 276 $^1$H NMR (300 MHz, CD$_3$OD) δ ppm 0.73 (s, 9H), 0.79 (d, J=8.82 Hz, 2H), 0.89 (s, 9H), 0.98 (m, 1H), 2.34 (d, J=9.56 Hz, 1H), 2.83 (m, 5H), 3.11 (m, 2H), 3.26 (m, 1H), 3.46 (s, 3H), 3.60 (s, 3H), 3.70 (s, 1H), 3.84 (s, 1H), 4.02 (m, 2H), 4.19 (s, 1H), 4.45 (m, 2H), 4.71 (s, 2H), 7.06 (m, 3H), 7.16 (m, 2H), 7.37 (s, 1H), 7.45 (d, J=4.78 Hz, 2H), 7.61 (m, 1H), 7.96 (s, 1H), 9.11 (s, 2H), 9.13 (d, J=3.68 Hz, 1H).

Example 277 $^1$H NMR (300 MHz, CD$_3$OD) δ ppm 0.86 (s, 9H), 0.92 (s, 9H), 2.36 (m, 2H), 2.51 (s, 3H), 2.83 (m, 5H), 3.10 (m, 3H), 3.26 (d, J=3.31 Hz, 2H), 3.46 (s, 3H), 3.62 (s, 3H), 3.76 (s, 1H), 3.86 (s, 1H), 4.05 (s, 1H), 4.14 (m, 3H), 4.46 (m, 2H), 4.71 (s, 2H), 6.67 (s, 1H), 7.07 (m, 3H), 7.16 (m, 2H), 7.38 (s, 1H), 7.67 (s, 1H).

Example 278 $^1$H NMR (300 MHz, CD$_3$OD) δ ppm 0.87 (s, 9H), 0.93 (m, 9H), 2.36 (d, J=9.56 Hz, 1H), 2.85 (m, 6H), 3.12 (m, 3H), 3.28 (m, 2H), 3.46 (s, 3H), 3.62 (s, 3H), 3.78 (s, 1H), 3.86 (s, 1H), 4.05 (s, 1H), 4.15 (d, J=16.18 Hz, 2H), 4.46 (m, 2H), 4.71 (s, 2H), 7.07 (m, 2H), 7.16 (m, 2H), 7.38 (s, 1H), 7.44 (dd, J=6.62, 4.78 Hz, 1H), 7.62 (s, 1H), 7.91 (m, 2H), 8.19 (d, J=8.09 Hz, 1H), 8.57 (d, J=4.41 Hz, 1H).

Example 279 $^1$H NMR (300 MHz, DMSO-d$_6$) δ ppm 0.95 (s, 9H), 0.86 (s, 9H), 1.30-1.27 (d, J=6.62 Hz, 6H), 2.46 (m, 1H), 2.77-2.63 (m, 4H), 3.26-2.96 (m, 5H), 3.38 (s, 2H), 3.53 (s, 3H), 3.62 (m, 1H), 3.71-3.68 (d, J=9.19 Hz, 1H), 4.02 (s, 3H), 4.09 (s, 1H), 4.46-4.27 (dd, J=15.44, 40.08 Hz, 2H), 4.68 (s, 2H), 4.79-4.78 (d, J=3.31 Hz, 1H), 7.13-7.01 (m, 5H), 7.31 (s, 1H), 7.43 (s, 1H), 7.65-7.62 (d, J=9.2 Hz, 1H), 9.19 (s, 1H).

Example 281 $^1$H NMR (300 MHz, DMSO-d$_6$), δ ppm 0.68 (m, 12H), 0.79 (t, J=7.17 Hz, 3H), 0.92 (m, 1H), 1.28 (s, 1H), 1.83 (m, 1H), 2.70 (m, 4H), 3.07 (m, 2H), 3.17 (s, 1H), 3.35 (m, 3H), 3.52 (d, J=6.62 Hz, 4H), 3.71 (m, 10H), 3.89 (m, 2H), 3.95 (d, J=11.03 Hz, 1H), 4.07 (s, 1H), 4.36 (m, 2H), 6.78 (m, 2H), 6.95 (d, J=9.56 Hz, 1H), 7.03 (d, J=8.82 Hz, 1H), 7.09 (m, 4H), 7.19 (m, 1H), 7.38 (d, J=9.19 Hz, 1H), 7.42 (s, 1H), 9.02 (s, 1H).

Example 282 $^1$H NMR (500 MHz, DMSO-d$_6$), δ ppm 0.64 (d, J=6.10 Hz, 3H), 0.68 (s, 9H), 0.76 (m, 3H), 0.89 (m, 2H), 1.26 (m, 2H), 1.49 (s, 1H), 1.74 (m, 1H), 2.00 (d, J=14.04 Hz, 1H), 2.14 (d, J=4.88 Hz, 6H), 3.38 (m, 3H), 3.48 (s, 1H), 3.52 (s, 3H), 3.56 (s, 1H), 3.68 (m, 2H), 3.81 (d, J=6.10 Hz, 2H), 3.86 (m, 1H), 3.91 (d, J=10.99 Hz, 1H), 4.00 (d, J=4.88 Hz, 1 H), 4.09 (s, 1H), 4.32 (d, J=15.26 Hz, 1H), 4.41 (m, 1H), 4.63 (d, J=16.48 Hz, 2H), 6.89 (d, J=9.77 Hz, 1H), 6.99 (d, J=5.49 Hz, 1H), 7.06 (s, 1H), 7.09 (m, 5H), 7.15 (dd, J=15.56, 7.02 Hz, 1H), 7.22 (m, 1H), 7.35 (d, J=9.16 Hz, 1H), 8.99 (s, 1H).

Example 283 $^1$H NMR (300 MHz, CDCl$_3$) δ ppm 0.67 (d, J=6.62 Hz, 3H), 0.79 (m, 6H), 0.87 (t, J=7.35 Hz, 3H), 0.93 (dd, J=7.17, 2.39 Hz, 1H), 1.04 (m, 1H), 1.27 (m, 1H), 1.42 (m, 1H), 1.64 (m, 2H), 1.94 (d, J=11.40 Hz, 1H), 2.53 (m, 3H), 2.77 (m, 1H), 2.93 (m, 3H), 3.16 (m, 4H), 3.59 (s, 1H), 3.61 (s, 3H), 3.77 (s, 1H), 3.78 (s, 3H), 3.79 (m, 1H), 3.87 (t, J=5.70 Hz, 1H), 3.92 (d, J=2.57 Hz, 1H), 4.08 (d, J=8.46 Hz, 1H), 4.49 (s, 2H), 4.72 (s, 1H), 5.08 (s, 1H), 6.58 (d, J=13.97 Hz, 2H), 6.83 (m, 2H), 7.12 (m, 7H), 7.20 (d, J=8.82 Hz, 2H), 7.58 (m, 1H).

Example 284 $^1$H NMR (300 MHz, CDCl$_3$) δ ppm 0.82 (d, J=6.62 Hz, 6H), 0.89 (m, 12H), 1.09 (m, 2H), 1.30 (m, 2H), 1.45 (m, 2H), 1.82 (m, 1H), 1.97 (s, 1H), 2.51 (d, J=4.41 Hz, 1 H), 2.55 (s, 3H), 2.69 (m, 3H), 2.93 (d, J=7.72 Hz, 2H), 3.08 (s, 1H), 3.19 (m, 3H), 3.58 (s, 3H), 3.61 (s, 1H), 3.83 (m, 1H), 3.95 (d, J=11.03 Hz, 1H), 4.01 (d, J=8.09 Hz, 1H), 4.49 (s, 2H), 4.82 (s, 1H), 5.16 (s, 1H), 6.76 (d, J=8.46 Hz, 1H), 6.86 (s, 1H), 7.05 (d, J=8.09 Hz, 1H), 7.10 (d, J=3.68 Hz, 1H), 7.17 (m, 5H), 7.58 (m, 1H).

Example 285 $^1$H NMR (300 MHz, CDCl$_3$) δ ppm 0.64 (d, J=6.62 Hz, 3H), 0.74 (t, J=7.35 Hz, 3H), 0.79 (d, J=6.62 Hz, 3H), 0.85 (m, 3H), 1.29 (s, 1H), 1.40 (s, 1H), 1.92 (s, 1H), 2.54 (s, 3H), 2.61 (d, J=13.97 Hz, 1H), 2.81 (d, J=9.93 Hz, 1H), 2.91 (m, 3H), 3.16 (m, 4H), 3.59 (s, 3H), 3.62 (s, 1H), 3.70 (t, J=8.09 Hz, 1H), 3.93 (m, 3H), 4.09 (d, J=8.82 Hz, 2H), 4.48 (s, 2H), 4.80 (s, 1H), 5.07 (s, 1H), 6.60 (s, 1H), 6.74 (s, 1H), 7.13 (m, 8H), 7.41 (d, J=8.09 Hz, 2H), 7.55 (t, #7.54 Hz, 1H), 7.73 (m, 2H), 7.94 (d, J=8.09 Hz, 2H), 8.68 (d, J=4.78 Hz, 1H).

Example 286 $^1$H NMR (300 MHz, CDCl$_3$), δ ppm 0.82 (s, 9H), 0.99 (m, 9H), 2.54 (m, 4H), 2.61 (d, J=9.19 Hz, 1H), 2.77 (m, 1H), 2.87 (m, 2H), 3.07 (m, 1H), 3.16 (m, 1H), 3.33 (dd, J=8.82, 3.31 Hz, 1H), 3.59 (d, J=9.56 Hz, 1H), 3.64 (s, 3H), 3.79 (s, 3H), 3.87 (q, J=13.48 Hz, 2H), 4.04 (s, 1H), 4.09 (d, J=8.09 Hz, 1H), 4.50 (m, 2H), 4.69 (s, 1H), 5.29 (d, J=9.93 Hz, 1H), 6.28 (d, J=9.56 Hz, 1H), 6.38 (s, 1H), 6.84 (m, 2H), 7.11 (m, 7H), 7.20 (m, 2H), 7.57 (t, J=7.72 Hz, 1H).

Example 287 $^1$H NMR (300 MHz, CDCl$_3$), δ ppm 0.72 (m, 1H), 0.83 (t, J=6.99 Hz, 6H), 1.02 (m, 18H), 1.33 (m, 1H), 1.65 (m, 2H), 2.32 (s, 1H), 2.51 (d, J=2.94 Hz, 1H), 2.55 (s, 3 H), 2.63 (s, 1H), 2.71 (m, 3H), 2.89 (m, 2H), 3.07 (m, 1H), 3.17 (m, 1H), 3.36 (m, 1H), 3.61 (s, 1H), 3.63 (s, 3H), 3.72 (d, J=9.56 Hz, 1H), 4.06 (d, J=7.35 Hz, 2H), 4.46 (d, J=16.18 Hz, 2H), 4.65 (s, 1H), 5.37 (d, J=9.56 Hz, 1H), 6.37 (s, 1H), 6.50 (s, 1H), 7.04 (s, 1H), 7.08 (m, 2H), 7.17 (m, 3H).

Example 288 $^1$H NMR (300 MHz, CDCl$_3$), δ ppm 0.82 (s, 9H), 0.85 (s, 1H), 0.96 (s, 9H), 1.04 (m, 2H), 2.35 (d, J=3.31 Hz, 1H), 2.38 (s, 3H), 2.55 (dd, J=12.13, 2.94 Hz, 2H), 2.75 (m, 1H), 2.96 (m, 1H), 3.35 (m, 1H), 3.58 (m, 1H), 3.64 (s, 3H), 3.79 (s, 3H), 3.87 (m, 2H), 4.02 (m, 1H), 4.11 (d, J=9.56 Hz, 1H), 4.30 (d, J=15.08 Hz, 1H), 4.50 (m, 1H), 4.68 (s, 1H), 5.29 (d, J=8.46 Hz, 1H), 6.26 (d, J=9.19 Hz, 1H), 6.41 (s, 1H), 6.85 (m, 2H), 7.06 (m, 2H), 7.14 (m, 3H), 7.22 (d, J=8.46 Hz, 2H), 8.38 (s, 1H), 8.43 (d, J=4.78 Hz, 1H).

Example 289 $^1$H NMR (300 MHz, CDCl$_3$), δ ppm 0.85 (t, J=7.17 Hz, 6H), 0.99 (m, 18H), 1.25 (s, 1H), 1.36 (m, 2H), 1.66 (m, 1H), 2.38 (s, 3H), 2.55 (d, J=2.94 Hz, 1H), 2.73 (m, 2H), 2.88 (t, #7.54 Hz, 3H), 2.96 (m, 1H), 3.33 (d, J=3.68 Hz, 1H), 3.58 (d, J=10.30 Hz, 1 H), 3.65 (s, 3H), 3.71 (d, J=9.19 Hz, 1H), 4.04 (s, 1H), 4.12 (m, 1H), 4.32 (d, J=14.71 Hz, 1 H), 4.49 (m, 1H), 4.60 (s, 1H), 5.37 (d, J=7.72 Hz, 1H), 6.33 (d, J=9.19 Hz, 1H), 6.49 (s, 1H), 7.07 (m, 3H), 7.15 (m, 3H), 8.39 (s, 1H), 8.44 (d, J=4.78 Hz, 1H).

Example 290 $^1$H NMR (300 MHz, CDCl$_3$), δ ppm 0.06 (d, J=4.04 Hz, 1H), 0.75 (m, 9H), 0.87 (m, 6H), 0.94 (s, 1H), 1.04 (d, J=5.15 Hz, 2H), 1.24 (m, 2H), 1.37 (d, J=14.34 Hz, 2H), 1.75 (s, 8H), 2.70 (s, 2H), 2.79 (s, 2H), 2.92 (d, J=7.72 Hz, 2H), 3.04 (d, J=8.82 Hz, 1H), 3.19 (m, 1H), 3.28 (d, J=9.19 Hz, 1H), 3.57 (s, 1H), 3.61 (s, 1H), 3.64 (m, 2H), 3.69 (s, 1H), 3.87 (d, J=11.03 Hz, 1H), 4.00 (s, 1H), 4.08 (m, 1H), 4.66 (s, 1H), 4.84 (s, 1H), 5.21 (s, 1H), 6.69 (d, J=8.46 Hz, 1H), 7.47 (s, 1H), 7.76 (s, 1H), 8.55 (d, J=5.88 Hz, 1H).

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound, stereoisomer of the compound, ester of the compound, prodrug of the compound, pharmaceutically acceptable salt of the compound, stereoisomer, ester, or prodrug, or combination thereof, wherein:

the compound corresponds in structure to formula (I):

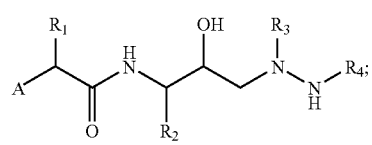

(I)

A is selected from the group consisting of

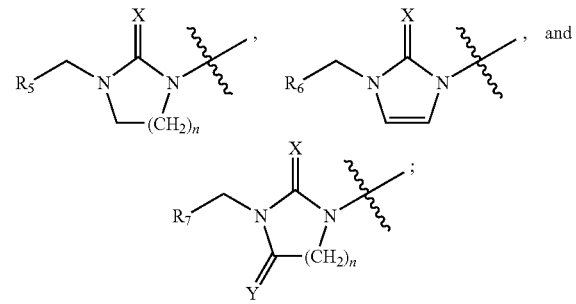

, and

;

X is selected from the group consisting of O, S, and NH;

Y is selected from the group consisting of O, S, and NH;

$R_1$ is selected from the group consisting of alkyl, alkenyl, alkynyl, cycloalkyl, cycloalkenyl, aryl, heteroaryl, arylalkyl, heteroarylalkyl, cycloalkylalkyl, and cycloalkenylalkyl, wherein:

each $R_1$ substituent is substituted with 0, 1, or 2 substituents independently selected from the group consisting of halo, haloalkyl, alkyl, alkenyl, cyano, nitro, —OR$_a$, —OalkylC(=O)NR$_a$R$_b$, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, N(R$_b$)SO$_2$R$_a$, —N(R$_b$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$, and C(=O)OR$_a$;

$R_2$ is selected from the group consisting of alkyl, alkenyl, alkynyl, cycloalkyl, cycloalkenyl, cycloalkylalkyl, cycloalkenylalkyl, arylalkyl, heterocycle, heterocyclealkyl, and heteroarylalkyl, wherein:

each $R_2$ substituent is substituted with 0, 1, or 2 substituents independently selected from the group consisting of alkyl, alkenyl, alkynyl, cyano, halo, formyl, nitro, hydroxy, alkoxy, —NH$_2$, —N(H)alkyl, —N(alkyl)$_2$, —N(H)C(=O)Oalkyl, —N(alkyl)C(=O)Oalkyl, —C(=O)OH, —C(=O)Oalkyl, —C(=O)NH$_2$, —C(=O)N(H)(alkyl), —C(=O)N(alkyl)$_2$, —C(=O)alkyl, cyanoalkyl, nitroalkyl, formylalkyl, haloalkyl, hydroxyalkyl, alkoxyalkyl, -alkylNH$_2$, -alkylN(H)alkyl, -alkylN(alkyl)$_2$, -alkylN(H)C(=O) Oalkyl, -alkylN(alkyl)C(=O)Oalkyl, -alkylC(=O) OH, -alkylC(=O)Oalkyl, -alkylC(=O)NH$_2$, -alkylC(=O)N(H)(alkyl), -alkylC(=O)N(alkyl)$_2$, and -alkylC(=O)alkyl;

$R_3$ is selected from the group consisting of hydrogen, alkyl, haloalkyl, alkenyl, haloalkenyl, alkynyl, haloalkynyl, cycloalkyl, cycloalkenyl, heterocycle, aryl, heteroaryl, cycloalkylalkyl, cycloalkenylalkyl, heterocyclealkyl, heteroarylalkyl, arylalkyl, hydroxyalkyl, alkoxyalkyl, -alkylSR$_a$, -alkylSOR$_a$, -alkylSO$_2$R$_a$, alkylNR$_a$R$_b$, -alkylC(=O)OR$_a$, -alkylN(R$_b$)C(=O)OR$_a$, -alkylN (R$_b$)C(=O)R$_a$, -alkylN(R$_b$)SO$_2$R$_a$, and -alkylN(R$_b$) SO$_2$NR$_a$R$_b$, wherein:

the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl, and aryl moiety of the arylalkyl are substituted with 0, 1, 2, or 3 substituents independently selected from the group consisting of halo, nitro, cyano, formyl, alkyl, alkenyl, alkynyl, hydroxy, alkoxy, —SH, —S(alkyl), —S(haloalkyl), —SO$_2$(alkyl), —SO$_2$(haloalkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$, -alkylC(=O)alkyl, and R$_{3a}$;

R$_{3a}$ is selected from the group consisting of cycloalkyl, cycloalkenyl, aryl, heteroaryl, heterocycle, aryloxy, heteroaryloxy, and heterocycleoxy, wherein:

each R$_{3a}$ substituent is substituted with 0, 1, 2, or 3 substituents independently selected from the group consisting of halo, nitro, cyano, formyl, alkyl, alkenyl, alkynyl, hydroxyl, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$, and -alkylC(=O)alkyl;

R$_4$ is selected from the group consisting of
a) C(O)CH(R$_8$)NHC(O)R$_9$,
b) —C(O)R$_9$,
c) —C(O)CH$_2$—O-aryl, substituted with 0, 1, 2, or 3 substituents independently selected from the group consisting of alkyl, alkenyl, halo, cyano, nitro, formyl, oxo, hydroxyl, alkoxy, hydroxyalkyl, alkoxyalkyl, haloalkyl, cyanoalkyl, aminoalkyl, alkylaminoalkyl, dialkylaminoalkyl, nitroalkyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), and —C(=O)N(alkyl)$_2$,
d) —C(O)CH$_2$—O-heteroaryl, substituted with 0, 1, 2, or 3 substituents independently selected from the group consisting of alkyl, alkenyl, halo, cyano, nitro, formyl, oxo, hydroxyl, alkoxy, hydroxyalkyl, alkoxyalkyl, haloalkyl, cyanoalkyl, aminoalkyl, alkylaminoalkyl, dialkylaminoalkyl, nitroalkyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), and —C(=O)N(alkyl)$_2$,

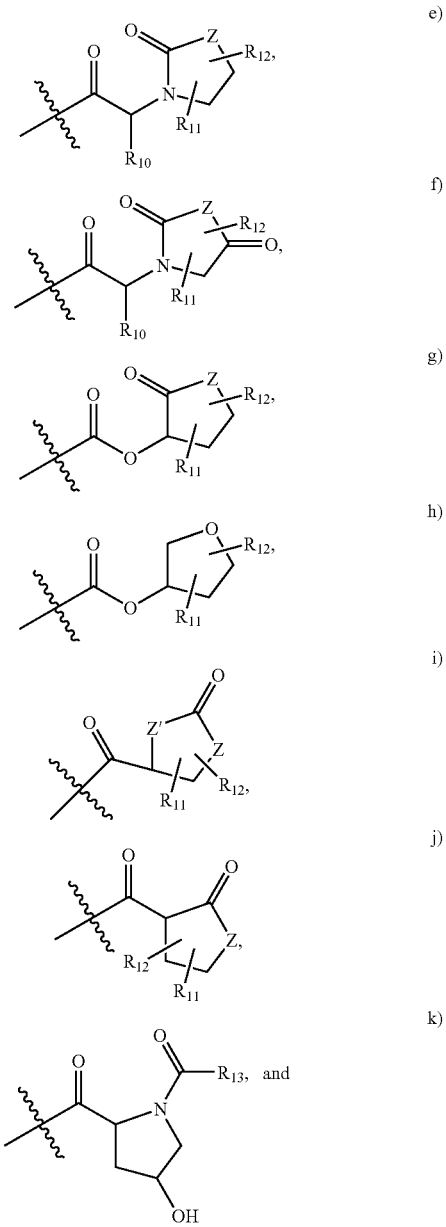

l) —SO$_2$R$_{14}$;

R$_5$ is selected from the group consisting of alkyl, alkenyl, alkynyl, cycloalkyl, cycloalkenyl, aryl, heteroaryl, and heterocycle, wherein:

each R$_5$ substituent is substituted with 0, 1, 2, or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NHR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NHR$_a$, -alkylSO$_2$OR$_a$, -alkylNR$_a$R$_b$, —C(H)=N(OR$_a$), —C(alkyl)=N(OR$_a$), —C(H)

=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$, and R$_{5a}$;

R$_{5a}$ is selected from the group consisting of cycloalkyl, cycloalkenyl, heterocycle, aryl, and heteroaryl, wherein:
each R$_{5a}$ substituent is substituted with 0, 1, 2, 3, or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)alkyl, -alkylN(alkyl)C(=O)alkyl, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), and -alkylC(=O)N(alkyl)$_2$;

R$_6$ is selected from the group consisting of alkyl, alkenyl, alkynyl, cycloalkyl, cycloalkenyl, aryl, heteroaryl, and heterocycle, wherein:
each R$_6$ substituent is substituted with 0, 1, 2, or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NHR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NHR$_a$, -alkylSO$_2$OR$_a$, -alkylNR$_a$R$_b$, —C(H)N(OR$_a$), —C(alkyl)N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, alkylC(=O)NR$_a$R$_b$, and R$_{6a}$;

R$_{6a}$ is selected from the group consisting of cycloalkyl, cycloalkenyl, heterocycle, aryl, and heteroaryl, wherein:
each R$_{6a}$ substituent is substituted with 0, 1, 2, 3, or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)alkyl, -alkylN(alkyl)C(=O)alkyl, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), and -alkylC(=O)N(alkyl)$_2$;

R$_7$ is selected from the group consisting of alkyl, alkenyl, alkynyl, cycloalkyl, cycloalkenyl, aryl, heteroaryl, and heterocycle, wherein:
each R$_7$ substituent is substituted with 0, 1, 2, or 3 substituents independently selected from the group consisting of alkyl, alkenyl, alkynyl, cyano, halo, nitro, OXO, —OR$_a$, —OC(=O)R$_a$, —SR$_a$, —SOR$_a$, —SO$_2$R$_a$, —SO$_2$NHR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NHR$_a$, -alkylSO$_2$OR$_a$, -alkylNR$_a$R$_b$, —C(H)N(OR$_a$), —C(alkyl)N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, alkylC(=O)OR$_a$, -alkylC(=O)NR$_a$R$_b$, and R$_{7a}$;

R$_{7a}$ is selected from the group consisting of cycloalkyl, cycloalkenyl, heterocycle, aryl, and heteroaryl, wherein:
each R$_{7a}$ substituent is substituted with 0, 1, 2, 3, or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)alkyl, -alkylN(alkyl)C(=O)alkyl, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), and -alkylC(=O)N(alkyl)$_2$;

R$_8$ is selected from the group consisting of alkyl, alkenyl, alkynyl, cycloalkyl, aryl, heteroaryl, cycloalkylalkyl, and arylalkyl, wherein:
each R$_8$ substituent is substituted with 0, 1, or 2 substituents independently selected from the group consisting of halo, cyano, formyl, nitro, alkyl, alkenyl, alkynyl, hydroxy, alkoxy, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), —C(=O)N(alkyl)$_2$, —C(=O)alkyl, hydroxyalkyl, alkoxyalkyl, -alkylNH$_2$, -alkylN(H)alkyl, -alkylN(alkyl)$_2$, -alkylC(=O)OH, -alkylC(=O)Oalkyl, -alkylC(=O)NH$_2$, -alkylC(=O)N(H)(alkyl), and -alkylC(=O)N(alkyl)$_2$;

R$_9$ is selected from the group consisting of alkyl, cycloalkyl, cycloalkylalkyl, aryl, heterocycle, heteroaryl, and OR$_{9a}$, wherein:
each R$_9$ substituent is substituted with 0, 1, 2, or 3 substituents independently selected from the group consisting of hydroxy, alkoxy, halo, cyano, nitro, formyl, alkyl, alkenyl, alkynyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), and —C(=O)N(alkyl)$_2$;

$R_{9a}$ is selected from the group consisting of alkyl, cycloalkyl, cycloalkylalkyl, aryl, arylalkyl, heterocycle, heteroaryl, heteroarylalkyl, and heterocyclealkyl, wherein:
  each $R_{9a}$ substituent is substituted with 0, 1, 2, or 3 substituents independently selected from the group consisting of hydroxy, alkoxy, halo, cyano, nitro, formyl, alkyl, alkenyl, alkynyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), and —C(=O)N(alkyl)$_2$;

$R_{10}$ is selected from the group consisting of alkyl, alkenyl, alkynyl, cycloalkyl or cycloalkenyl, aryl, heteroaryl, arylalkyl, cycloalkylalkyl, and heteroarylalkyl, wherein:
  each $R_{10}$ substituent is substituted with 0, 1, 2, or 3 substituents independently selected from the group consisting of halo, cyano, nitro, formyl, alkyl, alkenyl, hydroxy, alkoxy, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_b$)SO$_2$NR$_a$R$_b$, —N(R$_b$)C(NH)NR$_a$R$_b$, —N(R$_b$)C(=O)NR$_a$R$_b$, —C(=O)NR$_a$R$_b$, and —C(=O)OR$_a$;

$R_{11}$ is selected from the group consisting of hydrogen, alkyl, haloalkyl, hydroxyalkyl, and alkoxyalkyl;

$R_{12}$ is selected from the group consisting of hydrogen, alkyl, haloalkyl, hydroxyalkyl, and alkoxyalkyl;

$R_{13}$ is selected from the group consisting of alkyl and haloalkyl;

$R_{14}$ is selected from the group consisting of alkyl, cycloalkyl, cycloalkylalkyl, aryl, heteroaryl, and heterocycle, wherein:
  each $R_{14}$ substituent is substituted with 0, 1, 2, or 3 substituents independently selected from the group consisting of halo, cyano, nitro, formyl, alkyl, alkenyl, hydroxy, alkoxy, haloalkyl, —NH$_2$, —N(H)alkyl, —N(alkyl)$_2$, —C(=O)OH, —C(=O)Oalkyl, —C(=O)NH$_2$, —C(=O)N(H)(alkyl), and —C(=O)N(alkyl)$_2$;

Z is selected from the group consisting of —CH$_2$—, —NH—, —O—, and —S—;

Z' is selected from the group consisting of CH$_2$—, —NH—, —O—, and —S—;

R$_a$ and R$_b$ at each occurrence are independently selected from the group consisting of hydrogen, alkyl, haloalkyl, alkenyl, alkynyl, cycloalkyl, aryl, heteroaryl, heterocycle, arylalkyl, and heteroarylalkyl, wherein:
  each R$_a$ and R$_b$ substituent is substituted with 0, 1, 2, or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, —C(=O)alkyl, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), -alkylC(=O)N(alkyl)$_2$, and alkylC(=O)alkyl; and n is 1.

2. The compound, stereoisomer, ester, prodrug, salt, or combination of claim 1, wherein $R_1$ is alkyl.

3. The compound, stereoisomer, ester, prodrug, salt, or combination of claim 1, wherein:
  $R_1$ is alkyl, and
  $R_4$ is —C(O)C(H)(R$_8$)NHC(O)R$_9$.

4. The compound, stereoisomer, ester, prodrug, salt, or combination of claim 1, wherein:
  $R_1$ is alkyl,
  $R_4$ is —C(O)C(H)(R$_8$)NHC(O)R$_9$, and
  $R_9$ is —OR$_9$.

5. The compound, stereoisomer, ester, prodrug, salt, or combination of claim 1, wherein:
  $R_1$ is alkyl,
  $R_4$ is —C(O)C(H)(R$_8$)NHC(O)R$_9$,
  $R_8$ is alkyl, and
  $R_9$ is —OR$_{9a}$.

6. The compound, stereoisomer, ester, prodrug, salt, or combination of claim 1, wherein:
  $R_1$ is alkyl,
  $R_3$ is selected from the group consisting of arylalkyl, alkenyl, alkynyl, cycloalkyl, cycloalkylalkyl, hydroxyalkyl, alkoxyalkyl, arylalkyl, heteroarylalkyl, and heterocyclealkyl,
  $R_4$ is —C(O)C(H)(R$_8$)NHC(O)R$_9$,
  $R_8$ is alkyl, and
  $R_9$ is —OR$_{9a}$.

7. The compound, stereoisomer, ester, prodrug, salt, or combination of claim 1, wherein:
  $R_1$ is alkyl,
  $R_3$ is selected from the group consisting of alkyl, alkenyl, alkynyl, cycloalkyl, cycloalkylalkyl, hydroxyalkyl, alkoxyalkyl, arylalkyl, heteroarylalkyl, and heterocyclealkyl,
  $R_4$ is —C(O)C(H)(R$_8$)NHC(O)R$_9$,
  $R_8$ is alkyl,
  $R_9$ is —OR$_{9a}$, and
  $R_2$ is arylalkyl.

8. The compound, stereoisomer, ester, prodrug, salt, or combination of claim 1, wherein:
  $R_1$ is alkyl,
  $R_3$ is selected from the group consisting of alkyl, alkenyl, alkynyl, cycloalkyl, cycloalkylalkyl, hydroxyalkyl, alkoxyalkyl, arylalkyl, heteroarylalkyl, and heterocyclealkyl,
  $R_4$ is —C(O)C(H)(R$_8$)NHC(O)R$_9$,
  $R_8$ is alkyl,
  $R_9$ is —OR$_{9a}$,
  $R_{9a}$ is alkyl, and
  $R_2$ is arylalkyl.

9. A compound, stereoisomer of the compound, ester of the compound, prodrug of the compound, pharmaceutically acceptable salt of the compound, stereoisomer, ester, or prodrug, or combination thereof, wherein:
  the compound corresponds in structure to formula (II):

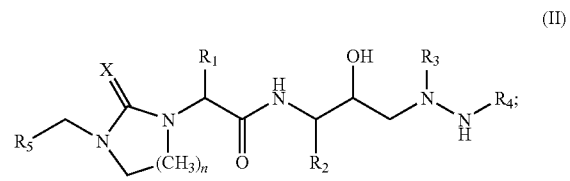

(II)

X is selected from the group consisting of O, S, and NH;

R₁ is selected from the group consisting of alkyl, alkenyl, alkynyl, cycloalkyl, cycloalkenyl, aryl, heteroaryl, arylalkyl, heteroarylalkyl, cycloalkylalkyl, and cycloalkenylalkyl, wherein:
  each R₁ substituent is substituted with 0, 1 or 2 substituents independently selected from the group consisting of halo, haloalkyl, alkyl, alkenyl, cyano, nitro, —OR$_a$, —OalkylC(=O)NR$_a$R$_b$, —SR$_a$, —SOR$_a$, —SO₂R$_a$, —SO₂NR$_a$R$_b$, —C(=O)R$_a$, —NR$_a$R$_b$, —N(R$_b$)C(=O)R$_a$, —N(R$_b$)C(=O)OR$_a$, —N(R$_b$)SO₂R$_a$, —N(R$_b$)SO₂NR$_a$R$_b$, —N(R$_b$)C(NH)NR$_a$R$_b$, —N(R$_b$)C(=O)NR$_a$R$_b$, —C(=O)NR$_a$R$_b$, and —C(=O)OR$_a$;

R₂ is selected from the group consisting of alkyl, alkenyl, alkynyl, cycloalkyl, cycloalkenyl, cycloalkylalkyl, cycloalkenylalkyl, arylalkyl, heterocycle, heterocyclealkyl, and heteroarylalkyl, wherein:
  each R₂ substituent is substituted with 0, 1, or 2 substituents independently selected from the group consisting of alkyl, alkenyl, alkynyl, cyano, halo, formyl, nitro, hydroxy, alkoxy, —NH₂, —N(H)alkyl, —N(alkyl)₂, —N(H)C(=O)Oalkyl, —N(alkyl)C(=O)Oalkyl, —C(=O)OH, —C(=O)Oalkyl, —C(=O)NH₂, —C(=O)N(H)(alkyl), —C(=O)N(alkyl)₂, —C(=O)alkyl, cyanoalkyl, nitroalkyl, formylalkyl, haloalkyl, hydroxyalkyl, alkoxyalkyl, -alkylNH₂, -alkylN(H)alkyl, -alkylN(alkyl)₂, -alkylN(H)C(=O)Oalkyl, -alkylN(alkyl)C(=O)Oalkyl, -alkylC(=O)OH, -alkylC(=O)Oalkyl, -alkylC(=O)NH₂, -alkylC(=O)N(H)(alkyl), -alkylC(=O)N(alkyl)₂, and -alkylC(=O)alkyl;

R₃ is selected from the group consisting of hydrogen, alkyl, haloalkyl, alkenyl, haloalkenyl, alkynyl, haloalkynyl, cycloalkyl, cycloalkenyl, heterocycle, aryl, heteroaryl, cycloalkylalkyl, cycloalkenylalkyl, heterocyclealkyl, heteroarylalkyl, arylalkyl, hydroxyalkyl, alkoxyalkyl, -alkylSR$_a$, -alkylSOR$_a$, -alkylSO₂R$_a$, alkylNR$_a$R$_b$, alkylC(=O)OR$_a$, -alkylN(R$_b$)C(=O)OR$_a$, -alkylN(R$_b$)C(=O)R$_a$, -alkylN(R$_b$)SO₂R$_a$, and -alkylN(R$_b$)SO₂NR$_a$R$_b$, wherein:
  the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl, and aryl moiety of the arylalkyl are substituted with 0, 1, 2, or 3 substituents independently selected from the group consisting of halo, nitro, cyano, formyl, alkyl, alkenyl, alkynyl, hydroxy, alkoxy, —SH, —S(alkyl), —S(haloalkyl), —SO₂(alkyl), —SO₂(haloalkyl), —NH₂, —N(H)(alkyl), —N(alkyl)₂, —N(H)C(=O)alkyl, —N(alkyl)C(=O)alkyl, —C(=O)OH, —C(=O)O(alkyl), —C(=O)NH₂, —C(=O)N(H)(alkyl), —C(=O)N(alkyl)₂, —C(=O)alkyl, haloalkyl, hydroxyalkyl, alkoxyalkyl, cyanoalkyl, formylalkyl, nitroalkyl, -alkylSH, -alkylS(alkyl), -alkylSO₂(alkyl), -alkylNH₂, -alkylN(H)(alkyl), -alkylN(alkyl)₂, -alkylN(H)C(=O)alkyl, -alkylN(alkyl)C(=O)alkyl, -alkylC(=O)OH, -alkylC(=O)O(alkyl), -alkylC(=O)NH₂, -alkylC(=O)N(H)(alkyl), -alkylC(=O)N(alkyl)₂, -alkylC(=O)alkyl, and R$_{3a}$;

R$_{3a}$ is selected from the group consisting of cycloalkyl, cycloalkenyl, aryl, heteroaryl, heterocycle, aryloxy, heteroaryloxy, and heterocycleoxy, wherein:
  each R$_{3a}$ substituent is independently substituted with 0, 1, 2, or 3 substituents independently selected from the group consisting of halo, nitro, cyano, formyl, alkyl, alkenyl, alkynyl, hydroxyl, alkoxy, —SH, —S(alkyl), —SO₂(alkyl), —NH₂, —N(H)(alkyl), —N(alkyl)₂, —N(H)C(=O)alkyl, —N(alkyl)C(=O)alkyl, —C(=O)OH, —C(=O)O(alkyl), —C(=O)NH₂, —C(=O)N(H)(alkyl), —C(=O)N(alkyl)₂, —C(=O)alkyl, haloalkyl, hydroxyalkyl, alkoxyalkyl, cyanoalkyl, formylalkyl, nitroalkyl, -alkylSH, -alkylS(alkyl), -alkylSO₂(alkyl), -alkylNH₂, -alkylN(H)(alkyl), -alkylN(alkyl)₂, -alkylN(H)C(=O)alkyl, -alkylN(alkyl)C(=O)alkyl, -alkylC(=O)OH, -alkylC(=O)O(alkyl), -alkylC(=O)NH₂, -alkylC(=O)N(H)(alkyl), -alkylC(=O)N(alkyl)₂, and -alkylC(=O)alkyl;

R₄ is selected from the group consisting of
  a) —C(O)CH(R₈)NHC(O)R₉,
  b) —C(O)R₉,
  c) —C(O)CH₂—O-aryl, substituted with 0, 1, 2, or 3 substituents independently selected from the group consisting of alkyl, alkenyl, halo, cyano, nitro, formyl, oxo, hydroxyl, alkoxy, hydroxyalkyl, alkoxyalkyl, haloalkyl, cyanoalkyl, aminoalkyl, alkylaminoalkyl, dialkylaminoalkyl, nitroalkyl, —NH₂, —N(H)alkyl, —N(alkyl)₂, —C(=O)alkyl, —C(=O)OH, —C(=O)Oalkyl, —C(=O)NH₂, —C(=O)N(H)(alkyl), and —C(=O)N(alkyl)₂,
  d) —C(=O)CH₂—O-heteroaryl, substituted with 0, 1, 2, or 3 substituents independently selected from the group consisting of alkyl, alkenyl, halo, cyano, nitro, formyl, oxo, hydroxyl, alkoxy, hydroxyalkyl, alkoxyalkyl, haloalkyl, cyanoalkyl, aminoalkyl, alkylaminoalkyl, dialkylaminoalkyl, nitroalkyl, —NH₂, —N(H)alkyl, —N(alkyl)₂, —C(=O)alkyl, —C(=O)OH, —C(=O)Oalkyl, —C(=O)NH₂, —C(=O)N(H)(alkyl), and —C(=O)N(alkyl)₂,

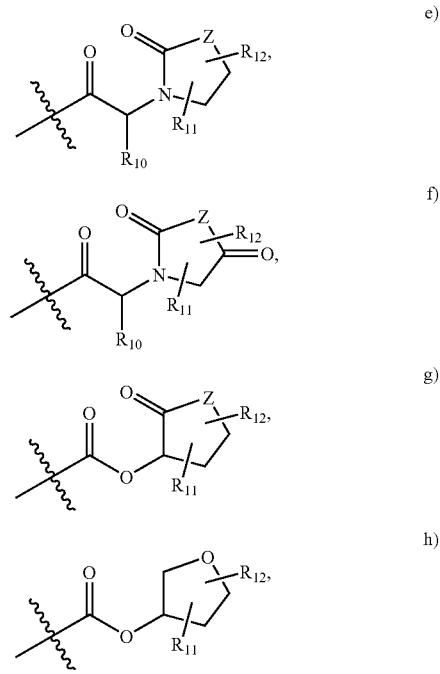

-continued

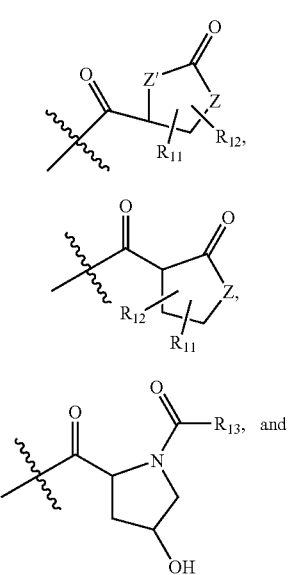

i)

j)

k)

l) —SO$_2$R$_{14}$;

R$_5$ is selected from the group consisting of alkyl, alkenyl, alkynyl, cycloalkyl, cycloalkenyl, aryl, heteroaryl, and heterocycle, wherein:
  each R$_5$ substituent is substituted with 0, 1, 2, or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NHR$_a$, —SO$_2$OR$_3$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NHR$_a$, -alkylSO$_2$OR$_a$, -alkylNR$_a$R$_b$, —C(H)=N(OR$_a$), —C(alkyl)N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$, and R$_{5a}$;

R$_{5a}$ is selected from the group consisting of cycloalkyl, cycloalkenyl, heterocycle, aryl, and heteroaryl, wherein:
  each R$_{5a}$ substituent is substituted with 0, 1, 2, 3, or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)alkyl, -alkylN(alkyl)C(=O)alkyl, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), and -alkylC(=O)N(alkyl)$_2$;

R$_8$ is selected from the group consisting of alkyl, alkenyl, alkynyl, cycloalkyl, aryl, heteroaryl, cycloalkylalkyl, and arylalkyl, wherein:
  each R$_8$ substituent is substituted with 0, 1, or 2 substituents independently selected from the group consisting of halo, cyano, formyl, nitro, alkyl, alkenyl, alkynyl, hydroxy, alkoxy, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), —C(=O)N(alkyl)$_2$, —C(=O)alkyl, hydroxyalkyl, alkoxyalkyl, -alkylNH$_2$, -alkylN(H)alkyl, -alkylN(alkyl)$_2$, -alkylC(=O)OH, -alkylC(=O)Oalkyl, -alkylC(=O)NH$_2$, -alkylC(=O)N(H)(alkyl), and -alkylC(=O)N(alkyl)$_2$;

R$_9$ is selected from the group consisting of alkyl, cycloalkyl, cycloalkylalkyl, aryl, heterocycle, heteroaryl, and OR$_{9a}$, wherein:
  each R$_9$ substituent is substituted with 0, 1, 2, or 3 substituents independently selected from the group consisting of hydroxy, alkoxy, halo, cyano, nitro, formyl, alkyl, alkenyl, alkynyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), and —C(=O)N(alkyl)$_2$;

R$_{9a}$ is selected from the group consisting of alkyl, cycloalkyl, cycloalkylalkyl, aryl, arylalkyl, heterocycle, heteroaryl, heteroarylalkyl, and heterocyclealkyl, wherein:
  each R$_{9a}$ substituent is substituted with 0, 1, 2, or 3 substituents independently selected from the group consisting of hydroxy, alkoxy, halo, cyano, nitro, formyl, alkyl, alkenyl, alkynyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), and —C(=O)N(alkyl)$_2$;

R$_{10}$ is selected from the group consisting of alkyl, alkenyl, alkynyl, cycloalkyl or cycloalkenyl, aryl, heteroaryl, arylalkyl, cycloalkylalkyl, and heteroarylalkyl, wherein:
  each R$_{10}$ substituent is substituted with 0, 1, 2, or 3 substituents independently selected from the group consisting of halo, cyano, nitro, formyl, alkyl, alkenyl, hydroxy, alkoxy, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_b$)SO$_2$NR$_a$R$_b$, —N(R$_b$)C(NH)NR$_a$R$_b$, —N(R$_b$)C(=O)NR$_a$R$_b$, —C(=O)NR$_a$R$_b$, and —C(=O)OR$_a$;

R$_{11}$ is selected from the group consisting of hydrogen, alkyl, haloalkyl, hydroxyalkyl, and alkoxyalkyl;

R$_{12}$ is selected from the group consisting of hydrogen, alkyl, haloalkyl, hydroxyalkyl, and alkoxyalkyl;

R$_{13}$ is selected from the group consisting of alkyl and haloalkyl;

R$_{14}$ is selected from the group consisting of alkyl, cycloalkyl, cycloalkylalkyl, aryl, heteroaryl, and heterocycle, wherein:
  each R$_{14}$ substituent is substituted with 0, 1, 2, or 3 substituents independently selected from the group consisting of halo, cyano, nitro, formyl, alkyl, alkenyl, hydroxy, alkoxy, haloalkyl, —NH$_2$, —N(H)alkyl, —N(alkyl)$_2$, —C(=O)OH, —C(=O)Oalkyl, —C(=O)NH$_2$, —C(=O)N(H)(alkyl), and —C(=O)N(alkyl)$_2$;

Z is selected from the group consisting of —CH$_2$—, —NH—, —O—, and S—;

Z' is selected from the group consisting of —CH$_2$—, —NH—, —O—, and S—;

R$_a$ and R$_b$ at each occurrence are independently selected from the group consisting of hydrogen, alkyl, haloalkyl, alkenyl, alkynyl, cycloalkyl, aryl, heteroaryl, heterocycle, arylalkyl, and heteroarylalkyl, wherein:

each R$_a$ and R$_b$ substituent is substituted with 0, 1, 2, or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, —C(=O)alkyl, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), -alkylC(=O)N(alkyl)$_2$, and alkylC(=O)alkyl; and n is 1.

10. The compound, stereoisomer, ester, prodrug, salt, or combination of claim 9, wherein X is O.

11. The compound, stereoisomer, ester, prodrug, salt, or combination of claim 9, wherein:
X is O, and
R$_1$ is alkyl.

12. The compound, stereoisomer, ester, prodrug, salt, or combination of claim 9, wherein:
X is O,
R$_1$ is alkyl, and
R$_4$ is —C(O)C(H)(R$_8$)NHC(O)R$_9$.

13. The compound, stereoisomer, ester, prodrug, salt, or combination of claim 9, wherein:
X is O,
R$_1$ is alkyl,
R$_4$ is —C(O)C(H)(R$_8$)NHC(O)R$_9$, and
R$_9$ is —OR$_{9a}$.

14. The compound, stereoisomer, ester, prodrug, salt, or combination of claim 9, wherein:
X is O,
R$_1$ is alkyl,
R$_4$ is —C(O)C(H)(R$_8$)NHC(O)R$_9$,
R$_8$ is alkyl, and
R$_9$ is —OR$_{9a}$.

15. The compound, stereoisomer, ester, prodrug, salt, or combination of claim 9, wherein:
X is O,
R$_1$ is alkyl,
R$_3$ is selected from the group consisting of alkyl, alkenyl, alkynyl, cycloalkyl, cycloalkylalkyl, hydroxyalkyl, alkoxyalkyl, arylalkyl, heteroarylalkyl, and heterocyclealkyl,
R$_4$ is —C(O)C(H)(R$_8$)NHC(O)R$_9$,
R$_8$ is alkyl, and
R$_9$ is —OR$_{9a}$.

16. The compound, stereoisomer, ester, prodrug, salt, or combination of claim 9, wherein:
X is O,
R$_1$ is alkyl,
R$_3$ is selected from the group consisting of alkyl, alkenyl, alkynyl, cycloalkyl, cycloalkylalkyl, hydroxyalkyl, alkoxyalkyl, arylalkyl, heteroarylalkyl, and heterocyclealkyl,
R$_4$ is —C(O)C(H)(R$_8$)NHC(O)R$_9$,
R$_8$ is alkyl,
R$_9$ is —OR$_{9a}$, and
R$_2$ is arylalkyl.

17. The compound, stereoisomer, ester, prodrug, salt, or combination of claim 9, wherein:
X is O,
R$_1$ is alkyl,
R$_3$ is selected from the group consisting of alkyl, alkenyl, alkynyl, cycloalkyl, cycloalkylalkyl, hydroxyalkyl, alkoxyalkyl, arylalkyl, heteroarylalkyl, and heterocyclealkyl,
R$_4$ is —C(O)C(H)(R$_8$)NHC(O)R$_9$,
R$_8$ is alkyl,
R$_9$ is —OR$_{9a}$,
R$_{9a}$ is alkyl, and
R$_2$ is arylalkyl.

18. The compound, stereoisomer, ester, prodrug, salt, or combination of claim 9, wherein:
X is O,
R$_1$ is alkyl,
R$_3$ is selected from the group consisting of alkyl, alkenyl, alkynyl, cycloalkyl, cycloalkylalkyl, hydroxyalkyl, alkoxyalkyl, arylalkyl, heteroarylalkyl, and heterocyclealkyl,
R$_4$ is —C(O)C(H)(R$_9$)NHC(O)R$_9$,
R$_8$ is alkyl,
R$_9$ is —OR$_{9a}$,
R$_{9a}$ is alkyl,
R$_2$ is arylalkyl, and
R$_5$ is heteroaryl.

19. The compound, stereoisomer, ester, prodrug, salt, or combination of claim 9, wherein the compound is selected from the group consisting of:

methyl (1S)-1-({2-{(2S,3S)-2-hydroxy-3-[((2S,3S)-3-methyl-2-{3-[2-(6-methyl-2-pyridinyl)ethyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate;

methyl (1S)-1-({2-{(2S,3S)-3-[((2S)-3,3-dimethyl-2-{3-[(1-methyl-1H-benzimidazol-2-yl)methyl]-2-oxo-1-imidazolidinyl}butanoyl)amino]-2-hydroxy-4-phenylbutyl}-2-[4-(2-pyridinyl)benzyl]hydrazino}carbonyl)-2,2-dimethylpropylcarbamate;

methyl (1S)-1-({2-((2S,3S)-2-hydroxy-3-({(2S,3S)-3-methyl-2-[2-oxo-3-(3-pyridinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

methyl (1S)-1-({2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate;

methyl (1S,2S)-1-({2-((2S,3S)-2-hydroxy-3-{[(2S,3S)-2-(3-([2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}carbonyl)-2-methylbutylcarbamate;

tert-butyl 2-[(2S,3S)-2-hydroxy-3-({(2S)-3-methyl-2-[2-oxo-3-(4-quinolinylmethyl)-1-imidazolidinyl]pentanoyl}amino)-4-phenylbutyl]-2-[4-(2-pyridinyl)benzyl]hydrazinecarboxylate;

methyl (1S,2S)-1-({2-((2S,3S)-3-[((2S)-3,3-dimethyl-2-{3-[(1-methyl-1H-benzimidazol-2-yl)methyl]-2-oxo-1-imidazolidinyl}butanoyl)amino]-2-hydroxy-4-phenylbutyl}-2-[4-(2-pyridinyl)benzyl]hydrazino) carbonyl)-2-methylbutylcarbamate;

methyl (1S,2S)-1-({2-((2S,3S)-2-hydroxy-3-{[(2S)-2-(3-{[2-(methoxymethyl)-1,3-thiazol-4-yl]methyl)-2-oxo-1-imidazolidinyl)-3,3-dimethylbutanoyl]amino)-4-phenylbutyl)-2-[4-(2-pyridinyl)benzyl]hydrazino) carbonyl)-2-methylbutylcarbamate;

methyl (1S)-1-({2-((2S,3S)-2-hydroxy-3-{[(2S)-2-(3-{[2-(methoxymethyl)-1,3-thiazol-4-yl]methyl)-2-oxo-1-imidazolidinyl)-3,3-dimethylbutanoyl]amino)-4-phenylbutyl)-2-[4-(2-pyridinyl)benzyl]hydrazino) carbonyl)-2,2-dimethylpropylcarbamate;

methyl (1S,2S)-1-({2-(4-bromobenzyl)-2-[(2S,3S)-2-hydroxy-3-(((2S,3S)-3-methyl-2-[2-oxo-3-(4-quinolinylmethyl)-1-imidazolidinyl]pentanoyl}amino)-4-phenylbutyl]hydrazino}carbonyl)-2-methyl butylcarbamate;

methyl (1S)-1-({2-benzyl-2-[(2S,3S)-2-hydroxy-3-({(2S,3S)-3-methyl-2-[2-oxo-3-(3-pyridinyl methyl)-1-imidazolidinyl]pentanoyl}amino)-4-phenylbutyl]hydrazino) carbonyl)-2,2-dimethylpropyl carbamate;

methyl (1S)-1-[(2-benzyl-2-((2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S,2S)-1-({2-benzyl-2-[(2S,3S)-2-hydroxy-3-({(2S,3S)-3-methyl-2-[2-oxo-3-(3-pyridinylmethyl)-1-imidazolidinyl]pentanoyl)amino)-4-phenylbutyl]hydrazino}carbonyl)-2-methyl butylcarbamate;

methyl (1S)-1-({2-((2S,3S)-3-{[(2S)-3,3-dimethyl-2-(3-{[2-(5-methyl-3-isoxazolyl)-1,3-thiazol-4-yl]methyl}-2-oxo-1-imidazolidinyl)butanoyl]amino]-2-hydroxy-4-phenylbutyl)-2-[4-(2-pyridinyl)benzyl]hydrazino}carbonyl)-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl)pentanoyl)amino]-4-phenylbutyl}-2-(4-methoxybenzyl)hydrazino]carbonyl]-2,2-dimethylpropylcarbamate;

methyl (1S)-1-({2-((2S,3S)-3-{[(2S)-3,3-dimethyl-2-(2-oxo-3-[2-(3-pyridinyl)-1,3-thiazol-4-yl]methyl}-1-imidazolidinyl)butanoyl]amino}-2-hydroxy-4-phenylbutyl)-2-[4-(2-pyridinyl)benzyl]hydrazino) carbonyl)-2,2-dimethylpropylcarbamate;

methyl (1S)-1-({2-((2S,3S)-2-hydroxy-3-{[(2S)-2-(3-{[6-(hydroxymethyl)-2-pyridinyl]methyl)-2-oxo-1-imidazolidinyl)-3,3-dimethylbutanoyl]amino)-4-phenylbutyl)-2-[4-(2-pyridinyl)benzyl]hydrazino}carbonyl)-2,2-dimethylpropylcarbamate;

methyl (1S)-1-({2-[(2S,3S)-2-hydroxy-3-({(2S,3S)-3-methyl-2-[2-oxo-3-((2-methyl-1,3-thiazol-4-yl)-1,3-thiazol-4-ylmethyl)-1-imidazolidinyl]pentanoyl}amino)-4-phenylbutyl]-2-(4-(2-pyridinyl)benzyl]hydrazino}carbonyl)-2,2-dimethylpropylcarbamate;

methyl (1S)-1-({2-{(2S,3S)-3-[((2S)-3,3-dimethyl-2-{3-[(6-methyl-3-pyridinyl)methyl]-2-oxo-1-imidazolidinyl}butanoyl)amino]-2-hydroxy-4-phenylbutyl}-2-[4-(2-pyridinyl)benzyl]hydrazino}carbonyl)-2,2-dimethylpropylcarbamate;

methyl (1S)-1-({2-((2S,3S)-2-hydroxy-3-{[(2S)-2-(3-{[6-(1-hydroxy-1-methylethyl)-2-pyridinyl]methyl}-2-oxo-1-imidazolidinyl)-3,3-dimethylbutanoyl]amino}-4-phenylbutyl)-2-[4-(2-pyridinyl)benzyl]hydrazino}carbonyl)-2,2-dimethylpropylcarbamate;

methyl (1S)-1-((2-((2S,3S)-3-{[(2S)-2-(3-{[2-(2-ethyl-4-pyridinyl)-1,3-thiazol-4-yl]methyl}-2-oxo-1-imidazolidinyl)-3-methylpentanoyl]amino)-2-hydroxy-4-phenylbutyl)-2-[4-(2-pyridinyl)benzyl]hydrazino}carbonyl)-2,2-dimethylpropylcarbamate;

methyl (1S)-1-({2-[(2S,3S)-2-hydroxy-3-(((2S,3S)-3-methyl-2-[2-oxo-3-(2-pyridinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

methyl (1S)-1-({2-((2S,3S)-2-hydroxy-3-[((2S,3S)-3-methyl-2-{3-[(4-methyl-3-pyridinyl)methyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate;

methyl (1S)-1-((2-((2S,3S)-3-[((2S)-3,3-dimethyl-2-{3-[(4-methyl-3-pyridinyl)methyl]-2-oxo-1-imidazolidinyl}butanoyl)amino]-2-hydroxy-4-phenylbutyl)-2-[4-(2-pyridinyl)benzyl]hydrazino}carbonyl)-2,2-dimethylpropylcarbamate;

methyl (1S)-1-({2-[(2S,3S)-3-({(2S)-3,3-dimethyl-2-[2-oxo-3-(4-quinolinylmethyl)-1-imidazolidinyl]butanoyl}amino)-2-hydroxy-4-phenylbutyl]-2-[4-(2-pyridinyl)benzyl]hydrazino}carbonyl)-2,2-dimethylpropylcarbamate;

methyl (1S)-1-({2-((2S,3S)-2-hydroxy-3-{[(2S,3S)-3-methyl-2-(2-oxo-3-{[2-(3-pyridinyl)-1,3-thiazol-4-yl]methyl}-1-imidazolidinyl)pentanoyl]amino}-4-phenylbutyl)-2-[4-(2-pyridinyl)benzyl]hydrazino}carbonyl)-2,2-dimethylpropylcarbamate;

methyl (1S)-1-([2-((2S,3S)-2-hydroxy-3-([(2S)-2-(3-([2-(methoxymethyl)-1,3-thiazol-4-yl]methyl]-2-oxo-1-imidazolidinyl)-3,3-dimethylbutanoyl]amino}-4-phenylbutyl)-2-(4-methoxybenzyl)hydrazino]carbonyl}-2,2-dimethylpropylcarbamate;

methyl (1S)-1-({2-[(2S,3S)-2-hydroxy-3-({(2S,3S)-3-methyl-2-[2-oxo-3-(4-pyridazinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

methyl (1S)-1-({2-((2S,3S)-2-hydroxy-3-{((2S,3S)-3-methyl-2-(2-oxo-3-([2-(trifluoromethyl)-1,3-thiazol-4-yl]methyl}-1-imidazolidinyl)pentanoyl]amino}-4-phenylbutyl)-2-[4-(2-pyridinyl)benzyl]hydrazino}carbonyl)-2,2-dimethylpropylcarbamate;

methyl (1S)-1-((2-{(2S,3S)-2-hydroxy-3-[((2S)-2-{3-[(2-isopropyl-1,3-thiazol-4-yl)methyl]-2-oxo-1-imidazolidinyl)-3,3-dimethylbutanoyl)amino]-4-phenylbutyl}-2-(4-(2-pyridinyl)benzyl]hydrazino}carbonyl)-2,2-dimethylpropylcarbamate;

methyl (1S)-1-[(2-{(2S,3S)-2-hydroxy-3-[((2S)-3-methyl-2-{3-[(6-methyl-2-pyridinyl)methyl]-2-oxo-1-imidazolidinyl}pentanoyl)amino]-4-phenylbutyl}-2-{[2-(5-methyl-3-isoxazolyl)-1,3-thiazol-4-yl]methyl}hydrazino) carbonyl]-2,2-dimethylpropylcarbamate;

methyl (1S,2S)-1-({2-{(2S,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}-2-[4-(2-pyridinyl)benzyl]hydrazino}carbonyl)-2-methylbutylcarbamate;

methyl (1S,2S)-1-({2-{(2S,3S)-3-[((2S)-3,3-dimethyl-2-{3-[(2-methyl-1,3-thiazol-4-yl)methyl]-2-oxo-1-imidazolidinyl}butanoyl)amino]-2-hydroxy-4-phenylbutyl}-2-[4-(2-pyridinyl)benzyl]hydrazino}carbonyl)-2-methylbutylcarbamate;

methyl (1S)-1-[(2-((2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-{[2-(2-pyridinyl)-1,3-thiazol-4-yl]methyl}hydrazino)carbonyl]-2,2-dimethylpropylcarbamate;

methyl (1S)-1-({2-{(2S,3S)-2-hydroxy-3-[((2S)-3-methyl-2-{3-[(2-methyl-1,3-thiazol-4-yl)methyl]-2-oxo-1- imidazolidinyl}butanoyl)amino]-4-phenylbutyl)-2-[4-(2-pyridinyl)benzyl]hydrazino}carbonyl)-2-methylpropylcarbamate;

methyl (1S)-1-({2-{(2S,3S)-3-[((2S)-3,3-dimethyl-2-{3-[(2-methyl-1,3-thiazol-4-yl)methyl]-2-oxo-1-imidazolidinyl}butanoyl)amino]-2-hydroxy-4-phenylbutyl)-2-[4-(2-pyridinyl)benzyl]hydrazino}carbonyl)-2-methylpropylcarbamate;

methyl (1S,2S)-1-({2-{(2S,3S)-2-hydroxy-3-[((2S,3S)-3-methyl-2-{3-[(2-methyl-1,3-thiazol-4-yl)methyl]-2-oxo-1-imidazolidinyl}pentanoyl)amino]-4-phenylbutyl)-2-[4-(2-pyridinyl)benzyl]hydrazino}carbonyl)-2-methylbutylcarbamate;

methyl (1S)-1-({2-{(2S,3S)-2-hydroxy-3-[((2S,3S)-3-methyl-2-{3-[(2-methyl-1,3-thiazol-4-yl)methyl]-2-oxo-1-imidazolidinyl}pentanoyl)amino]-4-phenylbutyl)-2-[4-(2-pyridinyl)benzyl]hydrazino) carbonyl)-2,2-dimethylpropylcarbamate;

methyl (1)-1-({2-{(2S,3S)-3-[((2S)-3,3-dimethyl-2-{3-[(2-methyl-1,3-thiazol-4-yl)methyl]-2-oxo-1-imidazolidinyl}butanoyl)amino]-2-hydroxy-4-phenylbutyl}-2-[4-(2-pyridinyl)benzyl]hydrazino}carbonyl)-2,2-dimethylpropylcarbamate;

methyl (1S)-1-{[2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)-2-(4-methoxybenzyl)hydrazino]carbonyl}-2,2-dimethylpropylcarbamate;

methyl (1S)-1-{[2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]-2-(4-methoxybenzyl)hydrazino]carbonyl)-2,2-dimethylpropylcarbamate;

(2S,3S)—N-((1S,2S)-1-benzyl-2-hydroxy-3-{2-[3-methyl-2-(2-oxo-1-pyrrolidinyl)butanoyl]-1-[4-(2-pyridinyl)benzyl]hydrazino}propyl)-3-methyl-2-{3-[(6-methyl-2-pyridinyl)methyl]-2-oxo-1-imidazolidinyl}pentanamide;

methyl (1S)-1-({2-[(2S,3S)-2-hydroxy-3-({(2S,3S)-3-methyl-2-[2-oxo-3-(3-pyridazinylmethyl)-1-imidazolidinyl]pentanoyl}amino)-4-phenylbutyl]-2-[4-(2-pyridinyl)benzyl]hydrazino) carbonyl)-2,2-dimethylpropylcarbamate;

methyl (1S)-1-((2-{(2S,3S)-3-[((2S)-2-{3-[(6-acetyl-2-pyridinyl)methyl]-2-oxo-1-imidazolidinyl}-3,3-dimethylbutanoyl)amino]-2-hydroxy-4-phenylbutyl}-2-[4-(2-pyridinyl)benzyl]hydrazino}carbonyl)-2,2-dimethylpropylcarbamate;

methyl 6-[(3-{(1S,4S,5S,10S)-4-benzyl-1,10-ditert-butyl-5-hydroxy-2,9,12-trioxo-7-[4-(2-pyridinyl)benzyl]-1,3-oxa-3,7,8,11-tetraazatetradec-1-yl)-2-oxo-1-imidazolidinyl)methyl]-2-pyridinecarboxylate;

methyl (1S)-1-((2-{(2S,3S)-2-hydroxy-3-[((2S,3S)-3-methyl-2-(3-[(6-methyl-2-pyridinyl)methyl]-2-oxo-1-imidazolidinyl}pentanoyl)amino]-4-phenylbutyl)-2-[4-(2-pyridinyl)benzyl]hydrazino}carbonyl)-2,2-dimethylpropylcarbamate;

(2S,3S)—N-((1S,2S)-1-benzyl-2-hydroxy-3-{2-[(2S,3S)-3-methyl-2-(2-oxo-1-imidazolidinyl)pentanoyl]-1-[4-(2-pyridinyl)benzyl]hydrazino) propyl)-3-methyl-2-{3-[(6-methyl-2-pyridinyl)methyl]-2-oxo-1-imidazolidinyl}pentanamide;

methyl (1S)-1-{[2-((2S,3S)-2-hydroxy-3-([(2S)-2-(3-{[6-(1-hydroxy-1-methylethyl)-2-pyridinyl]methyl}-2-oxo-1-imidazolidinyl)-3,3-dimethylbutanoyl]amino}-4-phenylbutyl)-2-(4-methoxybenzyl)hydrazino]carbonyl}-2,2-dimethylpropylcarbamate;

methyl (1S)-1-{[2-((2S,3S)-2-hydroxy-3-{[(2S,3S)-2-(3-{[6-(1-hydroxy-1-methylethyl)-2-pyridinyl]methyl}-2-oxo- 1-imidazolidinyl)-3-methylpentanoyl]amino}-4-phenylbutyl)-2-(4-methoxy benzyl)hydrazino]carbonyl)-2,2-dimethylpropylcarbamate;

methyl (1S)-1-{[2-((2S,3S)-2-hydroxy-3-{[(2S)-2-(3-{[6-(hydroxymethyl)-2-pyridinyl]methyl}-2-oxo-1-imidazolidinyl)-3,3-dimethylbutanoyl]amino)-4-phenylbutyl)-2-(4-methoxybenzyl)hydrazino]carbonyl)-2,2-dimethylpropylcarbamate;

methyl (1S)-1-{[2-((2S,3S)-2-hydroxy-3-{[(2S,3S)-2-(3-([6-(hydroxymethyl)-2-pyridinyl]methyl}-2-oxo-1-imidazolidinyl)-3-methylpentanoyl]amino}-4-phenylbutyl)-2-(4-methoxybenzyl)hydrazino]carbonyl}-2,2-dimethylpropylcarbamate;

methyl (1S)-1-{[2-[(2S,3S)-2-hydroxy-3-(((2S,3S)-3-methyl-2-[2-oxo-3-(8-quinolinylmethyl)-1-imidazolidinyl]pentanoyl}amino)-4-phenylbutyl]-2-(4-methoxybenzyl)hydrazino]carbonyl}-2,2-dimethyl propylcarbamate;

methyl (1S)-1-([2-{(2S,3S)-2-hydroxy-3-[((2S,3S)-3-methyl-2-{3-[(2-methyl-4-quinolinyl)methyl]-2-oxo-1-imidazolidinyl}pentanoyl)amino]-4-phenylbutyl)-2-(4-methoxybenzyl)hydrazino]carbonyl}-2,2-dimethylpropylcarbamate;

methyl (1S)-1-([2-{(2S,3S)-2-hydroxy-3-[((2S,3S)-3-methyl-2-{3-[(3-methyl-3H-imidazo[4,5-b]pyridin-2-yl)methyl]-2-oxo-1-imidazolidinyl}pentanoyl)amino]-4-phenylbutyl}-2-(4-methoxybenzyl)hydrazino]carbonyl}-2,2-dimethylpropylcarbamate;

methyl (1S)-1-({2-[(2S,3S)-2-hydroxy-3-({(2S,3S)-3-methyl-2-[2-oxo-3-(3-pyridazinylmethyl)-1-imidazolidinyl]pentanoyl}amino)-4-phenylbutyl]-2-(4-methoxybenzyl)hydrazino]carbonyl}-2,2-dimethylpropylcarbamate;

methyl (1S)-1-({2-{(2S,3S)-2-hydroxy-3-[((2S,3S)-3-methyl-2-{3-[(5-methyl-2-thienyl)methyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate;

methyl (1S,2S)-1-[(2-benzyl-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2-methylbutylcarbamate;

methyl (1S)-1-({2-[(2S,3S)-3-(((2S,3S)-2-[3-({2-[(1S)-1-(acetylamino)ethyl]-1,3-thiazol-4-yl}methyl)-2-oxo-1-imidazolidinyl]-3-methylpentanoyl}amino)-2-hydroxy-4-phenylbutyl]-2-[4-(2-pyridinyl)benzyl]hydrazino}carbonyl)-2,2-dimethylpropylcarbamate;

(2S,3S)—N-((1S,2S)-1-benzyl-2-hydroxy-3-{2-{[(4S,5R)-5-methyl-2-oxo-1,3-oxazolidin-4-yl]carbonyl}-1-[4-(2-pyridinyl)benzyl]hydrazino}propyl)-3-methyl-2-{3-[(6-methyl-2-pyridinyl)methyl]-2-oxo-1-imidazolidinyl) pentanamide;

methyl (1S) -1-[4-[2-((2S,3S)-2-hydroxy-3-4 [(2S)-2-(3-{[6-(1-hydroxy-1-methylethyl)-2-pyridinyl]methyl)-2-oxo-1-imidazolidinyl)-3,3-dimethylbutanoyl]amino}-4-phenylbutyl)-2-isopentylhydrazino]carbonyl}-2,2-dimethylpropylcarbamate;

methyl (1S)-1-([2-((2S,3S)-2-hydroxy-3-{[(2S,3S)-2-(3-{[6-(1-hydroxy-1-methylethyl)-2-pyridinyl]methyl)-2-oxo-1-imidazol idinyl)-3-methylpentanoyl]amino}-4-phenylbutyl)-2-isopentyl hydrazino]carbonyl}-2,2-dimethylpropylcarbamate;

methyl(1S)-1-{(2-((2S,3S)-2-hydroxy-3-{[(2S)-2-(3-{[6-(hydroxymethyl)-2-pyridinyl]methyl}-2-oxo-1-imidazolidinyl)-3,3-dimethylbutanoyl]amino}-4-phenylbutyl)-2-isopentylhydrazino]carbonyl}-2,2-dimethylpropylcarbamate;

methyl (1S)-1-{[2-((2S,3S)-2-hydroxy-3-([(2S,3S)-2-(3-{[6-(hydroxymethyl)-2-pyridinyl]methyl}-2-oxo-1-imidazolidinyl)-3-methylpentanoyl]amino}-4-phenylbutyl)-2-isopentylhydrazino]carbonyl)-2,2-dimethylpropylcarbamate;

(2S,3S)—N-((1S,2S)-1-benzyl-3-{2-[(2,2-dimethyl-5-oxotetrahydro-3-furanyl)carbonyl]-1-[4-(2-pyridinyl)benzyl]hydrazino}-2-hydroxypropyl)-3-methyl-2-{3-[(6-methyl-2-pyridinyl)methyl]-2-oxo-1-imidazolidinyl}pentanamide;

methyl (1S)-1-{[2-[(2S,3S)-2-hydroxy-3-(({2S,3S)-2-[3-(imidazo[1,5-a]pyridin-3-ylmethyl)-2-oxo-1-imidazolidinyl]-3-methylpentanoyl)amino)-4-phenylbutyl]-2-(4-methoxybenzyl)hydrazino]carbonyl)-2,2-dimethylpropylcarbamate;

(2S,3S)—N-((1S,2S)-1-benzyl-2-hydroxy-3-(2-{[(2S)-5-oxopyrrolidinyl]carbonyl}-1-[4-(2-pyridinyl)benzyl]hydrazino}propyl)-3-methyl-2-{3-[(6-methyl-2-pyridinyl)methyl]-2-oxo-1-imidazolidinyl}pentanamide;

(3S)-4,4-dimethyl-2-oxotetrahydro-3-furanyl 2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-[4-(2-pyridinyl)benzyl]hydrazinecarboxylate;

(3R)-4,4-dimethyl-2-oxotetrahydro-3-furanyl 2-{(2S,3S)-2-hydroxy-3-[((2S,3S)-3-methyl-2-(3-[(6-methyl-2-pyridinyl)methyl]-2-oxo-1-imidazolidinyl}pentanoyl)amino]-4-phenylbutyl}-2-[4-(2-pyridinyl)benzyl]hydrazinecarboxylate;

methyl (1S)-1-({2-((2S,3S)-3-[((2S)-3,3-dimethyl-2-(3-[(6-methyl-2-pyridinyl)methyl]-2-oxo-1-imidazolidinyl}butanoyl)amino]-2-hydroxy-4-phenylbutyl}-2-[4-(2-pyridinyl)benzyl]hydrazino}carbonyl)-2,2-dimethylpropylcarbamate;

methyl (1S)-1-{[2-(2,3-dihydro-1,4-benzodioxin-6-ylmethyl)-2-((2S,3S)-2-hydroxy-3-([(2S,3S)-2-(3-{[2-(methoxymethyl)-1,3-thiazol-4-yl]methyl}-2-oxo-1-imidazolidinyl)-3-methylpentanoyl]amino}-4-phenylbutyl)hydrazino]carbonyl)-2,2-dimethylpropylcarbamate;

methyl (1S)-1-([2-(3,3-dimethylbutyl)-2-((2S,3S)-2-hydroxy-3-([(2S,3S)-2-(3-([2-(methoxy methyl)-1,3-thiazol-4-yl]methyl}-2-oxo-1-imidazolidinyl)-3-methylpentanoyl]amino}-4-phenylbutyl)hydrazino]carbonyl}-2,2-dimethylpropylcarbamate;

(3R)-2-oxotetrahydro-3-furanyl 2-((2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-[4-(2-pyridinyl)benzyl]hydrazinecarboxylate;

(3S)-2-oxotetrahydro-3-furanyl 2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-[4-(2-pyridinyl)benzyl]hydrazinecarboxylate;

methyl (1S)-1-[(2-[4-(diethylamino)benzyl]-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

(2S,3S)—N-((1S,2S)-1-benzyl-3-{2-[(2S)-3,3-dimethyl-2-(2-oxo-1-imidazolidinyl)butanoyl]-1-[4-(2-pyridinyl)benzyl]hydrazino}-2-hydroxypropyl)-3-methyl-2-{3-[(6-methyl-2-pyridinyl)methyl]-2-oxo-1-imidazolidinyl}pentanamide;

methyl (1S)-1-{[2-(2,3-dihydro-1,4-benzodioxin-6-ylmethyl)-2-((2S,3S)-2-hydroxy-3-{[(2S)-2-(3-{[6-(1-hydroxy-1-methylethyl)-2-pyridinyl]methyl}-2-oxo-1-imidazol idinyl)-3,3-dimethylbutanoyl]amino}-4-phenylbutyl)hydrazino]carbonyl}-2,2-dimethylpropylcarbamate;

methyl (1S)-1-{[2-(2,3-dihydro-1,4-benzodioxin-6-ylmethyl)-2-((2S,3S)-2-hydroxy-3-{[(2S)-2-(3-([6-(1-hydroxy-1-methylethyl)-2-pyridinyl]methyl)-2-oxo-1-imidazolidinyl)-3-methylpentanoyl]amino}-4-phenylbutyl)hydrazino]carbonyl}-2,2-dimethylpropylcarbamate;

methyl (1S)-1-{[2-(2,3-dihydro-1,4-benzodioxin-6-ylmethyl)-2-((2S,3S)-2-hydroxy-3-{[(2S)-2-(3-{[6-(hydroxymethyl)-2-pyridinyl]methyl}-2-oxo-1-imidazolidinyl)-3,3-dimethylbutanoyl]amino}-4-phenylbutyl)hydrazino]carbonyl}-2,2-dimethylpropylcarbamate;

methyl (1S)-1-{[2-(2,3-dihydro-1,4-benzodioxin-6-ylmethyl)-2-((2S,3S)-2-hydroxy-3-{[(2S,3S)-2-(3-{[6-(hydroxymethyl)-2-pyridinyl]methyl}-2-oxo-1-imidazolidinyl)-3-methylpentanoyl]amino}-4-phenylbutyl)hydrazino]carbonyl}-2,2-dimethylpropylcarbamate;

(2S,3S)—N-((1S,2S)-1-benzyl-3-{2-[(4,4-dimethyl-2-oxotetrahydro-3-furanyl)carbonyl]-1-[4-(2-pyridinyl)benzyl]hydrazino}-2-hydroxypropyl)-3-methyl-2-{3-[(6-methyl-2-pyridinyl)methyl]-2-oxo-1-imidazolidinyl}pentanamide;

methyl (1S)-1-[(2-benzyl-2-{(2S,3S)-3-[((2S)-3,3-dimethyl-2-{3-[(4-methyl-3-pyridinyl)methyl]-2-oxo-1-imidazolidinyl}butanoyl)amino]-2-hydroxy-4-phenylbutyl}hydrazino)carbonyl]-2,2-dimethyl propylcarbamate;

methyl (1S)-1-{[2-(3,3-dimethylbutyl)-2-((2S,3S)-2-hydroxy-3-{((2S)-2-(3-{[6-(1-hydroxy-1-methylethyl)-2-pyridinyl]methyl}-2-oxo-1-imidazolidinyl)-3,3-dimethylbutanoyl]amino}-4-phenylbutyl)hydrazino]carbonyl}-2,2-dimethylpropylcarbamate;

methyl (1S)-1-{[2-(3,3-dimethylbutyl)-2-((2S,3S)-2-hydroxy-3-{((2S,3S)-2-(3-{[6-(1-hydroxy-1-methylethyl)-2-pyridinyl]methyl}-2-oxo-1-imidazolidinyl)-3-methylpentanoyl]amino}-4-phenylbutyl)hydrazino]carbonyl}-2,2-dimethylpropylcarbamate;

methyl (1S)-1-{[2-(3,3-dimethylbutyl)-2-((2S,3S)-2-hydroxy-3-{[(2S)-2-(3-{[6-(hydroxymethyl)-2-pyridinyl]methyl}-2-oxo-1-imidazolidinyl)-3,3-dimethylbutanoyl]amino}-4-phenylbutyl)hydrazino]carbonyl}-2,2-dimethylpropylcarbamate;

methyl (1S)-1-{[2-(3,3-dimethylbutyl)-2-((2S,3S)-2-hydroxy-3-{[(2S,3S)-2-(3-{[6-(hydroxy methyl)-2-pyridinyl]methyl}-2-oxo-1-imidazolidinyl)-3-methylpentanoyl]amino}-4-phenylbutyl)hydrazino]carbonyl}-2,2-dimethylpropylcarbamate;

methyl (1S)-1-([2-(cyclopropylmethyl)-2-((2S,3S)-2-hydroxy-3-{[(2S)-2-(3-([6-(1-hydroxy-1-methylethyl)-2-pyridinyl]methyl)-2-oxo-1-imidazolidinyl)-3,3-dimethylbutanoyl]amino}-4-phenylbutyl)hydrazino]carbonyl}-2,2-dimethylpropylcarbamate;

methyl (1S)-1-{[2-(cyclopropylmethyl)-2-((2S,3S)-2-hydroxy-3-{[(2S,3S)-2-(3-{[6-(1-hydroxy-1-methylethyl)-2-pyridinyl]methyl}-2-oxo-1-imidazolidinyl)-3-methylpentanoyl]amino}-4-phenylbutyl)hydrazino]carbonyl}-2,2-dimethylpropylcarbamate;

methyl (1S)-1-4 (2-(cyclopropylmethyl)-2-((2S,3S)-2-hydroxy-3-{[(2S)-2-(3-{[6-(hydroxymethyl)-2-pyridinyl]methyl}-2-oxo-1-imidazolidinyl)-3,3-dimethylbutanoyl]amino}-4-phenylbutyl)hydrazino]carbonyl}-2,2-dimethylpropylcarbamate;

methyl (1S)-1-{[2-(cyclopropylmethyl)-2-((2S,3S)-2-hydroxy-3-{[(2S)-2-(3-{[6-(hydroxymethyl)-2-pyridinyl]methyl}-2-oxo-1-imidazolidinyl)-3-methylpentanoyl]amino)-4-phenylbutyl)hydrazino]carbonyl}-2,2-dimethylpropylcarbamate;

methyl (1S,2S)-1-[(2-benzyl-2-{(2S,3S)-2-hydroxy-3-[((2S,3S)-3-methyl-2-{3-[(2-methyl-1,3-thiazol-4-yl)methyl]-2-oxo-1-imidazolidinyl}pentanoyl)amino]-4-phenylbutyl}hydrazino)carbonyl]-2-methylbutylcarbamate;

methyl (1S)-1-({[2-[(2S,3S)-2-hydroxy-3-({(2S,3S)-3-methyl-2-[2-oxo-3-(3-quinolinylmethyl)-1-imidazolidinyl]pentanoyl}amino)-4-phenylbutyl]-2-(4-methoxybenzyl)hydrazino]carbonyl}-2,2-dimethylpropylcarbamate;

methyl (1S)-1-({[2-[(2S,3S)-2-hydroxy-3-({(2S,3S)-3-methyl-2-[2-oxo-3-(2-quinolinylmethyl)-1-imidazolidinyl]pentanoyl}amino)-4-phenylbutyl]-2-(4-methoxybenzyl)hydrazino]carbonyl)-2,2-dimethylpropylcarbamate;

methyl (1S)-1-({2-{(2S,3S)-2-hydroxy-3-[((2S)-4-(methylamino)-2-{3-[(2-methyl-1,3-thiazol-4-yl)methyl]-2-oxo-1-imidazolidinyl}-4-oxobutanoyl)amino]-4-phenylbutyl}-2-(4-methoxybenzyl)hydrazino]carbonyl}-2,2-dimethylpropylcarbamate;

methyl (1S)-1-([2-{(2S,3S)-3-[((2S)-4-(ethylamino)-2-{3-[(2-methyl-1,3-thiazol-4-yl)methyl]-2-oxo-1-imidazolidinyl)-4-oxobutanoyl)amino]-2-hydroxy-4-phenylbutyl}-2-(4-methoxybenzyl)hydrazino]carbonyl}-2,2-dimethylpropylcarbamate;

methyl (1S)-1-[(2-benzyl-2-{(2S,3S)-3-[((2S)-3,3-dimethyl-2-(3-[(6-methyl-2-pyridinyl)methyl]-2-oxo-1-imidazolidinyl}butanoyl)amino]-2-hydroxy-4-phenylbutyl}hydrazino)carbonyl]-2,2-dimethylpropylcarbamate;

methyl (1S)-1-[(2-{(2S,3S)-3-[((2S)-3,3-dimethyl-2-{3-[(6-methyl-2-pyridinyl)methyl]-2-oxo-1-imidazolidinyl}butanoyl)amino]-2-hydroxy-4-phenylbutyl}-2-{[2-(3-pyridinyl)-1,3-thiazol-4-yl]methyl}hydrazino)carbonyl]-2,2-dimethylpropylcarbamate;

methyl (1S)-1-{(2-benzyl-2-((2S,3S)-2-hydroxy-3-{[(2S,3S)-3-methyl-2-(2-oxo-3-{[2-(3-pyridinyl)-1,3-thiazol-4-yl]methyl)-1-imidazolidinyl)pentanoyl]amino)-4-phenylbutyl)hydrazino]carbonyl)-2,2-dimethylpropylcarbamate;

methyl (1S)-1-({2-(3,3-dimethylbutyl)-2-[(2S,3S)-2-hydroxy-3-({(2S,3S)-2-[3-(imidazo[1,5-a]pyridin-3-ylmethyl)-2-oxo-1-imidazolidinyl]-3-methylpentanoyl}amino)-4-phenylbutyl]hydrazino}carbonyl)-2,2-dimethylpropylcarbamate;

methyl (1S)-1-({2-(3,3-dimethylbutyl)-2-[(2S,3S)-2-hydroxy-3-(((2S)-2-[3-(imidazo[1,5-a]pyridin-3-ylmethyl)-2-oxo-1-imidazolidinyl]-3,3-dimethylbutanoyl}amino)-4-phenylbutyl]hydrazino}carbonyl)-2,2-dimethylpropylcarbamate;

methyl (1S)-1-{[2-[(2S,3S)-2-hydroxy-3-({(2S)-2-[3-(imidazo[1,5-a]pyridin-3-ylmethyl)-2-oxo-1-imidazolidinyl]-3,3-dimethylbutanoyl}amino)-4-phenylbutyl]-2-(4-methoxybenzyl)hydrazino]carbonyl}-2,2-dimethylpropylcarbamate;

methyl (1S)-1-({2-(3,3-dimethylbutyl)-2-[(2S,3S)-2-hydroxy-3-(((2S,3S)-3-methyl-2-[2-oxo-3-(4-quinolinylmethyl)-1-imidazolidinyl]pentanoyl}amino)-4-phenylbutyl]hydrazino}carbonyl)-2,2-dimethylpropylcarbamate;

methyl (1S,2S)-1-{[2-((2S,3S)-2-hydroxy-3-[((2S,3S)-3-methyl-2-(3-[(2-methyl-1,3-thiazol-4-yl)methyl]-2-oxo-1-imidazolidinyl}pentanoyl)amino]-4-phenylbutyl}-2-(4-methoxybenzyl)hydrazino]carbonyl}-2-methylbutylcarbamate;

methyl (1S,2S)-1-({2-benzyl-2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]hydrazino}carbonyl)-2-methyl butylcarbamate;

methyl (1S)-1-[(2-(3,3-dimethylbutyl)-2-{(2S,3S)-2-hydroxy-3-[((2S,3S)-2-{3-[(2-isopropyl-1,3-thiazol-4-yl)methyl]-2-oxo-1-imidazolidinyl)-3-methylpentanoyl)amino]-4-phenylbutyl}hydrazino)carbonyl]-2,2-dimethylpropylcarbamate;

methyl (1S)-1-[(2-(3,3-dimethylbutyl)-2-{(2S,3S)-3-[((2S)-3,3-dimethyl-2-{3-[(6-methyl-2-pyridinyl)methyl]-2-oxo-1-imidazolidinyl}butanoyl)amino]-2-hydroxy-4-phenylbutyl}hydrazino)carbonyl]-2,2-dimethylpropylcarbamate;

methyl (1S)-1-{[2-{(2S,3S)-2-hydroxy-3-[((2S,3S)-2-{3-[(2-isopropyl-1,3-thiazol-4-yl)methyl]-2-oxo-1-imidazolidinyl}-3-methylpentanoyl)amino]-4-phenylbutyl}-2-(4-methoxybenzyl)hydrazino]carbonyl}-2,2-dimethylpropylcarbamate;

methyl (1S)-1-({2-{(2S,3S)-2-hydroxy-3-[((2S,3S)-2-{3-[(2-isopropyl-1,3-thiazol-4-yl)methyl]-2-oxo-1-imidazolidinyl}-3-methylpentanoyl)amino]-4-phenylbutyl}-2-[4-(2-pyridinyl)benzyl]hydrazino}carbonyl)-2,2-dimethylpropylcarbamate;

methyl (1S)-1-({2-((2S,3S)-2-hydroxy-3-[((2S,3S)-3-methyl-2-{3-[(6-methyl-3-pyridinyl)methyl]-2-oxo-1-imidazolidinyl}pentanoyl)amino]-4-phenylbutyl}-2-[4-(2-pyridinyl)benzyl]hydrazino}carbonyl)-2,2-dimethylpropylcarbamate;

methyl (1S)-1-{[2-((2S,3S)-2-hydroxy-3-([(2S,3S)-3-methyl-2-(2-oxo-3-{[2-(3-pyridinyl)-1,3-thiazol-4-yl]methyl}-1-imidazolidinyl)pentanoyl]amino}-4-phenylbutyl)-2-(4-methoxybenzyl)hydrazino]carbonyl}-2,2-dimethylpropylcarbamate;

methyl (1S)-1-{[2-((2S,3S)-2-hydroxy-{[(2S,3S)-3-methyl-2-(2-oxo-3-([2-(3-pyridinyl)-1,3-thiazol-4-yl]methyl}-1-imidazolidinyl)pentanoyl]amino}-4-phenylbutyl)-2-isopentylhydrazino]carbonyl}-2,2-dimethylpropylcarbamate;

methyl (1S)-1-{[2-(3,3-dimethylbutyl)-2-((2S,3S)-2-hydroxy-3-{[(2S,3S)-3-methyl-2-(2-oxo-3-([2-(3-pyridinyl)-1,3-thiazol-4-yl]methyl}-1-imidazolidinyl)pentanoyl]amino)-4-phenylbutyl)hydrazino]carbonyl}-2,2-dimethylpropylcarbamate;

methyl (1S)-1-([2-((2S,3S)-3-[((2S)-3,3-dimethyl-2-{3-[(3-methylimidazo[1,5-a]pyridin-1-yl)methyl]-2-oxo-1-imidazolidinyl}butanoyl)amino]-2-hydroxy-4-phenylbutyl}-2-(4-methoxybenzyl)hydrazino]carbonyl)-2,2-dimethylpropylcarbamate;

methyl (1S)-1-[(2-(3,3-dimethylbutyl)-2-{(2S,3S)-3-[((2S)-3,3-dimethyl-2-{3-[(3-methylimidazo[1,5-a]pyridin-1-yl)methyl]-2-oxo-1-imidazolidinyl}butanoyl)amino]-2-hydroxy-4-phenylbutyl}hydrazino)carbonyl]-2,2-dimethylpropylcarbamate;

methyl (1S)-1-{[2-[(2S,3S)-2-hydroxy-3-({(2S)-2-[3-(1H-indazol-3-ylmethyl)-2-oxo-1-imidazolidinyl]-3,3-dimethylbutanoyl}amino)-4-phenylbutyl]-2-(4-methoxybenzyl)hydrazino]carbonyl}-2,2-dimethylpropylcarbamate;

methyl (1S)-1-({2-(3,3-dimethylbutyl)-2-[(2S,3S)-2-hydroxy-3-({(2S)-2-[3-(1H-indazol-3-yl methyl)-2-oxo-1-imidazolidinyl]-3,3-dimethylbutanoyl}amino)-4-phenylbutyl]hydrazino}carbonyl)-2,2-dimethylpropylcarbamate;

methyl (1S)-1-({2-{(2S,3S)-2-hydroxy-3-[((2S,3S)-2-{3-[(6-isopropyl-2-pyridinyl)methyl]-2-oxo-1-imidazolidinyl}-3-methylpentanoyl)amino]-4-phenylbutyl)-2-[4-(2-pyridinyl)benzyl]hydrazino}carbonyl)-2,2-dimethylpropylcarbamate;

methyl (1S)-1-([2-{(2S,3S)-3-[((2S)-3,3-dimethyl-2-{3-[(1-methyl-1H-indazol-3-yl)methyl]-2-oxo-1-imidazolidinyl}butanoyl)amino]-2-hydroxy-4-phenylbutyl}-2-(4-methoxybenzyl)hydrazino]carbonyl}-2,2-dimethylpropylcarbamate;

methyl (1S)-1-[(2-(3,3-dimethylbutyl)-2-{(2S,3S)-3-[((2S)-3,3-dimethyl-2-{3-[(1-methyl-1H-indazol-3-yl)methyl]-2-oxo-1-imidazolidinyl}butanoyl)amino]-2-hydroxy-4-phenylbutyl}hydrazino) carbonyl]-2,2-dimethylpropylcarbamate;

methyl (1S)-1-[2-(3,3-dimethylbutyl)-2-{(2S,3S)-3-[((2S)-3,3-dimethyl-2-(34(2-methyl-1H-benzimidazol-5-yl)methyl]-2-oxo-1-imidazolidinyl}butanoyl)amino]-2-hydroxy-4-phenylbutyl}hydrazino)carbonyl]-2,2-dimethylpropylcarbamate;

methyl (1S)-1-({2-{(2S,3S)-3-[((2S)-2-{3-[(6-tert-butyl-2-pyridinyl)methyl]-2-oxo-1-imidazolidinyl}-3,3-dimethylbutanoyl)amino]-2-hydroxy-4-phenylbutyl}-2-[4-(2-pyridinyl)benzyl]hydrazino) carbonyl)-2,2-dimethylpropylcarbamate;

methyl (1S)-1-((2-((2S,3S)-2-hydroxy-3-{[(2S,3S)-2-(3-{[2-(methoxymethyl)-1,3-thiazol-4-yl]methyl)-2-oxo-1-imidazol idinyl)-3-methylpentanoyl]amino)-4-phenylbutyl)-2-[4-(2-pyridinyl)benzyl]hydrazino) carbonyl)-2,2-dimethylpropylcarbamate;

methyl (1S)-1-({2-((2S,3S)-2-hydroxy-3-{[(2S,3S)-2-(3-([2-(methoxymethyl)-1,3-thiazol-4-yl]methyl)-2-oxo-1-imidazolidinyl)-3-methylpentanoyl]amino}-4-phenylbutyl)-2-[4-(2-pyridinyl)benzyl]hydrazino) carbonyl)-2-methylpropylcarbamate;

methyl 4-hydroxy-2-({2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}carbonyl)-1-pyrrolidinecarboxylate;

methyl (1S,2R)-2-hydroxy-1-({2-((2S,3S)-2-hydroxy-3-(((2S,3S)-2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}carbonyl)propylcarbamate;

methyl (1S)-1-cyclohexyl-2-{2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino}-2-oxoethylcarbamate;

methyl (1S)-1-benzyl-2-(2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)-2-[4-(2-pyridinyl)benzyl]hydrazino)-2-oxoethylcarbamate;

methyl (1S)-1-(cyclohexylmethyl)-2-{2-((2S,3S)-2-hydroxy-3-{[(2S,3S)-2-(3-{[2-(methoxy methyl)-1,3-thiazol-4-yl]methyl)-2-oxo-1-imidazolidinyl)-3-methylpentanoyl]amino}-4-phenylbutyl)-2-[4-(2-pyridinyl)benzyl]hydrazino}-2-oxoethylcarbamate;

methyl (1S)-1-({2-{(2S,3S)-2-hydroxy-3-[((2S)-3-methyl-{3-[(2-methyl-1,3-thiazol-4-yl)methyl]-2-oxo-1-imidazolidinyl}butanoyl)amino]-4-phenylbutyl)-2-[4-(2-pyridinyl)benzyl]hydrazino}carbonyl)-2,2-dimethylpropylcarbamate;

tert-butyl (1S)-1-({2-((2S,3S)-2-hydroxy-3-({(2S,3S)-3-methyl-2-[2-oxo-3-(4-quinolinylmethyl)-1-imidazolidinyl]pentanoyl)amino)-4-phenylbutyl]-2-[4-(2-pyridinyl)benzyl]hydrazino}carbonyl)-2,2-dimethylpropylcarbamate;

methyl (1S)-1-({2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

(3S)-tetrahydro-3-furanyl 2-[(2S,3S)-2-hydroxy-3-({(2S,3S)-3-methyl-2-[2-oxo-3-(4-quinolinyl methyl)-1-imidazolidinyl]pentanoyl}amino)-4-phenylbutyl]-2-[4-(2-pyridinyl) benzyl]hydrazinecarboxylate;

(2S,3S)—N-((1S,2S)-1-benzyl-3-{2-[(2S)-3,3-dimethyl-2-(2-oxo-1-imidazolidinyl)butanoyl]-1-[4-(2-pyridinyl)benzyl]hydrazino)-2-hydroxypropyl)-3-methyl-2-[2-oxo-3-(4-quinolinylmethyl)-1-imidazolidinyl]pentanamide;

(2S,3S)—N-((1S,2S)-1-benzyl-3-{2-[(2,6-dimethylphenoxy)acetyl]-1-[4-(2-pyridinyl)benzyl]hydrazino)-2-hydroxypropyl)-3-methyl-2-[2-oxo-3-(4-quinolinylmethyl)-1-imidazolidinyl]pentanamide;

(2S,3S)—N-((1S,2S)-1-benzyl-2-hydroxy-3-{2-[(2-methylphenoxy)acetyl]-1-[4-(2-pyridinyl)benzyl] hydrazino}propyl)-3-methyl-2-[2-oxo-3-(4-quinolinylmethyl)-1-imidazolidinyl]pentanamide;

(2S,3S)—N-((1S,2S)-1-benzyl-2-hydroxy-3-{2-(3-hydroxy-2-methylbenzoyl)-1-[4-(2-pyridinyl)benzyl]hydrazino}propyl)-3-methyl-2-[2-oxo-3-(4-quinolinylmethyl)-1-imidazolidinyl]pentanamide;

(2S,3S)—N-((1S,2S)-1-benzyl-2-hydroxy-3-{2-[(2S,3S)-3-methyl-2-(2-oxo-1-imidazolidinyl)pentanoyl]-1-[4-(2-pyridinyl)benzyl]hydrazino}propyl)-3-methyl-2-[2-oxo-3-(4-quinolinylmethyl)-1-imidazolidinyl]pentanamide;

(2S,3S)—N-((1S,2S)-1-benzyl-3-{2-[(2S,3S)-2-(2,4-dioxo-1-imidazolidinyl)-3-methylpentanoyl]-1-[4-(2-pyridinyl)benzyl]hydrazino}-2-hydroxypropyl)-3-methyl-2-[2-oxo-3-(4-quinolinylmethyl)-1-imidazolidinyl]pentanamide;

benzyl 2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]-2-[4-(2-pyridinyl)benzyl]hydrazinecarboxylate;

ethyl (1S)-1-({2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]-2-[4-(2-pyridinyl)benzyl]hydrazino}carbonyl)-2,2-dimethylpropylcarbamate;

(2S,3S)—N-((1S,2S)-3-{2-[(2S)-2-(acetylamino)-3,3-dimethylbutanoyl]-1-[4-(2-pyridinyl)benzyl]hydrazino)-1-benzyl-2-hydroxypropyl)-3-methyl-2-[2-oxo-3-(4-quinolinylmethyl)-1-imidazolidinyl]pentanamide;

methyl (1S,2S)-1-({2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]2-[4-(3-pyridinyl)benzyl]hydrazino}carbonyl)-2-methylbutylcarbamate;

methyl (1S,2S)-1-({2-[4-(1,3-benzodioxol-5-yl)benzyl]-2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]hydrazino}carbonyl)-2-methylbutylcarbamate;

methyl (1S,2S)-1-({2-[4-(3,5-dimethyl-4-isoxazolyl)benzyl]-2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]hydrazino) carbonyl)-2-methylbutylcarbamate;

methyl (1S,2S)-1-({2-[(2S,3S)-2-hydroxy-3-({(2S,3S)-3-methyl-2-[2-oxo-3-(4-quinolinylmethyl)-1-imidazolidinyl]pentanoyl}amino)-4-phenylbutyl]-2-(4-(4-pyridinyl)benzyl]hydrazino}carbonyl)-2-methylbutylcarbamate;

methyl (1S)-1-[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethyl propylcarbamate;

methyl (1S)-1-[(2-{(2S,3S)-2-hydroxy-3-[((2S,3S)-3-methyl-2-{3-[2-(6-methyl-2-pyridinyl)ethyl]-2-oxo-1-imidazolidinyl}pentanoyl)amino]-4-phenylbutyl)-2-isopentylhydrazino)carbonyl]-2,2-dimethylpropylcarbamate;

methyl (1S)-1-({2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(4-methylbenzyl)hydrazino]carbonyl}-2,2-dimethylpropylcarbamate;

methyl (1S)-1-[(2-(cyclohexylmethyl)-2-{(2S,3S)-2-hydroxy-3-[((2S,3S)-3-methyl-2-{3-[(6-methyl-2-pyridinyl)

methyl]-2-oxo-1-imidazolidinyl}pentanoyl)amino]-4-phenylbutyl}hydrazino)carbonyl]-2,2-dimethylpropylcarbamate;

methyl (1.5°)-1-[(2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl)-2-isobutylhydrazino)carbonyl]-2,2-dimethylpropylcarbamate;

methyl (1S)-1-([2-((2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(2-phenylethyl)hydrazino]carbonyl)-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl)-2-(2-thienylmethyl)hydrazino]carbonyl}-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl)-2-(2-naphthylmethyl)hydrazino]carbonyl)-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(4-isopropylbenzyl)hydrazino]carbonyl}-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(4-isopropoxybenzyl)hydrazino]carbonyl}-2,2-dimethylpropylcarbamate;

methyl (1S)-1-[(2-(3,4-dimethylbenzyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-{[2-{(2S,3S)-2-hydroxy-3-[((2S,34S)-3-methyl-2-{3-[(6-methyl-2-pyridinyl)methyl]-2-oxo-1-imidazolidinyl}pentanoyl)amino]-4-phenylbutyl}-2-(3-methoxybenzyl)hydrazino]carbonyl}-2,2-dimethylpropylcarbamate;

methyl (1S)-1-[(2-(2-ethylbutyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(4-ethylbenzyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(3-methylbenzyl)hydrazino]carbonyl}-2,2-dimethylpropylcarbamate;

methyl (1S)-1-({2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl)-2-[4-(trifluoromethyl)benzyl]hydrazino}carbonyl)-2,2-dimethylpropylcarbamate;

methyl (1S)-1-[(2-(4-hydroxybenzyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(4-fluorobenzyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-({2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-[3-(4-methylphenoxy)benzyl]hydrazino) carbonyl)-2,2-dimethylpropylcarbamate;

methyl (1S)-1-[(2-[3-(4-chlorophenoxy)benzyl]-2-{(2S,3S)-2-hydroxy-3-{((2S,3S)-3-methyl-2-(3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(2-quinolinylmethyl)hydrazino]carbonyl}-2,2-dimethylpropylcarbamate;

methyl (1S)-1-[(2-[(5-ethyl-2-thienyl)methyl]-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1.5)-1-{[2-{(2S,3S)-2-hydroxy-3-[((2S,3S)-3-methyl-2-(3-[(6-methyl-2-pyridinyl)methyl]-2-oxo-1-imidazolidinyl}pentanoyl)amino]-4-phenylbutyl}-2-(2-octynyl)hydrazino]carbonyl}-2,2-dimethylpropylcarbamate;

methyl 6-(1-{(2S,3S)-2-hydroxy-3-[((2S,3S)-3-methyl-2-(3-[(6-methyl-2-pyridinyl)methyl]-2-oxo-1-imidazolidinyl}pentanoyl)amino]-4-phenylbutyl}-2-{(2.5)-2-[(methoxycarbonyl)amino]-3,3-dimethylbutanoyl}hydrazino)hexanoate;

methyl (1S)-1-[(2-[(5-ethyl-2-furyl)methyl]-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino) carbonyl]-2,2-dimethylpropylcarbamate;

methyl (1.5)-1-({2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl)-2-[4-(1H-imidazol-1-yl)benzyl]hydrazino}carbonyl)-2,2-dimethylpropylcarbamate;

methyl (1S)-1-((2-(3,3-dimethylbutyl)-2-((2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino) carbonyl]-2,2-dimethylpropylcarbamate;

methyl (1S)-1-[(2-[4-(acetylamino)benzyl]-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl 4-[(1-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl)-2-((2S)-2-[(methoxycarbonyl)amino]-3,3-dimethylbutanoyl}hydrazino)methyl]benzoate;

methyl (1S)-1-({2-((2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(3-phenoxybenzyl)hydrazino]carbonyl}-2,2-dimethylpropylcarbamate;

methyl (1S)-1-({2-{(2S,3S)-2-hydroxy-3-[((2S,3S)-3-methyl-2-{3-[(6-methyl-2-pyridinyl)methyl]-2-oxo-1- imidazolidinyl}pentanoyl)amino]-4-phenylbutyl}-2-[3-(4-methoxyphenoxy)benzyl]hydrazino}carbonyl)-2,2-dimethylpropylcarbamate;

methyl (1S)-1-[(2-(4-tert-butylbenzyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino) carbonyl]-2,2-dimethylpropylcarbamate;

methyl (1S)-1-[(2-(2,3-dihydro-1,4-benzodioxin-6-ylmethyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-{4-[(trifluoromethyl)sulfanyl]benzyl}hydrazino)carbonyl]-2,2-dimethylpropylcarbamate;

methyl (1S)-1-[(2-(3,7-dimethyl-6-octenyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(cyclopropylmethyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-[(2-ethyl-1H-imidazol-5-yl)methyl]-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(2,3-dihydro-1-benzofuran-5-ylmethyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(4-chlorobenzyl)-2-{(2S,3S)-2-hydroxy-3-[((2S,3S)-3-methyl-2-(3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(3,4-dimethoxybenzyl)-2-((2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(3-fluoro-4-methoxybenzyl)-2-((2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(1,3-benzodioxol-5-ylmethyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(4-methoxy-3-methylbenzyl)hydrazino]carbonyl}-2,2-dimethylpropylcarbamate;

methyl (1S)-1-[(2-(4-hydroxy-3-methoxybenzyl)-2-{(2S,3S)-2-hydroxy-3-{((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-({2-{(2S,3S)-2-hydroxy-3-[((2S,3S)-3-methyl-2-(3-[(6-methyl-2-pyridinyl)methyl]-2-oxo-1-imidazolidinyl}pentanoyl)amino]-4-phenylbutyl}-2-[4-(methylsulfonyl)benzyl]hydrazino}carbonyl)-2,2-dimethylpropylcarbamate;

methyl (1S)-1-([2-{(2S,3S)-2-hydroxy-3-[((2S,3S)-3-methyl-2-(3-[(6-methyl-2-pyridinyl)methyl]-2-oxo-1-imidazolidinyl}pentanoyl)amino]-4-phenylbutyl}-2-(1H-imidazol-2-ylmethyl)hydrazino]carbonyl]-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(5-hydroxypentyl)hydrazino]carbonyl}-2,2-dimethylpropylcarbamate;

methyl (1S)-1-[(2-[(4,5-dimethyl-2-furyl)methyl]-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(3-chlorobenzyl)-2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(3,5-dimethylbenzyl)-2-((2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-neopentylhydrazino)carbonyl]-2,2-dimethylpropylcarbamate;

methyl (1S)-1-[(2-(1,3-dimethylbutyl)-2-{(2S,3S)hydroxy-3-{((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(4-cyanobenzyl)-2-{(2S,3S)-2-hydroxy-3-[((2S,3S)-3-methyl-2-(3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-cyclohexyl-2-((2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino)carbonyl]-2,2-dimethylpropylcarbamate;

methyl (1S)-1-[(2-(3,4-dichlorobenzyl)-2-((2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}hydrazino) carbonyl]-2,2-dimethylpropylcarbamate;

methyl (1S)-1-[(2-((2S,3S)-2-hydroxy-3-{[(2S)-2-(3-{[2-(methoxymethyl)-1,3-thiazol-4-yl]methyl)-2-oxo-1-imidazolidinyl)-3,3-dimethylbutanoyl]amino]-4-phenylbutyl)-2-{[2-(4-pyridinyl)-1,3-thiazol-4-yl]methyl}hydrazino) carbonyl]-2,2-dimethylpropylcarbamate;

methyl (1S)-1-({2-((2S,3S)-2-hydroxy-3-{[(2S)-2-(3-{[2-(methoxymethyl)-1,3-thiazol-4-yl]methyl}-2-oxo-1-imidazolidinyl)-3,3-dimethylbutanoyl]amino]-4-phenylbutyl)-2-[3-(5-pyrimidinyl)benzyl]hydrazino}carbonyl]-2,2-dimethylpropylcarbamate;

methyl (1S)-1-[(2-((2S,3S)-2-hydroxy-3-{[(2S)-2-(3-{[2-(methoxymethyl)-1,3-thiazol-4-yl]methyl)-2-oxo-1-imidazolidinyl)-3,3-dimethylbutanoyl]amino)-4-phenylbutyl)-2-{[2-(5-methyl-3-isoxazolyl)-1,3-thiazol-4-yl]methyl}hydrazino)carbonyl]-2,2-dimethylpropylcarbamate;

methyl (1S)-1-[(2-((2S,3S)-2-hydroxy-3-{[(2S)-2-(3-{[2-(methoxymethyl)-1,3-thiazol-4-yl]methyl)-2-oxo-1-imidazolidinyl)-3,3-dimethylbutanoyl]amino)-4-phenylbutyl)-2-{[2-(2-pyridinyl)-1,3-thiazol-4-yl]methyl)hydrazino)carbonyl]-2,2-dimethylpropylcarbamate;

methyl (1S)-1-({2-((2S,3S)-2-hydroxy-3-{[(2S)-2-(3-{[2-(methoxymethyl)-1,3-thiazol-4-yl]methyl)-2-oxo-1-imidazolidinyl)-3,3-dimethylbutanoyl]amino)-4-phenylbutyl)-2-[(2-isopropyl-1,3-thiazol-4-yl)methyl]hydrazino}carbonyl)-2,2-dimethylpropylcarbamate;

methyl (1S)-1-{[2-((2S,3S)-2-hydroxy-3-{[(2S,3S)-2-(3-{(2-(methoxymethyl)-1,3-thiazol-4-yl]methyl)-2-oxo-1-imidazolidinyl)-3-methylpentanoyl]amino)-4-phenylbutyl)-2-isopentylhydrazino]carbonyl}-2,2-dimethylpropylcarbamate;

methyl (1S)-1-{[2-(3,4-dimethoxybenzyl)-2-((2S,3S)-2-hydroxy-3-{[(2S,3S)-2-(3-([2-(methoxymethyl)-1,3-thiazol-4-yl]methyl}-2-oxo-1-imidazolidinyl)-3-methylpentanoyl]amino}-4-phenylbutyl)hydrazino]carbonyl}-2,2-dimethylpropylcarbamate;

methyl (1S)-1-{[2-(3,4-dimethylbenzyl)-2-((2S,3S)-2-hydroxy-3-{[(2S,3S)-2-(3-{[2-(methoxymethyl)-1,3-thiazol-4-yl]methyl}-2-oxo-1-imidazolidinyl)-3-methylpentanoyl]amino}-4-phenylbutyl)hydrazino]carbonyl}-2,2-dimethylpropylcarbamate;

methyl (1S)-1-{[2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl}-2-(4-methoxybenzyl)hydrazino]carbonyl)-2-methylbutylcarbamate;

methyl (1S,2S)-1-[(2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl)-2-isopentylhydrazino)carbonyl]-2-methylbutylcarbamate;

methyl (1S,2S)-1-({2-{(2S,3S)-2-hydroxy-3-[((2S,3S)-3-methyl-2-{3-[(6-methyl-2-pyridinyl)methyl]-2-oxo-1-imidazolidinyl}pentanoyl)amino]-4-phenylbutyl)-2-[4-(2-pyridinyl)benzyl]hydrazino}carbonyl)-2-methylbutylcarbamate;

methyl (1S)-1-{[2-{(2S,3S)-3-[((2S)-3,3-dimethyl-2-{3-[2-(6-methyl-2-pyridinyl)ethyl]-2-oxo-1-imidazolidinyl}butanoyl)amino]-2-hydroxy-4-phenylbutyl)-2-(4-methoxybenzyl)hydrazino]carbonyl)-2,2-dimethylpropylcarbamate;

methyl (1S)-1-[(2-{(2S,3S)-3-[((2S)-3,3-dimethyl-2-{3-[2-(6-methyl-2-pyridinyl)ethyl]-2-oxo-1-imidazolidinyl}butanoyl)amino]-2-hydroxy-4-phenylbutyl)-2-isopentylhydrazino)carbonyl]-2,2-dimethylpropylcarbamate;

methyl (1S)-1-([2-{(2S,3S)-3-[((2S)-3,3-dimethyl-2-(3-[(4-methyl-3-pyridinyl)methyl]-2-oxo-1-imidazolidinyl}butanoyl)amino]-2-hydroxy-4-phenylbutyl)-2-(4-methoxybenzyl)hydrazino]carbonyl)-2,2-dimethylpropylcarbamate;

methyl (1S)-1-[(2-{(2S,3S)-3-[((2S)-3,3-dimethyl-2-(3-[(4-methyl-3-pyridinyl)methyl]-2-oxo-1-imidazolidinyl}butanoyl)amino]-2-hydroxy-4-phenylbutyl)-2-isopentylhydrazino)carbonyl]-2,2-dimethylpropylcarbamate; and methyl (1S)-1-([2-((2S,3S)-2-hydroxy-3-[((2S,3S)-3-methyl-2-(3-[2-(6-methyl-2-pyridinyl)ethyl]-2-oxo-1-imidazolidinyl}pentanoyl)amino]-4-phenylbutyl)-2-(4-pyridinylmethyl)hydrazino]carbonyl}-2,2-dimethylpropylcarbamate.

20. A compound, stereoisomer of the compound, ester of the compound, prodrug of the compound, pharmaceutically acceptable salt of the compound, stereoisomer, ester, or prodrug, or combination thereof, wherein:
the compound corresponds in structure to formula (III):

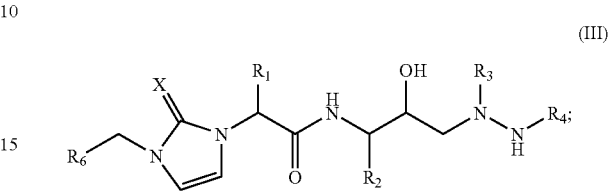

X is selected from the group consisting of O, S, and NH;
$R_1$ is selected from the group consisting of alkyl, alkenyl, alkynyl, cycloalkyl, cycloalkenyl, aryl, heteroaryl, arylalkyl, heteroarylalkyl, cycloalkylalkyl, and cycloalkenylalkyl, wherein:
each $R_1$ substituent is substituted with 0, 1, or 2 substituents independently selected from the group consisting of halo, haloalkyl, alkyl, alkenyl, cyano, nitro, —$OR_a$, —$OalkylC(=O)NR_aR_b$, —$SR_a$, —$SOR_a$, —$SO_2R_a$, —$SO_2NR_aR_b$, —$C(=O)R_a$, —$NR_aR_b$, —$N(R_b)C(=O)R_a$, —$N(R_b)C(=O)OR_a$, —$N(R_b)SO_2R_a$, —$N(R_b)SO_2NR_aR_b$, —$N(R_b)C(=NH)NR_aR_b$, —$N(R_b)C(=O)NR_aR_b$, —$C(=O)NR_aR_b$, and —$C(=O)OR_a$;
$R_2$ is selected from the group consisting of alkyl, alkenyl, alkynyl, cycloalkyl, cycloalkenyl, cycloalkylalkyl, cycloalkenylalkyl, arylalkyl, heterocycle, heterocyclealkyl, and heteroarylalkyl, wherein:
each $R_2$ substituent is substituted with 0, 1, or 2 substituents independently selected from the group consisting of alkyl, alkenyl, alkynyl, cyano, halo, formyl, nitro, hydroxy, alkoxy, —$NH_2$, —N(H)alkyl, —$N(alkyl)_2$, —N(H)C(=O)Oalkyl, —N(alkyl)C(=O)Oalkyl, —C(=O)OH, —C(=O)Oalkyl, —$C(=O)NH_2$, —C(=O)N(H)(alkyl), —$C(=O)N(alkyl)_2$, —C(=O)alkyl, cyanoalkyl, nitroalkyl, formylalkyl, haloalkyl, hydroxyalkyl, alkoxyalkyl, -alkyl$NH_2$, -alkylN(H)alkyl, -alkyl$N(alkyl)_2$, -alkylN(H)C(=O)Oalkyl, -alkylN(alkyl)C(=O)Oalkyl, -alkylC(=O)OH, -alkylC(=O)Oalkyl, -alkylC(=O)$NH_2$, -alkylC(=O)N(H)(alkyl), -alkylC(=O)$N(alkyl)_2$, and -alkylC(=O)alkyl;
$R_3$ is selected from the group consisting of hydrogen, alkyl, haloalkyl, alkenyl, haloalkenyl, alkynyl, haloalkynyl, cycloalkyl, cycloalkenyl, heterocycle, aryl, heteroaryl, cycloalkylalkyl, cycloalkenylalkyl, heterocyclealkyl, heteroarylalkyl, arylalkyl, hydroxyalkyl, alkoxyalkyl, -alkyl$SR_a$, -alkyl$SOR_a$, -alkyl$SO_2R_a$, -alkyl$NR_aR_b$, -alkylC(=O)$OR_a$, -alkylN($R_b$)C(=O)$OR_a$, -alkylN($R_b$)C(=O)$R_a$, -alkylN($R_b$)$SO_2R_a$, and -alkylN($R_b$)$SO_2NR_aR_b$, wherein:
the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl, and aryl moiety of the arylalkyl are substituted with 0, 1, 2, or 3 substituents independently selected from the group consisting of halo, nitro, cyano, formyl, alkyl, alkenyl, alkynyl, hydroxy, alkoxy, —SH, —S(alkyl), —S(haloalkyl), —SO$_2$(alkyl), —SO$_2$(haloalkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$, -alkylC(=O)alkyl, and R$_{3a}$;

R$_{3a}$ is selected from the group consisting of cycloalkyl, cycloalkenyl, aryl, heteroaryl, heterocycle, aryloxy, heteroaryloxy, and heterocycleoxy, wherein:

each R$_{3a}$ substituent is substituted with 0, 1, 2, or 3 substituents independently selected from the group consisting of halo, nitro, cyano, formyl, alkyl, alkenyl, alkynyl, hydroxyl, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$, and -alkylC(=O)alkyl;

R$_4$ is selected from the group consisting of
a) —C(O)CH(R$_8$)NHC(O)R$_9$,
b) —C(O)R$_9$,
c) —C(O)CH$_2$—O-aryl, substituted with 0, 1, 2, or 3 substituents independently selected from the group consisting of alkyl, alkenyl, halo, cyano, nitro, formyl, oxo, hydroxyl, alkoxy, hydroxyalkyl, alkoxyalkyl, haloalkyl, cyanoalkyl, aminoalkyl, alkylaminoalkyl, dialkylaminoalkyl, nitroalkyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), and —C(=O)N(alkyl)$_2$,
d) —C(O)CH$_2$—O-heteroaryl, substituted with 0, 1, 2, or 3 substituents independently selected from the group consisting of alkyl, alkenyl, halo, cyano, nitro, formyl, oxo, hydroxyl, alkoxy, hydroxyalkyl, alkoxyalkyl, haloalkyl, cyanoalkyl, aminoalkyl, alkylaminoalkyl, dialkylaminoalkyl, nitroalkyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), and —C(=O)N(alkyl)$_2$, e)
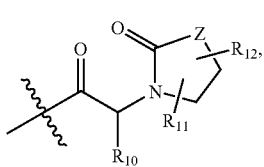

f)
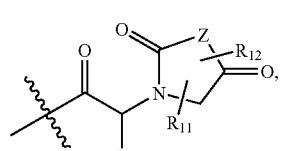

g)
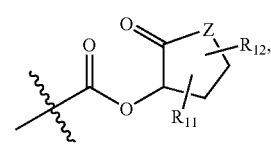

h)
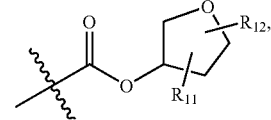

i)
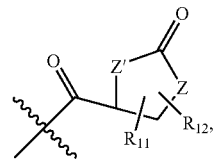

j)
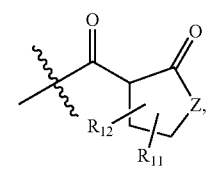

k)
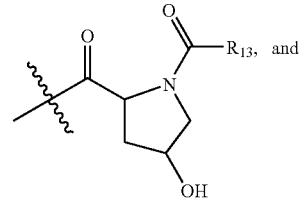

l) —SO$_2$R$_{14}$;

R$_6$ is selected from the group consisting of alkyl, alkenyl, alkynyl, cycloalkyl, cycloalkenyl, aryl, heteroaryl, and heterocycle, wherein:

each R$_6$ substituent is substituted with 0, 1, 2, or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NHR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NHR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN($R_b$)SO$_2$NR$_a$R$_b$, -alkylN($R_b$)SO$_2$R$_a$, -alkylC(=O)R$_a$, -alkylC(=O)OR$_a$, -alkylC(=O)NR$_a$R$_b$, and R$_{6a}$;

R$_{6a}$ is selected from the group consisting of cycloalkyl, cycloalkenyl, heterocycle, aryl, and heteroaryl, wherein:
  each R$_{6a}$ substituent is substituted with 0, 1, 2, 3, or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)alkyl, -alkylN(alkyl)C(=O)alkyl, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), and -alkylC(=O)N(alkyl)$_2$;

R$_8$ is selected from the group consisting of alkyl, alkenyl, alkynyl, cycloalkyl, aryl, heteroaryl, cycloalkylalkyl, and arylalkyl, wherein:
  each R$_8$ substituent is substituted with 0, 1, or 2 substituents independently selected from the group consisting of halo, cyano, formyl, nitro, alkyl, alkenyl, alkynyl, hydroxy, alkoxy, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), —C(=O)N(alkyl)$_2$, —C(=O)alkyl, hydroxyalkyl, alkoxyalkyl, -alkylNH$_2$, -alkylN(H)alkyl, -alkylN(alkyl)$_2$, -alkylC(=O)OH, -alkylC(=O)Oalkyl, -alkylC(=O)NH$_2$, -alkylC(=O)N(H)(alkyl), and -alkylC(=O)N(alkyl)$_2$;

R$_9$ is selected from the group consisting of alkyl, cycloalkyl, cycloalkylalkyl, aryl, heterocycle, heteroaryl, and OR$_{9a}$, wherein:
  each R$_9$ substituent is substituted with 0, 1, 2, or 3 substituents independently selected from the group consisting of hydroxy, alkoxy, halo, cyano, nitro, formyl, alkyl, alkenyl, alkynyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), and —C(=O)N(alkyl)$_2$;

R$_{9a}$ is selected from the group consisting of alkyl, cycloalkyl, cycloalkylalkyl, aryl, arylalkyl, heterocycle, heteroaryl, heteroarylalkyl, and heterocyclealkyl, wherein:
  each R$_{9a}$ substituent is substituted with 0, 1, 2, or 3 substituents independently selected from the group consisting of hydroxy, alkoxy, halo, cyano, nitro, formyl, alkyl, alkenyl, alkynyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), and —C(=O)N(alkyl)$_2$;

R$_{10}$ is selected from the group consisting of alkyl, alkenyl, alkynyl, cycloalkyl or cycloalkenyl, aryl, heteroaryl, arylalkyl, cycloalkylalkyl, and heteroarylalkyl, wherein:
  each R$_{10}$ substituent is substituted with 0, 1, 2, or 3 substituents independently selected from the group consisting of halo, cyano, nitro, formyl, alkyl, alkenyl, hydroxy, alkoxy, —SR$_a$, —SOR$_a$, —SO$_2$R$_a$, —SO$_2$NR$_a$R$_b$, —C(=O)R$_a$, —NR$_a$R$_b$, —N($R_b$)C(=O)R$_a$, —N($R_b$)C(=O)OR$_a$, —N($R_b$)SO$_2$R$_a$, —N($R_b$)SO$_2$NR$_a$R$_b$, —N($R_b$)C(=NH)NR$_a$R$_b$, IN($R_b$)C(=O)NR$_a$R$_b$, —C(=O)NR$_a$R$_b$, and —C(=O)OR$_a$;

R$_{11}$ is selected from the group consisting of hydrogen, alkyl, haloalkyl, hydroxyalkyl, and alkoxyalkyl;

R$_{12}$ is selected from the group consisting of hydrogen, alkyl, haloalkyl, hydroxyalkyl, and alkoxyalkyl;

R$_{13}$ is selected from the group consisting of alkyl and haloalkyl;

R$_{14}$ is selected from the group consisting of alkyl, cycloalkyl, cycloalkylalkyl, aryl, heteroaryl, and heterocycle, wherein:
  each R$_{14}$ substituent is substituted with 0, 1, 2, or 3 independently substituents selected from the group consisting of halo, cyano, nitro, formyl, alkyl, alkenyl, hydroxy, alkoxy, haloalkyl, —NH$_2$, —N(H)alkyl, —N(alkyl)$_2$, —C(=O)OH, —C(=O)Oalkyl, —C(=O)NH$_2$, —C(=O)N(H)(alkyl), and —C(=O)N(alkyl)$_2$;

Z is selected from the group consisting of —CH$_2$—, —NH—, —O—, and —S—;

Z' is selected from the group consisting of —CH$_2$—, —NH—, —O—, and —S—; and

R$_a$ and R$_b$ at each occurrence are independently selected from the group consisting of hydrogen, alkyl, haloalkyl, alkenyl, alkynyl, cycloalkyl, aryl, heteroaryl, heterocycle, arylalkyl, and heteroarylalkyl, wherein:
  each R$_a$ and R$_b$ substituent is substituted with 0, 1, 2, or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, —C(=O)alkyl, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), -alkylC(=O)N(alkyl)$_2$, and alkylC(=O)alkyl.

21. The compound, stereoisomer, ester, prodrug, salt, or combination of claim 20, wherein X is O.

22. The compound, stereoisomer, ester, prodrug, salt, or combination of claim 21, wherein:
  X is O, and
  R$_1$ is alkyl.

23. The compound, stereoisomer, ester, prodrug, salt, or combination of claim 20, wherein:
  X is O,
  R$_1$ is alkyl, and
  R$_4$ is —C(O)C(H)(R$_8$)NHC(O)R$_9$.

24. The compound, stereoisomer, ester, prodrug, salt, or combination of claim 20, wherein:
  X is O,
  R$_1$ is alkyl,
  R$_4$ is —C(O)C(H)(R$_8$)NHC(O)R$_9$, and
  R$_9$ is —OR$_{9a}$.

25. The compound, stereoisomer, ester, prodrug, salt, or combination of claim 20, wherein:
  X is O,
  R$_1$ is alkyl,
  R$_4$ is —C(O)C(H)(R$_8$)NHC(O)R$_9$, $R_8$ is alkyl, and $R_9$ is —$OR_{9a}$.

26. The compound, stereoisomer, ester, prodrug, salt, or combination of claim 20, wherein:

X is O, $R_1$ is alkyl, $R_3$ is selected from the group consisting of alkyl, alkenyl, alkynyl, cycloalkyl, cycloalkylalkyl, hydroxyalkyl, alkoxyalkyl, arylalkyl, heteroarylalkyl, and heterocyclealkyl, $R_4$ is —C(O)C(H)($R_8$)NHC(O)$R_9$, $R_8$ is alkyl, and $R_9$ is —$OR_{9a}$.

27. The compound, stereoisomer, ester, prodrug, salt, or combination of claim 20, wherein:

X is O, $R_1$ is alkyl, $R_3$ is selected from the group consisting of alkyl, alkenyl, alkynyl, cycloalkyl, cycloalkylalkyl, hydroxyalkyl, alkoxyalkyl, arylalkyl, heteroarylalkyl, and heterocyclealkyl, $R_4$ is —C(O)C(H)($R_8$)NHC(O)$R_9$, $R_8$ is alkyl, $R_9$ is —$OR_{9a}$, and $R_2$ is arylalkyl.

28. The compound, stereoisomer, ester, prodrug, salt, or combination of claim 20, wherein:

X is O, $R_1$ is alkyl, $R_3$ is selected from the group consisting of alkyl, alkenyl, alkynyl, cycloalkyl, cycloalkylalkyl, hydroxyalkyl, alkoxyalkyl, arylalkyl, heteroarylalkyl, and heterocyclealkyl, $R_4$ is —C(O)C(H)($R_8$)NHC(O)$R_9$, $R_8$ is alkyl, $R_9$ is —$OR_{9a}$, $R_{9a}$ is alkyl, and $R_2$ is arylalkyl.

29. The compound, stereoisomer, ester, prodrug, salt, or combination of claim 20, wherein:

X is O, $R_1$ is alkyl, $R_3$ is selected from the group consisting of alkyl, alkenyl, alkynyl, cycloalkyl, cycloalkylalkyl, hydroxyalkyl, alkoxyalkyl, arylalkyl, heteroarylalkyl, and heterocyclealkyl, $R_4$ is —C(O)C(H)($R_8$)NHC(O)$R_9$, $R_8$ is alkyl, $R_9$ is —$OR_{9a}$, $R_{9a}$ is alkyl, $R_2$ is arylalkyl, and $R_6$ is heteroaryl.

30. A compound, stereoisomer of the compound, ester of the compound, prodrug of the compound, pharmaceutically acceptable salt of the compound, stereoisomer, ester, or prodrug, or combination thereof, wherein:

the compound corresponds in structure to formula (IV):

(IV)

X is selected from the group consisting of O, S, and NH;

Y is selected from the group consisting of O, S, and NH;

$R_1$ is selected from the group consisting of alkyl, alkenyl, alkynyl, cycloalkyl, cycloalkenyl, aryl, heteroaryl, arylalkyl, heteroarylalkyl, cycloalkylalkyl, and cycloalkenylalkyl, wherein:

each $R_1$ substituent is substituted with 0, 1, or 2 substituents independently selected from the group consisting of halo, haloalkyl, alkyl, alkenyl, cyano, nitro, —$OR_a$, —OalkylC(=O)$NR_aR_b$, —$SR_a$, —$SOR_a$, —$SO_2R_a$, —$SO_2NR_aR_b$, —C(=O)$R_a$, —$NR_aR_b$, —N($R_b$)C(=O)$R_a$, —N($R_b$)C(=O)$OR_a$, —N($R_b$)$SO_2R_a$, —N($R_b$)$SO_2NR_aR_b$, —N($R_b$)C(=NH)$NR_aR_b$, —N($R_b$)C(=O)$NR_aR_b$, —C(=O)$NR_aR_b$, and —C(=O)$OR_a$;

$R_2$ is selected from the group consisting of alkyl, alkenyl, alkynyl, cycloalkyl, cycloalkenyl, cycloalkylalkyl, cycloalkenylalkyl, arylalkyl, heterocycle, heterocyclealkyl, and heteroarylalkyl, wherein:

each $R_2$ substituent is substituted with 0, 1, or 2 substituents independently selected from the group consisting of alkyl, alkenyl, alkynyl, cyano, halo, formyl, nitro, hydroxy, alkoxy, —$NH_2$, —N(H)alkyl, —N(alkyl)$_2$, —N(H)C(=O)Oalkyl, —N(alkyl)C(=O)Oalkyl, —C(=O)OH, —C(=O)Oalkyl, —C(=O)$NH_2$, —C(=O)N(H)(alkyl), —C(=O)N(alkyl)$_2$, —C(=O)alkyl, cyanoalkyl, nitroalkyl, formylalkyl, haloalkyl, hydroxyalkyl, alkoxyalkyl, -alkyl$NH_2$, -alkylN(H)alkyl, -alkylN(alkyl)$_2$, -alkylN(H)C(=O)Oalkyl, -alkylN(alkyl)C(=O)Oalkyl, -alkylC(=O)OH, -alkylC(=O)Oalkyl, -alkylC(=O)$NH_2$, -alkylC(=O)N(H)(alkyl), -alkylC(=O)N(alkyl)$_2$, and -alkylC(=O)alkyl;

$R_3$ is selected from the group consisting of hydrogen, alkyl, haloalkyl, alkenyl, haloalkenyl, alkynyl, haloalkynyl, cycloalkyl, cycloalkenyl, heterocycle, aryl, heteroaryl, cycloalkylalkyl, cycloalkenylalkyl, heterocyclealkyl, heteroarylalkyl, arylalkyl, hydroxyalkyl, alkoxyalkyl, -alkyl$SR_a$, -alkyl$SOR_a$, -alkyl$SO_2R_a$, alkyl$NR_aR_b$, -alkylC(=O)$OR_a$, -alkylN($R_b$)C(=O)$OR_a$, -alkylN($R_b$)C(=O)$R_a$, -alkylN($R_b$)$SO_2R_a$, and -alkylN($R_b$)$SO_2NR_aR_b$, wherein:

the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl, and aryl moiety of the arylalkyl are substituted with 0, 1, 2, or 3 substituents independently selected from the group consisting of halo, nitro, cyano, formyl, alkyl, alkenyl, alkynyl, hydroxy, alkoxy, —SH, —S(alkyl), —S(haloalkyl), —$SO_2$(alkyl), —$SO_2$(haloalkyl), —$NH_2$, —N(H)(alkyl), —N(alkyl)$_2$, —N(H)C(=O)alkyl, —N(alkyl)C(=O)alkyl, —C(=O)OH, —C(=O)O (alkyl), —C(=O)NH₂, —C(=O)N(H)(alkyl), —C(=O)N(alkyl)₂, —C(=O)alkyl, haloalkyl, hydroxyalkyl, alkoxyalkyl, cyanoalkyl, formylalkyl, nitroalkyl, -alkylSH, -alkylS(alkyl), -alkylSO₂ (alkyl), -alkylNH₂, -alkylN(H)(alkyl), -alkylN (alkyl)₂, -alkylN(H)C(=O)alkyl, -alkylN(alkyl)C (=O)alkyl, -alkylC(=O)OH, -alkylC(=O)alkyl, and R₃ₐ;

R₃ₐ is selected from the group consisting of cycloalkyl, cycloalkenyl, aryl, heteroaryl, heterocycle, aryloxy, heteroaryloxy, and heterocycleoxy, wherein:
  each R₃ substituent is substituted with 0, 1, 2, or 3 substituents independently selected from the group consisting of halo, nitro, cyano, formyl, alkyl, alkenyl, alkynyl, hydroxyl, alkoxy, —SH, —S(alkyl), —SO₂(alkyl), —NH₂, —N(H)(alkyl), —N(alkyl)₂, —N(H)C(=O)alkyl, —C(=O)N(alkyl), —C(=O)alkyl, haloalkyl, hydroxyalkyl, alkoxyalkyl, cyanoalkyl, formylalkyl, nitroalkyl, -alkylSH, -alkylS(alkyl), -alkylSO₂(alkyl), -alkylNH₂, -alkylN(H)(alkyl), -alkylN(alkyl)₂, -alkylN(H)C(=O)alkyl, -alkylN(alkyl)C(=O)alkyl, -alkylC(=O)OH, -alkylC(=O)O(alkyl), -alkylC(=O)NH₂, -alkylC(=O)N(H)(alkyl), -alkylC(=O)N(alkyl)₂, and -alkylC(=O)alkyl;

R₄ is selected from the group consisting of
  a) —C(O)CH(R₈)NHC(O)R₉,
  b) —C(O)R₉,
  c) —C(O)CH₂—O-aryl, substituted with 0, 1, 2, or 3 substituents independently selected from the group consisting of alkyl, alkenyl, halo, cyano, nitro, formyl, oxo, hydroxyl, alkoxy, hydroxyalkyl, alkoxyalkyl, haloalkyl, cyanoalkyl, aminoalkyl, alkylaminoalkyl, dialkylaminoalkyl, nitroalkyl, —NH₂, —N(H)alkyl, —N(alkyl)₂, —C(=O)alkyl, —C(=O)OH, —C(=O)Oalkyl, —C(=O)NH₂, —C(=O)N(H)(alkyl), and —C(=O)N(alkyl)₂,
  d) —C(=O)CH₂—O-heteroaryl, substituted with 0, 1, 2, or 3 substituents independently selected from the group consisting of alkyl, alkenyl, halo, cyano, nitro, formyl, oxo, hydroxyl, alkoxy, hydroxyalkyl, alkoxyalkyl, haloalkyl, cyanoalkyl, aminoalkyl, alkylaminoalkyl, dialkylaminoalkyl, nitroalkyl, —NH₂, —N(H)alkyl, —N(alkyl)₂, —C(=O)alkyl, —C(=O)OH, —C(=O)Oalkyl, —C(=O)NH₂, —C(=O)N(H)(alkyl), and —C(=O)N(alkyl)₂, e)
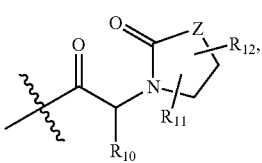

f)
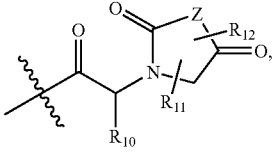

g)
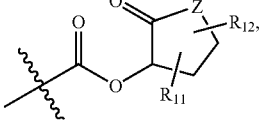

h)
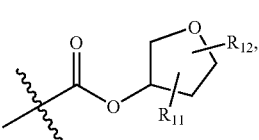

i)
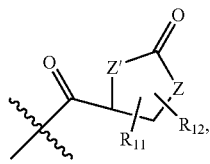

j)
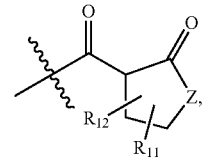

k)
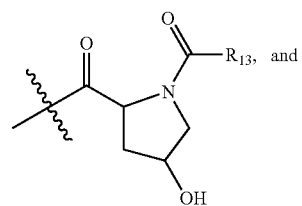

l) —SO₂R₁₄;

R₇ is selected from the group consisting of alkyl, alkenyl, alkynyl, cycloalkyl, cycloalkenyl, aryl, heteroaryl, and heterocycle, wherein:
  each R₇ substituent is substituted with 0, 1, 2, or 3 substituents independently selected from the group consisting of alkyl, alkenyl, alkynyl, cyano, halo, nitro, oxo, —ORₐ, —OC(=O)Rₐ, —SRₐ, —SORₐ, —SO₂Rₐ, SO₂NHR₂, —SO₂ORₐ, —NRₐRᵦ, —N(Rᵦ)NRₐRᵦ, —N(Rᵦ)C(=O)Rₐ, —N(Rᵦ)SO₂Rₐ, —N(Rᵦ)C(=O)ORₐ, —N(Rᵦ)C(=O)NRₐRᵦ, —N(Rᵦ)SO₂NRₐRᵦ, —C(=O)Rₐ, —C(=O)NRₐRᵦ, —C(=O)ORₐ, azidoalkyl, haloalkyl, nitroalkyl, cyanoalkyl, -alkylORₐ, -alkylOC(=O)Rₐ, -alkylSRₐ, -alkylSORₐ, -alkylSO₂Rₐ, -alkylSO₂NRₐ, -alkylSO₂ORₐ, -alkylNRₐRᵦ, —C(H)=N(ORₐ), —C(alkyl)N(ORₐ), —C(H)NNRₐRᵦ, —C(alkyl)=NNRₐRᵦ, —C(H)(=NORₐ)NRₐRᵦ, —C(alkyl)(=NORₐ)NRₐRᵦ, -alkylN(Rᵦ)NRₐRᵦ, -alkylN(Rᵦ)C(=O)Rₐ, -alkylN(Rᵦ)C(=O)ORₐ, alkylN(Rᵦ)C(=O)NRₐRᵦ, -alkylN(Rᵦ)SO₂NRₐRᵦ, -alkylN(Rᵦ)SO₂Rₐ, -alkylC(=O)Rₐ, -alkylC(=O)ORₐ, -alkylC(=O)NRₐRᵦ, and R₇ₐ;

R₇ₐ is selected from the group consisting of cycloalkyl, cycloalkenyl, heterocycle, aryl, and heteroaryl, wherein:
  each R₇ₐ substituent is substituted with 0, 1, 2, 3, or 4 substituents independently selected from the group consisting of cyano, halo, nitro, oxo, alkyl, alkenyl, alkynyl, hydroxy, alkoxy, —NH₂, —N(H)(alkyl), —N(alkyl)₂, —SH, —S(alkyl), —SO₂(alkyl), —N(H)C(=O)alkyl, —N(alkyl)C(=O)alkyl, —N(H)C(=O)NH₂, —N(H)C(=O)N(H)(alkyl), —N(H)C(=O)N(alkyl)₂, —C(=O)OH, —C(=O)Oalkyl, —C(=O)NH₂, —C(=O)N(H)(alkyl), —C(=O)N(alkyl)₂, cyanoalkyl, formylalkyl, haloalkyl, hydroxyalkyl, alkoxyalkyl, -alkylNH₂, -alkylN(H)(alkyl), -alkylN(alkyl)$_2$, -alkylN(H)C(=O)alkyl, -alkylN(alkyl)C(=O)alkyl, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), and -alkylC(=O)N(alkyl)$_2$;

$R_8$ is selected from the group consisting of alkyl, alkenyl, alkynyl, cycloalkyl, aryl, heteroaryl, cycloalkylalkyl, and arylalkyl, wherein:
  each $R_8$ substituent is substituted with 0, 1, or 2 substituents independently selected from the group consisting of halo, cyano, formyl, nitro, alkyl, alkenyl, alkynyl, hydroxy, alkoxy, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), —C(=O)N(alkyl)$_2$, —C(=O)alkyl, hydroxyalkyl, alkoxyalkyl, -alkylNH$_2$, -alkylN(H)alkyl, -alkylN(alkyl)$_2$, -alkylC(=O)OH, -alkylC(=O)Oalkyl, -alkylC(=O)NH$_2$, -alkylC(=O)N(H)(alkyl), and -alkylC(=O)N(alkyl)$_2$;

$R_9$ is selected from the group consisting of alkyl, cycloalkyl, cycloalkylalkyl, aryl, heterocycle, heteroaryl, and $OR_{9a}$, wherein:
  each $R_9$ substituent is substituted with 0, 1, 2, or 3 substituents independently selected from the group consisting of hydroxy, alkoxy, halo, cyano, nitro, formyl, alkyl, alkenyl, alkynyl, —NH$_2$, —N(H)alkyl, —N(alkyl)$_2$, —C(=O)alkyl, —C(=O)OH, —C(=O)Oalkyl, —C(=O)NH$_2$, —C(=O)N(H)(alkyl), and —C(=O)N(alkyl)$_2$;

$R_{9a}$ is selected from the group consisting of alkyl, cycloalkyl, cycloalkylalkyl, aryl, arylalkyl, heterocycle, heteroaryl, heteroarylalkyl, and heterocyclealkyl, wherein:
  each $R_{9a}$ substituent is substituted with 0, 1, 2, or 3 substituents independently selected from the group consisting of hydroxy, alkoxy, halo, cyano, nitro, formyl, alkyl, alkenyl, alkynyl, —C(=O)N(H)(alkyl), and —C(=O)N(alkyl)$_2$;

$R_{10}$ is selected from the group consisting of alkyl, alkenyl, alkynyl, cycloalkyl, and cycloalkenyl, aryl, heteroaryl, arylalkyl, cycloalkylalkyl or heteroarylalkyl, wherein:
  each $R_{10}$ substituent is substituted with 0, 1, 2, or 3 substituents independently selected from the group consisting of halo, cyano, nitro, formyl, alkyl, alkenyl, hydroxy, alkoxy, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_b$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$, and —C(=O)OR$_a$;

$R_{11}$ is selected from the group consisting of hydrogen, alkyl, haloalkyl, hydroxyalkyl, and alkoxyalkyl;

$R_{12}$ is selected from the group consisting of hydrogen, alkyl, haloalkyl, hydroxyalkyl, and alkoxyalkyl;

$R_{13}$ is selected from the group consisting of alkyl and haloalkyl;

$R_{14}$ is selected from the group consisting of alkyl, cycloalkyl, cycloalkylalkyl, aryl, heteroaryl, and heterocycle, wherein:
  each $R_{14}$ substituent is substituted with 0, 1, 2, or 3 substituents independently selected from the group consisting of halo, cyano, nitro, formyl, alkyl, alkenyl, hydroxy, alkoxy, haloalkyl, —NH$_2$, —N(H)alkyl, —N(alkyl)$_2$, —C(=O)OH, —C(=O)Oalkyl, —C(=O)NH$_2$, —C(=O)N(H)(alkyl), and —C(=O)N(alkyl)$_2$;

Z is selected from the group consisting of —CH$_2$—, —NH—, —O—, and S—;

Z' is selected from the group consisting of —CH$_2$—, —NH—, —O—, and S—;

$R_a$ and $R_b$ at each occurrence are independently selected from the group consisting of hydrogen, alkyl, haloalkyl, alkenyl, alkynyl, cycloalkyl, aryl, heteroaryl, heterocycle, arylalkyl, and heteroarylalkyl, wherein:
  each $R_a$ and $R_b$ substituent is substituted with 0, 1, 2, or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, —C(=O)alkyl, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), -alkylC(=O)N(alkyl)$_2$, and alkylC(=O)alkyl; and n is 1.

31. The compound, stereoisomer, ester, prodrug, salt, or combination of claim 30, wherein:
  X is O, and
  Y is O.

32. The compound, stereoisomer, ester, prodrug, salt, or combination of claim 30, wherein:
  X is O,
  Y is O, and
  $R_1$ is alkyl.

33. The compound, stereoisomer, ester, prodrug, salt, or combination of claim 30, wherein:
  X is O,
  Y is O,
  $R_1$ is alkyl, and
  $R_4$ is —C(O)C(H)(R$_8$)NHC(O)R$_9$.

34. The compound, stereoisomer, ester, prodrug, salt, or combination of claim 30, wherein:
  X is O,
  Y is O,
  $R_1$ is alkyl,
  $R_4$ is —C(O)C(H)(R$_8$)NHC(O)R$_9$, and
  $R_9$ is —OR$_{9a}$.

35. The compound, stereoisomer, ester, prodrug, salt, or combination of claim 30, wherein:
  X is O,
  Y is O
  $R_1$ is alkyl,
  $R_4$ is —C(O)C(H)(R$_8$)NHC(O)R$_9$,
  $R_8$ is alkyl, and
  $R_9$ is —OR$_{9a}$.

36. The compound, stereoisomer, ester, prodrug, salt, or combination of claim 30, wherein:
  X is O,
  Y is O,
  $R_1$ is alkyl,
  $R_3$ is selected from the group consisting of alkyl, alkenyl, alkynyl, cycloalkyl, cycloalkylalkyl, hydroxyalkyl, alkoxyalkyl, arylalkyl, heteroarylalkyl, and heterocyclealkyl,
  $R_4$ is —C(O)C(H)(R$_8$)NHC(O)R$_9$, $R_8$ is alkyl, and
$R_9$ is —$OR_{9a}$.

37. The compound, stereoisomer, ester, prodrug, salt, or combination of claim 30, wherein:
X is O,
Y is O,
$R_1$ is alkyl,
$R_3$ is selected from the group consisting of alkyl, alkenyl, alkynyl, cycloalkyl, cycloalkylalkyl, hydroxyalkyl, alkoxyalkyl, arylalkyl, heteroarylalkyl, and heterocyclealkyl,
$R_4$ is —$C(O)C(H)(R_8)NHC(O)R_9$,
$R_8$ is alkyl,
$R_9$ is —$OR_{9a}$, and
$R_2$ is arylalkyl.

38. The compound, stereoisomer, ester, prodrug, salt, or combination of claim 30, wherein:
X is O,
Y is O,
$R_1$ is alkyl;
$R_3$ is selected from the group consisting of alkyl, alkenyl, alkynyl, cycloalkyl, cycloalkylalkyl, hydroxyalkyl, alkoxyalkyl, arylalkyl, heteroarylalkyl, and heterocyclealkyl,
$R_4$ is —$C(O)C(H)(R_8)NHC(O)R_9$,
$R_8$ is alkyl,
$R_9$ is —$OR_{9a}$,
$R_{9a}$ is alkyl, and
$R_2$ is arylalkyl.

39. The compound, stereoisomer, ester, prodrug, salt, or combination of claim 30, wherein:
X is O,
Y is O,
$R_1$ is alkyl,
$R_3$ is selected from the group consisting of alkyl, alkenyl, alkynyl, cycloalkyl, cycloalkylalkyl, hydroxyalkyl, alkoxyalkyl, arylalkyl, heteroarylalkyl, and heterocyclealkyl,
$R_4$ is —$C(O)C(H)(R_8)NHC(O)R_9$,
$R_8$ is alkyl,
$R_9$ is —$OR_{9a}$,
$R_{9a}$ is alkyl,
$R_2$ is arylalkyl, and
$R_7$ is heteroaryl.

40. Methyl (1S)-1-({2-[(2S,3S)-3-({(2S,3S)-2-[2,4-dioxo-3-(2-pyridinylmethyl)-1-imidazolidinyl]-3-methylpentanoyl}amino)-2-hydroxy-4-phenylbutyl]-2-[4-(2-pyridinyl)benzyl]hydrazino}carbonyl)-2,2-dimethylpropylcarbamate, stereoisomer of the compound, ester of the compound, prodrug of the compound, pharmaceutically acceptable salt of the compound, stereoisomer, ester, or prodrug, or combination thereof.

41. A pharmaceutical composition comprising:
a therapeutically effective amount of one or more compounds, stereoisomers, esters, prodrugs, and/or salts of claim 1, and
a pharmaceutically acceptable carrier.

42. A pharmaceutical composition comprising:
a therapeutically effective amount of one or more compounds, stereoisomers, esters, prodrugs, and/or salts of claim 1, and
one, two, three, four, five, or six agents independently selected from the group consisting of a second HIV protease inhibitor, a HIV reverse transcriptase inhibitor, an HIV entry/fusion inhibitor, an HIV integrase inhibitor, and an HIV budding/maturation inhibitor, and
a pharmaceutically acceptable carrier.

43. The pharmaceutical composition of claim 42, wherein the second HIV protease inhibitor is selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684, and GW640385X.

44. The pharmaceutical composition of claim 42, wherein the HIV reverse transcriptase inhibitor is selected from the group consisting of lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120, and TMC-125.

45. The pharmaceutical composition of claim 42, wherein the HIV entry/fusion inhibitor is selected from the group consisting of enfuvirtide (T-20), T-1249, PRO 2000, PRO 542, PRO 140, AMD-3100, BMS-806, FP21399, GW873140, Schering C(SCH-C), Schering D (SCH-D), TNX-355, and UK-427857.

46. The pharmaceutical composition of claim 42, wherein the HIV integrase inhibitor is selected from the group consisting of S-1360, zintevir (AR-177), L-870812, and L-870810.

47. The pharmaceutical composition of claim 42, wherein the HIV budding/maturation inhibitor is PA-457.

48. A method of treating an HIV infection, wherein the method comprises administering to a patient in need of such treatment a therapeutically effective amount of one or more compounds, stereoisomers, esters, prodrugs, and/or salts of claim 1.

49. A method of treating an HIV infection, wherein the method comprises administering to a patient in need of such treatment a pharmaceutical composition of any one of claims 41, 42, 43, 44, 45, 46, and 47.

* * * * *

UNITED STATES PATENT AND TRADEMARK OFFICE
CERTIFICATE OF CORRECTION

PATENT NO. : 7,696,226 B2
APPLICATION NO. : 11/010177
DATED : April 13, 2010
INVENTOR(S) : John T. Randolph et al.

It is certified that error appears in the above-identified patent and that said Letters Patent is hereby corrected as shown below:

Column 224, line 9, claim 1: "OXO" to read as -- oxo --

Column 225, line 44, claim 1: "$CH_2$-" to read as -- —$CH_2$— --

Column 225, line 66, claim 1: "alkylC(=O)alkyl," to read as -- —alkylC(=O)alkyl --

Column 226, line 60, claim 9: "$(CH_3)_n$," to read as -- $(CH_2)_n$ --

Column 227, line 24, claim 9: "—C(=O)N(alkyl)$_z$," to read as-- —C(=O)N(alkyl)$_2$ --

Column 227, line 37, claim 9: "alkylNR$_a$R$_b$," to read as -- -alkylN(R$_b$)SO$_2$R$_a$ --

Column 229, line 35, claim 9: "—SO$_2$OR$_3$," to read as-- — SO$_2$OR$_a$ --

Column 229, line 48, claim 9: "-alkylN(R$_b$)SO$_2$R$_b$," to read as -- -alkylN(R$_b$)SO$_2$R$_a$ --

Column 230, line 35, claim 9: "—N(alkyl)$_z$," to read as-- —N(alkyl)$_2$ --

Column 236, line 52, claim 19: "methyl (1S) -1-[4-[2-((2S,3S)-2-hydroxy-3-4 [(2S)-2-" to read as -- methyl (1S)-1-{2-((2S,3S)-2-hydroxy-3-{[(2S)-2- --

Column 238, line 54, claim 19: "methyl (1S)-1-4 (2-(cyclopropylmethyl)-2-((2S,3S)-2hy-" to read as -- methyl (1S)-1-{[2-(cyclopropylmethyl)-2-((2S,3S)-2-hy- --

Column 241, line 2, claim 19: "[((2S)-3,3-dimethyl-2-(34(2-methyl-1H-benzimidazol-5-yl)" to read as -- [((2S)-3,3-dimethyl-2-{3-[(2-methyl-1H-benzimidazol-5-yl) --

Column 241, line 47, claim 19: "thyl-{3-[(2-methyl-1,3-thiazol-4-yl)methyl]-2-oxo-1-" to read as -- thyl-2-{3-[(2-methyl-1,3-thiazol-4-yl) methyl]-2-oxo-1- --

Column 243, line 4, claim 19: "(1.5°)" to read as -- (1S) --

Column 244, line 26, claim 19: "(1.5)" to read as -- (1S) --

Signed and Sealed this
First Day of March, 2011

David J. Kappos
*Director of the United States Patent and Trademark Office*

CERTIFICATE OF CORRECTION (continued)
U.S. Pat. No. 7,696,226 B2

Column 244, line 32, claim 19: "(2.5)" to read as -- (1S) --

Column 244, line 41, claim 19: "(1.5)" to read as -- (1S) --

Column 251, line 15, claim 20: "—C(=O)N(alkyl," to read as-- —C(=O)N(alkyl)$_2$ --

Column 252, line 2, claim 20: "IN(R$_b$)C(=O)NR$_a$R$_b$," to read as -- -N(R$_b$)C(=O)NR$_a$R$_b$ --

Column 255, line 7, claim 30: insert
-- -alkylC(=O)O(alkyl), -alkylC(=O)NH$_2$, -alkylC(=O)N(H)(alkyl), -alkylC(=O)N(alkyl)$_2$, -- after -alkylC(=O)OH, Column 255, line 17, claim 30: insert
-- -N(alkyl)C(=O)alkyl, -C(=O)OH, -C(=O)O(alkyl), -C(=O)NH$_2$, -C(=O)N(H)(alkyl), -C(O)N(alkyl)$_2$, -- after -N(H)C(=O)alkyl, Column 257, line 38, claim 30: insert -- -NH$_2$, -N(H)alkyl, -N(alkyl)$_2$, -C(=O)alkyl, -C(=O)OH, -C(=O)Oalkyl, -C(=O)NH$_2$, -- after alkynyl,